United States Patent
Boezio et al.

(10) Patent No.: US 9,115,127 B2
(45) Date of Patent: Aug. 25, 2015

(54) BENZIMIDAZOLE AND AZABENZIMIDAZOLE COMPOUNDS THAT INHIBIT ANAPLASTIC LYMPHOMA KINASE

(75) Inventors: Christiane M. Boezio, Somerville, MA (US); Alan C. Cheng, San Francisco, CA (US); Deborah Choquette, Medford, MA (US); Richard T. Lewis, Framingham, MA (US); Michele H. Potashman, Cambridge, MA (US); Karina Romero, Arlington, MA (US); John C. Stellwagen, Beverly, MA (US); Douglas A. Whittington, Waltham, MA (US)

(73) Assignee: AMGEN INC., Thousand Oaks, CA (US)

( * ) Notice: Subject to any disclaimer, the term of this patent is extended or adjusted under 35 U.S.C. 154(b) by 45 days.

(21) Appl. No.: 13/813,813

(22) PCT Filed: Jul. 28, 2011

(86) PCT No.: PCT/US2011/045703
§ 371 (c)(1),
(2), (4) Date: Apr. 11, 2013

(87) PCT Pub. No.: WO2012/018668
PCT Pub. Date: Feb. 9, 2012

(65) Prior Publication Data
US 2013/0217668 A1 Aug. 22, 2013

Related U.S. Application Data

(60) Provisional application No. 61/371,041, filed on Aug. 5, 2010.

(51) Int. Cl.
C07D 235/30 (2006.01)
C07D 235/32 (2006.01)
C07D 401/06 (2006.01)
C07D 401/12 (2006.01)
C07D 401/14 (2006.01)
C07D 403/04 (2006.01)
C07D 403/06 (2006.01)
C07D 403/08 (2006.01)
C07D 403/14 (2006.01)
C07D 417/04 (2006.01)
C07D 413/04 (2006.01)
A61P 35/00 (2006.01)
C07D 471/04 (2006.01)
C07D 417/06 (2006.01)
C07D 487/04 (2006.01)
C07D 401/10 (2006.01)
(Continued)

(52) U.S. Cl.
CPC ............ *C07D 471/04* (2013.01); *C07D 235/30* (2013.01); *C07D 401/06* (2013.01); *C07D 401/10* (2013.01); *C07D 401/12* (2013.01); *C07D 401/14* (2013.01); *C07D 403/04* (2013.01); *C07D 403/06* (2013.01); *C07D 403/08* (2013.01); *C07D 413/10* (2013.01); *C07D 413/14* (2013.01); *C07D 417/06* (2013.01); *C07D 417/12* (2013.01); *C07D 417/14* (2013.01); *C07D 487/04* (2013.01); *C07D 519/00* (2013.01)

(58) Field of Classification Search
CPC .. C07D 235/30; C07D 235/32; C07D 401/06; C07D 401/12; C07D 401/14; C07D 403/04; C07D 403/06; C07D 403/08; C07D 403/14; C07D 417/04; C07D 413/04
USPC ............ 514/388, 326, 339; 548/307.4, 308.7, 548/306.1
See application file for complete search history.

(56) References Cited

U.S. PATENT DOCUMENTS 3,624,096 A 11/1971 Abramovitch et al.
4,002,623 A 1/1977 Kadin
(Continued)

FOREIGN PATENT DOCUMENTS

CN 101405000 4/2009
JP 62025748 A 2/1987
(Continued)

OTHER PUBLICATIONS

Abramovitch et al., Direct Acylamination of Quinoline, Isoquinoline, Benzimidazole, Pyridazine, and Pyrimidine 1-Oxides. Novel 1,5-Sigmatropic Shift, Journal of Organic Chemistry, 40(1):41-48 (1975).
(Continued)

*Primary Examiner* — Sreeni Padmanabhan
*Assistant Examiner* — Irina Neagu
(74) *Attorney, Agent, or Firm* — Choate, Hall & Stewart LLP; Brenda Herschbach Jarrell; Kristen C. Buteau

(57) ABSTRACT

Compounds of Formula (I) are useful inhibitors of anaplastic lymphoma kinase. Compounds of Formula (I) have the following structure: where the definitions of the variables are provided herein.

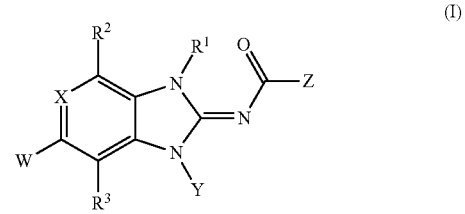

17 Claims, No Drawings

(51) Int. Cl.
  C07D 413/10    (2006.01)
  C07D 413/14    (2006.01)
  C07D 417/14    (2006.01)
  C07D 417/12    (2006.01)
  C07D 519/00    (2006.01)

(56) References Cited

U.S. PATENT DOCUMENTS

| | | | |
|---|---|---|---|
| 4,874,864 | A | 10/1989 | Schnur et al. |
| 5,376,665 | A | 12/1994 | Miyata et al. |
| 5,683,999 | A | 11/1997 | Jadhav et al. |
| 6,340,681 | B1 | 1/2002 | Ito |
| 7,011,700 | B2 | 3/2006 | Jung et al. |
| 7,132,438 | B2 | 11/2006 | Frenkel et al. |
| 7,256,196 | B1 | 8/2007 | Sabat et al. |
| 7,355,052 | B2 | 4/2008 | Poitout et al. |
| 2003/0144286 | A1* | 7/2003 | Frenkel et al. ............. 514/233.5 |
| 2004/0110808 | A1 | 6/2004 | Strobel et al. |
| 2004/0116388 | A1 | 6/2004 | Armistead et al. |
| 2004/0132758 | A1 | 7/2004 | Vaccaro et al. |
| 2005/0065179 | A1 | 3/2005 | Poitout et al. |
| 2005/0124638 | A1 | 6/2005 | Swayze et al. |
| 2005/0165007 | A1 | 7/2005 | Seth et al. |
| 2005/0176792 | A1 | 8/2005 | Moriarty et al. |
| 2005/0209284 | A1 | 9/2005 | Bentzien et al. |
| 2005/0245547 | A1 | 11/2005 | Kim et al. |
| 2006/0173036 | A1 | 8/2006 | Poitout et al. |
| 2008/0200371 | A1 | 8/2008 | Cheruvallath et al. |

FOREIGN PATENT DOCUMENTS

| | | |
|---|---|---|
| JP | 63159861 A | 7/1988 |
| JP | 05088812 B2 | 12/1993 |
| JP | 11302177 A | 11/1999 |
| JP | 2000154188 A | 6/2000 |
| JP | 2001199968 A | 7/2001 |
| WO | WO-0008013 A2 | 2/2000 |
| WO | WO-0020358 A2 | 4/2000 |
| WO | WO-0125220 A1 | 4/2001 |
| WO | WO-0170705 A1 | 9/2001 |
| WO | WO-03037332 A1 | 5/2003 |
| WO | WO-03041708 A1 | 5/2003 |
| WO | WO-2004075823 A2 | 9/2004 |
| WO | WO-2005/009389 A2 | 2/2005 |
| WO | WO-2005021547 A2 | 3/2005 |
| WO | WO-2006099379 A2 | 9/2006 |
| WO | WO-2007008541 A2 | 1/2007 |
| WO | WO-2007022305 A2 | 2/2007 |
| WO | WO-2007084728 A2 | 7/2007 |
| WO | WO-2007133983 A2 | 11/2007 |
| WO | WO-2008079277 A1 | 7/2008 |
| WO | WO-2010067067 A1 | 6/2010 |

OTHER PUBLICATIONS

Abramovitch et al., Direct Alkyl and Aryl Amination of Heteroaromatic Nitrogen Compounds, Journal of the American Chemical Society, 91(20): 5672-3 (1969).

Baell et al., Design and Synthesis of Type-III Mimetics of ShK Toxin, Journal of Computer-Aided Molecular Design, 16(4): 245-262 (2002).

Bischof, D. et al., Role of the Nucleophosmin (NPM) Portion of the Non-Hodgkin's Lymphoma-Associated NPM-Anaplastic Lymphoma Kinase Fusion Protein in Oncogenesis, Molecular and Cellular Biology, 17(4):2312-2325 (1997).

Calhorda et al., Synthesis and Ligand Properties Towards Gold and Silver of the Ferrocenylamidobenzimidazole Ligand, Journal of Organometallic Chemistry, 691(20): 4181-4188 (2006).

Caroti et al., A Facile Synthesis of 5,7-dihydro-5-oxopyrido[3',2':5,6]pyrimido[1,2-a]benzimidazoles. A New Heterocyclic Ring System., Journal of Heterocyclic Chemistry, 23(6): 1833-1836 (1986).

Chern et al., An Efficient Synthesis of 8-Amino-9-Benzylguanine, Journal of the Chinese Chemical Society, 36(6): 615-618 (1989).

Daniels et al., Food Intake Inhibition and Reduction in Body Weight Gain in Lean and Obese Rodents Treated with GW438014A, a Potent and Selective NPY-Y5 Receptor Antagonist, Regulatory Peptides, 106(1-3): 47-54 (2002).

Gerritz et al., High-Throughput Manual Parallel Synthesis Using SynPhase Crowns and Lanterns, Journal of Combinatorial Chemistry, 5(2): 110-117 (2003).

He et al., Structural Modification and Cytotoxic Activity of Adenosine Analogs, National Research Laboratories of Natural and Biomimetic Drugs, Acta Pharmaceutica Sinica, 34(1): 29-33 (1998).

Ladanyi, M. et al., Reverse Transcriptase Polymerase Chain Reaction for the Ki-1 Anaplastic Large Cell Lymphoma-Associated t(2;5) Translocation in Hodgkin's Disease, The American Journal of Pathology, 145(6):1296-1300 (1994).

Lawrence, B. et al., TPM3-ALK and TPM4-ALK Oncogenes in Inflammatory Myofibroblastic Tumors, The American Journal of Pathology, 157(2):377-384 (2000).

Li et al., Synthesis and Biological Evaluation of Purine Derivatives Incorporating Metal Chelating Ligands as HIV Integrase Inhibitors, Bioorganic & Medicinal Chemistry, 14(16): 5742-5755 (2006).

Lin, E. et al., Exon Array Profiling Detects EML4-ALK Fusion in Breast, Colorectal, and Non-Small Cell Lung Cancers, Molecular Cancer Research 7:1466-1476 (2009).

Mallesha et al., Synthesis and Characterization of Model Ultimate Carcinogens/Metabolites Derived from Lead Tetraacetate Oxidation of Arylnitrones: 2'-Deoxyguanosine Adducts, Synthesis, 10: 1459-1461 (2001).

Mallesha et al., Synthesis and Characterization of Nucleoside Derivatives, N-(benzoyl)-N-(deoxyguanosin-8-yl)-4-aminobiphenyl and N-(2'-deoxyguanosin-8-yl)-4-aminobiphenyl via α-Phenyl-N-(4-biphenyl)nitrone, Nucleosides, Nucleotides & Nucleic Acids, 21(4&5):385-392 (2002).

Mallesha et al., Synthesis of N-Acetoxy-N-benzoyl-2-aminofluorene, an Ultimate Carcinogen by LTA Oxidation of α-Phenyl-N-(2-aminofluorenyl)nitrone, and N-(2'-Deoxyguanosine-8-yl)-2-aminofluorene, Synthesis, 16: 2415-2418 (2001).

Manfredini et al., Hindered Nucleoside Aanalogs as Antiflaviviridae Agents, Pure and Applied Chemistry, 76(5): 1007-1015 (2004).

Martinho et al., New Polynuclear Mo-Fe Complexes with Ferrocenylamidobenzimidazole Ligands, European Journal of Inorganic Chemistry, 4096-4103 (2006).

Moriarty et al., Discovery, SAR and X-ray Structure of 1H-benzimidazole-5-Carboxylic Acid Cyclohexylmethylamides as Inhibitors of Inducible T-cell Kinase (Itk), Bioorganic & Medicinal Chemistry Letters, 18(20): 5545-5549 (2008).

Morris, S.W. et al., Fusion of a Kinase Gene, ALK, to a Nucleolar Protein Gene, NPM, in Non-Hodgkin's Lymphoma, Science, 263:1281-1284 (1994).

Mosse, Y.P. et al., Identification of ALK as a Major Familial Neuroblastoma Predisposition Gene, Nature, 455(7215):930-935 (2008).

Powers et al., Discovery and Initial SAR of Inhibitors of Interleukin-1 Receptor-Associated Kinase-4, Bioorganic & Medicinal Chemistry Letters, 16(11): 2842-2845 (2006).

Pulford, K. et al., The Emerging Normal and Disease-Related Roles of Anaplastic Lymphoma Kinase, Cellular and Molecular Life Sciences, 61:2939-2953 (2004).

Rao et al., Synthesis of 2-aryl-1H-s-triazolo[1,5-a]benzimidazoles, Synthetic Communications, 18(16&17): 1995-2001 (1988).

Rastogi et al., Synthesis of 2-(N-aroylamino) benzimidazoles as Potential Anthelmintics and Antimicrobial Agents, European Journal of Medicinal Chemistry—Chimica Therapeutica, 14(6): 489-491 (1979).

Rega et al., Structure-Based Discovery of a New Class of BCl-xl Antagonists, Bioorganic Chemistry, 35(4): 344-353 (2007).

Sabat et al., The Development of Novel C-2, C-8, and N-9 Trisubstituted Purines as Inhibitors of TNF-α Production, Bioorganic & Medicinal Chemistry Letters, 16(16): 4360-4365 (2006).

(56) References Cited

OTHER PUBLICATIONS

Seth et al., Efficient Solution Phase Synthesis of 2-(N-acylamino)benzimidazoles, Tetrahedron Letters, 43(41): 7303-7306 (2002).
Seth et al., SAR by MS: Discovery of a New Class of RNA-Binding Small Molecules for the Hepatitis C Virus: Internal Ribosome Entry Site IIA Subdomain, Journal of Medicinal Chemistry, 48(23): 7099-7102 (2005).
Simonov et al., Benzimidazole Drivatives. XIV. Amination of 1-Cyclohexyland 1-Phenylbenzimidazole, Journal of General Chemistry of the USSR (Zhurnal Obshchei Khimii), 33(7): 2350-2354 (1963).
Simonov et al., Reaction of 2-Iminobenzimidazoline Derivatives with Chlorosulfonic Acid, Khimiya Geterotsiklicheskikh Soedinenii, 5(3): 539-542 (1969).
Snow et al., Hit-to-lead Studies on Benzimidazole Inhibitors of ITK: Discovery of a novel class of kinase inhibitors, Bioorganic & Medicinal Chemistry Letters, 17(13): 3660-3665 (2007).
Soda, M. et al., Identification of the Transforming EML4-ALK Fusion Gene in Non-Small-Cell Lung Cancer, Nature, 448:561-566 (2007).
Stahura et al., Molecular Scaffold-Based Design and Comparison of Combinatorial Libraries Focused on the ATP-Binding Site of Protein Kinases, Journal of Molecular Graphics & Modelling 17(1): 1-9 (1999).
Touriol, C. et al., Further Demonstration of the Diversity of Chromosomal Changes Involving 2p23 in ALK-Positive Lymphoma: 2 Cases Expressing ALK Kinase Fused to CLTCL (Clathrin Chain Polypeptide-Like), Blood, 95(10):3204-3207 (2000).
Vanallan et al., Reaction of Certain Heterocyclic Azides with Triphenylphosphine, Journal of Heterocyclic Chemistry, 5(4): 471-476 (1968).
Vitkevich et al., Benzimidazole Derivatives. VII. Dual Reactivity of 2-Amino-1-Methylbenzimidazole, Journal of General Chemistry of the USSR (Zhurnal Obshchei Khimii), 30(9): 2868-2871 (1960).
Zhao et al., New Developments in Diketo-Containing Inhibitors of HIV-1 Integrase, Mini-Reviews in Medicinal Chemistry, 7(7): 707-725 (2007).
International Preliminary Report on Patentability of PCT/US11/45703, 7 pages (mailed Feb. 14, 2013).
International Search Report of PCT/US11/45703, 3 pages (mailed Dec. 23, 2011).
Written Opinion of PCT/US11/45703, 9 pages (mailed Dec. 23, 2011).
European Search Report of EP 11815100.0, 5 pages (dated Dec. 5, 2013).

\* cited by examiner

BENZIMIDAZOLE AND AZABENZIMIDAZOLE COMPOUNDS THAT INHIBIT ANAPLASTIC LYMPHOMA KINASE

CROSS-REFERENCE TO RELATED APPLICATIONS

This application is a National Stage Entry of International Patent Application No. PCT/US11/45703, filed Jul. 28, 2011, which claims the benefit of, and priority to, U.S. Provisional Application No. 61/371,041, filed on Aug. 5, 2010, which are hereby incorporated by reference in their entirety and for all purposes as if fully set forth herein.

FIELD OF THE INVENTION

The present invention relates to compounds capable of inhibiting the kinase activity of anaplastic lymphoma kinase (ALK), and compositions that include compounds that inhibit ALK. The compounds and compositions may be used to treat diseases or conditions modulated by ALK such as cancer and may be used to treat neurological disorders such as depression and are especially useful in treating patients with cancers expressing modified ALK or cancers related to ALK expression. For example, the compounds and compositions are especially useful in treating cancers that are positive for ALK fusion proteins EML4-ALK and/or NPM-ALK or have kinase activating point mutations in the ALK protein as well as amplifications of the ALK locus on chromosome 2p23.

BACKGROUND OF THE INVENTION

ALK is a receptor tyrosine kinase conserved across species and plays a key role in the growth and differentiation of neural tissues in the developing embryo. The receptor belongs in the insulin receptor superfamily and was initially identified as a member of a novel intracellular fusion protein with constitutive kinase activity in anaplastic large-cell lymphoma (ALCL). Bischof, D. et al., "Role of the Nucleophosmin (NPM) Portion of the Non-Hodgkin's Lymphoma-Associated NPM-Anaplastic Lymphoma Kinase Fusion Protein in Oncogenesis," Molecular and Cellular Biology. 17, 2312-2325 (1997); Pulford, K. et al., "The Emerging Normal and Disease-Related Roles of Anaplastic Lymphoma Kinase," Cell Mol Life Sci. 61, 2939-2953 (2004). Subsequent studies have identified ALK fusion proteins in diffuse large B-cell lymphomas, systemic histiocytosis, inflammatory myofibroblastic tumors, breast cancers, colorectal carcinomas, and non-small cell lung cancers. Morris, S. W. et al., "Fusion of a Kinase Gene, ALK, to a Nucleolar Protein Gene, NPM, in Non-Hodgkin's Lymphoma", Science (New York, N.Y. 263, 1281-1284 (1994)); Lawrence, B. et al., "TPM3-ALK and TPM4-ALK Oncogenes in Inflammatory Myofibroblastic Tumors," The American Journal of Pathology. 157, 377-384 (2000); Touriol, C. et al., "Further Demonstration of the Diversity of Chromosomal Changes Involving 2p23 in ALK-Positive Lymphoma: 2 Cases Expressing ALK Kinase Fused to CLTCL (Clathrin Chain Polypeptide-Like)," Blood. 95, 3204-3207 (2000); Soda, M. et al., "Identification of the Transforming EML4-ALK Fusion Gene in Non-Small-Cell Lung Cancer," Nature. 448, 561-566 (2007); Lin, E. et al., "Exon Array Profiling Detects EML4-ALK Fusion in Breast, Colorectal, and Non-Small Cell Lung Cancers," Mol Cancer Res. 7, 1466-1476 (2009). In addition, activating point mutations, as well as genomic DNA amplification and overexpression of ALK have recently been described in neuroblastomas. Mosse, Y. P. et al., "Identification of ALK as a Major Familial Neuroblastoma Predisposition Gene," Nature. 455, 930-935 (2008).

Using immunostaining and other methods, 60-80% of ALCLs have been found to be ALK fusion-positive. Morris, S. W. et al., "Fusion of a Kinase Gene, ALK, to a Nucleolar Protein Gene, NPM, in Non-Hodgkin's Lymphoma", Science (New York, N.Y. 263, 1281-1284 (1994)); Ladanyi, M. et al., "Reverse Transcriptase Polymerase Chain Reaction for the Ki-1 Anaplastic Large Cell Lymphoma-Associated t(2; 5) Translocation in Hodgkin's Disease," The American Journal of Pathology. 145, 1296-1300 (1994). ALK-positive ALCL cells express the cell surface protein CD30 and exhibit a cytotoxic T-cell or null phenotype. This lymphoma entity is now officially classified as 'ALK-positive ALCL' in the WHO classification of NHL.

More recently, ALK has been identified in a subset of non small cell lung carcinoma patients (NSCLC). In 2006, genetic analysis of a patient with NSCLC led to the discovery of a novel fusion gene between the echinoderm microtubule-associated protein-like 4 (EML4) and the anaplastic lymphoma kinase (ALK) genes. Oncogenic activity of EML4-ALK requires the N-terminal coiled-coil domain within EML4 that leads to the constitutive dimerization and, thereby, activation of the fusion protein. Soda, M. et al., "Identification of the Transforming EML4-ALK Fusion Gene in Non-Small-Cell Lung Cancer," Nature. 448, 561-566 (2007). Since both of the EML4 and ALK genes are closely mapped in an opposite direction to the same short arm of human chromosome 2, a small chromosome inversion involving the two genes is likely to be the underlying mechanism for the generation of the gene fusion, which was indeed evidenced by both of FISH and genomic PCR analyses.

SUMMARY OF THE INVENTION

In one aspect, the invention provides a compound of Formula I:

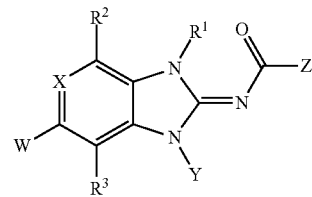

or a pharmaceutically acceptable salt thereof, tautomer thereof, a pharmaceutically acceptable salt of the tautomer, a stereoisomer of any of the foregoing, or a mixture thereof, wherein:

$R^1$ is —H;
$R^2$ is —H;
$R^3$ is selected from —H, —F, —Cl, —Br, —I; —($C_1$-$C_6$) alkyl, —($C_2$-$C_6$)alkenyl, —($C_2$-$C_6$)alkynyl, —$CF_3$, —OH, —$OCF_3$, —O—($C_1$-$C_6$)alkyl, —$OCHF_2$, —SH, —S—($C_1$-$C_6$)alkyl, —$NH_2$, —N(H)—($C_1$-$C_6$)alkyl, —N(($C_1$-$C_6$) alkyl)$_2$, —$NO_2$, —C≡N, —C(=O)OH, —C(=O)O—($C_1$-$C_6$)alkyl, —C(=O)$NH_2$, —C(=O)N(H)—($C_1$-$C_6$)alkyl, —C(=O)N(($C_1$-$C_6$)alkyl)$_2$, —N(H)—C(=O)—($C_1$-$C_6$) alkyl, —N(($C_1$-$C_6$)alkyl)-C(=O)—($C_1$-$C_6$)alkyl, —($C_1$-$C_4$) alkylene-OH, —($C_1$-$C_4$)alkylene-$NH_2$, —($C_1$-$C_4$)alkylene-N(H)—($C_1$-$C_6$)alkyl, —($C_1$-$C_4$)alkylene-N(($C_1$-$C_6$)alkyl)$_2$, or phenyl optionally substituted with 1, 2, or 3 substituents selected from —F, —Cl, —Br, —I; —(C$_1$-C$_6$)alkyl, —(C$_2$-C$_6$)alkenyl, —(C$_2$-C$_6$)alkynyl, —CF$_3$, —OH, —OCF$_3$, —O—(C$_1$-C$_6$)alkyl, —OCHF$_2$, —SH, —S—(C$_1$-C$_6$)alkyl, —NH$_2$, —N(H)—(C$_1$-C$_6$)alkyl, —N((C$_1$-C$_6$)alkyl)$_2$, —NO$_2$, —C≡N, —C(═O)OH, —C(═O)O—(C$_1$-C$_6$)alkyl, —C(═O)NH$_2$, —C(═O)N(H)—(C$_1$-C$_6$)alkyl, or —C(═O)N((C$_1$-C$_6$)alkyl)$_2$;

X is selected from CR$^4$ or N;

R$^4$ is absent if X is N, or is selected from —H, —F, —Cl, —Br, —I; —(C$_1$-C$_6$)alkyl, —(C$_2$-C$_6$)alkenyl, —(C$_2$-C$_6$)alkynyl, —CF$_3$, —OH, —OCF$_3$, —O—(C$_1$-C$_6$)alkyl, —OCHF$_2$, —SH, —S—(C$_1$-C$_6$)alkyl, —NH$_2$, —N(H)—(C$_1$-C$_6$)alkyl, —N((C$_1$-C$_6$)alkyl)$_2$, —NO$_2$, —C≡N, —C(═O)OH, —C(═O)O—(C$_1$-C$_6$)alkyl, —C(═O)NH$_2$, —C(═O)N(H)—(C$_1$-C$_6$)alkyl, —C(═O)N((C$_1$-C$_6$)alkyl)$_2$, —(C$_1$-C$_4$)alkylene-OH, —(C$_1$-C$_4$)alkylene-NH$_2$, —(C$_1$-C$_4$)alkylene-N(H)—(C$_1$-C$_6$)alkyl, —(C$_1$-C$_4$)alkylene-N((C$_1$-C$_6$)alkyl)$_2$, or phenyl optionally substituted with 1, 2, or 3 substituents selected from —F, —Cl, —Br, —I; —(C$_1$-C$_6$)alkyl, —(C$_2$-C$_6$)alkenyl, —(C$_2$-C$_6$)alkynyl, —CF$_3$, —OH, —OCF$_3$, —O—(C$_1$-C$_6$)alkyl, —OCHF$_2$, —SH, —S—(C$_1$-C$_6$)alkyl, —NH$_2$, —N(H)—(C$_1$-C$_6$)alkyl, —N((C$_1$-C$_6$)alkyl)$_2$, —NO$_2$, —C≡N, —C(═O)OH, —C(═O)O—(C$_1$-C$_6$)alkyl, —C(═O)NH$_2$, —C(═O)N(H)—(C$_1$-C$_6$)alkyl, or —C(═O)N((C$_1$-C$_6$)alkyl)$_2$;

Y is selected from a C$_3$-C$_{12}$ cycloalkyl or a 3-10 membered heterocyclyl comprising 1, 2, or 3 heteroatoms selected from O, S, or N; wherein the C$_3$-C$_{12}$ cycloalkyl and the 3-10 membered heterocyclyl may be monocyclic, bicyclic, or tricyclic, and further wherein the C$_3$-C$_{12}$ cycloalkyl and the 3-10 membered heterocyclyl are unsubstituted or are optionally substituted with 1, 2, or 3 substituents independently selected from —Y', —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —(C$_2$-C$_6$)alkenyl, —(C$_2$-C$_6$)alkynyl, —NH$_2$, —NH((C$_1$-C$_4$)alkyl), —N((C$_1$-C$_4$)alkyl)$_2$, SO$_2$—(C$_1$-C$_6$)alkyl, —NHC(═O)—(C$_1$-C$_6$)alkyl, —C(═O)NH$_2$, —C(═O)NH((C$_1$-C$_6$)alkyl), —C(═O)NH—(C$_1$-C$_4$)alkylene-CF$_3$, —C(═O)NH—(C$_1$-C$_4$)alkylene-F, —C(═O)NH—(C$_2$-C$_4$)alkenyl, —C(═O)N((C$_1$-C$_6$)alkyl)$_2$, —C(═O)NH—OH, —C(═O)NH—O—(C$_1$-C$_6$)alkyl, —C(═O)NH—Y", —C(═O)—(C$_1$-C$_4$)alkylene-CF$_3$, —C(═O)N—(C$_1$-C$_4$)alkylene-F, —C(═O)—(C$_2$-C$_4$)alkenyl, —C(═O)—(C$_1$-C$_4$)alkylene-NH$_2$, —C(═O)—(C$_1$-C$_4$)alkylene-NH((C$_1$-C$_4$)alkyl), —C(═O)—(C$_1$-C$_4$)alkylene-N((C$_1$-C$_4$)alkyl)$_2$, —C(═O)NH—(C$_1$-C$_4$)alkylene-OH, —C(═O)NH—(C$_1$-C$_4$)alkylene-O—(C$_1$-C$_6$)alkyl, —C(═O)NH—(C$_1$-C$_4$)alkylene-Y", —C(═O)—(C$_1$-C$_6$)alkyl, —C(═O)—Y", —CO$_2$H, —C(═O)—O—(C$_1$-C$_6$)alkyl, —C(═O)NH—(C$_1$-C$_4$)alkylene-NH$_2$, —C(═O)NH—(C$_1$-C$_4$)alkylene-NH((C$_1$-C$_6$)alkyl), —C(═O)NH—(C$_1$-C$_4$)alkylene-N((C$_1$-C$_6$)alkyl)$_2$, —SO$_2$NH$_2$, —SO$_2$NH((C$_1$-C$_6$)alkyl), —SO$_2$N((C$_1$-C$_6$)alkyl)$_2$, —SO$_2$NH((C$_2$-C$_4$)alkenyl), —SO$_2$NH((C$_2$-C$_4$)alkynyl), —SO$_2$NH—Y", —SO$_2$NH—(C$_1$-C$_4$)alkylene-OH, —SO$_2$NH—(C$_1$-C$_4$)alkylene-O—(C$_1$-C$_4$)alkyl, —SO$_2$—(C$_1$-C$_6$)alkyl, —SO$_2$—Y", —SO—(C$_1$-C$_6$)alkyl, —(C$_1$-C$_4$)alkylene-NH—C(═O)—(C$_1$-C$_6$)alkyl, —(C$_1$-C$_4$)alkylene-NH—(C$_1$-C$_6$)alkyl, —(C$_1$-C$_4$)alkylene-N((C$_1$-C$_6$)alkyl)$_2$, —(C$_1$-C$_4$)alkylene-OH, —(C$_1$-C$_4$)alkylene-O—(C$_1$-C$_6$)alkyl, —(C$_1$-C$_4$)alkylene-C(═O)—(C$_1$-C$_6$)alkyl, —(C$_1$-C$_4$)alkylene-C(═O)—O—(C$_1$-C$_6$)alkyl, or —(C$_1$-C$_4$)alkylene-C(═O)—OH; wherein two substituents on a carbon ring member of the Y cycloalkyl or heterocyclyl may join to form a 3-7 membered cycloalkyl group or a 3-7 membered heterocyclyl group that comprises 1 to 3 heteroatoms selected from N, O, or S; and further wherein 1 or 2 carbon atom ring members of the 3-7 membered cycloalkyl or the 3-7 membered heterocyclyl group formed from the two substituents on the carbon ring member of the Y cycloalkyl or heterocyclyl may be double bonded to an O atom;

Y' may be absent or is a C$_6$-C$_{10}$ aryl, a 5-10 membered heteroaryl comprising 1, 2, 3, or 4 heteroatoms independently selected from O, S, or N, or a 3-7 membered heterocyclyl comprising 1, 2, or 3 heteroatoms selected from O, S, or N, wherein the C$_6$-C$_{10}$ aryl, the 5-10 membered heteroaryl, or the 3-7 membered heterocyclyl Y' groups are unsubstituted or are optionally substituted with 1, 2, or 3 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(═O)NH$_2$, —C(═O)NH((C$_1$-C$_4$)alkyl), —C(═O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(═O)—(C$_1$-C$_4$)alkyl, —SO$_2$—(C$_1$-C$_6$)alkyl, —SO—(C$_1$-C$_4$)alkyl, —(C$_1$-C$_4$)alkylene-NH—C(═O)—(C$_1$-C$_4$)alkyl, —CF$_3$, —C(═O)—(C$_1$-C$_4$)alkyl, —CO$_2$H, —C(═O)—O—(C$_1$-C$_4$)alkyl, —C(═O)NH—(C$_1$-C$_4$)alkylene-NH$_2$, —C(═O)NH—(C$_1$-C$_4$)alkylene-NH((C$_1$-C$_4$)alkyl), —C(═O)NH—(C$_1$-C$_4$)alkylene-N((C$_1$-C$_4$)alkyl)$_2$, —C(═O)NH—(C$_1$-C$_4$)alkylene-OH, —C(═O)NH—(C$_1$-C$_4$)alkylene-CF$_3$, —C(═O)NH—(C$_1$-C$_4$)alkylene-O—(C$_1$-C$_4$)alkyl, —(C$_1$-C$_4$)alkylene-C(═O)—(C$_1$-C$_4$)alkyl, —(C$_1$-C$_4$)alkylene-C(═O)—O—(C$_1$-C$_4$)alkyl, —(C$_1$-C$_4$)alkylene-C(═O)—OH, —OH, —O—(C$_1$-C$_6$)alkyl, —SH, —S—(C$_1$-C$_6$)alkyl, —OCF$_3$, or —OCHF$_2$;

Y" may be absent or is selected from a C$_3$-C$_{10}$ cycloalkyl; a 3-10 membered heterocyclyl comprising 1, 2, or 3 heteroatoms selected from N, O, and S; a C$_6$-C$_{10}$ aryl; or a 5-10 membered heteroaryl comprising 1, 2, 3, or 4 heteroatoms independently selected from N, O, or S; wherein the C$_3$-C$_{10}$ cycloalkyl and the 3-10 membered heterocyclyl may be monocyclic or bicyclic, and further wherein the C$_3$-C$_{10}$ cycloalkyl, the 3-10 membered heterocyclyl, the C$_6$-C$_{10}$ aryl, or the 5-10 membered heteroaryl Y" groups are unsubstituted or are optionally substituted with 1, 2, or 3 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(═O)NH$_2$, —C(═O)NH((C$_1$-C$_4$)alkyl), —C(═O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(═O)—(C$_1$-C$_4$)alkyl, —SO$_2$—(C$_1$-C$_6$)alkyl, —SO—(C$_1$-C$_4$)alkyl, —(C$_1$-C$_4$)alkylene-NH—C(═O)—(C$_1$-C$_4$)alkyl, —CF$_3$, —C(═O)—(C$_1$-C$_4$)alkyl, —CO$_2$H, —C(═O)—O—(C$_1$-C$_4$)alkyl, —C(═O)NH—(C$_1$-C$_4$)alkylene-NH$_2$, —C(═O)NH—(C$_1$-C$_4$)alkylene-NH((C$_1$-C$_4$)alkyl), —C(═O)NH—(C$_1$-C$_4$)alkylene-N((C$_1$-C$_4$)alkyl)$_2$, —C(═O)NH—(C$_1$-C$_4$)alkylene-OH, —C(═O)NH—(C$_1$-C$_4$)alkylene-CF$_3$, —C(═O)NH—(C$_1$-C$_4$)alkylene-O—(C$_1$-C$_4$)alkyl, —(C$_1$-C$_4$)alkylene-C(═O)—(C$_1$-C$_4$)alkyl, —(C$_1$-C$_4$)alkylene-C(═O)—O—(C$_1$-C$_4$)alkyl, —(C$_1$-C$_4$)alkylene-C(═O)—OH, —OH, —O—(C$_1$-C$_6$)alkyl, —SH, —S—(C$_1$-C$_6$)alkyl, —OCF$_3$, or —OCHF$_2$;

W is selected from —H, —F, —Cl, —Br, —I, —(C$_1$-C$_6$)alkyl, —(CR$^a$R$^{a'}$)$_q$—OH, —(CR$^a$R$^{a'}$)$_q$—O—(C$_1$-C$_6$)alkyl, —(CR$^a$R$^{a'}$)$_q$—O—W', —O—(CR$^a$R$^{a'}$)$_q$—W', —O—(CR$^a$R$^{a'}$)$_q$—OH, —O—(CR$^a$R$^{a'}$)$_q$—O—(C$_1$-C$_6$)alkyl, —(CR$^a$R$^{a'}$)$_q$—O—(CR$^a$R$^{a'}$)$_q$—OH, —(CR$^a$R$^{a'}$)$_q$—O—(CR$^a$R$^{a'}$)$_q$—O—(C$_1$-C$_6$)alkyl, —(CR$^a$R$^{a'}$)$_q$—SH, —(CR$^a$R$^{a'}$)$_q$—S—(C$_1$-C$_6$)alkyl, —(CR$^a$R$^{a'}$)$_q$—S—W', —S—(CR$^a$R$^{a'}$)$_q$—W', —(CR$^a$R$^{a'}$)$_q$—S(O)$_2$—(C$_1$-C$_6$)alkyl, —(CR$^a$R$^{a'}$)$_q$—S(O)$_2$—W', —S(O)$_2$—(CR$^a$R$^{a'}$)$_q$—W', —(CR$^a$R$^{a'}$)$_q$—NH$_2$, —(CR$^a$R$^{a'}$)$_q$—NH—(C$_1$-C$_6$)alkyl, —(CR$^a$R$^{a'}$)$_q$—N—((C$_1$-C$_6$)alkyl,)$_2$, —(CR$^a$R$^{a'}$)$_q$—N$^+$—((C$_1$-C$_6$)alkyl,)$_3$, —(CR$^a$R$^{a'}$)$_q$—NH—W', —(CR$^a$R$^{a'}$)$_q$—NH—(CR$^a$R$^{a'}$)$_q$—OH, —NH—(CR$^a$R$^{a'}$)$_q$—W', or —(CR$^a$R$^{a'}$)$_q$—W';

W' may be absent or is selected from a C$_3$-C$_{10}$ cycloalkyl; a 3-10 membered heterocyclyl comprising 1, 2, or 3 heteroatoms selected from N, O, and S; a C$_6$-C$_{10}$ aryl; or a 5-10 membered heteroaryl comprising 1, 2, 3, or 4 heteroatoms independently selected from N, O, or S; wherein the C$_3$-C$_{10}$ cycloalkyl and the 3-10 membered heterocyclyl may be monocyclic or bicyclic, and further wherein the C$_3$-C$_{10}$ cycloalkyl, the 3-10 membered heterocyclyl, the C$_6$-C$_{10}$ aryl, or the 5-10 membered heteroaryl W' groups are unsubstituted or are optionally substituted with 1, 2, 3, or 4 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —CH(CF$_3$)(OH), —(C$_1$-C$_4$)alkylene-NH$_2$, —(C$_1$-C$_4$)alkylene-NH((C$_1$-C$_4$)alkyl), —(C$_1$-C$_4$)alkylene-NH—(C$_1$-C$_4$)alkylene-CF$_3$, —(C$_1$-C$_4$)alkylene-N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_6$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —C(=O)NH—(C$_1$-C$_4$)alkylene-OH, —C(=O)NH—(C$_1$-C$_4$)alkylene-CF$_3$, —C(=O)NH—(C$_1$-C$_4$)alkylene-O—(C$_1$-C$_4$)alkyl, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —(C$_1$-C$_4$)alkylene-OH, —OH, —O—(C$_1$-C$_6$)alkyl, —SH, —S—(C$_1$-C$_6$)alkyl, —SO$_3$H, —OCF$_3$, —OCHF$_2$, or —C(=O)—W'''; and further wherein W' may include 0, 1, or 2=O groups when W' is a C$_3$-C$_{10}$ cycloalkyl or a 3-10 membered heterocyclyl, and further wherein the =O groups may be bonded to a ring carbon atom or a ring S atom;

W''' may be absent or is selected from a C$_3$-C$_{10}$ cycloalkyl; a 3-10 membered heterocyclyl comprising 1, 2, or 3 heteroatoms selected from N, O, and S; a C$_6$-C$_{10}$ aryl; or a 5-10 membered heteroaryl comprising 1, 2, 3, or 4 heteroatoms independently selected from N, O, or S; wherein the C$_3$-C$_{10}$ cycloalkyl and the 3-10 membered heterocyclyl may be monocyclic or bicyclic, and further wherein the C$_3$-C$_{10}$ cycloalkyl, the 3-10 membered heterocyclyl, the C$_6$-C$_{10}$ aryl, or the 5-10 membered heteroaryl W''' groups are unsubstituted or are optionally substituted with 1, 2, 3, or 4 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —OH, —NH$_2$, —NH((C$_1$-C$_4$)alkyl), —N((C$_1$-C$_4$)alkyl)$_2$, —CF$_3$, —CO$_2$H, —C(=O)—O—(C$_1$-C$_4$)alkyl, —SH, —S—(C$_1$-C$_6$)alkyl, —OCF$_3$, or —OCHF$_2$; and further wherein W''' may include 0, 1, or 2 =O groups when W''' is a C$_3$-C$_{10}$ cycloalkyl or a 3-10 membered heterocyclyl, and further wherein the =O groups may be bonded to a ring carbon atom or a ring S atom;

the subscript q is, in each instance, independently selected from 0, 1, 2, 3, or 4;

R$^a$ is, in each instance, independently selected from —H, —CH$_3$, —CH$_2$CH$_3$, —F, —CF$_3$, or —C≡N;

R$^{a'}$ is, in each instance, independently selected from —H, —CH$_3$, —CH$_2$CH$_3$, —F, —CF$_3$, or —C≡N; or R$^a$ and R$^{a'}$ may join to form a cyclopropyl ring together with the carbon atom to which they are attached;

Z is selected from a C$_6$-C$_{10}$ aryl; a 5-10 membered heteroaryl comprising 1, 2, 3 or 4 heteroatoms independently selected from O, S, or N; a 4-7 membered heterocyclyl comprising 1, 2, or 3 heteroatoms selected from O, S, or N; a C$_3$-C$_7$ cycloalkyl; a —N(H)-heterocyclyl, wherein the heterocyclyl of —N(H)-heterocyclyl is a 4-7 membered heterocyclyl comprising 1, 2, or 3 heteroatoms selected from O, S, or N; a —N(H)—(C$_3$-C$_7$)cycloalkyl; or Z is a —O—(C$_1$-C$_6$) alkyl; wherein the C$_6$-C$_{10}$ aryl, the 5-10 membered heteroaryl, the 4-7 membered heterocyclyl, the C$_3$-C$_7$ cycloalkyl; the —N(H)-heterocyclyl, and the —N(H)—(C$_3$-C$_7$)cycloalkyl are unsubstituted or are optionally substituted with 1, 2, or 3 substituents independently selected from —F, —Cl, —Br, —I, —C≡N, —NO$_2$, —CF$_3$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_6$)alkyl), —N((C$_1$-C$_6$)alkyl)$_2$, —C(=O)NH$_2$, —C(=O)NH((C$_1$-C$_6$)alkyl), —C(=O)N((C$_1$-C$_6$)alkyl)$_2$, —SO$_2$NH$_2$, —SO$_2$NH((C$_1$-C$_6$)alkyl), —SO$_2$N((C$_1$-C$_6$)alkyl)$_2$, —SO$_2$NH((C$_2$-C$_6$)alkenyl), —SO$_2$NH((C$_2$-C$_6$)alkynyl), —SO$_2$NH—(C$_1$-C$_4$)alkylene-OH, —SO$_2$NH—(C$_1$-C$_4$)alkylene-O—(C$_1$-C$_6$)alkyl, —NHSO$_2$—(C$_1$-C$_6$)alkyl, —NHC(=O)—(C$_1$-C$_6$)alkyl, —SO$_2$—(C$_1$-C$_6$)alkyl, —SO—(C$_1$-C$_6$)alkyl, —(C$_1$-C$_4$)alkylene-NH—C(=O)—(C$_1$-C$_6$)alkyl, —C(=O)—(C$_1$-C$_6$)alkyl, —CO$_2$H, —C(=O)—O—(C$_1$-C$_6$)alkyl, —C(=O)NH—(C$_1$-C$_4$)alkylene-NH$_2$, —C(=O)NH—(C$_1$-C$_4$)alkylene-NH((C$_1$-C$_6$)alkyl), —C(=O)NH—(C$_1$-C$_4$)alkylene-N((C$_1$-C$_6$)alkyl)$_2$, —(C$_1$-C$_4$)alkylene-C(=O)—(C$_1$-C$_6$)alkyl, —(C$_1$-C$_4$)alkylene-C(=O)—O—(C$_1$-C$_6$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$;

W is not —H, —F, —Cl, —Br, —I, or unsubstituted —(C$_1$-C$_6$)alkyl if X is CR$^4$;

Y is not unsubstituted cyclopropyl, cyclobutyl, or cyclopentyl if W is —H, —F, —Br, —I, or —(C$_1$-C$_6$)alkyl;

W is not —CH$_2$OH or —CH$_2$O(C$_1$-C$_4$alkyl) if Y is a group of formula

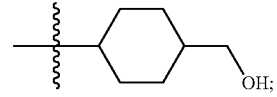

and

W is not —SH, —OH, —S—(C$_1$-C$_6$)alkyl), or —S—(C$_1$-C$_6$)alkyl) if Z is —O—(C$_1$-C$_6$)alkyl);

wherein the symbol ∿∿∿, when drawn across a bond, indicates the point of attachment to the rest of the molecule.

In some embodiments, X is N.

In some embodiments, X is CR$^4$. In some such embodiments, R$^4$ is —H.

In some embodiments, R$^3$ is —H.

In some embodiments, Z is selected from —OMe or —NH-cyclohexyl; or an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, piperidinyl, isothiazolyl, or thiomorpholinyl group. In some such embodiments, Z is selected from —OMe or —NH-cyclohexyl; or an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl.

In some embodiments, Z is an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, piperidinyl, isothiazolyl, or thiomorpholinyl group. In some embodiments, Z is an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl group. In some such embodiments, Z is a substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl group.

In some embodiments, Z is an unsubstituted or substituted phenyl or pyridyl. In some such embodiments, Z is a substituted phenyl or pyridyl. In some other such embodiments, Z is a substituted phenyl.

In some embodiments, Y is an unsubstituted or substituted cycloheptyl, cyclohexyl, cyclopentyl, cyclobutyl, piperidinyl, pyrrolidinyl, azetidinyl, adamantyl, bicyclo[2.2.2]octyl, bicyclo[3.2.1]octyl, bicyclo[4.1.1]octyl, bicyclo[2.2.1]heptyl, bicyclo[3.1.1]heptyl, or bicyclo[2.1.1]hexyl. In some such embodiments, Y is a substituted cycloheptyl, cyclohexyl, cyclopentyl, cyclobutyl, piperidinyl, pyrrolidinyl, adamantyl, bicyclo[2.2.2]octyl, bicyclo[3.2.1]octyl, bicyclo[4.1.1]octyl, bicyclo[2.2.1]heptyl, bicyclo[3.1.1]heptyl, or bicyclo[2.1.1]hexyl group. In some such embodiments, Y is an unsubstituted or substituted cyclohexyl. In some such embodiments, Y is a substituted cyclohexyl. In other embodiments, Y is an unsubstituted or substituted adamantyl. In some such embodiments, Y is an unsubstituted adamantyl. In other embodiments, Y is a substituted adamantyl. In other such embodiments, Y is an unsubstituted or substituted cyclobutyl. In some such embodiments, Y is a substituted cyclobutyl. In still other embodiments, Y is an unsubstituted or substituted cyclopentyl or cycloheptyl. In some such embodiments Y is a substituted cyclopentyl or cycloheptyl. In still other embodiments, Y is an unsubstituted or substituted piperidinyl. In some such embodiments, Y is a substituted piperidinyl. In some embodiments where Y is substituted, Y is substituted with a group that includes a carbonyl (C=O) functional group. Examples include, but are not limited to ketones, esters, and amides.

In some embodiments, W is selected from —$CH_2OH$, —$CH_2OCH_3$, —$CH_2OCH_2CH_2OH$, —$CH_2OCH_2CH_2OCH_3$, —$OCH_2CH_2OH$, —$OCH_2CH_2OMe$, —W', —$CH_2W'$, —OW', —$OCH_2W'$, —$OCH_2CH_2W'$, —$OCH_2CH_2CH_2W'$, —NHW', —$NHCH_2W'$, —$NHCH_2CH_2W'$, —$NHCH_2CH_2CH_2W'$, or —W'—C(=O)—W"; wherein W', if present, is selected from a 3-10 membered heterocyclyl comprising 1 or 2 heteroatoms selected from N, O, and S; a $C_6$-$C_{10}$ aryl; or a 5-10 membered heteroaryl comprising 1, 2, 3, or 4 heteroatoms independently selected from N, O, or S; wherein the 3-10 membered heterocyclyl W' group may be monocyclic or bicyclic, and further wherein the 3-10 membered heterocyclyl, the $C_6$-$C_{10}$ aryl, or the 5-10 membered heteroaryl W' groups are unsubstituted or are substituted with 1, 2, 3, or 4 substituents independently selected from —F, —Cl, —Br, —($C_1$-$C_6$)alkyl, —$CH(CF_3)$(OH), —($C_1$-$C_4$)alkylene-$NH_2$, —($C_1$-$C_4$)alkylene-NH—($C_1$-$C_4$)alkylene-$CF_3$, —C(=O)$NH_2$, —$SO_2$—($C_1$-$C_6$)alkyl, —$CF_3$, —$CO_2H$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —($C_1$-$C_4$)alkylene-OH, —OH, —O—($C_1$-$C_6$)alkyl, or —$SO_3H$; and further wherein W' may include 0, 1, or 2 =O groups when W' is a 3-10 membered heterocyclyl, and further wherein the =O groups may be bonded to a ring carbon atom or a ring S atom; and further wherein W", if present, is a 3-10 membered heterocyclyl comprising 1, 2, or 3 heteroatoms selected from N, O, and S, wherein the 3-10 membered heterocyclyl W" group may be monocyclic or bicyclic, and further wherein the 3-10 membered heterocyclyl W" group is unsubstituted or is optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —OH, —$NH_2$, —NH(($C_1$-$C_4$)alkyl), —N(($C_1$-$C_4$)alkyl)$_2$, —$CF_3$, —$CO_2H$, —C(=O)—O—($C_1$-$C_4$)alkyl, —SH, —S—($C_1$-$C_6$)alkyl, —$OCF_3$, or —$OCHF_2$, or a pharmaceutically acceptable salt thereof, tautomer thereof, a pharmaceutically acceptable salt of the tautomer, a stereoisomer of any of the foregoing, or a mixture thereof.

In some embodiments, W is selected from —W', —$CH_2W'$, —OW', —$OCH_2W'$, —$OCH_2CH_2W'$, —$OCH_2CH_2CH_2W'$, —NHW', —$NHCH_2W'$, —$NHCH_2CH_2W'$, —$NHCH_2CH_2CH_2W'$, or —W'—C(=O)—W"; wherein W', is selected from a 3-10 membered heterocyclyl comprising 1 or 2 heteroatoms selected from N, O, and S; a $C_6$-$C_{10}$ aryl; or a 5-10 membered heteroaryl comprising 1, 2, 3, or 4 heteroatoms independently selected from N, O, or S; wherein the 3-10 membered heterocyclyl W' group may be monocyclic or bicyclic, and further wherein the 3-10 membered heterocyclyl, the $C_6$-$C_{10}$ aryl, or the 5-10 membered heteroaryl W' groups are unsubstituted or are substituted with 1, 2, 3, or 4 substituents independently selected from —F, —Cl, —Br, —($C_1$-$C_6$)alkyl, —$CH(CF_3)$(OH), —($C_1$-$C_4$)alkylene-$NH_2$, —($C_1$-$C_4$)alkylene-NH—($C_1$-$C_4$) alkylene-$CF_3$, —C(=O)$NH_2$, —$SO_2$—($C_1$-$C_6$)alkyl, —$CF_3$, —$CO_2H$, —($C_1$-$C_4$)alkylene-C(=O)—($C_1$-$C_4$) alkyl, —($C_1$-$C_4$)alkylene-C(=O)—O—($C_1$-$C_4$)alkyl, —($C_1$-$C_4$)alkylene-C(=O)—OH, —($C_1$-$C_4$)alkylene-OH, —OH, —O—($C_1$-$C_6$)alkyl, or —$SO_3H$; and further wherein W' may include 0, 1, or 2 =O groups when W' is a 3-10 membered heterocyclyl, and further wherein the =O groups may be bonded to a ring carbon atom or a ring S atom; and further wherein W", if present, is a 3-10 membered heterocyclyl comprising 1, 2, or 3 heteroatoms selected from N, O, and S, wherein the 3-10 membered heterocyclyl W" group may be monocyclic or bicyclic, and further wherein the 3-10 membered heterocyclyl W" group is unsubstituted or is optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —OH, —$NH_2$, —NH(($C_1$-$C_4$)alkyl), —N(($C_1$-$C_4$)alkyl)$_2$, —$CF_3$, —$CO_2H$, —C(=O)—O—($C_1$-$C_4$)alkyl, —SH, —S—($C_1$-$C_6$)alkyl, —$OCF_3$, or —$OCHF_2$.

In some embodiments, W is not —H, —F, —Cl, —OH, or —OMe.

In some embodiments of any of those described above, the compound is a pharmaceutically acceptable salt of the compound, a tautomer of the compound, a pharmaceutically acceptable salt of the tautomer, a stereoisomer of any of the foregoing, or is a mixture of any of these. In some such embodiments, the compound is a tautomer. In some such embodiments, the compound is a pharmaceutically acceptable salt of the tautomer. In still other embodiments, the compound is a single stereoisomer whereas in other embodiments, the compound is a mixture of enantiomers or is a mixture of stereoisomers and such a mixture may include equal or unequal amount of specific stereioisomers. In some embodiments, the compound is a racemic mixture of stereoisomers.

In some embodiments, the compound is any one of the Example compounds.

In some embodiments, the compound is a salt. Such salts may be anhydrous or associated with water as a hydrate.

In some embodiments, the compound is a prodrug.

Also provided are pharmaceutical formulations that include at least one pharmaceutically acceptable carrier, excipient or diluent and a therapeutically effective amount of the compound of any of the embodiments described herein. In some such embodiments, the compound is present in an amount effective for the treatment of cancer.

Further provided are pharmaceutical formulations that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. Such methods typically include administering to a subject an effective amount of a compound of any one of the embodiments or a pharmaceutical composition that includes any of the compounds of any of the embodiments. In some such embodiments, the subject has a cancer that expresses an ALK fusion protein, point mutation, or overexpression. In other such embodiments, the ALK fusion protein is EML4-ALK fusion protein or NPM-ALK fusion protein. In some embodiments, the subject is a human cancer patient, and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma diffuse large B-cell lymphomas, systemic histiocytosis, or inflammatory myofibroblastic tumors. In some such embodiments, the cancer is non-small cell lung carcinoma (NSCLC). In some embodiments, the cancer is an EML4-ALK positive cancer or is a NPM-ALK positive cancer.

In still other embodiments, the invention provides a method of treating a condition where it is desired to inhibit ALK activity. Such methods typically include administering to a subject an effective amount of a compound of any of the embodiments or a pharmaceutical composition that includes a compound of any of the embodiments.

In some embodiments, the compound of any of the embodiments is used in the preparation of a medicament. In some such embodiments, the medicament is for use in treating cancer. In some such embodiments, a medicament is for use in inhibiting ALK. In still other such embodiments, the medicament is for use in treating a cancer that expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein.

In some embodiments, a compound or pharmaceutical formulation of any of the embodiments is provided for use in treating cancer. In some such embodiments, the cancer expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein. In some embodiments, a compound or pharmaceutical formulation of any of the embodiments is provided for use in treating cancer and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma diffuse large B-cell lymphomas, systemic histiocytosis, or inflammatory myofibroblastic tumors. In some such embodiments, the cancer is non-small cell lung carcinoma (NSCLC). In still other embodiments, a compound or pharmaceutical formulation of any of the embodiments is provided for use in inhibiting ALK or for use in treating a disease or condition wherein inhibition of ALK is desired.

Other objects, features and advantages of the invention will become apparent to those skilled in the art from the following description and claims.

DETAILED DESCRIPTION OF THE INVENTION

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention, where, and if, appropriate.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line from one atom to the other indicates that both stereoisomers are encompassed. A wavy line drawn across a bond, indicates point of attachment of a group to the rest of the molecule.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, 1N, 1972).

Compounds of the invention may exist in multiple tautomeric forms. These forms are illustrated below as "Tautomer A" and "Tautomer B":

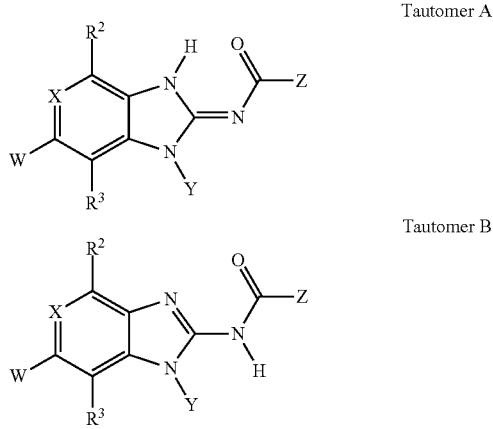

Because one chemical structure may only be used to represent one tautomeric form, it will be understood that for convenience, referral to a compound of a given structural formula includes tautomers of the structure represented by the structural formula. Furthermore, the compounds may exist as mixtures of tautomers in equal or unequal amounts or may exist solely in one tautomeric form. The same may apply to salts and stereoisomers.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound" encompasses the compound itself, pharmaceutically acceptable salts thereof, tautomers of the compound, pharmaceutically acceptable salts of the tautomers.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I.

The term "solvate" refers to the compound formed by the interaction of a solvent and a compound. Suitable solvates are pharmaceutically acceptable solvates, such as hydrates, including monohydrates and hemi-hydrates.

Certain structures are drawn to include standard abbreviations such as Me to represent methyl and Et to represent ethyl. Other structures may be drawn such that H atoms are not shown on hydroxyl groups or N containing groups where the N is singly bonded to two other substituents. It will be recognized that such compounds include a H at such locations. Finally, some structures may be drawn that include a bond that does not show the terminal carbon as $CH_3$ or Me. It will be recognized that such structures include a $CH_3$ group in such compounds.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

"ALK" refers to anaplastic lymphoma kinase, tyrosine kinase. ALK was originally identified as part of the chimeric nucleophosmin-ALK protein in the t(2; 5) chromosomal rearrangement associated with anaplastic large cell lymphoma.

"EML4-ALK fusion protein" refers to a protein that results from a fusion of echinoderm microtubule-associated protein-like 4 (EML4) and ALK.

"NPM-ALK fusion protein" refers to a protein that results from a fusion of nucleophosmin (NPM) with ALK.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises 1 to 20 carbon atoms. In some embodiments, alkyl groups include 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a —($C_1$-$C_6$)alkyl group and an alkyl group having 1 to 4 carbon atoms may be referred to as a —($C_1$-$C_4$)alkyl.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a —($C_2$-$C_6$) alkenyl group "Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group "Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O($C_{1-6}$) alkyl or as —O—($C_{1-6}$) alkyl groups. In some embodiments, an alkoxy group may include 1 to 4 carbon atoms and may be designated as an —O($C_{1-4}$) alkyl or as an —O—($C_{1-4}$) alkyl group.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —CH($CH_3$)—, —$CH_2$C($CH_3$)$_2$—, —$CH_2CH_2CH_2$—, —$CH_2$CH($CH_3$)—, and the like, and may include a cyclic hydrocarbon group such as a —CH(cyclopropyl)-alkylene group. In some embodiments an alkylene may include 1 to 6 carbon atoms and in other embodiments may include 1 to 4 carbon atoms. Such groups may be designated as —($C_1$-$C_6$)alkylene- and —($C_1$-$C_4$) alkylene-groups.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl groups may include fused ring systems where one ring is a carbocyclic aromatic ring and the other ring(s) are not aromatic and may be heterocyclic or carcocyclic. For example, aryl groups include systems where a carbocyclic aromatic ring is fused to a 5- to 7-membered heterocyclic ring containing 1 or more heteroatoms chosen from N, O, and S. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with a heterocyclic aromatic ring, the resulting ring system is heteroaryl, not aryl, as defined herein. Bicyclic and tricyclic aryl groups include at least one ring that is aromatic. The other rings in such systems may be partially unsaturated. For example, tetralin (1,2,3,4-tetrahydronaphthalene) includes a benzene ring fused to a ring that includes saturation and is therefore, partially saturated. Examples of other aryl groups with a partially saturated ring include, but are not limited to, indane, 1,4-dihydronaphthalene, chroman, 2,3-dihydrobenzo[b][1,4]dioxine, 1,2,3,4-tetrahydroquinoline, and indoline. The nonaromatic rings of such systems may also include a carbon that is double-bonded to an O. Examples of such aryl groups include, but are not limited to, 2-indanone, 1-indanone, 3,4-dihydronaphthalen-2(1H)-one, chroman-3-one, indolin-2-one, and 1,2-dihydroquinolin-3(4H)-one.

"Carbonyl" refers to the radical —C(O) or —C(=O) group.

"Carboxy" refers to the radical —C(O)OH.

"Cyano" refers to the radical —CN which can also be represented by —C≡N.

"Cycloalkyl" refers to a saturated or partially unsaturated, but non-aromatic, cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl. In some embodiments, a cycloalkyl group is a saturated cycloalkyl group.

"Heterocyclic", "heterocyclo" or "heterocyclyl" refer to saturated or partially unsaturated, but non-aromatic, cyclic hydrocarbon groups in which one or more carbon atoms (and any associated hydrogen atoms) are independently replaced with the same or a different heteroatom and its associated hydrogen atoms, where appropriate. Typical heteroatoms to replace the carbon atom(s) include, but are not limited to, N, O, and S. In some embodiments, a heterocyclyl group includes 3 to 10 ring members of which 1, 2, or 3 ring members are independently selected from N, O, or S. In other embodiments, a heterocyclyl group includes 5 to 7 ring members of which 1, 2, or 3 are heteroatoms independently selected from N, O, or S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—$O^-$) substituents, such as piperidinyl N-oxide, morpholinyl-N-oxide, 1-oxo-1-thiomorpholinyl and 1,1-dioxo-1-thiomorpholinyl.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 10-membered aromatic, monocyclic and bicyclic rings containing one or more, for example, 1, 2, 3, or 4, or in certain embodiments, 1, 2, or 3, heteroatoms chosen from N, O, and S, with the remaining ring atoms being carbon. The term heteroaryl may also encompass tricyclic ring systems containing one or more, for example, 1, 2, 3, or 4, or in certain embodiments, 1, 2, or 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or to a carbocyclic aromatic ring or to a 5-7 membered heteroaromatic ring, and heteroaryl includes a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, carbazole, β-carboline, cinnoline, furan, imidazole, indazole, indole, indolizine, isobenzofuran, isochromene, isoindole, isoquinoline, isothiazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, benzimidazole, oxazole, tetrazole, and pyrazine.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides a compound of Formula I:

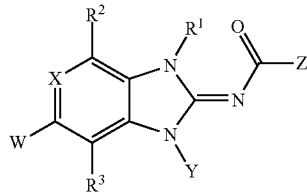

or a pharmaceutically acceptable salt thereof, tautomer thereof, a pharmaceutically acceptable salt of the tautomer, a stereoisomer of any of the foregoing, or a mixture thereof,
wherein:
$R^1$ is —H;
$R^2$ is —H;
$R^3$ is selected from —H, —F, —Cl, —Br, —I; —$(C_1$-$C_6)$ alkyl, —$(C_2$-$C_6)$alkenyl, —$(C_2$-$C_6)$alkynyl, —$CF_3$, —OH, —$OCF_3$, —O—$(C_1$-$C_6)$alkyl, —$OCHF_2$, —SH, —S—$(C_1$-$C_6)$alkyl, —$NH_2$, —N(H)—$(C_1$-$C_6)$alkyl, —N$((C_1$-$C_6)$ alkyl$)_2$, —$NO_2$, —C≡N, —C(=O)OH, —C(=O)O—$(C_1$-$C_6)$alkyl, —C(=O)$NH_2$, —C(=O)N(H)—$(C_1$-$C_6)$alkyl, —C(=O)N$((C_1$-$C_6)$alkyl$)_2$, —N(H)—C(=O)—$(C_1$-$C_6)$ alkyl, —N$((C_1$-$C_6)$alkyl)-C(=O)—$(C_1$-$C_6)$alkyl, —$(C_1$-$C_4)$ alkylene-OH, —$(C_1$-$C_4)$alkylene-$NH_2$, —$(C_1$-$C_4)$alkylene-N(H)—$(C_1$-$C_6)$alkyl, —$(C_1$-$C_4)$alkylene-N$((C_1$-$C_6)$alkyl$)_2$, or phenyl optionally substituted with 1, 2, or 3 substituents selected from —F, —Cl, —Br, —I; —$(C_1$-$C_6)$alkyl, —$(C_2$-$C_6)$alkenyl, —$(C_2$-$C_6)$alkynyl, —$CF_3$, —OH, —$OCF_3$, —O—$(C_1$-$C_6)$alkyl, —$OCHF_2$, —SH, —S—$(C_1$-$C_6)$alkyl, —$NH_2$, —N(H)—$(C_1$-$C_6)$alkyl, —N$((C_1$-$C_6)$alkyl$)_2$, —$NO_2$, —C≡N, —C(=O)OH, —C(=O)O—$(C_1$-$C_6)$ alkyl, —C(=O)$NH_2$, —C(=O)N(H)—$(C_1$-$C_6)$alkyl, or —C(=O)N$((C_1$-$C_6)$alkyl$)_2$;

X is selected from $CR^4$ or N;
$R^4$ is absent if X is N, or is selected from —H, —F, —Cl, —Br, —I; —$(C_1$-$C_6)$alkyl, —$(C_2$-$C_6)$alkenyl, —$(C_2$-$C_6)$ alkynyl, —$CF_3$, —OH, —$OCF_3$, —O—$(C_1$-$C_6)$alkyl, —$OCHF_2$, —SH, —S—$(C_1$-$C_6)$alkyl, —$NH_2$, —N(H)— $(C_1$-$C_6)$alkyl, —N$((C_1$-$C_6)$alkyl$)_2$, —$NO_2$, —C≡N, —C(=O)OH, —C(=O)O—$(C_1$-$C_6)$alkyl, —C(=O)$NH_2$, —C(=O)N(H)—$(C_1$-$C_6)$alkyl, —C(=O)N$((C_1$-$C_6)$alkyl$)_2$, —$(C_1$-$C_4)$alkylene-OH, —$(C_1$-$C_4)$alkylene-$NH_2$, —$(C_1$-$C_4)$ alkylene-N(H)—$(C_1$-$C_6)$alkyl, —$(C_1$-$C_4)$alkylene-N$((C_1$-$C_6)$alkyl$)_2$, or phenyl optionally substituted with 1, 2, or 3 substituents selected from —F, —Cl, —Br, —I; —$(C_1$-$C_6)$ alkyl, —$(C_2$-$C_6)$alkenyl, —$(C_2$-$C_6)$alkynyl, —$CF_3$, —OH, —$OCF_3$, —O—$(C_1$-$C_6)$alkyl, —$OCHF_2$, —SH, —S—$(C_1$-$C_6)$alkyl, —$NH_2$, —N(H)—$(C_1$-$C_6)$alkyl, —N$((C_1$-$C_6)$ alkyl$)_2$, —$NO_2$, —C≡N, —C(=O)OH, —C(=O)O—$(C_1$-$C_6)$alkyl, —C(=O)$NH_2$, —C(=O)N(H)—$(C_1$-$C_6)$alkyl, or —C(=O)N$((C_1$-$C_6)$alkyl$)_2$;

Y is selected from a $C_3$-$C_{12}$ cycloalkyl or a 3-10 membered heterocyclyl comprising 1, 2, or 3 heteroatoms selected from O, S, or N; wherein the $C_3$-$C_{12}$ cycloalkyl and the 3-10 membered heterocyclyl may be monocyclic, bicyclic, or tricyclic, and further wherein the $C_3$-$C_{12}$ cycloalkyl and the 3-10 membered heterocyclyl are unsubstituted or are optionally substituted with 1, 2, or 3 substituents independently selected from —Y', —F, —Cl, —Br, —I, —C≡N, —$NO_2$, —OH, —O— $(C_1$-$C_6)$alkyl, —SH, —S—$(C_1$-$C_6)$alkyl, —$OCF_3$, —$OCHF_2$, —$CF_3$, —$(C_1$-$C_6)$alkyl, —$(C_2$-$C_6)$alkenyl, —$(C_2$-$C_6)$alkynyl, —$NH_2$, —NH$((C_1$-$C_4)$alkyl), —N$((C_1$-$C_4)$alkyl$)_2$, —$NHSO_2$—$(C_1$-$C_6)$alkyl, —NHC(=O)—$(C_1$-$C_6)$alkyl, —C(=O)$NH_2$, —C(=O)NH$((C_1$-$C_6)$alkyl), —C(=O)NH—$(C_1$-$C_4)$alkylene-$CF_3$, —C(=O)NH—$(C_1$-$C_4)$alkylene-F, —C(=O)NH—$(C_2$-$C_4)$alkenyl, —C(=O)N $((C_1$-$C_6)$alkyl$)_2$, —C(=O)NH—OH, —C(=O)NH—O— $(C_1$-$C_6)$alkyl, —C(=O)NH—Y'', —C(=O)—$(C_1$-$C_4)$ alkylene-$CF_3$, —C(=O)N—$(C_1$-$C_4)$alkylene-F, —C(=O)—$(C_2$-$C_4)$alkenyl, —C(=O)—$(C_1$-$C_4)$alkylene-$NH_2$, —C(=O)—$(C_1$-$C_4)$alkylene-NH$((C_1$-$C_4)$alkyl), —C(=O)—$(C_1$-$C_4)$alkylene-N$((C_1$-$C_4)$alkyl$)_2$, —C(=O) NH—$(C_1$-$C_4)$alkylene-OH, —C(=O)NH—$(C_1$-$C_4)$alkylene-O—$(C_1$-$C_6)$alkyl, —C(=O)NH—$(C_1$-$C_4)$alkylene-Y'', —C(=O)—$(C_1$-$C_6)$alkyl, —C(=O)—Y'', —$CO_2$H, —C(=O)—O—$(C_1$-$C_6)$alkyl, —C(=O)NH—$(C_1$-$C_4)$alkylene-$NH_2$, —C(=O)NH—$(C_1$-$C_4)$alkylene-NH$((C_1$-$C_6)$ alkyl), —C(=O)NH—$(C_1$-$C_4)$alkylene-N$((C_1$-$C_6)$alkyl$)_2$, —$SO_2NH_2$, —$SO_2$NH$((C_1$-$C_6)$alkyl), —$SO_2$N$((C_1$-$C_6)$ alkyl$)_2$, —$SO_2$NH$((C_2$-$C_4)$alkenyl), —$SO_2$NH$((C_2$-$C_4)$alkynyl), —$SO_2$NH—Y'', —$SO_2$NH—$(C_1$-$C_4)$alkylene-OH, —$SO_2$NH—$(C_1$-$C_4)$alkylene-O—$(C_1$-$C_4)$alkyl, —$SO_2$— $(C_1$-$C_6)$alkyl, —$SO_2$—Y'', —SO—$(C_1$-$C_6)$alkyl, —$(C_1$-$C_4)$ alkylene-NH—C(=O)$(C_1$-$C_6)$alkyl, —$(C_1$-$C_4)$alkylene-NH—$(C_1$-$C_6)$alkyl, —$(C_1$-$C_4)$alkylene-N$((C_1$-$C_6)$alkyl$)_2$-$(C_1$-$C_4)$alkylene-OH, —$(C_1$-$C_4)$alkylene-O—$(C_1$-$C_6)$alkyl, —$(C_1$-$C_4)$alkylene-C(=O)—$(C_1$-$C_6)$alkyl, —$(C_1$-$C_4)$alkylene-C(=O)—O—$(C_1$-$C_6)$alkyl, or —$(C_1$-$C_4)$alkylene-C (=O)—OH; wherein two substituents on a carbon ring member of the Y cycloalkyl or heterocyclyl may join to form a 3-7 membered cycloalkyl group or a 3-7 membered heterocyclyl group that comprises 1 to 3 heteroatoms selected from N, O, or S; and further wherein 1 or 2 carbon atom ring members of the 3-7 membered cycloalkyl or the 3-7 membered heterocyclyl group formed from the two substituents on the carbon ring member of the Y cycloalkyl or heterocyclyl may be double bonded to an O atom;

Y' may be absent or is a $C_6$-$C_{10}$ aryl, a 5-10 membered heteroaryl comprising 1, 2, 3, or 4 heteroatoms independently selected from O, S, or N, or a 3-7 membered heterocyclyl comprising 1, 2, or 3 heteroatoms selected from O, S, or N, wherein the $C_6$-$C_{10}$ aryl, the 5-10 membered heteroaryl, or the 3-7 membered heterocyclyl Y' groups are unsubstituted or are optionally substituted with 1, 2, or 3 substituents independently selected from —F, —Cl, —Br, —I, —C≡N, —$NO_2$, —$(C_1$-$C_6)$alkyl, —$(C_2$-$C_6)$alkenyl, —$(C_2$-$C_6)$alkynyl, —$(C_1$-$C_4)$alkylene-OH, —$NH_2$, —NH$((C_1$-$C_4)$alkyl), —N$((C_1$-$C_4)$alkyl$)_2$, —C(=O)$NH_2$, —C(=O)NH$((C_1$-$C_4)$ alkyl), —C(=O)N$((C_1$-$C_4)$alkyl$)_2$, —$SO_2NH_2$, —$SO_2$NH $((C_1$-$C_4)$alkyl), —$SO_2$N$((C_1$-$C_4)$alkyl$)_2$, —$NHSO_2$—$(C_1$-$C_4)$alkyl, —NHC(=O)—$(C_1$-$C_4)$alkyl, —$SO_2$—$(C_1$-$C_6)$ alkyl, —SO—$(C_1$-$C_4)$alkyl, —$(C_1$-$C_4)$alkylene-NH—C (=O)—$(C_1$-$C_4)$alkyl, —$CF_3$, —C(=O)—$(C_1$-$C_4)$alkyl, —$CO_2$H, —C(=O)—O—$(C_1$-$C_4)$alkyl, —C(=O)NH— $(C_1$-$C_4)$alkylene-$NH_2$, —C(=O)NH—$(C_1$-$C_4)$alkylene-NH $((C_1$-$C_4)$alkyl), —C(=O)NH—$(C_1$-$C_4)$alkylene-N$((C_1$-$C_4)$ alkyl$)_2$, —C(=O)NH—$(C_1$-$C_4)$alkylene-OH, —C(=O) NH—$(C_1$-$C_4)$alkylene-$CF_3$, —C(=O)NH—$(C_1$-$C_4)$ alkylene-O—$(C_1$-$C_4)$alkyl, —$(C_1$-$C_4)$alkylene-C(=O)— $(C_1$-$C_4)$alkyl, —$(C_1$-$C_4)$alkylene-C(=O)—O—$(C_1$-$C_4)$ alkyl, —$(C_1$-$C_4)$alkylene-C(=O)—OH, —OH, —O—$(C_1$-$C_6)$alkyl, —SH, —S—$(C_1$-$C_6)$alkyl, —$OCF_3$, or —$OCHF_2$;

Y'' may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl Y" groups are unsubstituted or are optionally substituted with 1, 2, or 3 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_6$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-$CF_3$, —C(=O)NH—($C_1$-$C_4$)alkylene-O—($C_1$-$C_4$)alkyl, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

W is selected from —H, —F, —Cl, —Br, —I, —($C_1$-$C_6$)alkyl, —($CR^aR^{a'}$)$_q$—OH, —($CR^aR^{a'}$)$_q$—O—($C_1$-$C_6$)alkyl, —($CR^aR^{a'}$)$_q$—O—W', —O—($CR^aR^{a'}$)$_q$—W', —O—($CR^aR^{a'}$)$_q$—OH, —O—($CR^aR^{a'}$)$_q$—O—($C_1$-$C_6$)alkyl, —($CR^aR^{a'}$)$_q$—O—($CR^aR^{a'}$)$_q$—OH, —($CR^aR^{a'}$)$_q$—O—($CR^aR^{a'}$)$_q$—O—($C_1$-$C_6$)alkyl, —($CR^aR^{a'}$)$_q$—SH, —($CR^aR^{a'}$)$_q$—S—($C_1$-$C_6$)alkyl, —($CR^aR^{a'}$)$_q$—S—W', —S—($CR^aR^{a'}$)$_q$—W', —($CR^aR^{a'}$)$_q$—S(O)$_2$—($C_1$-$C_6$)alkyl, —($CR^aR^{a'}$)$_q$—S(O)$_2$—W', —S(O)$_2$—($CR^aR^{a'}$)$_q$—W', —($CR^aR^{a'}$)$_q$—$NH_2$, —($CR^aR^{a'}$)$_q$—NH—($C_1$-$C_6$)alkyl, —($CR^aR^{a'}$)$_q$—N—(($C_1$-$C_6$)alkyl,)$_2$, —($CR^aR^{a'}$)$_q$—N$^+$(($C_1$-$C_6$)alkyl,)$_3$, —($CR^aR^{a'}$)$_q$—NH—W', —($CR^aR^{a'}$)$_q$—NH—($CR^aR^{a'}$)$_q$—OH, —NH—($CR^aR^{a'}$)$_q$—W', or —($CR^aR^{a'}$)$_q$—W';

W' may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl W' groups are unsubstituted or are optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —CH($CF_3$)(OH), —($C_1$-$C_4$)alkylene-$NH_2$, —($C_1$-$C_4$)alkylene-NH(($C_1$-$C_4$)alkyl), —($C_1$-$C_4$)alkylene-NH—($C_1$-$C_4$)alkylene-$CF_3$, —($C_1$-$C_4$)alkylene-N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_6$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-$CF_3$, —C(=O)NH—($C_1$-$C_4$)alkylene-O—($C_1$-$C_4$)alkyl, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —($C_1$-$C_4$)alkylene-OH, —OH, —O—($C_1$-$C_6$)alkyl, —SH, —S—($C_1$-$C_6$)alkyl, —$SO_3$H, —$OCF_3$, —$OCHF_2$, or —C(=O)—W"; and further wherein W' may include 0, 1, or 2 =O groups when W' is a $C_3$-$C_{10}$ cycloalkyl or a 3-10 membered heterocyclyl, and further wherein the =O groups may be bonded to a ring carbon atom or a ring S atom;

W" may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl W" groups are unsubstituted or are optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —OH, —$NH_2$, —NH(($C_1$-$C_4$)alkyl), —N(($C_1$-$C_4$)alkyl)$_2$, —$CF_3$, —$CO_2$H, —C(=O)—O—($C_1$-$C_4$)alkyl, —SH, —S—($C_1$-$C_6$)alkyl, —$OCF_3$, or —$OCHF_2$; and further wherein W" may include 0, 1, or 2 =O groups when W" is a $C_3$-$C_{10}$ cycloalkyl or a 3-10 membered heterocyclyl, and further wherein the =O groups may be bonded to a ring carbon atom or a ring S atom;

the subscript q is, in each instance, independently selected from 0, 1, 2, 3, or 4;

$R^a$ is, in each instance, independently selected from —H, —$CH_3$, —$CH_2CH_3$, —F, —$CF_3$, or —C≡N;

$R^{a'}$ is, in each instance, independently selected from —H, —$CH_3$, —$CH_2CH_3$, —F, —$CF_3$, or —C≡N; or $R^a$ and $R^{a'}$ may join to form a cyclopropyl ring together with the carbon atom to which they are attached;

Z is selected from a $C_6$-$C_{10}$ aryl; a 5-10 membered heteroaryl comprising 1, 2, 3 or 4 heteroatoms independently selected from O, S, or N; a 4-7 membered heterocyclyl comprising 1, 2, or 3 heteroatoms selected from O, S, or N; a $C_3$-$C_7$ cycloalkyl; a —N(H)-heterocyclyl, wherein the heterocyclyl of —N(H)-heterocyclyl is a 4-7 membered heterocyclyl comprising 1, 2, or 3 heteroatoms selected from O, S, or N; a —N(H)—($C_3$-$C_7$)cycloalkyl; or Z is a —O—($C_1$-$C_6$)alkyl; wherein the $C_6$-$C_{10}$ aryl, the 5-10 membered heteroaryl, the 4-7 membered heterocyclyl, the $C_3$-$C_7$ cycloalkyl; the —N(H)-heterocyclyl, and the —N(H)—($C_3$-$C_7$)cycloalkyl are unsubstituted or are optionally substituted with 1, 2, or 3 substituents independently selected from —F, —Cl, —Br, —I, —C≡N, —$NO_2$, —$CF_3$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_6$)alkyl), —N(($C_1$-$C_6$)alkyl)$_2$, —C(=O)$NH_2$, —C(=O)NH(($C_1$-$C_6$)alkyl), —C(=O)N(($C_1$-$C_6$)alkyl)$_2$, —$SO_2NH_2$, —$SO_2$NH(($C_1$-$C_6$)alkyl), —$SO_2$N(($C_1$-$C_6$)alkyl)$_2$, —$SO_2$NH(($C_2$-$C_6$)alkenyl), —$SO_2$NH(($C_2$-$C_6$)alkynyl), —$SO_2$NH—($C_1$-$C_4$)alkylene-OH, —$SO_2$NH—($C_1$-$C_4$)alkylene-O—($C_1$-$C_6$)alkyl, —$NHSO_2$—($C_1$-$C_6$)alkyl, —NHC(=O)—($C_1$-$C_6$)alkyl, —$SO_2$—($C_1$-$C_6$)alkyl, —SO—($C_1$-$C_6$)alkyl, —($C_1$-$C_4$)alkylene-NH—C(=O)—($C_1$-$C_6$)alkyl, —C(=O)—($C_1$-$C_6$)alkyl, —$CO_2$H, —C(=O)—O—($C_1$-$C_6$)alkyl, —C(=O)NH—($C_1$-$C_4$)alkylene-$NH_2$, —C(=O)NH—($C_1$-$C_4$)alkylene-NH(($C_1$-$C_6$)alkyl), —C(=O)NH—($C_1$-$C_4$)alkylene-N(($C_1$-$C_6$)alkyl)$_2$, —($C_1$-$C_4$)alkylene-C(=O)—($C_1$-$C_6$)alkyl, —($C_1$-$C_4$)alkylene-C(=O)—O—($C_1$-$C_6$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

W is not —H, —F, —Cl, —Br, —I, or unsubstituted —($C_1$-$C_6$)alkyl if X is $CR^4$;

Y is not unsubstituted cyclopropyl, cyclobutyl, or cyclopentyl if W is —H, —F, —Cl, —Br, —I, or —($C_1$-$C_6$)alkyl;

W is not —CH$_2$OH or —CH$_2$O(C$_1$-C$_4$alkyl) if Y is a group of formula

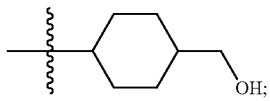

and

W is not —SH, —OH, —S—(C$_1$-C$_6$)alkyl), or —S—(C$_1$-C$_6$)alkyl) if Z is —O—(C$_1$-C$_6$)alkyl);

wherein the symbol ∿, when drawn across a bond, indicates the point of attachment to the rest of the molecule.

In some embodiments, X is N.

In some embodiments, X is CR$^4$. In some such embodiments, R$^4$ is —H.

In some embodiments, R$^3$ is —H.

In some embodiments, Z is selected from —OMe or —NH-cyclohexyl; or an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, piperidinyl, isothiazolyl, or thiomorpholinyl group. In some such embodiments, Z is selected from —OMe or —NH-cyclohexyl; or an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl.

In some embodiments, Z is an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, piperidinyl, isothiazolyl, or thiomorpholinyl group. In some embodiments, Z is an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl group. In some such embodiments, Z is a substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl group.

In some embodiments, Z is an unsubstituted or substituted phenyl or pyridyl. In some such embodiments, Z is a substituted phenyl or pyridyl. In some other such embodiments, Z is a substituted phenyl.

In some embodiments, Z is selected from

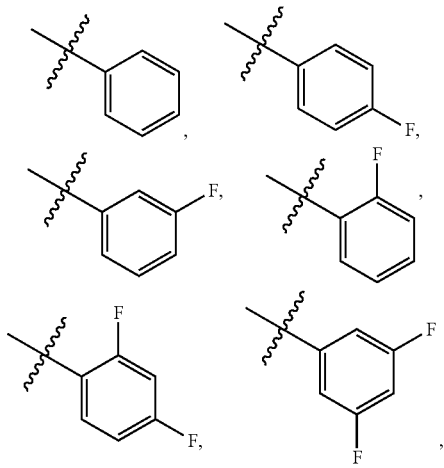

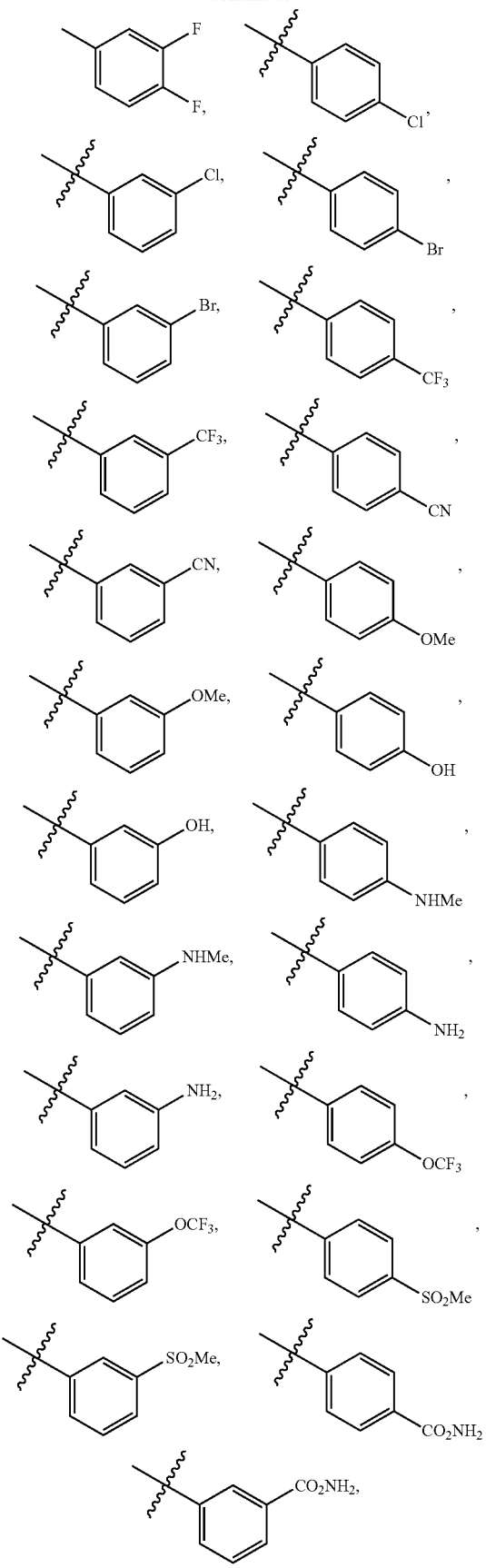

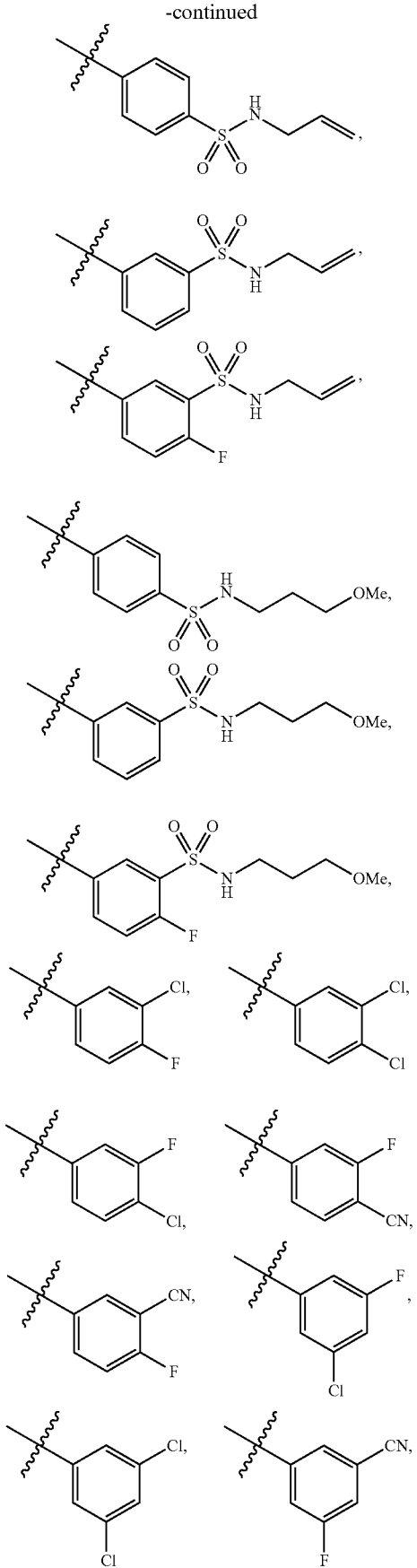
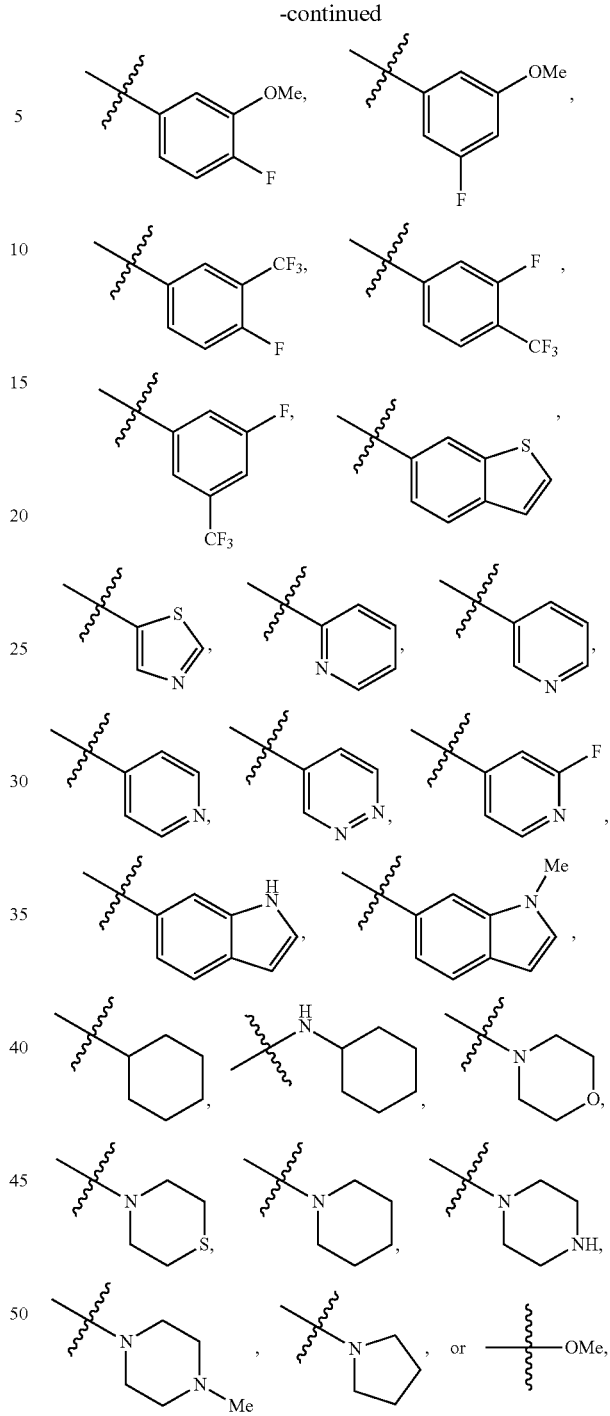
wherein the symbol ⌇, when drawn across a bond, indicates the point of attachment to the rest of the molecule.
In some embodiments, Z is selected from
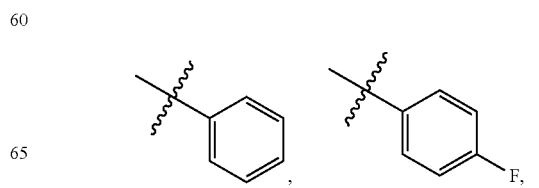

-continued

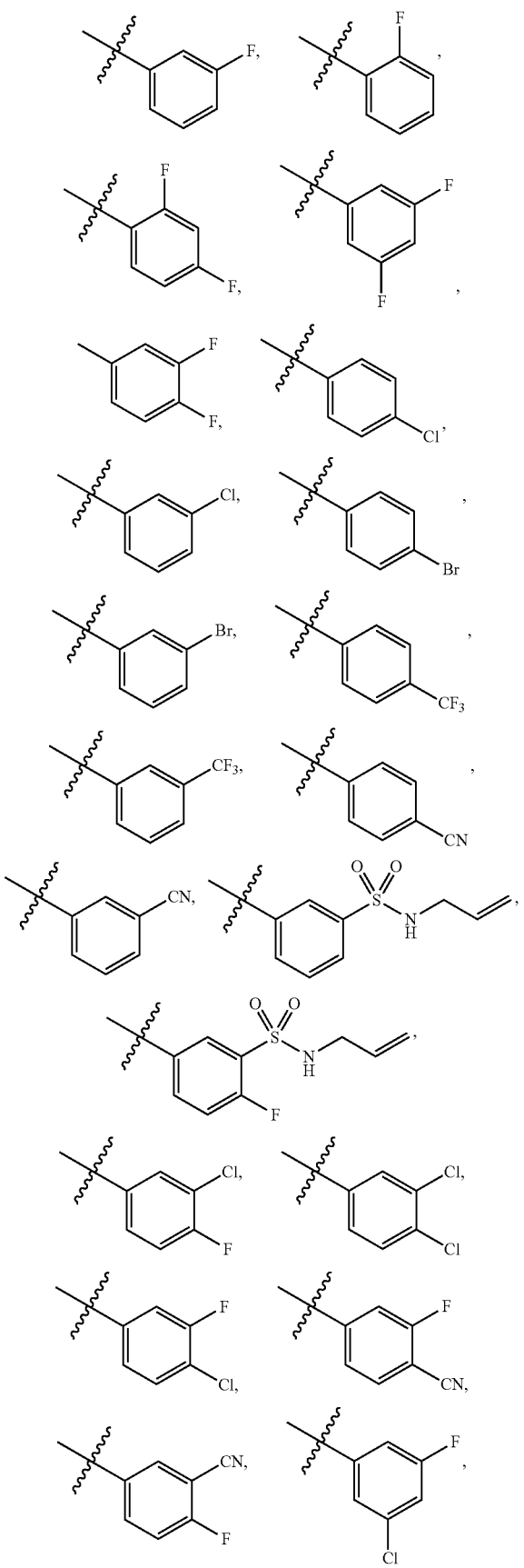

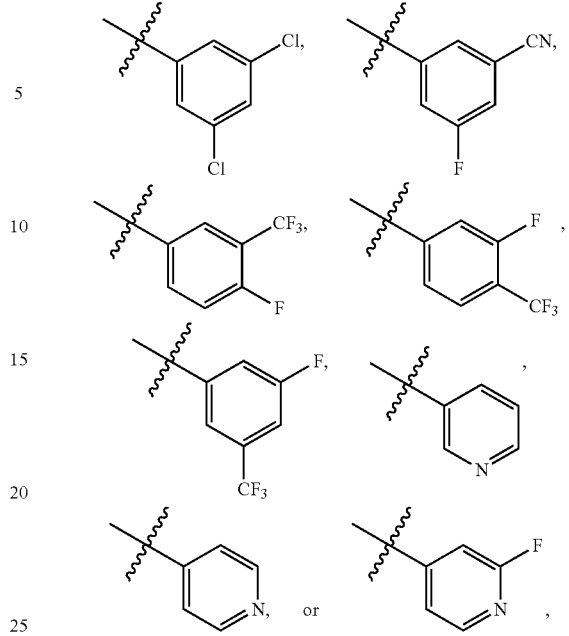

wherein the symbol ∿, when drawn across a bond, indicates the point of attachment to the rest of the molecule.

In some embodiments, Y is an unsubstituted or substituted cycloheptyl, cyclohexyl, cyclopentyl, cyclobutyl, piperidinyl, pyrrolidinyl, azetidinyl, adamantyl, bicyclo[2.2.2]octyl, bicyclo[3.2.1]octyl, bicyclo[4.1.1]octyl, bicyclo[2.2.1]heptyl, bicyclo[3.1.1]heptyl, or bicyclo[2.1.1]hexyl. In some such embodiments, Y is a substituted cycloheptyl, cyclohexyl, cyclopentyl, cyclobutyl, piperidinyl, pyrrolidinyl, adamantyl, bicyclo[2.2.2]octyl, bicyclo[3.2.1]octyl, bicyclo[4.1.1]octyl, bicyclo[2.2.1]heptyl, bicyclo[3.1.1]heptyl, or bicyclo[2.1.1]hexyl group. In some such embodiments, Y is an unsubstituted or substituted cyclohexyl. In some such embodiments, Y is a substituted cyclohexyl. In other such embodiments, Y is an unsubstituted or substituted adamantyl. In some such embodiments, Y is an unsubstituted adamantyl. In other embodiments, Y is a substituted adamantyl. In other such embodiments, Y is an unsubstituted or substituted cyclobutyl. In some such embodiments, Y is a substituted cyclobutyl. In still other embodiments, Y is an unsubstituted or substituted cyclopentyl or cycloheptyl. In some such embodiments Y is a substituted cyclopentyl or cycloheptyl. In still other embodiments, Y is an unsubstituted or substituted piperidinyl. In some such embodiments, Y is a substituted piperidinyl. In some embodiments where Y is substituted, Y is substituted with a group that includes a carbonyl (C=O) functional group. Examples include, but are not limited to ketones, esters, and amides.

In some embodiments, Y is selected from

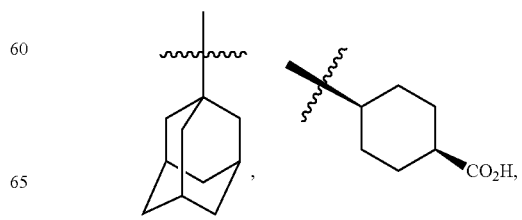

27
-continued
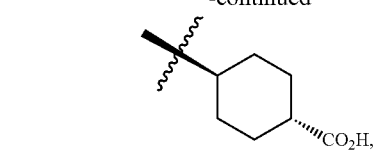
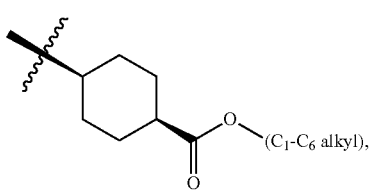
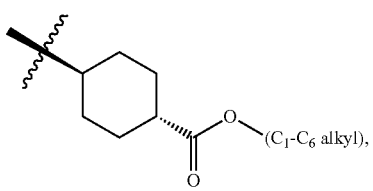
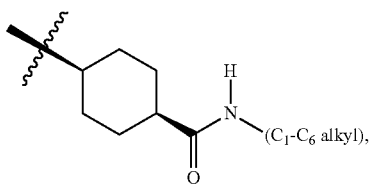
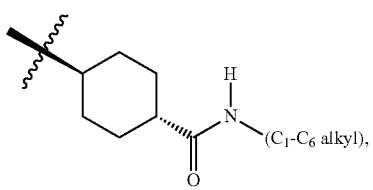
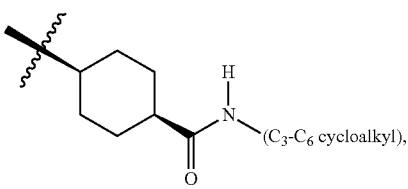
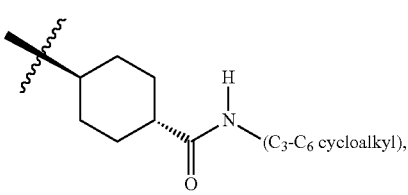
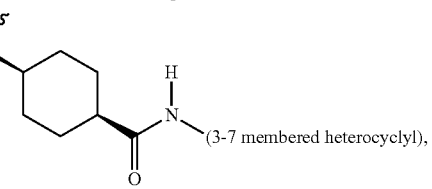
28
-continued
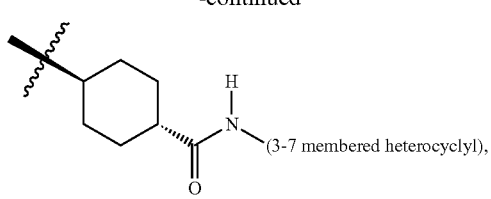
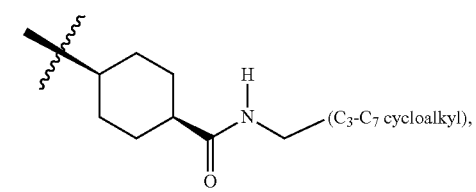
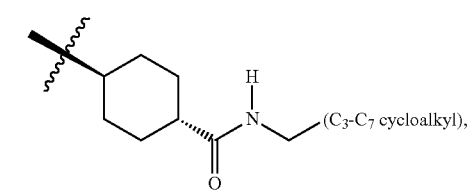
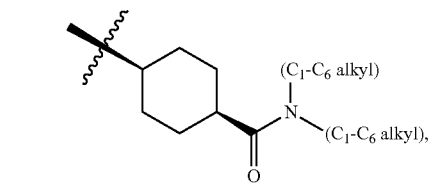
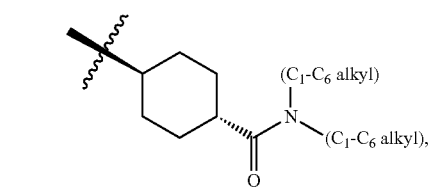
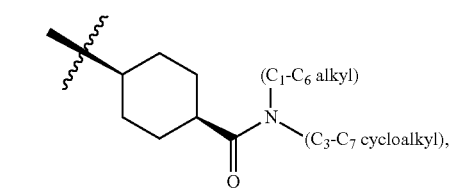
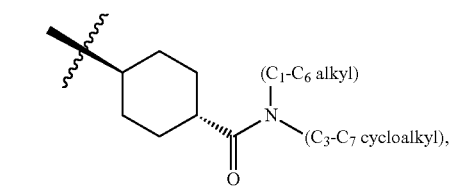
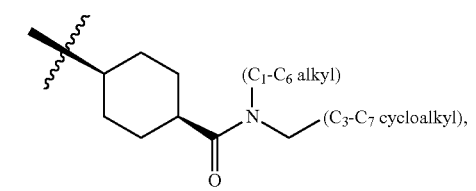
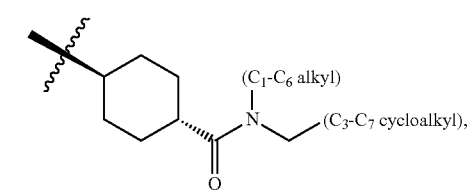

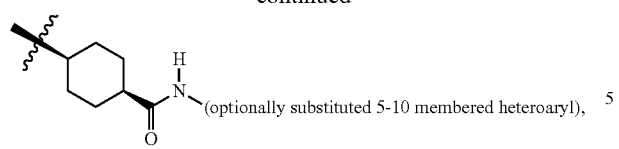
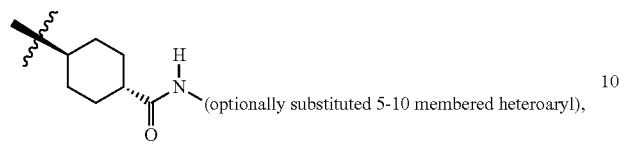
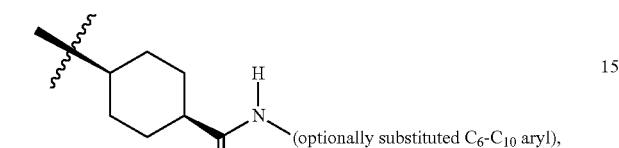
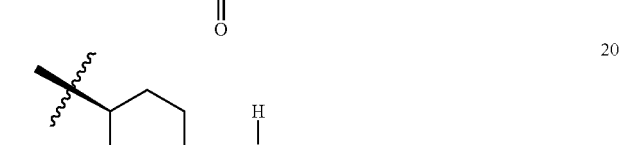
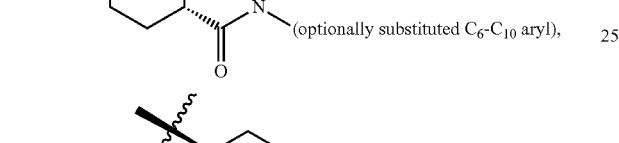
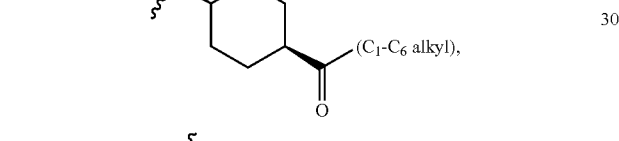
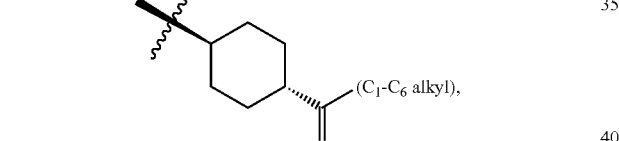
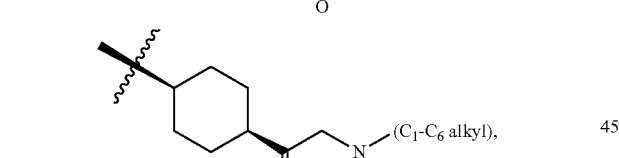
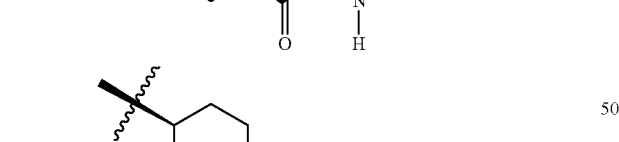
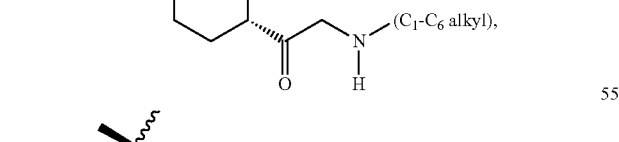
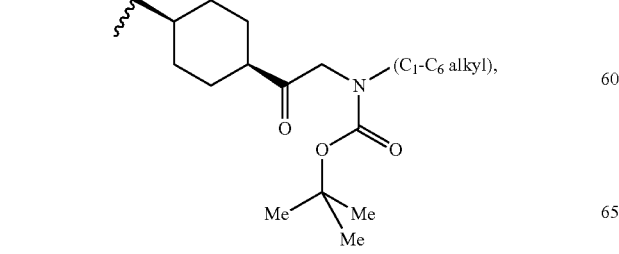
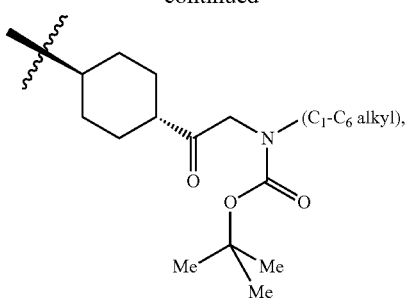
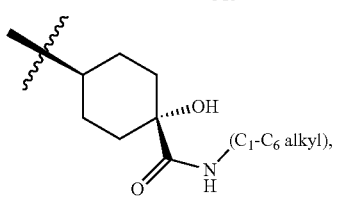
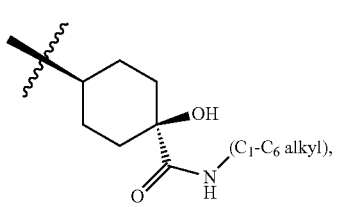
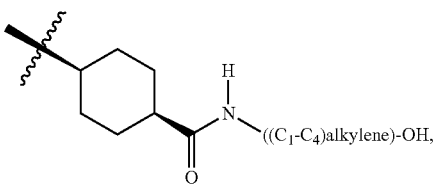
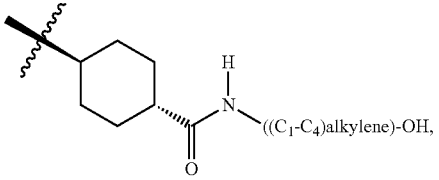
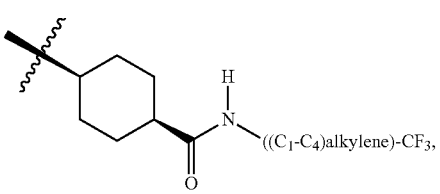
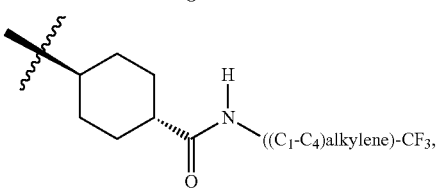
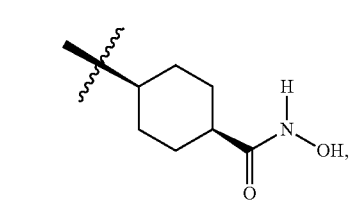

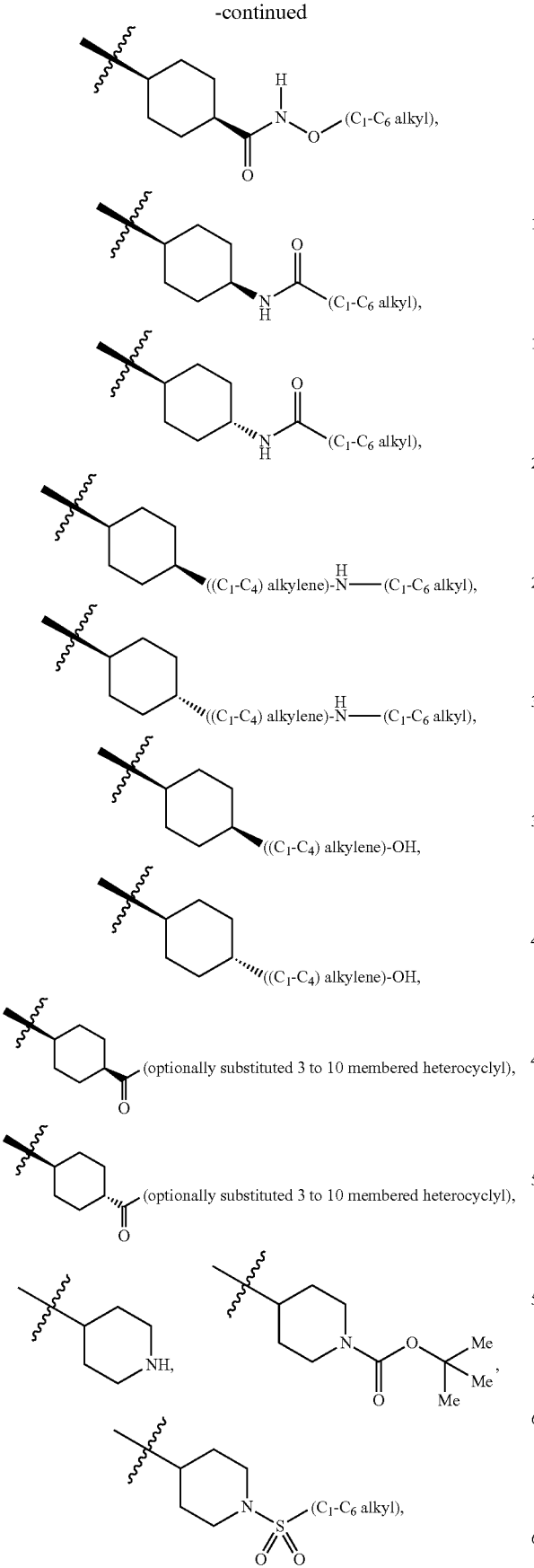
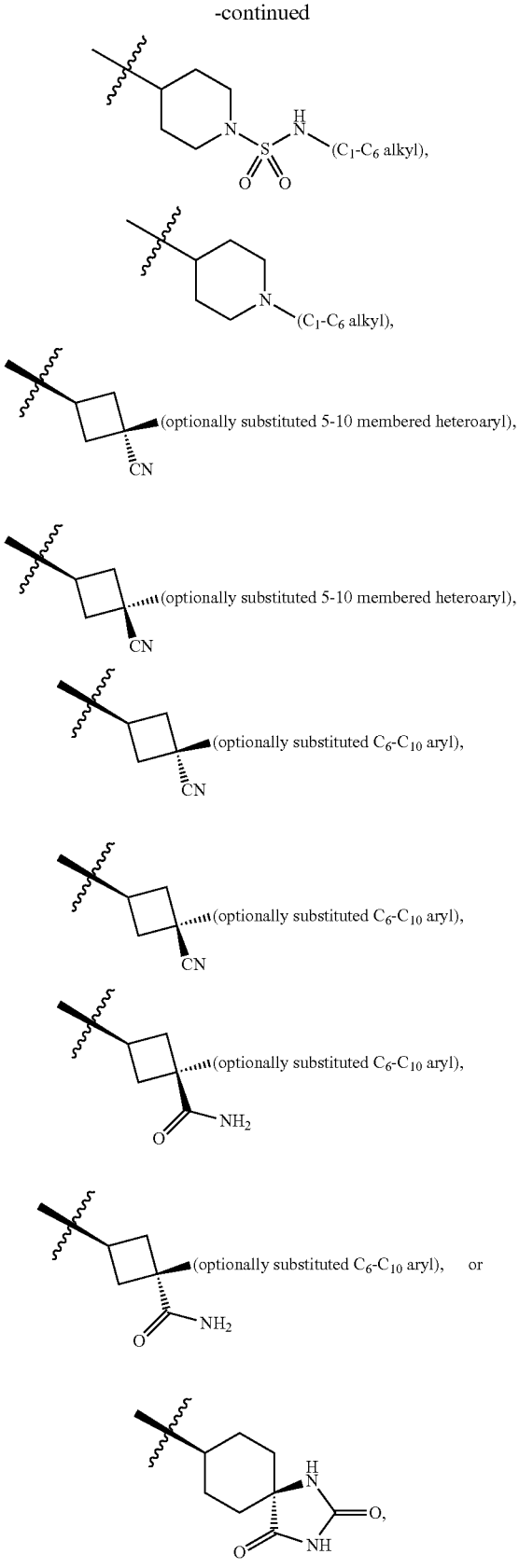
wherein the symbol ⁓⁓⁓, when drawn across a bond, indicates the point of attachment to the rest of the molecule.

In some embodiments, Y is selected from
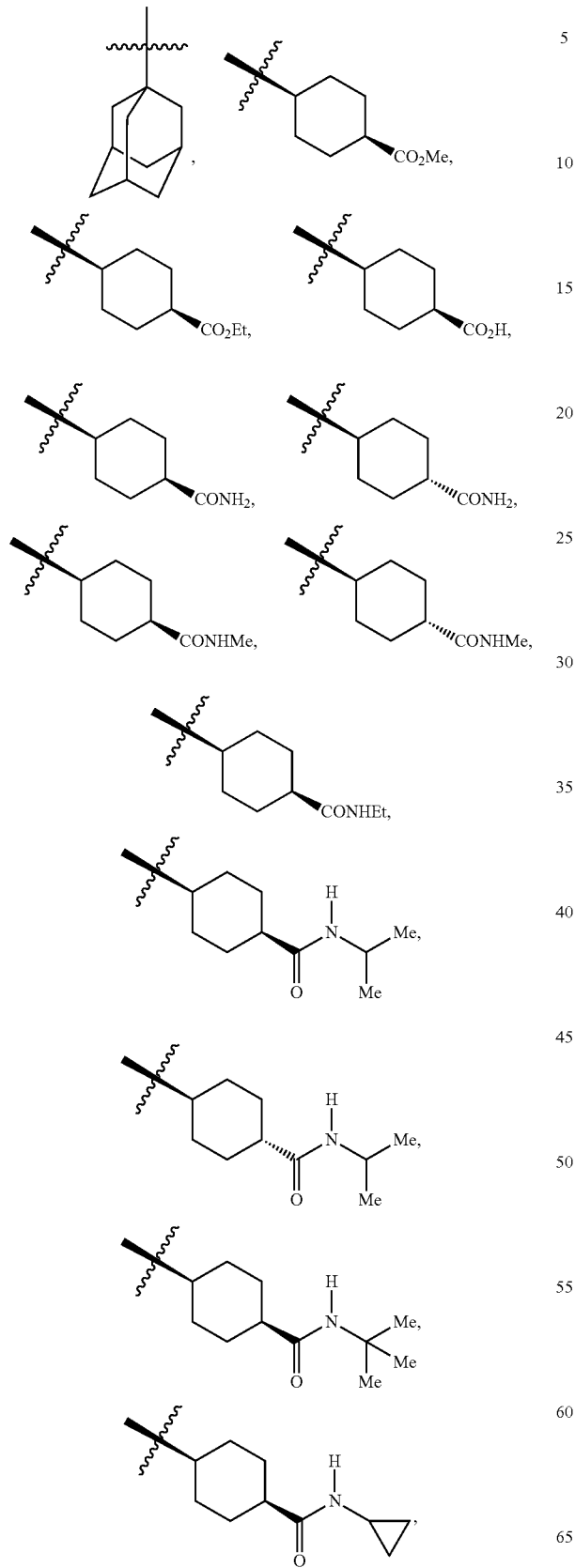
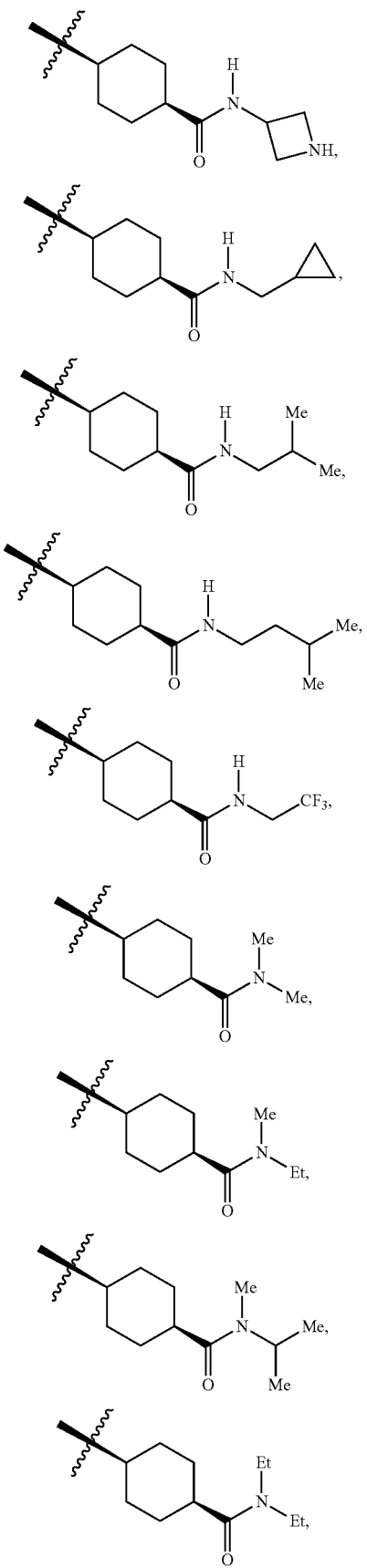

-continued
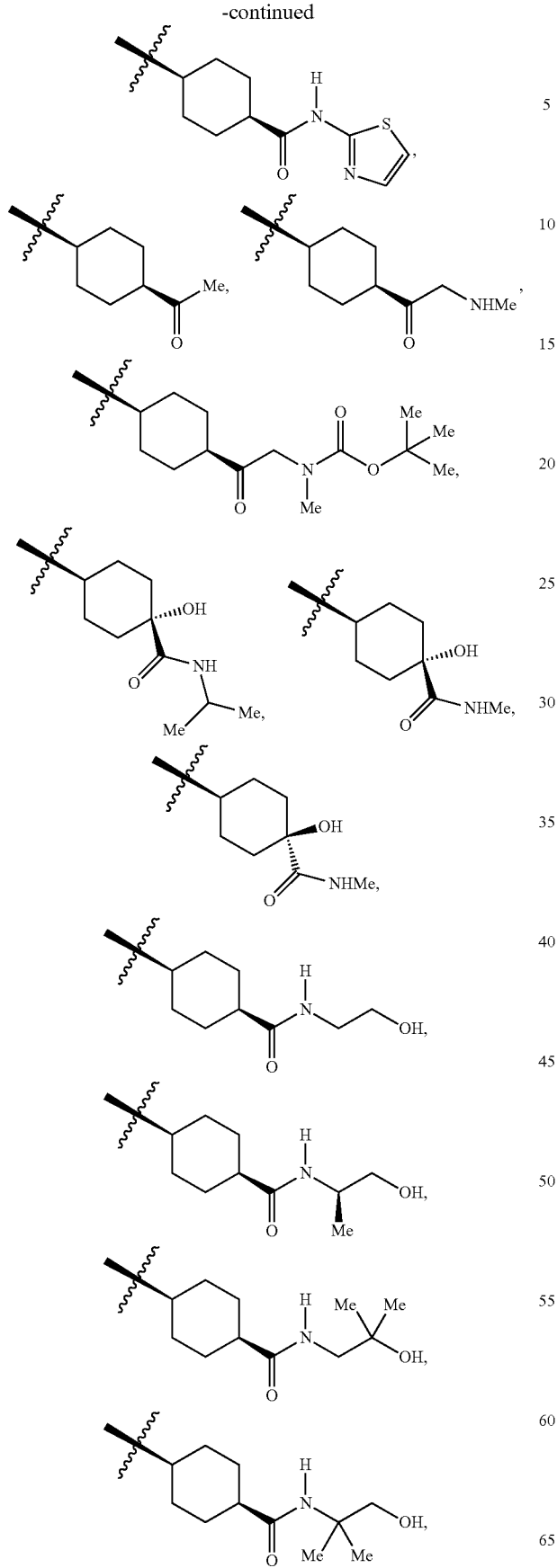
-continued
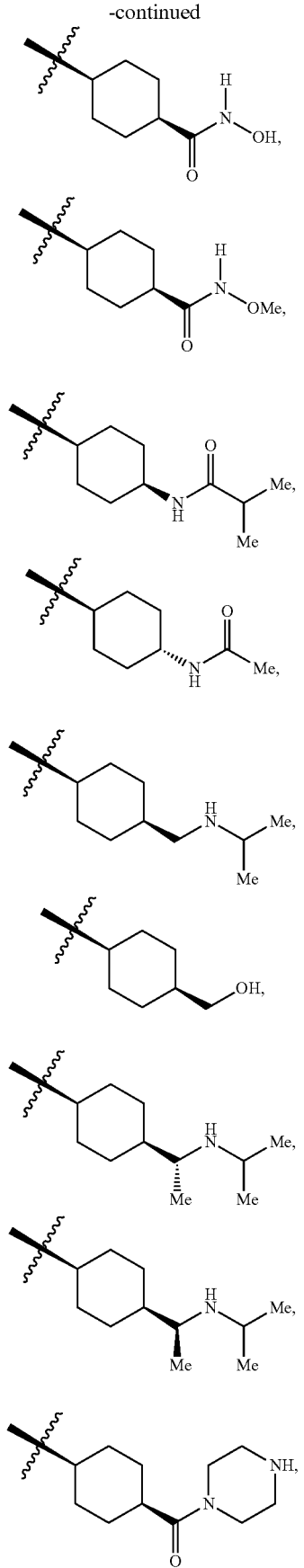

37
-continued
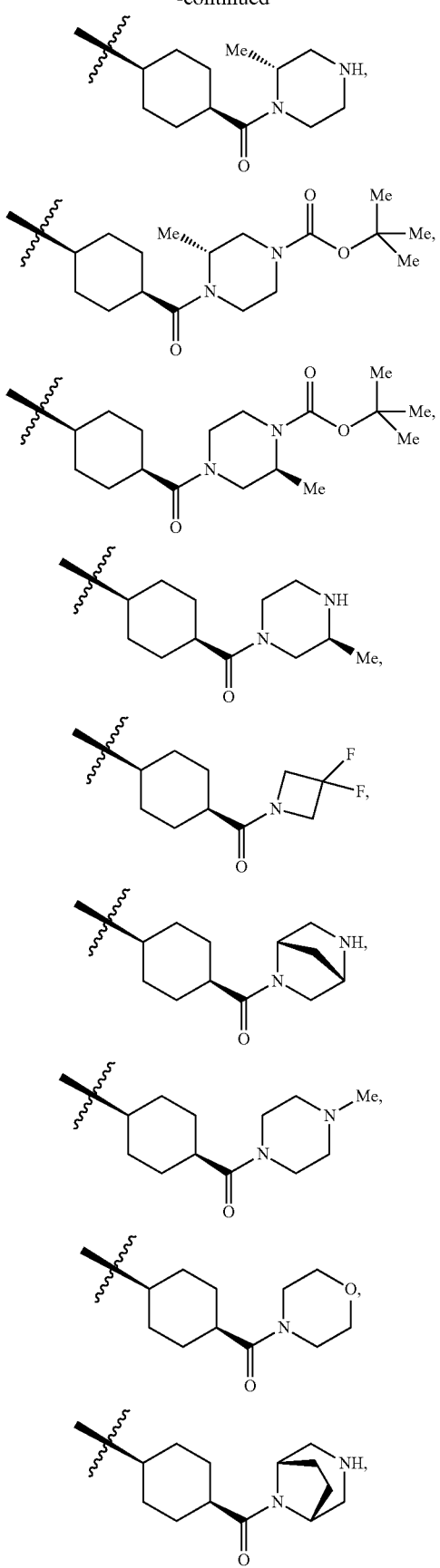
38
-continued
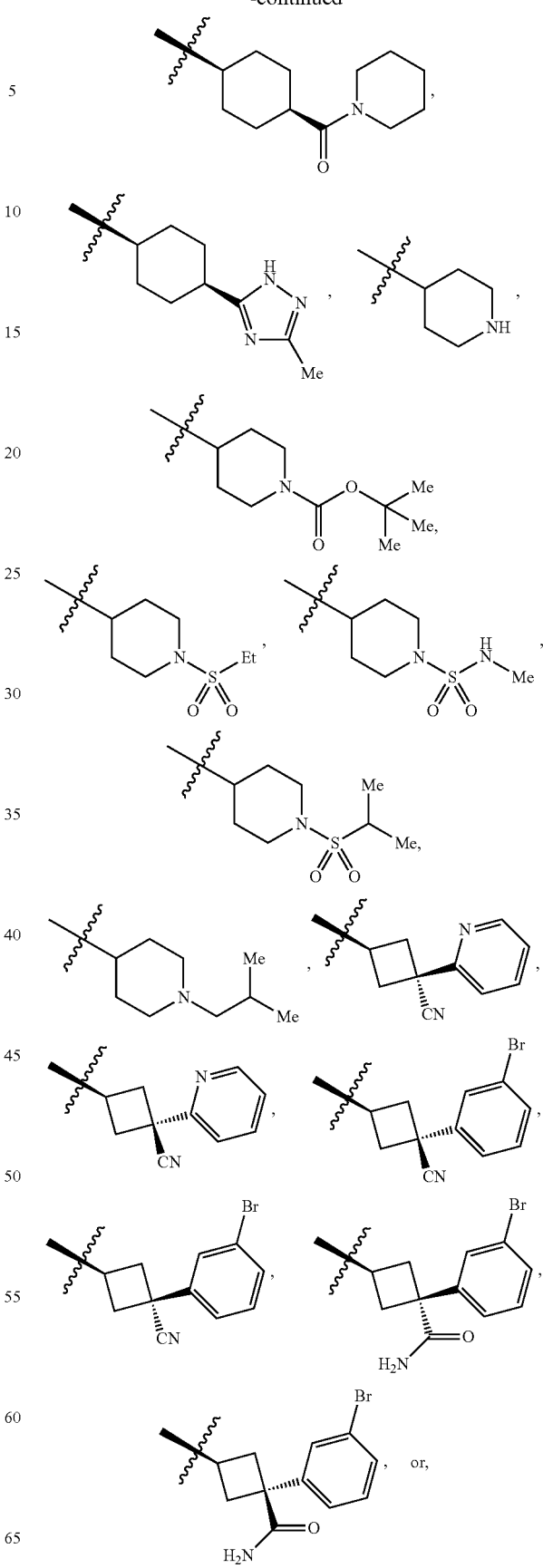

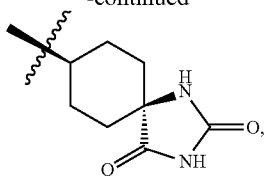
wherein the symbol ∿, when drawn across a bond, indicates the point of attachment to the rest of the molecule.
In some embodiments, Y is selected from
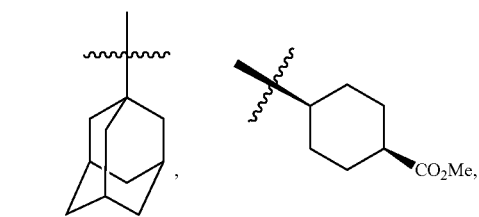
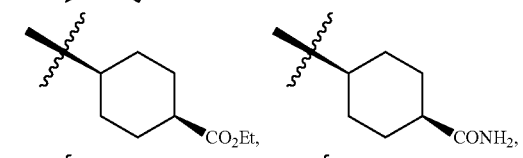
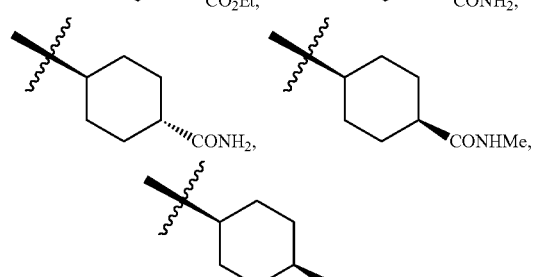
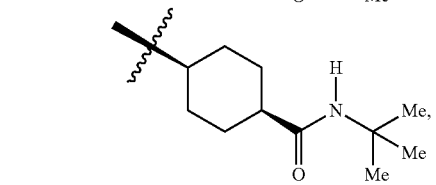
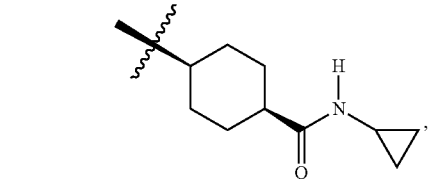
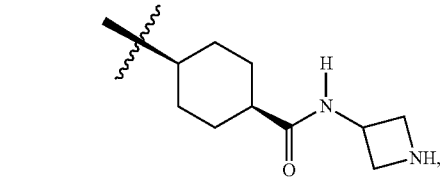
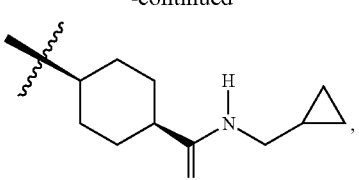
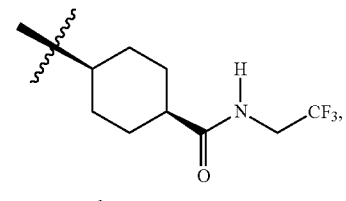
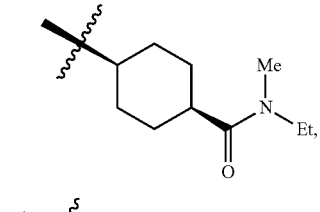
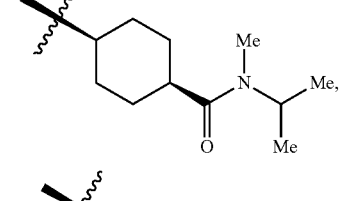
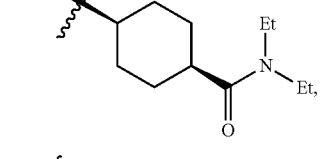
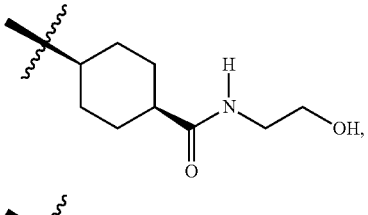
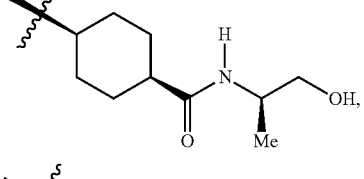
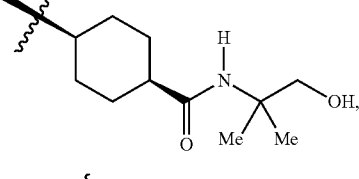
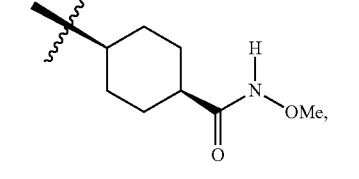

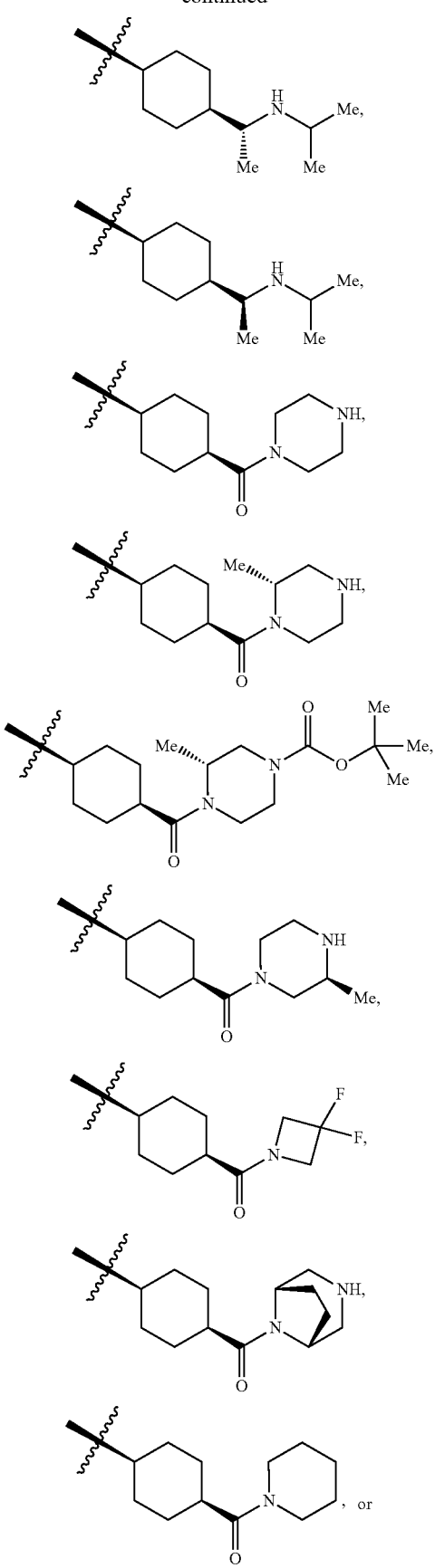

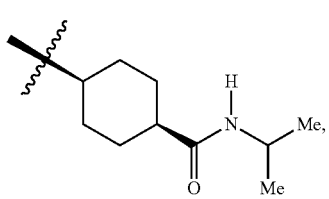

wherein the symbol ⌇, when drawn across a bond, indicates the point of attachment to the rest of the molecule.

In some embodiments, Y is wherein the symbol ⌇, when drawn across a bond, indicates the point of attachment to the rest of the molecule.

In some embodiments, W is selected from —CH$_2$OH, —CH$_2$OCH$_3$, —CH$_2$OCH$_2$CH$_2$OH, —CH$_2$OCH$_2$CH$_2$OCH$_3$, —OCH$_2$CH$_2$OH, —OCH$_2$CH$_2$OMe, —W', —CH$_2$W', —OW', —OCH$_2$W', —OCH$_2$CH$_2$W', —OCH$_2$CH$_2$CH$_2$W', —NHW', —NHCH$_2$W', —NHCH$_2$CH$_2$W', —NHCH$_2$CH$_2$CH$_2$W', or —W'—C(=O)—W''; wherein W', if present, is selected from a 3-10 membered heterocyclyl comprising 1 or 2 heteroatoms selected from N, O, and S; a C$_6$-C$_{10}$ aryl; or a 5-10 membered heteroaryl comprising 1, 2, 3, or 4 heteroatoms independently selected from N, O, or S; wherein the 3-10 membered heterocyclyl W' group may be monocyclic or bicyclic, and further wherein the 3-10 membered heterocyclyl, the C$_6$-C$_{10}$ aryl, or the 5-10 membered heteroaryl W' groups are unsubstituted or are substituted with 1, 2, 3, or 4 substituents independently selected from —F, —Cl, —Br, —(C$_1$-C$_6$)alkyl, —CH(CF$_3$)(OH), —(C$_1$-C$_4$)alkylene-NH$_2$, —(C$_1$-C$_4$)alkylene-NH—(C$_1$-C$_4$)alkylene-CF$_3$, —C(=O)NH$_2$, —SO$_2$—(C$_1$-C$_6$)alkyl, —CF$_3$, —CO$_2$H, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —(C$_1$-C$_4$)alkylene-OH, —OH, —O—(C$_1$-C$_6$)alkyl, or —SO$_3$H; and further wherein W' may include 0, 1, or 2 =O groups when W' is a 3-10 membered heterocyclyl, and further wherein the =O groups may be bonded to a ring carbon atom or a ring S atom; and further wherein W'', if present, is a 3-10 membered heterocyclyl comprising 1, 2, or 3 heteroatoms selected from N, O, and S, wherein the 3-10 membered heterocyclyl W'' group may be monocyclic or bicyclic, and further wherein the 3-10 membered heterocyclyl W'' group is unsubstituted or is optionally substituted with 1, 2, 3, or 4 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —OH, —NH$_2$, —NH((C$_1$-C$_4$)alkyl), —N((C$_1$-C$_4$)alkyl)$_2$, —CF$_3$, —CO$_2$H, —C(=O)—O—(C$_1$-C$_4$)alkyl, —SH, —S—(C$_1$-C$_6$)alkyl, —OCF$_3$, or —OCHF$_2$, or a pharmaceutically acceptable salt thereof, tautomer thereof, a pharmaceutically acceptable salt of the tautomer, a stereoisomer of any of the foregoing, or a mixture thereof.

In some embodiments, W is selected from —W', —CH₂W', —OW', —OCH₂W', —OCH₂CH₂W', —OCH₂CH₂CH₂W', —NHW', —NHCH₂W', —NHCH₂CH₂W', —NHCH₂CH₂CH₂W', or —W'—C(=O)—W"; wherein W', is selected from a 3-10 membered heterocyclyl comprising 1 or 2 heteroatoms selected from N, O, and S; a $C_6$-$C_{10}$ aryl; or a 5-10 membered heteroaryl comprising 1, 2, 3, or 4 heteroatoms independently selected from N, O, or S; wherein the 3-10 membered heterocyclyl W' group may be monocyclic or bicyclic, and further wherein the 3-10 membered heterocyclyl, the $C_6$-$C_{10}$ aryl, or the 5-10 membered heteroaryl W' groups are unsubstituted or are substituted with 1, 2, 3, or 4 substituents independently selected from —F, —Cl, —Br, —($C_1$-$C_6$)alkyl, —CH(CF₃)(OH), —($C_1$-$C_4$)alkylene-NH₂, —($C_1$-$C_4$)alkylene-NH—($C_1$-$C_4$)alkylene-CF₃, —C(=O)NH₂, —SO₂—($C_1$-$C_6$)alkyl, —CF₃, —CO₂H, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —($C_1$-$C_4$)alkylene-OH, —OH, —O—($C_1$-$C_6$)alkyl, or —SO₃H; and further wherein W' may include 0, 1, or 2 =O groups when W' is a 3-10 membered heterocyclyl, and further wherein the =O groups may be bonded to a ring carbon atom or a ring S atom; and further wherein W", if present, is a 3-10 membered heterocyclyl comprising 1, 2, or 3 heteroatoms selected from N, O, and S, wherein the 3-10 membered heterocyclyl W" group may be monocyclic or bicyclic, and further wherein the 3-10 membered heterocyclyl W" group is unsubstituted or is optionally substituted with 1, 2, 3, or 4 substituents independently selected from —F, —Cl, —Br, —I, —C≡N, —NO₂, —($C_1$-$C_6$)alkyl, —($C_2$-$C_6$)alkenyl, —($C_2$-$C_6$)alkynyl, —OH, —NH₂, —NH(($C_1$-$C_4$)alkyl), —N(($C_1$-$C_4$)alkyl)₂, —CF₃, —CO₂H, —C(=O)—O—($C_1$-$C_4$)alkyl, —SH, —S—($C_1$-$C_6$)alkyl, —OCF₃, or —OCHF₂.

In some embodiments, W is selected from —H, —F, —Cl, —OH, —OMe, —SO₂Me, —CH₂OH, —CH₂OMe, —OCH₂CH₂OH, —OCH₂CH₂OMe, or a group selected from

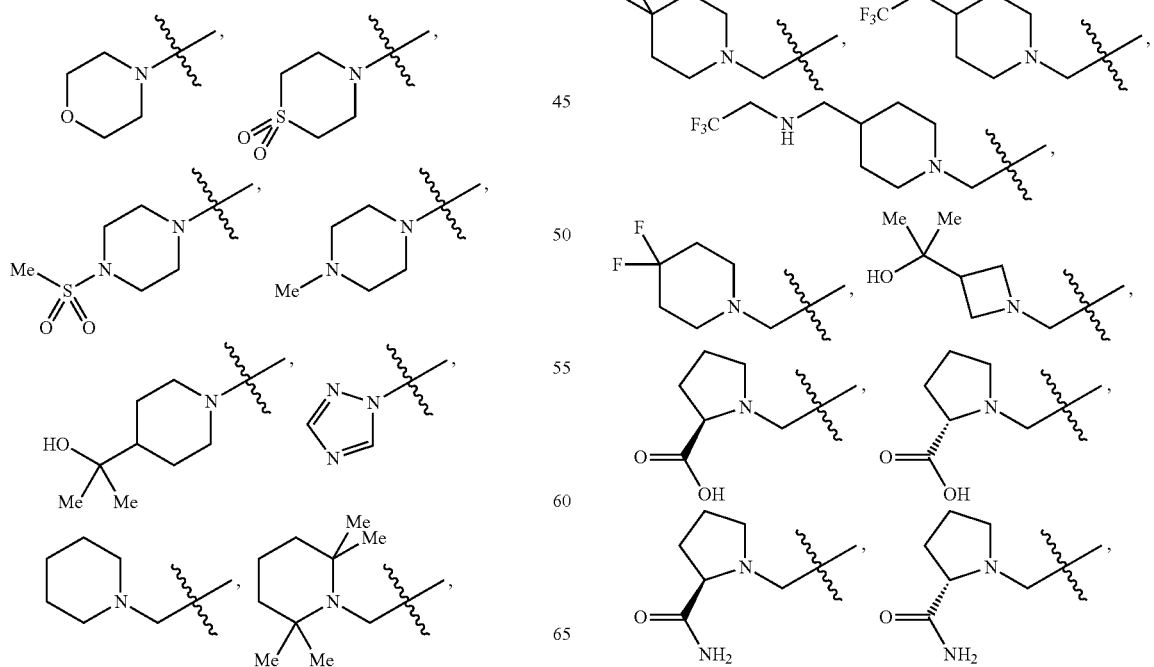

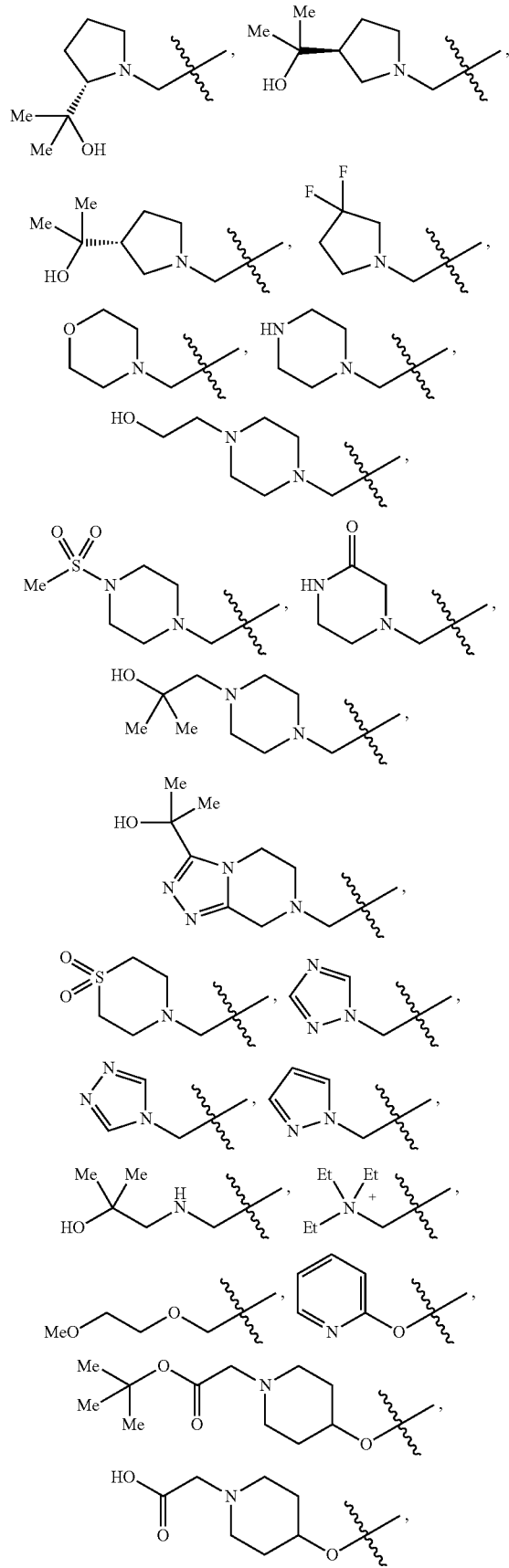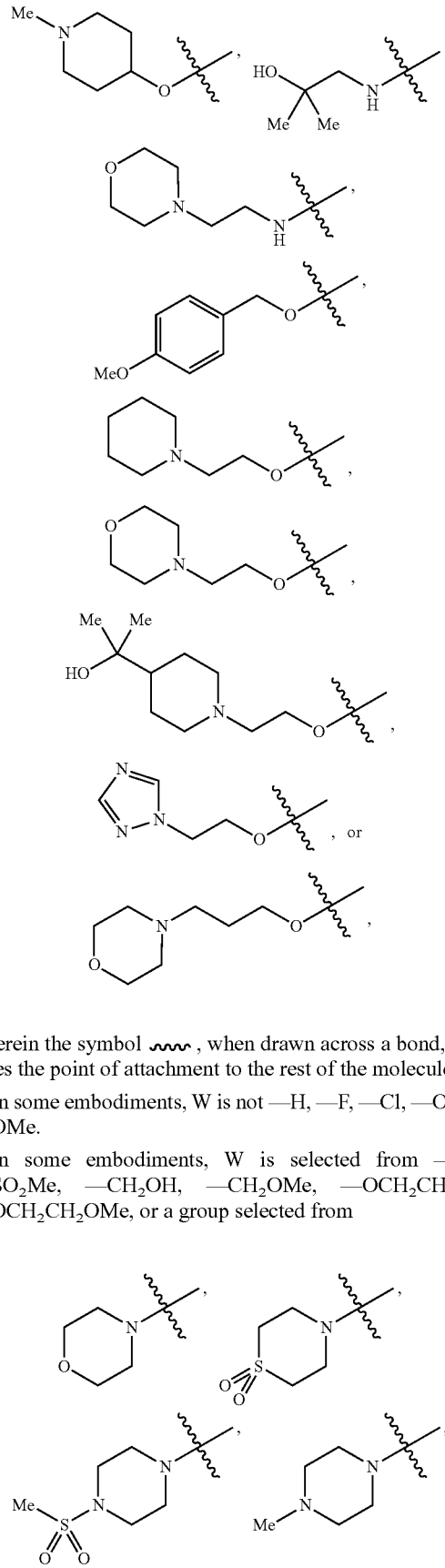
wherein the symbol ~~~, when drawn across a bond, indicates the point of attachment to the rest of the molecule.
In some embodiments, W is not —H, —F, —Cl, —OH, or —OMe.
In some embodiments, W is selected from —OH, —SO$_2$Me, —CH$_2$OH, —CH$_2$OMe, —OCH$_2$CH$_2$OH, —OCH$_2$CH$_2$OMe, or a group selected from -continued
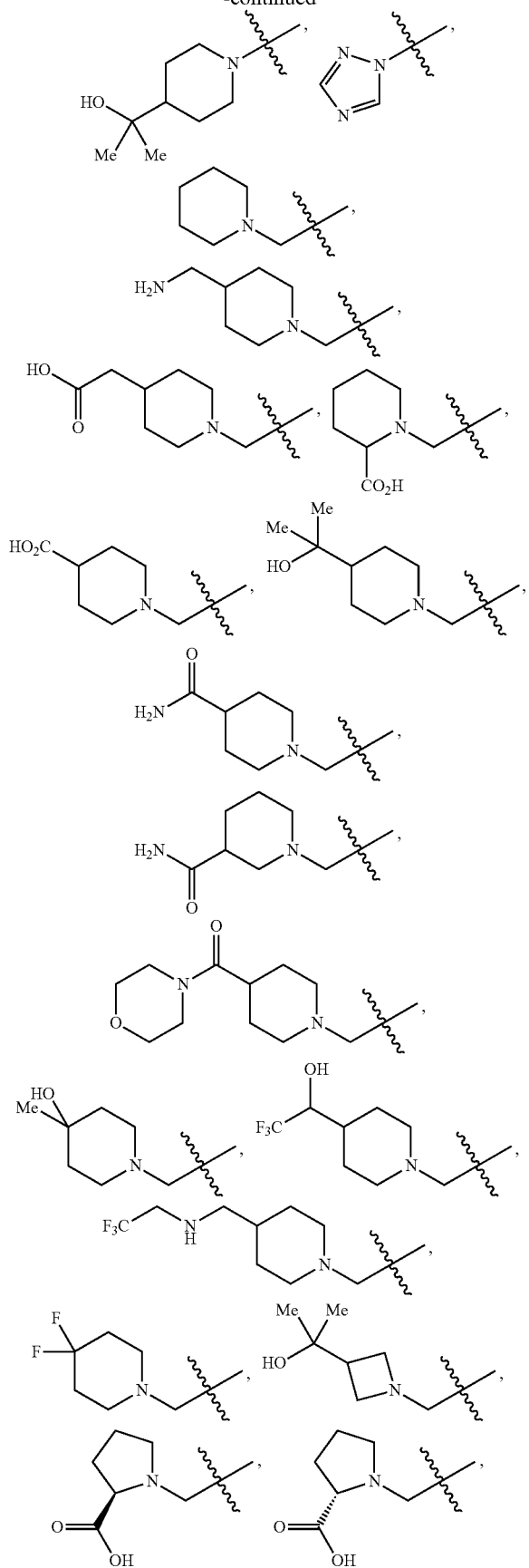
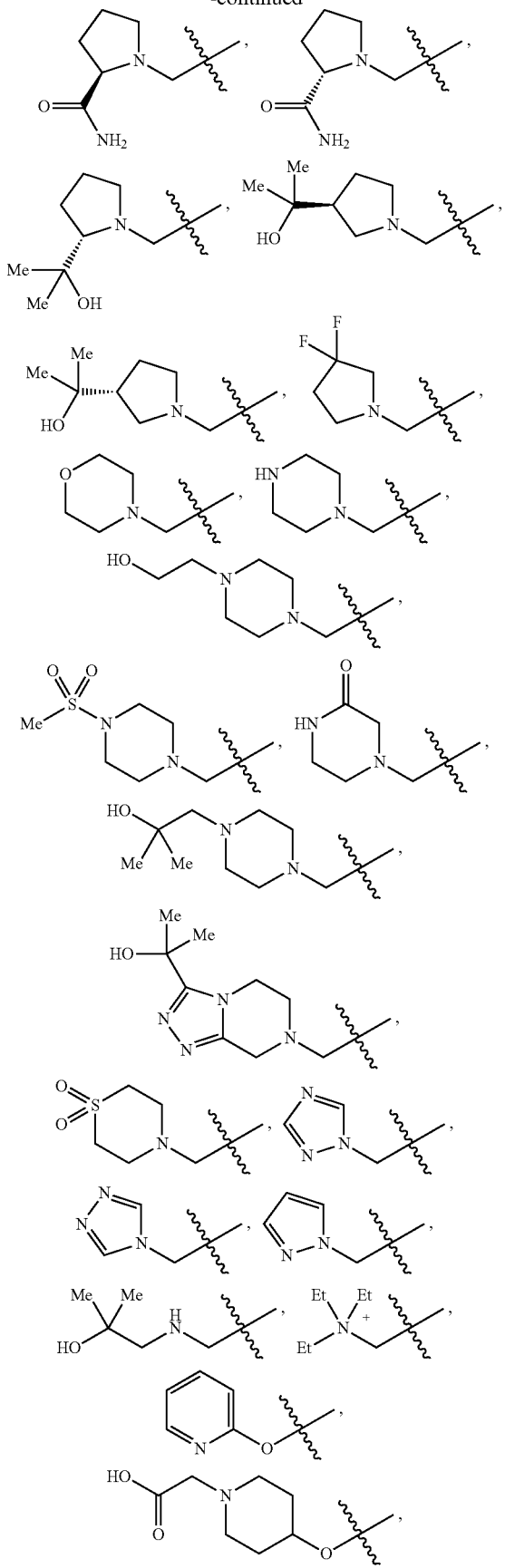

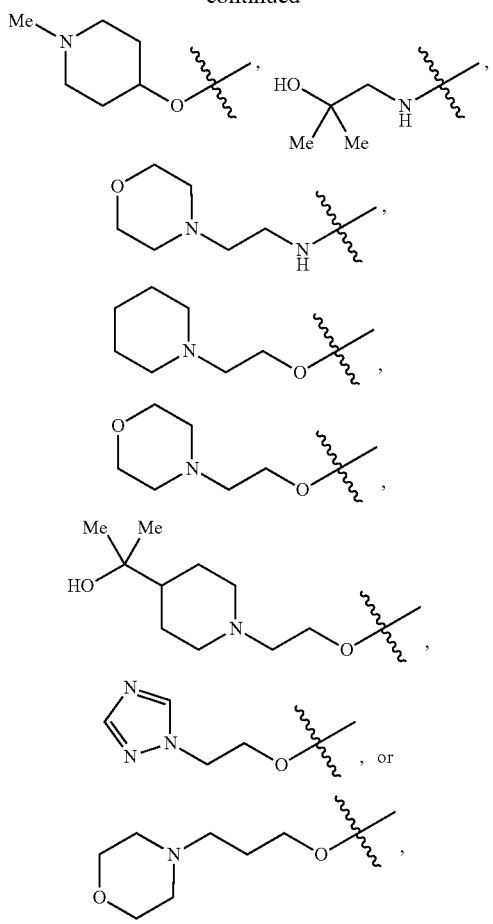
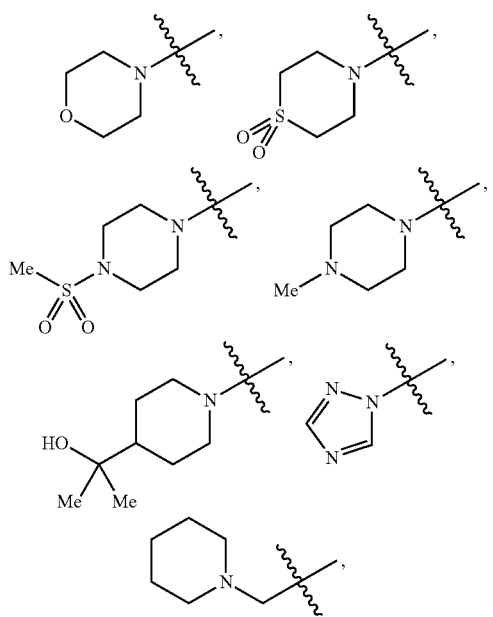
wherein the symbol ⌇, when drawn across a bond, indicates the point of attachment to the rest of the molecule.
In some embodiments, W is selected from
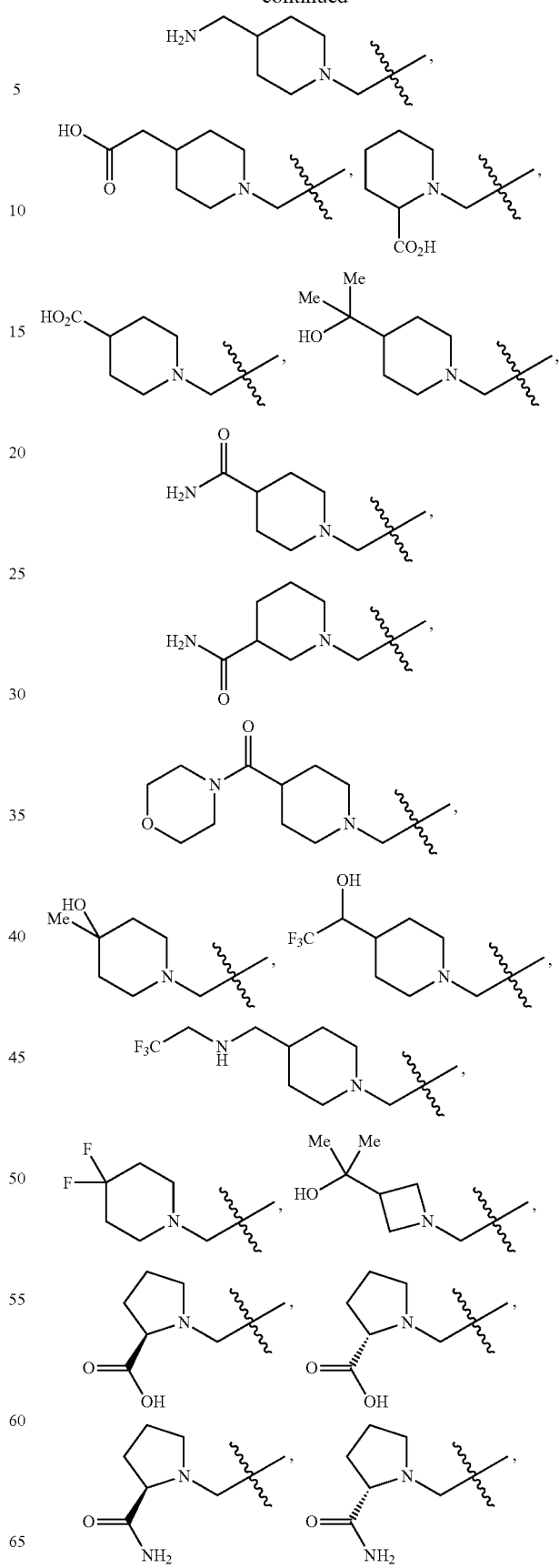

51
-continued
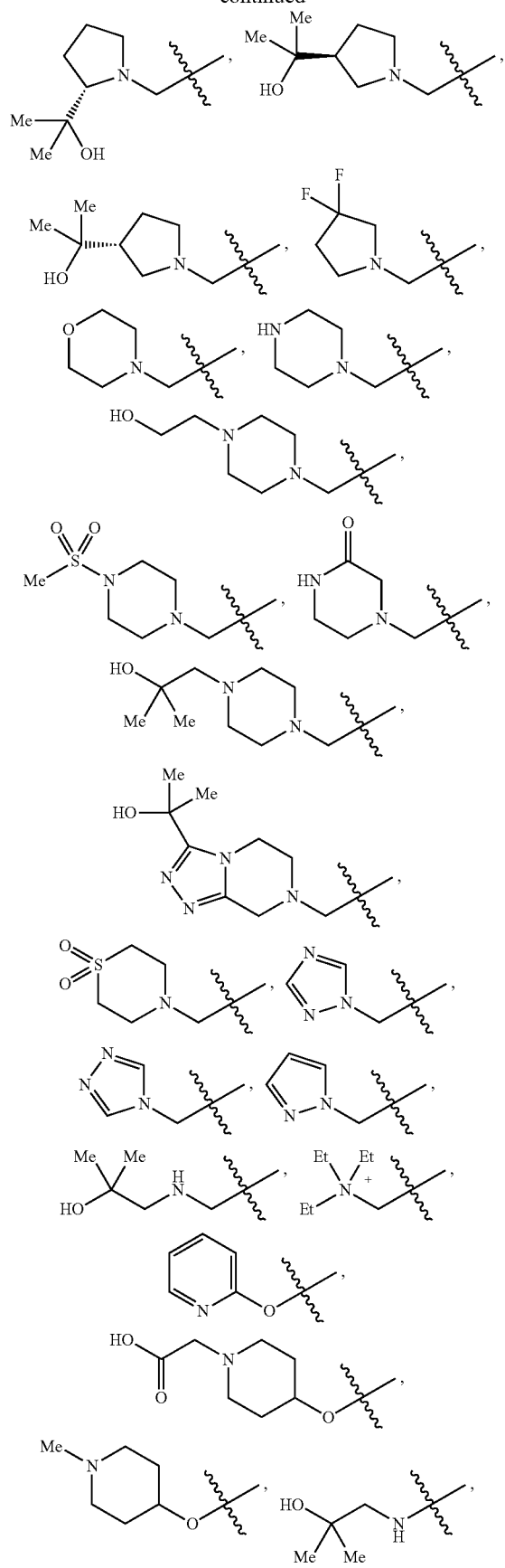
52
-continued
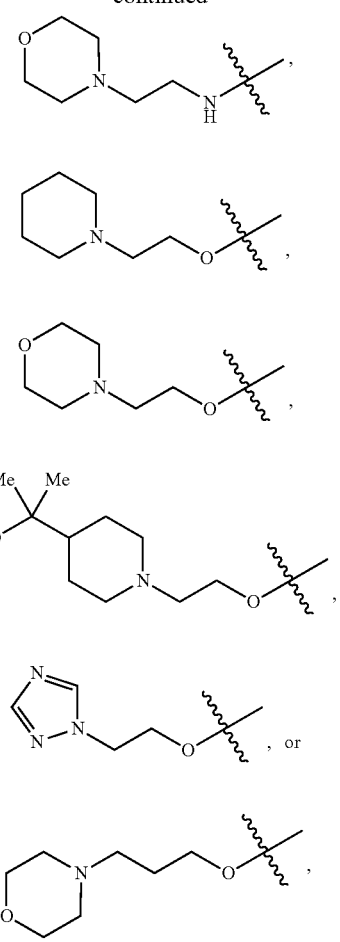
wherein the symbol ⌇, when drawn across a bond, indicates the point of attachment to the rest of the molecule.
In some embodiments, the compound is selected from
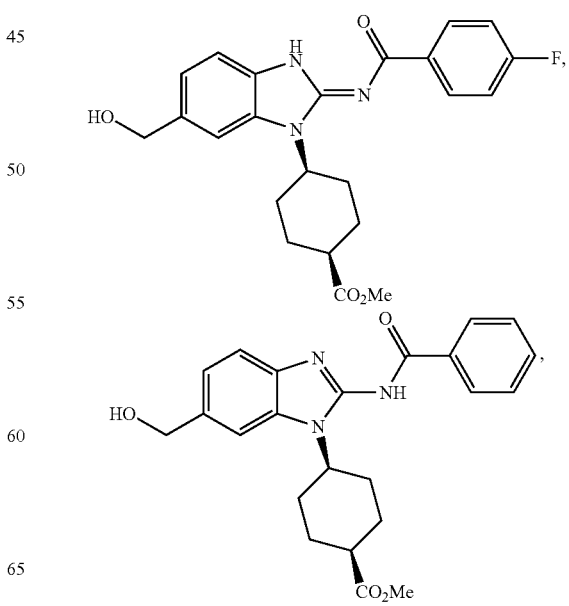

| 53 | 54 |
|---|---|
| -continued | -continued |
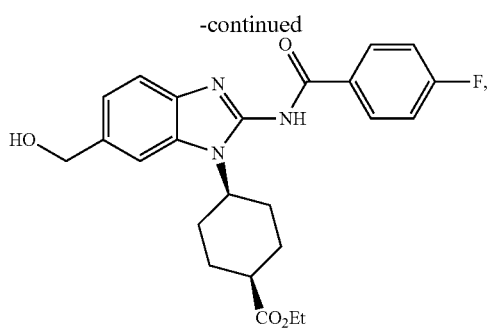
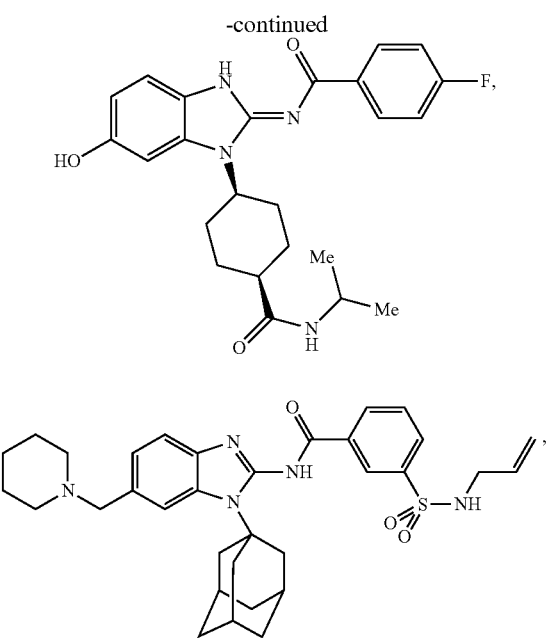
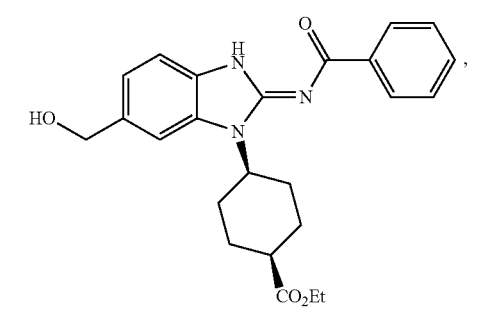
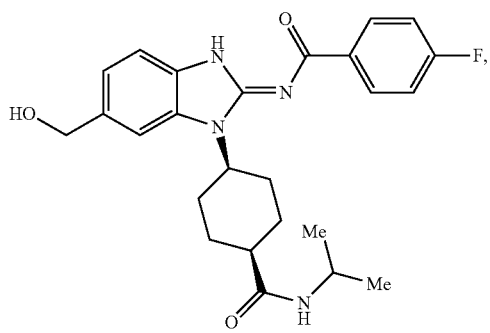
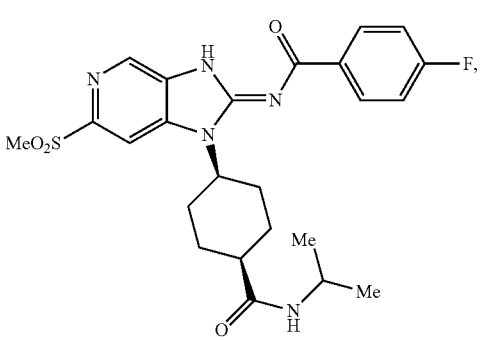
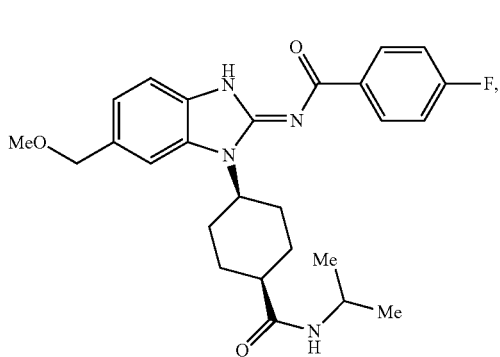
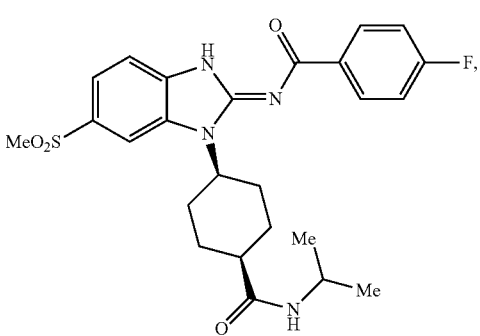
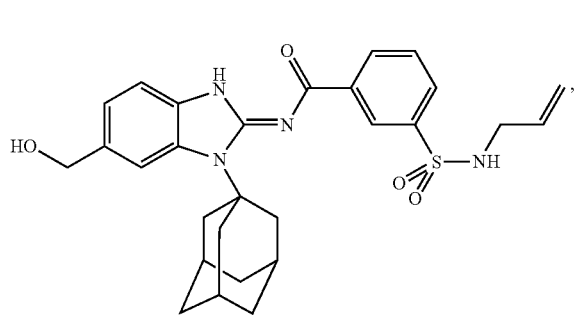
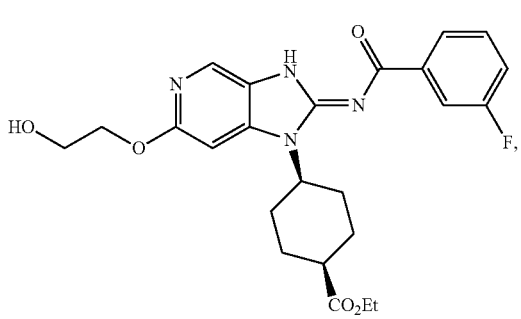

55
-continued
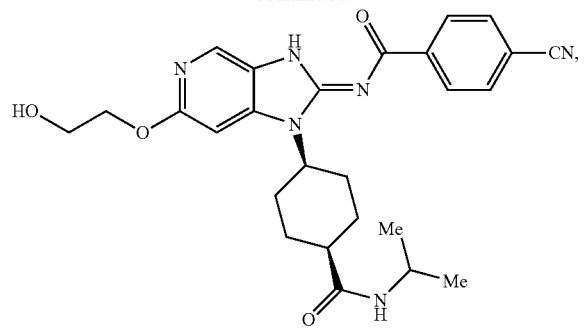
56
-continued
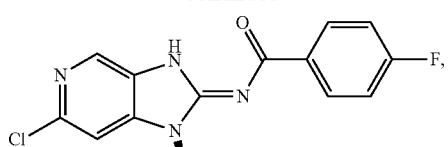
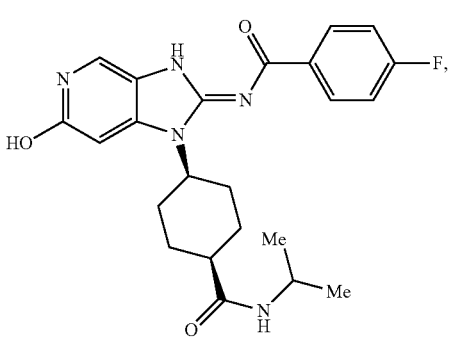
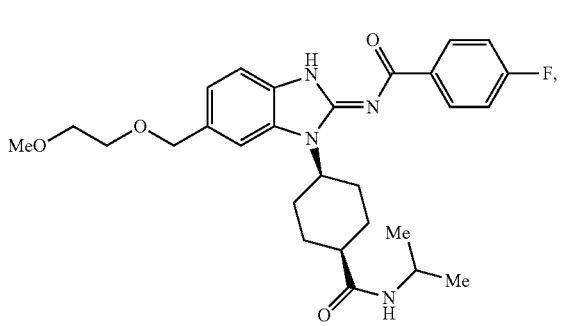
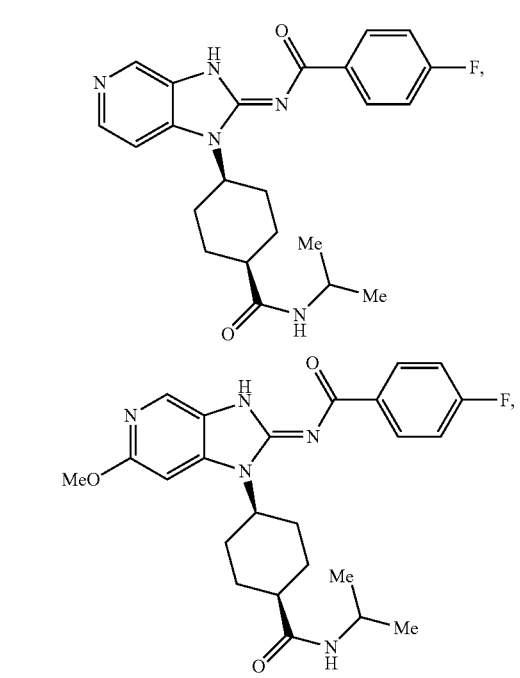
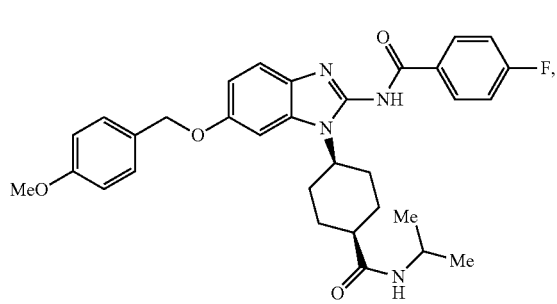
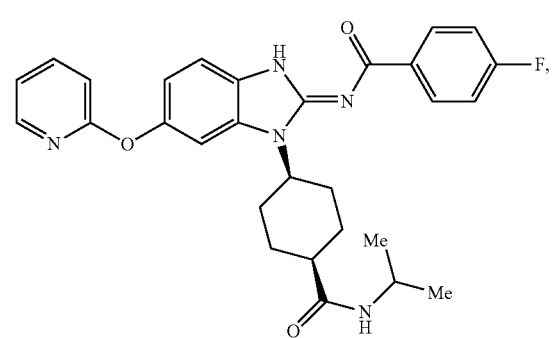

57
-continued
58
-continued
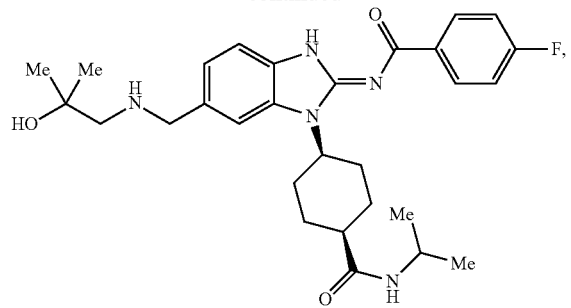
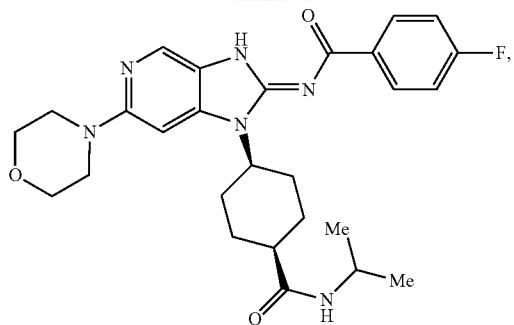
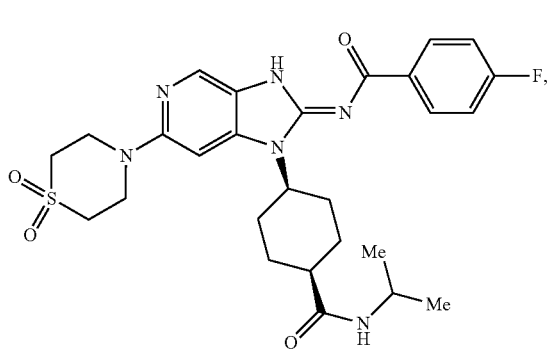
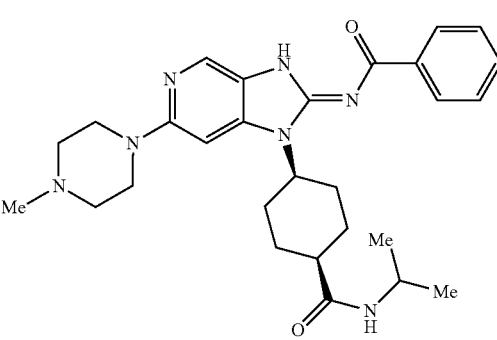
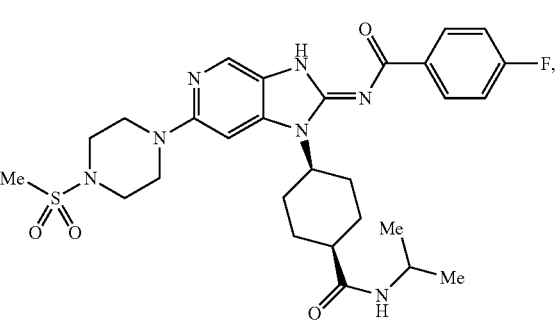
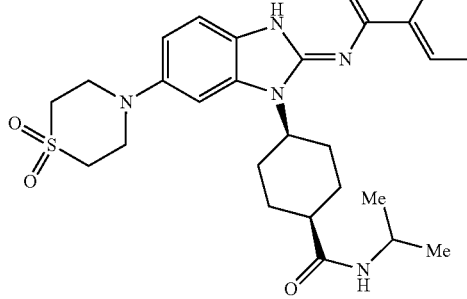

59
-continued
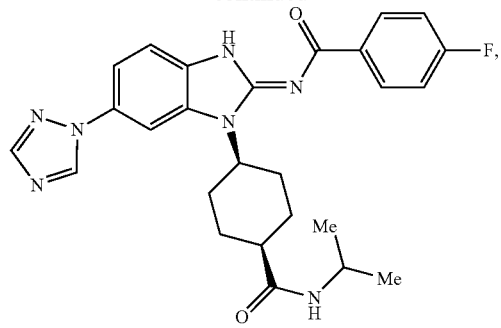
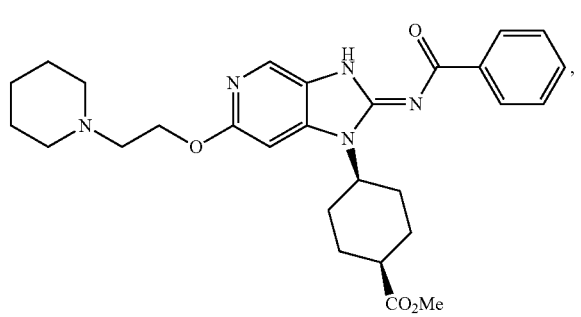
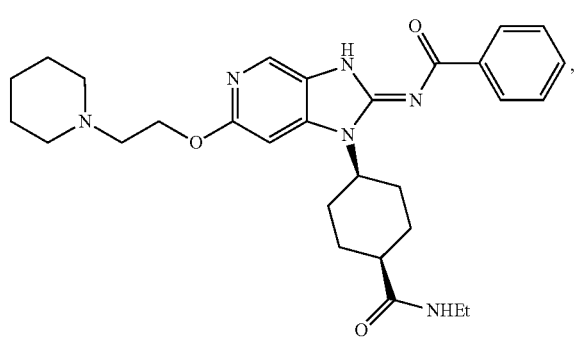
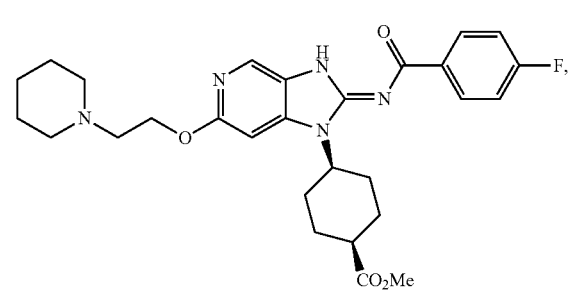
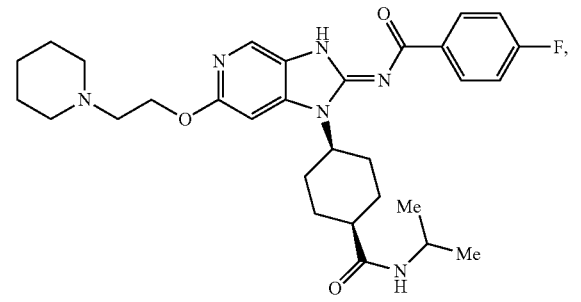
60
-continued
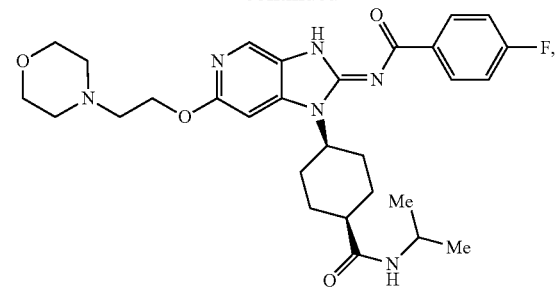
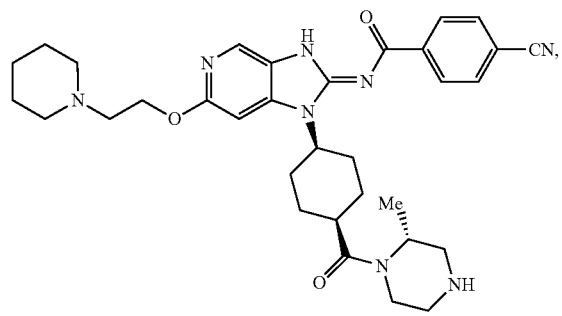
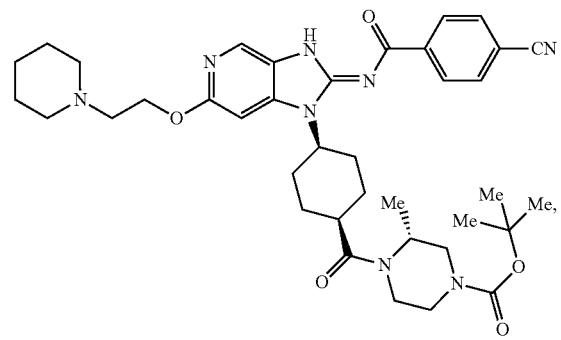
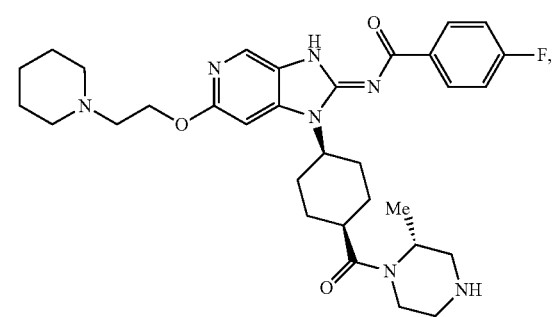
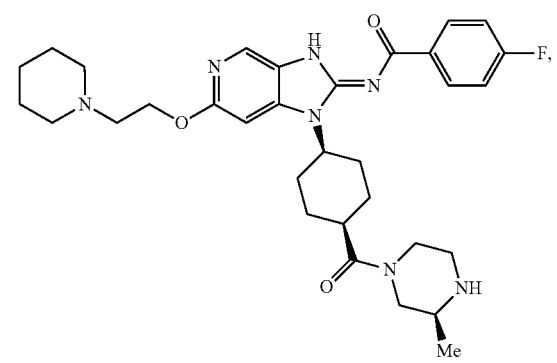

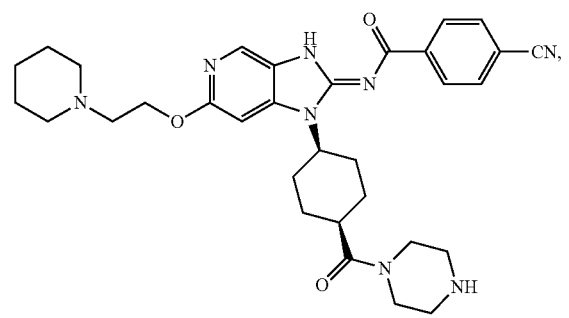
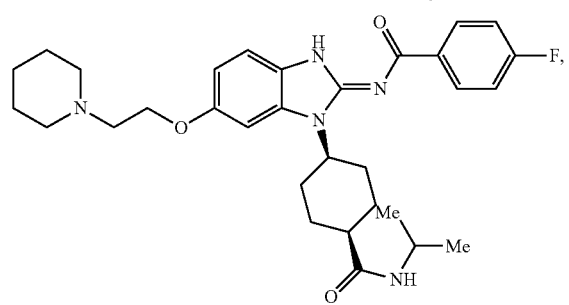
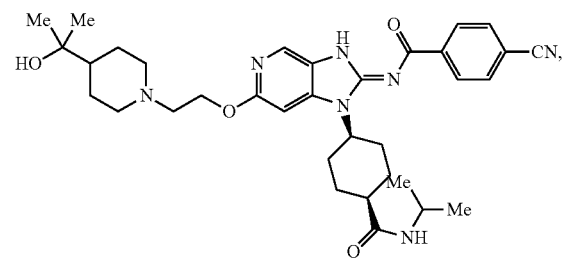
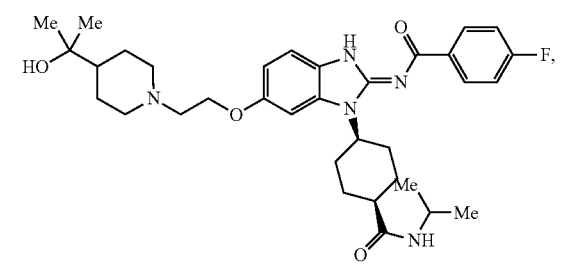
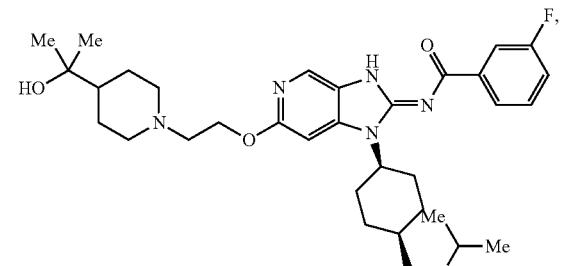
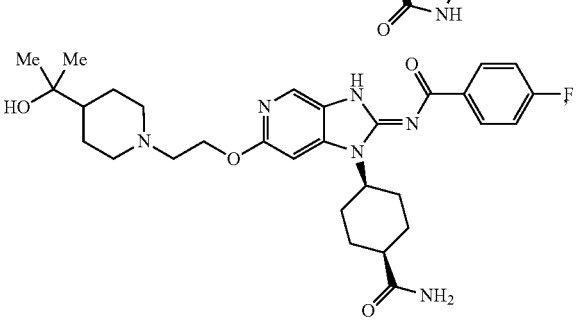
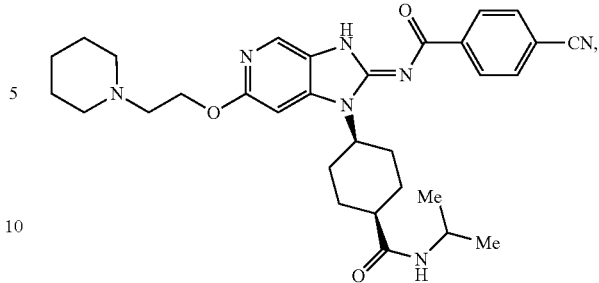
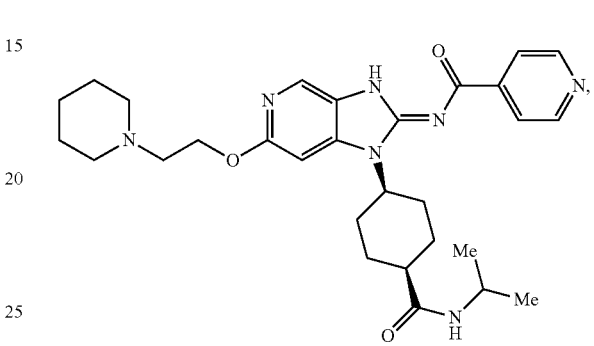
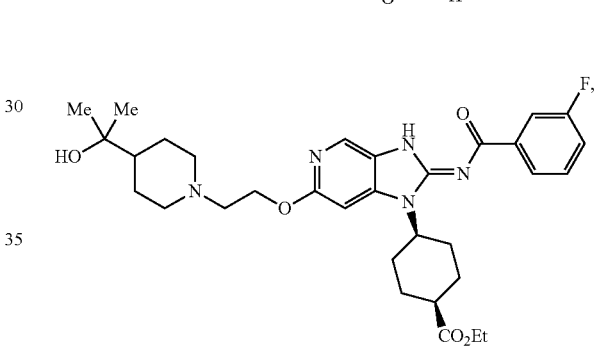
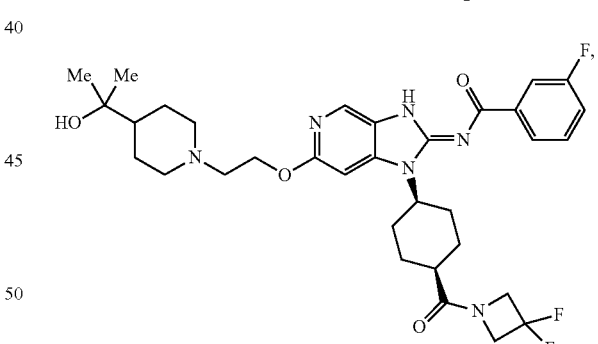
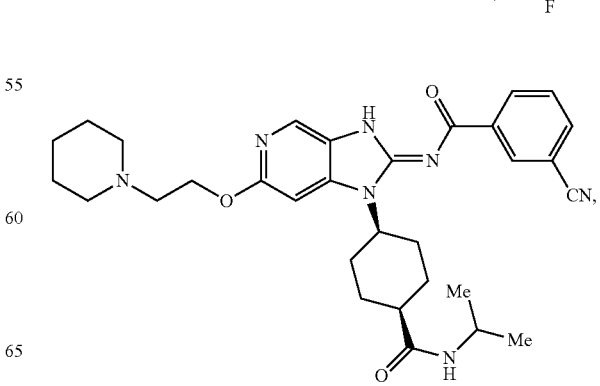

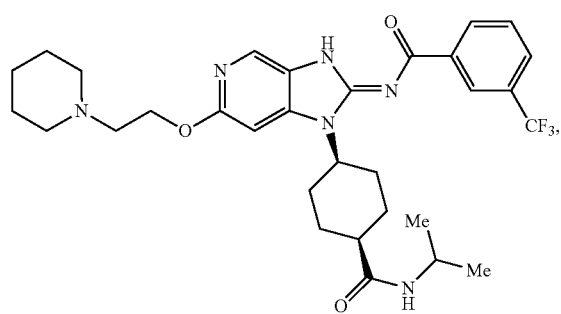
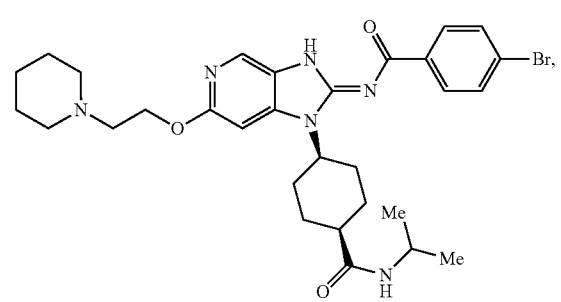
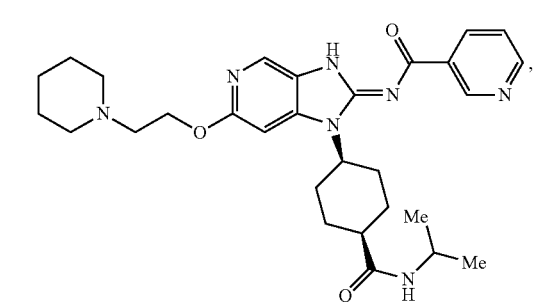
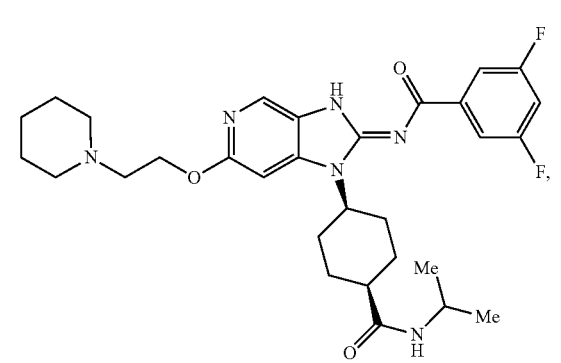
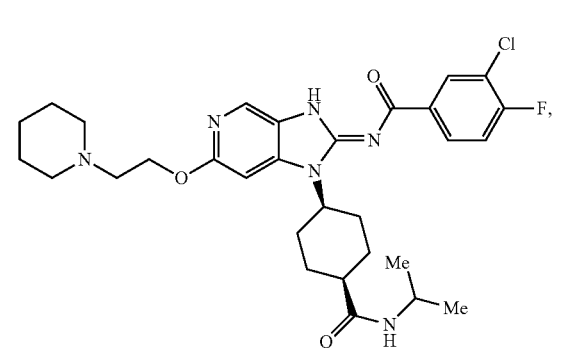
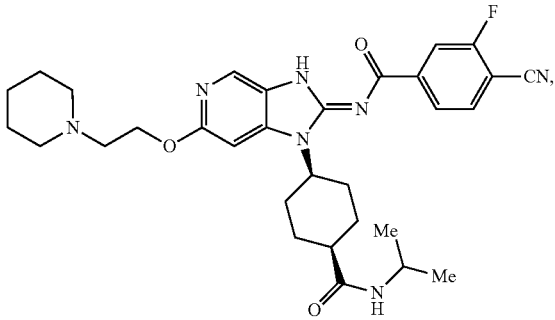
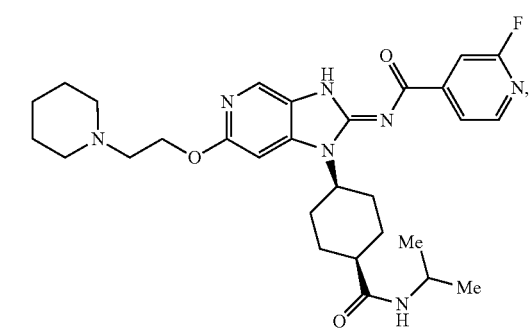
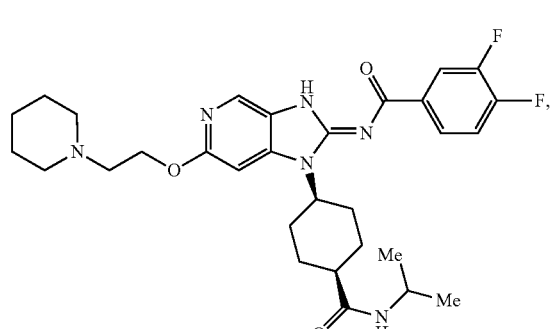
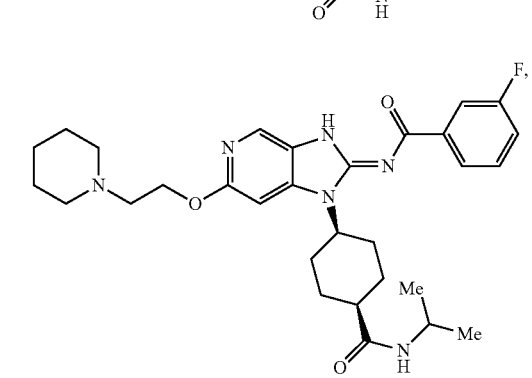
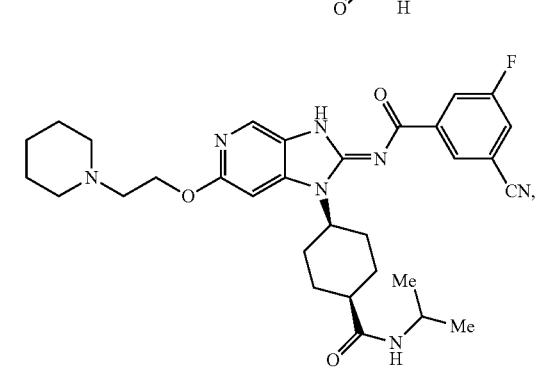

-continued
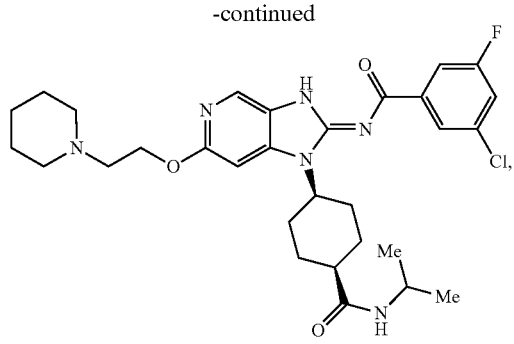
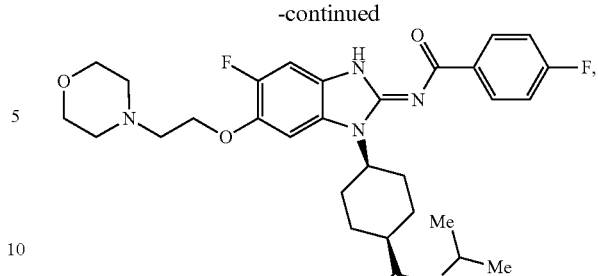
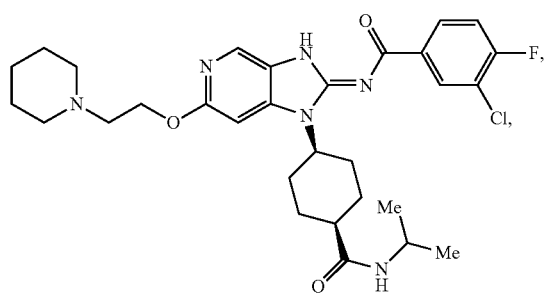
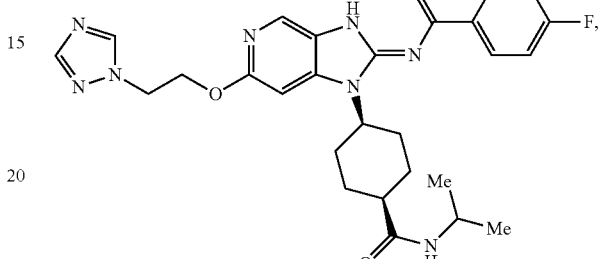
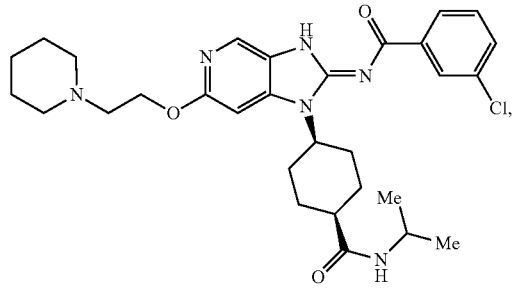
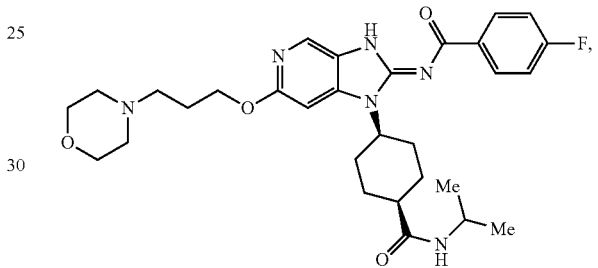
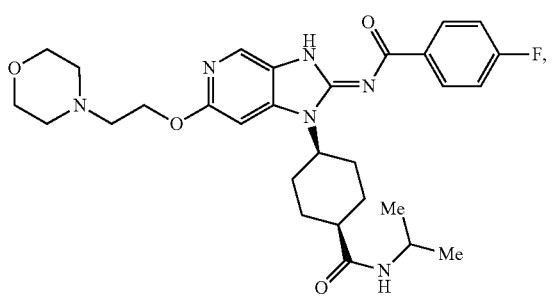
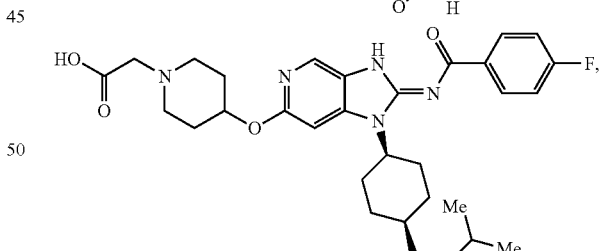
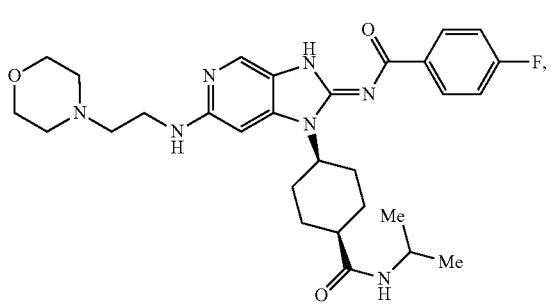
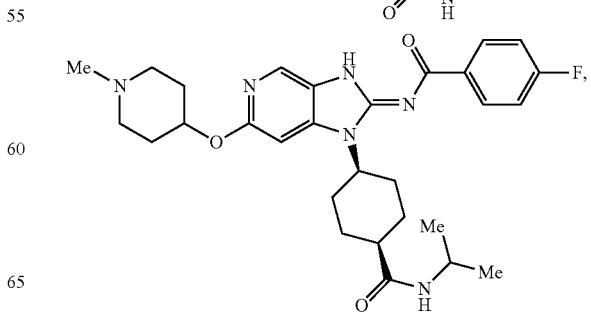

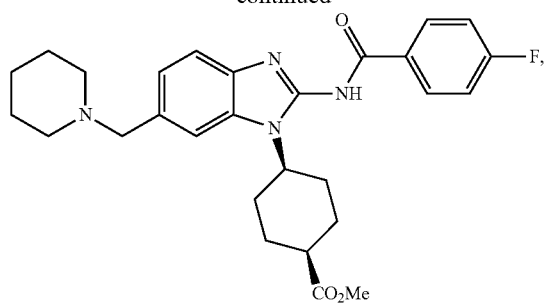
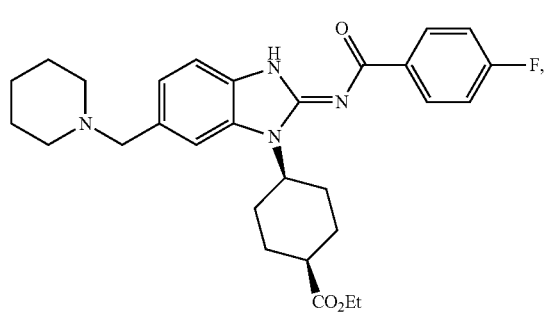
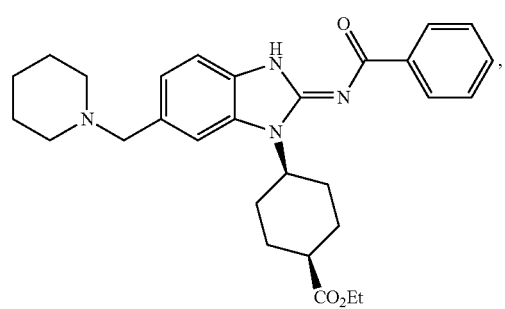
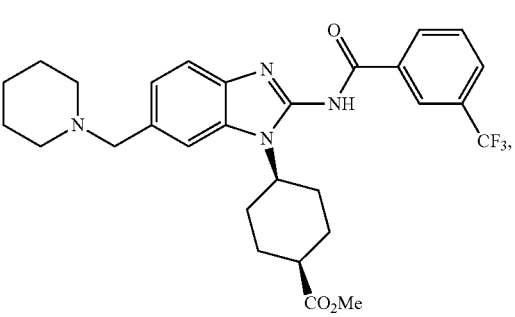
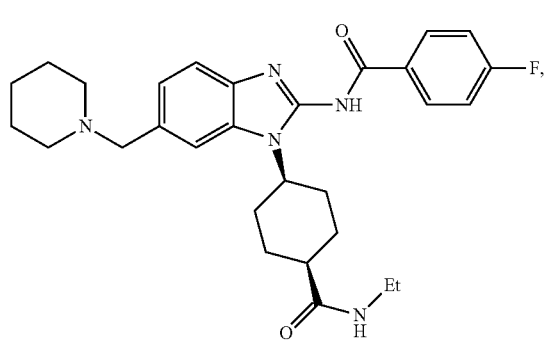
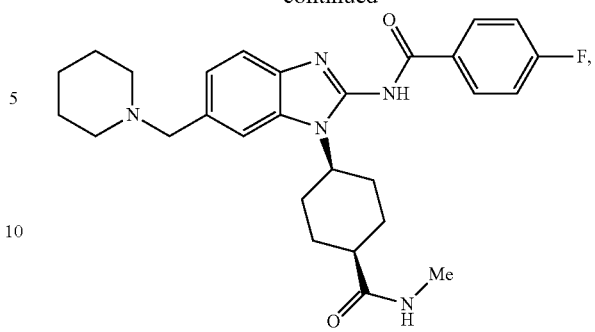
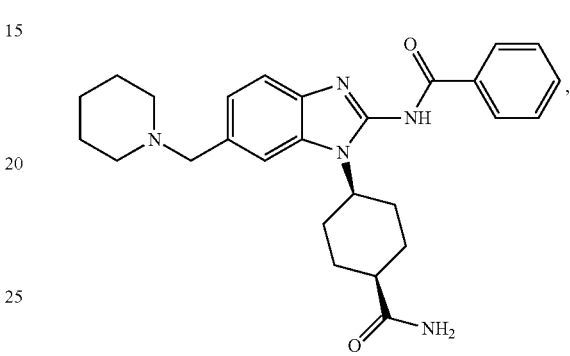
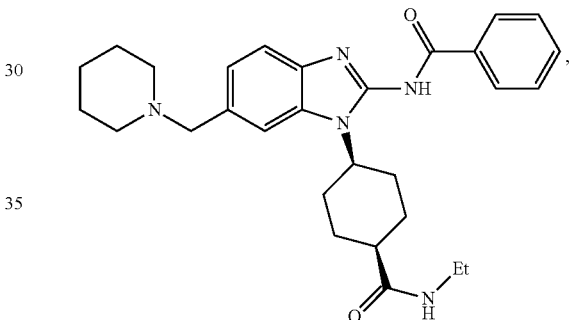
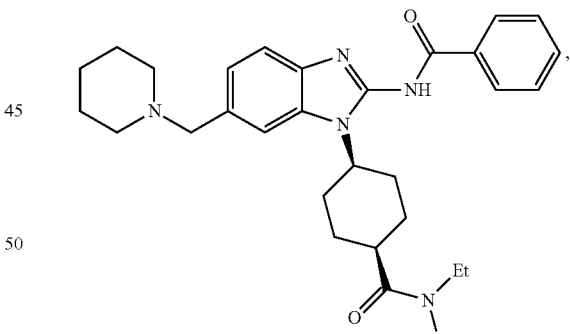
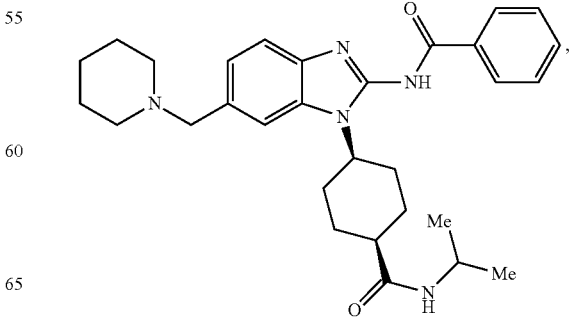

69
-continued
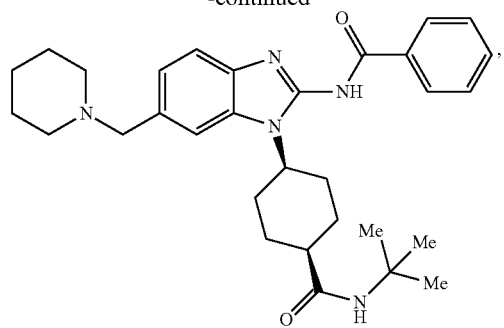
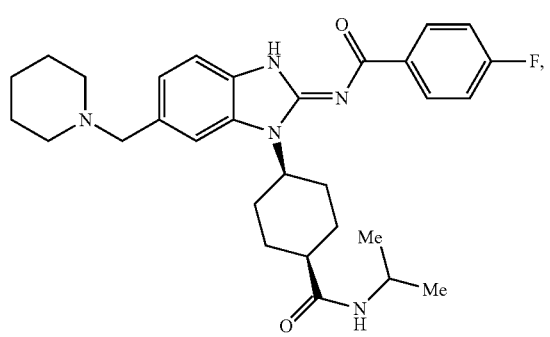
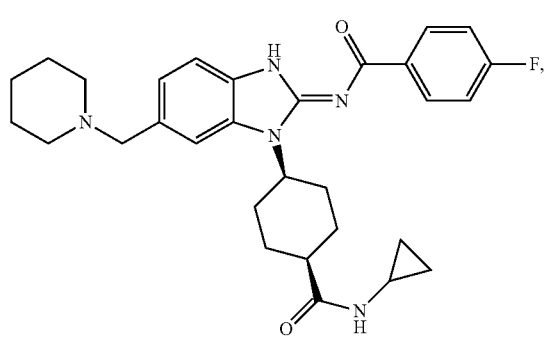
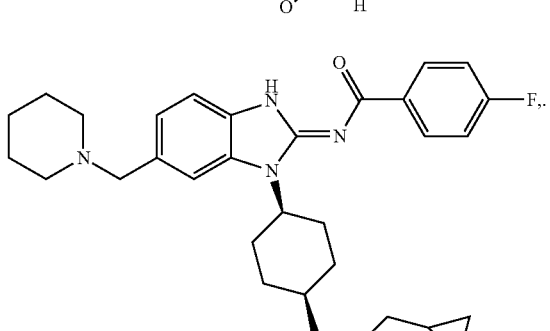
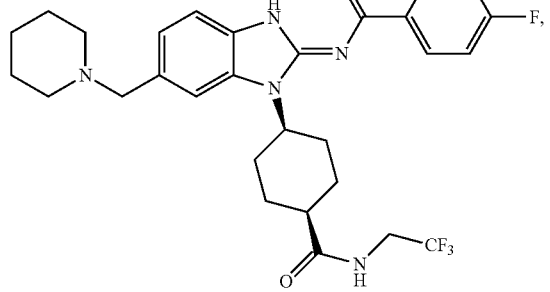
70
-continued
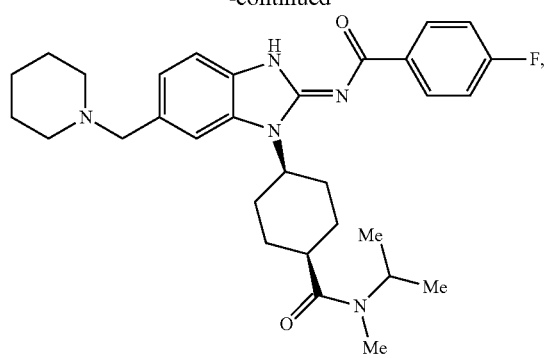
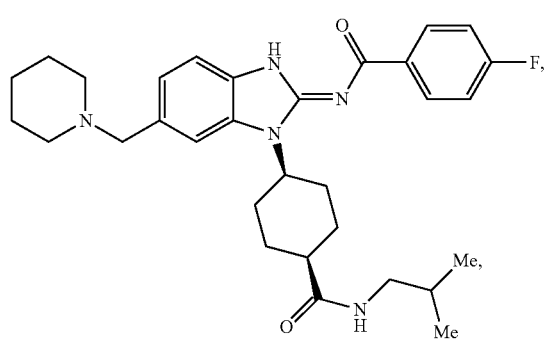
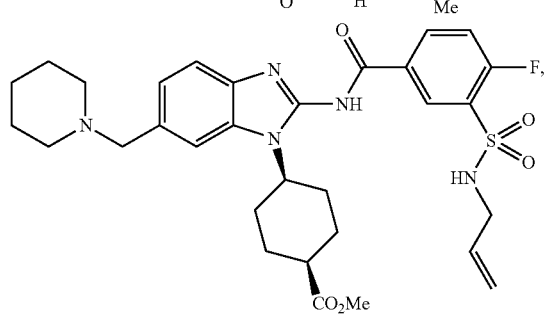
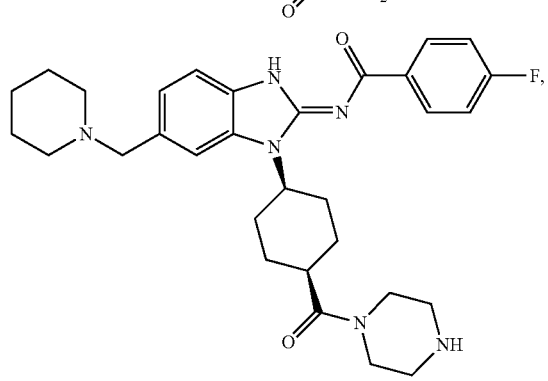

71
-continued
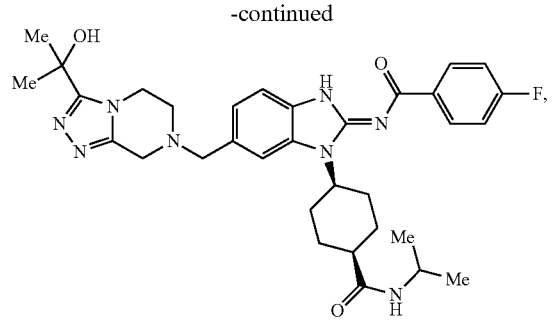
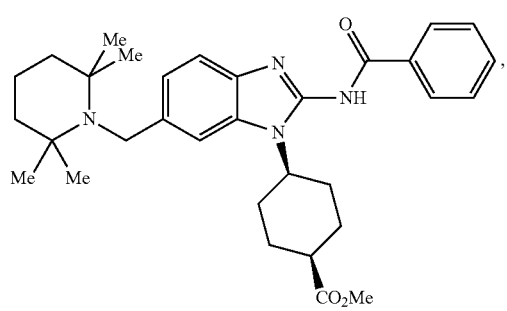
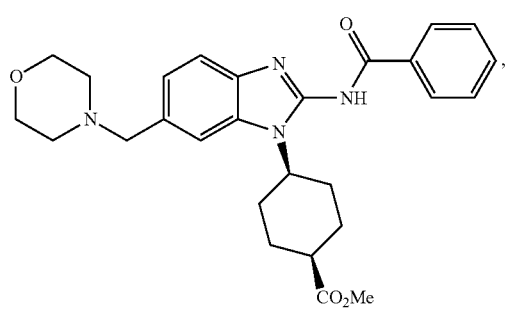
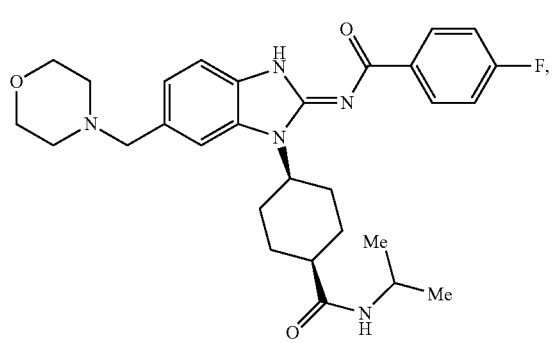
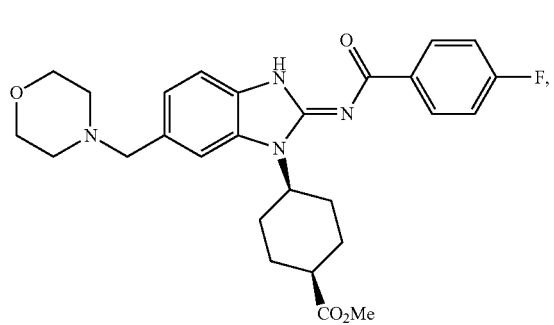
72
-continued
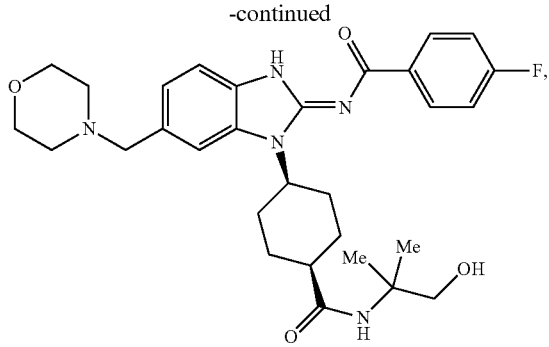
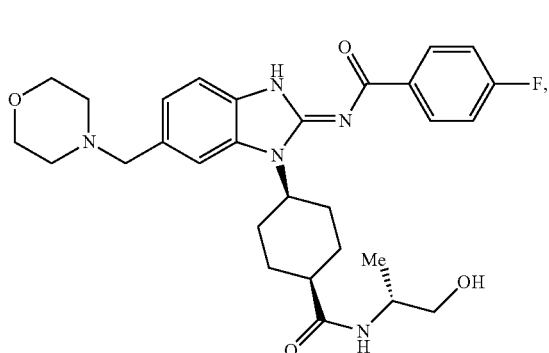
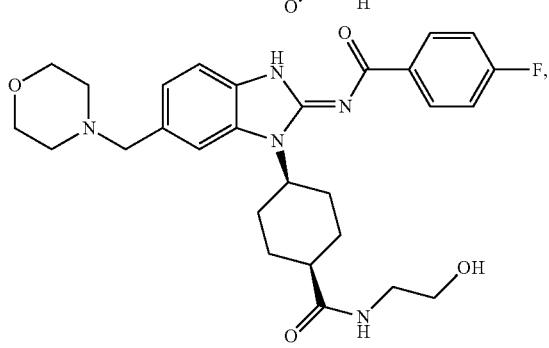
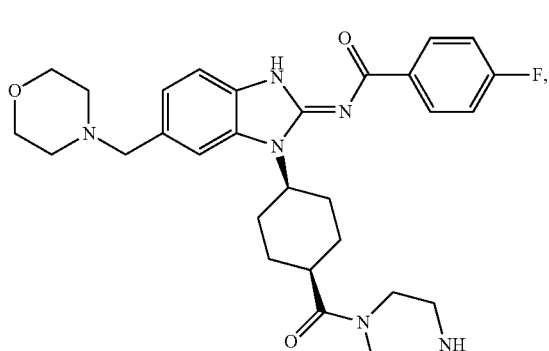
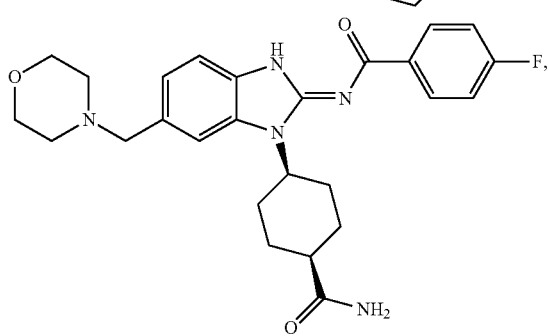

73
-continued
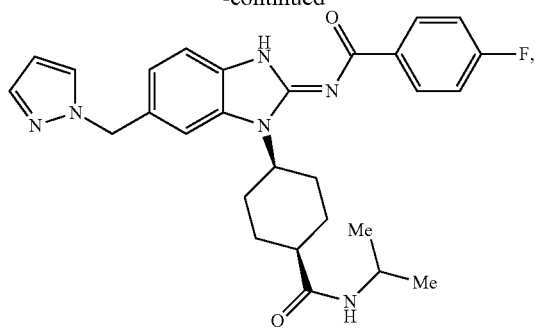
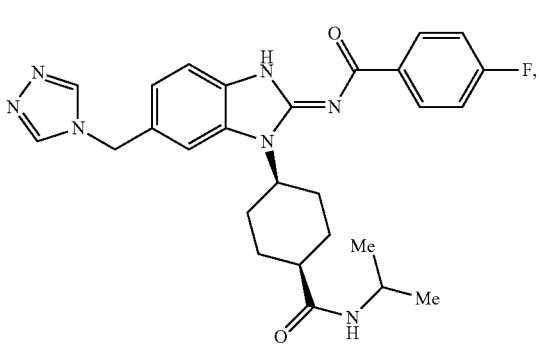
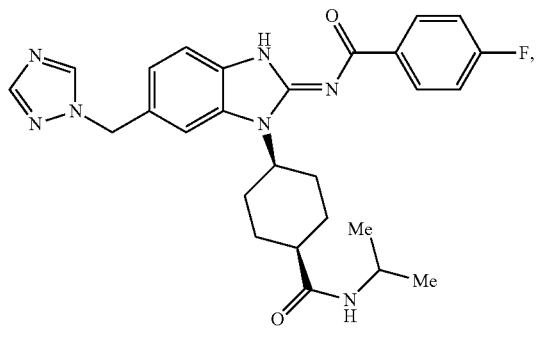
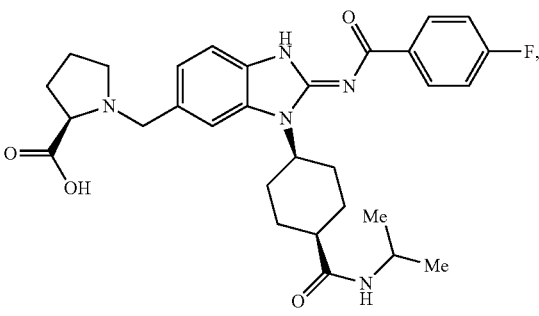
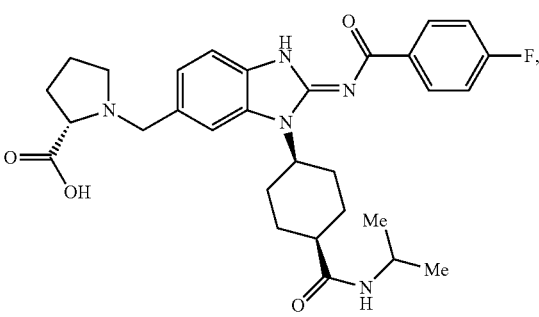
74
-continued
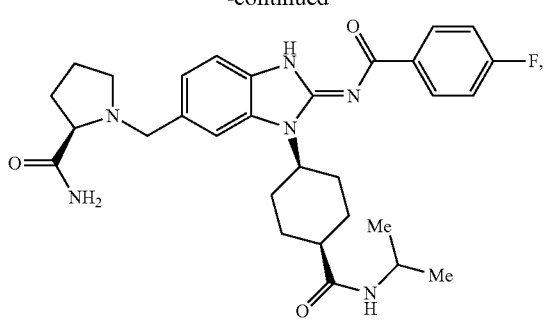
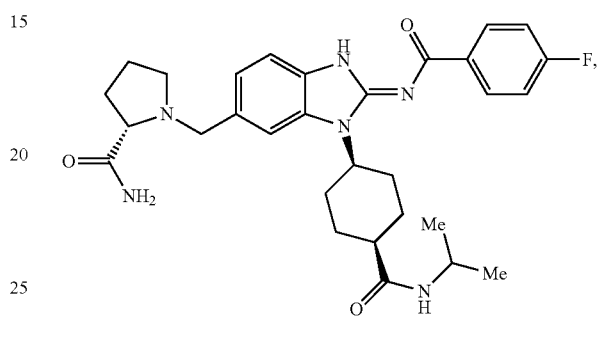
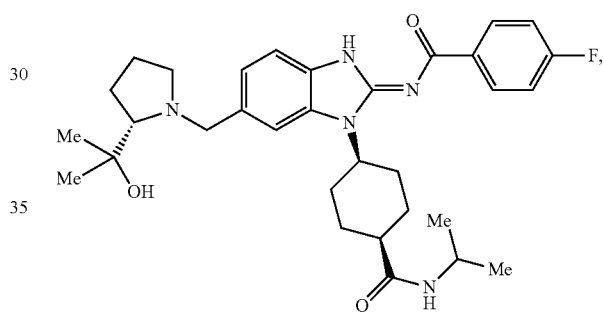
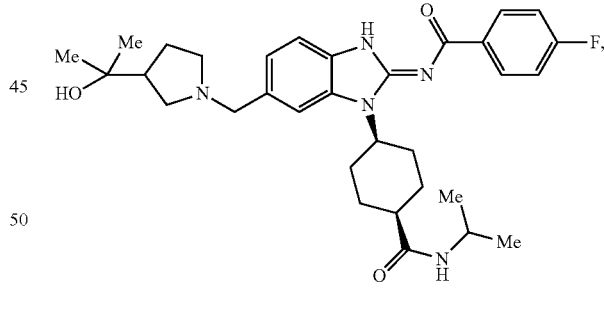
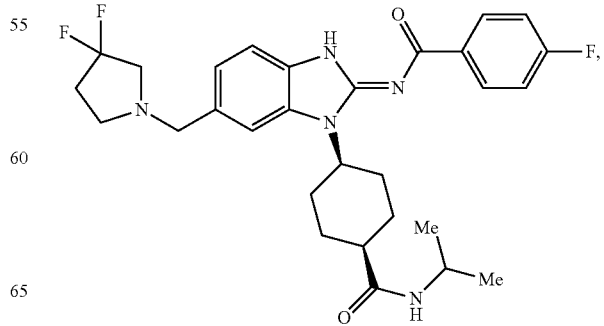

75
-continued
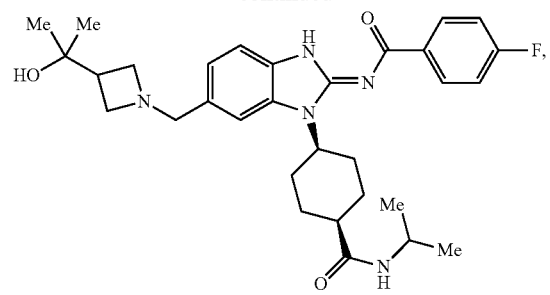
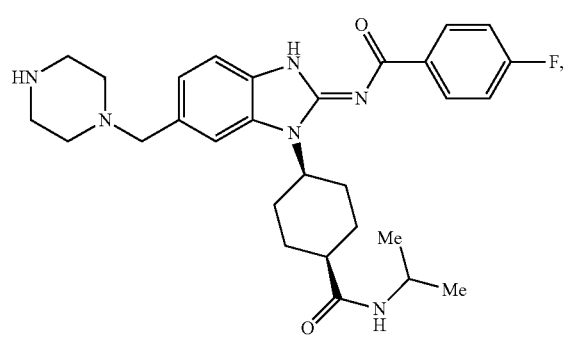
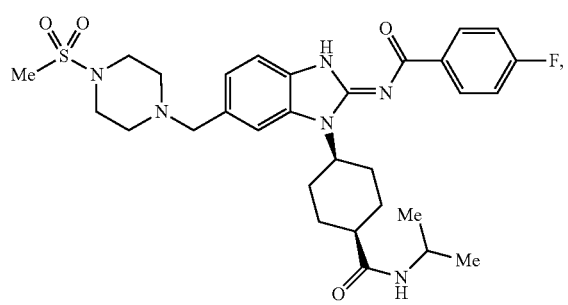
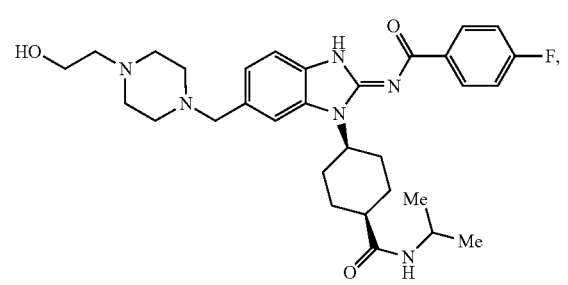
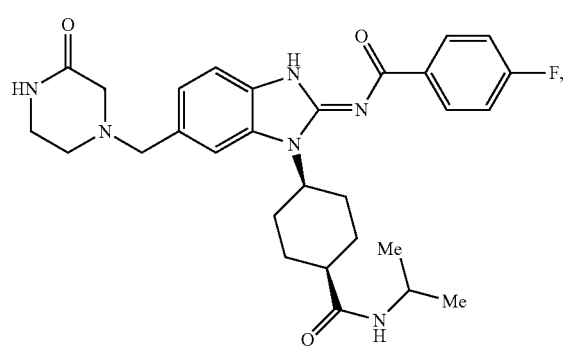
76
-continued
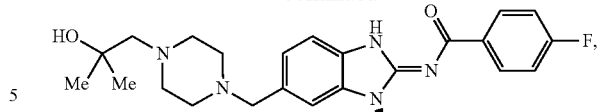
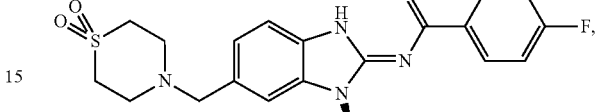

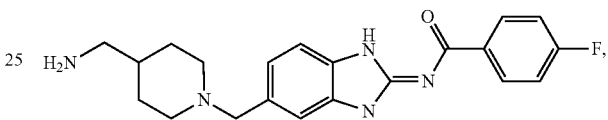
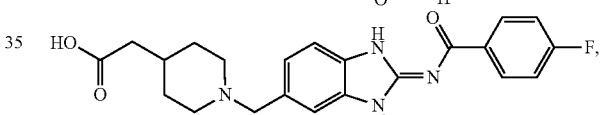

77
-continued
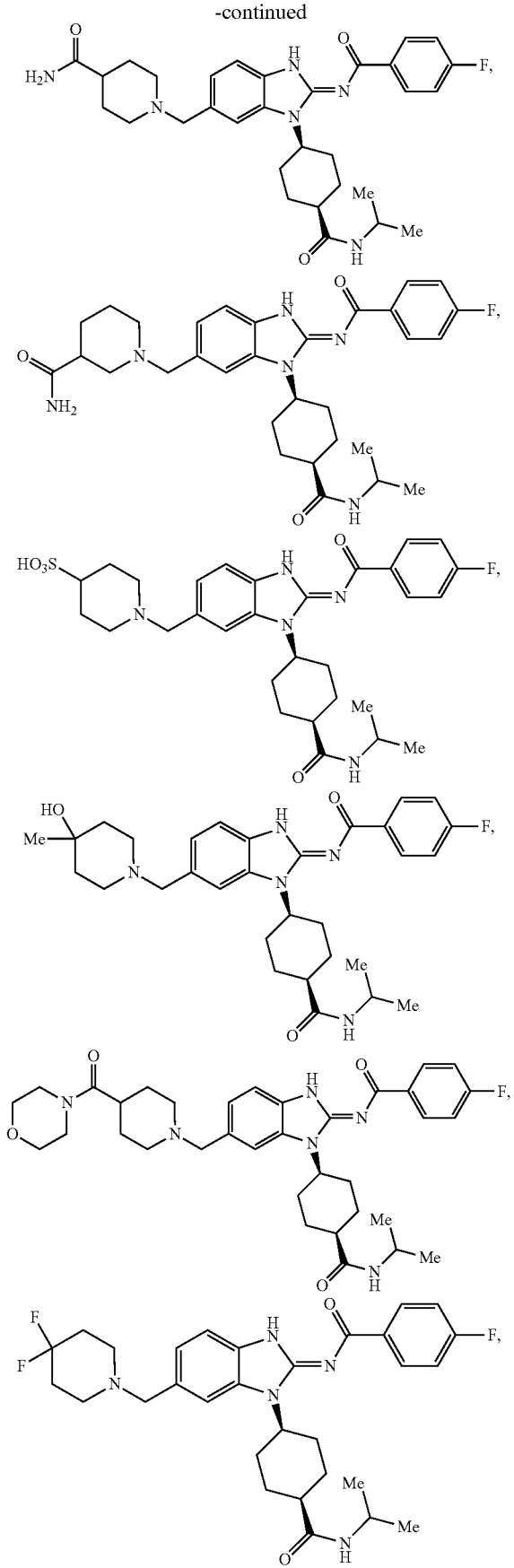
78
-continued
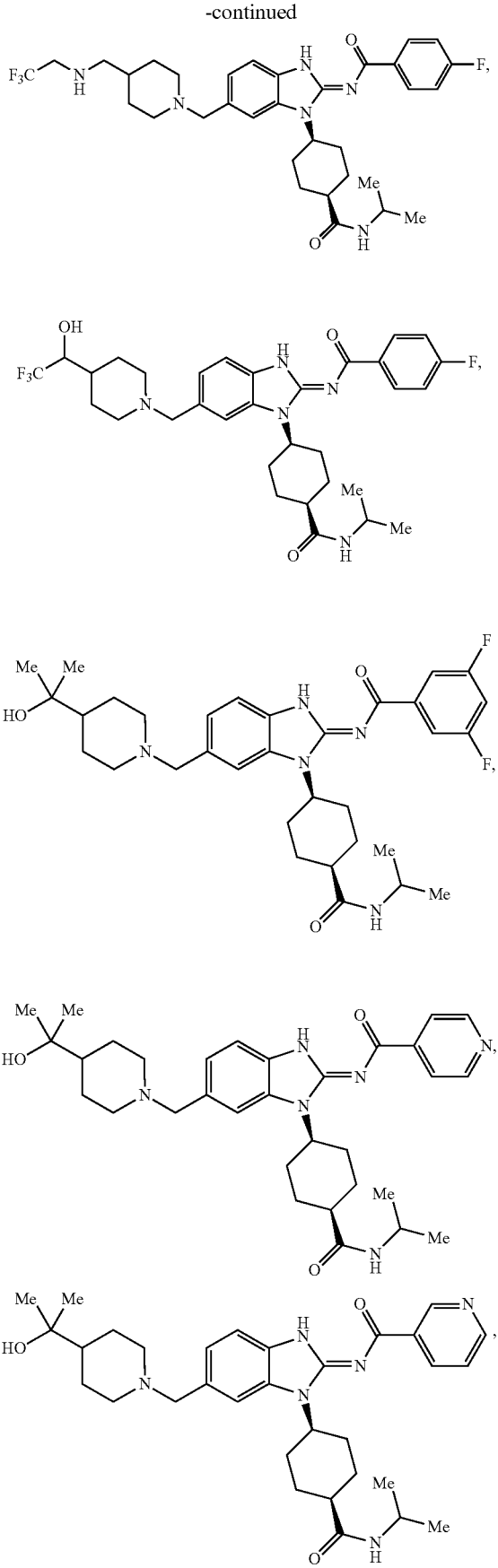

79
-continued
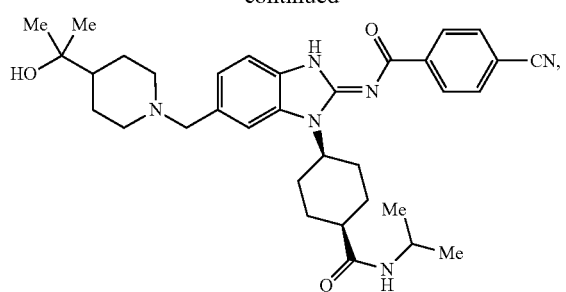
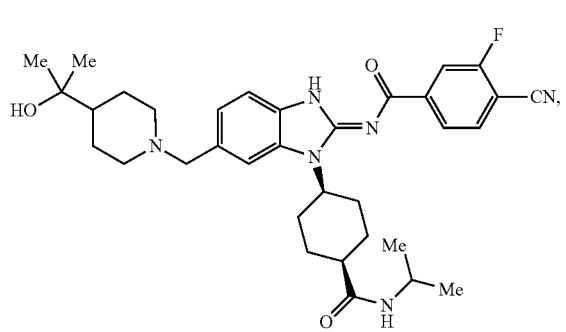
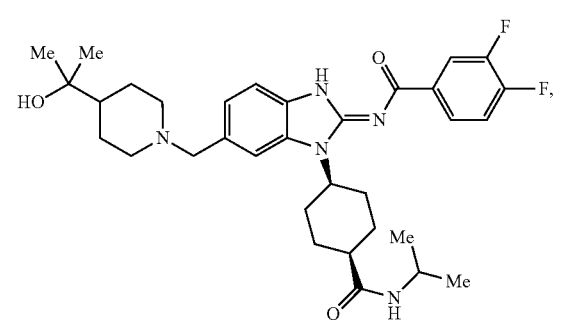
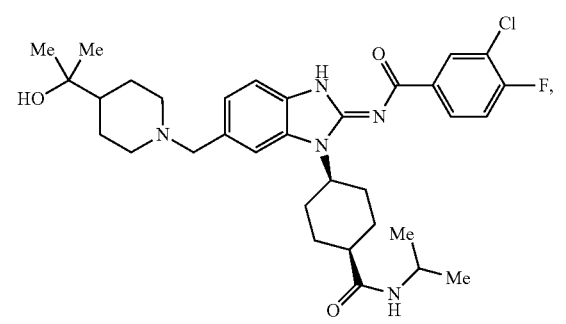
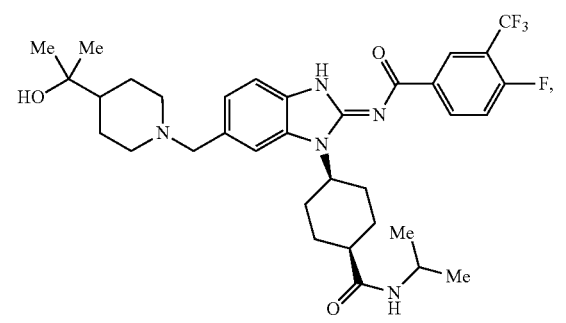
80
-continued
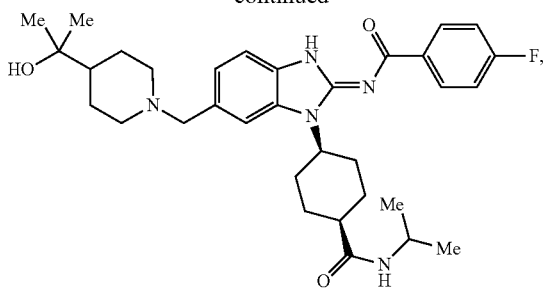
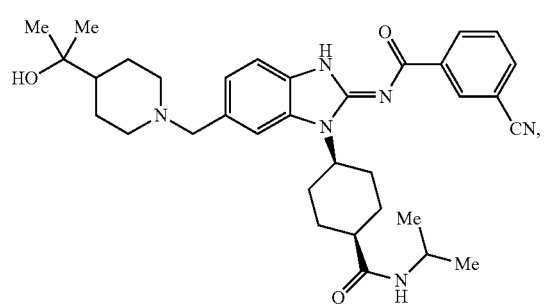
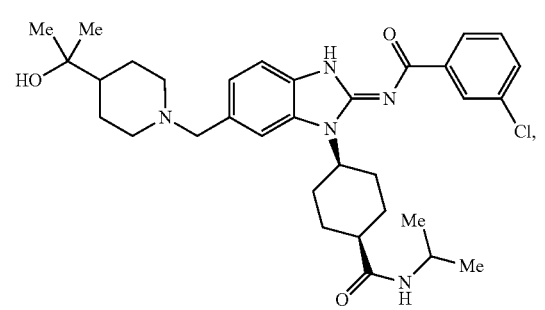
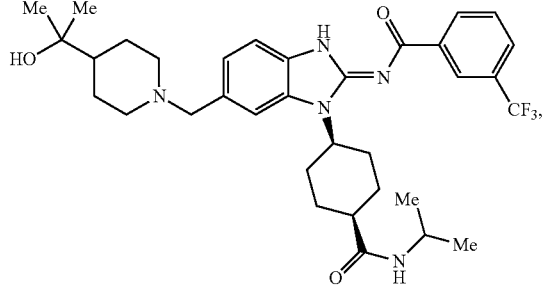
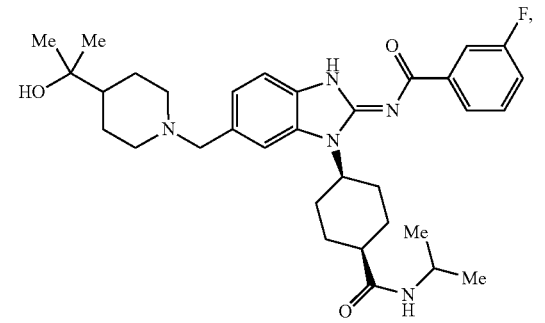

81
-continued
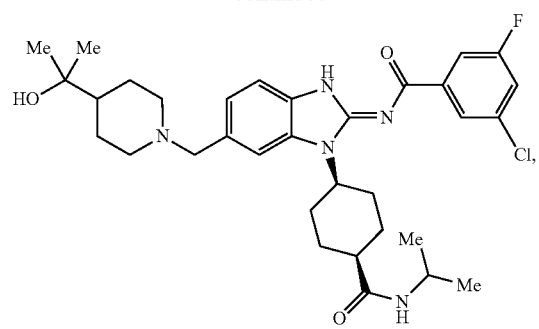
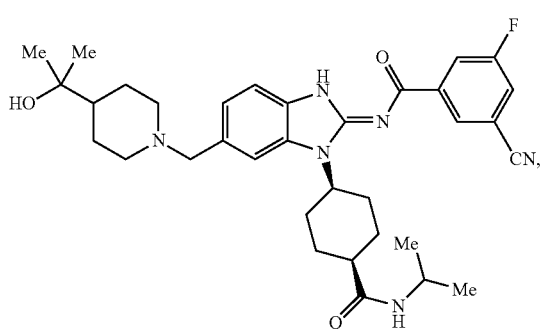
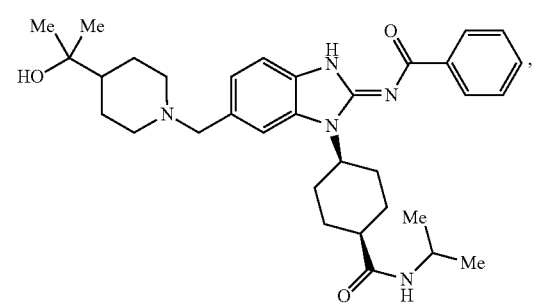
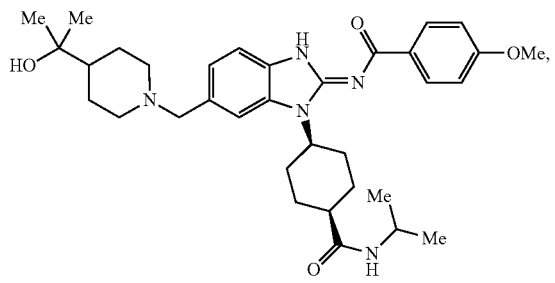
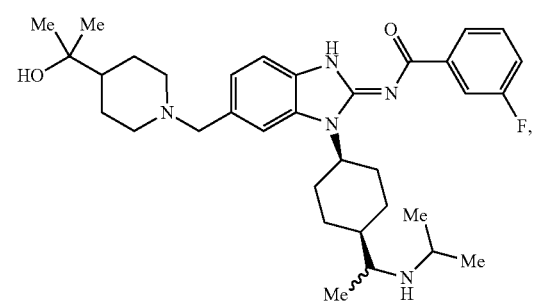
82
-continued
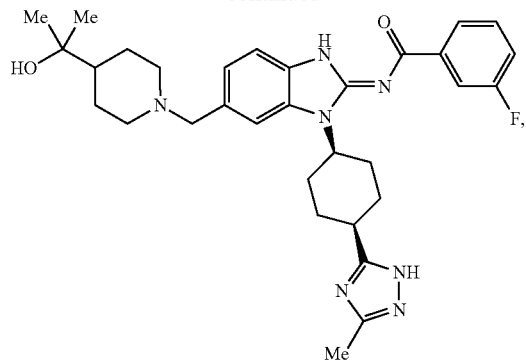
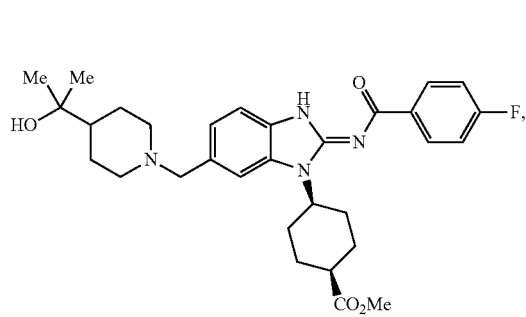
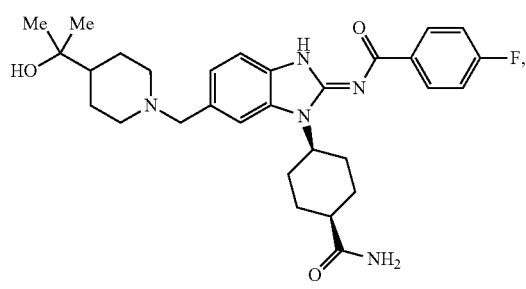
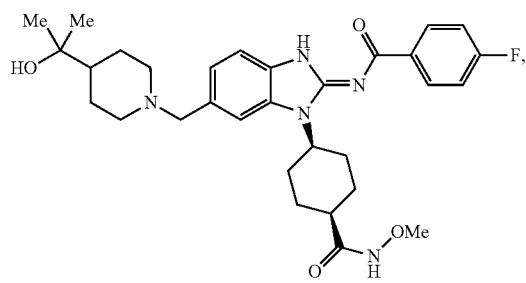
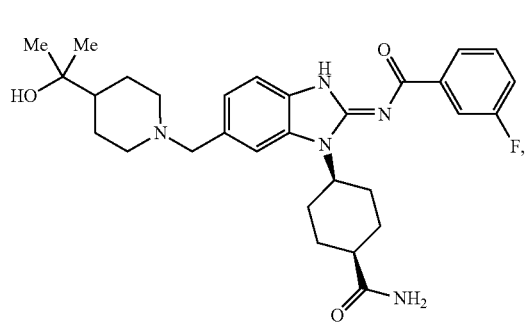

83
-continued

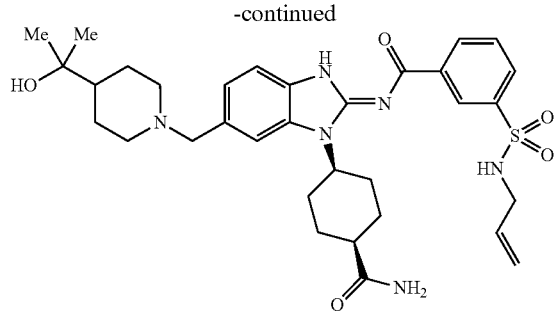

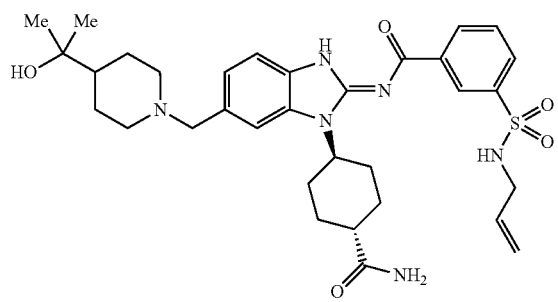

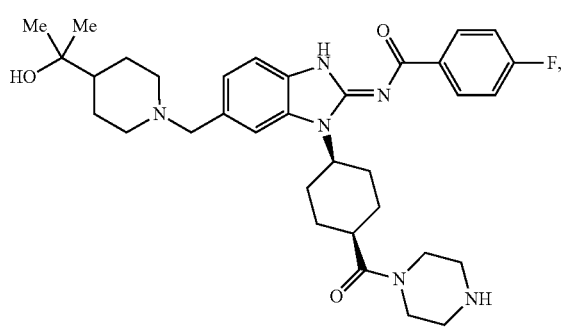

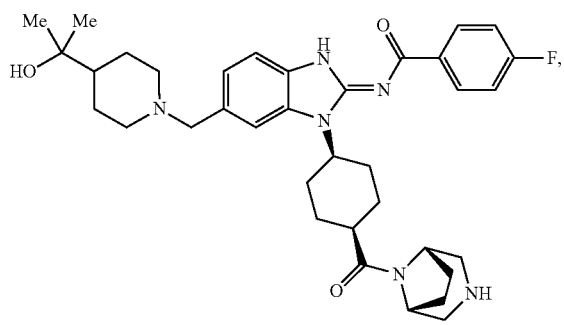

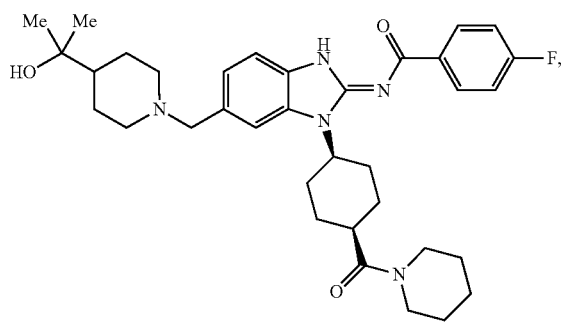

84
-continued

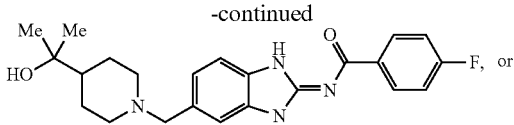

or a pharmaceutically acceptable salt thereof, tautomer thereof, a pharmaceutically acceptable salt of the tautomer, a stereoisomer of any of the foregoing, or a mixture thereof.

In some embodiments of any of those described above, the compound is a pharmaceutically acceptable salt of the compound, a tautomer of the compound, a pharmaceutically acceptable salt of the tautomer, a stereoisomer of any of the foregoing, or is a mixture of any of these. In some such embodiments, the compound is a tautomer. In some such embodiments, the compound is a pharmaceutically acceptable salt of the tautomer. In still other embodiments, the compound is a single stereoisomer whereas in other embodiments, the compound is a mixture of enantiomers or is a mixture of stereoisomers and such a mixture may include equal or unequal amount of specific stereioisomers. In some embodiments, the compound is a racemic mixture of stereoisomers.

In some embodiments, the compound is any one of the Example compounds.

In some embodiments, the compound is a salt. Such salts may be anhydrous or associated with water as a hydrate.

In some embodiments, the compound is a prodrug.

Also provided are pharmaceutical formulations that include at least one pharmaceutically acceptable carrier, excipient or diluent and a therapeutically effective amount of the compound of any of the embodiments described herein. In some such embodiments, the compound is present in an amount effective for the treatment of cancer.

Further provided are pharmaceutical formulations that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. Such methods typically include administering to a subject an effective amount of a compound of any one of the embodiments or a pharmaceutical composition that includes any of the compounds of any of the embodiments. In some such embodiments, the subject has a cancer that expresses an ALK fusion protein. In other such embodiments, the ALK fusion protein is EML4-ALK fusion protein or NPM-ALK fusion protein. In some embodiments, the subject is a human cancer patient, and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC).

In still other embodiments, the invention provides a method of treating a condition where it is desired to inhibit ALK activity. Such methods typically include administering to a subject an effective amount of a compound of any of the embodiments or a pharmaceutical composition that includes a compound of any of the embodiments.

In some embodiments, the compound of any of the embodiments is used in the preparation of a medicament. In some such embodiments, the medicament is for use in treating cancer. In some such embodiments, a medicament is for use in inhibiting ALK. In still other such embodiments, the medicament is for use in treating a cancer that expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein.

In some such embodiments, a compound or pharmaceutical formulation of any of the embodiments is provided for use in treating cancer. In some such embodiments, the cancer expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein. In some embodiments, a compound or pharmaceutical formulation of any of the embodiments is provided for use in treating cancer and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC). In still other embodiments, a compound or pharmaceutical formulation of any of the embodiments is provided for use in inhibiting ALK or for use in treating a disease or condition wherein inhibition of ALK is desired.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, ALK KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, JAK, or a CDK complex. In some such embodiments, the disorder is mediated by a JAK family member such as JAK2. In other such embodiments, the disorder is mediated by ALK. In some such embodiments, the administration of the compound or pharmaceutical composition produces selective inhibition of ALK. In some embodiments, the disorder is cancer. The present invention thus provides methods for treating or preventing ALK-mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCl (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVEC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, c-met inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

The compounds of the invention can be prepared using the general synthetic routes shown below in Scheme 1, Scheme 2, and Scheme 3 and described more fully in the Examples.

Scheme 1

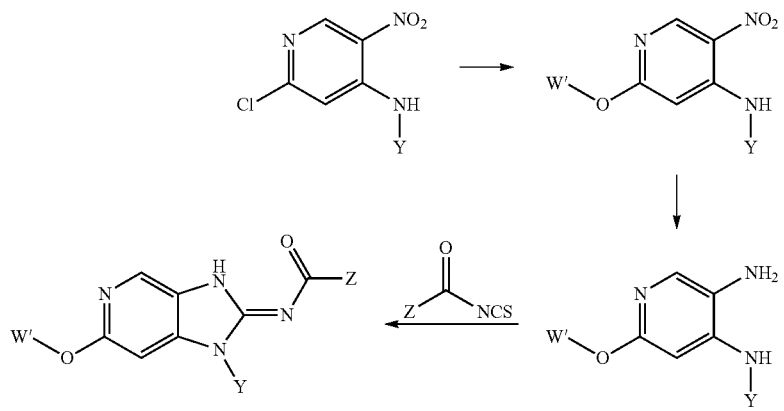

Scheme 2

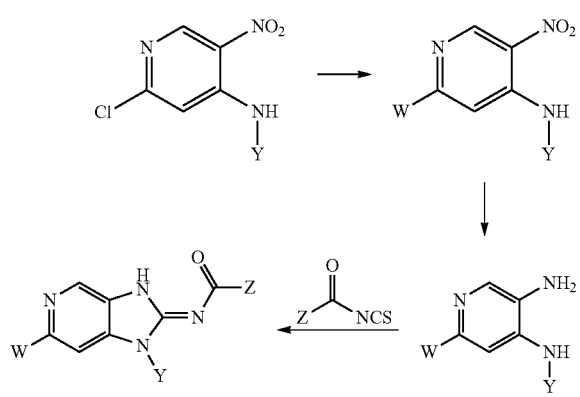

As shown in Schemes 1 and 2, Y-substituted 4-amino-2-chloro-5-nitropyridines provide excellent access to compounds of Formula I where X is N. As shown in Schemes 1 and 2, nucleophiles, such as 2-(piperidin-1-yl)ethanol (Example 20) or morpholine (see Example 222) can be reacted with Y-substituted 4-amino-2-chloro-5-nitropyridine compounds to displace the chlorine group and form the appropriate bond to a selected W group. Reduction of the nitro group to an amine using hydrogenation conditions followed by reaction with a selected isothiocyanate such as 4-fluorobenzoyl isothiocyanate (see Example 222) to form the five-membered ring and provide the appropriate Z group allows ready access to the compounds of Formula I where X is N.

Scheme 3

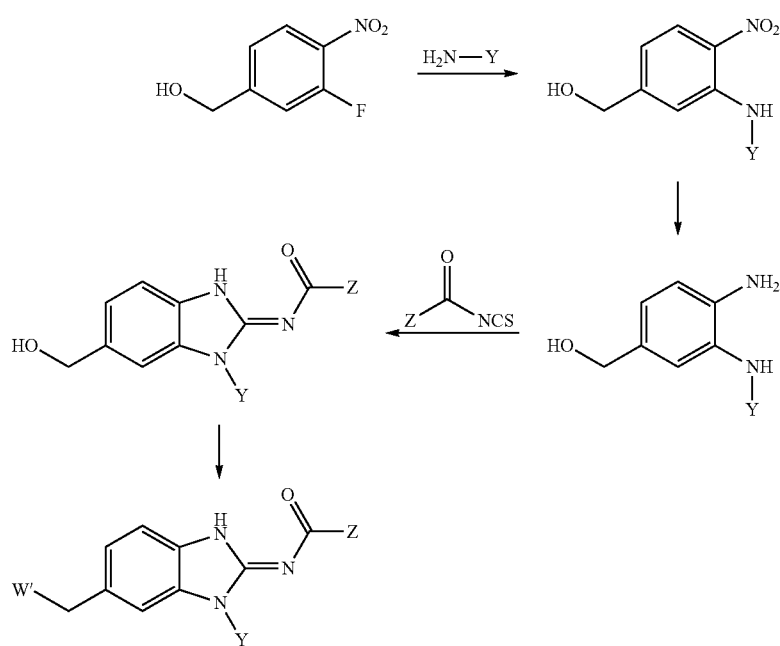

As shown in Scheme 3, (3-fluoro-4-nitrophenyl)methanol provides a convenient starting material for the preparation of various compounds of Formula I where X is C. For example, an amine nucleophile bearing a selected Y group such as N-(cis-4-aminocyclohexyl)isobutyramide (see Example 227) may be reacted with (3-fluoro-4-nitrophenyl)methanol to form the Y substituted (3-amino-4-nitrophenyl)methanol compound. Reduction of the nitro group to form the amino compound followed by reaction with an appropriate isothiocyanate such as 4-benzoyl isothiocyanate (see Example 227) forms the five-membered ring and adds the desired Z group to provide a useful hydroxymethyl compound that can be readily converted to various compounds of Formula I. For example, the hydroxymethyl compound may be converted to a reactive chloromethyl intermediate by reaction with thionyl chloride. The chloromethyl intermediate may then be reacted with an appropriate nucleophile such as 2-(piperidin-4-yl)propan-2-ol (see Example 227) to obtain the compound of Formula I.

Modification of the above Schemes can be used to synthesize numerous compounds of the invention as will be apparent to those skilled in the art.

The invention is further described by reference to the following examples, which are intended to exemplify the claimed invention but not to limit it in any way.

EXAMPLES

Unless otherwise stated, all starting material compounds and reagents were obtained from commercial sources, including, but not limited to, Sigma Aldrich, Alfa Aesar, Oakwood, TCI America, Fluka, Frontier, AstaTech, Strem, Maybridge, Ark Pharma, Acros Organics, Combi-Blocks, Lancaster, Enamine, Matrix, and JRD Fluorochemicals, or were prepared using known synthetic procedures, or were prepared using the methods and experimental procedures described herein.

The following Abbreviations are used to refer to various reagents and solvents:
ACN Acetonitrile
AcOH Acetic Acid
CDI Carbonyldiimidazole
DBU 1,8-Diazabicycloundec-7-ene
DCE Dichloroethane
DCM Dichloromethane
DIPEA Diisopropylethylamine
DMF N,N-Dimethylformamide
DMSO Dimethylsulfoxide
EDC 1-(3-Dimethylaminopropyl)-3-ethylcarbodiimide hydrochloride
EtOAc Ethyl Acetate
EtOH Ethanol
HATU 0-(7-Azabenzotriazol-1-O—N,N,N',N'-tetramethyluronium hexafluorophosphate
HCl Hydrochloric acid
HOBT 1-Hydroxybenzotriazole
IPA Isopropanol
MeOH Methanol
NaHCO$_3$ Sodium bicarbonate
NaOH Sodium hydroxide
NH$_4$Cl Ammonium chloride
NMP N-methyl-2-pyrrolidone
NMR Nuclear Magnetic Resonance Spectroscopy
PS Polystyrene
RT Room Temperature
TEA Triethylamine
TBAF Tetrabutylammonium fluoride
THF Tetrahydrofuran
TFA Trifluoroacetic acid

EXAMPLES

Example 1

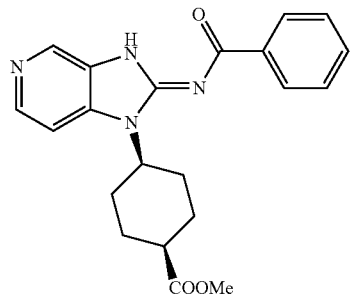 [SMILES: COC(=O)[C@H]1CC[C@@H](n2/c(=N/C(=O)c3ccccc3)[nH]c3cnccc32)CC1]

cis-Methyl 4-((E)-2-(benzoylimino)-2,3-dihydro-1H-imidazo[4,5-c]pyridin-1-yl)cyclohexanecarboxylate

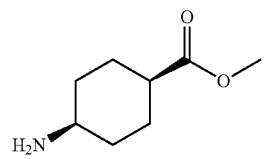

Step A: cis-Methyl 4-aminocyclohexanecarboxylate

A resealable pressure bottle was charged with cis-4-aminocyclohexanecarboxylic acid (10 g, 69.8 mmol), MeOH (100 mL), and sulfuric acid (7.45 mL, 140 mmol). The vessel was sealed and the mixture stirred at 80° C. for 24 hours. The mixture was cooled to 0° C. via an ice bath and made basic with NH$_4$OH to a pH of approximately 10. The aqueous layer was extracted with DCM (4×50 mL) and the organic layers combined, dried over sodium sulfate and concentrated to afford cis-methyl 4-aminocyclohexanecarboxylate (9 g, 82% yield) as a colorless oil. MS m/z=158.2 [M+H]. Calc'd for C$_8$H$_{15}$NO$_2$: 157.1.

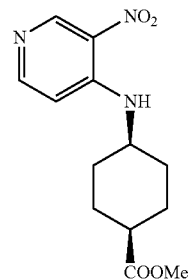

Step B: cis-Methyl 4-(3-nitropyridin-4-ylamino)cyclohexanecarboxylate

A round bottom flask under nitrogen atmosphere was charged with 4-chloro-3-nitropyridine (1.65 g, 10.41 mmol), cis-ethyl 4-aminocyclohexanecarboxylate (2.454 g, 15.61 mmol), and ACN (26 mL). To the mixture was added DIPEA (3.63 mL, 20.81 mmol). The resulting mixture was stirred at 60° C. for 17 hours. The reaction was stopped, cooled to RT and diluted with water (20 mL) and DCM (50 mL). The layers were separated, and the organic layer was collected, dried over sodium sulfate and concentrated to afford an orange oil. The oil was purified by silica gel chromatography to afford the title compound (2.2 g, 76% yield) as a bright yellow solid. MS m/z=280.2 [M+H]. Calc'd for $C_{13}H_{17}N_3O_4$: 279.1.

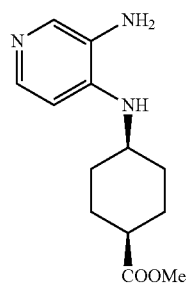 [SMILES: COC(=O)[C@H]1CC[C@@H](Nc2ccncc2[N+](=O)[O-])CC1]

Step C: cis-Methyl 4-(3-aminopyridin-4-ylamino)cyclohexanecarboxylate

A round bottom flask under nitrogen atmosphere was charged with cis-methyl 4-(3-nitropyridin-4-ylamino)cyclohexanecarboxylate (1.1 g, 3.94 mmol) and Pd/C (10% wt) (0.419 g, 0.394 mmol). EtOH (16 mL) was added, and the reaction mixture was purged with nitrogen 3 times. A $H_2$-filled balloon was attached to the top of the flask, and the mixture stirred at RT for 2 hours. The reaction mixture was diluted with EtOH and filtered through Celite® brand filter aid. The pad was washed with DCM (50 mL), EtOH (50 mL), and MeOH (50 mL). The filtrate was concentrated to dryness to afford cis-methyl 4-(3-aminopyridin-4-ylamino)cyclohexanecarboxylate as a purple oil. (0.9 g, 92.0% yield). MS m/z=250.2 [M+H]. Calc'd for $C_{13}H_{19}N_3O_2$: 249.2.

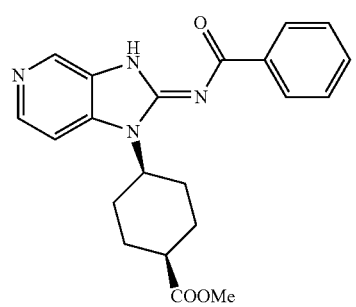 [SMILES: COC(=O)[C@H]1CC[C@@H](n2/c(=N/C(=O)c3ccccc3)[nH]c3cnccc32)CC1]

Step D: cis-Methyl 4-((E)-2-(benzoylimino)-2,3-dihydro-1H-imidazo[4,5-c]pyridin-1-yl)cyclohexanecarboxylate To a solution of cis-methyl 4-(3-aminopyridin-4-ylamino) cyclohexanecarboxylate (70 mg, 0.281 mmol) in ACN (5.6 mL) under nitrogen was added benzoyl isothiocyanate (0.045 mL, 0.337 mmol). The reaction mixture was stirred for 30 minutes at RT. To the mixture was added polymer-supported-carbodiimide (936 mg, 1.123 mmol; Loading: 1.2 mmol/g;), and the resulting mixture was stirred at 70° C. for 16 hours. The reaction mixture was cooled to RT and filtered, and the resin was washed with 1% MeOH/DCM. The filtrate was concentrated and purified by silica gel chromatography (1-4% MeOH/DCM) to afford cis-methyl 4-((E)-2-(benzoylimino)-2,3-dihydro-1H-imidazo[4,5-c]pyridin-1-yl)cyclohexanecarboxylate as an off-white solid (18 mg, 17% yield). MS m/z=379.2 [M+H]. Calc'd for $C_{21}H_{22}N_4O_3$: 378.2.

Example 2

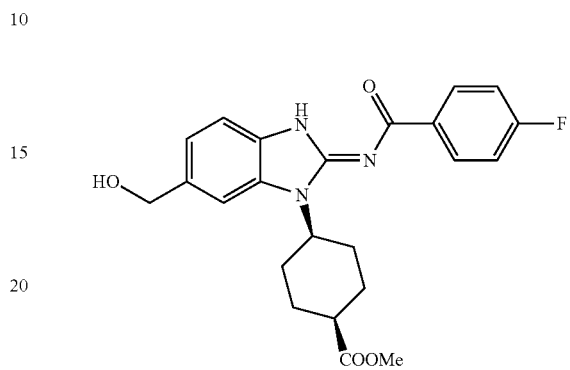

cis-Methyl 4-((E)-2-((4-fluorobenzoylimino)-6-(hydroxymethyl)-2,3-dihydro-1H-benzo[d]imidazol-1-yl)cyclohexanecarboxylate

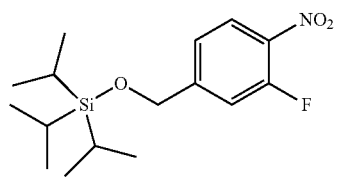 [SMILES: CC(C)[Si](OCc1ccc([N+](=O)[O-])c(F)c1)(C(C)C)C(C)C]

Step A: (3-Fluoro-4-nitrobenzyloxy)triisopropylsilane

To a 3-L round-bottomed flask was added (3-fluoro-4-nitrophenyl)methanol (4.7 g, 27.5 mmol) and DCM (47 mL). To the mixture was added triisopropylsilyl trifluoromethanesulfonate (9.26 g, 30.2 mmol) and 2,6-dimethylpyridine (3.53 g, 33.0 mmol). The resulting mixture was stirred for 3 hours at RT, and washed with $NH_4Cl$ (5-250 mL) and $H_2O$ (5-250 mL). The organic layer was collected and dried over sodium sulfate and concentrated to afford (3-fluoro-4-nitrobenzyloxy)triisopropylsilane (8.9 g, 99% yield) as a light yellow oil.

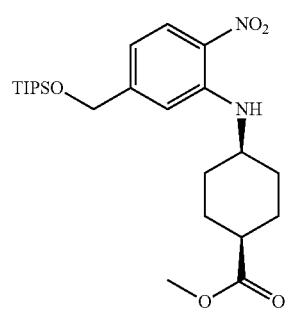

Step B: cis-Methyl 4-(2-nitro-5-((triisopropylsilyloxy)methyl)phenylamino)cyclohexanecarboxylate The title compound was prepared from (3-fluoro-4-nitrobenzyloxy)triisopropylsilane using the preparation for cis-methyl 4-(3-nitropyridin-4-ylamino)cyclohexanecarboxylate described above. The yield was 3.5 g (39.2% yield).

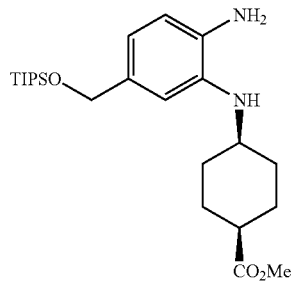

Step C: cis-Methyl 4-(2-amino-5-((triisopropylsilyloxy)methyl)phenylamino)cyclohexanecarboxylate A round bottom flask under nitrogen atmosphere was charged with cis-methyl 4-(2-nitro-5-((triisopropylsilyloxy)methyl)phenylamino)cyclohexanecarboxylate (2.77 g, 5.96 mmol) and palladium (10% on carbon) (0.634 g, 0.596 mmol). To this was added EtOH (48.5 mL) followed by ammonium formate (3.76 g, 59.6 mmol). The reaction mixture was stirred at RT for 2 hours and then diluted with EtOH and filtered through Celite® brand filter aid. The filter cake was washed sequentially with DCM (100 mL), EtOH (100 mL), and MeOH (100 mL). The filtrate was concentrated, re-diluted with DCM (100 mL) and washed with brine. The organic layer was collected, dried over sodium sulfate and concentrated to afford cis-methyl 4-(2-amino-5-((triisopropylsilyloxy)methyl)phenylamino)cyclohexanecarboxylate as a brown oil (2.58 g, 100% yield). MS m/z=435.2 [M+H]. Calc'd for $C_{24}H_{42}N_2O_3Si$: 434.3.

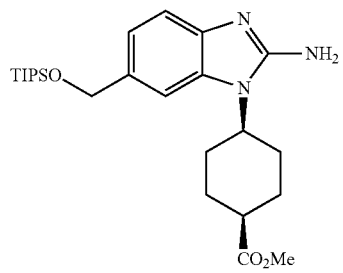

Step D: cis-Methyl 4-(2-amino-6-((triisopropylsilyloxy)methyl)-1H-benzo[d]imidazol-1-yl)cyclohexanecarboxylate A round bottom flask under nitrogen atmosphere was charged with cis-methyl 4-(2-amino-5-((triisopropylsilyloxy)methyl)phenylamino)cyclohexanecarboxylate (2.5 g, 5.75 mmol) and EtOH (23.96 mL) To this was added cyanogen bromide (0.914 g, 8.63 mmol), and the reaction mixture was stirred overnight at RT. The reaction mixture was diluted with DCM (80 mL) and washed with 1N aqueous NaOH (50 mL). The organic layer was collected, dried over sodium sulfate, and concentrated to dryness to afford cis-methyl 4-(2-amino-6-((triisopropylsilyloxy)methyl)-1H-benzo[d]imidazol-1-yl)cyclohexanecarboxylate as a brown solid (2.64 g, 100% yield). MS m/z=460.2 [M+H]. Calc'd for $C_{25}H_{41}N_3O_3Si$: 459.3.

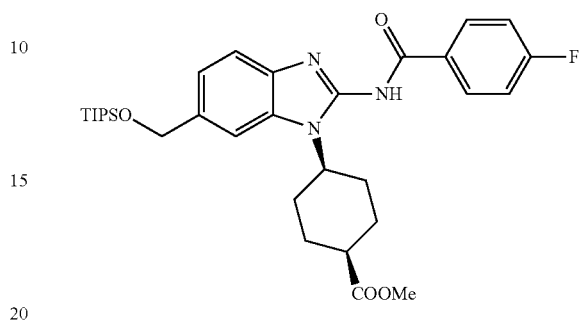

Step E: cis-Methyl 4-(2-(4-fluorobenzamido)-6-((triisopropylsilyloxy)methyl)-1H-benzo[d]imidazol-1-yl)cyclohexanecarboxylate A solution of 4-fluorobenzoyl chloride (0.113 mL, 0.957 mmol) in DCM (2.90 mL) was cooled to 0° C. under nitrogen. To this was added cis-methyl 4-(2-amino-6-((triisopropylsilyloxy)methyl)-1H-benzo[d]imidazol-1-yl)cyclohexanecarboxylate (0.4 g, 0.870 mmol) followed by TEA (0.482 mL, 3.48 mmol). The resulting mixture was stirred at 0° C. for 30 minutes. The ice bath was removed, and the mixture was stirred for 2 hours. The reaction mixture was diluted with DCM (20 mL) and washed with water (10 mL). The organic layer was collected, dried over sodium sulfate, concentrated, and dried under vacuum to afford cis-methyl 4-(2-(4-fluorobenzamido)-6-((triisopropylsilyloxy)methyl)-1H-benzo[d]imidazol-1-yl)cyclohexanecarboxylate (0.5 g, 100% yield).

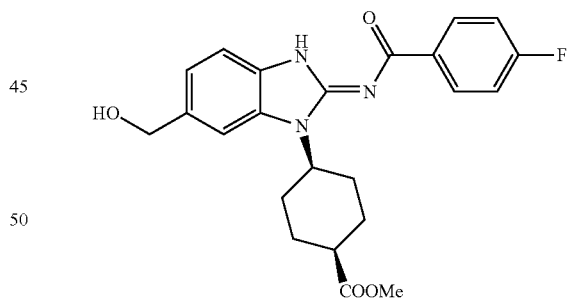

Step F: cis-Methyl 4-((E)-2-(4-fluorobenzoylimino)-6-(hydroxymethyl)-2,3-dihydro-1H-benzo[d]imidazol-1-yl)cyclohexanecarboxylate cis-Methyl 4-((E)-2-(4-fluorobenzoylimino)-6-((triisopropylsilyloxy)methyl)-2,3-dihydro-1H-benzo[d]imidazol-1-yl)cyclohexanecarboxylate (0.61 g, 1.048 mmol) was suspended in 2.1 mL of THF and cooled to 0° C. under nitrogen. To this mixture was added TBAF (1 M in THF) (1.573 mL, 1.573 mmol) dropwise via syringe, and the resulting mixture was stirred for 30 minutes at 0° C. The ice bath was removed, and the mixture was stirred for another 30 minutes at RT. The resulting mixture was diluted with DCM and washed with water. The organic layer was collected, dried over sodium sulfate, and concentrated, and the residue was purified by silica gel chromatography (30-50% EtOAc/Hexanes) to provide the title compound (190 mg, 42.6% yield). MS m/z=426.2 [M+H]. Calc'd for $C_{23}H_{24}FN_3O_4$: 425.2. $^1$H NMR (400 MHz, DMSO-$d_6$) δ ppm 1.63-1.92 (m, 4H) 2.15-2.30 (m, 2H) 2.53-2.74 (m, 2H) 2.78-2.94 (m, 1H) 3.76 (s, 3H) 4.58 (d, J=5.58 Hz, 2H) 4.62-4.82 (m, 1H) 5.24 (t, J=5.58 Hz, 1H) 7.11-7.20 (m, 1H) 7.20-7.33 (m, 2H) 7.35-7.66 (m, 2H) 7.84-8.46 (m, 2H) 12.78 (s, 1H).

Example 3

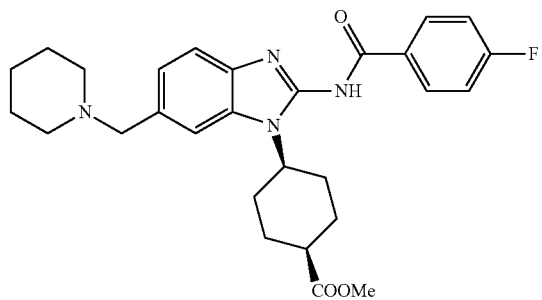 [SMILES: COC(=O)[C@H]1CC[C@@H](n2c(NC(=O)c3ccc(F)cc3)nc3ccc(CN4CCCCC4)cc32)CC1]

cis-Methyl 4-(2-(4-fluorobenzoylimino)-6-(piperidin-1-ylmethyl)-2,3-dihydro-1H-benzo[d]imidazol-1-yl)cyclohexanecarboxylate cis-Methyl 4-(2-(4-fluorobenzamido)-6-(hydroxymethyl)-1H-benzo[d]imidazol-1-yl)cyclohexanecarboxylate (0.19 g, 0.447 mmol) was suspended in DCM (4.47 mL) and cooled to 0° C. under a nitrogen atmosphere. To this mixture was added thionyl chloride (0.652 mL, 8.93 mmol) dropwise, and the reaction mixture was stirred at 0° C. for 1 hour. The ice bath was removed, and the mixture was stirred at RT for 2 hours. The reaction mixture was concentrated under reduced pressure and dried under high vacuum to afford a yellow foam. The foam was suspended in 2 mL of DMSO and treated with piperidine (0.441 mL, 4.47 mmol) followed by TEA (0.248 mL, 1.786 mmol). The resulting mixture was stirred at RT for 2 hours. The reaction mixture was diluted with DCM (2-20 mL) and washed with water (2-20 mL). The organic layer was collected, dried over sodium sulfate, and concentrated. The residue was purified by HPLC (10-70% ACN/H$_2$O; 0.1% TFA) to afford cis-methyl 4-((E)-2-(4-fluorobenzoylimino)-6-(piperidin-1-ylmethyl)-2,3-dihydro-1H-benzo[d]imidazol-1-yl)cyclohexanecarboxylate as a white solid (150 mg, 68.2% yield). MS m/z=493.2 [M+H]. Calc'd for $C_{28}H_{33}FN_4O_3$: 492.3. $^1$H NMR (400 MHz, DMSO-$d_6$) δ ppm 1.33-1.45 (m, 2H) 1.44-1.61 (m, 4H) 1.66-1.93 (m, 4H) 2.19-2.32 (m, 2H) 2.29-2.43 (m, 4H) 2.53-2.65 (m, 2H) 2.81-2.94 (m, 1H) 3.51 (s, 2H) 3.78 (s, 3H) 4.57-4.89 (m, 1H) 7.10-7.18 (m, 1H) 7.21-7.32 (m, 2H) 7.42-7.52 (m, 2H) 8.02-8.48 (m, 2H) 12.78 (s, 1H).

Example 4

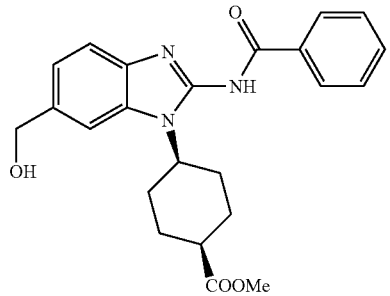 [SMILES: COC(=O)[C@H]1CC[C@@H](n2c(NC(=O)c3ccccc3)nc3ccc(CO)cc32)CC1]

cis-Methyl 4-(2-benzamido-6-(hydroxymethyl)-1H-benzo[d]imidazol-1-yl)cyclohexanecarboxylate The title compound was prepared in 2 steps from (cis-methyl 4-(2-amino-6-((triisopropylsilyloxy)methyl)-1H-benzo[d]imidazol-1-yl)cyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate (430 mg, 48.8% yield). MS m/z=408.2 [M+H]. Calc'd for $C_{23}H_{25}N_3O_4$: 407.2. $^1$H NMR (400 MHz, DMSO-$d_6$) δ ppm 1.65-1.91 (m, 4H) 2.20-2.33 (m, 2H) 2.55-2.73 (m, 2H) 2.77-2.93 (m, 1H) 3.22-3.48 (m, 1H) 3.77 (s, 3H) 4.56 (s, 2H) 4.63-4.82 (m, 1H) 7.17-7.23 (m, 1H) 7.42-7.58 (m, 5H) 7.95-8.37 (m, 2H) 12.82 (s, 1H).

Example 5

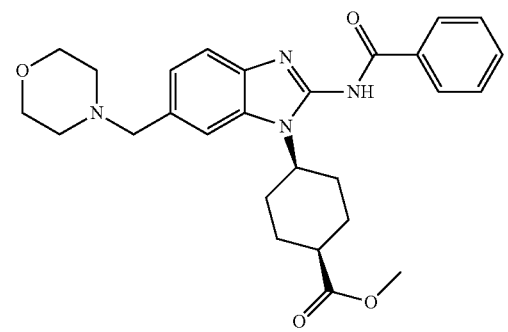 [SMILES: COC(=O)[C@H]1CC[C@@H](n2c(NC(=O)c3ccccc3)nc3ccc(CN4CCOCC4)cc32)CC1]

cis-Methyl 4-(2-benzamido-6-(morpholinomethyl)-1H-benzo[d]imidazol-1-yl)cyclohexanecarboxylate The title compound was prepared from cis-methyl 4-(2-benzamido-6-(hydroxymethyl)-1H-benzo[d]imidazol-1-yl)cyclohexanecarboxylate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (60 mg, 36.6% yield). MS m/z=477.2 [M+H]. Calc'd for $C_{27}H_{32}N_4O_4$: 476.3.

Example 6

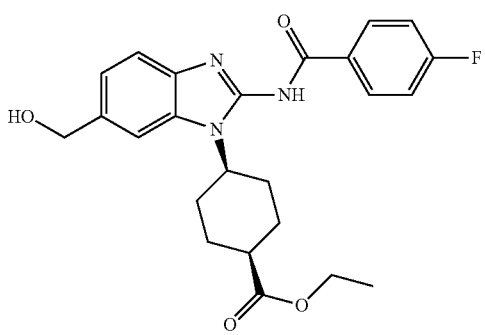 [SMILES: CCOC(=O)[C@H]1CC[C@@H](n2c(NC(=O)c3ccc(F)cc3)nc3ccc(CO)cc32)CC1]

cis-Ethyl 4-(2-(4-fluorobenzamido)-6-(hydroxymethyl)-1H-benzo[D]imidazol-1-yl)cyclohexanecarboxylate The title compound was prepared in 6 steps from cis-ethyl 4-aminocyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate. MS m/z=440.2 [M+H]. Calc'd for $C_{24}H_{26}FN_3O_4$: 439.2.

Example 7

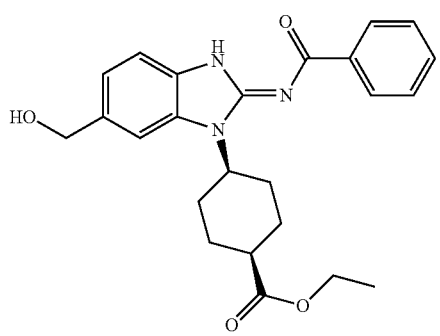 [SMILES: CCOC(=O)[C@H]1CC[C@@H](n2/c(=N/C(=O)c3ccccc3)[nH]c3ccc(CO)cc32)CC1]

cis-Ethyl 4-((E)-2-(benzoylimino)-6-(hydroxymethyl)-2,3-dihydro-1H-benzo[d]imidazol-1-yl)cyclohexanecarboxylate The title compound was prepared in 6 steps from cis-ethyl 4-aminocyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate. MS m/z=422.2 [M+H]. Calc'd for $C_{24}H_{27}N_3O_4$: 421.2.

Example 8

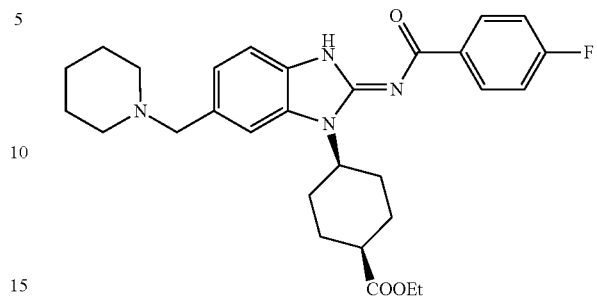

cis-Ethyl 4-((E)-2-(4-fluorobenzoylimino)-6-(piperidin-1-ylmethyl)-2,3-dihydro-1H-benzo[d]imidazol-1-yl)cyclohexanecarboxylate The title compound was prepared from cis-ethyl 4-((E)-2-(4-fluorobenzoylimino)-6-(hydroxymethyl)-2,3-dihydro-1H-benzo[d]imidazol-1-yl)cyclohexanecarboxylate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (40 mg, 57.8% yield). MS m/z=507.2 [M+H]. Calc'd for $C_{29}H_{35}FN_4O_3$: 506.3. $^1$H NMR (400 MHz, CDCl$_3$) δ ppm 1.35 (t, 3H) 1.42-1.51 (m, 2H) 1.52-1.69 (m, 5H) 1.71-1.94 (m, 4H) 2.30-2.51 (m, 6H) 2.56-2.75 (m, 2H) 2.77-2.91 (m, 1H) 3.51-3.64 (m, 1H) 4.32 (q, J=7.17 Hz, 2H) 4.70-4.90 (m, 1H) 7.08-7.16 (m, 2H) 7.18-7.26 (m, 2H) 7.35-7.44 (m, 1H) 8.13-8.55 (m, 2H) 12.54 (s, 1H).

Example 9

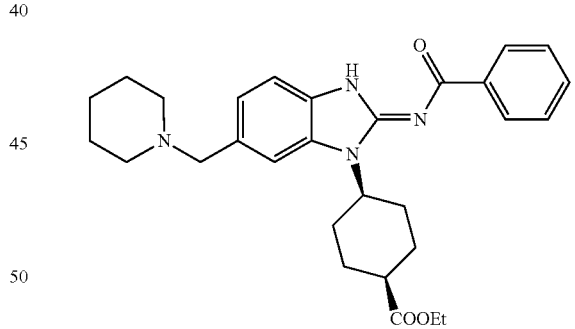

cis-Ethyl 4-((E)-2-(benzoylimino)-6-(piperidin-1-ylmethyl)-2,3-dihydro-1H-benzo[d]imidazol-1-yl)cyclohexanecarboxylate The title compound was prepared from cis-ethyl 4-((E)-2-(benzoylimino)-6-(hydroxymethyl)-2,3-dihydro-1H-benzo[d]imidazol-1-yl)cyclohexanecarboxylate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (80 mg, 69% yield). MS m/z=489.2 [M+H]. Calc'd for $C_{29}H_{36}N_4O_3$: 488.3

Example 10

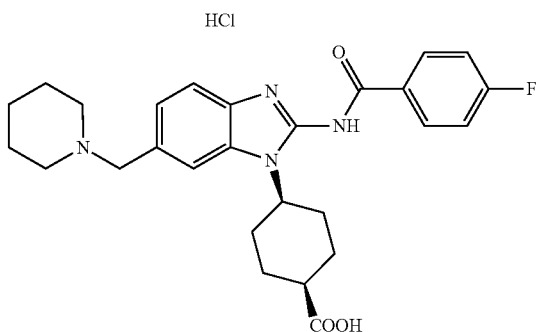 [SMILES: Cl ; O=C(Nc1nc2ccc(CN3CCCCC3)cc2n1[C@H]1CC[C@@H](C(=O)O)CC1)c1ccc(F)cc1]

cis-4-(2-(4-Fluorobenzamido)-6-(piperidin-1-ylmethyl)-1H-benzo[d]imidazol-1-yl)cyclohexanecarboxylic acid hydrochloride A round bottom flask under nitrogen atmosphere was charged with cis-methyl 4-(2-(4-fluorobenzamido)-6-(piperidin-1-ylmethyl)-1H-benzo[d]imidazol-1-yl)cyclohexanecarboxylate (0.10 g, 0.203 mmol), MeOH (2.90 mL) and 1N aqueous NaOH (3.05 mL, 3.05 mmol) and stirred at RT overnight. The reaction mixture was adjusted to a pH of approximately 2 by treatment with 6N HCl and was extracted with DCM (3×50 mL). The organic layers were combined, dried over sodium sulfate and concentrated under vacuum to afford an off-white solid. Trituration with ether afforded cis-4-(2-(4-fluorobenzamido)-6-(piperidin-1-ylmethyl)-1H-benzo[d]imidazol-1-yl)cyclohexanecarboxylic acid hydrochloride as a white solid (0.095 g, 91% yield). MS m/z=479.2 [M+H]. Calc'd for $C_{27}H_{31}N_4O_3$: 478.2.

Example 11

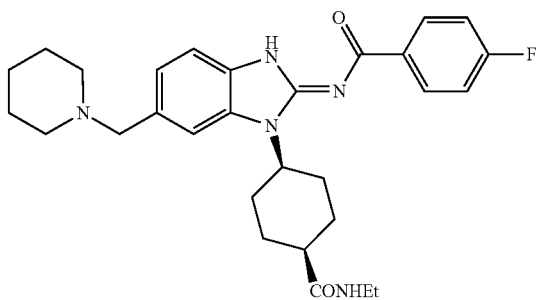

(E)-N-(1-(cis-4-(Ethylcarbamoyl)cyclohexyl)-6-(piperidin-1-ylmethyl)-1H-benzo[d]imidazol-2(3H)-ylidene)-4-fluorobenzamide cis-4-((E)-2-(4-Fluorobenzoylimino)-6-(piperidin-1-ylmethyl)-2,3-dihydro-1H-benzo[d]imidazol-1-yl)cyclohexanecarboxylic acid (0.025 g, 0.052 mmol) was cooled to 0° C. under nitrogen. To this mixture was added thionyl chloride (0.381 mL, 5.22 mmol), and the resulting reaction mixture was stirred for 10 minutes. The mixture was concentrated under reduced pressure and dried under high vacuum. The residue was suspended in THF (0.5 mL) and cooled to 0° C. under a nitrogen atmosphere. To this mixture was added ethanamine (2M in THF) (0.059 mL, 1.045 mmol) dropwise, and the reaction was stirred at 0° C. for 30 minutes. The reaction mixture was diluted with water (10 mL) and DCM (20 mL), and the layers were separated. The organic phase was dried over sodium sulfate, filtered, and solvent was concentrated under reduced pressure to afford (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (0.025 g, 95% yield). MS m/z=506.2 [M+H]. Calc'd for $C_{29}H_{36}FN_5O_2$: 505.3. $^1$H NMR (400 MHz, DMSO-$d_6$) δ ppm 1.14 (t, J=7.19 Hz, 3H) 1.42-1.50 (m, 2H) 1.50-1.63 (m, 4H) 1.63-1.89 (m, 4H) 2.14-2.28 (m, 2H) 2.32-2.47 (m, 4H) 2.57-2.66 (m, 1H) 2.67-2.89 (m, 2H) 3.21-3.32 (m, 2H) 3.56 (s, 2H) 4.77-5.03 (m, 1H) 7.17-7.23 (m, 1H) 7.25-7.35 (m, 2H) 7.53 (d, J=8.12 Hz, 1H) 7.63 (s, 1H) 7.83-7.94 (m, 1H) 8.29-8.43 (m, 2H) 12.79 (s, 1H).

Example 12

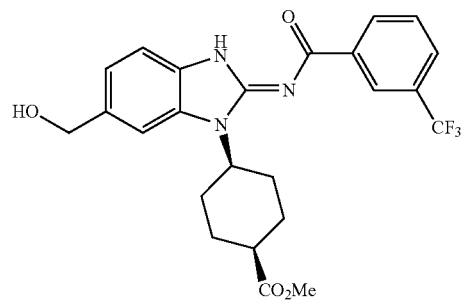 [SMILES: COC(=O)[C@H]1CC[C@@H](n2/c(=N/C(=O)c3cccc(C(F)(F)F)c3)[nH]c3ccc(CO)cc32)CC1]

cis-Methyl 4-((E)-6-(hydroxymethyl)-2-(3-(trifluoromethyl)benzoylimino)-2,3-dihydro-1H-benzo[d]imidazol-1-yl)cyclohexanecarboxyl The title compound was prepared in 2 steps from cis-methyl 4-(2-amino-6-((triisopropylsilyloxy)methyl)-1H-benzo[d]imidazol-1-yl)cyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate (250 mg, 60.4% yield). MS m/z=476.2 [M+H]. Calc'd for $C_{24}H_{24}F_3N_3O_4$: 475.2. $^1$H NMR (400 MHz, DMSO-$d_6$) δ ppm 1.69-1.89 (m, 4H) 2.22-2.33 (m, 2H) 2.54-2.69 (m, 2H) 2.80-2.94 (m, 1H) 3.76 (s, 3H) 4.60 (d, J=5.58 Hz, 2H) 4.70-4.88 (m, 1H) 5.27 (t, J=5.58 Hz, 1H) 7.14-7.23 (m, 1H) 7.48-7.57 (m, 2H) 7.70-7.79 (m, 1H) 7.86-7.95 (m, 1H) 8.41 (s, 1H) 8.49-8.60 (m, 1H) 12.86 (s, 1H).

Example 13

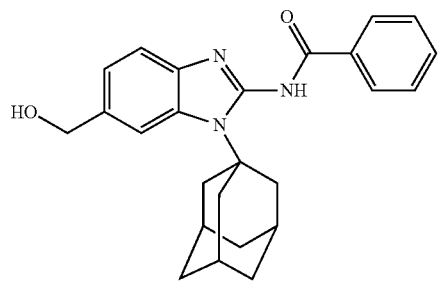 [SMILES: O=C(Nc1nc2ccc(CO)cc2n1C12CC3CC(CC(C3)C1)C2)c1ccccc1]

N-(1-adamantyl-6-(hydroxymethyl)-1H-benzo[d]imidazol-2-yl)benzamide

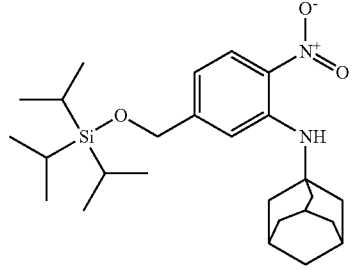 [SMILES: CC(C)[Si](OCc1ccc([N+](=O)[O-])c(NC23CC4CC(CC(C4)C2)C3)c1)(C(C)C)C(C)C]

Step A: N-Adamantyl-2-nitro-5-((triisopropylsilyloxy)methyl)aniline

The title compound was prepared from (3-fluoro-4-nitrobenzyloxy)triisopropylsilane using a method analogous to that used to prepare cis-methyl 4-(3-nitropyridin-4-ylamino)cyclohexanecarboxylate (1.7 g, 40.5% yield).

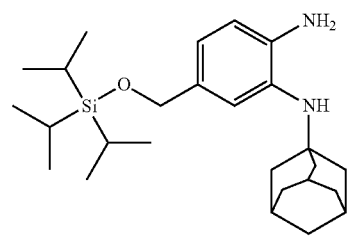 [SMILES: CC(C)[Si](OCc1ccc(N)c(NC23CC4CC(CC(C4)C2)C3)c1)(C(C)C)C(C)C]

Step B: N1-Adamantyl-5-((triisopropylsilyloxy)methyl)benzene-1,2-diamine

The title compound was prepared from N-adamantyl-2-nitro-5-((triisopropylsilyloxy)methyl)aniline using a method analogous to that used to prepare cis-methyl 4-(3-aminopyridin-4-ylamino)cyclohexanecarboxylate (869 mg, 100% yield). MS m/z=429.2 [M+H]. Calc'd for $C_{26}H_{44}N_2OSi$: 428.3.

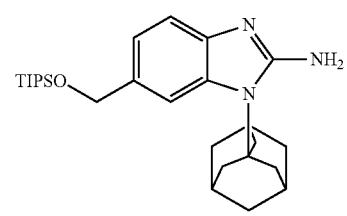

Step C: N-1-Adamantyl-6-((triisopropylsilyloxy)methyl)-1H-benzo[d]imidazol-2-amine The title compound was prepared from N1-adamantyl-5-((triisopropylsilyloxy)methyl)benzene-1,2-diamine using a method analogous to that used to prepare cis-methyl 4-(2-amino-6-((triisopropylsilyloxy)methyl)-1H-benzo[d]imidazol-1-yl)cyclohexanecarboxylate (984 mg, 100% yield). MS m/z=454.2 [M+H]. Calc'd for $C_{27}H_{43}N_3OSi$: 453.3.

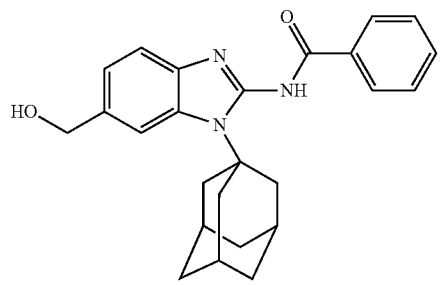 [SMILES: O=C(Nc1nc2ccc(CO)cc2n1C12CC3CC(CC(C3)C1)C2)c1ccccc1]

Step D: N-(1-Adamanty-6-(hydroxymethyl)-1H-benzo[d]imidazol-2-yl)benzamide

The title compound was prepared in 2 steps from N-1-adamantyl-6-((triisopropylsilyloxy)methyl)-1H-benzo[d]imidazol-2-amine using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate. The yield was 200 mg (37.7%, 2 steps). MS m/z=402.2 [M+H]. Calc'd for $C_{25}H_{27}N_3O_2$: 401.2.

Example 14

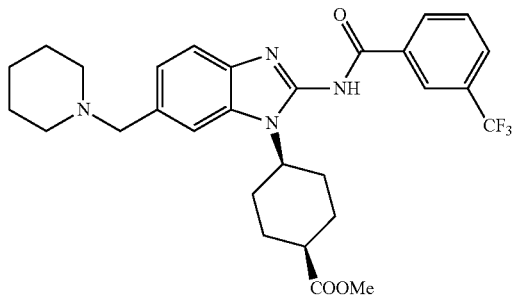 [SMILES: COC(=O)[C@H]1CC[C@@H](n2c(NC(=O)c3cccc(C(F)(F)F)c3)nc3ccc(CN4CCCCC4)cc32)CC1]

cis-Methyl 4-(6-(piperidin-1-ylmethyl)-2-(3-(trifluoromethyl)benzamido)-1H-benzo[d]imidazol-1-yl)cyclohexanecarboxylate The title compound was prepared in 3 steps from cis-methyl 4-(2-amino-6-((triisopropylsilyloxy)methyl)-1H-benzo[d]imidazol-1-yl)cyclohexanecarboxylate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (148 mg, 47.3% yield). MS m/z=543.2 [M+H]. Calc'd for $C_{29}H_{33}F_3N_4O_3$: 542.2. $^1$H NMR (400 MHz, DMSO-$d_6$) δ ppm 1.28-1.46 (m, 2H) 1.47-1.61 (m, 4H) 1.69-1.89 (m, 4H) 2.21-2.32 (m, 2H) 2.29-2.41 (m, 4H) 2.53-2.63 (m, 2H) 2.82-2.96 (m, 1H) 3.52 (s, 2H) 3.77 (s, 3H) 4.69-4.93 (m, 1H) 7.13-7.20 (m, 1H) 7.48 (s, 1H) 7.51 (d, J=8.12 Hz, 1H) 7.69-7.78 (m, 1H) 7.90 (d, J=7.63 Hz, 1H) 8.42 (s, 1H) 8.55 (d, J=7.53 Hz, 1H) 12.84 (s, 1H).

Example 15

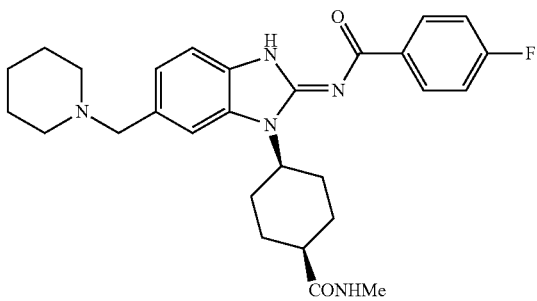

(E)-N-(1-(cis-4-(Methylcarbamoyl)cyclohexyl)-6-(piperidin-1-ylmethyl)-1H-benzo[d]imidazol-2(3H)-ylidene)-4-fluorobenzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (23 mg, 90% yield). MS m/z=492.2 [M+H]. Calc'd for $C_{28}H_{34}FN_5O_2$: 491.3. $^1$H NMR (400 MHz, DMSO-$d_6$) δ ppm 1.42-1.50 (m, 2H) 1.52-1.62 (m, 4H) 1.64-1.74 (m, 2H) 1.71-1.87 (m, 2H) 2.16-2.28 (m, 2H) 2.35-2.47 (m, 4H) 2.59-2.66 (m, 1H) 2.77 (d, J=4.60 Hz, 3H) 2.78-2.85 (m, 2H) 3.57 (s, 2H) 4.68-5.04 (m, 1H) 7.13-7.24 (m, 1H) 7.25-7.36 (m, 2H) 7.53 (d, J=8.12 Hz, 1H) 7.64 (s, 1H) 7.76-7.87 (m, 1H) 8.27-8.41 (m, 2H) 12.80 (s, 1H).

Example 16

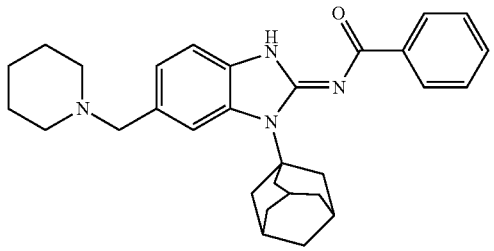 [SMILES: O=C(/N=c1\[nH]c2ccc(CN3CCCCC3)cc2n1C12CC3CC(CC(C3)C1)C2)c1ccccc1]

(E)-N—O-Adamantyl-6-(piperidin-1-ylmethyl)-1H-benzo[d]imidazol-2(3H)-ylidene)benzamide The title compound was prepared from N-(1-adamanty-6-(hydroxymethyl)-1H-benzo[d]imidazol-2-yl)benzamide using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (60 mg, 68.2% yield). MS m/z=469.2 [M+H]. Calc'd for $C_{30}H_{36}N_4O$: 468.3.

Example 17

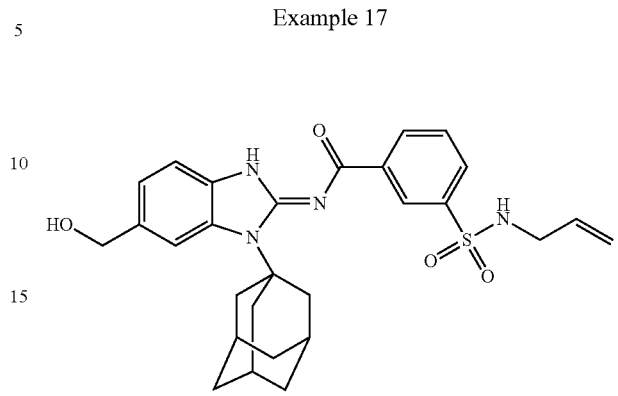

(E)-3-(N-Allylsulfamoyl)-N-(1-adamantyl-6-(hydroxymethyl)-1H-benzo[d]imidazol-2(3H)-ylidene)benzamide The title compound was prepared in 2 steps from N-1-adamantyl-6-((triisopropylsilyloxy)methyl)-1H-benzo[d]imidazol-2-amine using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate. The yield was 100 mg (21.8%, 2 steps). MS m/z=521.2 [M+H]. Calc'd for $C_{28}H_{32}N_4O_4S$: 520.2.

Example 18

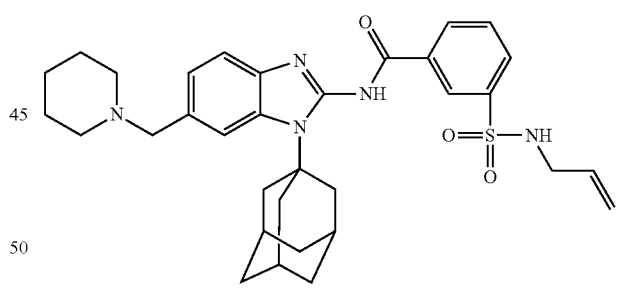

3-(N-Allylsulfamoyl)-N-(1-adamantyl-6-(piperidin-1-ylmethyl)-1H-benzo[d]imidazol-2-yl)benzamide The title compound was prepared from (E)-3-(N-allylsulfamoyl)-N-(1-adamantyl-6-(hydroxymethyl)-1H-benzo[d]imidazol-2(3H)-ylidene)benzamide using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (50 mg, 63.3% yield). MS m/z=588.2 [M+H]. Calc'd for $C_{28}H_{32}N_4O_4S$: 587.3.

Example 19

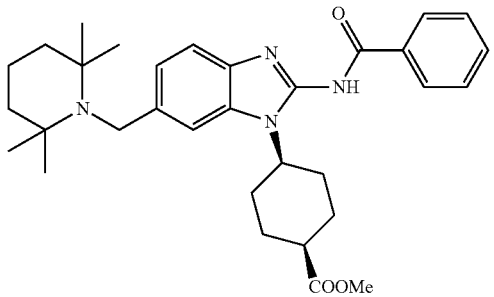 [SMILES: COC(=O)[C@H]1CC[C@@H](n2c(NC(=O)c3ccccc3)nc3ccc(CN4C(C)(C)CCCC4(C)C)cc32)CC1]

cis-Methyl 4-(2-benzamido-6-((2,2,6,6-tetramethylpiperidin-1-yl)methyl)-1H-benzo[d]imidazol-1-yl)cyclohexanecarboxylate cis-Methyl 4-(2-benzamido-6-(hydroxymethyl)-1H-benzo[d]imidazol-1-yl)cyclohexanecarboxylate (0.05 g, 0.123 mmol) was suspended in DCM (1.2 mL) and cooled to 0° C. under nitrogen atmosphere. To this mixture was added thionyl chloride (0.292 g, 2.454 mmol), and the mixture was stirred for 30 minutes. The resulting mixture was concentrated under reduced pressure and dried under high vacuum. The residue was suspended in 2 mL of DMSO and cooled in an ice bath under nitrogen atmosphere. To this mixture was added 2,2,6,6-tetramethylpiperidine (0.173 g, 1.227 mmol) dropwise, and the reaction was stirred in an ice bath for 30 minutes and at RT for another 30 minutes. The reaction mixture was diluted with DCM (20 mL) and washed with water (10 mL). The organic layer was collected, dried over sodium sulfate, and concentrated under vacuum. The residual yellow oil was triturated with 10% water/MeOH to afford cis-methyl 4-(2-benzamido-6-((2,2,6,6-tetramethylpiperidin-1-yl)methyl)-1H-benzo[d]imidazol-1-yl)cyclohexanecarboxylate (20 mg, 30.8% yield). MS m/z=531.2 [M+H]. Calc'd for $C_{32}H_{42}N_4O_3$: 530.3. $^1$H NMR (400 MHz, DMSO-$d_6$) δ ppm 1.04 (s, 12H) 1.54-1.73 (m, 6H) 1.73-1.99 (m, 4H) 2.25-2.41 (m, 2H) 2.46-2.54 (m, 2H) 2.84-3.02 (m, 1H) 3.81 (s, 3H) 3.93 (s, 2H) 4.73-5.08 (m, 1H) 7.25 (d, J=8.31 Hz, 1H) 7.39-7.62 (m, 4H) 7.74 (s, 1H) 8.23-8.35 (m, 2H) 12.76 (s, 1H).

Example 20

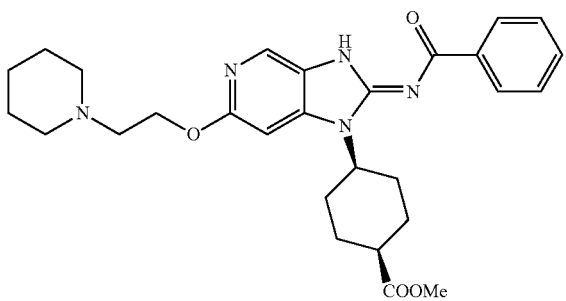

cis-Methyl 4-((E)-2-(benzoylimino)-6-(2-(piperidin-1-yl)ethoxy)-2,3-dihydro-1H-imidazo[4,5-c]pyridin-1-yl)cyclohexanecarboxylate

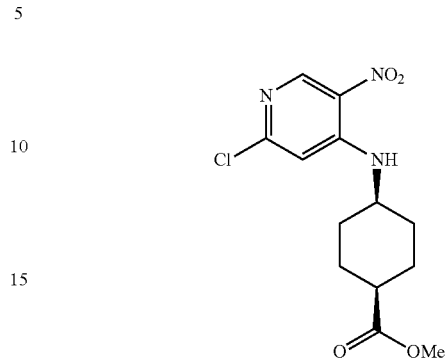

Step A: cis-Methyl 4-(2-chloro-5-nitropyridin-4-ylamino)cyclohexanecarboxylate The title compound was prepared from 2,4-dichloro-5-nitropyridine using a method analogous to the preparation of cis-methyl 4-(3-nitropyridin-4-ylamino)cyclohexanecarboxylate (2.7 g, 98% yield). MS m/z=314.2 [M+H]. Calc'd for $C_{13}H_{16}ClN_3O_4$: 313.1.

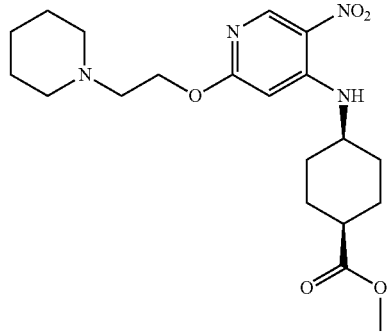

Step B: cis-Methyl 4-(5-nitro-2-(2-(piperidin-1-yl)ethoxy)pyridin-4-ylamino)cyclohexanecarboxylate To a nitrogen purged, cooled (0° C.) suspension of 2-(piperidin-1-yl)ethanol (0.577 g, 4.46 mmol) in THF was added sodium hydride (0.196 g of 60% oil dispersion, 4.91 mmol), and the resulting mixture was stirred for 30 minutes. A solution of cis-methyl 4-(2-chloro-5-nitropyridin-4-ylamino)cyclohexanecarboxylate (1.40 g, 4.46 mmol) in THF (14 mL) was added, and the reaction was stirred overnight at RT. The reaction mixture was quenched with water (10 mL) and the product extracted with DCM (30 mL). The organic layer was collected, dried over sodium sulfate and concentrated under reduced pressure. The residue was purified by silica gel chromatography (10-30% of 90/10/1 DCM/MeOH/NH$_4$OH in DCM) to afford cis-methyl 4-(5-nitro-2-(2-(piperidin-1-yl)ethoxy)pyridin-4-ylamino)cyclohexanecarboxylate (0.6 g, 33.1% yield). MS m/z=407.2 [M+H]. Calc'd for $C_{20}H_{30}N_4O_5$: 406.2.

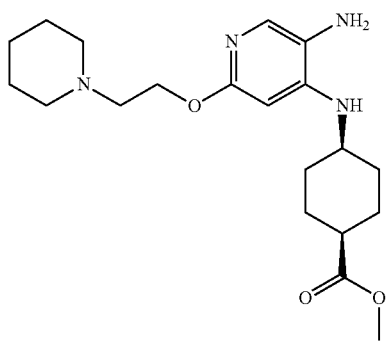 [SMILES: COC(=O)[C@H]1CC[C@@H](Nc2cc(OCCN3CCCCC3)ncc2N)CC1]

Step C: cis-Methyl 4-(5-amino-2-(2-(piperidin-1-yl)ethoxy)pyridin-4-ylamino)cyclohexanecarboxylate The title compound was prepared from cis-methyl 4-(5-nitro-2-(2-(piperidin-1-yl)ethoxy)pyridin-4-ylamino)cyclohexanecarboxylate using a method analogous to that used to prepare to cis-methyl 4-(2-amino-5-((triisopropylsilyloxy)methyl)phenylamino)cyclohexanecarboxylate (398 mg, 100% yield). MS m/z=377.2 [M+H]. Calc'd for $C_{20}H_{32}N_4O_3$: 376.2.

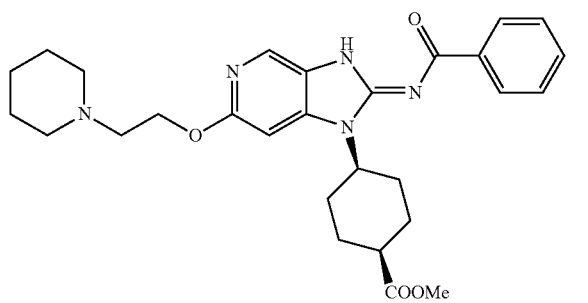 [SMILES: COC(=O)[C@H]1CC[C@@H](n2/c(=N/C(=O)c3ccccc3)[nH]c3cnc(OCCN4CCCCC4)cc32)CC1]

Step D: cis-Methyl 4-((E)-2-(benzoylimino)-6-(2-(piperidin-1-yl)ethoxy)-2,3-dihydro-1H-imidazo[4,5-c]pyridin-1-yl)cyclohexanecarboxylate The title compound was prepared from cis-methyl 4-(5-amino-2-(2-(piperidin-1-yl)ethoxy)pyridin-4-ylamino)cyclohexanecarboxylate using a method analogous to that used to prepare cis-methyl 4-((E)-2-(benzoylimino)-2,3-dihydro-1H-imidazo[4,5-c]pyridin-1-yl)cyclohexanecarboxylate (96 mg, 65% yield). MS m/z=506.2 [M+H]. Calc'd for $C_{28}H_{35}N_5O_4$: 505.3. $^1$H NMR (500 MHz, DMSO-$d_6$) δ ppm 1.31-1.43 (m, 2H) 1.44-1.56 (m, 4H) 1.65-1.85 (m, 4H) 2.17-2.28 (m, 2H) 2.37-2.46 (m, 4H) 2.53-2.61 (m, 2H) 2.65 (t, J=5.98 Hz, 2H) 2.79-2.87 (m, 1H) 3.74 (s, 3H) 4.35 (t, J=5.98 Hz, 2H) 4.50-4.69 (m, 1H) 6.92 (s, 1H) 7.43-7.51 (m, 2H) 7.51-7.58 (m, 1H) 8.12-8.25 (m, 3H) 12.64 (s, 1H).

Example 21

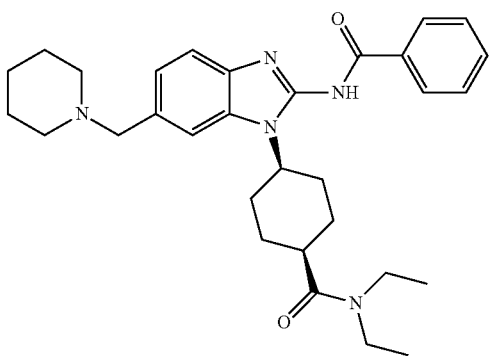 [SMILES: CCN(CC)C(=O)[C@H]1CC[C@@H](n2c(NC(=O)c3ccccc3)nc3ccc(CN4CCCCC4)cc32)CC1]

N-(1-(cis-4-(Diethylcarbamoyl)cyclohexyl)-6-(piperidin-1-ylmethyl)-1H-benzo[d]imidazol-2-yl)benzamide The title compound was prepared in 5 steps from cis-methyl 4-(2-amino-6-((triisopropylsilyloxy)methyl)-1H-benzo[d]imidazol-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (35 mg, last step=62.5% yield). MS m/z=516.2 [M+H]. Calc'd for $C_{31}H_{41}N_5O_2$: 515.3.

Example 22

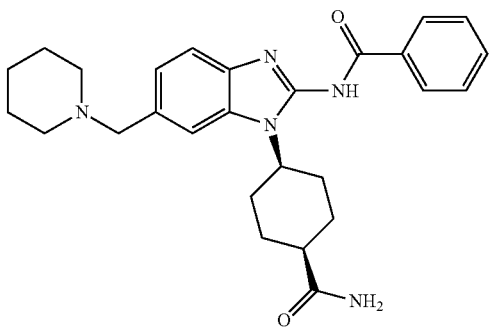 [SMILES: NC(=O)[C@H]1CC[C@@H](n2c(NC(=O)c3ccccc3)nc3ccc(CN4CCCCC4)cc32)CC1]

N-(1-(cis-4-Carbamoylcyclohexyl)-6-(piperidin-1-ylmethyl)-1H-benzo[d]imidazol-2-yl)benzamide The title compound was prepared in 5 steps from cis-methyl 4-(2-amino-6-((triisopropylsilyloxy)methyl)-1H-benzo[d]imidazol-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide. MS m/z=460.2 [M+H]. Calc'd for $C_{27}H_{33}N_5O_2$: 459.3. $^1$H NMR (400 MHz, DMSO-$d_6$) δ ppm 1.28-1.45 (m, 2H) 1.46-1.58 (m, 4H) 1.60-1.82 (m, 4H) 2.08-2.25 (m, 2H) 2.29-2.45 (m, 4H) 2.54-2.61 (m, 4H) 2.61-2.87 (m, 2H) 3.40-3.56 (m, 2H) 4.56-5.01 (m, 1H) 6.87-6.94 (m, 1H) 7.12-7.22 (m, 1H) 7.31-7.41 (m, 1H) 7.43-7.53 (m, 4H) 7.54-7.63 (m, 1H) 7.96-8.52 (m, 2H) 12.76 (s, 1H).

Example 23

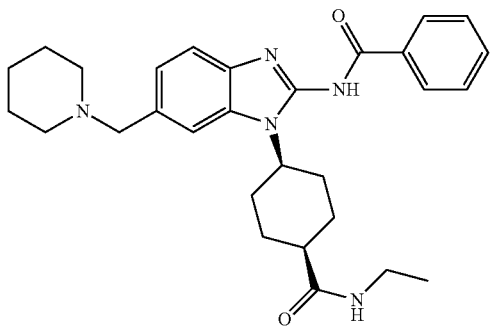 [SMILES: CCNC(=O)[C@H]1CC[C@@H](n2c(NC(=O)c3ccccc3)nc3ccc(CN4CCCCC4)cc32)CC1]

N-(1-(cis-4-(Ethylcarbamoyl)cyclohexyl)-6-(piperidin-1-ylmethyl)-1H-benzo[d]imidazol-2-yl)benzamide The title compound was prepared in 5 steps from cis-methyl 4-(2-amino-6-((triisopropylsilyloxy)methyl)-1H-benzo[d]imidazol-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2 (3H)-ylidene)-4-fluorobenzamide. MS m/z=488.2 [M+H]. Calc'd for $C_{29}H_{37}N_5O_2$: 487.3.

Example 24

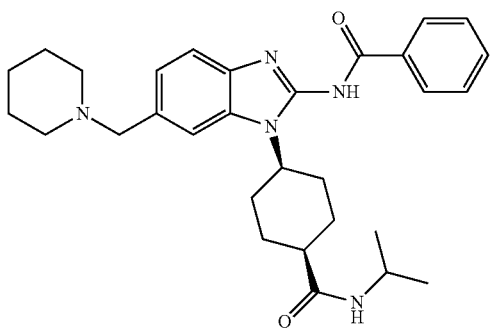 [SMILES: CC(C)NC(=O)[C@H]1CC[C@@H](n2c(NC(=O)c3ccccc3)nc3ccc(CN4CCCCC4)cc32)CC1]

N—O-(cis-4-(Isopropylcarbamoyl)cyclohexyl)-6-(piperidin-1-ylmethyl)-1H-benzo[d]imidazol-2-yl)benzamide The title compound was prepared in 5 steps from cis-methyl 4-(2-amino-6-((triisopropylsilyloxy)methyl)-1H-benzo[d]imidazol-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide. MS m/z=502.2 [M+H]. Calc'd for $C_{30}H_{39}N_5O_2$: 501.3. $^1$H NMR (400 MHz, DMSO-$d_6$) δ ppm 1.09 (d, J=6.55 Hz, 6H) 1.23-1.28 (m, 1H) 1.64-1.76 (m, 6H) 1.78-1.86 (m, 2H) 2.07-2.20 (m, 2H) 2.53-2.57 (m, 1H) 2.78-2.98 (m, 4H) 3.31-3.44 (m, 2H) 3.97-4.14 (m, 1H) 4.26-4.36 (m, 3H) 4.66-4.77 (m, 1H) 7.37-7.42 (m, 1H) 7.44-7.50 (m, 2H) 7.50-7.56 (m, 1H) 7.57-7.62 (m, 1H) 7.65-7.74 (m, 1H) 7.90 (s, 1H) 8.22-8.32 (m, 2H) 9.94 (s, 1H).

Example 25

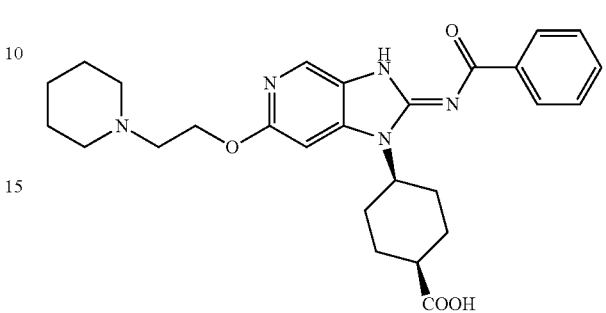

cis-4-((E)-2-(Benzoylimino)-6-(2-(piperidin-1-yl)ethoxy)-2,3-dihydro-1H-imidazo[4,5-c]pyridin-1-yl)cyclohexanecarboxylic acid To a suspension of cis-methyl 4-((E)-2-(benzoylimino)-6-(2-(piperidin-1-yl)ethoxy)-2,3-dihydro-1H-imidazo[4,5-c]pyridin-1-yl)cyclohexanecarboxylate (0.052 g, 0.103 mmol) in MeOH (1.0 mL) was added 1N aqueous NaOH (1.028 mL, 1.028 mmol), and the resulting mixture was stirred at RT for 48 hours. The reaction mixture was concentrated under vacuum to remove MeOH and neutralized with 2 N HCl. The product was extracted with DCM (5-20 mL) to afford cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid as an off-white solid (50 mg, 99% yield). MS m/z=492.2 [M+H]. Calc'd for $C_{27}H_{33}N_5O_4$: 491.3.

Example 26

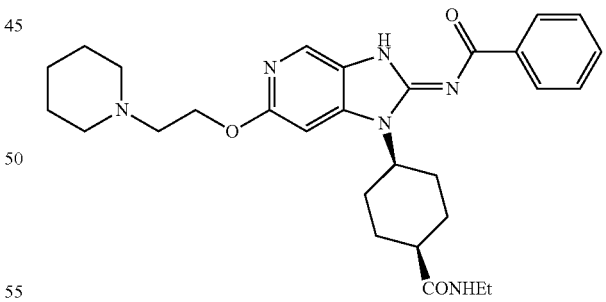

cis-4-((E)-2-(Benzoylimino)-6-(2-(piperidin-1-yl)ethoxy)-2,3-dihydro-1H-imidazo[4,5-c]pyridin-1-yl)cyclohexanecarboxylic acid The title compound was prepared from cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid using a method analogous to the preparation of (E)-N-(1-(cis-4-(ethylcarbamoyl)cyclohexyl)-6-(piperidin-1-ylmethyl)-

1H-benzo[d]imidazol-2(3H)-ylidene)-4-fluorobenzamide (25 mg, 99% yield). MS m/z=519.2 [M+H]. Calc'd for $C_{29}H_{38}N_6O_3$: 518.3.

Example 27

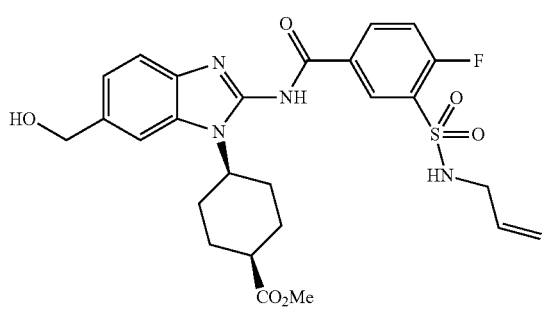 [SMILES: C=CCNS(=O)(=O)c1cc(C(=O)Nc2nc3ccc(CO)cc3n2[C@H]2CC[C@@H](C(=O)OC)CC2)ccc1F]

cis-Methyl 4-(2-(3-(N-allylsulfamoyl)-4-fluorobenzamido)-6-(hydroxymethyl)-1H-benzo[d]imidazol-1-yl)cyclohexanecarboxylate The title compound was prepared in 2 steps from cis-methyl 4-(2-amino-6-((triisopropylsilyloxy)methyl)-1H-benzo[d]imidazol-1-yl)cyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate (340 mg, 70% yield, 2 steps). MS m/z=545.2 [M+H]. Calc'd for $C_{26}H_{29}FN_4O_6S$: 544.2.

Example 28

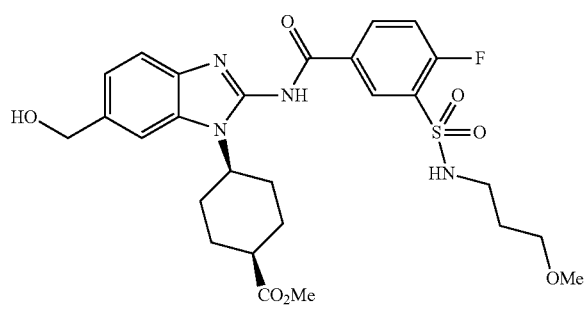 [SMILES: COCCCNS(=O)(=O)c1cc(C(=O)Nc2nc3ccc(CO)cc3n2[C@H]2CC[C@@H](C(=O)OC)CC2)ccc1F]

cis-Methyl 4-(2-(4-fluoro-3-(N-(3-methoxypropyl)sulfamoyl)benzamido)-6-(hydroxymethyl)-1H-benzo[d]imidazol-1-yl)cyclohexanecarboxylate The title compound was prepared in 2 steps from cis-methyl 4-(2-amino-6-((triisopropylsilyloxy)methyl)-1H-benzo[d]imidazol-1-yl)cyclohexanecarboxylate using a method analogous to the preparation of cis-methyl 4-((E)-2-(4-fluorobenzoylimino)-6-(hydroxymethyl)-2,3-dihydro-1H-benzo[d]imidazol-1-yl)cyclohexanecarboxylate (290 mg, 65.1% yield, 2 steps). MS m/z=577.2 [M+H]. Calc'd for $C_{27}H_{33}FN_4O_7S$: 576.2. $^1$H NMR (400 MHz, DMSO-d$_6$) δ ppm 1.22-1.28 (m, 2H) 1.70-1.86 (m, 4H) 2.21-2.30 (m, 2H) 2.54-2.58 (m, 1H) 2.80-2.91 (m, 1H) 3.30 (s, 3H) 3.55-3.66 (m, 2H) 3.76 (s, 3H) 4.54-4.62 (m, 2H) 4.74-4.88 (m, 1H) 4.99-5.06 (m, 1H) 5.09-5.20 (m, 1H) 5.26 (t, J=5.04 Hz, 1H) 5.62-5.77 (m, 1H) 7.18 (d, J=8.12 Hz, 1H) 7.45-7.55 (m, 3H) 8.22-8.29 (m, 1H) 8.48-8.54 (m, 1H) 8.54-8.59 (m, 1H) 12.80 (s, 1H).

Example 29

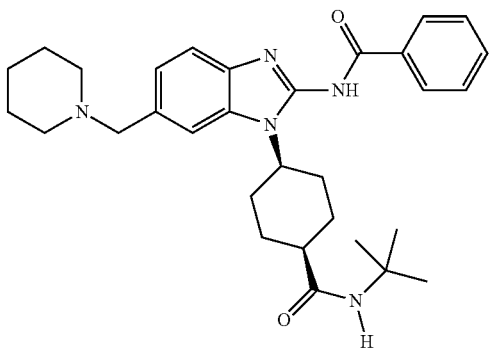 [SMILES: CC(C)(C)NC(=O)[C@H]1CC[C@@H](n2c(NC(=O)c3ccccc3)nc3ccc(CN4CCCCC4)cc32)CC1]

N-(1-(cis-4-(tert-Butylcarbamoyl)cyclohexyl)-6-(piperidin-1-ylmethyl)-1H-benzo[d]imidazol-2-yl)benzamide The title compound was prepared in 5 steps from cis-methyl 4-(2-amino-6-((triisopropylsilyloxy)methyl)-1H-benzo[d]imidazol-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide. MS m/z=516.2 [M+H]. Calc'd for $C_{31}H_{41}N_5O_2$: 515.3.

Example 30

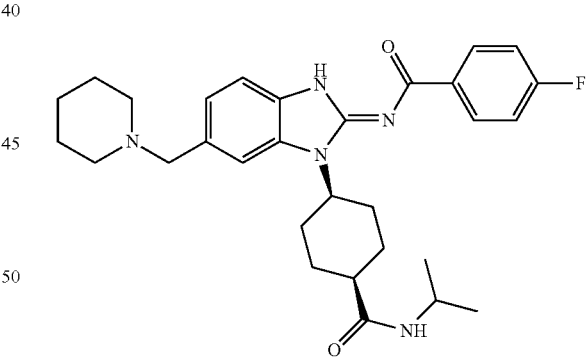

(E)-4-Fluoro-N-(1-(cis-4-(isopropylcarbamoyl)cyclohexyl)-6-(piperidin-1-ylmethyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (40 mg, 73.7% yield). MS m/z=520.2 [M+H]. Calc'd for $C_{30}H_{38}FN_5O_2$: 519.3. $^1$H NMR (400 MHz, DMSO-d$_6$) δ ppm 1.15 (d, J=6.55 Hz, 6H) 1.27-1.34 (m, 2H) 1.68-1.79 (m, 4H) 1.81-1.89 (m, 3H) 2.12-2.25 (m, 2H) 2.59-2.64 (m, 1H) 2.84-3.03 (m, 4H) 3.33-3.47 (m, 2H) 3.89-4.03 (m, 1H) 4.05-4.19 (m, 1H) 4.29-4.44 (m, 2H) 4.63-4.82 (m, 1H) 7.25-7.34 (m, 2H) 7.47-7.53 (m, 1H) 7.64 (d, J=8.22 Hz, 1H) 7.76 (d, J=7.73 Hz, 1H) 8.01 (s, 1H) 8.32-8.47 (m, 2H) 10.54 (s, 1H).

Example 31

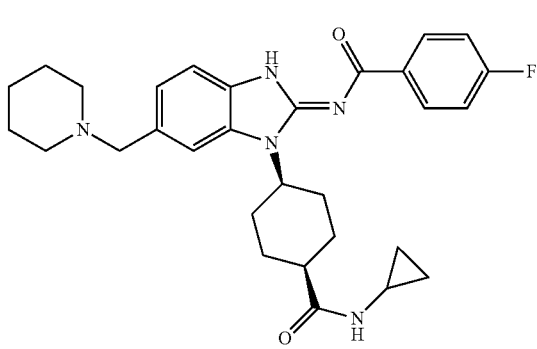 [SMILES: O=C(/N=c1\[nH]c2ccc(CN3CCCCC3)cc2n1[C@H]1CC[C@@H](C(=O)NC2CC2)CC1)c1ccc(F)cc1]

(E)-N-(1-(cis-4-(Cyclopropylcarbamoyl)cyclohexyl)-6-(piperidin-1-ylmethyl)-1H-benzo[d]imidazol-2(3H)-ylidene)-4-fluorobenzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (45 mg, 83% yield). MS m/z=518.2 [M+H]. Calc'd for $C_{30}H_{36}FN_5O_2$: 517.3.

Example 32

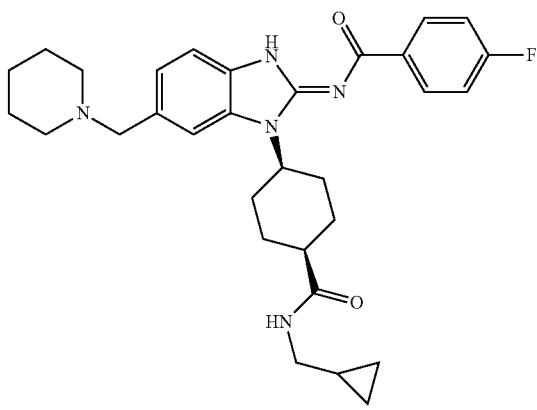 [SMILES: O=C(/N=c1\[nH]c2ccc(CN3CCCCC3)cc2n1[C@H]1CC[C@@H](C(=O)NCC2CC2)CC1)c1ccc(F)cc1]

(E)-N-(1-(cis-4-(Cyclopropylmethylcarbamoyl)cyclohexyl)-6-(piperidin-1-ylmethyl)-1H-benzo[d]imidazol-2(3H)-ylidene)-4-fluorobenzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (35 mg, 63% yield). MS m/z=532.2 [M+H]. Calc'd for $C_{31}H_{38}FN_5O_2$: 531.3.

Example 33

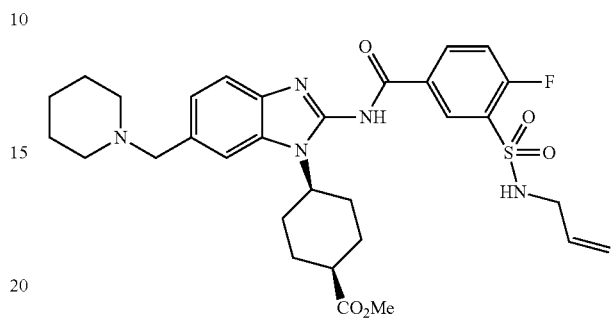

cis-Methyl 4-(2-(3-(N-allylsulfamoyl)-4-fluorobenzamido)-6-(piperidin-1-ylmethyl)-1H-benzo[d]imidazol-1-yl)cyclohexanecarboxylate The title compound was prepared from cis-methyl 4-(2-(3-(N-allylsulfamoyl)-4-fluorobenzamido)-6-(hydroxymethyl)-1H-benzo[d]imidazol-1-yl)cyclohexanecarboxylate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (180 mg, 68.5% yield). MS m/z=612.2 [M+H]. Calc'd for $C_{31}H_{38}FN_5O_5S$: 611.3. $^1H$ NMR (400 MHz, DMSO-$d_6$) δ ppm 1.04-1.14 (m, 2H) 1.21-1.31 (m, 2H) 1.32-1.44 (m, 4H) 1.54-1.73 (m, 4H) 2.03-2.16 (m, 2H) 2.15-2.27 (m, 4H) 2.68-2.79 (m, 1H) 3.37 (s, 2H) 3.40-3.52 (m, 2H) 3.63 (s, 3H) 4.62-4.77 (m, 1H) 4.84-4.92 (m, 1H) 4.97-5.06 (m, 1H) 5.49-5.63 (m, 1H) 6.97-7.07 (m, 1H) 7.28-7.41 (m, 3H) 8.09-8.15 (m, 1H) 8.34-8.41 (m, 1H) 8.40-8.46 (m, 1H) 12.65 (s, 1H).

Example 34

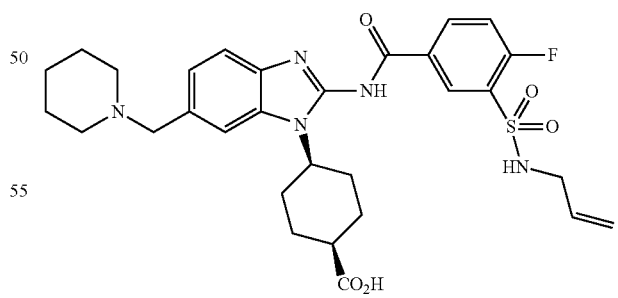

cis-4-(2-(3-(N-Allylsulfamoyl)-4-fluorobenzamido)-6-(piperidin-1-ylmethyl)-1H-benzo[d]imidazol-1-yl)cyclohexanecarboxylic acid The title compound was prepared from cis-methyl 4-(2-(3-(N-allylsulfamoyl)-4-fluorobenzamido)-6-(piperidin-1-ylmethyl)-1H-benzo[d]imidazol-1-yl)cyclohexanecarboxylate using a method analogous to the preparation of cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid (145 mg, 99% yield). MS m/z=598.2 [M+H]. Calc'd for $C_{30}H_{36}FN_5O_5S$: 597.2.

Example 35

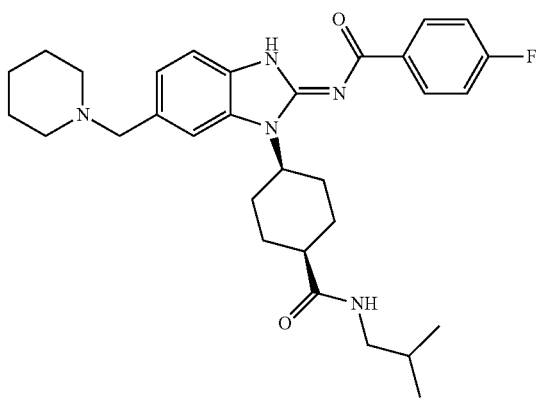 [SMILES: CC(C)CNC(=O)[C@H]1CC[C@@H](n2/c(=N/C(=O)c3ccc(F)cc3)[nH]c3ccc(CN4CCCCC4)cc32)CC1]

(E)-4-Fluoro-N-(1-(cis-4-(isobutylcarbamoyl)cyclo-hexyl)-6-(piperidin-1-ylmethyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (30 mg, 63% yield). MS m/z=534.2 [M+H]. Calc'd for $C_{31}H_{40}FN_5O_2$: 533.3.

Example 36

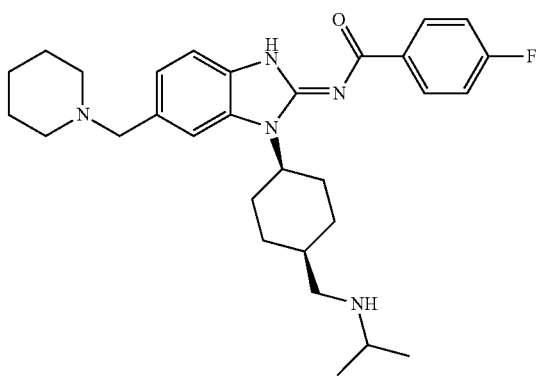 [SMILES: CC(C)NC[C@H]1CC[C@@H](n2/c(=N/C(=O)c3ccc(F)cc3)[nH]c3ccc(CN4CCCCC4)cc32)CC1]

(E)-4-Fluoro-N-(1-(cis-4-((isopropylamino)methyl)cyclohexyl)-6-(piperidin-1-ylmethyl)-1H-benzo[d]imidazol-2(3H)-ylidene)benzamide A suspension of (E)-4-fluoro-N-(1-(cis-4-formylcyclohexyl)-6-(piperidin-1-ylmethyl)-1H-benzo[d]imidazol-2(3H)-ylidene)benzamide (75 mg, 0.162 mmol) in MeOH (3.2 mL) was cooled to 0° C. under nitrogen atmosphere. To this mixture was added isopropylamine (0.208 mL, 2.432 mmol) followed by AcOH (0.056 mL, 0.973 mmol). The resulting mixture was stirred for 15 minutes. Solid sodium cyanoborohydride (15.28 mg, 0.243 mmol) was added in one portion, and the resulting mixture was stirred for 18 hours at RT. The reaction mixture was quenched with water (10 mL), and the aqueous layer was extracted with DCM (30 mL). The organic layer was collected, dried over sodium sulfate, and concentrated to dryness under vacuum. The residue was purified by silica gel chromatography (10-30% of 90/10/1 DCM/MeOH/NH$_4$OH in DCM) to afford (E)-4-fluoro-N-(1-(cis-4-((isopropylamino)methyl)cyclohexyl)-6-(piperidin-1-ylmethyl)-1H-benzo[d]imidazol-2(3H)-ylidene)benzamide (10 mg, 12.20% yield). MS m/z=506.2 [M+H]. Calc'd for $C_{30}H_{40}FN_5O$: 505.3.

Example 37

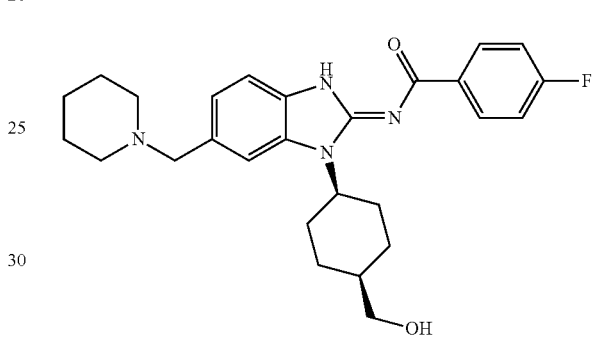

(E)-4-Fluoro-N-(1-(cis-4-(hydroxymethyl)cyclohexyl)-6-(piperidin-1-ylmethyl)-1H-benzo[d]imidazol-2(3H)-ylidene)benzamide The title compound was a byproduct isolated during preparation of (E)-4-fluoro-N-(1-(cis-4-((isopropylamino)methyl)cyclohexyl)-6-(piperidin-1-ylmethyl)-1H-benzo[d]imidazol-2(3H)-ylidene)benzamide (20 mg, 26.6% yield). MS m/z=465.2 [M+H]. Calc'd for $C_{27}H_{33}FN_4O_2$: 464.3. $^1$H NMR (400 MHz, DMSO-d$_6$) δ ppm 1.21-1.32 (m, 4H) 1.34-1.46 (m, 2H) 1.44-1.57 (m, 4H) 1.56-1.70 (m, 1H) 1.78-1.92 (m, 2H) 1.91-2.01 (m, 2H) 2.31-2.42 (m, 4H) 3.33-3.38 (m, 2H) 3.53 (s, 2H) 4.53 (t, J=5.18 Hz, 1H) 4.69-4.88 (m, 1H) 7.13-7.19 (m, 1H) 7.26-7.34 (m, 2H) 7.49 (d, J=8.12 Hz, 1H) 7.55 (s, 1H) 8.19-8.31 (m, 2H) 12.76 (s, 1H).

Example 38

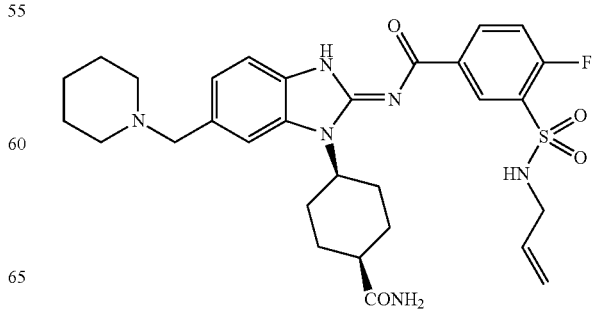

(E)-3-(N-Allylsulfamoyl)-N-(1-(cis-4-carbamoylcyclohexyl)-6-(piperidin-1-ylmethyl)-1H-benzo[d]imidazol-2(3H)-ylidene)-4-fluorobenzamide The title compound was prepared from cis-4-((E)-2-(3-(N-allylsulfamoyl)-4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (10 mg, 20.0% yield). MS m/z=597.2 [M+H]. Calc'd for $C_{30}H_{37}FN_6O_4S$: 596.3. $^1$H NMR (400 MHz, CDCl$_3$) δ ppm 1.25-1.30 (m, 4H) 1.45-1.54 (m, 2H) 1.56-1.69 (m, 5H) 1.76-1.85 (m, 3H) 2.29-2.38 (m, 2H) 2.40-2.50 (m, 2H) 2.68-2.77 (m, 1H) 3.02-3.13 (m, 1H) 3.57-3.66 (m, 1H) 3.69-3.79 (m, 2H) 4.21-4.41 (m, 1H) 5.01-5.15 (m, 1H) 5.20-5.32 (m, 1H) 5.72-5.92 (m, 1H) 6.76-6.87 (m, 1H) 7.19-7.27 (m, 4H) 7.32-7.48 (m, 1H) 8.21 (s, 1H) 8.34-8.49 (m, 1H) 8.56-8.74 (m, 1H) 12.84 (s, 1H).

Example 39

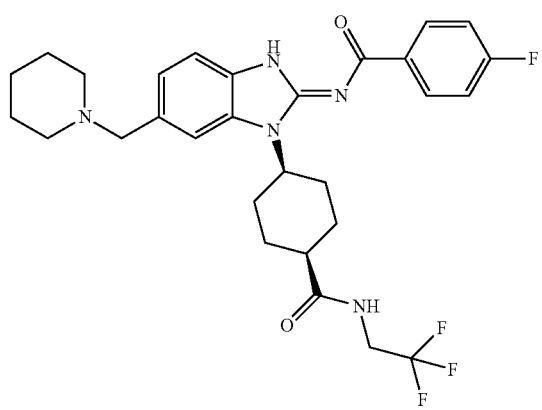 [SMILES: O=C(/N=c1\[nH]c2ccc(CN3CCCCC3)cc2n1[C@H]1CC[C@@H](C(=O)NCC(F)(F)F)CC1)c1ccc(F)cc1]

(E)-4-Fluoro-N-(6-(piperidin-1-ylmethyl)-1-(cis-4-(2,2,2-trifluoroethylcarbamoyl)cyclohexyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (15 mg, 42.8% yield). MS m/z=560.2 [M+H]. Calc'd for $C_{29}H_{33}F_4N_5O_2$: 559.3. $^1$H NMR (400 MHz, DMSO-d$_6$) δ ppm 1.34-1.46 (m, 2H) 1.46-1.60 (m, 4H) 1.62-1.72 (m, 2H) 1.74-1.89 (m, 2H) 2.08-2.21 (m, 2H) 2.22-2.44 (m, 4H) 2.63-2.83 (m, 3H) 3.50 (s, 2H) 3.92-4.13 (m, 2H) 4.72-4.98 (m, 1H) 7.09-7.20 (m, 1H) 7.20-7.33 (m, 2H) 7.43-7.52 (m, 1H) 7.55 (s, 1H) 8.22-8.39 (m, 2H) 8.46-8.62 (m, 1H) 12.76 (s, 1H).

Example 40

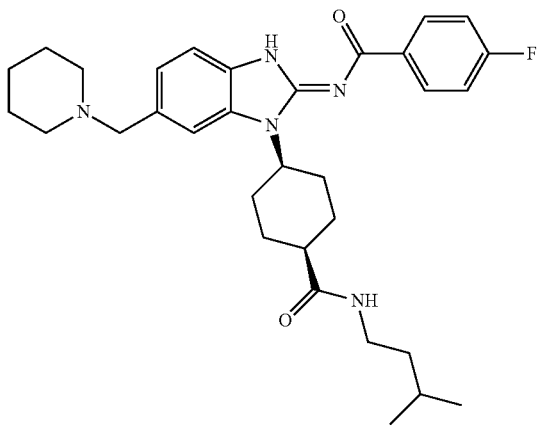 [SMILES: CC(C)CCNC(=O)[C@H]1CC[C@@H](n2/c(=N/C(=O)c3ccc(F)cc3)[nH]c3ccc(CN4CCCCC4)cc32)CC1]

(E)-4-Fluoro-N-(1-(cis-4-(isopentylcarbamoyl)cyclohexyl)-6-(piperidin-1-ylmethyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (15 mg, 43.7% yield). MS m/z=548.2 [M+H]. Calc'd for $C_{32}H_{42}FN_5O_2$: 547.3.

Example 41

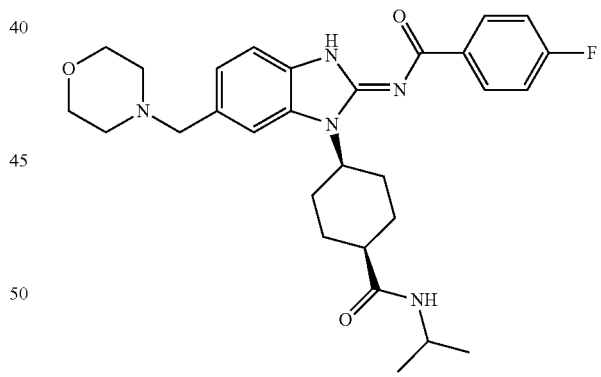

(E)-4-Fluoro-N-(1-(cis-4-(isopropylcarbamoyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (15 mg, 25.1% yield). MS m/z=522.2 [M+H]. Calc'd for $C_{29}H_{36}FN_5O_3$: 521.3. $^1$H NMR (400 MHz, DMSO-d$_6$) δ ppm 1.17 (d, J=6.55 Hz, 6H) 1.63-1.72 (m, 2H) 1.72-1.87 (m, 2H) 2.14-2.27 (m, 2H) 2.37-2.48 (m, 4H) 2.58-2.63 (m, 1H) 2.69-2.89 (m, 2H) 3.60 (s, 2H) 3.62-3.74 (m, 4H) 4.01-4.19 (m, 1H) 4.82-5.02 (m, 1H) 7.21 (d, J=8.31 Hz, 1H) 7.26-7.35 (m, 2H) 7.55 (d, J=8.12 Hz, 1H) 7.65-7.73 (m, 2H) 8.22-8.49 (m, 2H) 12.80 (s, 1H).

Example 42

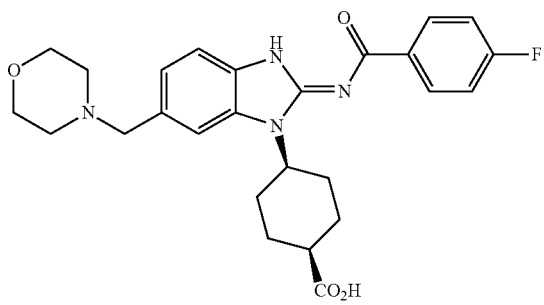 [SMILES: O=C(/N=c1\[nH]c2ccc(CN3CCOCC3)cc2n1[C@H]1CC[C@@H](C(=O)O)CC1)c1ccc(F)cc1]

cis-4-((E)-2-(4-Fluorobenzoylimino)-6-(morpholinomethyl)-2,3-dihydro-1H-benzo[d]imidazol-1-yl)cyclohexanecarboxylic acid The title compound was prepared in 4 steps from cis-methyl 4-(2-amino-6-((triisopropylsilyloxy)methyl)-1H-benzo[d]imidazol-1-yl)cyclohexanecarboxylate using a method analogous to the preparation of cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid. MS m/z=481.2 [M+H]. Calc'd for $C_{26}H_{29}FN_4O_4$: 480.2.

Example 43

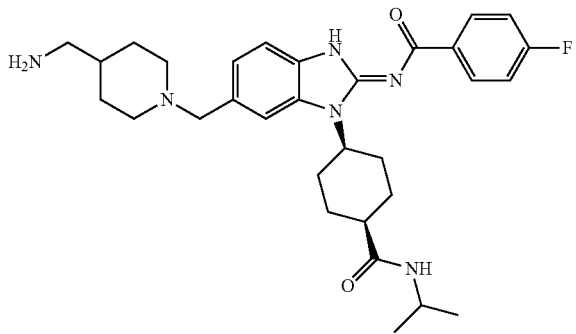 [SMILES: CC(C)NC(=O)[C@H]1CC[C@@H](n2/c(=N/C(=O)c3ccc(F)cc3)[nH]c3ccc(CN4CCC(CN)CC4)cc32)CC1]

(E)-N-(6-((4-(Aminomethyl)piperidin-1-yl)methyl)-1-(cis-4-(isopropylcarbamoyl)cyclohexyl)-1H-benzo[d]imidazol-2(3H)-ylidene)-4-fluorobenzamide

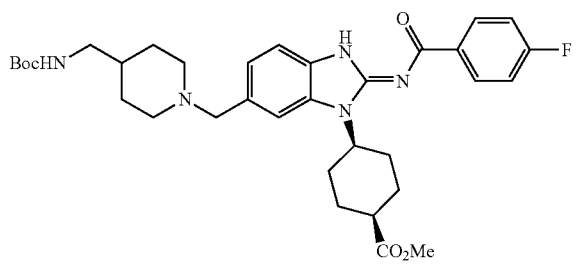 [SMILES: COC(=O)[C@H]1CC[C@@H](n2/c(=N/C(=O)c3ccc(F)cc3)[nH]c3ccc(CN4CCC(CNC(=O)OC(C)(C)C)CC4)cc32)CC1]

Step A: cis-Methyl 4-((E)-6-((4-((tert-butoxycarbonylamino)methyl)piperidin-1-yl)methyl)-2-(4-fluorobenzoylimino)-2,3-dihydro-1H-benzo[d]imidazol-1-yl)cyclohexanecarboxylate The title compound was prepared from cis-methyl 4-((E)-2-(4-fluorobenzoylimino)-6-(hydroxymethyl)-2,3-dihydro-1H-benzo[d]imidazol-1-yl)cyclohexanecarboxylate and tert-butyl piperidin-4-ylmethylcarbamate using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (45 mg, 77% yield). MS m/z=622.2 [M+H]. Calc'd for $C_{34}H_{44}FN_5O_5$: 621.3.

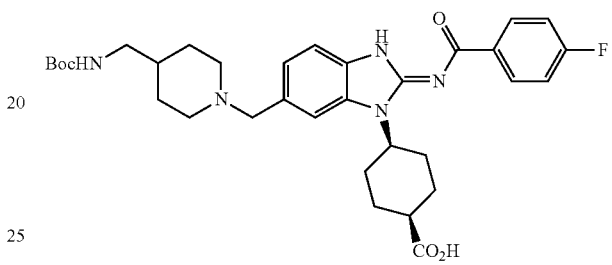

Step B: cis-4-((E)-6-((4-((tert-Butoxycarbonylamino)methyl)piperidin-1-yl)methyl)-2-(4-fluorobenzoylimino)-2,3-dihydro-1H-benzo[d]imidazol-1-yl)cyclohexanecarboxylic acid The title compound was prepared from cis-methyl 4-((E)-6-((4-((tert-butoxycarbonylamino)methyl)piperidin-1-yl)methyl)-2-(4-fluorobenzoylimino)-2,3-dihydro-1H-benzo[d]imidazol-1-yl)cyclohexanecarboxylate using a method analogous to the preparation of cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid (440 mg, 100% yield). MS m/z=608.2 [M+H]. Calc'd for $C_{33}H_{42}FN_5O_5$: 607.3.

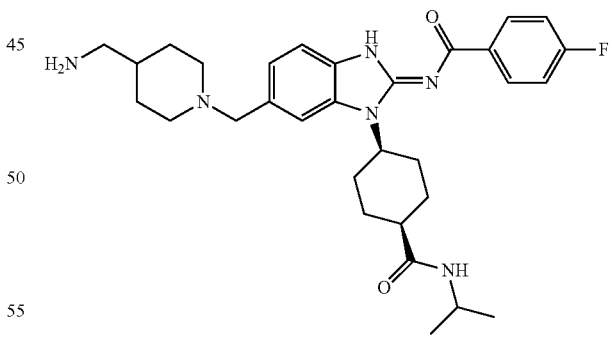

Step C: (E)-N-(6-((4-(Aminomethyl)piperidin-1-yl)methyl)-1-(cis-4-(isopropylcarbamoyl)cyclohexyl)-1H-benzo[d]imidazol-2(3H)-ylidene)-4-fluorobenzamide A suspension of cis-4-((E)-6-((4-((tert-butoxycarbonylamino)methyl)piperidin-1-yl)methyl)-2-(4-fluorobenzoylimino)-2,3-dihydro-1H-benzo[d]imidazol-1-yl)cyclohexanecarboxylic acid (0.57 g, 0.94 mmol) in thionyl chloride (6.85 mL, 94 mmol) under nitrogen atmosphere was stirred for 30 minutes at RT and then concentrated to dryness. The residue was suspended in THF (9.4 mL) and cooled in an ice bath under nitrogen atmosphere. To the resulting mixture was added isopropylamine (0.804 mL, 9.38 mmol) as a solution in THF (1 mL). The ice bath was removed and the mixture was stirred for 1 hour at RT. The resulting mixture was diluted with water (10 mL) and the aqueous layer extracted with DCM (30 mL). The organic layer was dried over sodium sulfate and concentrated to dryness under high vacuum to afford a tan solid. The solid was suspended in HCl (4.0M in dioxanes) (23.45 mL, 94 mmol) and stirred for 16 hours. The mixture was concentrated, suspended in DCM and washed with aqueous NaHCO$_3$ solution. The organic portion was collected, dried over sodium sulfate, and concentrated to dryness under high vacuum to afford a tan solid. The solid was purified by silica gel chromatography (1-10% MeOH/DCM (1% NH$_4$OH)) to afford (E)-N-(6-((4-(aminomethyl)piperidin-1-yl)methyl)-1-(cis-4-(isopropylcarbamoyl)cyclohexyl)-1H-benzo[d]imidazol-2(3H)-ylidene)-4-fluorobenzamide (0.3 g, 58.3% yield). MS m/z=549.2 [M+H]. Calc'd for C$_{31}$H$_{41}$FN$_6$O$_2$: 548.3.

Example 44

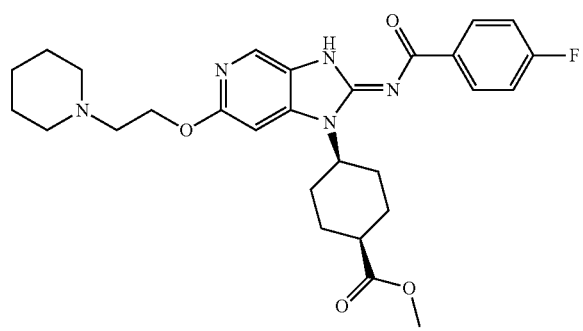 [SMILES: COC(=O)[C@H]1CC[C@@H](n2/c(=N/C(=O)c3ccc(F)cc3)[nH]c3cnc(OCCN4CCCCC4)cc32)CC1]

cis-Methyl 4-((E)-2-(4-fluorobenzoylimino)-6-(2-(piperidin-1-yl)ethoxy)-2,3-dihydro-1H-imidazo[4,5-c]pyridin-1-yl)cyclohexanecarboxylate The title compound was prepared from cis-methyl 4-(5-amino-2-(2-(piperidin-1-yl)ethoxy)pyridin-4-ylamino)cyclohexanecarboxylate and 4-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (100 mg, 55.3% yield). MS m/z=524.2 [M+H]. Calc'd for C$_{28}$H$_{34}$FN$_5$O$_4$: 523.3. $^1$H NMR (400 MHz, DMSO-d$_6$) δ ppm 1.19-1.30 (m, 2H) 1.34-1.45 (m, 2H) 1.46-1.60 (m, 4H) 1.66-1.91 (m, 5H) 2.17-2.27 (m, 2H) 2.35-2.49 (m, 3H) 2.53-2.62 (m, 2H) 2.78-2.90 (m, 1H) 3.75 (s, 3H) 4.29-4.46 (m, 2H) 4.55-4.70 (m, 1H) 6.94 (s, 1H) 7.23-7.36 (m, 2H) 8.19-8.31 (m, 3H) 12.70 (s, 1H).

Example 45

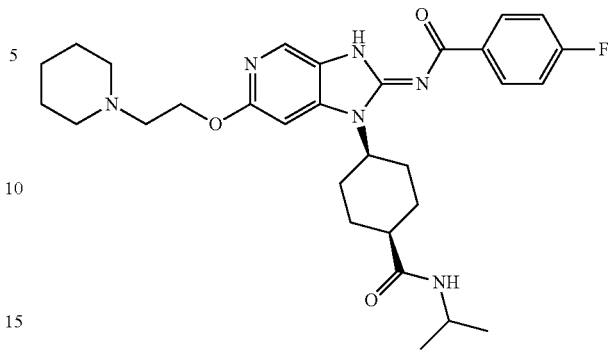

(E)-4-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The title compound was prepared in 2 steps from cis-methyl 4-((E)-2-(4-fluorobenzoylimino)-6-(2-(piperidin-1-yl)ethoxy)-2,3-dihydro-1H-imidazo[4,5-c]pyridin-1-yl)cyclohexanecarboxylate using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (15 mg, 25.2% yield). MS m/z=551.2 [M+H]. Calc'd for C$_{30}$H$_{39}$FN$_6$O$_3$: 550.3. $^1$H NMR (400 MHz, DMSO-d$_6$) δ ppm 1.15 (d, J=6.46 Hz, 6H) 1.24-1.35 (m, 1H) 1.35-1.48 (m, 2H) 1.48-1.62 (m, 4H) 1.61-1.88 (m, 4H) 2.02-2.25 (m, 2H) 2.37-2.53 (m, 4H) 2.64-2.87 (m, 4H) 3.90-4.16 (m, 1H) 4.29-4.50 (m, 2H) 4.74-4.95 (m, 1H) 7.08 (s, 1H) 7.23-7.44 (m, 2H) 7.58-7.89 (m, 1H) 8.03-8.56 (m, 3H) 12.68 (s, 1H).

Example 46

(E)-4-Fluoro-N-(1-(cis-4-(isopropyl(methyl)carbamoyl)cyclohexyl)-6-(piperidin-1-ylmethyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (10 mg, 22.4% yield). MS m/z=534.2 [M+H]. Calc'd for C$_{31}$H$_{40}$FN$_5$O$_2$: 533.3

Example 47

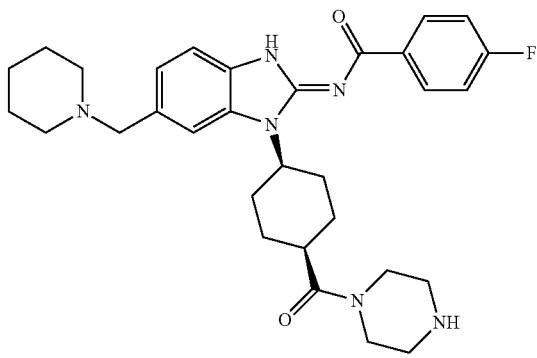 [SMILES: O=C(/N=c1\[nH]c2ccc(CN3CCCCC3)cc2n1[C@H]1CC[C@@H](C(=O)N2CCNCC2)CC1)c1ccc(F)cc1]

(E)-4-Fluoro-N-(1-(cis-4-(piperazine-1-carbonyl)cyclohexyl)-6-(piperidin-1-ylmethyl)-1H-benzo[d]imidazol-2(3H)-ylidene)benzamide The title compound was prepared from cis-4-((E)-2-(4-fluorobenzoylimino)-6-(piperidin-1-ylmethyl)-2,3-dihydro-1H-benzo[d]imidazol-1-yl)cyclohexanecarboxylic acid using a method analogous to the preparation of (E)-N-(1-(cis-4-(ethylcarbamoyl)cyclohexyl)-6-(piperidin-1-ylmethyl)-1H-benzo[d]imidazol-2(3H)-ylidene)-4-fluorobenzamide (12 mg, 26.3% yield). MS m/z=547.2 [M+H]. Calc'd for $C_{31}H_{39}FN_6O_2$: 546.3. $^1$H NMR (400 MHz, MeOH) δ ppm 1.25-1.38 (m, 1H) 1.49-1.66 (m, 1H) 1.76-2.05 (m, 9H) 2.08-2.21 (m, 2H) 2.87-3.00 (m, 2H) 2.99-3.11 (m, 2H) 3.17-3.26 (m, 1H) 3.32-3.37 (m, 4H) 3.48-3.66 (m, 2H) 3.84-4.06 (m, 4H) 4.49 (s, 2H) 4.89-5.01 (m, 1H) 7.25-7.36 (m, 2H) 7.57-7.65 (m, 1H) 7.73-7.81 (m, 1H) 8.13-8.20 (m, 1H) 8.22-8.33 (m, 2H).

Example 48

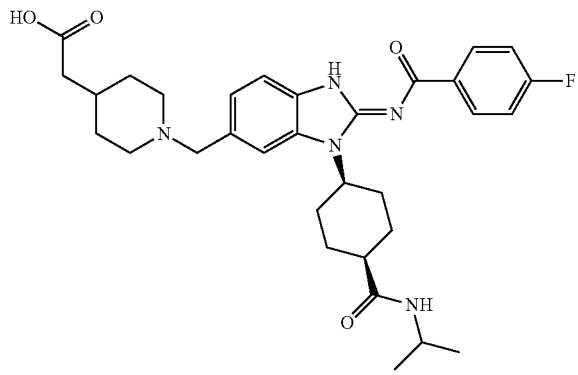 [SMILES: CC(C)NC(=O)[C@H]1CC[C@@H](n2/c(=N/C(=O)c3ccc(F)cc3)[nH]c3ccc(CN4CCC(CC(=O)O)CC4)cc32)CC1]

2-(1-(((E)-2-(4-Fluorobenzoylimino)-3-(cis-4-(isopropylcarbamoyl)cyclohexyl)-2,3-dihydro-1H-benzo[d]imidazol-5-yl)methyl)piperidin-4-yl)acetic acid The title compound was prepared from with (E)-4-fluoro-N-(6-(hydroxymethyl)-1-(cis-4-(isopropylcarbamoyl)cyclohexyl)-1H-benzo[d]imidazol-2(3H)-ylidene)benzamide using a method analogous to the preparation of 1-(((E)-2-(4-fluorobenzoylimino)-3-(cis-4-(isopropylcarbamoyl)cyclohexyl)-2,3-dihydro-1H-benzo[d]imidazol-5-yl)methyl)piperidine-2-carboxylic acid (20 mg, 18.6% yield, 3 steps). MS m/z=578.2 [M+H]. Calc'd for $C_{32}H_{40}FN_5O_4$: 577.3.

Example 49

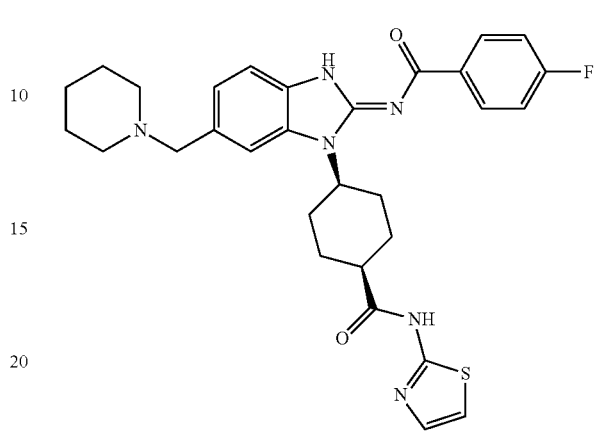

(E)-4-Fluoro-N-(6-(piperidin-1-ylmethyl)-1-(cis-4-(thiazol-2-ylcarbamoyl)cyclohexyl)-1H-benzo[d]imidazol-2(3H)-ylidene)benzamide A round bottom flask under nitrogen atmosphere was charged with cis-4-((E)-2-(4-fluorobenzoylimino)-6-(piperidin-1-ylmethyl)-2,3-dihydro-1H-benzo[d]imidazol-1-yl)cyclohexanecarboxylic acid (50 mg, 0.104 mmol), N,N-dimethylpyridin-4-amine (31.9 mg, 0.261 mmol), thiazol-2-amine (15.69 mg, 0.157 mmol), and DMF (2 mL). To this mixture was added EDC (40.1 mg, 0.209 mmol), and the reaction was stirred for 48 hours. The resulting mixture was diluted with water (10 mL) and DCM (30 mL). The organic layer was collected, dried over sodium sulfate and concentrated to afford a brown oil. The residual oil was purified by HPLC (10-70% ACN/H$_2$O; 0.1% TFA) to afford (E)-4-fluoro-N-(6-(piperidin-1-ylmethyl)-1-(cis-4-(thiazol-2-ylcarbamoyl)cyclohexyl)-1H-benzo[d]imidazol-2(3H)-ylidene)benzamide (0.027 g, 46.1% yield). MS m/z=561.2 [M+H]. Calc'd for $C_{30}H_{33}FN_6O_2S$: 560.2. $^1$H NMR (400 MHz, DMSO-d$_6$) δ ppm 1.23-1.36 (m, 1H) 1.36-1.48 (m, 2H) 1.50-1.60 (m, 4H) 1.68-1.84 (m, 2H) 1.86-2.01 (m, 2H) 2.26-2.37 (m, 2H) 2.40-2.50 (m, 3H) 2.75-2.90 (m, 2H) 2.98-3.10 (m, 1H) 3.63 (s, 2H) 4.77-5.08 (m, 1H) 7.18-7.24 (m, 1H) 7.24-7.32 (m, 2H) 7.36 (d, J=3.62 Hz, 1H) 7.52-7.59 (m, 2H) 7.66 (s, 1H) 8.30-8.42 (m, 2H) 12.21 (s, 1H) 12.83 (s, 1H).

Example 50

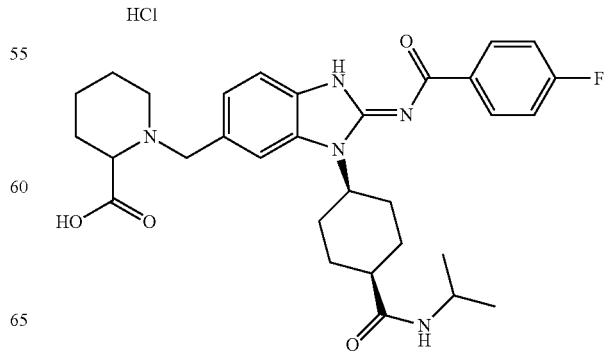

1-(((E)-2-(4-Fluorobenzoylimino)-3-(cis-4-(isopropylcarbamoyl)cyclohexyl)-2,3-dihydro-1H-benzo[d]imidazol-5-yl)methyl)piperidine-2-carboxylic acid hydrochloride A round bottom flask was charged with (E)-4-fluoro-N-(6-(hydroxymethyl)-1-(cis-4-(isopropylcarbamoyl)cyclohexyl)-1H-benzo[d]imidazol-2(3H)-ylidene)benzamide (0.042 g, 0.093 mmol) and DCM (1 mL). The resulting suspension was cooled to 0° C. under nitrogen atmosphere. To this mixture was added thionyl chloride (0.110 g, 0.928 mmol), and the resulting mixture was stirred at RT for 30 minutes. The mixture was concentrated under reduced pressure, and the residue was dissolved in DMSO (2 mL). To this mixture was added tert-butyl piperidine-2-carboxylate (0.100 g, 0.538 mmol), and the reaction mixture was stirred for 2 hours. The reaction mixture was diluted with water (2 mL) and extracted with DCM (10 mL). The organic layer was collected and dried over sodium sulfate and concentrated. The residue was purified by HPLC (10-70% ACN/Water, 0.1% TFA) to afford the t-butyl ester intermediate. This material was dissolved in HCl (4M in dioxanes) (1.160 mL, 4.64 mmol) and stirred for 16 hours. The resulting mixture was concentrated and dried under high vacuum to afford 1-(((E)-2-(4-fluorobenzoylimino)-3-(cis-4-(isopropylcarbamoyl)cyclohexyl)-2,3-dihydro-1H-benzo[d]imidazol-5-yl)methyl)piperidine-2-carboxylic acid hydrochloride (0.02 g, 35.9% yield). MS m/z=564.2 [M+H]. Calc'd for $C_{31}H_{38}FN_5O_4$: 563.3.

Example 51

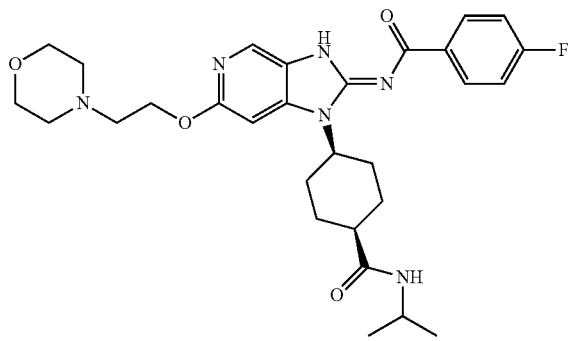 [SMILES: CC(C)NC(=O)[C@H]1CC[C@@H](n2/c(=N/C(=O)c3ccc(F)cc3)[nH]c3cnc(OCCN4CCOCC4)cc32)CC1]

(E)-4-Fluoro-N-(1-(cis-4-(isopropylcarbamoyl)cyclohexyl)-6-(2-morpholinoethoxy)-1H-imidazo[4,5-c]pyridin-2(3H)-ylidene)benzamide The title compound was prepared in 3 steps from cis-4-(2-chloro-5-nitropyridin-4-ylamino)-N-isopropylcyclohexanecarboxamide using a method analogous to the preparation of tert-butyl 2-(4-((E)-2-(4-fluorobenzoylimino)-1-(cis-4-(isopropylcarbamoyl)cyclohexyl)-2,3-dihydro-1H-imidazo[4,5-c]pyridin-6-yloxy)piperidin-1-yl)acetate (60 mg, 33.9% yield, last step). MS m/z=553.2 [M+H]. Calc'd for $C_{29}H_{37}FN_6O_4$: 552.3. $^1$H NMR (400 MHz, DMSO-$d_6$) δ ppm 1.15 (d, J=6.55 Hz, 6H) 1.25-1.35 (m, 2H) 1.59-1.71 (m, 2H) 1.72-1.86 (m, 2H) 2.05-2.21 (m, 2H) 2.49-2.55 (m, 4H) 2.66-2.84 (m, 4H) 3.54-3.69 (m, 4H) 3.96-4.12 (m, 1H) 4.36-4.54 (m, 2H) 4.77-4.97 (m, 1H) 7.08 (s, 1H) 7.27-7.37 (m, 2H) 7.75 (d, J=7.63 Hz, 1H) 8.29 (s, 1H) 8.33-8.43 (m, 2H) 12.75 (s, 1H).

Example 52

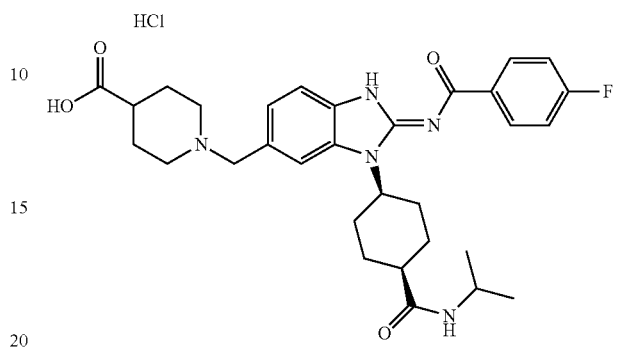

1-(((E)-2-(4-Fluorobenzoylimino)-3-(cis-4-(isopropylcarbamoyl)cyclohexyl)-2,3-dihydro-1H-benzo[d]imidazol-5-yl)methyl)piperidine-4-carboxylic acid hydrochloride To a cooled (0° C.) suspension of (E)-4-fluoro-N-(6-(hydroxymethyl)-1-(cis-4-(isopropylcarbamoyl)cyclohexyl)-1H-benzo[d]imidazol-2(3H)-ylidene)benzamide (0.062 g, 0.137 mmol) in DCM (2 mL) under nitrogen atmosphere was added thionyl chloride (0.163 g, 1.370 mmol) dropwise via syringe. The reaction mixture was stirred at RT for 30 minutes and was concentrated under reduced pressure. The resulting residue was dissolved in DMSO (2 mL) and tert-butyl piperidine-4-carboxylate (230 mg, 1.24 mmol) was added in one portion. The resulting mixture was stirred for 2 hours at RT. The mixture was diluted with water (10 mL) and extracted with DCM (20 mL). The organic layer was collected, dried over sodium sulfate, concentrated, and purified by HPLC (10-70% ACN/Water, 0.1% TFA) to afford the t-Butyl ester intermediate. This intermediate was suspended in HCl (4M in dioxanes) (1.028 mL, 4.11 mmol) and stirred for 16 hours. The reaction mixture was concentrated to dryness, and the residue was triturated with 1 mL of anhydrous dioxane to afford 1-(((E)-2-(4-fluorobenzoylimino)-3-(cis-4-(isopropylcarbamoyl)cyclohexyl)-2,3-dihydro-1H-benzo[d]imidazol-5-yl)methyl)piperidine-4-carboxylic acid hydrochloride (0.02 g, 24.32% yield). MS m/z=564.2 [M+H]. Calc'd for $C_{31}H_{38}FN_5O_4$: 563.3.

Example 53

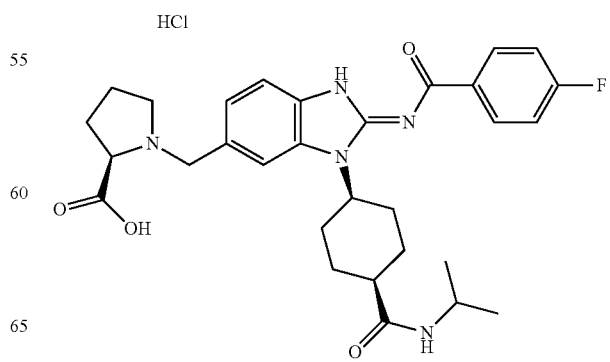

(R)-1-(((E)-2-(4-Fluorobenzoylimino)-3-(cis-4-(isopropylcarbamoyl)cyclohexyl)-2,3-dihydro-1H-benzo[d]imidazol-5-yl)methyl)pyrrolidine-2-carboxylic acid hydrochloride The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide using a method analogous to the preparation of 1-(((E)-2-(4-fluorobenzoylimino)-3-(cis-4-(isopropylcarbamoyl)cyclohexyl)-2,3-dihydro-1H-benzo[d]imidazol-5-yl)methyl)piperidine-4-carboxylic acid hydrochloride (10 mg, 11.9% yield). MS m/z=550.2 [M+H]. Calc'd for $C_{30}H_{36}FN_5O_4$: 549.3.

Example 54

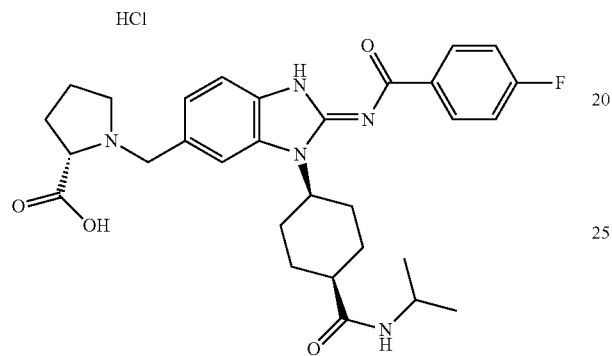

(S)-1-(((E)-2-(4-Fluorobenzoylimino)-3-(cis-4-(isopropylcarbamoyl)cyclohexyl)-2,3-dihydro-1H-benzo[d]imidazol-5-yl)methyl)pyrrolidine-2-carboxylic acid hydrochloride The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide using a method analogous to the preparation of 1-(((E)-2-(4-fluorobenzoylimino)-3-(cis-4-(isopropylcarbamoyl)cyclohexyl)-2,3-dihydro-1H-benzo[d]imidazol-5-yl)methyl)piperidine-4-carboxylic acid hydrochloride (23 mg, 27.4% yield). MS m/z=550.2 [M+H]. Calc'd for $C_{30}H_{36}FN_5O_4$: 549.3.

Example 55

There is no Example that corresponds to Example 55.

Example 56

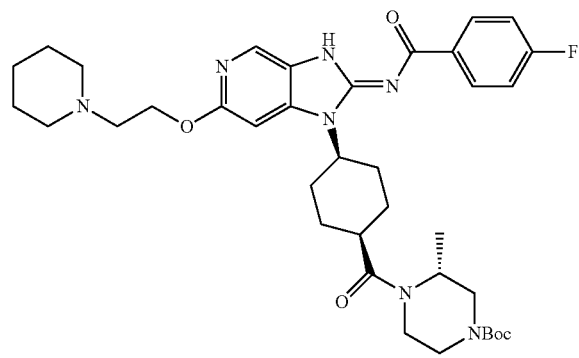 [SMILES: C[C@@H]1CN(C(=O)OC(C)(C)C)CCN1C(=O)[C@H]1CC[C@@H](n2/c(=N/C(=O)c3ccc(F)cc3)[nH]c3cnc(OCCN4CCCCC4)cc32)CC1]

(R)-tert-Butyl 4-(cis-4-((E)-2-(4-fluorobenzoylimino)-6-(2-(piperidin-1-yl)ethoxy)-2,3-dihydro-1H-imidazo[4,5-c]pyridin-1-yl)cyclohexanecarbonyl)-3-methylpiperazine-1-carboxylate

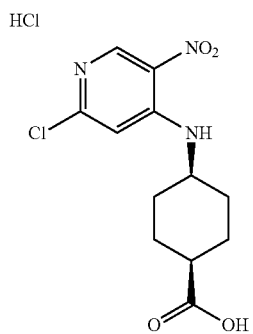 [SMILES: Cl ; O=C(O)[C@H]1CC[C@@H](Nc2cc(Cl)ncc2[N+](=O)[O-])CC1]

Step A: cis-4-(2-Chloro-5-nitropyridin-4-ylamino)cyclohexanecarboxylic acid hydrochloride To a suspension of cis-methyl 4-(2-chloro-5-nitropyridin-4-ylamino)cyclohexanecarboxylate (2.51 g, 8.00 mmol) in dioxane (10 mL) was added 4N aqueous HCl (52.0 mL, 208 mmol), and the resulting mixture was stirred at 60° C. for 3 hours. The mixture was concentrated to dryness to afford cis-4-(2-chloro-5-nitropyridin-4-ylamino)cyclohexanecarboxylic acid hydrochloride as a yellow solid (2.69 g, 100% yield). MS m/z=300.2 [M+H]. Calc'd for $C_{12}H_{14}ClN_3O_4$: 299.1.

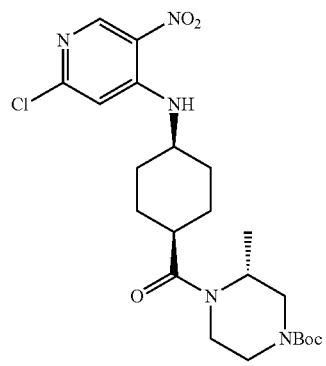 [SMILES: C[C@@H]1CN(C(=O)OC(C)(C)C)CCN1C(=O)[C@H]1CC[C@@H](Nc2cc(Cl)ncc2[N+](=O)[O-])CC1]

Step B: (R)-tert-Butyl 4-(cis-4-(2-chloro-5-nitropyridin-4-ylamino)cyclohexanecarbonyl)-3-methylpiperazine-1-carboxylate A suspension of cis-4-(2-chloro-5-nitropyridin-4-ylamino)cyclohexanecarboxylic acid hydrochloride (0.5 g, 1.487 mmol) in thionyl chloride (10.86 mL, 149 mmol) was heated at 70° C. for 1.5 hours. The mixture was concentrated under reduced pressure and dried under high vacuum for 1 hour. The resulting solid was suspended in THF (14.87 mL) and cooled to 0° C. under nitrogen atmosphere. To this mixture was added (R)-tert-butyl 3-methylpiperazine-1-carboxylate (0.357 g, 1.785 mmol) as a solution in THF (5 mL). The ice bath was removed, and the reaction mixture was stirred overnight at RT. The resulting mixture was diluted with DCM (100 mL) and washed with saturated aqueous $NaHCO_3$ solution (30 mL) and then with saturated aqueous ammonium chloride solution (2×). The organic phase was collected, dried over sodium sulfate, and concentrated under reduced pressure to afford (R)-tert-butyl 4-(cis-4-(2-chloro-5-nitropyridin-4-ylamino)cyclohexanecarbonyl)-3-methylpiperazine-1-carboxylate as a light yellow solid (0.55 g, 77% yield). MS m/z=482.2 [M+H]. Calc'd for $C_{22}H_{32}ClN_5O_5$: 481.2.

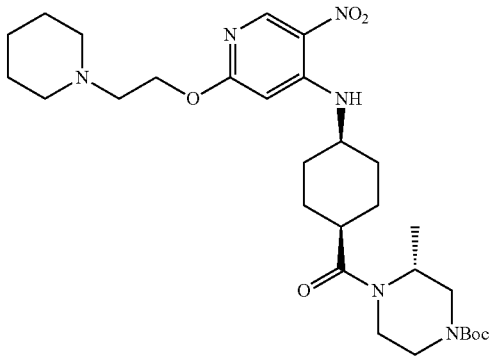 [SMILES: C[C@@H]1CN(C(=O)OC(C)(C)C)CCN1C(=O)[C@H]1CC[C@@H](Nc2cc(OCCN3CCCCC3)ncc2[N+](=O)[O-])CC1]

Step C: (R)-tert-Butyl 3-methyl-4-(cis-4-(5-nitro-2-(2-(piperidin-1-yl)ethoxy)pyridin-4-ylamino)cyclohexanecarbonyl)piperazine-1-carboxylate To a solution of (R)-tert-butyl 4-(cis-4-(2-chloro-5-nitropyridin-4-ylamino)cyclohexanecarbonyl)-3-methylpiperazine-1-carboxylate (0.4 g, 0.830 mmol) in toluene (8.30 mL) was added 2-(piperidin-1-yl)ethanol (0.536 g, 4.15 mmol), 18-crown-6 (0.329 g, 1.245 mmol), and cesium carbonate (0.811 g, 2.490 mmol). The reaction was purged with argon and stirred at 75° C. overnight. The mixture was diluted with EtOAc to about 50 mL total volume and washed sequentially with water (50 mL), brine (50 mL), and aqueous $NH_4Cl$ (2×50 mL). The organic layer was dried over sodium sulfate and concentrated to afford an orange residue. The residue was purified by silica gel chromatography (1-5% MeOH/DCM, 1% $NH_4OH$) to afford (R)-tert-butyl 3-methyl-4-(cis-4-(5-nitro-2-(2-(piperidin-1-yl)ethoxy)pyridin-4-ylamino)cyclohexanecarbonyl)piperazine-1-carboxylate as a tan solid (0.33 g, 69.2% yield). MS m/z=575.4 [M+H]. Calc'd for $C_{29}H_{46}N_6O_6$: 574.4.

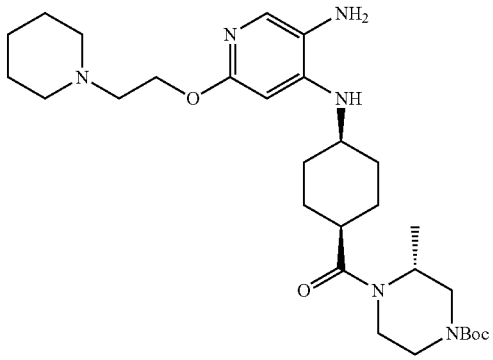

Step D: (R)-tert-Butyl 4-(cis-4-(5-amino-2-(2-(piperidin-1-yl)ethoxy)pyridin-4-ylamino)cyclohexanecarbonyl)-3-methylpiperazine-1-carboxylate To a suspension of (R)-tert-butyl 3-methyl-4-(cis-4-(5-nitro-2-(2-(piperidin-1-yl)ethoxy)pyridin-4-ylamino)cyclohexanecarbonyl)piperazine-1-carboxylate (0.2 g, 0.348 mmol) in MeOH (3.48 mL) was added tin(II) chloride (0.264 g, 1.392 mmol). The resulting suspension was stirred at 80° C. for 2 hours. The mixture was cooled to RT, diluted with EtOAc and washed with 1N aqueous NaOH. The organic layer was collected, dried over sodium sulfate and concentrated to afford (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate as a tan solid (190 mg, 100%). MS m/z=545.4 [M+H]. Calc'd for $C_{29}H_{48}N_6O_4$: 544.4.

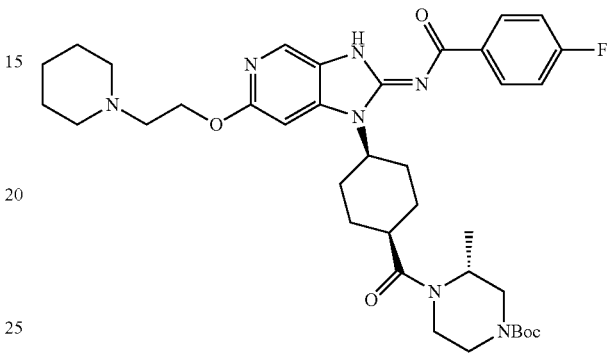

Step E: (R)-tert-Butyl 4-(cis-4-((E)-2-(4-fluorobenzoylimino)-6-(2-(piperidin-1-yl)ethoxy)-2,3-dihydro-1H-imidazo[4,5-c]pyridin-1-yl)cyclohexanecarbonyl)-3-methylpiperazine-1-carboxylate The title compound was prepared from (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate and 4-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (80 mg, 67.0% yield). MS m/z=692.4 [M+H]. Calc'd for $C_{37}H_{50}FN_7O_5$: 691.4.

Example 57

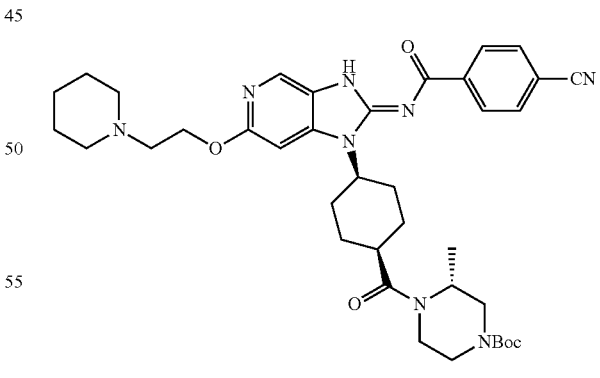

(R)-tert-Butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexanecarbonyl)-3-methylpiperazine-1-carboxylate The title compound was prepared from (R)-tert-butyl 4-(cis-4-(5-amino-2-(2-(piperidin-1-yl)ethoxy)pyridin-4-

141 ylamino)cyclohexanecarbonyl)-3-methylpiperazine-1-carboxylate and 4-cyanobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (84 mg, 57.4% yield). MS m/z=699.4 [M+H]. Calc'd for $C_{38}H_{50}N_8O_5$: 698.4.

Example 58

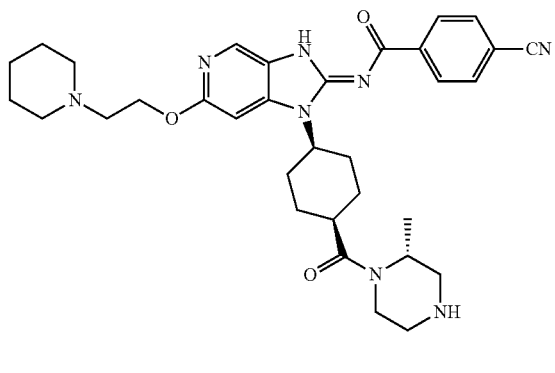 [SMILES: C[C@@H]1CNCCN1C(=O)[C@H]1CC[C@@H](n2/c(=N/C(=O)c3ccc(C#N)cc3)[nH]c3cnc(OCCN4CCCCC4)cc32)CC1]

(E)-4-Cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide A suspension of (R)-tert-butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexanecarbonyl)-3-methylpiperazine-1-carboxylate (0.07 g, 0.100 mmol) in HCl (4M in dioxanes) (1.252 mL, 5.01 mmol) was stirred at RT for 16 hours. The mixture was concentrated under reduced pressure, and the residue was suspended in DCM (20 mL) and washed with aqueous $NaHCO_3$ solution (10 mL). The organic layer was collected, dried over sodium sulfate and concentrated to afford a brown solid. This material was purified by silica gel chromatography to afford (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide (10 mg, 16.7% yield). MS m/z=599.4 [M+H]. Calc'd for $C_{33}H_{42}N_8O_3$: 598.3.

Example 59

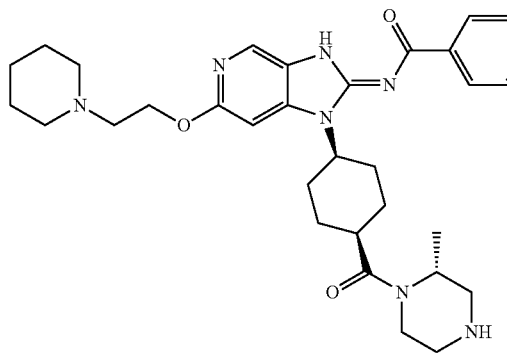

142

(E)-4-Fluoro-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide The title compound was prepared from (R)-tert-butyl 4-(cis-4-((E)-2-(4-fluorobenzoylimino)-6-(2-(piperidin-1-yl)ethoxy)-2,3-dihydro-1H-imidazo[4,5-c]pyridin-1-yl)cyclohexanecarbonyl)-3-methylpiperazine-1-carboxylate using a method analogous to the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide (30 mg, 50.1% yield). MS m/z=592.2 [M+H]. Calc'd for $C_{32}H_{42}FN_7O_3$: 591.3. $^1$H NMR (400 MHz, DMSO-$d_6$) δ ppm 1.23-1.26 (m, 1H) 1.36-1.43 (m, 2H) 1.48 (s, 9H) 1.49-1.54 (m, 4H) 1.76-1.86 (m, 2H) 2.40-2.47 (m, 4H) 2.54-2.59 (m, 1H) 2.61-2.70 (m, 2H) 2.84-3.08 (m, 2H) 4.09-4.23 (m, 2H) 4.29-4.43 (m, 2H) 4.73-4.91 (m, 1H) 7.00 (s, 1H) 7.41-7.48 (m, 2H) 7.49-7.59 (m, 1H) 8.15-8.20 (m, 2H) 8.23 (s, 1H) 12.72 (s, 1H).

Example 60

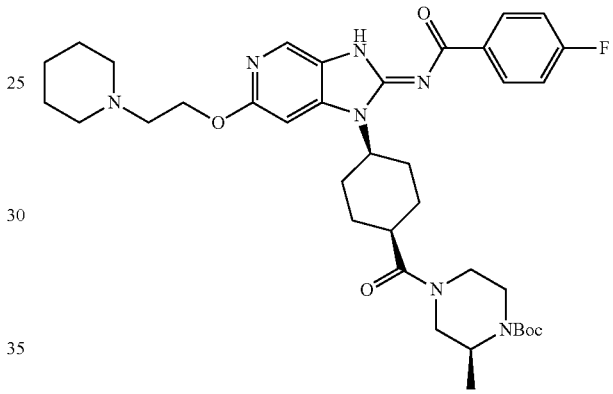

(S)-tert-Butyl 4-(cis-4-((E)-2-(4-fluorobenzoylimino)-6-(2-(piperidin-1-yl)ethoxy)-2,3-dihydro-1H-imidazo[4,5-c]pyridin-1-yl)cyclohexanecarbonyl)-2-methylpiperazine-1-carboxylate The title compound was prepared in 4 steps from (S)-tert butyl 2-methylpiperazine-1-carboxylate using a method analogous to the preparation of cis-methyl 4-((E)-2-(benzoylimino)-2,3-dihydro-1H-imidazo[4,5-c]pyridin-1-yl)cyclohexanecarboxylate (90 mg, 59.1% yield, last step). MS m/z=692.2 [M+H]. Calc'd for $C_{37}H_{50}FN_7O_5$: 691.4.

Example 61

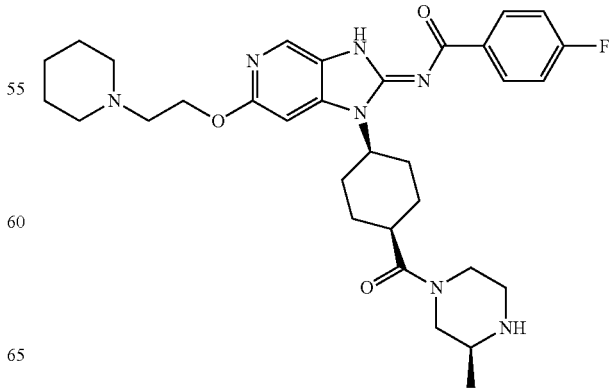

143

(E)-4-Fluoro-N-(1-(cis-4-((S)-3-methylpiperazine-1-carbonyl)cyclohexyl)-6-(2-(piperidin-1-yl)ethoxy)-1H-imidazo[4,5-c]pyridin-2(3H)-ylidene)benzamide The title compound was prepared from (5)-tert-butyl 4-(cis-4-((E)-2-(4-fluorobenzoylimino)-6-(2-(piperidin-1-yl)ethoxy)-2,3-dihydro-1H-imidazo[4,5-c]pyridin-1-yl)cyclohexanecarbonyl)-2-methylpiperazine-1-carboxylate using a method analogous to the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide (30 mg, 50.1% yield). MS m/z=592.2 [M+H]. Calc'd for $C_{32}H_{42}FN_7O_3$: 591.3.

Example 62

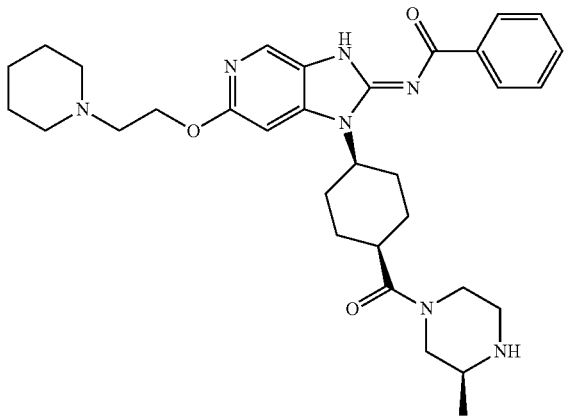 [SMILES: C[C@H]1CN(C(=O)[C@H]2CC[C@@H](n3/c(=N/C(=O)c4ccccc4)[nH]c4cnc(OCCN5CCCCC5)cc43)CC2)CCN1]

(E)-4-Fluoro-N-(1-(cis-4-((S)-3-methylpiperazine-1-carbonyl)cyclohexyl)-6-(2-(piperidin-1-yl)ethoxy)-1H-imidazo[4,5-c]pyridin-2(3H)-ylidene)benzamide The title compound was prepared in 5 steps from (S)-tert butyl 2-methylpiperazine-1-carboxylate using a method analogous to the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide. MS m/z=574.2 [M+H]. Calc'd for $C_{32}H_{43}N_7O_3$: 573.3.

Example 63

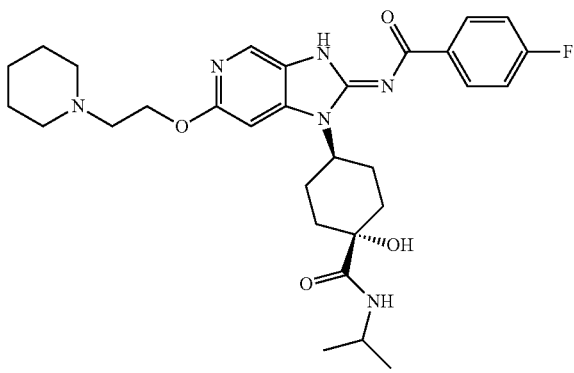 [SMILES: CC(C)NC(=O)[C@]1(O)CC[C@H](n2/c(=N/C(=O)c3ccc(F)cc3)[nH]c3cnc(OCCN4CCCCC4)cc32)CC1]

144

(E)-4-Fluoro-N-(1-(trans-4-hydroxy-4-(isopropylcarbamoyl)cyclohexyl)-6-(2-(piperidin-1-yl)ethoxy)-1H-imidazo[4,5-c]pyridin-2(3H)-ylidene)benzamide

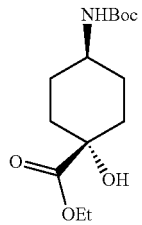 [SMILES: CCOC(=O)[C@]1(O)CC[C@H](NC(=O)OC(C)(C)C)CC1]

Step A: trans-Ethyl 4-(tert-butoxycarbonylamino)-1-hydroxycyclohexanecarboxylate To dry THF (60 mL) was added diisopropylamine (6.41 mL, 45.7 mmol). The mixture was cooled to −78° C. and n-butyllithium solution (29.9 mL, 47.8 mmol of 1.6M solution in hexanes) was added with stirring. The resulting mixture was stirred at −78° C. for 1 hour. A solution of ethyl 4-(tert-butoxycarbonylamino)cyclohexanecarboxylate (5.64 g, 20.78 mmol) in dry THF (40 mL) was added dropwise with stirring over 10 minutes via cannula, and the resulting mixture was stirred at −78° C. for 1.5 hours. A stream of dry air was passed through the mixture for 1.5 hours. The cooling bath was removed, and the mixture was stirred at RT for 60 hours. Saturated aqueous $Na_2S_2O_3$ and EtOAc were then added, and the mixture was stirred vigorously for 30 minutes. The organic layer was separated, washed with brine, and the solvent was removed. The residue was purified by silica gel chromatography (50% EtOAc/Hexane) ($KMnO_4$ stain) to afford cis-ethyl 4-(tert-butoxycarbonylamino)-1-hydroxycyclohexanecarboxylate (346 mg, 5.8%).

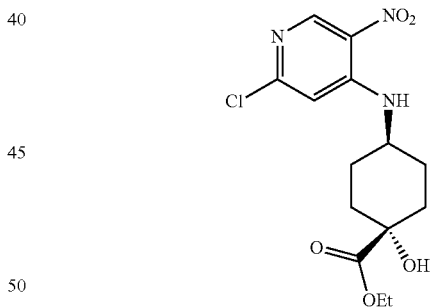

Step B: trans-Ethyl 4-(2-chloro-5-nitropyridin-4-ylamino)-1-hydroxycyclohexanecarboxylate To trans-ethyl 4-(tert-butoxycarbonylamino)-1-hydroxycyclohexanecarboxylate (346 mg, 1.20 mmol) was added saturated EtOH/HCl, and the resulting solution was allowed to stand at RT for 24 hours. The solvent was removed at reduced pressure, and the residue was dried in vacuo to afford the amine hydrochloride (269 mg, 1.20 mmol) as a colourless solid. The amine hydrochloride was suspended in ACN (5 mL) and 2,4-dichloro-5-nitropyridine (0.232 g, 1.20 mmol) and DIPEA (0.732 mL, 4.21 mmol) were added. The mixture was heated at 70° C. under argon for 5 hours and allowed to stand at RT overnight. The solvent was removed at reduced pressure, and the residue was purified by silica gel chromatography (40% EtOAc/Hexane). The desired fractions were collected and concentrated to afford a residue which was crystallized from toluene/hexane to afford trans-4-(2-chloro-5-nitropyridin-4-ylamino)-1-ethoxycyclohexanecarboxylic acid as yellow needles (289 mg, 69.9%). MS m/z=344.0 [M+H]. Calc'd for $C_{14}H_{18}ClN_3O_5$: 343.1.

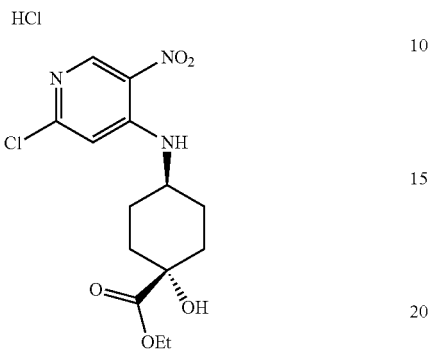

Step C: trans-4-(2-Chloro-5-nitropyridin-4-ylamino)-1-hydroxycyclohexanecarboxylic acid To a suspension of trans-ethyl 4-(2-chloro-5-nitropyridin-4-ylamino)-1-hydroxycyclohexanecarboxylate (220 mg, 0.640 mmol) in dioxane (0.8 mL) was added 4N aqueous HCl (4.16 mL, 16.64 mmol), and the resulting reaction mixture was stirred at 60° C. for 3 hours. The mixture was concentrated to afford trans-4-(2-chloro-5-nitropyridin-4-ylamino)-1-hydroxycyclohexanecarboxylic acid hydrochloride as a yellow solid (225 mg, 100% yield). MS m/z=316.0 [M+H]. Calc'd for $C_{12}H_{14}ClN_3O_5$: 315.1.

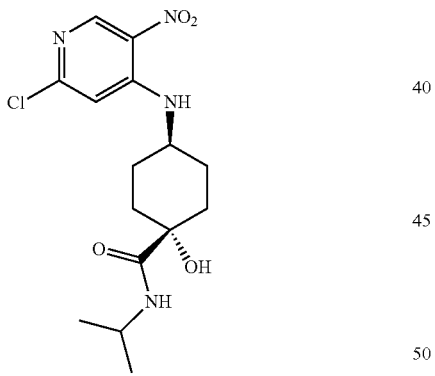

Step D: trans-4-(2-Chloro-5-nitropyridin-4-ylamino)-1-hydroxy-N-isopropylcyclohexanecarboxamide To a suspension of trans-4-(2-chloro-5-nitropyridin-4-ylamino)-1-hydroxycyclohexanecarboxylic acid hydrochloride (225 mg, 0.639 mmol) in DMF (6.4 mL) was added CDI (207 mg, 1.278 mmol). The resulting mixture was stirred at RT for 1 hour. The mixture was cooled to 0° C. and isopropylamine (1.095 mL, 12.78 mmol) was added dropwise as a solution in THF (1 mL). The ice bath was removed and the mixture stirred at RT for 1 hour. The mixture was diluted with DCM (20 mL) and washed with aqueous $NH_4Cl$ (10 mL) and brine (10 mL). The organic layer was collected, dried over sodium sulfate, and concentrated under reduced pressure to afford trans-4-(2-chloro-5-nitropyridin-4-ylamino)-1-hydroxy-N-isopropylcyclohexanecarboxamide as a yellow solid (0.22 g, 97% yield). MS m/z=357.2 [M+H]. Calc'd for $C_{15}H_{21}ClN_4O_4$: 356.1.

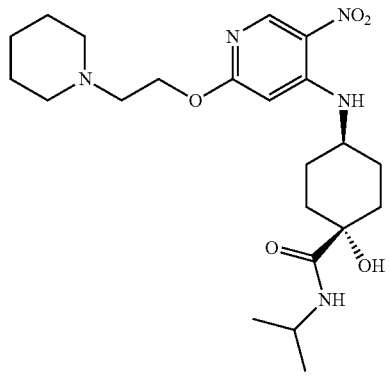 [SMILES: CC(C)NC(=O)[C@]1(O)CC[C@H](Nc2cc(OCCN3CCCCC3)ncc2[N+](=O)[O-])CC1]

Step E: trans-1-Hydroxy-N-isopropyl-4-(5-nitro-2-(2-(piperidin-1-yl)ethoxy)pyridin-4-ylamino)cyclohexanecarboxamide The title compound was prepared from trans-4-(2-chloro-5-nitropyridin-4-ylamino)-1-hydroxy-N-isopropylcyclohexanecarboxamide using a method analogous to the preparation of (R)-tert-butyl 3-methyl-4-(cis-4-(5-nitro-2-(2-(piperidin-1-yl)ethoxy)pyridin-4-ylamino)cyclohexanecarbonyl)piperazine-1-carboxylate and isolated as a tan solid (100 mg, 79.0%). MS m/z=450.2 [M+H]. Calc'd for $C_{22}H_{35}N_5O_5$: 449.3

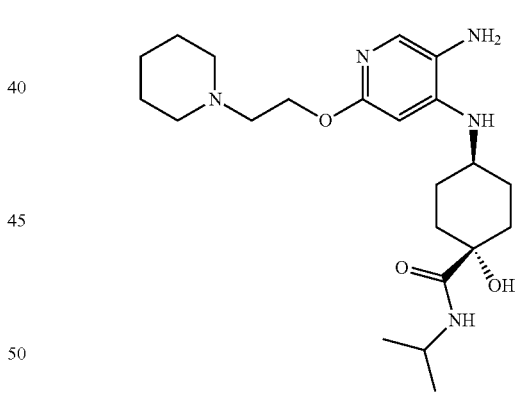

Step F: trans-4-(5-Amino-2-(2-(piperidin-1-yl)ethoxy)pyridin-4-ylamino)-1-hydroxy-N-isopropylcyclohexanecarboxamide The title compound was prepared from trans-1-hydroxy-N-isopropyl-4-(5-nitro-2-(2-(piperidin-1-yl)ethoxy)pyridin-4-ylamino)cyclohexanecarboxamide using a method analogous to the preparation of (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate (70 mg, 75.0% yield). MS m/z=420.2 [M+H]. Calc'd for $C_{22}H_{37}N_5O_3$: 419.3

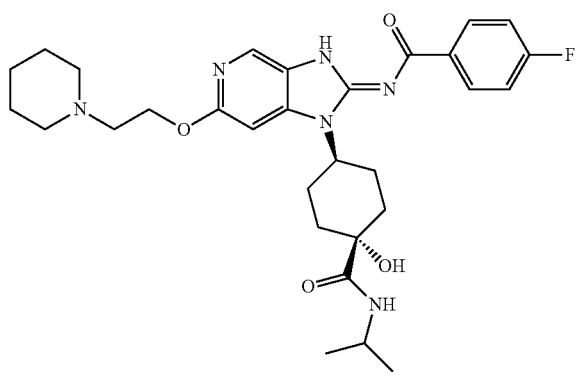 [SMILES: CC(C)NC(=O)[C@]1(O)CC[C@H](n2/c(=N/C(=O)c3ccc(F)cc3)[nH]c3cnc(OCCN4CCCCC4)cc32)CC1]

Step G: trans-4-(5-Amino-2-(2-(piperidin-1-yl)ethoxy)pyridin-4-ylamino)-1-hydroxy-N-isopropyl-cyclohexanecarboxamide The title compound was prepared from trans-4-(5-amino-2-(2-(piperidin-1-yl)ethoxy)pyridin-4-ylamino)-1-hydroxy-N-isopropylcyclohexanecarboxamide and 4-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (10 mg, 10.0% yield). MS m/z=567.2 [M+H]. Calc'd for $C_{30}H_{39}FN_6O_4$: 566.3

Example 64

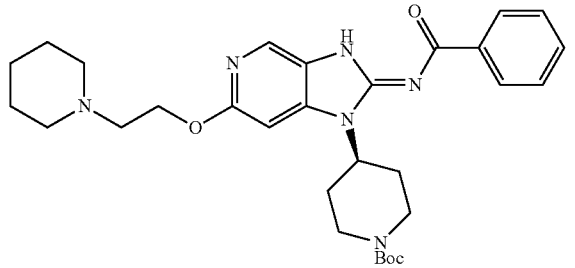

(E)-tert-Butyl 4-(2-(benzoylimino)-6-(2-(piperidin-1-yl)ethoxy)-2,3-dihydro-1H-imidazo[4,5-c]pyridin-1-yl)piperidine-1-carboxylate

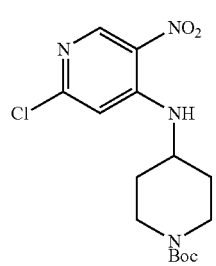 [SMILES: CC(C)(C)OC(=O)N1CCC(Nc2cc(Cl)ncc2[N+](=O)[O-])CC1]

Step A: tert-Butyl 4-(2-chloro-5-nitropyridin-4-ylamino)piperidine-1-carboxylate The title compound was prepared from 2,4-dichloro-5-nitropyridine and tert-butyl 4-aminopiperidine-1-carboxy-late using a method analogous to the preparation of cis-methyl 4-(3-nitropyridin-4-ylamino)cyclohexanecarboxylate (10.2 g, 55.2% yield). MS m/z=357.2 [M+H]. Calc'd for $C_{15}H_{21}ClN_4O_4$: 356.1.

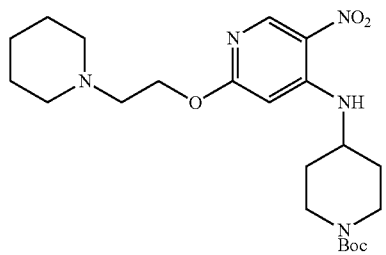

Step B: tert-Butyl 4-(5-nitro-2-(2-(piperidin-1-yl)ethoxy)pyridin-4-ylamino)piperidine-1-carboxylate The title compound was prepared from tert-butyl 4-(2-chloro-5-nitropyridin-4-ylamino)piperidine-1-carboxylate using a method analogous to the preparation of (R)-tert-butyl 3-methyl-4-(cis-4-(5-nitro-2-(2-(piperidin-1-yl)ethoxy)pyridin-4-ylamino)cyclohexanecarbonyl)piperazine-1-carboxylate (3.0 g, 59.5% yield). MS m/z=450.2 [M+H]. Calc'd for $C_{22}H_{35}N_5O_5$: 449.3

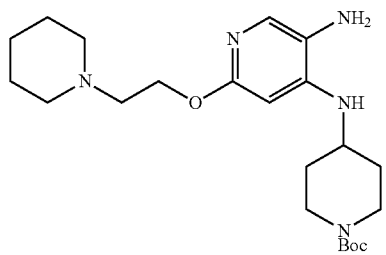 [SMILES: CC(C)(C)OC(=O)N1CCC(Nc2cc(OCCN3CCCCC3)ncc2[N+](=O)[O-])CC1]

Step C: tert-Butyl 4-(5-amino-2-(2-(piperidin-1-yl)ethoxy)pyridin-4-ylamino)piperidine-1-carboxylate The title compound was prepared from tert-butyl 4-(5-nitro-2-(2-(piperidin-1-yl)ethoxy)pyridin-4-ylamino)piperidine-1-carboxylate using a method analogous to the preparation of (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate (2.56 g, 91% yield). MS m/z=420.2 [M+H]. Calc'd for $C_{22}H_{37}N_5O_3$: 419.3

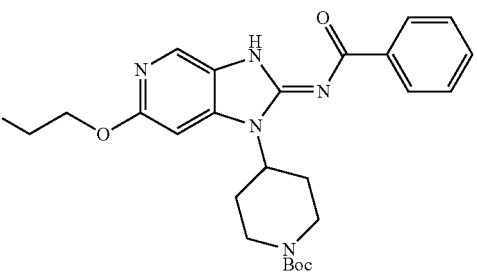

Step D: (E)-tert-Butyl 4-(2-(benzoylimino)-6-(2-(piperidin-1-yl)ethoxy)-2,3-dihydro-1H-imidazo[4,5-c]pyridin-1-yl)piperidine-1-carboxylate The title compound was prepared from tert-butyl 4-(5-amino-2-(2-(piperidin-1-yl)ethoxy)pyridin-4-ylamino)piperidine-1-carboxylate using a method analogous to the preparation of cis-methyl 4-((E)-2-(benzoylimino)-2,3-dihydro-1H-imidazo[4,5-c]pyridin-1-yl)cyclohexanecarboxylate (2.4 g, 65.5% yield). MS m/z=549.2 [M+H]. Calc'd for $C_{30}H_{40}N_6O_4$: 548.3.

Example 65

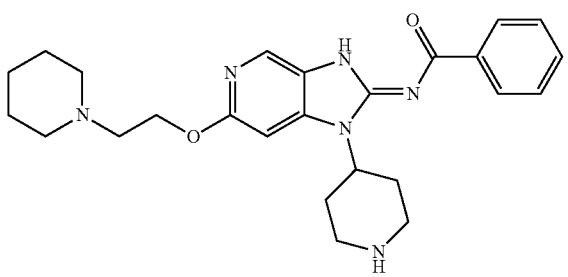 [SMILES: O=C(/N=c1\[nH]c2cnc(OCCN3CCCCC3)cc2n1C1CCNCC1)c1ccccc1]

(E)-N-(6-(2-(Piperidin-1-yl)ethoxy)-1-(piperidin-4-yl)-1H-imidazo[4,5-c]pyridin-2(3H)-ylidene)benzamide The title compound was prepared from (E)-tert-butyl 4-(2-(benzoylimino)-6-(2-(piperidin-1-yl)ethoxy)-2,3-dihydro-1H-imidazo[4,5-c]pyridin-1-yl)piperidine-1-carboxylate using a method analogous to the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide (1.9 g, 97%). MS m/z=449.2 [M+H]. Calc'd for $C_{25}H_{32}N_6O_2$: 448.3. $^1$H NMR (400 MHz, DMSO-$d_6$) δ ppm 1.16-1.29 (m, 2H) 1.31-1.42 (m, 2H) 1.41-1.55 (m, 4H) 1.60-1.77 (m, 2H) 2.26-2.37 (m, 1H) 2.37-2.45 (m, 4H) 2.58-2.70 (m, 4H) 3.04-3.17 (m, 2H) 4.29-4.39 (m, 2H) 4.72-4.89 (m, 1H) 7.04-7.06 (m, 1H) 7.47-7.51 (m, 2H) 7.51-7.54 (m, 1H) 8.19-8.20 (m, 1H) 8.21-8.22 (m, 1H) 8.22-8.24 (m, 1H).

Example 66

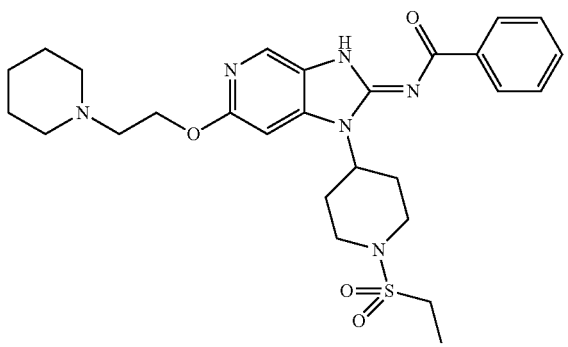 [SMILES: CCS(=O)(=O)N1CCC(n2/c(=N/C(=O)c3ccccc3)[nH]c3cnc(OCCN4CCCCC4)cc32)CC1]

(E)-N-(1-(1-(Ethylsulfonyl)piperidin-4-yl)-6-(2-(piperidin-1-yl)ethoxy)-1H-imidazo[4,5-c]pyridin-2(3H)-ylidene)benzamide A suspension of (E)-N-(6-(2-(piperidin-1-yl)ethoxy)-1-(piperidin-4-yl)-1H-imidazo[4,5-c]pyridin-2(3H)-ylidene)benzamide (0.10 g, 0.223 mmol) in DMF (1.12 mL) was cooled to 0° C. under nitrogen atmosphere. To this mixture was added TEA (0.045 g, 0.446 mmol) followed by ethanesulfonyl chloride (0.043 g, 0.334 mmol). The resulting mixture was stirred for 30 minutes and diluted with water (10 mL) and DCM (20 mL). The organic layer was collected and concentrated to yield a brown residue. The residue was purified by HPLC (10-70% ACN/$H_2O$; 0.1% TFA) to afford (E)-N-(1-(1-(ethylsulfonyl)piperidin-4-yl)-6-(2-(piperidin-1-yl)ethoxy)-1H-imidazo[4,5-c]pyridin-2(3H)-ylidene)benzamide as an off-white solid (15 mg, 12.4%). MS m/z=541.2 [M+H]. Calc'd for $C_{27}H_{36}N_6O_4S$: 540.3.

Example 67

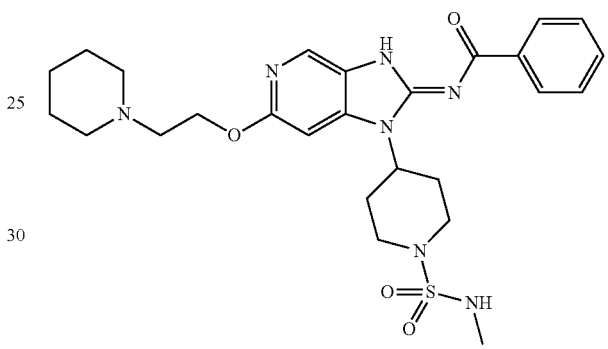

(E)-N-(1-(1-(N-Methylsulfamoyl)piperidin-4-yl)-6-(2-(piperidin-1-yl)ethoxy)-1H-imidazo[4,5-c]pyridin-2(3H)-ylidene)benzamide The title compound was prepared from (E)-N-(6-(2-(piperidin-1-yl)ethoxy)-1-(piperidin-4-yl)-1H-imidazo[4,5-c]pyridin-2(3H)-ylidene)benzamide and methylsulfamoyl chloride using a method analogous to the preparation of (E)-N-(1-(1-(ethylsulfonyl)piperidin-4-yl)-6-(2-(piperidin-1-yl)ethoxy)-1H-imidazo[4,5-c]pyridin-2(3H)-ylidene)benzamide (15 mg, 12.4% yield). MS m/z=542.2 [M+H]. Calc'd for $C_{26}H_{35}N_7O_4S$: 541.3

Example 68

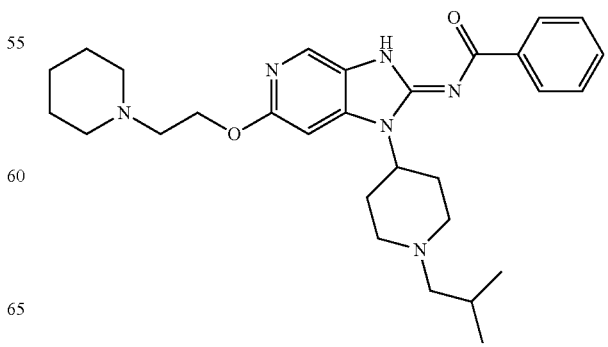

(E)-N-(1-(1-Isobutylpiperidin-4-yl)-6-(2-(piperidin-1-yl)ethoxy)-1H-imidazo[4,5-c]pyridin-2(3H)-ylidene)benzamide A suspension of (E)-N-(6-(2-(piperidin-1-yl)ethoxy)-1-(piperidin-4-yl)-1H-imidazo[4,5-c]pyridin-2(3H)-ylidene)benzamide (0.089 g, 0.198 mmol) and potassium carbonate (0.082 g, 0.595 mmol) in DMF (2 mL) was cooled to 0° C. under nitrogen. To this mixture was added 1-bromo-2-methylpropane (0.054 g, 0.397 mmol). The ice bath was removed, and the resulting mixture was stirred for 16 hours at RT. The reaction mixture was diluted with water (10 mL) and DCM (30 mL), and the organic layer was collected, concentrated and purified by silica gel chromatography (5-30% MeOH/DCM) to afford (E)-N-(1-(1-isobutylpiperidin-4-yl)-6-(2-(piperidin-1-yl)ethoxy)-1H-imidazo[4,5-c]pyridin-2(3H)-ylidene)benzamide as an off-white solid (20 mg, 19.97% yield). MS m/z=505.2 [M+H]. Calc'd for $C_{29}H_{40}N_6O_2$: 504.3.

Example 69

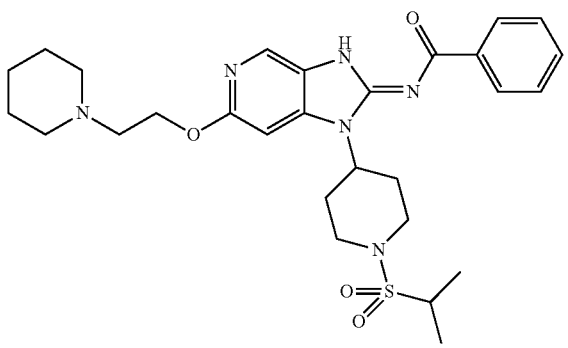 [SMILES: CC(C)S(=O)(=O)N1CCC(n2/c(=N/C(=O)c3ccccc3)[nH]c3cnc(OCCN4CCCCC4)cc32)CC1]

(E)-N-(1-(1-(Isopropylsulfonyl)piperidin-4-yl)-6-(2-(piperidin-1-yl)ethoxy)-1H-imidazo[4,5-c]pyridin-2(3H)-ylidene)benzamide The title compound was prepared from (E)-N-(6-(2-(piperidin-1-yl)ethoxy)-1-(piperidin-4-yl)-1H-imidazo[4,5-c]pyridin-2(3H)-ylidene)benzamide and 2-propanesulphonyl chloride using a method analogous to the preparation of (E)-N-(1-(1-(ethylsulfonyl)piperidin-4-yl)-6-(2-(piperidin-1-yl)ethoxy)-1H-imidazo[4,5-c]pyridin-2(3H)-ylidene)benzamide (20 mg, 19.0% yield). MS m/z=555.2 [M+H]. Calc'd for $C_{28}H_{38}N_6O_4S$: 554.3

Example 70

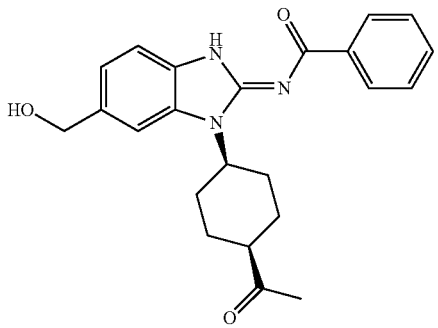 [SMILES: CC(=O)[C@H]1CC[C@@H](n2/c(=N/C(=O)c3ccccc3)[nH]c3ccc(CO)cc32)CC1]

(E)-N-(1-(cis-4-Acetylcyclohexyl)-6-(hydroxymethyl)-1H-benzo[d]imidazol-2(3H)-ylidene)-3-fluorobenzamide

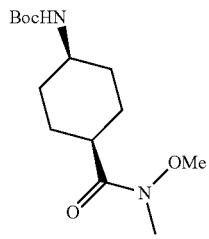 [SMILES: CON(C)C(=O)[C@H]1CC[C@@H](NC(=O)OC(C)(C)C)CC1]

Step A: tert-Butyl cis-4-(methoxy(methyl)carbamoyl)cyclohexylcarbamate

To a suspension of cis-4-(tert-butoxycarbonylamino)cyclohexanecarboxylic acid (3 g, 12.33 mmol) in DCM (35 mL) was added CDI (4.00 g, 24.66 mmol) portion-wise. The resulting mixture was stirred for 1 hour, and then O,N-dimethylhydroxylamine hydrochloride (1.804 g, 18.50 mmol) was added, and the mixture was stirred at RT for 16 hours. Water (30 mL) was added, and the mixture was stirred for 1 hour and then extracted with DCM (50 mL). The organic layer was washed with brine (30 mL), dried over sodium sulfate and concentrated to afford tert-butyl cis-4-(methoxy(methyl)carbamoyl)cyclohexylcarbamate (3.3 g, 93% yield).

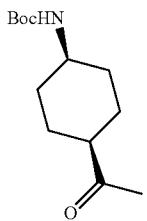

Step B: tert-Butyl cis-4-acetylcyclohexylcarbamate

A suspension of tert-butyl cis-4-(methoxy(methyl)carbamoyl)cyclohexylcarbamate (4.7 g, 16.41 mmol) in THF (109 mL) was cooled to 0° C. under nitrogen atmosphere. To this was added methylmagnesium iodide (3M in ether solution)(10.94 mL, 32.8 mmol) dropwise via syringe, and the mixture was stirred at 0° C. for 1 hour. The ice bath was removed, and the reaction mixture was stirred for 18 hours at RT. The reaction mixture was again cooled to 0° C. under nitrogen atmosphere and quenched with aqueous NH$_4$Cl (100 mL). DCM (200 mL) was added, and the layers were separated. The organic layer was washed with brine (30 mL), dried over sodium sulfate and concentrated to afford a yellow oil which was purified by silica gel chromatography (5-30% MeOH/DCM) to afford tert-butyl cis-4-acetylcyclohexylcarbamate as an off-white solid (1.8 g, 45.4% yield).

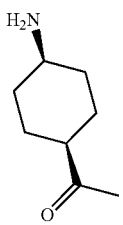

Step C: 1-(cis-4-Aminocyclohexyl)ethanone hydrochloride

A suspension of tert-butyl cis-4-acetylcyclohexylcarbamate (1.8 g, 7.46 mmol) in HCl (4M in dioxane) (93 mL, 373 mmol) was stirred at RT for 16 hours. The resulting mixture was concentrated to dryness to afford 1-(cis-4-aminocyclohexyl)ethanone hydrochloride as a white solid (1.33 g, 100% yield).

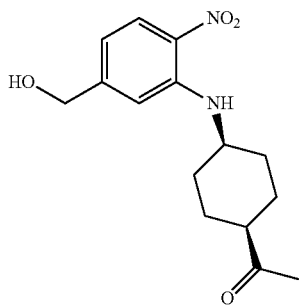

Step D: 1-(cis-4-(5-(Hydroxymethyl)-2-nitrophenylamino)cyclohexyl)ethanone

The title compound was prepared from (3-fluoro-4-nitrophenyl)methanol and 1-(cis-4-aminocyclohexyl)ethanone hydrochloride using a method analogous to the preparation of cis-methyl 4-(2-nitro-5-((triisopropylsilyloxy)methyl)phenylamino)cyclohexanecarboxylate (0.7 g, 41.0% yield). MS m/z=293.2 [M+H]. Calc'd for $C_{15}H_{20}N_2O_4$: 292.1.

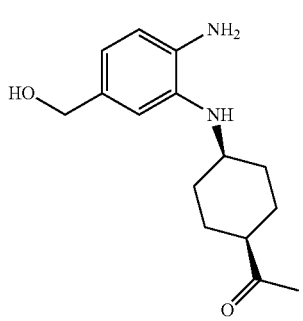 [SMILES: CC(=O)[C@H]1CC[C@@H](Nc2cc(CO)ccc2[N+](=O)[O-])CC1]

Step E: 1-(cis-4-(2-Amino-5-(hydroxymethyl)phenylamino)cyclohexyl)ethanone

The title compound was prepared from 1-(cis-4-(5-(hydroxymethyl)-2-nitrophenylamino)cyclohexyl)ethanone using a method analogous to the preparation of cis-methyl 4-(3-aminopyridin-4-ylamino)cyclohexanecarboxylate (0.14 g, 98.0% yield). MS m/z=263.2 [M+H]. Calc'd for $C_{15}H_{22}N_2O_2$: 262.2.

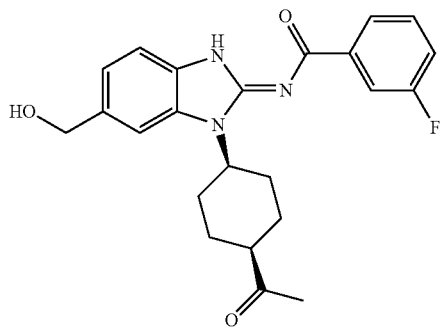 [SMILES: CC(=O)[C@H]1CC[C@@H](n2/c(=N/C(=O)c3cccc(F)c3)[nH]c3ccc(CO)cc32)CC1]

Step F: (E)-N-(1-(cis-4-Acetylcyclohexyl)-6-(hydroxymethyl)-1H-benzo[d]imidazol-2(3H)-ylidene)-3-fluorobenzamide The title compound was prepared from 1-(cis-4-(2-amino-5-(hydroxymethyl)phenylamino)cyclohexyl)ethanone and 4-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (0.15 g, 66.7% yield). MS m/z=410.2 [M+H]. Calc'd for $C_{15}H_{20}N_2O_4$: 409.2. $^1$H NMR (400 MHz, DMSO-$d_6$) δ ppm 1.22-1.27 (m, 1H) 1.48-1.66 (m, 2H) 1.85-1.95 (m, 2H) 2.06-2.16 (m, 2H) 2.21 (s, 3H) 2.40-2.48 (m, 1H) 2.57-2.73 (m, 1H) 4.60 (d, J=5.77 Hz, 2H) 4.73-4.91 (m, 1H) 5.22 (t, J=5.77 Hz, 1H) 7.16-7.22 (m, 1H) 7.32-7.40 (m, 1H) 7.48-7.58 (m, 2H) 7.65 (s, 1H) 7.86-7.93 (m, 1H) 8.05-8.10 (m, 1H) 12.82 (s, 1H).

Example 71

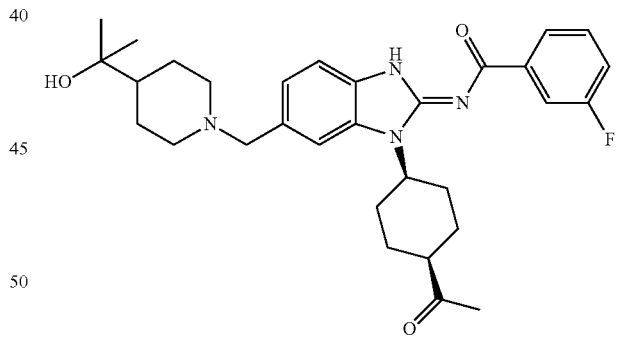

(E)-N-(1-(cis-4-Acetylcyclohexyl)-6-((4-(2-hydroxypropan-2-yl)piperidin-1-yl)methyl)-1H-benzo[d]imidazol-2(3H)-ylidene)-3-fluorobenzamide The title compound was prepared from (E)-N-(1-(cis-4-acetylcyclohexyl)-6-(hydroxymethyl)-1H-benzo[d]imidazol-2(3H)-ylidene)-3-fluorobenzamide using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (65 mg, 35.6%). MS m/z=535.2 [M+H]. Calc'd for $C_{31}H_{39}FN_4O_3$: 534.3

Example 72

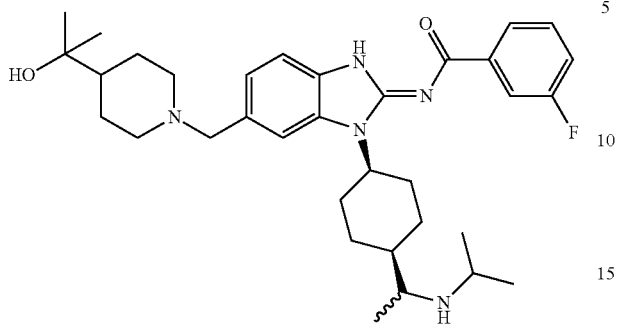

(E)-3-Fluoro-N-(6-((4-(2-hydroxypropan-2-yl)piperidin-1-yl)methyl)-1-(cis-4-(1-(isopropylamino)ethyl)cyclohexyl)-1H-benzo[d]imidazol-2(3H)-ylidene)benzamide (E)-N-(1-(cis-4-acetylcyclohexyl)-6-((4-(2-hydroxypropan-2-yl)piperidin-1-yl)methyl)-1H-benzo[d]imidazol-2(3H)-ylidene)-3-fluorobenzamide (0.06 g, 0.112 mmol) was suspended in 0.37 mL of dichloroethane. To this mixture was added propan-2-amine (7.30 mg, 0.123 mmol) followed by sodium triacetoxyborohydride (0.033 g, 0.157 mmol) and AcOH (6.42 pt, 0.112 mmol). The resulting mixture was stirred for 6 hours at RT and quenched with 1N aqueous NaOH (5 mL). DCM (20 mL) was added and the layers were separated. The organic portion was dried over sodium sulfate and concentrated to afford a yellow residue which was purified by silica gel chromatography (5-30% MeOH/DCM) to afford (E)-3-fluoro-N-(6-((4-(2-hydroxypropan-2-yl)piperidin-1-yl)methyl)-1-(cis-4-(1-(isopropylamino)ethyl)cyclohexyl)-1H-benzo[d]imidazol-2(3H)-ylidene)benzamide as an off-white solid (10 mg, 15.42% yield). MS m/z=578.4 [M+H]. Calc'd for $C_{34}H_{48}FN_5O_2$: 577.4

Example 73

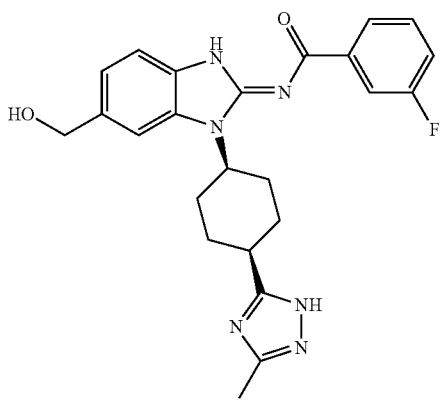 [SMILES: Cc1n[nH]c([C@H]2CC[C@@H](n3/c(=N/C(=O)c4cccc(F)c4)[nH]c4ccc(CO)cc43)CC2)n1]

Example 72

(E)-3-Fluoro-N-(6-(hydroxymethyl)-1-(cis-4-(3-methyl-1H-1,2,4-triazol-5-yl)cyclohexyl)-1H-benzo[d]imidazol-2(3H)-ylidene)benzamide

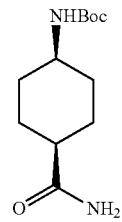 [SMILES: CC(C)(C)OC(=O)N[C@H]1CC[C@@H](C(N)=O)CC1]

Step A: tert-Butyl cis-4-carbamoylcyclohexylcarbamate

The title compound was prepared from cis-4-(tert-butoxycarbonylamino)cyclohexanecarboxylic acid using a method analogous to the preparation of tert-butyl cis-4-(methoxy(methyl)carbamoyl)cyclohexylcarbamate (0.86 g, 78% yield).

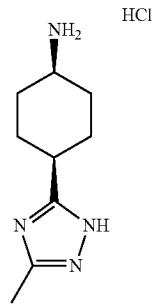

Step B: cis-4-(3-Methyl-1H-1,2,4-triazol-5-yl)cyclohexanamine hydrochloride

To a suspension of tert-butyl cis-4-carbamoylcyclohexylcarbamate (0.24 g, 0.990 mmol) in toluene (0.8 mL) was added N,N-dimethylacetamide dimethyl acetal (2.90 mL, 19.81 mmol), and the resulting mixture was refluxed for 16 hours with a Dean-Stark trap attached. The mixture was allowed to cool, was diluted with EtOAc (30 mL), and was washed with water (2-10 mL) and then brine (10 mL). The organic layer was dried over $Na_2SO_4$, filtered and concentrated under reduced pressure to give a brown oil. A premixed solution of hydrazine (0.078 mL, 2.476 mmol) and AcOH (8.22 mL, 144 mmol) was added to the residual oil, and the resulting mixture was heated at 90° C. for 3 hours. The mixture was allowed to cool and poured into water (30 mL). The mixture was extracted with EtOAc (50 mL), and the organic layer was separated and washed sequentially with water (10 mL), aqueous $NaHCO_3$ (10 mL), and brine (10 mL), then dried over $Na_2SO_4$, filtered and concentrated under reduced pressure to give a tan solid. The solid was suspended in HCl (4M in dioxanes) (12.38 mL, 49.5 mmol) and stirred at RT for 16 hours. The mixture was concentrated to dryness under reduced pressure to afford cis-4-(3-methyl-1H-1,2,4-triazol-5-yl)cyclohexanamine hydrochloride as a tan solid (0.15 g, 0.692 mmol, 69.9% yield). MS m/z=181.2 [M+H]. Calc'd for $C_9H_{16}N_5$: 180.1.

157

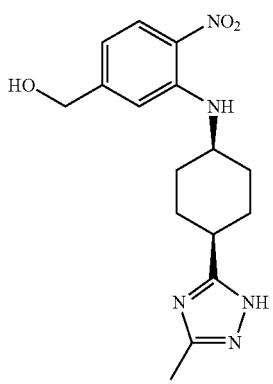 [SMILES: Cc1n[nH]c([C@H]2CC[C@@H](Nc3cc(CO)ccc3[N+](=O)[O-])CC2)n1]

Step C: (3-(cis-4-(3-Methyl-1H-1,2,4-triazol-5-yl)cyclohexylamino)-4-nitrophenyl)methanol The title compound was prepared from (3-fluoro-4-nitrophenyl)methanol and cis-4-(3-methyl-1H-1,2,4-triazol-5-yl)cyclohexanamine hydrochloride using a method analogous to the preparation of cis-methyl 4-(2-nitro-5-(((triisopropylsilyloxy)methyl)phenylamino)cyclohexanecarboxylate (0.12 g, 78.0% yield). MS m/z=332.2 [M+H]. Calc'd for $C_{16}H_{21}N_5O_3$: 331.2.

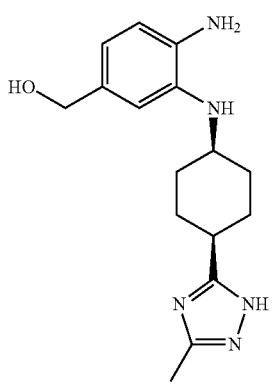

Step D: (4-Amino-3-(cis-4-(3-methyl-1H-1,2,4-triazol-5-yl)cyclohexylamino)phenyl)methanol The title compound was prepared from (3-(cis-4-(3-methyl-1H-1,2,4-triazol-5-yl)cyclohexylamino)-4-nitrophenyl)methanol using a method analogous to the preparation of cis-methyl 4-(3-aminopyridin-4-ylamino)cyclohexanecarboxylate (0.10 g, 92.0% yield). MS m/z=302.2 [M+H]. Calc'd for $C_{16}H_{23}N_5O$: 301.2.

158

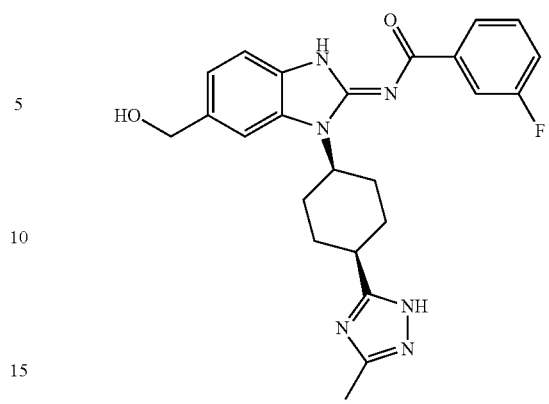

Step E: (E)-3-Fluoro-N-(6-(hydroxymethyl)-1-(cis-4-(3-methyl-1H-1,2,4-triazol-5-yl)cyclohexyl)-1H-benzo[d]imidazol-2(3H)-ylidene)benzamide The title compound was prepared from (4-amino-3-(cis-4-(3-methyl-1H-1,2,4-triazol-5-yl)cyclohexylamino)phenyl)methanol and 3-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (45 mg, 27.5% yield). MS m/z=449.2 [M+H]. Calc'd for $C_{24}H_{25}FN_6O_2$: 448.2.

Compound 74

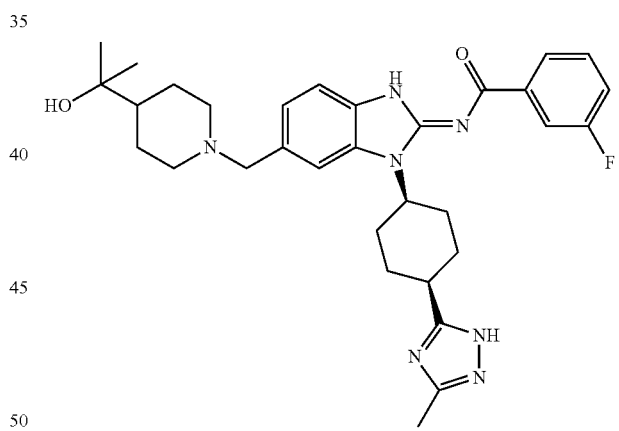

(E)-3-Fluoro-N-(6-((4-(2-hydroxypropan-2-yl)piperidin-1-yl)methyl)-1-(cis-4-(3-methyl-1H-1,2,4-triazol-5-yl)cyclohexyl)-1H-benzo[d]imidazol-2(3H)-ylidene)benzamide The title compound was prepared from (E)-3-fluoro-N-(6-(hydroxymethyl)-1-(cis-4-(3-methyl-1H-1,2,4-triazol-5-yl)cyclohexyl)-1H-benzo[d]imidazol-2(3H)-ylidene)benzamide and 2-(piperidin-4-yl)propan-2-ol using a method analogous to the preparation of cis-methyl 4-(2-benzamido-6-((2,2,6,6-tetramethylpiperidin-1-yl)methyl)-1H-benzo[d]imidazol-1-yl)cyclohexanecarboxylate (22 mg, 41.9% yield). MS m/z=574.2 [M+H]. Calc'd for $C_{32}H_{40}FN_7O_2$: 573.3.

Compound 75

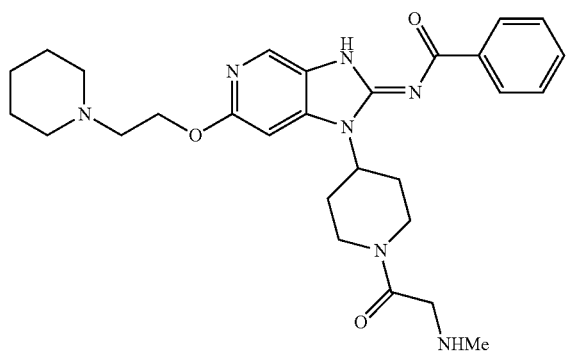 [SMILES: CNCC(=O)N1CCC(n2/c(=N/C(=O)c3ccccc3)[nH]c3cnc(OCCN4CCCCC4)cc32)CC1]

(E)-N-(1-(1-(2-(Methylamino)acetyl)piperidin-4-yl)-6-(2-(piperidin-1-yl)ethoxy)-1H-imidazo[4,5-c]pyridin-2(3H)-ylidene)benzamide The title compound was prepared from (E)-tert-butyl 2-(4-(2-(benzoylimino)-6-(2-(piperidin-1-yl)ethoxy)-2,3-dihydro-1H-imidazo[4,5-c]pyridin-1-yl)piperidin-1-yl)-2-oxoethyl(methyl)carbamate using a method analogous to the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide (30 mg, 25.9% yield). MS m/z=520.2 [M+H]. Calc'd for $C_{28}H_{37}N_7O_3$: 519.3.

Example 76

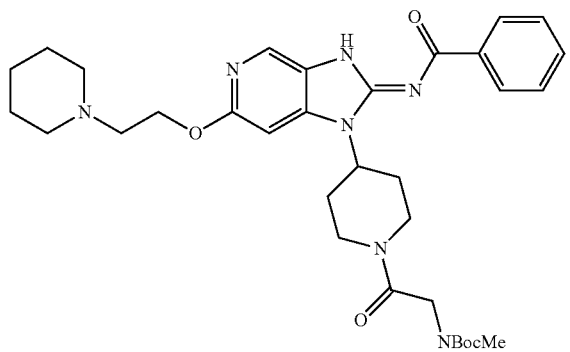

(E)-tert-Butyl 2-(4-(2-(benzoylimino)-6-(2-(piperidin-1-yl)ethoxy)-2,3-dihydro-1H-imidazo[4,5-c]pyridin-1-yl)piperidin-1-yl)-2-oxoethyl(methyl)carbamate To a cooled (0° C.) solution of 2-(tert-butoxycarbonyl(methyl)amino)acetic acid (0.046 g, 0.245 mmol) in DMF (1.12 mL) under nitrogen atmosphere was added EDC (0.047 g, 0.245 mmol), HOBT (0.038 g, 0.245 mmol), (E)-N-(6-(2-(piperidin-1-yl)ethoxy)-1-(piperidin-4-yl)-1H-imidazo[4,5-c]pyridin-2(3H)-ylidene)benzamide (0.1 g, 0.223 mmol), and DIPEA (0.047 mL, 0.268 mmol). The resulting mixture was stirred for 16 hours and was diluted with water (10 mL) and EtOAc (20 mL). The organic layers were separated, dried over Na$_2$SO$_4$, filtered and concentrated under reduced pressure to give a brown oil. The oil was purified by silica gel chromatography (1-5% MeOH/DCM) to afford (E)-tert-butyl 24442-(benzoylimino)-6-(2-(piperidin-1-yl)ethoxy)-2,3-dihydro-1H-imidazo[4,5-c]pyridin-1-yl)piperidin-1-yl)-2-oxoethyl(methyl)carbamate (50 mg, 36.2% yield). MS m/z=620.2 [M+H]. Calc'd for $C_{33}H_{45}N_7O_5$: 619.4.

Example 77

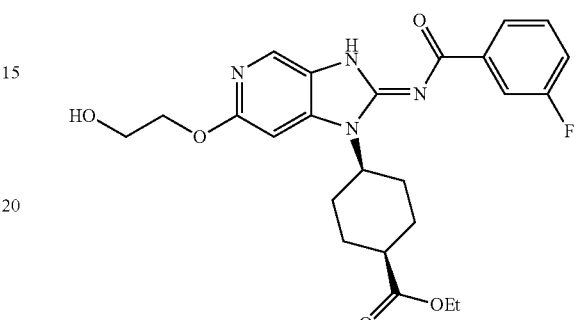

cis-Ethyl 4-((E)-2-(3-fluorobenzoylimino)-6-(2-hydroxyethoxy)-2,3-dihydro-1H-imidazo[4,5-c]pyridin-1-yl)cyclohexanecarboxylate

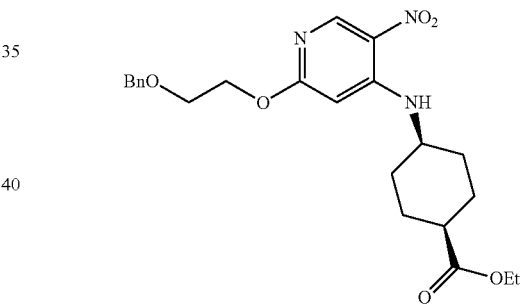

Step A: cis-Ethyl 4-(2-(2-(benzyloxy)ethoxy)-5-nitropyridin-4-ylamino)cyclohexanecarboxylate To a suspension of cis-4-(2-chloro-5-nitropyridin-4-ylamino)cyclohexanecarboxylic acid (5 g, 16.68 mmol) in toluene (111 mL) was added 2-(benzyloxy)ethanol (7.62 g, 50.0 mmol), cesium carbonate (16.31 g, 50.0 mmol), and 18-crown-6 (6.61 g, 25.02 mmol). The resulting mixture was purged with argon and stirred at 75° C. overnight. The mixture was allowed to cool to RT and diluted with EtOAc to about 150 mL total volume and washed sequentially with brine (2-150 mL), aqueous NH$_4$Cl (2-150 mL) and water (150 mL). The organic phase was collected, dried over sodium sulfate and concentrated under reduced pressure. The residue was suspended in EtOH (111 mL) and thionyl chloride (36.5 mL, 500 mmol) was added dropwise via syringe. The reaction mixture was stirred at RT for 16 hours. The mixture was concentrated to ⅓ volume and diluted with DCM (150 mL). The organic portion was washed with aqueous NaHCO$_3$ (100 mL), dried over sodium sulfate and concentrated. The residue was purified by silica gel chromatography (10-50% EtOAc/Hexanes) to afford cis-ethyl 4-(2-(2-(benzyloxy)ethoxy)-5-nitropyridin-4-ylamino)cyclohexanecarboxylate (5.6 g, 76% yield). MS m/z=444.2 [M+H]. Calc'd for $C_{23}H_{29}N_3O_6$: 443.2.

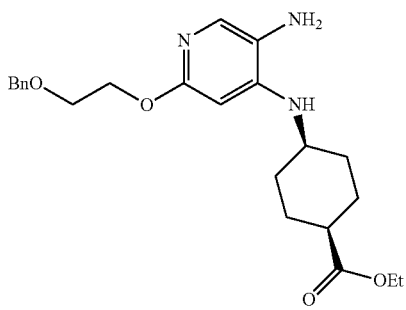 [SMILES: CCOC(=O)[C@H]1CC[C@@H](Nc2cc(OCCOCc3ccccc3)ncc2N)CC1]

Step B: cis-Ethyl 4-(5-amino-2-(2-(benzyloxy)ethoxy)pyridin-4-ylamino)cyclohexanecarboxylate The title compound was prepared from cis-ethyl 4-(2-(2-(benzyloxy)ethoxy)-5-nitropyridin-4-ylamino)cyclohexanecarboxylate using a method analogous to the preparation of (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate (4.4 g, 86.0% yield). MS m/z=414.2 [M+H] Calc'd for $C_{23}H_{31}N_3O_4$: 413.2.

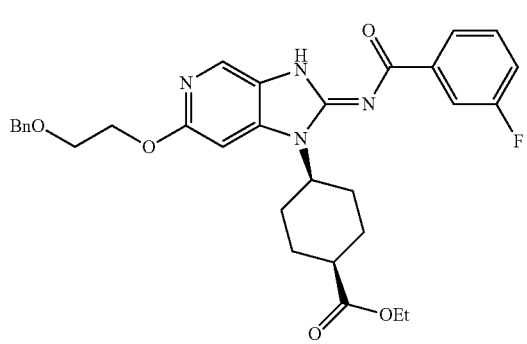 [SMILES: CCOC(=O)[C@H]1CC[C@@H](n2/c(=N/C(=O)c3cccc(F)c3)[nH]c3cnc(OCCOCc4ccccc4)cc32)CC1]

Step C: cis-Ethyl 4-((E)-6-(2-(benzyloxy)ethoxy)-2-(3-fluorobenzoylimino)-2,3-dihydro-1H-imidazo[4,5-c]pyridin-1-yl)cyclohexanecarboxylate The title compound was prepared from cis-ethyl 4-(5-amino-2-(2-(benzyloxy)ethoxy)pyridin-4-ylamino)cyclohexanecarboxylate and 3-fluorobenzoyl isothiocyanate using a method analogous to the preparation of cis-methyl 4-((E)-2-(benzoylimino)-2,3-dihydro-1H-imidazo[4,5-c]pyridin-1-yl)cyclohexanecarboxylate (2.5 g, 82% yield). MS m/z=561.2 [M+H]. Calc'd for $C_{31}H_{33}FN_4O_5$: 560.2.

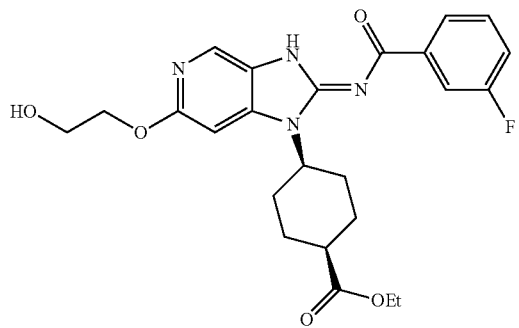 [SMILES: CCOC(=O)[C@H]1CC[C@@H](n2/c(=N/C(=O)c3cccc(F)c3)[nH]c3cnc(OCCO)cc32)CC1]

Step D: cis-Ethyl 4-((E)-2-(3-fluorobenzoylimino)-6-(2-hydroxyethoxy)-2,3-dihydro-1H-imidazo[4,5-c]pyridin-1-yl)cyclohexanecarboxylate A round bottom flask under nitrogen was charged with cis-ethyl 4-((E)-6-(2-(benzyloxy)ethoxy)-2-(3-fluorobenzoylimino)-2,3-dihydro-1H-imidazo[4,5-c]pyridin-1-yl)cyclohexanecarboxylate (2.5 g, 4.46 mmol), 10% Pd/C (0.712 g, 0.669 mmol), EtOH (8.92 mL), and concentrated HCl (0.372 mL, 4.46 mmol). The reaction mixture was stirred under an atmosphere of hydrogen for 24 hours. The mixture was diluted with EtOH (50 mL) and filtered through Celite® brand filter aid. The cake was washed with DCM (50 mL), EtOH (50 mL), and MeOH (50 mL), and the filtrate was concentrated to dryness. The residue was dissolved in 2% MeOH/DCM (100 mL) and washed with aqueous NaHCO₃ (50 mL). The organic layer was dried over sodium sulfate and concentrated under reduced pressure to afford cis-ethyl 4-((E)-2-(3-fluorobenzoylimino)-6-(2-hydroxyethoxy)-2,3-dihydro-1H-imidazo[4,5-c]pyridin-1-yl)cyclohexanecarboxylate as a tan solid (2.1 g, 100% yield). MS m/z=471.2 [M+H]. Calc'd for $C_{24}H_{27}FN_4O_5$: 470.2.

Example 78

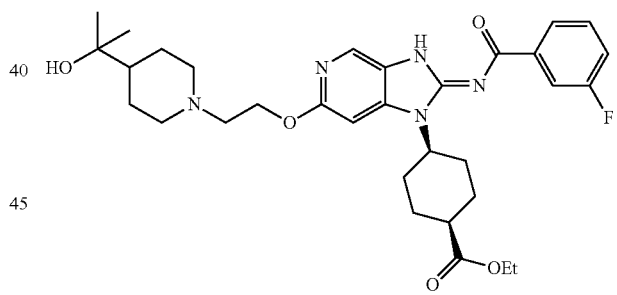

cis-Ethyl 4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylate

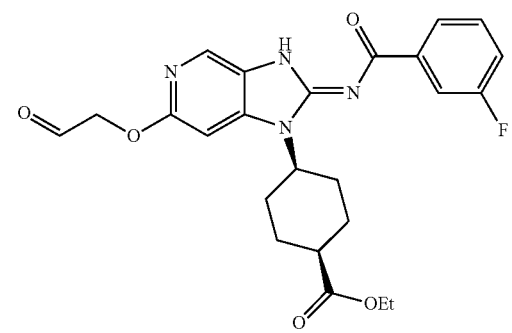 [SMILES: CCOC(=O)[C@H]1CC[C@@H](n2/c(=N/C(=O)c3cccc(F)c3)[nH]c3cnc(OCC=O)cc32)CC1]

Step B: cis-Ethyl 4-((E)-2-(3-fluorobenzoylimino)-6-(2-oxoethoxy)-2,3-dihydro-1H-imidazo[4,5-c]pyridin-1-yl)cyclohexanecarboxylate The title compound was prepared from cis-ethyl 4-((E)-2-(3-fluorobenzoylimino)-6-(2-hydroxyethoxy)-2,3-dihydro-1H-imidazo[4,5-c]pyridin-1-yl)cyclohexanecarboxylate using a method analogous to the preparation of (E)-4-fluoro-N-(1-(cis-4-(isopropylcarbamoyl)cyclohexyl)-6-(2-oxoethoxy)-1H-imidazo[4,5-c]pyridin-2(3H)-ylidene)benzamide (1.8 g, 90% yield). MS m/z=469.2 [M+H]. Calc'd for $C_{24}H_{25}FN_4O_5$: 468.2.

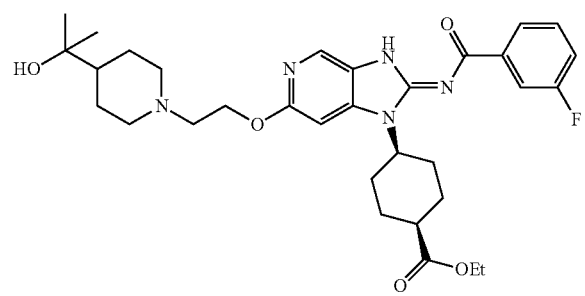 [SMILES: CCOC(=O)[C@H]1CC[C@@H](n2/c(=N/C(=O)c3cccc(F)c3)[nH]c3cnc(OCCN4CCC(C(C)(C)O)CC4)cc32)CC1]

Step B: cis-Ethyl 4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylate The title compound was prepared from cis-ethyl 4-((E)-2-(3-fluorobenzoylimino)-6-(2-oxoethoxy)-2,3-dihydro-1H-imidazo[4,5-c]pyridin-1-yl)cyclohexanecarboxylate using a method analogous to the preparation of (E)-4-fluoro-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide (0.9 g, 35.4% yield). MS m/z=596.2 [M+H]. Calc'd for $C_{32}H_{42}FN_5O_5$: 595.3.

Example 79

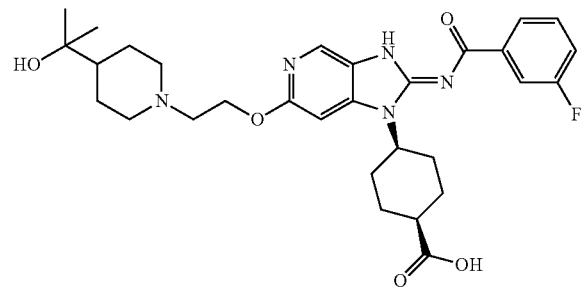 [SMILES: CC(C)(O)C1CCN(CCOc2cc3c(cn2)[nH]/c(=N\C(=O)c2cccc(F)c2)n3[C@H]2CC[C@@H](C(=O)O)CC2)CC1]

cis-4-((E)-2-(3-Fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylic acid The title compound was prepared from cis-ethyl 4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylate using a method analogous to the preparation of cis-4-((E)-2-(benzoylimino)-6-(2-(piperidin-1-yl)ethoxy)-2,3-dihydro-1H-imidazo[4,5-c]pyridin-1-yl)cyclohexanecarboxylic acid (0.65 g, 97% yield). MS m/z=568.2 [M+H]. Calc'd for $C_{30}H_{38}FN_5O_5$: 567.2.

Example 80

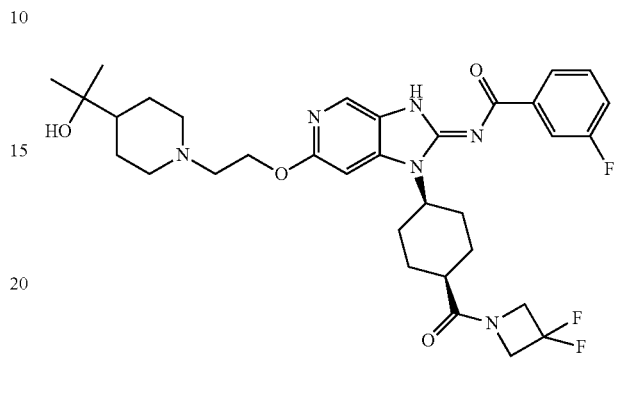

(E)-N-(1-(cis-4-(3,3-Difluoroazetidine-1-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide To a suspension of cis-4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylic acid (0.05 g, 0.088 mmol) in DMF (1 mL) was added CDI (0.029 g, 0.176 mmol), and the resulting mixture was stirred at RT for 1 hour. To this mixture was added 3,3-difluoroazetidine hydrochloride (0.057 g, 0.440 mmol), and the mixture was stirred at RT for 1 hour. The mixture was diluted with DCM (10 mL) and washed with aqueous NH₄Cl (5 mL) and brine (5 mL). The organic layer was collected, dried over sodium sulfate, and concentrated under reduced pressure. The residue was purified by HPLC (5-75% ACN/H₂O; 0.1% TFA) to afford (E)-N-(1-(cis-4-(3,3-difluoroazetidine-1-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide (35 mg, 61.8% yield). MS m/z=643.2 [M+H]. Calc'd for $C_{33}H_{41}F_3N_6O_4$: 642.3.

Example 81

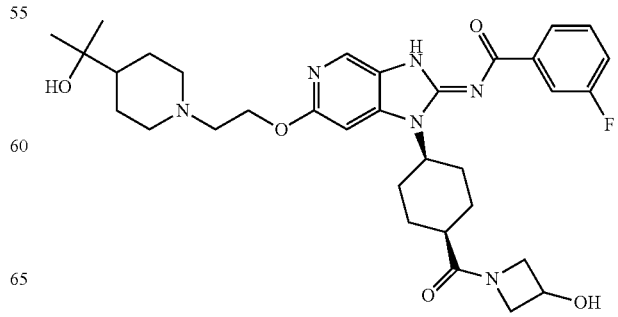

(E)-3-Fluoro-N-(1-(cis-4-(3-hydroxyazetidine-1-carbonyl)cyclohexyl)-6-(2-(4-(2-hydroxypropan-2-yl)piperidin-1-yl)ethoxy)-1H-imidazo[4,5-c]pyridin-2(3H)-ylidene)benzamide The title compound was prepared from cis-4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylic acid using a method analogous to the preparation of (E)-N-(1-(cis-4-(3,3-difluoroazetidine-1-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide (15 mg, 27.3% yield). MS m/z=623.2 [M+H]. Calc'd for $C_{33}H_{43}FN_6O_5$: 622.3. $^1$H NMR (400 MHz, DMSO-$d_6$) δ ppm 1.08 (s, 6H) 1.27-1.37 (m, 4H) 1.62-1.75 (m, 4H) 1.72-1.87 (m, 2H) 1.95-2.12 (m, 3H) 2.68-2.76 (m, 3H) 2.76-2.88 (m, 2H) 3.00-3.13 (m, 2H) 3.69-3.77 (m, 1H) 3.94-4.01 (m, 1H) 4.03-4.09 (m, 1H) 4.13-4.25 (m, 1H) 4.38-4.47 (m, 3H) 4.47-4.57 (m, 1H) 4.74-4.98 (m, 1H) 5.74 (d, J=6.26 Hz, 1H) 7.13 (s, 1H) 7.38-7.48 (m, 1H) 7.53-7.62 (m, 1H) 7.94-8.02 (m, 1H) 8.16 (d, J=7.73 Hz, 1H) 8.31 (s, 1H) 12.78 (s, 1H).

Example 82

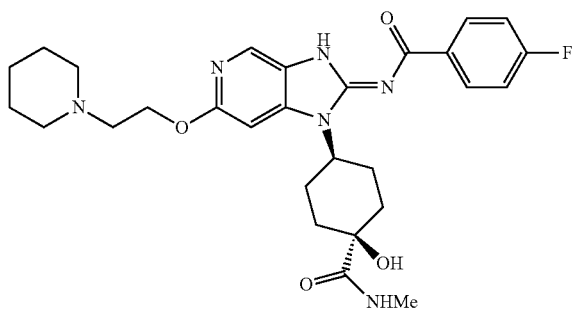 [SMILES: CNC(=O)[C@]1(O)CC[C@@H](n2/c(=N/C(=O)c3ccc(F)cc3)[nH]c3cnc(OCCN4CCCCC4)cc32)CC1]

(E)-4-Fluoro-N-(1-(cis-4-hydroxy-4-(methylcarbamoyl)cyclohexyl)-6-(2-(piperidin-1-yl)ethoxy)-1H-imidazo[4,5-c]pyridin-2(3H)-ylidene)benzamide

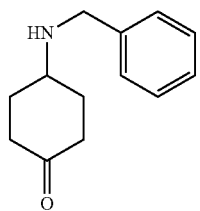 [SMILES: O=C1CCC(NCc2ccccc2)CC1]

Step A: 4-(Benzylamino)cyclohexanone

To a suspension of 1,4-dioxaspiro[4.5]decan-8-one (10 g, 64.0 mmol) in DCE (200 mL) was added phenylmethanamine (7.34 mL, 67.2 mmol), AcOH (3.67 mL, 64.0 mmol) and sodium triacetoxyborohydride (19.00 g, 90 mmol). The reaction was stirred at RT for 16 hours and then the mixture was diluted with 1N NaOH (100 mL) and DCM (250 mL). The organic layer was collected, dried over sodium sulfate and concentrated under reduced pressure. The residue was suspended in acetone (66.7 mL) and treated with HCl (2N aqueous) (64.0 mL, 128 mmol), and the mixture was stirred at RT for 16 hours. The reaction mixture was concentrated to half its volume and diluted with 1 N aqueous NaOH (100 mL) and DCM (300 mL). The layers were separated, and the organic portion was dried over sodium sulfate and concentrated under reduced pressure to afford a white solid. The solid was purified by silica gel chromatography (5-10% MeOH/DCM) to afford 4-(benzylamino)cyclohexanone (9.1 g, 69.9% yield). MS m/z=204.2 [M+H]. Calc'd for $C_{13}H_{17}NO$: 203.1.

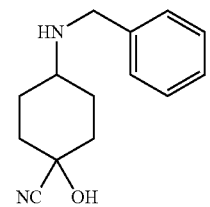

Step B:
4-(Benzylamino)-1-hydroxycyclohexanecarbonitrile

A suspension of 4-(benzylamino)cyclohexanone (5.8 g, 28.5 mmol) in ether (112 mL) was cooled to 0° C. To this mixture was added NaCN (1.538 g, 31.4 mmol) as a solution in NaHCO$_3$ (4.79 g, 57.1 mmol) and water (71.4 mL, 3966 mmol). The reaction mixture was stirred at RT for 16 hours. The resulting mixture was diluted with ether (110 mL) and water (50 mL). The layers were separated, and the organic portion was dried over sodium sulfate and concentrated under reduced pressure to afford 4-(benzylamino)-1-hydroxycyclohexanecarbonitrile as a light yellow solid (5.6 g, 85% yield). MS m/z=231.2 [M+H]. Calc'd for $C_{14}H_{18}N_2O$: 230.1.

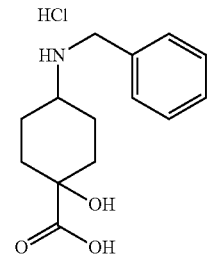 [SMILES: Cl ; O=C(O)C1(O)CCC(NCc2ccccc2)CC1]

Step C: 4-(Benzylamino)-1-hydroxycyclohexanecarboxylic acid hydrochloride.

A suspension of 4-(benzylamino)-1-hydroxycyclohexanecarbonitrile (6 g, 26.1 mmol) in aqueous HCl (10 N) (67.1 mL, 782 mmol) was stirred at 65° C. for 16 hours. The mixture was concentrated under reduced pressure to afford 4-(benzylamino)-1-hydroxycyclohexanecarboxylic acid hydrochloride as a light yellow solid (7.0 g, 94% yield). MS m/z=250.2 [M+H]. Calc'd for $C_{14}H_{19}NO_3$: 249.1.

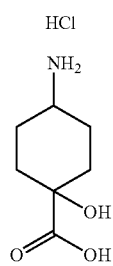

Step D: 4-Amino-1-hydroxycyclohexanecarboxylic acid hydrochloride 4-(Benzylamino)-1-hydroxycyclohexanecarboxylic acid (0.44 g, 1.765 mmol) and 10% palladium on carbon (0.282 g, 0.265 mmol) were charged into a round bottom flask under nitrogen atmosphere. To this was added EtOH (8.82 mL), and the mixture was stirred under an atmosphere of hydrogen at RT for 72 hours. The mixture was diluted with EtOH (10 mL) and filtered through Celite® brand filter aid, rinsing with DCM (10 mL), EtOH (10 mL), and MeOH (10 mL). The filtrate was concentrated under reduced pressure to afford 4-amino-1-hydroxycyclohexanecarboxylic acid as a yellow solid (0.28 g, 100% yield). MS m/z=160.2 [M+H]. Calc'd for $C_7H_{13}NO_3$: 159.1.

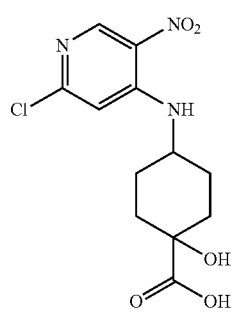 [SMILES: O=C(O)C1(O)CCC(Nc2cc(Cl)ncc2[N+](=O)[O-])CC1]

Step E: 4-(2-Chloro-5-nitropyridin-4-ylamino)-1-hydroxycyclohexanecarboxylic acid A 100 mL round bottom flask was charged with 4-amino-1-hydroxycyclohexanecarboxylic acid hydrochloride (0.28 g, 1.431 mmol), potassium carbonate (0.435 g, 3.15 mmol) and water (1.908 mL). To the mixture was added 2,4-dichloro-5-nitropyridine (0.276 g, 1.431 mmol) as a solution in dioxane (0.954 mL). After the resulting mixture was stirred at 60° C. for 24 hours, it was cooled to RT and treated with 2N aqueous HCl to bring the pH to about 4-5. The aqueous layer was extracted with DCM (3×40 mL). The combined organic portions were dried over sodium sulfate and concentrated to afford 4-(2-chloro-5-nitropyridin-4-ylamino)-1-hydroxycyclohexanecarboxylic acid as a yellow solid (0.28 g, 62.0% yield). MS m/z=316.2 [M+H]. Calc'd for $C_{12}H_{14}ClN_3O_5$: 315.1.

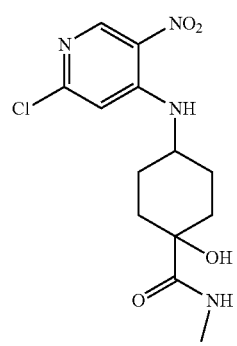 [SMILES: CNC(=O)C1(O)CCC(Nc2cc(Cl)ncc2[N+](=O)[O-])CC1]

Step F: 4-(2-Chloro-5-nitropyridin-4-ylamino)-1-hydroxy-N-methylcyclohexanecarboxamide The title compound was prepared from 4-(2-chloro-5-nitropyridin-4-ylamino)-1-hydroxycyclohexanecarboxylic acid using a method analogous to that used for the synthesis of cis-4-(2-chloro-5-nitropyridin-4-ylamino)-1-hydroxy-N-isopropylcyclohexanecarboxamide (240 mg, 82% yield). MS m/z=329.2 [M+H]. Calc'd for $C_{13}H_{17}ClN_4O_4$: 328.1.

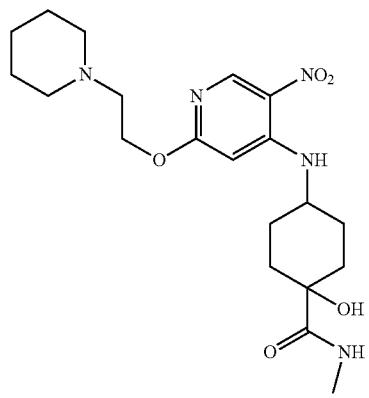 [SMILES: CNC(=O)C1(O)CCC(Nc2cc(OCCN3CCCCC3)ncc2[N+](=O)[O-])CC1]

Step G: 1-Hydroxy-N-methyl-4-(5-nitro-2-(2-(piperidin-1-yl)ethoxy)pyridin-4-ylamino)cyclohexanecarboxamide The title compound was prepared from 4-(2-chloro-5-nitropyridin-4-ylamino)-1-hydroxy-N-methylcyclohexanecarboxamide using a method analogous to the preparation of (R)-tert-butyl 3-methyl-4-(cis-4-(5-nitro-2-(2-(piperidin-1-yl)ethoxy)pyridin-4-ylamino)cyclohexanecarbonyl)piperazine-1-carboxylate (150 mg, 49.8% yield). MS m/z=422.2 [M+H]. Calc'd for $C_{20}H_{31}N_5O_5$: 421.2.

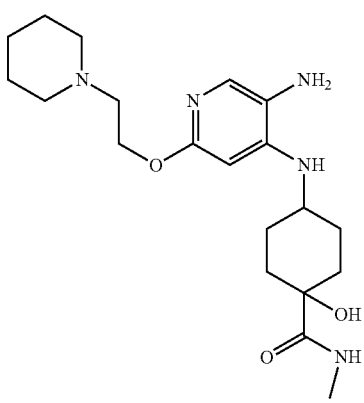

Step H: 4-(5-Amino-2-(2-(piperidin-1-yl)ethoxy)
pyridin-4-ylamino)-1-hydroxy-N-methylcyclohexan-
ecarboxamide The title compound was prepared from 1-hydroxy-N-methyl-4-(5-nitro-2-(2-(piperidin-1-yl)ethoxy)pyridin-4-ylamino)cyclohexanecarboxamide using a method analogous to the preparation of (R)-tert-butyl 4-(cis-4-(5-amino-2-(2-(piperidin-1-yl)ethoxy)pyridin-4-ylamino)cyclohexanecarbonyl)-3-methylpiperazine-1-carboxylate (46 mg, 100% yield). MS m/z=392.2 [M+H]. Calc'd for $C_{20}H_{33}N_5O_3$: 391.3.

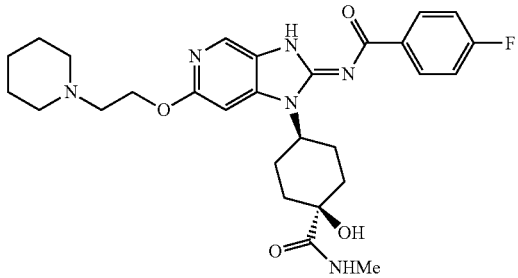 [SMILES: CNC(=O)[C@]1(O)CC[C@@H](n2/c(=N/C(=O)c3ccc(F)cc3)[nH]c3cnc(OCCN4CCCCC4)cc32)CC1]

Step I: (E)-4-Fluoro-N-(1-(cis-4-hydroxy-4-(methylcarbamoyl)cyclohexyl)-6-(2-(piperidin-1-yl)ethoxy)-1H-imidazo[4,5-c]pyridin-2(3H)-ylidene)benzamide The title compound was prepared from 4-(5-amino-2-(2-(piperidin-1-yl)ethoxy)pyridin-4-ylamino)-1-hydroxy-N-methylcyclohexanecarboxamide using a method analogous to the preparation of cis-methyl 4-((E)-2-(benzoylimino)-2,3-dihydro-1H-imidazo[4,5-c]pyridin-1-yl)cyclohexanecarboxylate (10 mg, 18.2% yield). MS m/z=539.2 [M+H]. Calc'd for $C_{28}H_{35}FN_6O_4$: 538.3.

Example 83

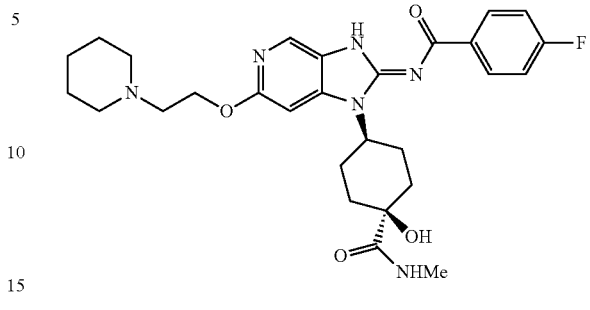

(E)-4-Fluoro-N-(1-(trans-4-hydroxy-4-(methylcarbamoyl)cyclohexyl)-6-(2-(piperidin-1-yl)ethoxy)-1H-imidazo[4,5-c]pyridin-2(3H)-ylidene)benzamide The title compound was isolated from the reaction to prepare (E)-4-fluoro-N-(1-(cis-4-hydroxy-4-(methylcarbamoyl)cyclohexyl)-6-(2-(piperidin-1-yl)ethoxy)-1H-imidazo[4,5-c]pyridin-2(3H)-ylidene)benzamide (8 mg, 14.5% yield). MS m/z=539.2 [M+H]. Calc'd for $C_{28}H_{35}FN_6O_4$: 538.3.

Example 84

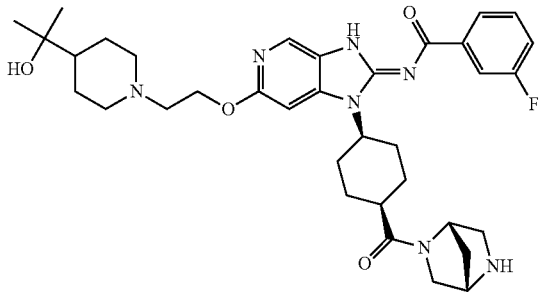 [SMILES: CC(C)(O)C1CCN(CCOc2cc3c(cn2)[nH]/c(=N\C(=O)c2cccc(F)c2)n3[C@H]2CC[C@@H](C(=O)N3C[C@@H]4C[C@H]3CN4)CC2)CC1]

(E)-N-(1-(cis-4-(cis-2,5-Diazabicyclo[2.2.1]heptane-2-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide Intermediate cis-tert-butyl 5-(cis-4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarbonyl)-2,5-diazabicyclo[2.2.1]heptane-2-carboxylate was prepared from cis-4-((E)-2-(3-fluorobenzoylimino)-6-(2-(4-(2-hydroxypropan-2-yl)piperidin-1-yl)ethoxy)-2,3-dihydro-1H-imidazo[4,5-c]pyridin-1-yl)cyclohexanecarboxylic acid using a method analogous to the preparation of (E)-N-(1-(cis-4-(3,3-difluoroazetidine-1-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide. The unpurified intermediate compound was deprotected using a procedure analogous to that used in the preparation of (E)-4-cyano-N-(1-(cis-4-((R)-2-methylpiperazine-1-carbonyl)cyclohexyl)-6-(2-(piperidin-1-yl)ethoxy)-1H-imidazo[4,5-c]pyridin-2(3H)-ylidene)benzamide to afford the title compound (10 mg, 17.5% yield). MS m/z=648.2 [M+H]. Calc'd for $C_{35}H_{46}FN_7O_4$: 647.4.

Example 85

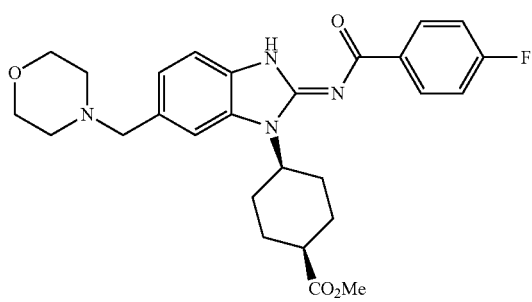 [SMILES: COC(=O)[C@H]1CC[C@@H](n2/c(=N/C(=O)c3ccc(F)cc3)[nH]c3ccc(CN4CCOCC4)cc32)CC1]

cis-Methyl 4-((E)-2-(4-fluorobenzoylimino)-6-(morpholinomethyl)-2,3-dihydro-1H-benzo[d]imidazol-1-yl)cyclohexanecarboxylate The title compound was prepared from cis-methyl 4-((E)-2-(4-fluorobenzoylimino)-6-(hydroxymethyl)-2,3-dihydro-1H-benzo[d]imidazol-1-yl)cyclohexanecarboxylate and morpholine using a method analogous to the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate (20 mg, 31.3% yield). MS m/z=495.2 [M+H]. Calc'd for $C_{27}H_{31}FN_4O_4$: 494.2.

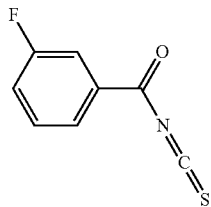 [SMILES: O=C(N=C=S)c1cccc(F)c1]

3-Fluorobenzoyl isothiocyanate

Potassium thiocyanate (11.03 g, 114 mmol) was suspended in acetone (63.1 mL) and heated to 40° C. under nitrogen atmosphere. To this was added 3-fluorobenzoyl chloride (11.35 mL, 95 mmol), and the resulting mixture was stirred at 50° C. for 6 hours. The heterogeneous mixture was filtered, and the solid was further washed with acetone. The filtrate was concentrated and purified by silica gel chromatography (10% EtOAc/Hexanes as the eluent) to afford 3-fluorobenzoyl isothiocyanate (6.5 g, 37.9% yield) as a light orange oil.

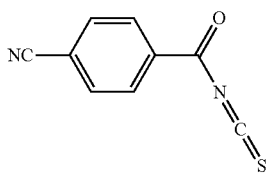 [SMILES: N#Cc1ccc(C(=O)N=C=S)cc1]

4-Cyanobenzoyl isothiocyanate

The title compound was prepared from 4-cyanobenzoyl chloride using a method analogous to that used in the preparation of 3-fluorobenzoyl isothiocyanate (1.0 g, 16.0% yield).

4-Fluorobenzoyl isothiocyanate

The title compound was prepared from 4-fluorobenzoyl chloride using a method analogous to that used in the preparation of 3-fluorobenzoyl isothiocyanate (11.1 g, 44% yield).

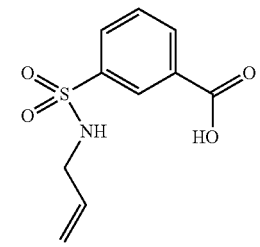 [SMILES: C=CCNS(=O)(=O)c1cccc(C(=O)O)c1]

3-(N-allylsulfamoyl)benzoic acid

To a solution of 3-(chlorosulfonyl)benzoic acid (5 g, 22.66 mmol) in THF (50.4 mL) at 0° C. was added allylamine (2.038 mL, 27.2 mmol) followed by NaOH (1N aqueous) (49.9 mL, 49.9 mmol). The mixture was allowed to warm to RT over 1 hour and stirred an additional 16 hours. The mixture was diluted with 1N HCl (250 mL), and the aqeuous layer was extracted with EtOAc (300 mL). The organic layer was dried over sodium sulfate and concentrated to dryness to afford 3-(N-allylsulfamoyl)benzoic acid as white solid (5.2 g, 95% yield). MS m/z=242.0 [M+H]. Calc'd for $C_{10}H_{11}NO_4S$: 241.0.

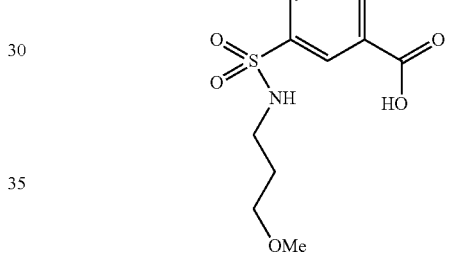

2-Fluoro-5-(N-(3-methoxypropyl)sulfamoyl)benzoic acid

The title compound was prepared from 5-(chlorosulfonyl)-2-fluorobenzoic acid using a method analogous to the preparation of 3-(N-allylsulfamoyl)benzoic acid (1.0 g, 82% yield). MS m/z=292.0 [M+H]. Calc'd for $C_{11}H_{14}FNO_5S$: 291.1.

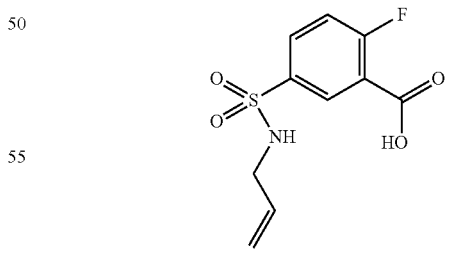

5-(N-allylsulfamoyl)-2-fluorobenzoic acid

The title compound was prepared from 5-(chlorosulfonyl)-2-fluorobenzoic acid using a method analogous to the preparation of 3-(N-allylsulfamoyl)benzoic acid (0.8 g, 73.7% yield). MS m/z=260.0 [M+H]. Calc'd for $C_{10}H_{10}FNO_4S$: 259.0.

173
cis-Ethyl 4-aminocyclohexanecarboxylate
The title compound was prepared from cis-4-aminocyclohexanecarboxylic acid using a method analogous to cis-methyl 4-aminocyclohexanecarboxylate.
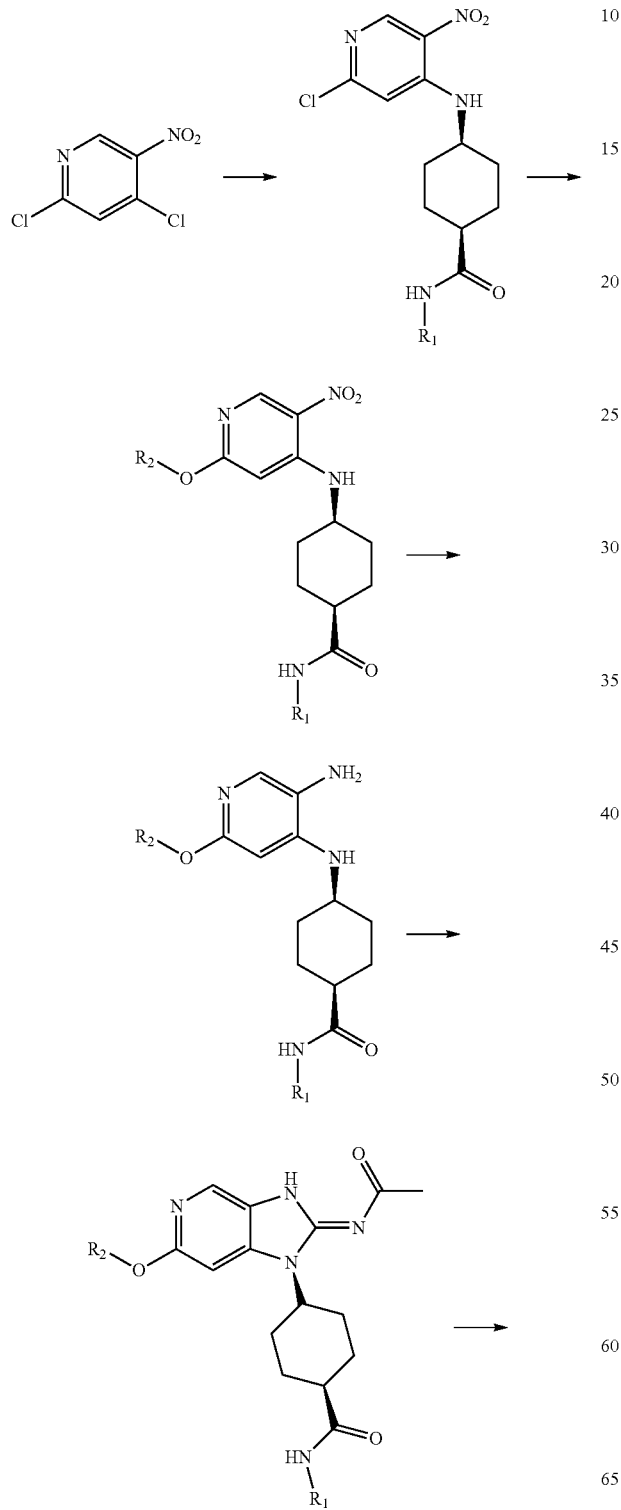
Scheme A
174
-continued
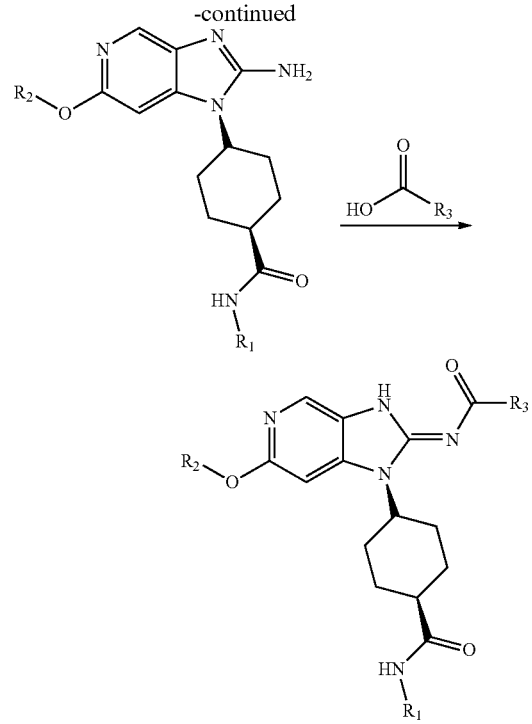
Example 86
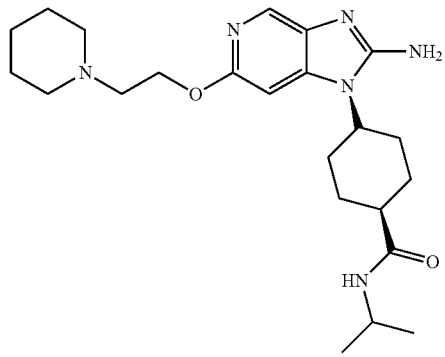
cis-4-(2-Amino-6-(2-(piperidin-1-yl)ethoxy)-1H-imidazo[4,5-c]pyridin-1-yl)-N-isopropylcyclohexanecarboxamide
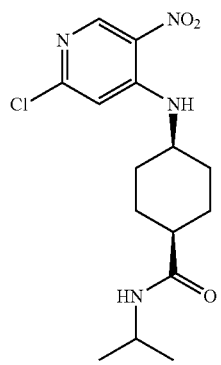 [SMILES: CC(C)NC(=O)[C@H]1CC[C@@H](Nc2cc(Cl)ncc2[N+](=O)[O-])CC1]

Step A: cis-4-(2-Chloro-5-nitropyridin-4-ylamino)-N-isopropylcyclohexanecarboxamide To a solution of cis-4-amino-N-isopropylcyclohexanecarboxamide hydrochloride (12.58 g, 57.0 mmol) and DIPEA (29.0 mL, 166 mmol) in ACN (104 mL) was added 2,4-dichloro-5-nitropyridine (10.00 g, 51.8 mmol). The resulting mixture was stirred at RT for 24 hours. The reaction mixture was diluted with water and washed with DCM (×2). The combined organic layers were washed with a minimal volume of brine, dried over sodium sulfate, filtered and concentrated in vacuo. After almost complete concentration of solvent, EtOAc was added, and the solid precipitate was collected yielding cis-4-(2-chloro-5-nitropyridin-4-ylamino)-N-isopropylcyclohexanecarboxamide as a yellow solid (12.97 g, 73.4% yield).

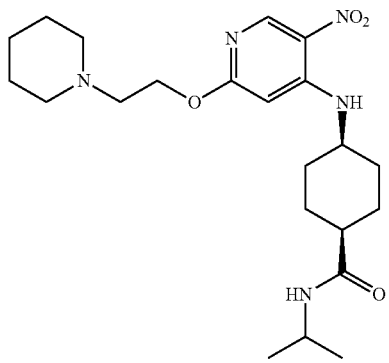 [SMILES: CC(C)NC(=O)[C@H]1CC[C@@H](Nc2cc(OCCN3CCCCC3)ncc2[N+](=O)[O-])CC1]

Step B: cis-N-Isopropyl-4-(5-nitro-2-(2-(piperidin-1-yl)ethoxy)pyridin-4-ylamino)cyclohexanecarboxamide A round-bottom flask under nitrogen was charged with 1-piperidineethanol (19.34 mL, 147 mmol), 18-crown-6 (11.63 g, 44.0 mmol), cis-4-(2-chloro-5-nitropyridin-4-ylamino)-N-isopropylcyclohexanecarboxamide (10.00 g, 29.3 mmol), cesium carbonate (28.7 g, 88 mmol) and toluene (196 mL). The reaction mixture was purged with nitrogen and heated at 75° C. for 12 hours. The reaction mixture was diluted with EtOAc, and washed with brine, followed by saturated NH$_4$Cl (aq). The aqueous layers were back-extracted with EtOAc, and the combined organic layers were dried over magnesium sulfate, filtered and concentrated in vacuo. The residual material was purified via silica gel chromatography eluting with isocratic 90:10:1 DCM:MeOH:NH$_4$OH, to provide cis-N-isopropyl-4-(5-nitro-2-(2-(piperidin-1-yl)ethoxy)pyridin-4-ylamino)cyclohexanecarboxamide (10.79 g, 85% yield) as a rust-colored solid, which was taken forward without further purification. MS m/z=434.2 [M+H], calc 433.54 for C$_{22}$H$_{35}$N$_5$O$_4$.

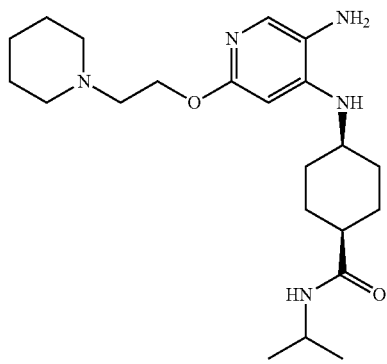 [SMILES: CC(C)NC(=O)[C@H]1CC[C@@H](Nc2cc(OCCN3CCCCC3)ncc2N)CC1]

Step C: cis-4-(5-Amino-2-(2-(piperidin-1-yl)ethoxy)pyridin-4-ylamino)-N-isopropylcyclohexanecarboxamide To a solution of cis-N-isopropyl-4-(5-nitro-2-(2-(piperidin-1-yl)ethoxy)pyridin-4-ylamino)cyclohexanecarboxamide (10.79 g, 24.89 mmol) in MeOH (124 mL) was added tin (II) chloride (18.88 g, 100 mmol), and the reaction was stirred at 80° C. for 2 hours. The reaction mixture was concentrated in vacuo, and the residue was dissolved in EtOAc, then diluted with 1N aqueous NaOH. The layers were separated, and the organic layer was washed with brine, dried over magnesium sulfate, filtered, and concentrated in vacuo to yield cis-4-(5-amino-2-(2-(piperidin-1-yl)ethoxy)pyridin-4-ylamino)-N-isopropylcyclohexanecarboxamide (8.06 g, 80% yield). MS m/z=404.2 [M+H], calc 403.56 for C$_{22}$H$_{37}$N$_5$O$_2$.

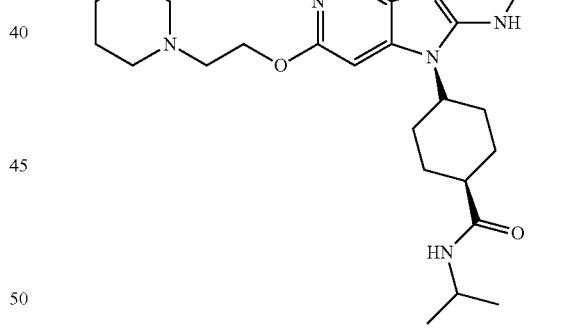

Step D: cis-4-(2-Acetamido-6-(2-(piperidin-1-yl)ethoxy)-1H-imidazo[4,5-c]pyridin-1-yl)-N-isopropylcyclohexanecarboxamide Acetyl isothiocyanate (1.755 mL, 19.97 mmol) was added to a heated (100° C. oil bath) solution of cis-4-(5-amino-2-(2-(piperidin-1-yl)ethoxy)pyridin-4-ylamino)-N-isopropyl-cyclohexanecarbox-amide (8.06 g, 19.97 mmol) in dioxane (100 mL). After 5 minutes, complete conversion to the thiourea intermediate was observed. The reaction was cooled to RT, and EDC (11.49 g, 59.9 mmol) and DIPEA (12.56 mL, 71.9 mmol) were added. Heating was resumed at 60° C. for 2.5 hours. The reaction mixture was pre-absorbed onto silica gel, and purified via silica gel chromatography, eluting with 90:10:1 DCM:MeOH:NH₄OH to yield cis-4-(2-acetamido-6-(2-(piperidin-1-yl)ethoxy)-1H-imidazo[4,5-c]pyridin-1-yl)-N-isopropylcyclohexanecarboxamide (8.56 g, 18.19 mmol, 91% yield) as an orange solid. MS m/z=471.2 [M+H], calc 470.61 for $C_{25}H_{38}N_6O_3$.

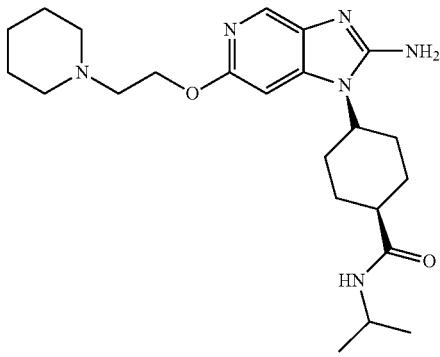

Step E: cis-4-(2-Amino-6-(2-(piperidin-1-yl)ethoxy)-1H-imidazo[4,5-c]pyridin-1-yl)-N-isopropylcyclohexanecarboxamide cis-4-(2-Acetamido-6-(2-(piperidin-1-yl)ethoxy)-1H-imidazo[4,5-c]pyridin-1-yl)-N-isopropylcyclohexanecarboxamide (8.56 g, 18.19 mmol) was diluted with 2N HCl (aq) (91 mL, 182 mmol) and heated at 50° C. overnight. The reaction mixture was concentrated in vacuo, and purified via silica gel chromatography using 0-100% 90:10:1 DCM:MeOH:NH₄OH in DCM to yield cis-4-(2-amino-6-(2-(piperidin-1-yl)ethoxy)-1H-imidazo[4,5-c]pyridin-1-yl)-N-isopropylcyclohexanecarboxamide (6.39 g, 82% yield). MS m/z=429.2 [M+H], calc 428.57 for $C_{23}H_{36}N_6O_2$.

Example 87

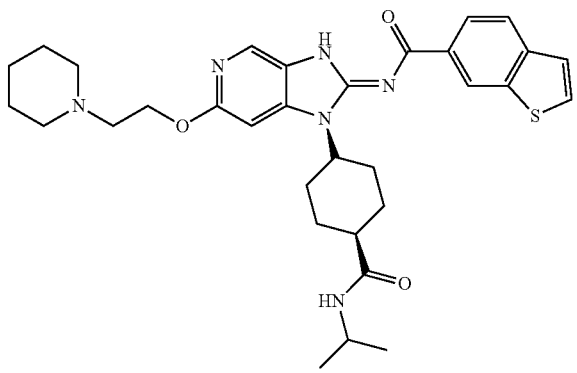

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide 1-Benzothiophene-5-carboxylic acid (0.022 g, 0.124 mmol), EDC (0.036 g, 0.186 mmol) and HOBT (0.019 g, 0.124 mmol) were combined in DMF (0.124 mL). A solution of cis-4-(2-amino-6-(2-(piperidin-1-yl)ethoxy)-1H-imidazo[4,5-c]pyridin-1-yl)-N-isopropylcyclohexanecarboxamide (0.053 g, 0.124 mmol) in DMF (0.124 mL) was added, followed by DIPEA (0.086 mL, 0.495 mmol). The reaction mixture was stirred at RT for 16 h. The mixture was diluted with EtOAc and washed with water (x1) and brine (×1). The organic layer was dried over sodium sulfate, filtered and concentrated in vacuo. The residual material was purified via silica gel chromatography, eluting with a gradient of 0% to 100% 90:10:1 DCM:MeOH:NH₄OH in DCM to provide a residual material, which was further purified via reverse-phase preparative HPLC (0.1% TFA in ACN/H₂O, gradient 10% to 90% over 20 min) to provide the TFA salt of (E)-N-(1-(cis-4-(isopropylcarbamoyl)cyclohexyl)-6-(2-(piperidin-1-yl)ethoxy)-1H-imidazo-[4,5-c]pyridin-2(3H)-ylidene)benzo[b]thiophene-6-carboxamide as a white solid (0.020 g, 23.01% yield). MS m/z=589.2 [M+H], calc 588.76 for $C_{32}H_{40}N_6O_3S$.

Example 88

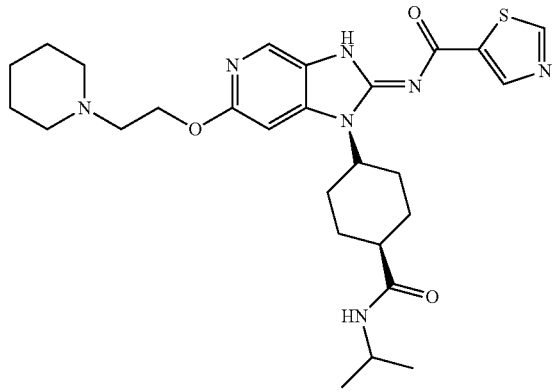

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)thiazole-5-carboxamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using thiazole-5-carboxylic acid. After preparative HPLC purification in the last step, the TFA salt was free-based using an SCX-ion exchange column to obtain (Z)—N—((R)-3-(cis-4-(isopropylcarbamoyl)cyclohexyl)-5-(2-(piperidin-1-yl)ethoxy)-1H-pyrrolo[2,3-c]pyridin-2(3H)-ylidene)thiazole-5-carboxamide as a white solid (20.68% yield). MS m/z=540.2 [M+H], calc 539.69 for $C_{27}H_{37}N_7O_3S$. ¹H NMR (400 MHz, DMSO-d₆) δ ppm 1.09 (d, J=6.55 Hz, 6H) 1.32-1.42 (m, 2H) 1.44-1.55 (m, 4H) 1.55-1.76 (m, 4H) 2.01-2.13 (m, 2H) 2.37-2.48 (m, 4H) 2.58-2.72 (m, 6H) 4.01 (dq, J=13.77, 6.99 Hz, 1H) 4.35 (t, J=6.06 Hz, 2H) 4.65-4.83 (m, 1H) 7.67 (d, J=7.24 Hz, 1H) 8.23 (s, 1H) 8.53 (s, 1H) 9.18 (s, 1H) 12.56 (br. s., 1H).

Example 89

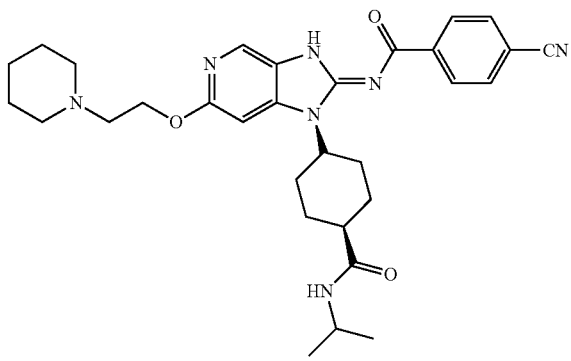

(E)-4-Cyano-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-cyanobenzoic acid. After preparative HPLC purification, the TFA salt was free-based using an SCX-ion exchange column to obtain (E)-4-cyano-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide as a light yellow solid (34.6% yield). MS m/z=558.2 [M+H], calc 557.69 for $C_{31}H_{39}N_7O_3$.

Example 90

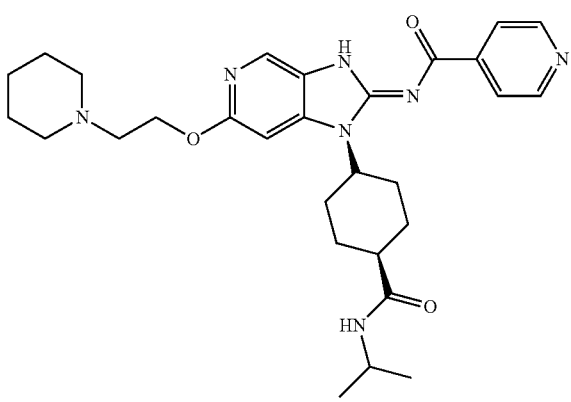

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)isonicotinamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using isonicotinic acid. After preparative HPLC purification, the TFA salt was free-based using an SCX-ion exchange column to obtain (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)isonicotinamide as a tan solid (44.2% yield). MS m/z=534.2 [M+H], calc 533.67 for $C_{29}H_{39}N_7O_3$.

Example 91

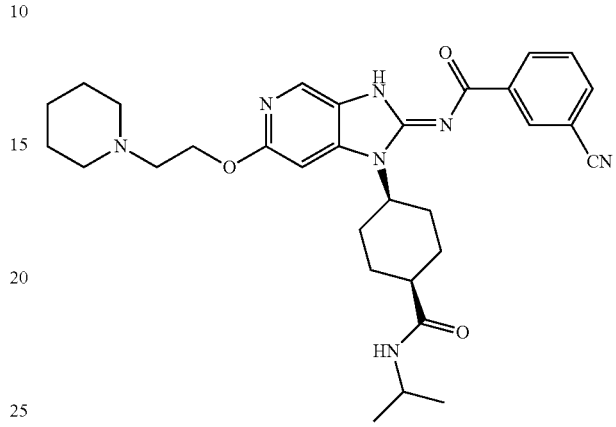

(E)-3-Cyano-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-cyanobenzoic acid (35% yield; white solid). MS m/z=558.2 [M+H], calc 557.69 for $C_{31}H_{39}N_7O_3$. $^1$H NMR (400 MHz, CDCl$_3$) δ ppm 1.22 (d, J=6.55 Hz, 6H) 1.37-1.56 (m, 1H) 1.75-2.11 (m, 9H) 2.18-2.27 (m, 2H) 2.51-2.56 (m, 1H) 2.73-2.98 (m, 4H) 3.52-3.58 (m, 2H) 3.75-3.85 (m, 2H) 4.11-4.21 (m, 1H) 4.75-4.81 (m, 2H) 4.85-4.96 (m, 1H) 5.40-5.46 (m, 1H) 7.31 (s, 1H) 7.61 (t, J=7.9 Hz, 1H) 7.80 (dt, J=7.68, 1.39 Hz, 1H) 8.17 (s, 1H) 8.53 (dt, J=7.95, 1.41 Hz, 1H) 8.63-8.66 (m, 1H) 11.49 (br. s., 1H).

Example 92

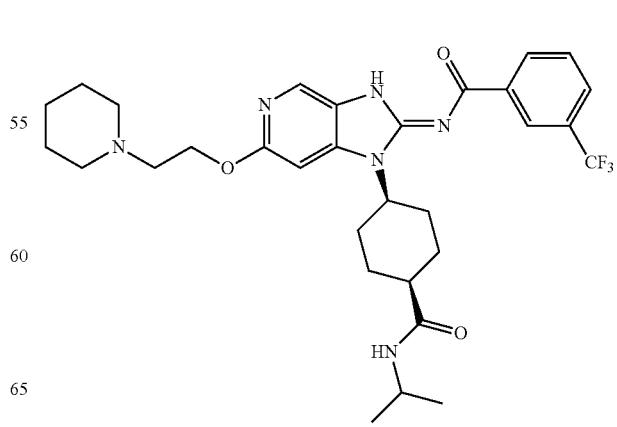

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-3-(trifluoromethyl)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-(trifluoromethyl)benzoic acid (32.3% yield; white solid). MS m/z=601.2 [M+H], calc 600.67 for $C_{31}H_{39}F_3N_6O_3$.

Example 93

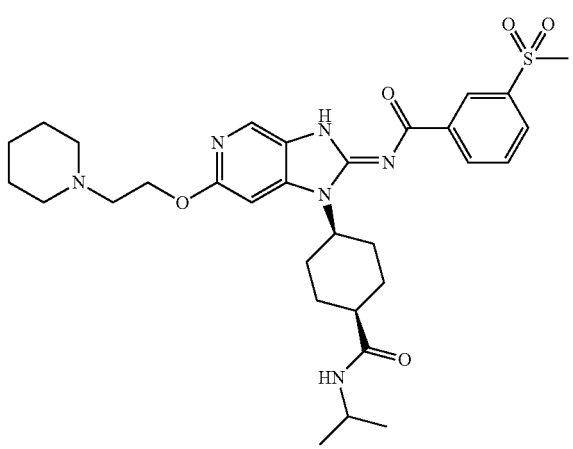 [SMILES: CC(C)NC(=O)[C@H]1CC[C@@H](n2/c(=N/C(=O)c3cccc(S(C)(=O)=O)c3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-3-(methylsulfonyl)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-(methylsulfonyl)benzoic acid (50.7% yield; white solid). MS m/z=611.4 [M+H], calc 610.77 for $C_{31}H_{42}N_6O_5S$.

Example 94

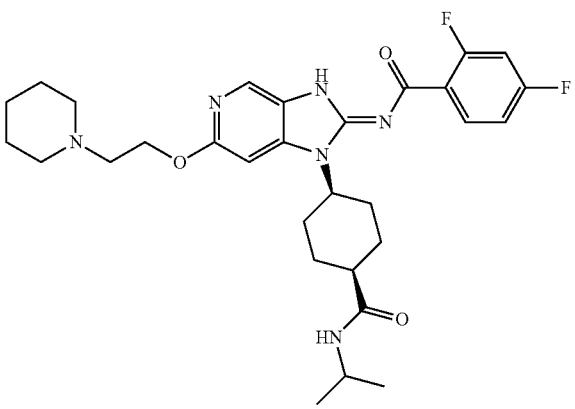 [SMILES: CC(C)NC(=O)[C@H]1CC[C@@H](n2/c(=N/C(=O)c3ccc(F)cc3F)[nH]c3cnc(OCCN4CCCCC4)cc32)CC1]

(E)-2,4-Difluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 2,4-difluorobenzoic acid (14.5% yield; white solid). MS m/z=569.2 [M+H], calc 568.66 for $C_{30}H_{38}F_2N_6O_3$. $^1$H NMR (400 MHz, CDCl$_3$) δ ppm 1.20 (d, J=6.46 Hz, 6H) 1.35-1.52 (m, 2H) 1.72-1.85 (m, 4H) 1.85-1.97 (m, 3H) 1.96-2.12 (m, 2H) 2.13-2.21 (m, 2H) 2.45-2.51 (m, 1H) 2.64-2.82 (m, 2H) 2.83-94 (m, 2H) 3.49-3.61 (m, 2H) 3.75-3.80 (m, 2H) 4.05-4.19 (m, 1H) 4.71-4.91 (m, 3H) 5.43-5.47 (m, 1H) 6.82-6.91 (m, 1H) 6.93-6.98 (m, 1H) 8.12-8.28 (m, 2H) 11.79 (br. s., 1H).

Example 95

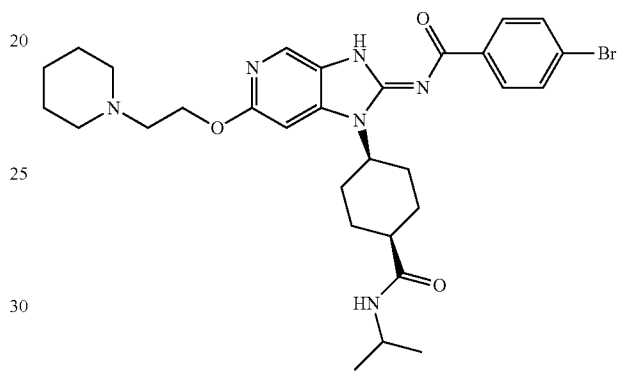

(E)-4-Bromo-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-bromobenzoic acid (22.4% yield; white solid). MS m/z=612.2 [M+H], calc 611.57 for $C_{30}H_{39}BrN_6O_3$. $^1$H NMR (400 MHz, CDCl$_3$) δ ppm 1.21 (d, J=6.55 Hz, 6H) 1.33-1.55 (m, 1H) 1.73-2.27 (m, 11H) 2.48-2.54 (m, 1H) 2.67-2.99 (m, 4H) 3.51-3.59 (m, 2H) 3.74-3.82 (d, 2H) 4.10-4.20 (m, 1H) 4.75-4.90 (m, 3H) 5.39-5.44 (m, 1H) 7.30 (s, 1H) 7.45-7.73 (m, 2H) 7.97-8.33 (m, 3H) 11.52 (br. s., 1H)

Example 96

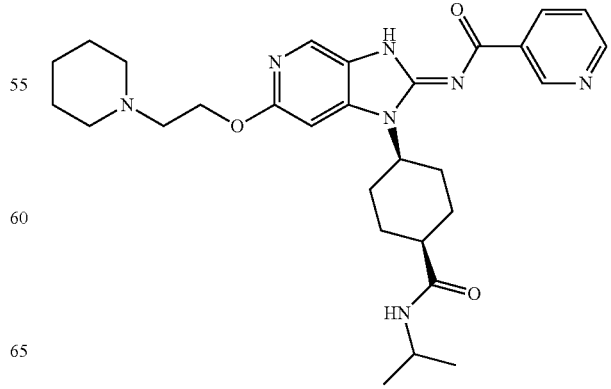

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)nicotinamide The TFA salt of the compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using nicotinic acid (60.9% yield; white solid). MS m/z=534.2 [M+H], calc 533.67 for $C_{29}H_{39}N_7O_3$.

Example 97

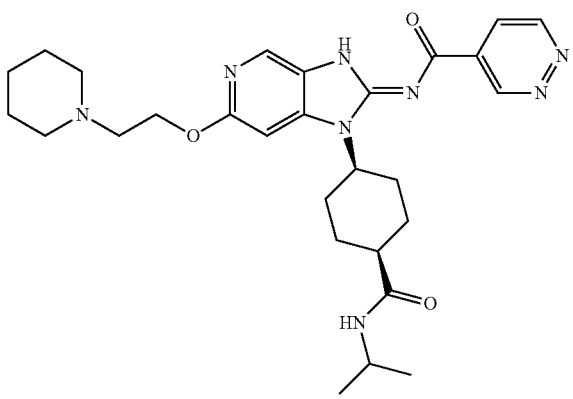 [SMILES: CC(C)NC(=O)[C@H]1CC[C@@H](n2/c(=N/C(=O)c3ccnnc3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)pyridazine-4-carboxamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using pyridazine-4-carboxylic acid (32.4% yield; yellow solid). MS m/z=535.2 [M+H], calc 534.65 for $C_{28}H_{38}N_8O_3$. $^1$H NMR (400 MHz, CDCl$_3$) δ ppm 1.22 (d, J=6.55 Hz, 6H) 1.38-1.54 (m, 1H) 1.76-1.97 (m, 7H) 2.04-2.26 (m, 4H) 2.52-2.56 (m, 1H) 2.77-2.95 (m, 4H) 3.48-3.55 (m, 2H) 3.75-3.82 (m, 2H) 4.11-4.23 (m, 1H) 4.77-4.91 (m, 3H) 5.40-5.45 (m, 1H) 7.23 (s, 1H) 8.23 (s, 1H) 8.56 (dd, J=5.04, 2.01 Hz, 1H) 9.47 (dd, J=5.28, 1.17 Hz, 1H) 10.09 (dd, J=1.96, 1.17 Hz, 1H) 11.73 (br. s., 1H).

Example 98

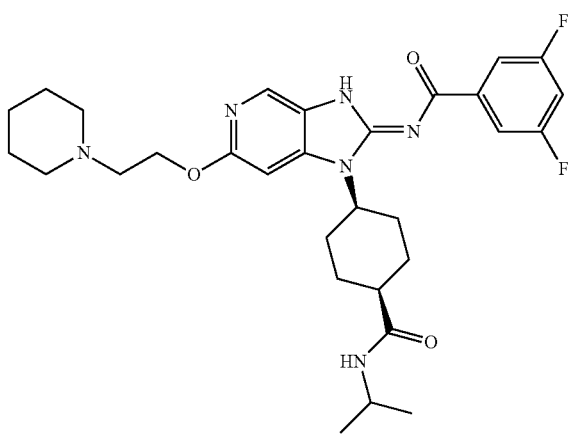 [SMILES: CC(C)NC(=O)[C@H]1CC[C@@H](n2/c(=N/C(=O)c3cc(F)cc(F)c3)[nH]c3cnc(OCCN4CCCCC4)cc32)CC1]

(E)-3,5-Difluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3,5-difluorobenzoic acid (50.8% yield; white solid). MS m/z=569.2 [M+H], calc 568.66 for $C_{30}H_{38}F_2N_6O_3$. $^1$H NMR (400 MHz, CDCl$_3$) δ ppm 1.22 (d, J=6.55 Hz, 6H) 1.38-1.54 (m, 1H) 1.74-2.25 (m, 11H) 2.48-2.57 (m, 1H) 2.70-2.97 (m, 4H) 3.52-3.59 (m, 2H) 3.74-3.84 (m, 2H) 4.10-4.21 (m, 1H) 4.78-4.83 (m, 2H) 4.83-4.96 (m, 1H) 5.40-5.45 (m, 1H) 6.93-7.02 (m, 1H) 7.33 (s, 1H) 7.83 (dd, J=8.17, 2.30 Hz, 2H) 8.18 (s, 1H) 11.44 (br. s., 1H)

Example 99

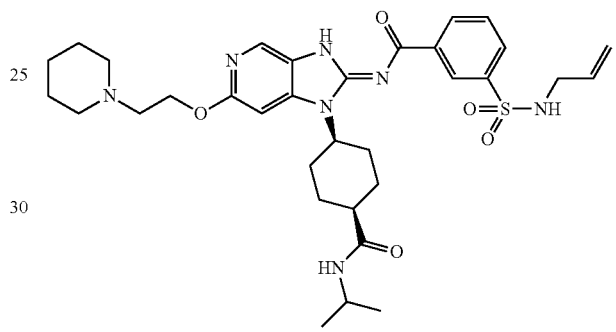

(E)-3-(N-Allylsulfamoyl)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-(N-allylsulfamoyl)benzoic acid (27.4% yield; white solid). MS m/z=652.2 [M+H], calc 651.82 for $C_{33}H_{45}N_7O_5S$.

Example 100

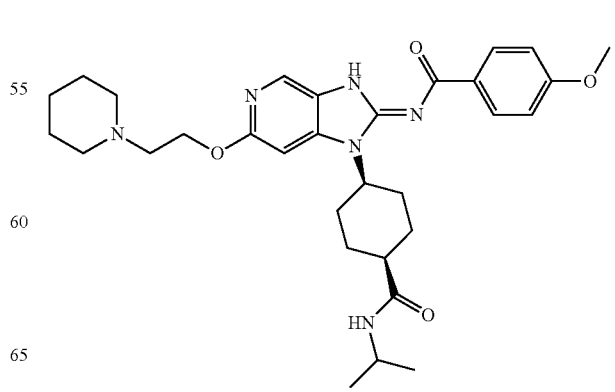

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-4-methoxybenzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-e]pyridin-2(3H)-ylidene)benzo[b]thiophene-6-carboxamide, using 4-methoxybenzoic acid (38.0% yield; white solid). MS m/z=563.2 [M+H], calc 562.70 for $C_{31}H_{42}N_6O_4$. $^1$H NMR (400 MHz, DMSO-$d_6$) δ ppm 1.09 (d, J=6.55 Hz, 6H) 1.30-1.51 (m, 1H) 1.56-1.91 (m, 9H) 2.01-2.10 (m, 2H) 2.56-2.73 (m, 2H) 2.94-3.11 (m, 2H) 3.47-3.60 (m, 4H) 3.83 (s, 3H) 3.90-4.01 (m, 2H) 4.61-4.67 (m, 2H) 6.98-7.01 (m, 2H) 7.09 (s, 1H) 7.74 (d, J=7.82 Hz, 1H) 8.19 (d, J=8.71 Hz, 2H) 8.26 (s, 1H) 9.31 (br. s., 1H) 12.55 (br. s., 1H).

Example 101

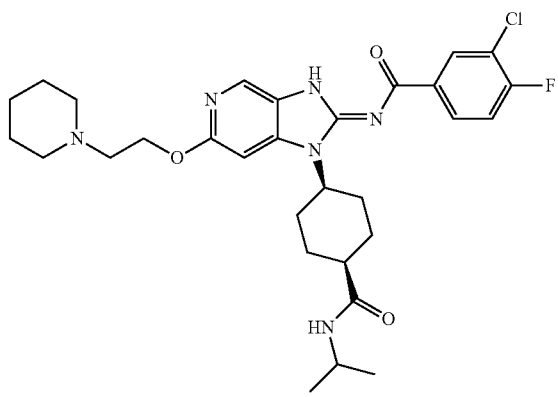 [SMILES: CC(C)NC(=O)[C@H]1CC[C@@H](n2/c(=N/C(=O)c3ccc(F)c(Cl)c3)[nH]c3cnc(OCCN4CCCCC4)cc32)CC1]

(E)-3-Chloro-4-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-chloro-4-fluorobenzoic acid (44.7% yield; white solid). MS m/z=585.2 [M+H], calc 585.11 for $C_{30}H_{38}ClFN_6O_3$. $^1$H NMR (400 MHz, CDCl$_3$) δ ppm 1.22 (d, J=6.6 Hz, 6H) 1.40-1.53 (m, 1H) 1.74-2.13 (m, 9H) 2.15-2.26 (m, 2H) 2.48-2.55 (m, 1H) 2.72-2.96 (m, 4H) 3.51-3.57 (m, 2H) 3.74-3.83 (m, 2H) 4.10-4.22 (m, 1H) 4.75-4.81 (m, 2H) 4.81-4.92 (m, 1H) 5.38-5.44 (m, 1H) 7.22 (t, J=8.61 Hz, 1H) 7.30 (s, 1H) 8.16 (s, 1H) 8.23 (ddd, J=8.6, 4.9, 2.2 Hz, 1H) 8.36 (dd, J=7.29, 2.10 Hz, 1H) 11.46 (br. s., 1H).

Example 102

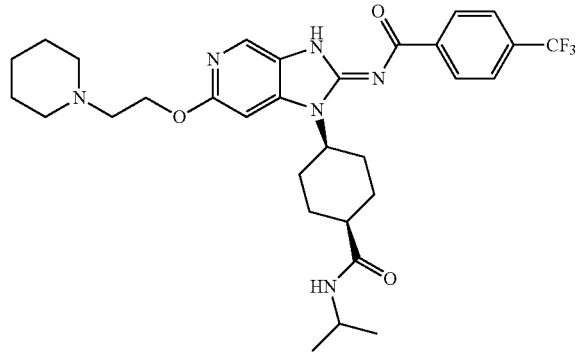 [SMILES: CC(C)NC(=O)[C@H]1CC[C@@H](n2/c(=N/C(=O)c3ccc(C(F)(F)F)cc3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-4-(trifluoromethyl)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-(trifluoromethyl)benzoic acid (48.0% yield; white solid). MS m/z=601.2 [M+H], calc 600.67 for $C_{31}H_{39}F_3N_6O_3$. $^1$H NMR (400 MHz, CDCl$_3$) δ ppm 1.21 (d, J=6.6 Hz, 6H) 1.35-1.57 (m, 1H) 1.76-2.29 (m, 11H) 2.49-2.56 (m, 1H) 2.73-2.98 (m, 4H) 3.51-3.60 (m, 2H) 3.73-3.84 (m, 2H) 4.09-4.21 (m, 1H) 4.75-4.96 (m, 3H) 5.39-5.46 (m, 1H) 7.31 (s, 1H) 7.73 (d, J=8.4 Hz, 2H) 8.18 (s, 1H) 8.42 (d, J=8.0 Hz, 2H) 11.49 (br. s., 1H).

Example 103

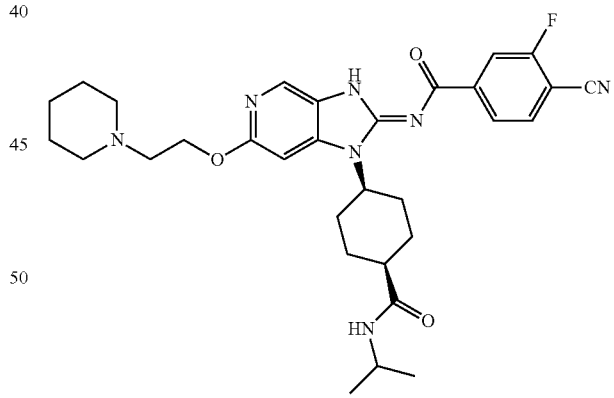

(E)-4-Cyano-3-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-cyano-3-fluorobenzoic acid (40.4% yield; white solid). MS m/z=576.2 [M+H], calc 575.68 for $C_{31}H_{38}FN_7O_3$.

Example 104

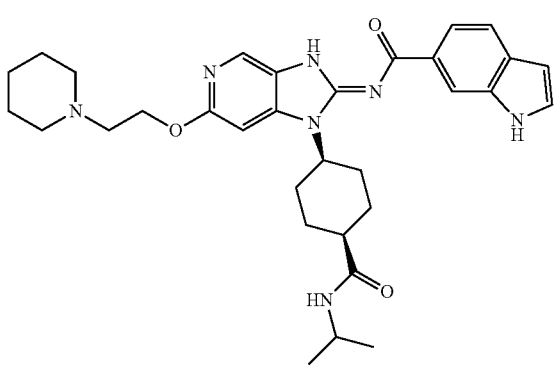 [SMILES: CC(C)NC(=O)[C@H]1CC[C@@H](n2/c(=N/C(=O)c3ccc4cc[nH]c4c3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-1H-indole-6-carboxamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using indole-6-carboxylic acid (6.9% yield; off-white solid). MS m/z=572.2 [M+H], calc 571.71 for $C_{32}H_{41}N_7O_3$.

Example 105

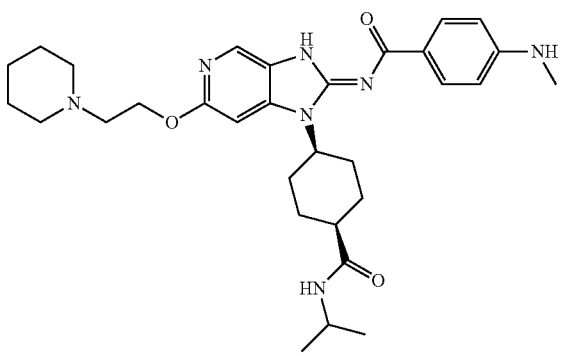 [SMILES: CNc1ccc(C(=O)/N=c2\[nH]c3cnc(OCCN4CCCCC4)cc3n2[C@H]2CC[C@@H](C(=O)NC(C)C)CC2)cc1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-4-(methylamino)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-(methylamino)benzoic acid (26.6% yield; off-white solid). MS m/z=562.2 [M+H], calc 561.72 for $C_{31}H_{43}N_7O_3$.

Example 106

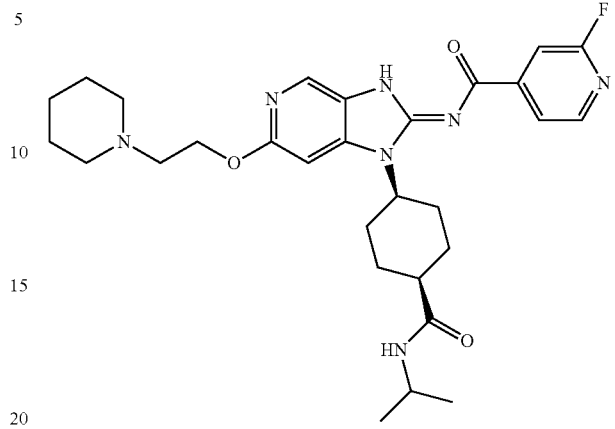

(E)-2-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)isonicotinamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 2-fluoroisonicotinic acid (6.4% yield; white solid). MS m/z=552.2 [M+H], calc 551.66 for $C_{29}H_{38}FN_7O_3$. $^1$H NMR (400 MHz, CDCl$_3$) δ ppm 1.21 (d, J=6.6 Hz, 6H) 1.38-1.54 (m, 1H) 1.73-2.11 (m, 9H) 2.16-2.27 (m, 2H) 2.49-2.57 (m, 1H) 2.75-2.97 (m, 4H) 3.52-3.59 (m, 2H) 3.75-3.87 (m, 2H) 4.10-4.21 (m, 1H) 4.76-4.89 (m, 3H) 5.40-5.49 (m, 1H) 7.31 (s, 1H) 7.80 (s, 1H) 8.03 (dt, J=5.06, 1.53 Hz, 1H) 8.21 (s, 1H) 8.37 (d, J=5.18 Hz, 1H) 11.05 (br. s., 1H).

Example 107

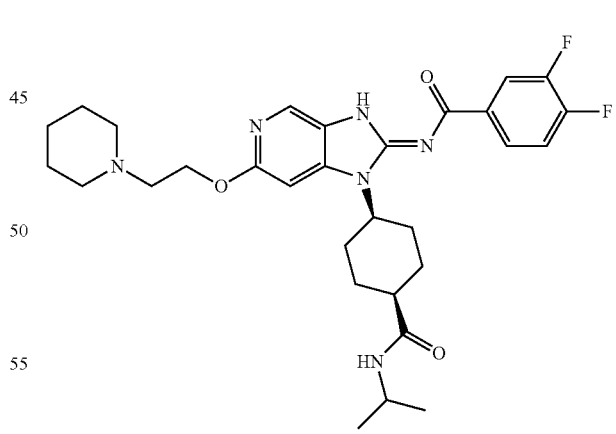

(E)-3,4-Difluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide. The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3,4-difluorobenzoic acid (36.4% yield; white solid). MS m/z=569.2 [M+H], calc 568.66 for $C_{30}H_{38}F_2N_6O_3$.

Example 108

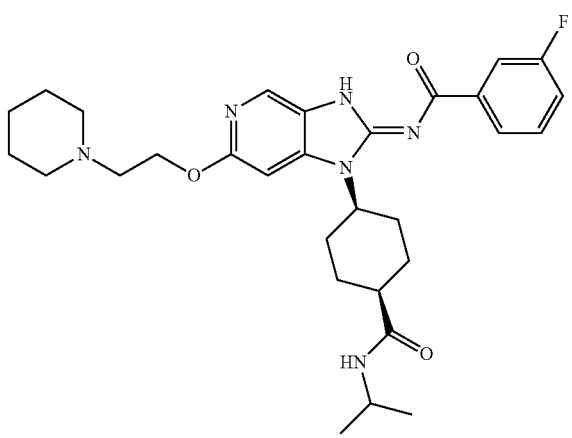 [SMILES: CC(C)NC(=O)[C@H]1CC[C@@H](n2/c(=N/C(=O)c3cccc(F)c3)[nH]c3cnc(OCCN4CCCCC4)cc32)CC1]

(E)-3-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-fluorobenzoic acid (53.5% yield; white solid). MS m/z=551.2 [M+H], calc 550.67 for $C_{30}H_{39}FN_6O_3$. $^1H$ NMR (400 MHz, CDCl$_3$) δ ppm 1.21 (d, J=6.6 Hz, 6H) 1.33-1.56 (m, 1H) 1.75-2.11 (m, 9H) 2.15-2.26 (m, 2H) 2.46-2.56 (m, 1H) 2.65-2.99 (m, 4H) 3.48-3.59 (m, 2H) 3.75-3.82 (m, 2H) 4.08-4.23 (m, 1H) 4.75-4.80 (m, 2H) 4.83-4.97 (m, 1H) 5.36-5.46 (m, 1H) 7.20-7.26 (m, 1H) 7.28 (s, 1H) 7.45 (td, J=7.97, 5.58 Hz, 1H) 8.00 (ddd, J=9.85, 2.57, 1.47 Hz, 1H) 8.09 (dt, J=7.82, 1.17 Hz, 1H) 8.16 (d, J=0.59 Hz, 1H) 11.68 (br. s., 1H).

Example 109

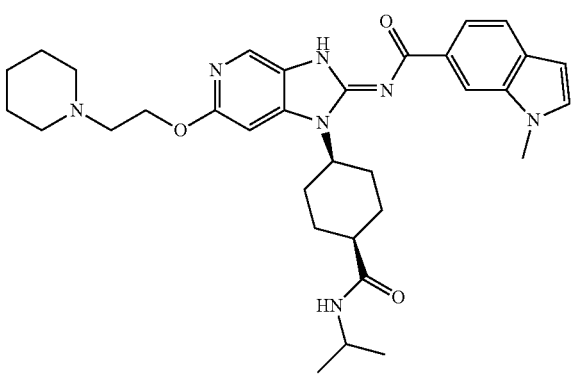 [SMILES: CC(C)NC(=O)[C@H]1CC[C@@H](n2/c(=N/C(=O)c3ccc4ccn(C)c4c3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-1-methyl-1H-indole-6-carboxamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 1-methyl-1H-indole-6-carboxylic acid (33.7% yield; white solid). MS m/z=586.2 [M+H], calc 585.74 for $C_{33}H_{43}N_7O_3$. $^1H$ NMR (400 MHz, DMSO-d$_6$) δ ppm 1.09 (d, J=6.6 Hz, 6H) 1.27-1.53 (m, 1H) 1.61-1.79 (m, 7H) 1.79-1.91 (m, 2H) 1.96-2.14 (m, 2H) 2.56-2.74 (m, 3H) 2.93-3.13 (m, 2H) 3.46-3.60 (m, 4H) 3.85-4.02 (m, 5H) 4.60-4.69 (m, 2H) 6.50 (dd, J=3.1, 0.7 Hz, 1H) 7.12 (s, 1H) 7.52 (d, J=3.1 Hz, 1H) 7.61 (d, J=8.3 Hz, 1H) 7.74 (d, J=7.4 Hz, 1H) 7.95 (br. s., 1H) 8.27-8.35 (m, 2H) 9.30 (br. s., 1H).

Example 110

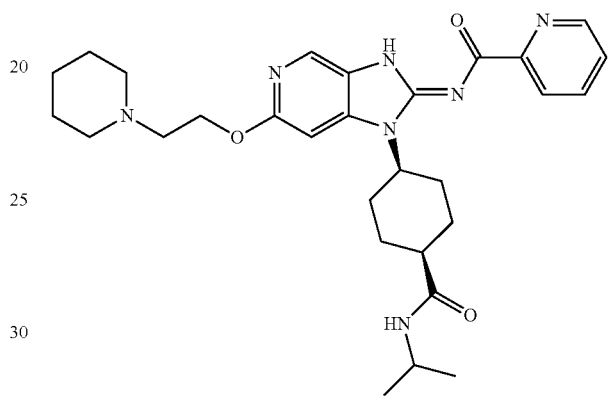

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)picolinamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using picolinic acid (45.7% yield; white solid). MS m/z=534.2 [M+H], calc 533.67 for $C_{29}H_{39}N_7O_3$.

Example 111

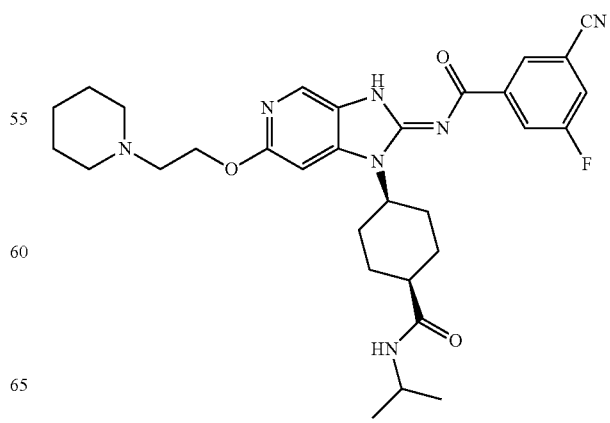

191

(E)-3-Cyano-5-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-cyano-5-fluorobenzoic acid (9.94% yield; white solid). MS m/z=576.2 [M+H], calc 575.68 for $C_{31}H_{38}FN_7O_3$.

Example 112

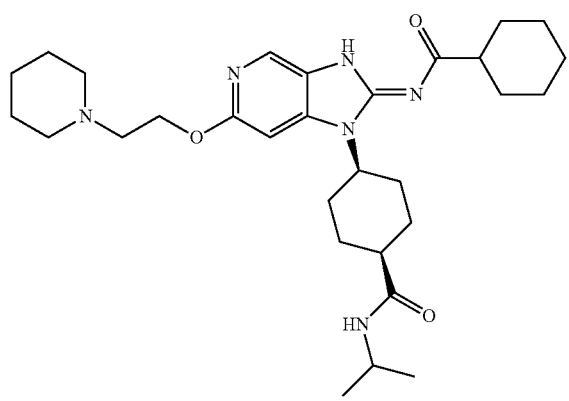 [SMILES: CC(C)NC(=O)[C@H]1CC[C@@H](n2/c(=N/C(=O)C3CCCCC3)[nH]c3cnc(OCCN4CCCCC4)cc32)CC1]

cis-4-((E)-2-(Cyclohexanecarbonylimino)-6-(2-(piperidin-1-yl)ethoxy)-2,3-dihydro-1H-imidazo[4,5-c]pyridin-1-yl)-N-isopropylcyclohexanecarboxamide The TFA salt of the title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using cyclohexanecarboxylic acid (52.5% yield; colorless oil). MS m/z=539.2 [M+H], calc 538.72 for $C_{30}H_{46}N_6O_3$.

Example 113

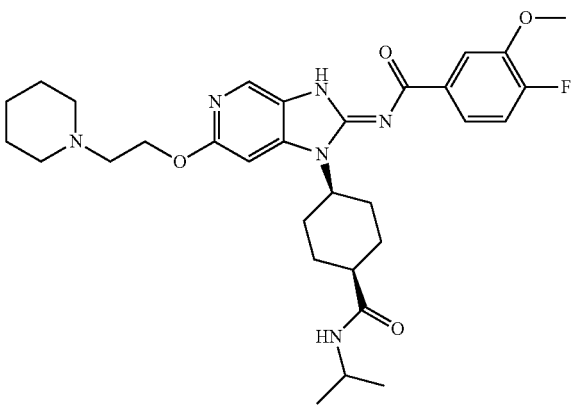 [SMILES: COc1cc(C(=O)/N=c2\[nH]c3cnc(OCCN4CCCCC4)cc3n2[C@H]2CC[C@@H](C(=O)NC(C)C)CC2)ccc1F]

192

(E)-4-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)-3-methoxybenzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-fluoro-3-methoxybenzoic acid. The material was purified via preparative HPLC (0.1% $NH_4OH$ in $ACN/H_2O$) to provide (E)-4-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)-3-methoxybenzamide (43.1% yield). MS m/z=581.4 [M+H], calc 580.69 for $C_{31}H_{41}FN_6O_4$.

Example 114

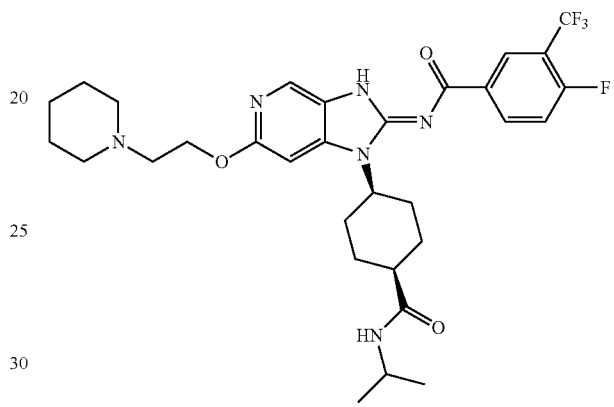

(E)-4-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)-3-(trifluoromethyl)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-fluoro-3-(trifluoromethyl)benzoic acid. The material was purified via preparative HPLC (0.1% $NH_4OH$ in $ACN/H_2O$) to provide (E)-4-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)-3-(trifluoromethyl)benzamide (43.8% yield). MS m/z=619.4 [M+H], calc 618.67 for $C_{31}H_{38}F_4N_6O_3$.

Example 115

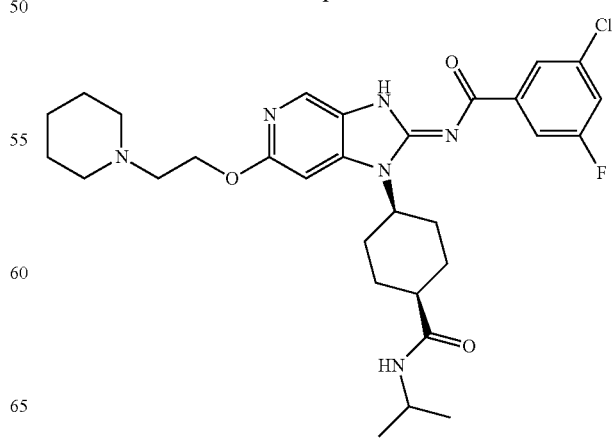

(E)-3-Chloro-5-fluoro-N-(1-(cis-4-(isopropylcarbamoyl)cyclohexyl)-6-(2-(piperidin-1-yl)ethoxy)-1H-imidazo[4,5-c]pyridin-2 (3H)-ylidene)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-chloro-5-fluorobenzoic acid. The material was purified via preparative HPLC (0.1% NH$_4$OH in ACN/H$_2$O) to provide (E)-3-chloro-5-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide (38.5% yield). MS m/z=585.4 [M+H], calc 585.11 for C$_{30}$H$_{38}$ClFN$_6$O$_3$.

Example 116

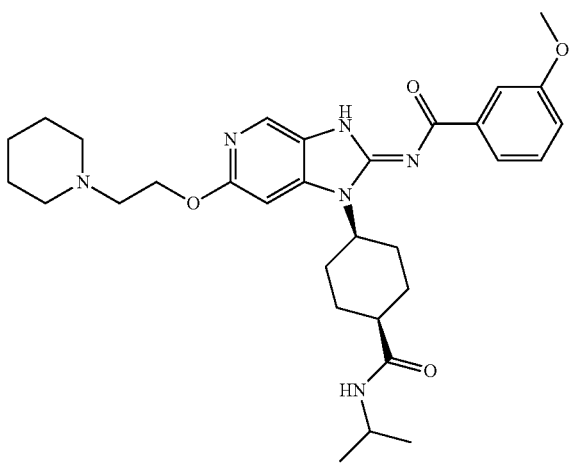 [SMILES: COc1cccc(C(=O)/N=c2\[nH]c3cnc(OCCN4CCCCC4)cc3n2[C@H]2CC[C@@H](C(=O)NC(C)C)CC2)c1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-3-methoxybenzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-methoxybenzoic acid. The material was purified via preparative HPLC (0.1% NH$_4$OH in ACN/H$_2$O) to provide (E)-N(1-(cis-4-(isopropylcarbamoyl)cyclohexyl)-6-(2-(piperidin-1-yl)ethoxy)-1H-imidazo[4,5-c]pyridin-2(3H)-ylidene)-3-methoxy-benzamide (42.5% yield). MS m/z=563.4 [M+H], calc 562.71 for C$_{31}$H$_{42}$N$_6$O$_4$.

Example 117

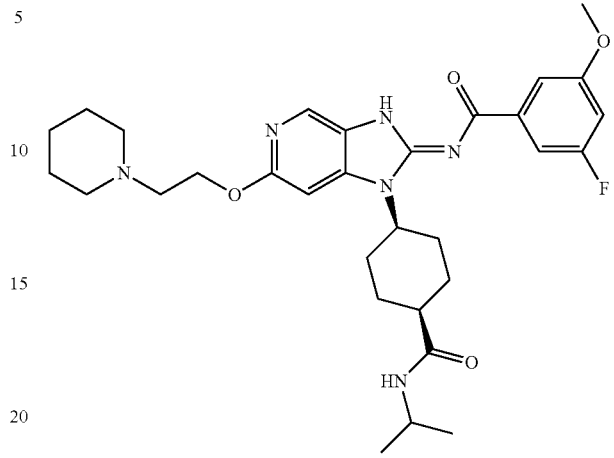

(E)-3-Fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)-5-methoxybenzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-fluoro-5-methoxybenzoic acid. The material was purified via preparative HPLC (0.1% NH$_4$OH in ACN/H$_2$O) to provide (E)-3-fluoro-N-(1-(cis-4-(isopropylcarbamoyl)cyclohexyl)-6-(2-(piperidin-1-yl)ethoxy)-1H-imidazo[4,5-c]-pyridin-2(3H)-ylidene)-5-methoxybenzamide (43.8% yield). MS m/z=581.4 [M+H], calc 580.69 for C$_{31}$H$_{41}$FN$_6$O$_4$.

Example 118

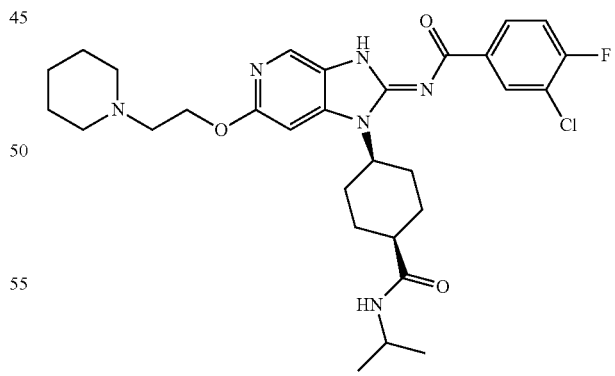

(E)-3-Chloro-4-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-chloro-4-fluorobenzoic acid. The material was purified via preparative HPLC (0.1% NH$_4$OH in ACN/H$_2$O) to provide (E)-3-chloro-4-fluoro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide (45.4% yield). MS m/z=585.4 [M+H], calc 585.12 for C$_{30}$H$_{38}$ClFN$_6$O$_3$.

Example 119

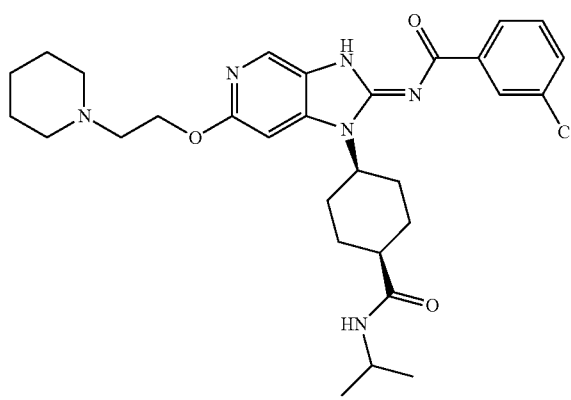

(E)-3-Chloro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-chlorobenzoic acid. The material was purified via preparative HPLC (0.1% NH$_4$OH in ACN/H$_2$O) to provide (E)-3-chloro-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide (37.4% yield). MS m/z=567.4 [M+H], calc 567.12 for C$_{30}$H$_{39}$ClN$_6$O$_3$.

Example 120

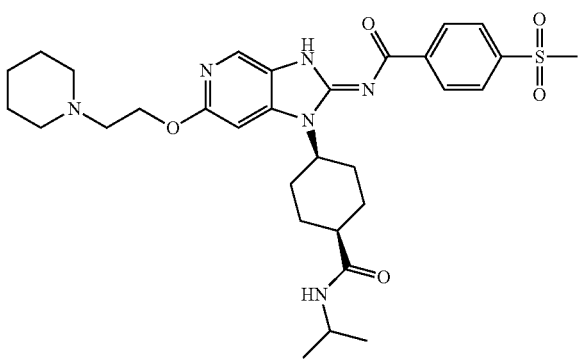 [SMILES: CC(C)NC(=O)[C@H]1CC[C@@H](n2/c(=N/C(=O)c3ccc(S(C)(=O)=O)cc3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-4-(methylsulfonyl)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-(methylsulfonyl)benzoic acid. The material was purified via preparative HPLC (0.1% NH$_4$OH in ACN/H$_2$O) to provide (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)-4-(methylsulfonyl)benzamide (22.0% yield). MS m/z=611.4 [M+H], calc 610.77 for C$_{31}$H$_{42}$N$_6$O$_5$S.

Example 121

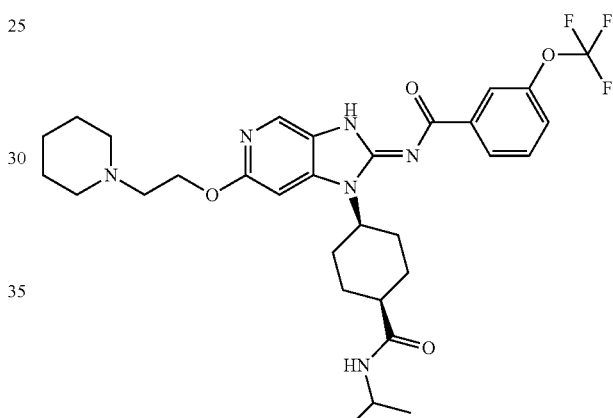

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)-3-(trifluoromethoxy)benzamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 3-(trifluoromethoxy)benzoic acid. The material was purified via preparative HPLC (0.1% NH$_4$OH in ACN/H$_2$O) to provide (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)-3-(trifluoromethoxy)benzamide (50.3% yield). MS m/z=617.4 [M+H], calc 616.67 for C$_{31}$H$_{39}$F$_3$N$_6$O$_4$. $^1$H NMR (CDCl$_3$) δ ppm: 12.32 (br. s., 1H), 8.30-8.43 (m, 2H), 8.10 (d, J=0.8 Hz, 1H), 7.28-7.31 (m, 1H), 7.01 (s, 1H), 5.34 (d, J=1.0 Hz, 1H), 4.77-4.91 (m, 1H), 4.45-4.55 (m, 2H), 4.14-4.29 (m, 1H), 2.46-2.95 (m, 8H), 2.20-2.27 (m, 2H), 1.73-1.89 (m, 4H), 1.58-1.73 (m, 5H), 1.41-1.57 (m, 3H), 1.22 (d, J=6.6 Hz, 6H).

Example 122

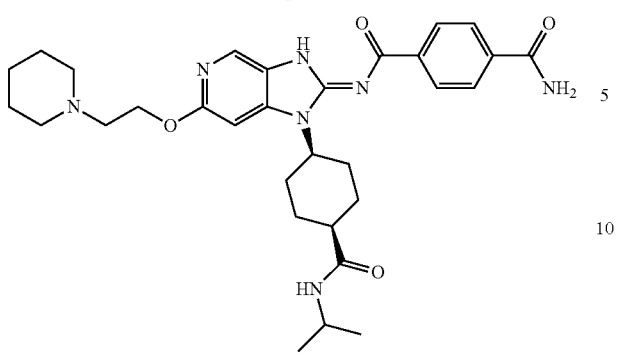

(E)-N-1-(1-(cis-4-(Isopropylcarbamoyl)cyclohexyl)-6-(2-(piperidin-1-yl)ethoxy)-1H-imidazo[4,5-c]pyridin-2(3H)-ylidene)terephthalamide The title compound was prepared using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzo[b]thiophene-6-carboxamide, using 4-carbamoylbenzoic acid. The material was purified via preparative HPLC (0.1% NH$_4$OH in ACN/H$_2$O) to provide (E)-N1-(1-(cis-4-(isopropylcarbamoyl)cyclohexyl)-6-(2-(piperidin-1-yl)ethoxy)-1H-imidazo[4,5-c]pyridin-2(3H)-ylidene)terephthalamide (11.9% yield). MS m/z=576.2 [M+H], calc 575.71 for $C_{31}H_{41}N_7O_4$.

Example 123

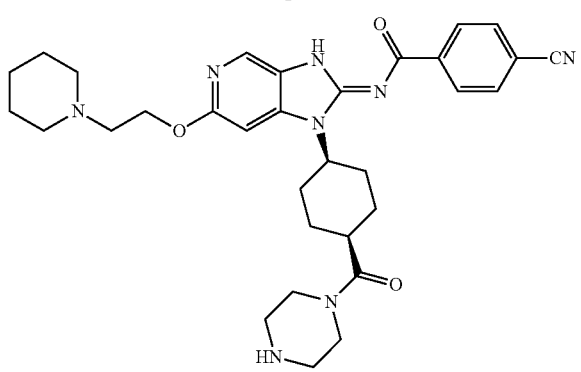 [SMILES: N#Cc1ccc(C(=O)/N=c2\[nH]c3cnc(OCCN4CCCCC4)cc3n2[C@H]2CC[C@@H](C(=O)N3CCNCC3)CC2)cc1]

(E)-4-Cyano-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide Step A: cis-4-(2-Chloro-5-nitropyridin-4-ylamino)cyclohexanecarboxylic acid

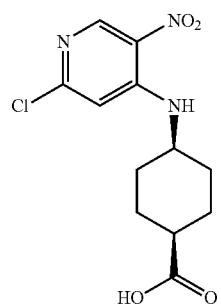 [SMILES: O=C(O)[C@H]1CC[C@@H](Nc2cc(Cl)ncc2[N+](=O)[O-])CC1]

The compound was made using a procedure analogous to that used in the preparation of cis-4-(2-chloro-5-nitropyridin-4-ylamino)-N-isopropylcyclohexanecarboxamide using cis-4-aminocyclohexanecarboxylic acid.

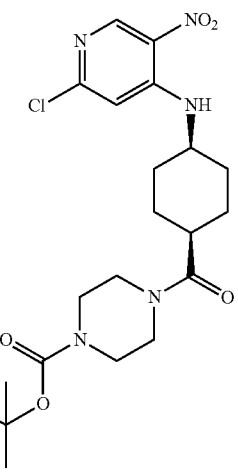

Step B: tert-butyl-4-(cis-4-(2-chloro-5-nitropyridin-4-ylamino)cyclohexanecarbonyl)-piperazine-1-carboxylate cis-4-(2-Chloro-5-nitropyridin-4-ylamino)cyclohexanecarboxylic acid (1.000 g, 3.34 mmol) was suspended in thionyl chloride (12.18 mL, 167 mmol), and the mixture was stirred at RT for 30 minutes. The reaction mixture was concentrated in vacuo, dissolved in THF (33.4 mL), and then cooled to 0° C. under a nitrogen atmosphere. To the cooled reaction was added tert-butyl-piperazine-1-carboxylate (0.684 g, 3.67 mmol) as a solution in THF (1 mL). The reaction mixture was stirred at 0° C. for 15 minutes and allowed to warm to RT and stirred overnight. To the reaction mixture was added additional tert-butyl-piperazine-1-carboxylate (0.684 g, 3.67 mmol) in THF (1 mL) (×2, stirring for about 1 h after each addition). Upon completion, the reaction mixture was diluted with aqueous NH$_4$Cl and extracted with DCM (×2). The organic layers were dried over sodium sulfate, filtered and concentrated in vacuo. The residual material was purified via silica gel chromatography, eluting with isocratic 90:10:1 DCM:MeOH:NH$_4$OH, to provide tert-butyl 4-(cis-4-(2-chloro-5-nitropyridin-4-ylamino)cyclohexanecarbonyl)piperazine-1-carboxylate (1.51 g, 70% yield) as a yellow solid. MS m/z=468.0 [M+H], calc 467.95 for $C_{21}H_{30}ClN_5O_5$.

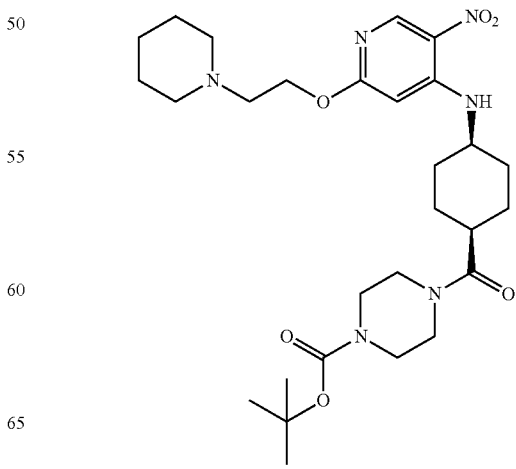

Step C: tert-butyl 4-(cis-4-(5-nitro-2-(2-(piperidin-1-yl)ethoxy)pyridin-4-ylamino)cyclohexanecarbonyl)piperazine-1-carboxylate The title compound was made analogous to the preparation of cis-N-isopropyl-4-(5-nitro-2-(2-(piperidin-1-yl)ethoxy)pyridin-4-ylamino)cyclohexanecarboxamide using tert-butyl 4-(cis-4-(2-chloro-5-nitropyridin-4-ylamino)cyclohexanecarbonyl)piperazine-1-carboxylate. MS m/z=561.2 [M+H], calc 560.69 for $C_{28}H_{44}N_6O_6$.

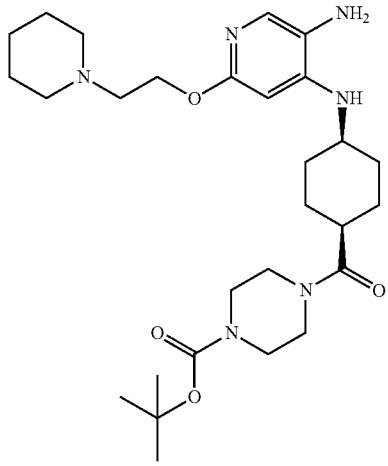 [SMILES: CC(C)(C)OC(=O)N1CCN(C(=O)[C@H]2CC[C@@H](Nc3cc(OCCN4CCCCC4)ncc3[N+](=O)[O-])CC2)CC1]

Step D: tert-butyl 4-(cis-4-(5-amino-2-(2-(piperidin-1-yl)ethoxy)pyridin-4-ylamino)cyclo-hexanecarbonyl)piperazine-1-carboxylate The title compound made analogous to the preparation of cis-4-(5-amino-2-(2-(piperidin-1-yl)ethoxy)pyridin-4-ylamino)-N-isopropylcyclohexanecarboxamide. MS m/z=531.3 [M+H], calc 530.70 for $C_{28}H_{46}N_6O_4$.

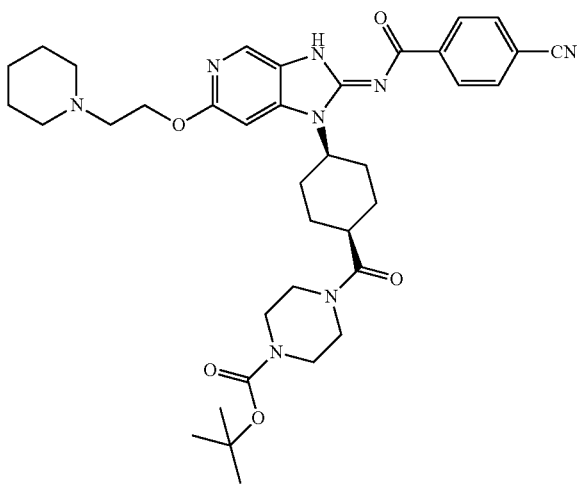 [SMILES: CC(C)(C)OC(=O)N1CCN(C(=O)[C@H]2CC[C@@H](n3/c(=N/C(=O)c4ccc(C#N)cc4)[nH]c4cnc(OCCN5CCCCC5)cc43)CC2)CC1]

Step E: tert-butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexanecarbonyl)piperazine-1-carboxylate tert-Butyl 4-(cis-4-(5-amino-2-(2-(piperidin-1-yl)ethoxy)pyridin-4-ylamino)cyclohexanecarbonyl)piperazine-1-carboxylate (0.200 g, 0.377 mmol) was suspended in THF (3.77 mL), and the mixture was cooled to 0° C. under a nitrogen atmosphere. To this mixture was added a solution of 4-cyanobenzoyl isothiocyanate (0.078 g, 0.415 mmol) in 1.5 mL of THF. The reaction was stirred at RT for 30 minutes. PS-CDI (1.417 g, 1.884 mmol) was added (along with 6 mL of THF to account for swelling of the polymer-supported reagent) and the reaction was heated at 60° C. for 1 hour. The solids were filtered off (rinsing well with THF) and the filtrate was concentrated in vacuo. The residual material was purified via silica gel chromatography eluting with a gradient of 0% to 100% 90:10:1 DCM:MeOH:NH$_4$OH, to provide tert-butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexane-carbonyl)piperazine-1-carboxylate as an orange solid (0.227 g, 88% yield). MS m/z=685.2 [M+H], calc 684.83 for $C_{37}H_{48}N_8O_5$.

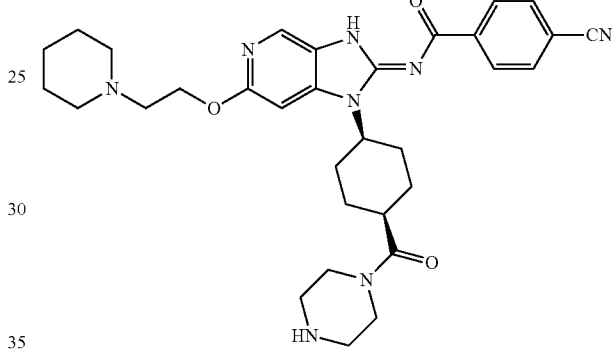

Step F: (E)-4-Cyano-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide tert-Butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexanecarbonyl)piperazine-1-carboxylate (0.227 g, 0.331 mmol) was suspended in HCl (4M in dioxanes) (4.14 mL, 16.57 mmol), and the resulting mixture was stirred at RT for 3 hour. The reaction mixture was concentrated in vacuo, resuspended in DCM and washed with aqueous NaHCO$_3$ solution. The aqueous layer was washed with DCM, and then the combined organics were dried over sodium sulfate, filtered and concentrated in vacuo. The material was purified via preparative HPLC to yield the TFA salt, which was free-based using an SCX-ion exchange column to yield (E)-4-cyano-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide (0.076 g, 39.2% yield). MS m/z=585.2 [M+H], calc 584.71 for $C_{32}H_{40}N_8O_3$. $^1$H NMR (CDCl$_3$) δ ppm: 8.36-8.49 (m, 2H), 8.14 (d, J=0.7 Hz, 1H), 7.71-7.78 (m, 2H), 7.10 (s, 1H), 4.74-4.88 (m, 1H), 4.46-4.59 (m, 2H), 3.66-3.75 (m, 2H), 3.47-3.57 (m, 2H), 2.82-3.05 (m, 9H), 2.55-2.70 (m, 3H), 2.08-2.19 (m, 2H), 1.58-1.91 (m, 10H), 1.42-1.54 (m, 3H).

Example 124

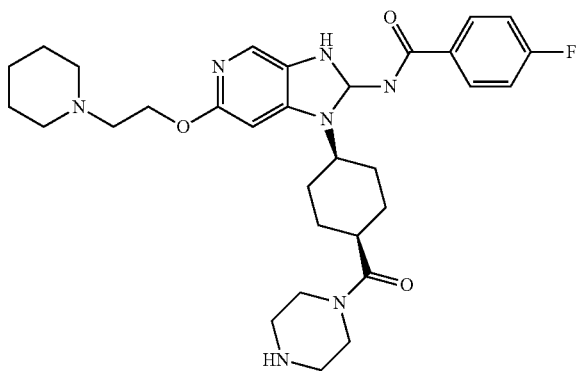 [SMILES: O=C(NC1Nc2cnc(OCCN3CCCCC3)cc2N1[C@H]1CC[C@@H](C(=O)N2CCNCC2)CC1)c1ccc(F)cc1]

(E)-4-Fluoro-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide The title compound was prepared using a method analagous to the preparation of (E)-4-cyano-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide, using 4-fluorobenzoyl isothiocyanate. MS m/z=578.2 [M+H], calc 577.69 for $C_{31}H_{40}FN_7O_3$. $^1$H NMR (CDCl$_3$) δ ppm: 8.35 (dd, J=8.7, 5.7 Hz, 2H), 8.09 (s, 1H), 7.01-7.20 (m, 3H), 4.75-4.96 (m, 1H), 4.50 (t, J=1.0 Hz, 2H), 3.64-3.77 (m, 2H), 3.46-3.59 (m, 2H), 2.80-3.03 (m, 10H), 2.53-2.69 (m, 4H), 2.08-2.19 (m, 2H), 1.72-1.90 (m, 5H), 1.60-1.71 (m, 4H), 1.40-1.55 (m, 2H).

Example 125

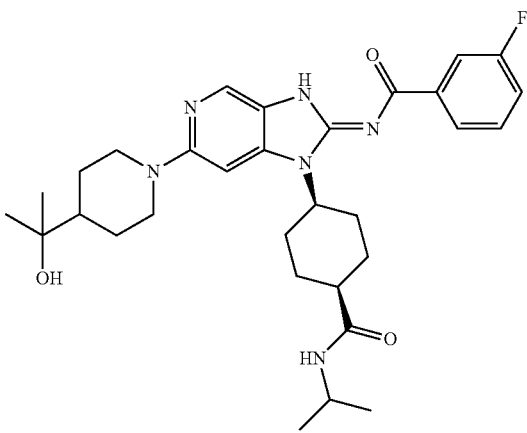 [SMILES: CC(C)NC(=O)[C@H]1CC[C@@H](n2/c(=N/C(=O)c3cccc(F)c3)[nH]c3cnc(N4CCC(C(C)(C)O)CC4)cc32)CC1]

(E)-3-Fluoro-N-(6-(4-(2-hydroxypropan-2-yl)piperidin-1-yl)-1-(cis-4-(isopropylcarbamoyl)cyclohexyl)-1H-imidazo[4,5-c]pyridin-2(3H)-ylidene)benzamide

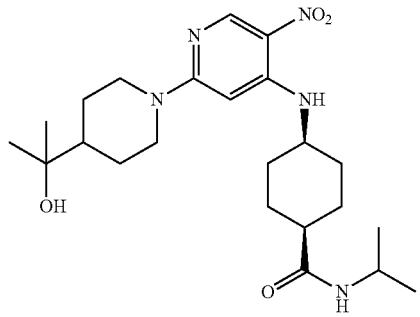 [SMILES: CC(C)NC(=O)[C@H]1CC[C@@H](Nc2cc(N3CCC(C(C)(C)O)CC3)ncc2[N+](=O)[O-])CC1]

Step A: cis-4-(2-(4-(2-Hydroxypropan-2-yl)piperidin-1-yl)-5-nitropyridin-4-ylamino)-N-isopropylcyclohexanecarboxamide A suspension of cis-4-(2-chloro-5-nitropyridin-4-ylamino)-N-isopropylcyclohexanecarboxamide (0.200 g, 0.587 mmol) and 2-(piperidin-4-yl)propan-2-ol (0.420 g, 2.93 mmol) in 2-propanol (2.003 mL) was microwave irradiated for 1 hour at 150° C. The reaction mixture was concentrated in vacuo, and the residual material was purified via silica gel chromatography eluting with isocratic 90:10:1 DCM:MeOH:NH$_4$OH, to provide cis-4-(2-(4-(2-hydroxypropan-2-yl)piperidin-1-yl)-5-nitropyridin-4-ylamino)-N-isopropylcyclohexanecarboxamide as a yellow solid (0.263 g, 100% yield). MS m/z=448.2 [M+H], calc 447.57 for $C_{23}H_{37}FN_5O_4$.

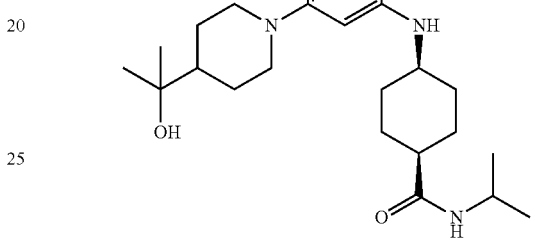

Step B: cis-4-(5-Amino-2-(4-(2-hydroxypropan-2-yl)piperidin-1-yl)pyridin-4-ylamino)-N-isopropylcyclohexanecarboxamide The title compound was synthesized using a method analogous to the preparation of cis-4-(5-amino-2-(2-(piperidin-1-yl)ethoxy)pyridin-4-ylamino)-N-isopropylcyclohexanecarboxamide starting from cis-4-(2-(4-(2-hydroxypropan-2-yl)piperidin-1-yl)-5-nitropyridin-4-ylamino)-N-isopropylcyclohexanecarboxamide (yellow solid). MS m/z=418.2 [M+H], calc 417.59 for $C_{23}H_{39}N_5O_2$.

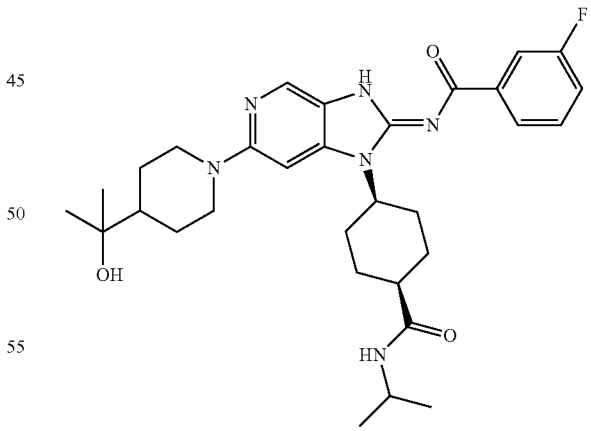

Step C: (E)-3-Fluoro-N-(6-(4-(2-hydroxypropan-2-yl)piperidin-1-yl)-1-(cis-4-(isopropy-lcarbamoyl)cyclohexyl)-1H-imidazo[4,5-c]pyridin-2(3H)-ylidene)benzamide The title compound was synthesized using a method analogous to that used to prepare tert-butyl 4-(cis-4-((E)-2-(4- cyanobenzoylimino)-6-(2-(piperidin-1-yl)ethoxy)-2,3-dihydro-1H-imidazo[4,5-c]pyridin-1-yl)cyclohexane-carbonyl)piperazine-1-carboxylate starting from cis-4-(5-amino-2-(4-(2-hydroxypropan-2-yl)piperidin-1-yl)pyridin-4-ylamino)-N-isopropylcyclohexanecarboxamide (65.9% yield). MS m/z=565.2 [M+H], calc 564.69 for $C_{31}H_{41}FN_6O_3$. $^1$H NMR (CDCl$_3$) δ ppm: 12.22 (br. s., 1H), 8.19 (d, J=0.5 Hz, 1H), 8.09 (dt, J=7.8, 1.2 Hz, 1H), 8.01 (ddd, J=10.0, 2.6, 1.5 Hz, 1H), 7.42 (td, J=7.9, 5.7 Hz, 1H), 7.15-7.22 (m, 1H), 5.30-5.35 (m, 1H), 4.93-5.07 (m, 1H), 4.50-4.62 (m, 2H), 4.05-4.18 (m, 1H), 2.75-2.91 (m, 3H), 2.47-2.54 (m, 1H), 2.13-2.21 (m, 2H), 1.71-1.98 (m, 6H), 1.36-1.64 (m, 6H), 1.23 (s, 6H), 1.22 (d, J=6.55 Hz, 6H).

Example 126

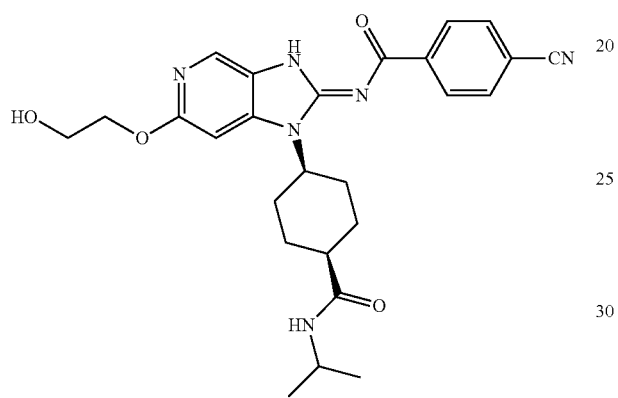

(E)-4-Cyano-N-(6-(2-hydroxyethoxy)-1-(cis-4-(isopropylcarbamoyl)cyclohexyl)-1H-imidazo[4,5-c]pyridin-2(3H)-ylidene)benzamide

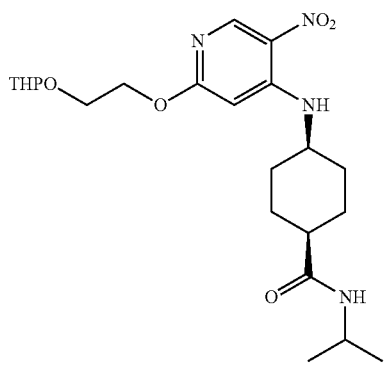

Step A: cis-N-Isopropyl-4-(5-nitro-2-(2-(tetrahydro-2H-pyran-2-yloxy)ethoxy)pyridin-4-ylamino)cyclohexanecarboxamide The title compound was synthesized using a method analogous to that used to prepare cis-N-isopropyl-4-(5-nitro-2-(2-(piperidin-1-yl)ethoxy)pyridin-4-ylamino)cyclohexanecarboxamide, using 2-(tetrahydro-2H-pyran-2-yloxy)ethanol (61.0% yield). MS m/z=451.2 [M+H], calc 450.53 for $C_{22}H_{34}N_4O_6$.

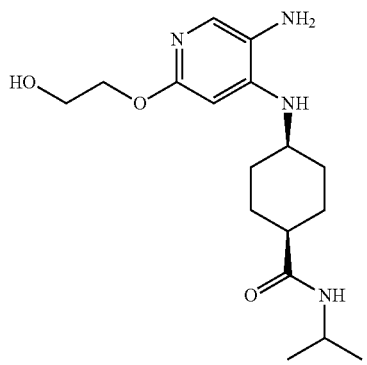 [SMILES: CC(C)NC(=O)[C@H]1CC[C@@H](Nc2cc(OCCO)ncc2N)CC1]

Step B: cis-4-(5-Amino-2-(2-hydroxyethoxy)pyridin-4-ylamino)-N-isopropylcyclohexane-carboxamide The title compound was synthesized using a method analogous to the preparation of cis-4-(5-amino-2-(2-(piperidin-1-yl)ethoxy)pyridin-4-ylamino)-N-isopropylcyclohexanecarboxamide starting from cis-N-isopropyl-4-(5-nitro-2-(2-(tetrahydro-2H-pyran-2-yloxy)ethoxy)pyridin-4-ylamino) cyclohexanecarboxamide, resulting in the deprotection of the -THP alcohol. MS m/z=337.2 [M+H], calc 336.43 for $C_{17}H_{28}N_4O_3$.

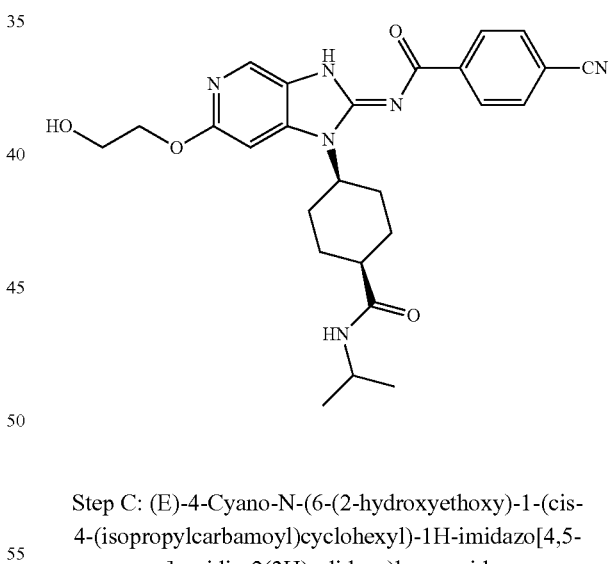

Step C: (E)-4-Cyano-N-(6-(2-hydroxyethoxy)-1-(cis-4-(isopropylcarbamoyl)cyclohexyl)-1H-imidazo[4,5-c]pyridin-2(3H)-ylidene)benzamide The title compound was synthesized using a method analogous to the preparation of tert-butyl 4-(cis-4-((E)-2-(4-cyanobenzoylimino)-6-(2-(piperidin-1-yl)ethoxy)-2,3-dihydro-1H-imidazo[4,5-c]pyridin-1-yl)cyclohexane-carbonyl)piperazine-1-carboxylate starting from cis-4-(5-amino-2-(2-hydroxyethoxy)pyridin-4-ylamino)-N-isopropylcyclohexane-carboxamide (50.8% yield). MS m/z=491.1 [M+H], calc 490.55 for $C_{26}H_{30}N_6O_4$.

Example 127

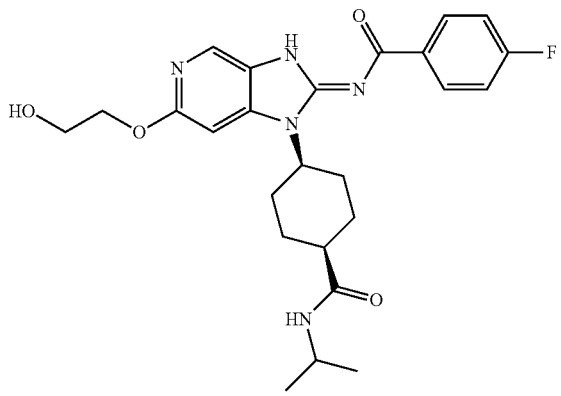 [SMILES: CC(C)NC(=O)[C@H]1CC[C@@H](n2/c(=N/C(=O)c3ccc(F)cc3)[nH]c3cnc(OCCO)cc32)CC1]

(E)-4-Fluoro-N-(6-(2-hydroxyethoxy)-1-(cis-4-(isopropylcarbamoyl)cyclohexyl)-1H-imidazo[4,5-c]pyridin-2(3H)-ylidene)benzamide The title compound was synthesized using a method analogous to the preparation of (E)-4-cyano-N-(1-(cis-4-(piperazine-1-carbonyl)cyclohexyl)-6-(2-(piperidin-1-yl)ethoxy)-1H-imidazo[4,5-c]pyridin-2(3H)-ylidene)benzamide (51.5% yield). MS m/z=484.2 [M+H], calc 483.54 for $C_{25}H_{30}FN_5O_4$.

Example 128

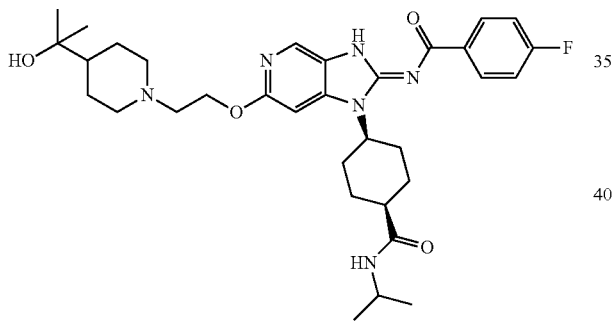

(E)-4-Fluoro-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide

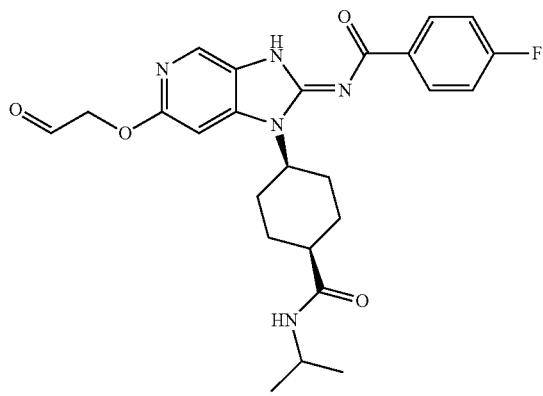 [SMILES: CC(C)NC(=O)[C@H]1CC[C@@H](n2/c(=N/C(=O)c3ccc(F)cc3)[nH]c3cnc(OCC=O)cc32)CC1]

Step A: (E)-4-Fluoro-N-(1-(cis-4-(isopropylcarbamoyl)cyclohexyl)-6-(2-oxoethoxy)-1H-imidazo[4,5-c]pyridin-2(3H)-ylidene)benzamide (E)-4-Fluoro-N-(6-(2-hydroxyethoxy)-1-(cis-4-(isopropylcarbamoyl)cyclohexyl)-1H-imidazo[4,5-e]pyridin-2(3H)-ylidene)benzamide (0.043 g, 0.089 mmol) was suspended in DCM (3.56 mL) under nitrogen, and the reaction flask was cooled to 0° C. To the flask was added Dess-Martin periodinane (0.057 g, 0.133 mmol), and the reaction was allowed to warm to RT and stirred for 1 hour. The reaction was quenched with aqueous NaHCO₃ (8 mL) and sodium thiosulfate (85 mg). The product was extracted with 5% MeOH/DCM. The organic layer was dried over sodium sulfate, filtered and concentrated in vacuo to afford (E)-4-fluoro-N-(1-(cis-4-(isopropylcarbamoyl)cyclohexyl)-6-(2-oxoethoxy)-1H-imidazo[4,5-e]pyridin-2(3H)-ylidene)benzamide as a light pink solid. MS m/z=482.0 [M+H], calc 481.52 for $C_{25}H_{28}FN_5O_4$.

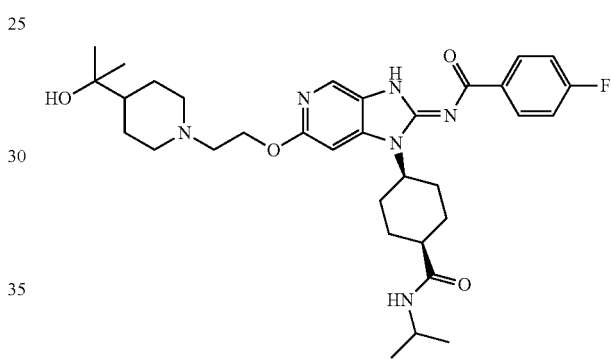

Step B: (E)-4-Fluoro-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide To a round bottom flask cooled at 0° C. charged with (E)-4-fluoro-N-(1-(cis-4-(isopropylcarbamoyl)cyclohexyl)-6-(2-oxoethoxy)-1H-imidazo[4,5-e]pyridin-2(3H)-ylidene)benzamide (0.056 g, 0.116 mmol) in DCE (0.775 mL) was added 2-(piperidin-4-yl)propan-2-ol (0.083 g, 0.581 mmol) and NaBH(OAc)₃ (0.074 g, 0.349 mmol). The reaction mixture was stirred at 0° C. for 1 hour. The resulting mixture was quenched with saturated aqueous NaHCO₃, and extracted with DCM and EtOAc. The combined organic layers were dried over magnesium sulfate, filtered and concentrated in vacuo. The residual material was purified via silica gel chromatography, eluting with a gradient of 0% to 10% MeOH in EtOAc, followed by straight 90:10:1 DCM:MeOH:NH₄OH to provide (E)-4-fluoro-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide as an off-white solid (0.062 g, 88% yield). MS m/z=609.3 [M+H], calc 608.75 for $C_{33}H_{45}FN_6O_4$.

Example 129

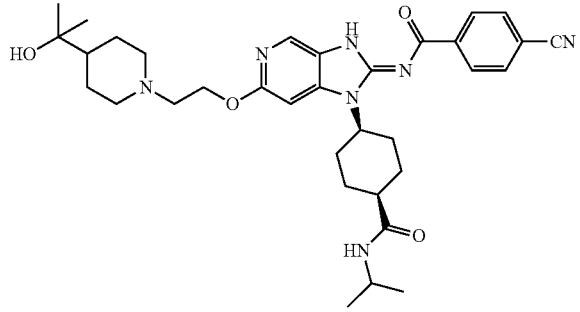 [SMILES: CC(C)NC(=O)[C@H]1CC[C@@H](n2/c(=N/C(=O)c3ccc(C#N)cc3)[nH]c3cnc(OCCN4CCC(C(C)(C)O)CC4)cc32)CC1]

(E)-4-Cyano-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide The title compound was synthesized using a method analogous to the preparation of (E)-4-fluoro-N-(6-(2-(4-(2-hydroxypropan-2-yl)piperidin-1-yl)ethoxy)-1-(cis-4-(isopropylcarbamoyl)-cyclohexyl)-1H-imidazo[4,5-c]pyridin-2(3H)-ylidene)benzamide (39.7% yield). MS m/z=616.2 [M+H], calc 615.77 for $C_{34}H_{45}N_7O_4$. $^1$H NMR (CDCl$_3$) δ ppm: 12.32 (br. s, 1H), 8.38-8.47 (m, 2H), 8.14 (d, J=0.6 Hz, 1H), 7.73-7.77 (m, 2H), 7.04 (s, 1H), 5.34 (d, J=1.0 Hz, 1H), 4.77-4.89 (m, 1H), 4.74 (s, 1H), 4.50 (t, J=1.0 Hz, 2H), 4.22 (dd, J=7.7, 6.7 Hz, 1H), 3.11-3.23 (m, 2H), 2.72-2.93 (m, 4H), 2.50-2.55 (m, 1H), 2.03-2.30 (m, 4H), 1.72-1.89 (m, 6H), 1.28-1.56 (m, 3H), 1.23 (d, J=6.6 Hz, 6H), 1.20 (s, 6H).

Example 130

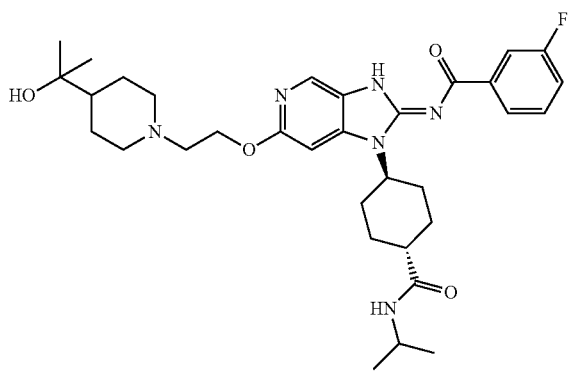 [SMILES: CC(C)NC(=O)[C@H]1CC[C@H](n2/c(=N/C(=O)c3cccc(F)c3)[nH]c3cnc(OCCN4CCC(C(C)(C)O)CC4)cc32)CC1]

(E)-3-Fluoro-N-(6-(2-(4-(2-hydroxypropan-2-yl)piperidin-1-yl)ethoxy)-1-(cis-4-(isopropylcarbamoyl)cyclohexyl)-1H-imidazo[4,5-c]pyridin-2(3H)-ylidene)benzamide The title compound was synthesized using a method analogous to the preparation of (E)-4-fluoro-N-(6-(2-(4-(2-hydroxypropan-2-yl)piperidin-1-yl)ethoxy)-1-(cis-4-(isopropylcarbamoyl)-cyclohexyl)-1H-imidazo[4,5-c]pyridin-2(3H)-ylidene)benzamide (32.1% yield). MS m/z=609.2 [M+H], calc 608.75 for $C_{33}H_{45}FN_6O_4$.

Example 131

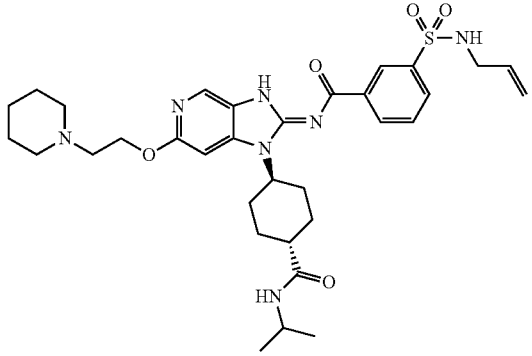 [SMILES: C=CCNS(=O)(=O)c1cccc(C(=O)/N=c2\[nH]c3cnc(OCCN4CCCCC4)cc3n2[C@H]2CC[C@H](C(=O)NC(C)C)CC2)c1]

(E)-3-(N-Allylsulfamoyl)-N-(1-(trans-4-(isopropylcarbamoyl)cyclohexyl)-6-(2-(piperidin-1-yl)ethoxy)-1H-imidazo[4,5-c]pyridin-2(3H)-ylidene)benzamide

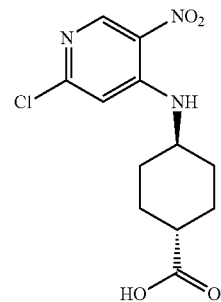 [SMILES: O=C(O)[C@H]1CC[C@H](Nc2cc(Cl)ncc2[N+](=O)[O-])CC1]

Step A: trans-4-(2-Chloro-5-nitropyridin-4-ylamino)cyclohexanecarboxylic acid trans-4-Aminocyclohexanecarboxylic acid (5.01 g, 35.0 mmol) and potassium carbonate (4.83 g, 35.0 mmol) were dissolved in water (20 mL). 2,4-Dichloro-5-nitropyridine (6.75 g, 35.0 mmol) was added as a solution in dioxane (40 mL), and the reaction was stirred at 80° C. for 8 hours. The dioxane solvent was removed under vacuum. The remaining aqueous solution was acidified with aqueous 2N HCl (approx. pH 2-3), and the resulting precipitate was collected and washed with water, and then DCM. The solid was dried under high vacuum to yield trans-4-(2-chloro-5-nitropyridin-4-ylamino)cyclohexanecarboxylic acid hydrochloride as a yellow solid (8.79 g, 74.8% yield). MS m/z=300.0 [M+H], calc 299.71 for $C_{12}H_{14}ClN_3O_4$.

Step B: trans-4-(2-Chloro-5-nitropyridin-4-ylamino)-N-isopropylcyclohexanecarboxamide trans-4-(2-Chloro-5-nitropyridin-4-ylamino)cyclohexanecarboxylic acid hydrochloride (0.500 g, 1.487 mmol) was suspended in THF (3 mL). Thionyl chloride (0.434 mL, 5.95 mmol) was added to the suspension, and the reaction mixture was stirred at 20° C. for 2 hours. The resulting mixture was concentrated in vacuo. The solid was resuspended in THF (5 mL) and then propan-2-amine (0.153 mL, 1.785 mmol) was added. The mixture was stirred at RT for 16 hours, and additional propan-2-amine (0.128 mL, 1.487 mmol) was added. Stirring at RT was continued for 1 hour. The reaction mixture was diluted with DCM and washed with saturated aqueous NaHCO$_3$ and brine. The organic layer was concentrated in vacuo, and the residual material was purified via silica gel chromatography, eluting with 20-100% EtOAc in hexanes, to yield trans-4-(2-chloro-5-nitropyridin-4-ylamino)-N-isopropylcyclohexanecarboxamide as a yellow solid (0.312 g, 61.6% yield). MS m/z=341.0 [M+H], calc 340.81 for C$_{15}$H$_{21}$ClN$_4$O$_3$.

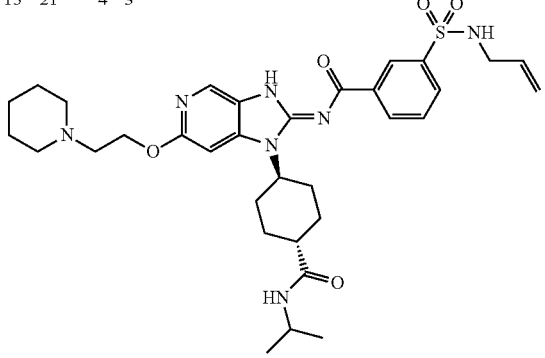

Step C: (E)-3-(N-Allylsulfamoyl)-N-(1-(trans-4-(isopropylcarbamoyl)cyclohexyl)-6-(2-(piperidin-1-yl)ethoxy)-1H-imidazo[4,5-c]pyridin-2(3H)-ylidene)benzamide The title compound was synthesized using a method analogous to the preparation of the remaining steps used to prepare (E)-N-(1-(cis-4-(isopropylcarbamoyl)cyclohexyl)-6-(2-(piperidin-1-yl)ethoxy)-1H-imidazo-[4,5-c]pyridin-2(3H)-ylidene)benzo[b]thiophene-6-carboxamide. MS m/z=652.2 [M+H], calc 651.82 for C$_{33}$H$_{45}$N$_7$O$_5$S. $^1$H NMR (DMSO-d$_6$) δ ppm: 12.72 (br. s., 1H), 8.57-8.63 (m, 1H), 8.45 (dt, J=7.75, 1.21 Hz, 1H), 8.26 (s, 1H), 7.90-8.00 (m, 2H), 7.75 (t, J=7.8 Hz, 1H), 7.44 (d, J=1.0 Hz, 1H), 7.04 (s, 1H), 5.61-5.77 (m, 1H), 5.10-5.20 (dq, J=17.1, 1.63 Hz, 1H), 4.98-5.07 (dq, J=10.27, 1.47 Hz, 1H), 4.63-4.75 (m, 1H), 4.35 (t, J=5.9 Hz, 2H), 3.77-3.92 (m, J=7.5 Hz, 1H), 3.46-3.52 (m, 2H), 2.65 (t, J=5.9 Hz, 2H), 2.28-2.48 (m, J=4.4 Hz, 7H), 1.80-1.98 (m, 4H), 1.55-1.72 (m, 2H), 1.43-1.54 (m, 4H), 1.32-1.42 (m, 2H), 1.07 (d, J=6.6 Hz, 6H).

Example 132

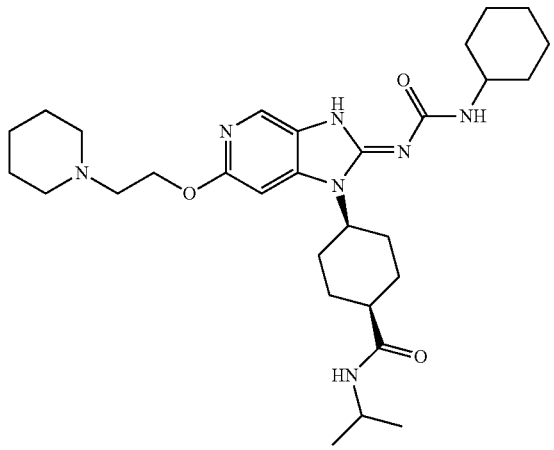 [SMILES: CC(C)NC(=O)[C@H]1CC[C@@H](n2/c(=N/C(=O)NC3CCCCC3)[nH]c3cnc(OCCN4CCCCC4)cc32)CC1]

cis-4-((E)-2-(Cyclohexylcarbamoylimino)-6-(2-(piperidin-1-yl)ethoxy)-2,3-dihydro-1H-imidazo[4,5-c]pyridin-1-yl)-N-isopropylcyclohexanecarboxamide To a solution of cis-4-(2-amino-6-(2-(piperidin-1-yl)ethoxy)-1H-imidazo[4,5-c]pyridin-1-yl)-N-isopropylcyclohexanecarboxamide (0.150 g, 0.350 mmol) in THF (2.92 mL) was added cyclohexyl isocyanate (0.067 mL, 0.525 mmol). The resulting mixture was stirred at reflux overnight. The reaction mixture was concentrated in vacuo and purified via silica gel chromatography, eluting with a gradient of 0% to 100% 90:10:1 DCM:MeOH:NH$_4$OH. The product was further purified via reverse-phase preparative HPLC (0.1% TFA in ACN/H$_2$O, gradient 10% to 90% over 25 minutes) to provide the TFA salt of the desired product. The material was free-based using an SCX ion-exchange column to yield cis-4-((E)-2-(cyclohexylcarbamoylimino)-6-(2-(piperidin-1-yl)ethoxy)-2,3-dihydro-1H-imidazo[4,5-c]pyridin-1-yl)-N-isopropylcyclohexanecarboxamide as a white solid (18.0% yield). MS m/z=554.2 [M+H], calc 553.74 for C$_{30}$H$_{47}$N$_7$O$_3$.

Example 133

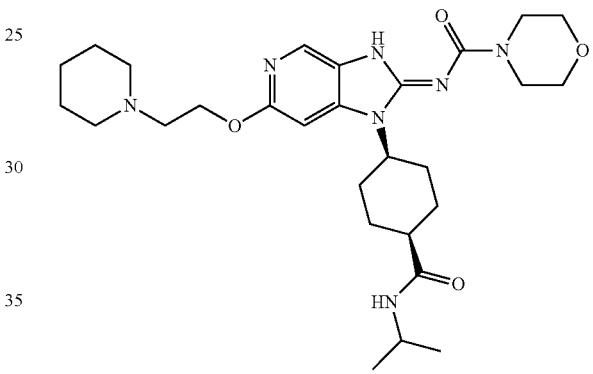

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)morpholine-4-carboxamide cis-4-(2-Amino-6-(2-(piperidin-1-yl)ethoxy)-1H-imidazo[4,5-c]pyridin-1-yl)-N-isopropylcyclohexanecarboxamide (0.200 g, 0.467 mmol), DIPEA (0.408 mL, 2.333 mmol) and phenyl carbonochloridate (0.235 mL, 1.867 mmol) were dissolved in THF (1.3 mL), and the reaction was stirred at 60° C. for 1 hour. Morpholine (0.407 mL, 4.67 mmol) was added in DCM (1 mL), and heating was resumed at 50° C. for 2 hours. The solids were filtered and washed with DCM and the filtrate was concentrated in vacuo. The residual material was purified via reverse-phase preparative HPLC (0.1% TFA in ACN/H$_2$O, gradient 10% to 90% over 25 min) to provide the TFA salt of the desired product. The free base was isolated using an SCX ion-exchange column to obtain (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)morpholine-4-carboxamide as a light purple solid (0.027 g, 10.68% yield). MS m/z=542.2 [M+H], calc 541.69 for C$_{28}$H$_{43}$N$_7$O$_4$.

Example 134

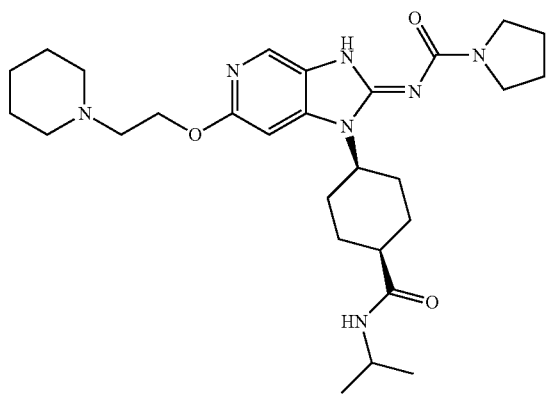 [SMILES: CC(C)NC(=O)[C@H]1CC[C@@H](n2/c(=N/C(=O)N3CCCC3)[nH]c3cnc(OCCN4CCCCC4)cc32)CC1]

(E)-N-(1-(cis-4-(Isopropylcarbamoyl)cyclohexyl)-6-(2-(piperidin-1-yl)ethoxy)-1H-imidazo[4,5-c]pyridin-2(3H)-ylidene)pyrrolidine-1-carboxamide The title compound was synthesized using a method analogous to the preparation of (E)-N-(1-(cis-4-(isopropylcarbamoyl)cyclohexyl)-6-(2-(piperidin-1-yl)ethoxy)-1H-imidazo[4,5-c]pyridin-2(3H)-ylidene)morpholine-4-carboxamide, using pyrrolidine as the amine source (4.5% yield). MS m/z=526.5 [M+H], calc 525.69 for $C_{28}H_{43}N_7O_3$. $^1$H NMR (DMSO-d$_6$) δ ppm: 11.77 (s., 1H), 7.98 (s, 1H), 7.62 (d, J=1.0 Hz, 1H), 6.79 (s, 1H), 4.45-4.58 (m, 1H), 4.30 (t, J=1.0 Hz, 2H), 3.85-4.00 (m, 1H), 3.43-3.53 (m, 2H), 3.30-3.36 (m, 2H), 2.61 (t, J=1.0 Hz, 2H), 2.52-2.59 (m, 2H), 2.36-2.47 (m, 5H), 2.01-2.10 (m, 2H), 1.75-1.86 (m, 4H), 1.53-1.65 (m, 2H), 1.43-1.53 (m, 6H), 1.32-1.42 (m, 2H), 1.08 (d, J=6.6 Hz, 6H).

Example 135

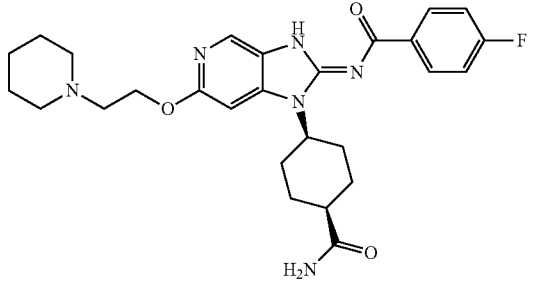 [SMILES: NC(=O)[C@H]1CC[C@@H](n2/c(=N/C(=O)c3ccc(F)cc3)[nH]c3cnc(OCCN4CCCCC4)cc32)CC1]

(E)-N-(1-(cis-4-Carbamoylcyclohexyl)-6-(2-(piperidin-1-yl)ethoxy)-1H-imidazo[4,5-c]pyridin-2(3H)-ylidene)-4-fluorobenzamide The title compound was synthesized using a method analogous to the preparation of (E)-3-(N-allylsulfamoyl)-N-(1-(cis-4-(isopropylcarbamoyl)cyclohexyl)-6-(2-(piperidin-1-yl)ethoxy)-1H-imidazo[4,5-c]pyridin-2(3H)-ylidene)benzamide. MS m/z=509.2 [M+H], calc 508.59 for $C_{27}H_{33}FN_6O_3$. $^1$H NMR (DMSO-d$_6$) δ ppm: 12.63 (br. s., 1H), 8.28 (dd, J=8.7, 5.8 Hz, 2H), 8.22 (s, 1H), 7.37 (br. s, 1H), 7.26-7.34 (m, 2H), 6.98 (s, 1H), 6.94 (br. s, 1H), 4.66-4.80 (m, 1H), 4.34 (t, J=6.0 Hz, 2H), 2.60-2.69 (m, 3H), 2.52-2.58 (m, 2H), 2.38-2.45 (m, 4H), 2.11-2.19 (m, 2H), 1.55-1.78 (m, J=17.2 Hz, 4H), 1.44-1.55 (m, 4H), 1.32-1.43 (m, 2H).

Scheme B

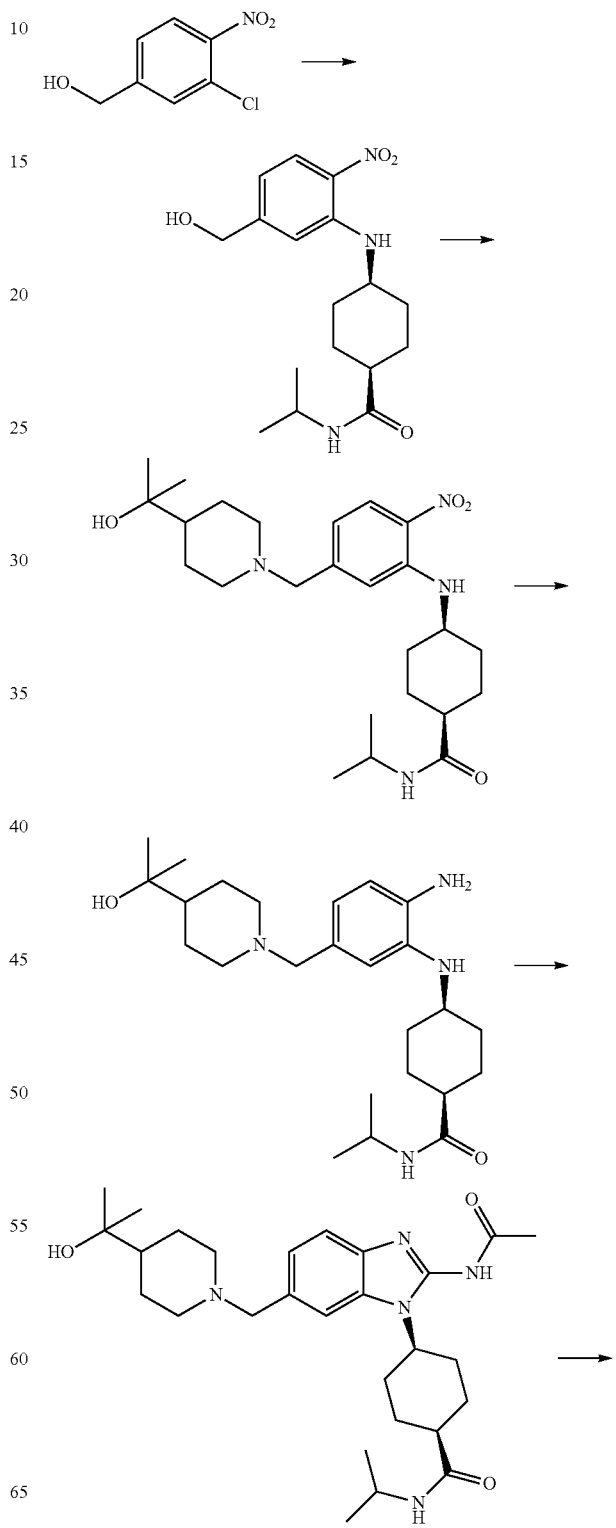

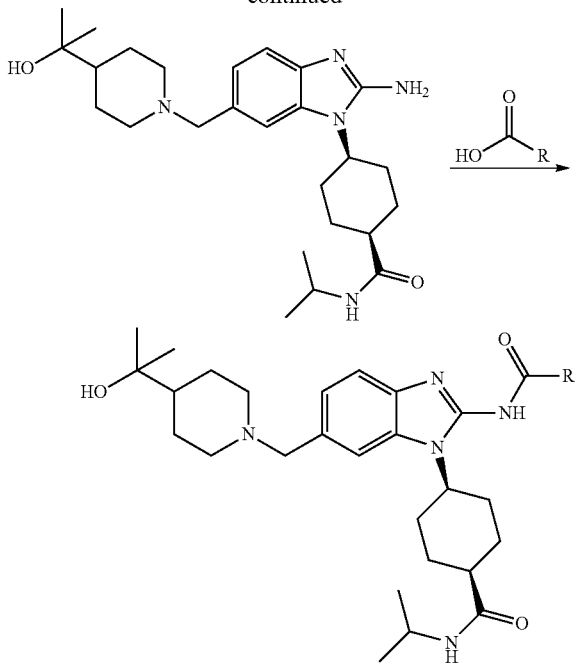

Example 136 cis-4-(2-Amino-6-((4-(2-hydroxypropan-2-yl)piperidin-1-yl)methyl)-1H-benzo[d]imidazol-1-yl)-N-isopropylcyclohexanecarboxamide

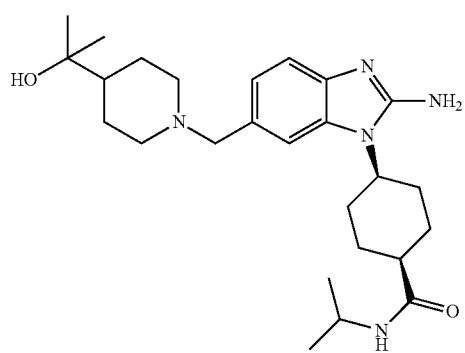 [SMILES: CC(C)NC(=O)[C@H]1CC[C@@H](n2c(N)nc3ccc(CN4CCC(C(C)(C)O)CC4)cc32)CC1]

Step A: cis-4-(5-(4-(2-Hydroxypropan-2-yl)piperidin-1-yl)methyl)-2-nitrophenylamino)-N-isopropylcyclohexanecarboxamide To a solution of cis-4-(5-(hydroxymethyl)-2-nitrophenylamino)-N-isopropylcyclohexanecarboxamide (3.75 g, 11.18 mmol) in DCM (127 mL) at 0° C. was added thionyl chloride (4.08 mL, 55.9 mmol) dropwise. The reaction was stirred at 0° C. for 3 hours and then at RT for 2 hours. The reaction was concentrated in vacuo and suspended in ACN and re-concentrated to remove residual thionyl chloride. The residue was resuspended in ACN (102 mL, 11.18 mmol), cooled to 0° C., and to it was added 2-(piperidin-4-yl)propan-2-ol (5.60 g, 39.1 mmol). The reaction was stirred at RT overnight. The mixture was filtered, and the filtrate concentrated in vacuo. The residual material was purified via silica gel chromatography, eluting with 90:10:1 DCM:MeOH:NH$_4$OH to provide cis-4-(5-((4-(2-hydroxypropan-2-yl)piperidin-1-yl)methyl)-2-nitrophenylamino)-N-isopropylcyclohexanecarboxamide (4.64 g, 10.07 mmol, 90% yield) as an orange solid. MS m/z=461.4 [M+H], calc 460.61 for $C_{25}H_{40}N_4O_4$.

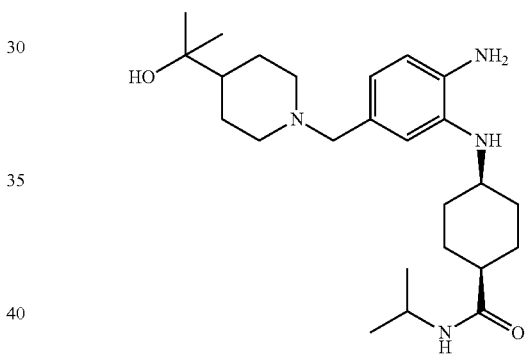

Step B: cis-4-(2-Amino-5-((4-(2-hydroxypropan-2-yl)piperidin-1-yl)methyl)phenylamino)-N-isopropylcyclohexanecarboxamide To a flask under nitrogen atmosphere, Pd/C (10%) (0.460 g, 0.432 mmol) (water wet) was diluted with MeOH (28.8 mL). To the slurry was added cis-4-(5-(4-(2-hydroxypropan-2-yl)piperidin-1-yl)methyl)-2-nitrophenylamino)-N-isopropylcyclohexanecarboxamide (1.99 g, 4.32 mmol), followed by ammonium formate (2.72 g, 43.2 mmol). The flask was closed and stirred at RT for 30 minutes. The reaction was filtered through a pad of Celite® brand filter aid, washing with MeOH. The filtrate was concentrated in vacuo, and was dissolved in 90:10:1 DCM:MeOH:NH$_4$OH and washed with water (×2). The organic layer was dried with sodium sulfate, filtered and concentrated in vacuo to yield cis-4-(2-amino-5-4-((2-hydroxypropan-2-yl)piperidin-1-yl)methyl)phenylamino)-N-isopropylcyclohexanecarboxamide as a red solid. MS m/z=431.2, calc 430.63 $C_{25}H_{42}N_4O_2$.

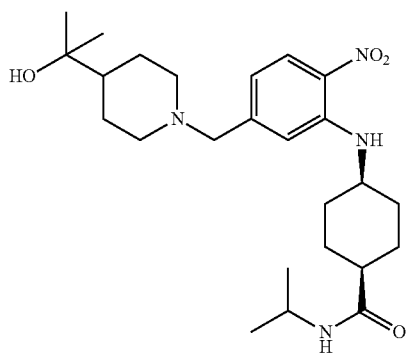 [SMILES: CC(C)NC(=O)[C@H]1CC[C@@H](Nc2cc(CN3CCC(C(C)(C)O)CC3)ccc2[N+](=O)[O-])CC1]

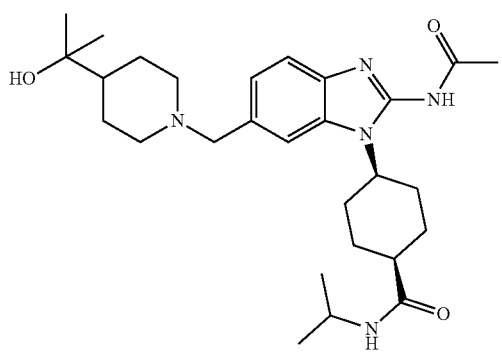 [SMILES: CC(=O)Nc1nc2ccc(CN3CCC(C(C)(C)O)CC3)cc2n1[C@H]1CC[C@@H](C(=O)NC(C)C)CC1]

Step C: cis-4-(2-Acetamido-6-((4-(2-hydroxypropan-2-yl)piperidin-1-yl)methyl)-1H-benzo[d]imidazol-1-yl)-N-isopropylcyclohexanecarboxamide The title compound was synthesized using a method analogous to the preparation of cis-4-(2-acetamido-6-(2-(piperidin-1-yl)ethoxy)-1H-imidazo[4,5-c]pyridin-1-yl)-N-isopropylcyclohexanecarboxamide. MS m/z=498.2 [M+H], calc 497.67 for $C_{28}H_{43}N_5O_3$.

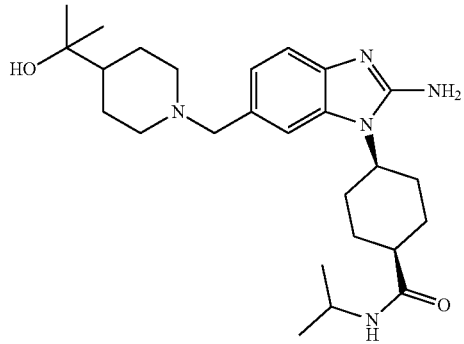 [SMILES: CC(C)NC(=O)[C@H]1CC[C@@H](n2c(N)nc3ccc(CN4CCC(C(C)(C)O)CC4)cc32)CC1]

Step D: cis-4-(2-Amino-6-((4-(2-hydroxypropan-2-yl)piperidin-1-yl)methyl)-1H-benzo[d]imidazol-1-yl)-N-isopropylcyclohexanecarboxamide The title compound was synthesized using a method analogous to the preparation of cis-4-(2-amino-6-(2-(piperidin-1-yl)ethoxy)-1H-imidazo[4,5-c]pyridin-1-yl)-N-isopropylcyclohexanecarboxamide. MS m/z=456.2 [M+H], calc 455.64 for $C_{26}H_{41}N_5O_2$.

Example 137

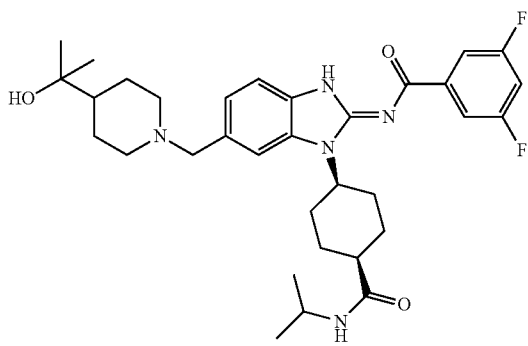 [SMILES: CC(C)NC(=O)[C@H]1CC[C@@H](n2/c(=N/C(=O)c3cc(F)cc(F)c3)[nH]c3ccc(CN4CCC(C(C)(C)O)CC4)cc32)CC1]

(E)-3,5-Difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-N-(1-(cis-4-(isopropylcarbamoyl)cyclohexyl)-6-(2-(piperidin-1-yl)ethoxy)-1H-imidazo-[4,5-c]pyridin-2(3H)-ylidene)benzo[b]thiophene-6-carboxamide (19.9% yield). MS m/z=596.2 [M+H], calc 575.72 for $C_{33}H_{43}F_2N_5O_3$. $^1$H NMR (DMSO-$d_6$) δ ppm: 12.81 (s, 1H), 7.85 (dd, J=8.4, 2.3 Hz, 2H), 7.56-7.64 (m, J=7.6 Hz, 2H), 7.50 (d, J=8.2 Hz, 1H), 7.38 (tt, J=9.0, 2.4 Hz, 1H), 7.18 (dd, J=8.2, 1.0 Hz, 1H), 4.78-4.90 (m, 1H), 4.00-4.11 (m, 1H), 3.99 (s, 1H), 3.50 (s, 2H), 2.85-2.92 (m, 2H), 2.63-2.82 (m, 2H), 2.51-2.56 (m, 1H), 2.06-2.19 (m, 2H), 1.69-1.91 (m, 4H), 1.56-1.69 (m, 4H), 1.18-1.35 (m, 2H), 1.12-1.18 (m, 1H), 1.09 (d, J=3.6 Hz, 6H), 1.02 (s, 6H).

Example 138

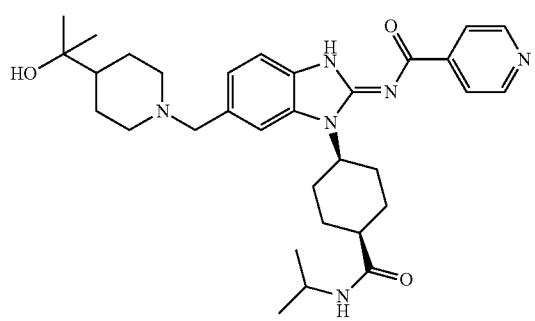 [SMILES: CC(C)NC(=O)[C@H]1CC[C@@H](n2/c(=N/C(=O)c3ccncc3)[nH]c3ccc(CN4CCC(C(C)(C)O)CC4)cc32)CC1]

(E)-N-(6-((4-(2-Hydroxypropan-2-yl)piperidin-1-yl)methyl)-1-(cis-4-(isopropylcarbamoyl)cyclohexyl)-1H-benzo[d]imidazol-2(3H)-ylidene)isonicotinamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using isonicotinic acid (21.3% yield). MS m/z=561.4 [M+H], calc 560.73 for $C_{32}H_{44}N_6O_3$.

Example 139

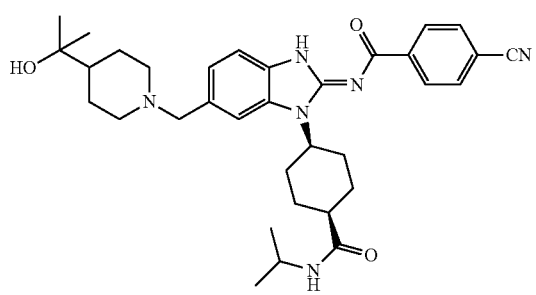 [SMILES: CC(C)NC(=O)[C@H]1CC[C@@H](n2/c(=N/C(=O)c3ccc(C#N)cc3)[nH]c3ccc(CN4CCC(C(C)(C)O)CC4)cc32)CC1]

217

(E)-4-Cyano-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 4-cyanobenzoic acid (20.5% yield). MS m/z=585.4 [M+H], calc 584.75 for $C_{34}H_{44}N_6O_3$. $^1$H NMR (DMSO-d$_6$) δ ppm: 12.83 (br. s., 1H), 8.41 (d, J=8.4 Hz, 2H), 7.91 (d, J=8.4 Hz, 2H), 7.64 (d, J=7.6 Hz, 1H), 7.58 (s, 1H), 7.50 (d, J=8.1 Hz, 1H), 7.18 (d, J=8.2 Hz, 1H), 4.81-4.92 (m, 1H), 4.01-4.09 (m, 1H), 4.00 (s, 1H), 3.50 (s, 2H), 2.83-2.93 (m, 2H), 2.66-2.80 (m, 2H), 2.52-2.56 (m, 2H), 2.10-2.19 (m, 2H), 1.79-1.89 (m, 2H), 1.68-1.79 (m, 2H), 1.58-1.67 (m, 4H), 1.18-1.31 (m, 2H), 1.11 (d, J=6.5 Hz, 6H), 1.02 (s, 6H).

Example 140

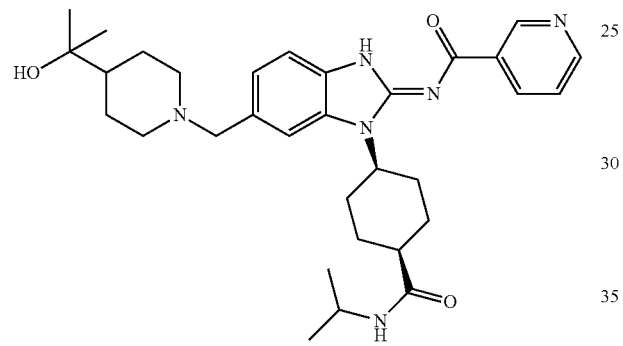

(E)-N-(6-((4-(2-Hydroxypropan-2-yl)piperidin-1-yl)methyl)-1-(cis-4-(isopropylcarbamoyl)cyclohexyl)-1H-benzo[d]imidazol-2(3H)-ylidene)nicotinamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using nicotinic acid (23.2% yield). MS m/z=561.3 [M+H], calc 560.73 for $C_{32}H_{44}N_6O_3$.

Example 141

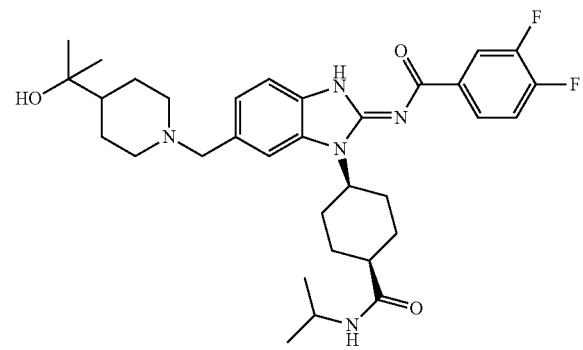 [SMILES: CC(C)NC(=O)[C@H]1CC[C@@H](n2/c(=N/C(=O)c3ccc(F)c(F)c3)[nH]c3ccc(CN4CCC(C(C)(C)O)CC4)cc32)CC1]

218

(E)-3,4-Difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3,4-difluorobenzoic acid (16.4% yield). MS m/z=596.3 [M+H], calc 595.72 for $C_{33}H_{43}F_2N_5O_3$.

Example 142

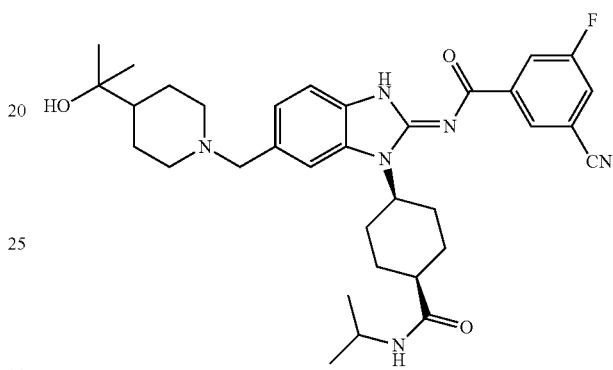

(E)-3-Cyano-5-fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-cyano-5-fluorobenzoic acid (17.6% yield). MS m/z=603.4 [M+H], calc 602.74 for $C_{34}H_{43}FN_6O_3$. $^1$H NMR (DMSO-d$_6$) δ ppm: 12.87 (br. s., 1H), 8.43 (s, 1H), 8.32 (d, J=1.0 Hz, 1H), 7.96-8.03 (m, 1H), 7.58-7.65 (m, 2H), 7.52 (d, J=8.1 Hz, 1H), 7.19 (d, J=8.2 Hz, 1H), 4.78-4.90 (m, 1H), 4.02-4.13 (m, 1H), 4.00 (s, 1H), 3.50 (s, 2H), 2.85-2.92 (m, 2H), 2.72-2.84 (m, 2H), 2.52-2.57 (m, 1H), 2.06-2.15 (m, 2H), 1.68-1.90 (m, 4H), 1.58-1.67 (m, 4H), 1.19-1.31 (m, 2H), 1.11-1.18 (m, 1H), 1.08 (d, J=1.0 Hz, 6H), 1.02 (s, 6H).

Example 143

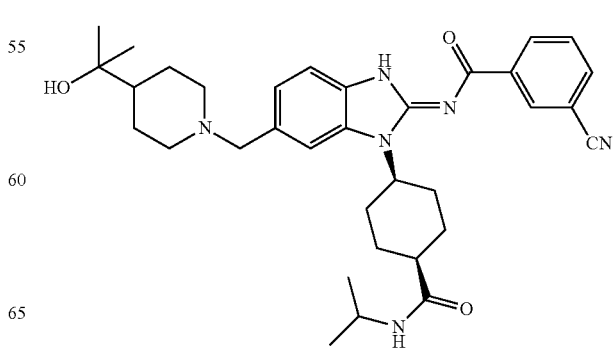

(E)-3-Cyano-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-cyanobenzoic acid (20.2% yield). MS m/z=585.4 [M+H], calc 584.76 for $C_{34}H_{44}N_6O_3$.

Example 144

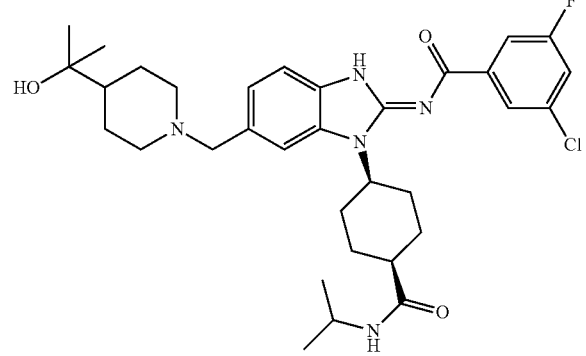

(E)-3-Chloro-5-fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-chloro-5-fluorobenzoic acid (21.4% yield). MS m/z=612.3 [M+H], calc 612.19 for $C_{33}H_{43}ClFN_5O_3$. $^1$H NMR (DMSO-d$_6$) δ ppm: 12.82 (br. s., 1H), 7.96-8.05 (m, 2H), 7.54-7.66 (m, 3H), 7.51 (d, J=8.1 Hz, 1H), 7.18 (d, J=8.1 Hz, 1H), 4.80-4.91 (m, 1H), 4.01-4.10 (m, 1H), 4.00 (s, 1H), 3.50 (s, 2H), 2.84-2.92 (m, 2H), 2.64-2.79 (m, 2H), 2.51-2.56 (m, 2H), 2.05-2.19 (m, 2H), 1.79-1.89 (m, 2H), 1.67-1.79 (m, 2H), 1.59-1.67 (m, 4H), 1.18-1.31 (m, 2H), 1.10 (d, J=6.5 Hz, 6H), 1.02 (s, 6H).

Example 145

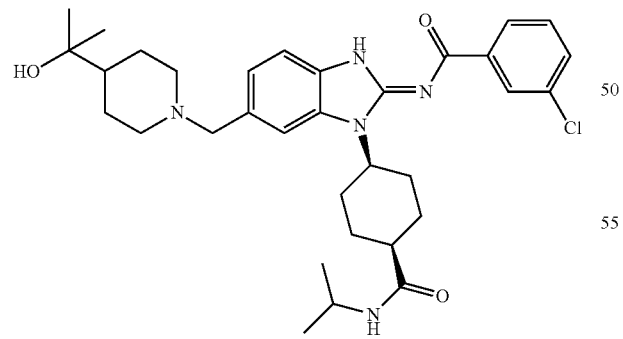

(E)-3-Chloro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-chlorobenzoic acid (21.4% yield). MS m/z=594.4 [M+H], calc 594.20 for $C_{33}H_{44}ClN_5O_3$.

Example 146

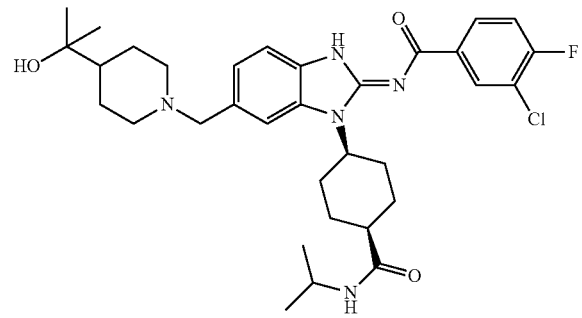 [SMILES: CC(C)NC(=O)[C@H]1CC[C@@H](n2/c(=N/C(=O)c3ccc(F)c(Cl)c3)[nH]c3ccc(CN4CCC(C(C)(C)O)CC4)cc32)CC1]

(E)-3-Chloro-4-fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-chloro-4-fluorobenzoic acid (21.4% yield). MS m/z=612.3 [M+H], calc 612.19 for $C_{33}H_{43}ClFN_5O_3$.

Example 147

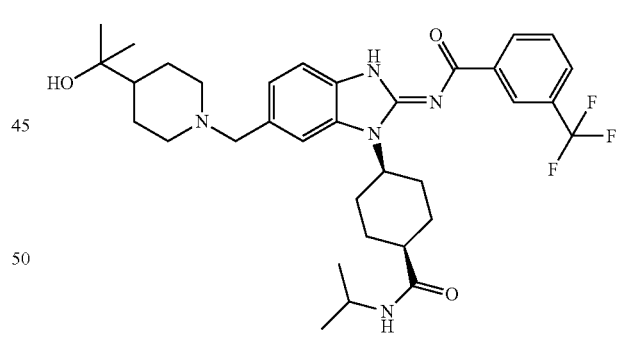

(E)-N-(6-((4-(2-Hydroxypropan-2-yl)piperidin-1-yl)methyl)-1-(cis-4-(isopropylcarbamoyl)cyclohexyl)-1H-benzo[d]imidazol-2(3H)-ylidene)-3-(trifluoromethyl)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 3-(trifluoromethyl)benzoic acid (16.1% yield). MS m/z=628.4 [M+H], calc 627.75 for $C_{34}H_{44}F_3N_5O_3$.

Example 148

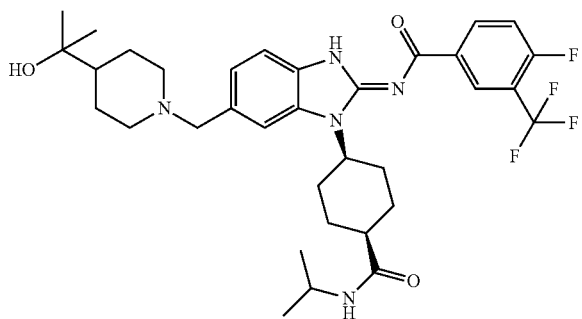 [SMILES: CC(C)NC(=O)[C@H]1CC[C@@H](n2/c(=N/C(=O)c3ccc(F)c(C(F)(F)F)c3)[nH]c3ccc(CN4CCC(C(C)(C)O)CC4)cc32)CC1]

(E)-4-Fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)-3-(trifluoromethyl)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 4-fluoro-3-(trifluoromethyl)benzoic acid (14.5% yield). MS m/z=646.4 [M+H], calc 645.74 for $C_{34}H_{43}F_4N_5O_3$.

Example 149

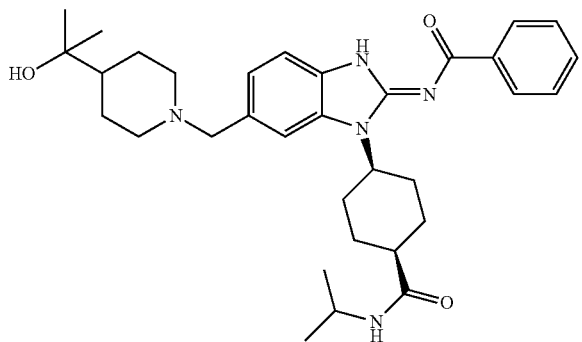 [SMILES: CC(C)NC(=O)[C@H]1CC[C@@H](n2/c(=N/C(=O)c3ccccc3)[nH]c3ccc(CN4CCC(C(C)(C)O)CC4)cc32)CC1]

(E)-N-(6-((4-(2-Hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2 (3H)-ylidene)benzamide, using benzoic acid (22.3% yield). MS m/z=560.4 [M+H], calc 559.75 for $C_{33}H_{45}N_5O_3$.

Example 150

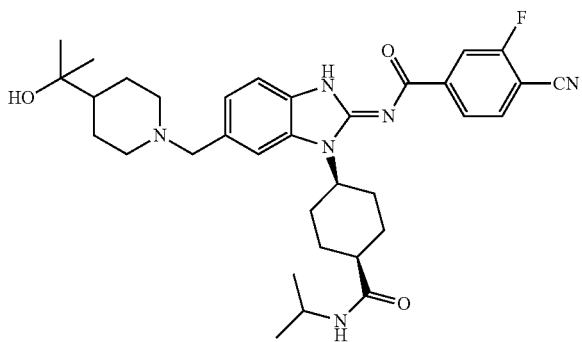 [SMILES: CC(C)NC(=O)[C@H]1CC[C@@H](n2/c(=N/C(=O)c3ccc(C#N)c(F)c3)[nH]c3ccc(CN4CCC(C(C)(C)O)CC4)cc32)CC1]

(E)-4-Cyano-3-fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 4-cyano-3-fluorobenzoic acid (21.5% yield). MS m/z=603.4 [M+H], calc 602.75 for $C_{34}H_{43}FN_6O_3$.

Example 151

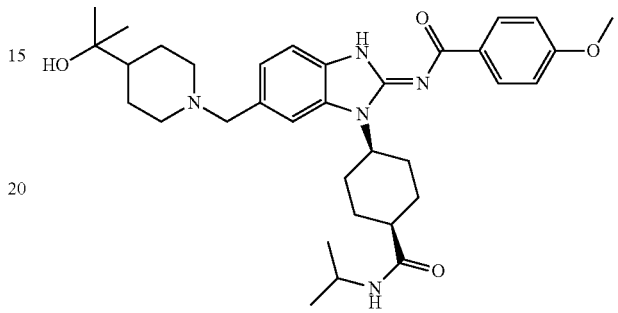

(E)-N-(6-((4-(2-Hydroxypropan-2-yl)piperidin-1-yl)methyl)-1-(cis-4-(isopropylcarbamoyl)cyclohexyl)-1H-benzo[d]imidazol-2(3H)-ylidene)-4-methoxybenzamide The title compound was synthesized using a method analogous to the preparation of (E)-3,5-difluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide, using 4-methoxybenzoic acid (7.8% yield). MS m/z=590.2 [M+H], calc 589.77 for $C_{34}H_{47}N_5O_4$.

Example 152

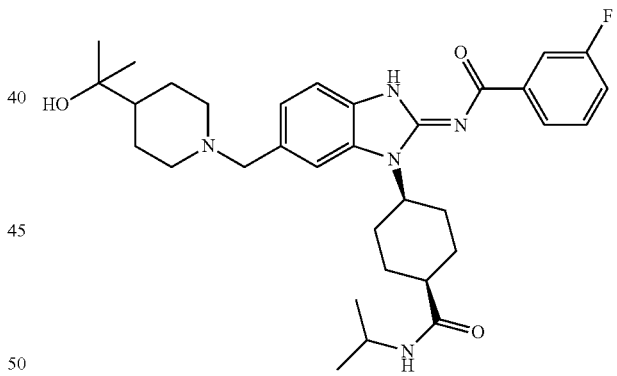

(E)-3-Fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide The title compound was synthesized synthesized using a method analogous to the preparation of (E)-4-fluoro-N-(6-((4-(2-hydroxypropan-2-yl)piperidin-1-yl)methyl)-1-(cis-4-(isopropylcarbamoyl)cyclohexyl)-1H-benzo[d]imidazol-2(3H)-ylidene)benzamide (39.5% yield). MS m/z=578.2 [M+H], calc 577.73 for $C_{33}H_{44}FN_5O_3$. $^1$H NMR (DMSO-$d_6$) δ ppm: 12.80 (br. s., 1H), 8.10 (d, J=1.0 Hz, 1H), 7.93 (d, J=1.0 Hz, 1H), 7.43-7.69 (m, J=5.8 Hz, 4H), 7.29-7.39 (m, 1H), 7.11-7.23 (m, 1H), 4.80-4.92 (m, 1H), 4.56 (s, 1H), 3.94-4.13 (m, 2H), 3.44-3.58 (m, 2H), 2.81-2.96 (m, 2H), 2.64-2.80 (m, 2H), 2.51-2.56 (m, 2H), 2.09-2.21 (m, 2H), 1.54-1.92 (m, 7H), 1.20-1.37 (m, 2H), 1.10 (d, J=6.6 Hz, 6H), 1.02 (s, 6H)

Example 153

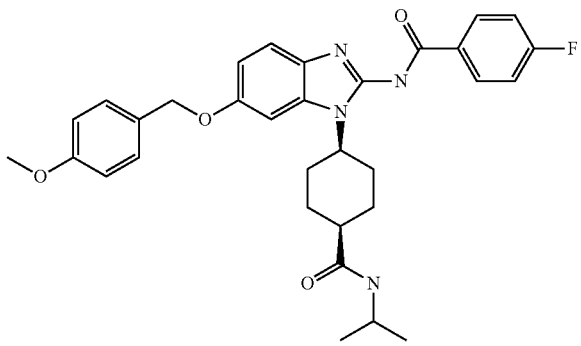 [SMILES: COc1ccc(COc2ccc3nc(NC(=O)c4ccc(F)cc4)n([C@H]4CC[C@@H](C(=O)NC(C)C)CC4)c3c2)cc1]

4-Fluoro-N-(6-((4-methoxybenzyl)oxy)-1-(cis-4-((1-methylethyl)carbamoyl)cyclohexyl)-1H-benzimidazol-2-yl)benzamide

Step A: 2-Fluoro-4-(4-methoxybenzyloxy)-1-nitrobenzene

To a solution of 3-fluoro-4-nitrophenol (2.96 g, 18.81 mmol) in DMF (18.81 mL) was added 1-(chloromethyl)-4-methoxybenzene (2.55 mL, 18.81 mmol) and potassium carbonate (5.20 g, 37.6 mmol). The reaction mixture was stirred at 50° C. for 16 hours. The mixture was diluted with EtOAc (100 mL), washed with water, and the aqueous layer was back-extracted with EtOAc (25 mL). The combined organic layers were washed with 1 M aqueous NaOH (20 mL) and then with brine. The organic layer was dried over $Na_2SO_4$, filtered and evaporated. The yellow solid was triturated with ether (20 mL), and the solid was collected, rinsing with ether (5 mL). The title compound was obtained as a yellow solid (4.39 g, 84% yield).

Step B: cis-N-Isopropyl-4-(5-(4-methoxybenzyloxy)-2-nitrophenylamino)cyclohexanecarboxamide A mixture of 2-fluoro-4-(4-methoxybenzyloxy)-1-nitrobenzene (507 mg, 1.82 mmol), cis-4-amino-N-isopropylcyclohexanecarboxamide hydrochloride (404 mg, 1.82 mmol), DIPEA (0.70 mL, 4.02 mmol) and ACN (3.6 mL) were placed in a sealed tube, and the tube was heated at 80° C. for 6 hours. The mixture was allowed to cool and evaporated. The residue was diluted with DCM (15 mL), washed with water (×2), and then washed with brine. The organic layer was dried over $Na_2SO_4$. The mixture was purified via flash chromatography using a linear gradient of 0% to 10% MeOH in DCM. The title compound was collected as a yellow solid (476 mg, 59% yield).

Step C: 4-Fluoro-N-(4-fluorobenzoyl)-N-(1-(cis-4-(isopropylcarbamoyl)cyclohexyl)-6-(4-methoxybenzyloxy)-1H-benzo[d]imidazol-2-yl)benzamide To a solution of cis-N-isopropyl-4-(5-(4-methoxybenzyloxy)-2-nitrophenylamino)cyclohexanecarboxamide (452 mg, 1.024 mmol) in MeOH (5 mL) was added AcOH (0.293 mL, 5.12 mmol) and zinc (669 mg, 10.24 mmol), and the resulting mixture was stirred at RT for 3 hours. The mixture was filtered through a pad of Celite® brand filter aid and evaporated to afford cis-4-(2-amino-5-(4-methoxybenzyloxy)phenylamino)-N-isopropylcyclohexanecarboxamide (400 mg).

To a solution of cis-4-(2-amino-5-(4-methoxybenzyloxy)phenylamino)-N-isopropylcyclohexanecarboxamide (400 mg, 0.972 mmol) in EtOH (4.8 mL) was added cyanic bromide (165 mg, 1.555 mmol) and the mixture was stirred at RT for 2 hours. The solvent was evaporated, and the residue was diluted with DCM (about 10 mL), washed with water, 1N aqueous NaOH, and brine. The organic layer was dried over $Na_2SO_4$, filtered and the solvent was removed to afford cis-4-(2-amino-6-(4-methoxybenzyloxy)-1H-benzo[d]imidazol-1-yl)-N-isopropylcyclohexanecarboxamide (424 mg).

To a solution of cis-4-(2-amino-6-(4-methoxybenzyloxy)-1H-benzo[d]imidazol-1-yl)-N-isopropylcyclohexanecarboxamide (424 mg, 0.971 mmol) and 4-fluorobenzoyl chloride (0.172 mL, 1.457 mmol) in DCM was added TEA (0.271 mL, 1.943 mmol), and the resulting mixture was stirred at RT for 10 minutes. The mixture was evaporated, and the residue diluted with DCM, washed with water, brine, and the organic layer dried over $Na_2SO_4$. The mixture was purified via flash chromatography using a linear gradient of 0% to 10% MeOH in DCM. The title compound was obtained as a tan foam (442 mg, max 80% yield, mixture of the mono and bis-acylated products).

Step D: 4-Fluoro-N—O-(cis-4-(isopropylcarbamoyl)cyclohexyl)-6-(4-methoxybenzyloxy)-1H-benzo[d]imidazol-2-yl)benzamide To a solution of 4-fluoro-N-(4-fluorobenzoyl)-N-(1-(cis-4-(isopropylcarbamoyl)cyclohexyl)-6-(4-methoxybenzyloxy)-1H-benzo[d]imidazol-2-yl)benzamide (442 mg, 0.649 mmol, as a mixture with the mono-acylated material) in MeOH (3.2 mL) and dioxane (3.2 mL) was added a flake of sodium hydroxide (46.7 mg, 1.169 mmol), and the mixture was stirred at RT for 1 hour. The mixture was evaporated and the residue diluted with DCM, washed with 1 N aqueous NaOH, brine, and the organic layer dried over $Na_2SO_4$. The residue was purified via flash chromatography using a linear gradient of 0% to 50% EtOAc in hexanes. The title compound was collected as a white solid (275 mg, 76% yield). M/Z calc'd for $C_{32}H_{35}FN_4O_4$: 558.65. found 559 [M+H].

Example 154

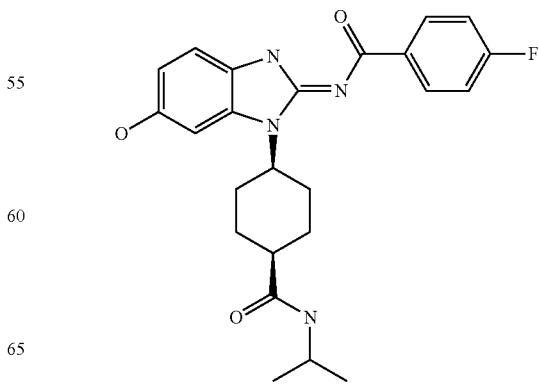

4-Fluoro-N-(6-hydroxy-1-(cis-4-(isopropylcarbamoyl)cyclohexyl)-1H-benzo[d]imidazol-2-yl)benzamide To a solution of 4-fluoro-N-(1-(cis-4-(isopropylcarbamoyl)cyclohexyl)-6-(4-methoxybenzyloxy)-1H-benzo[d]imidazol-2-yl)benzamide (232 mg, 0.415 mmol) in DCM was added TFA (0.96 mL, 1.246 mmol), and the mixture was stirred at RT for 90 minutes. Additional TFA (0.96 mL, 1.246 mmol) was added, and the mixture was stirred at RT for 1 hour longer. The mixture was diluted with DCM, washed with 1 N aqueous NaOH, and the water layer back-extracted with DCM. The aqueous layer was adjusted to pH 8, and the pale green solid was collected and rinsed with 2 mL water. The solid was dissolved in ether and washed with brine, dried over Na$_2$SO$_4$, filtered, and evaporated. The title compound was obtained as a white sold (153 mg, 84% yield). $^1$H NMR (400 MHz, DMSO-d$_6$) δ ppm 1.10 (d, J=8 Hz, 6H) 1.59 (m, 2H) 1.65-1.82 (m, 2H) 2.02-2.19 (m, 2H) 2.46-2.58 (m, 1H) 2.62-2.79 (m, 2H) 3.93-4.07 (m, 1H) 4.70-4.85 (m, 1H) 6.67 (dd, J=8.61, 2.15 Hz, 1H) 7.03 (d, J=2.05 Hz, 1H) 7.14-7.28 (m, 2H) 7.33 (d, J=8.51 Hz, 1H) 7.64 (d, J=7.82 Hz, 1H) 8.16-8.38 (m, 2H) 9.40 (s, 1H) 12.58 (s, 1H). M/Z calc'd for C$_{24}$H$_{27}$FN$_4$O$_3$: 438.50. found 439 [M+H].

Example 155

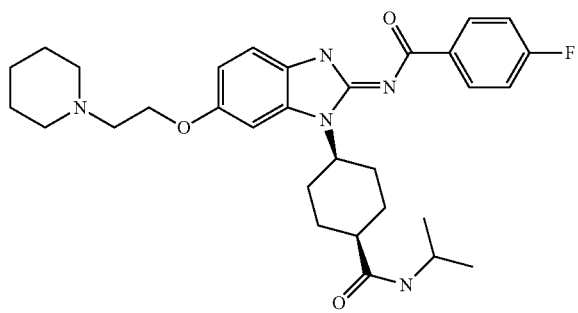 [SMILES: CC(C)NC(=O)[C@H]1CC[C@@H](n2/c(=N/C(=O)c3ccc(F)cc3)[nH]c3ccc(OCCN4CCCCC4)cc32)CC1]

(E)-4-Fluoro-N-(1-(cis-4-(isopropylcarbamoyl)cyclohexyl)-6-(2-(piperidin-1-yl)ethoxy)-1H-benzo[d]imidazol-2(3H)-ylidene)benzamide

Step A: 1-(2-(3-Fluoro-4-nitrophenoxy)ethyl)piperidine

A mixture of 3-fluoro-4-nitrophenol (3.07 g, 19.54 mmol), 1-(2-chloroethyl)piperidine hydrochloride (3.60 g, 19.54 mmol), cesium carbonate (19.10 g, 58.6 mmol) and potassium iodide (1.622 g, 9.77 mmol) were combined with DMF (19.54 mL), and the mixture was heated at 50° C. for 36 hours. The resulting mixture was diluted with EtOAc (50 mL), washed with water (100 mL) and the water layer extracted with EtOAc (30 mL). The combined organic layers were washed with water (20 mL×2), 1N aqueous NaOH, and brine, and the organic layer was dried over Na$_2$SO$_4$, filtered and evaporated. The residue was purified via flash chromatography using a linear gradient of 0% to 5% of 1% NH$_4$OH in MeOH in DCM. The title compound was isolated as a yellow liquid (662 mg, 13% yield).

Step B: (E)-4-Fluoro-N-(1-(cis-4-(isopropylcarbamoyl)cyclohexyl)-6-(2-(piperidin-1-yl)ethoxy)-1H-benzo[d]imidazol-2(3H)-ylidene)benzamide To a solution of 1-(2-(3-fluoro-4-nitrophenoxy)ethyl)piperidine (220 mg, 0.820 mmol) and cis-4-amino-N-isopropylcyclohexanecarboxamide hydrochloride (190 mg, 0.861 mmol) in ACN (0.8 mL) was added DIPEA (0.301 mL, 1.722 mmol). The mixture was heated at 80° C. in a sealed tube for 14 hours, and then additional cis-4-amino-N-isopropylcyclohexanecarboxamide hydrochloride (38 mg, 0.172 mmol) and DIPEA (0.100 mL, 0.574 mmol) were added. The resulting mixture was heated an additional 24 hours. The mixture was diluted with DCM (5 mL), washed with water/brine mixture, brine, and the organic layer was dried over Na$_2$SO$_4$, filtered and evaporated to afford cis-N-isopropyl-4-(2-nitro-5-(2-(piperidin-1-yl)ethoxy)phenylamino)cyclohexanecarboxamide.

To a solution of cis-N-isopropyl-4-(2-nitro-5-(2-(piperidin-1-yl)ethoxy)phenylamino)cyclohexanecarboxamide (350 mg, 0.809 mmol) in MeOH (4.0 mL) was added AcOH (0.463 mL, 8.09 mmol) and zinc (423 mg, 6.47 mmol), and the mixture was stirred at RT for 1 hour. The mixture was filtered through a pad of Celite® brand filter aid and evaporated to afford cis-4-(2-amino-5-(2-(piperidin-1-yl)ethoxy)phenylamino)-N-isopropylcyclohexanecarboxamide.

The title compound was prepared from cis-4-(2-amino-5-(2-(piperidin-1-yl)ethoxy)phenylamino)-N-isopropylcyclohexanecarboxamide using a procedure analogous to that used in the preparation of (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. The product was isolated as an off-white solid (96 mg, 15% yield). M/Z calc'd for C$_{31}$H$_{40}$FN$_5$O$_3$: 549.68. found 550 [M+H].

Example 156

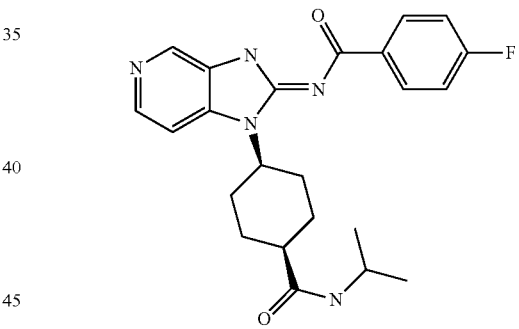

(E)-4-Fluoro-N-(1-(cis-4-(isopropylcarbamoyl)cyclohexyl)-1H-imidazo[4,5-c]pyridin-2(3H)-ylidene)benzamide To a solution of cis-4-(2-chloro-5-nitropyridin-4-ylamino)-N-isopropylcyclohexanecarboxamide (100 mg, 0.293 mmol) and conc. HCl (0.072 mL, 0.880 mmol) in EtOH (3.0 mL) under nitrogen was added Pd/C (10% wt) (156 mg, 0.147 mmol) and ammonium formate (185 mg, 2.93 mmol), and the mixture was stirred at RT for 30 minutes. The mixture was filtered through a pad of Celite® brand filter aid and evaporated. The residue was diluted with 10% IPA in DCM, and washed with 1 N NaOH and then with saturated aqueous NaHCO$_3$. The organic layer was dried over Na$_2$SO$_4$, filtered and the solvent was removed to afford 4-(3-aminopyridin-4-ylamino)-N-isopropylcyclohexanecarboxamide as an off-white solid.

The title compound was prepared from 4-(3-aminopyridin-4-ylamino)-N-isopropylcyclohexanecarboxamide using a procedure analogous to the preparation of cis-methyl 4-((E)-2-(benzoylimino)-2,3-dihydro-1H-imidazo[4,5-c]pyridin-1-yl)cyclohexanecarboxylate isolated as an off-white solid (8 mg, 1% yield). M/Z calc'd for $C_{23}H_{26}FN_5O_2$: 423.48. found 424 [M+H].

Example 157

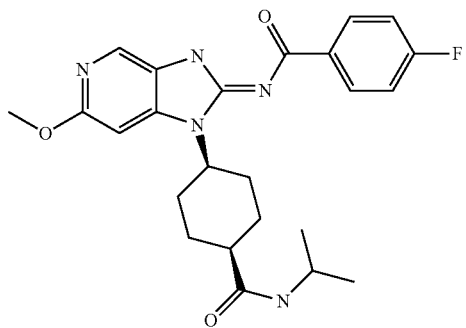 [SMILES: COc1cc2c(cn1)[nH]/c(=N\C(=O)c1ccc(F)cc1)n2[C@H]1CC[C@@H](C(=O)NC(C)C)CC1]

(E)-4-Fluoro-N-(1-(cis-4-(isopropylcarbamoyl)cyclohexyl)-6-methoxy-1H-imidazo[4,5-c]pyridin-2(3H)-ylidene)benzamide Step A: cis-N-Isopropyl-4-(2-methoxy-5-nitropyridin-4-ylamino)cyclohexanecarboxamide To an ice-bath cooled suspension of cis-4-(2-chloro-5-nitropyridin-4-ylamino)-N-isopropylcyclohexanecarboxamide (400 mg, 1.174 mmol) in THF (2.3 mL) was added sodium methoxide (25 wt. % in MeOH (0.859 mL, 3.76 mmol)). The mixture was stirred in an ice bath for 1 minute. The ice bath was removed and the reaction was stirred for 30 minutes. The mixture was diluted with 10% IPA/DCM (5 mL) and washed with saturated aqueous $NaHCO_3$ (1 mL). The layers were separated, and the organic layer was dried with $Na_2SO_4$ and the mixture purified via flash chromatography using a linear gradient of 0% to 5% of 1% $NH_4OH$ in MeOH in DCM. The title compound was collected as a yellow solid (289 mg, 73%).

Step B: (E)-4-Fluoro-N-(1-(cis-4-(isopropylcarbamoyl)cyclohexyl)-6-methoxy-1H-imidazo[4,5-c]pyridin-2(3H)-ylidene)benzamide To solution of cis-N-isopropyl-4-(2-methoxy-5-nitropyridin-4-ylamino)cyclohexanecarboxamide (264 mg, 0.785 mmol) in AcOH (1.5 µmL) was added iron powder (219 mg, 3.92 mmol), and the mixture was heated to 100° C. for 5 minutes. The mixture was allowed to cool to RT, was diluted with 10% MeOH/DCM, and was filtered through a pad of Celite® brand filter aid and concentrated. The mixture was purified via flash chromatography using a linear gradient of 0% to 10% of 1% $NH_4OH$ in MeOH in DCM. Cis-4-(5-amino-2-methoxypyridin-4-ylamino)-N-isopropylcyclohexanecarboxamide was isolated as a red film (211 mg).

To a 0° C. cooled solution of cis-4-(5-amino-2-methoxypyridin-4-ylamino)-N-isopropylcyclohexanecarboxamide (211 mg, 0.689 mmol) in 1 mL THF, was added a suspension of 4-fluorobenzoyl isothiocyanate (250 mg, 1.377 mmol) in THF (3.4 mL). The resulting reaction mixture was stirred at 0° C. for 15 minutes. The ice bath was removed, and the mixture was stirred for 15 minutes at RT. To the mixture were added EDC (396 mg, 2.066 mmol) and DIPEA (0.433 mL, 2.479 mmol), and the flask was heated at 60° C. for 1 hour. The resulting mixture was allowed to cool to RT, and the solvents were removed. The residue was dissolved in 10% IPA in DCM and was washed with water and brine. The organic layer was dried over $Na_2SO_4$ and filtered. The mixture was purified via flash chromatography using a linear gradient of 0% to 5% of 1% $NH_4OH$ in MeOH in DCM. The title compound was collected as an off-white solid. The solid was partitioned with 10% IPA/EtOAc and was washed with 1 mL:2 mL saturated aqueous $NH_4Cl$/water, and brine. The organic layer was dried over $Na_2SO_4$, filtered and the solvents were removed to afford the title compound as an off-white solid (212 mg, 68%). M/Z calc'd for $C_{24}H_{28}FN_5O_3$: 453.51. found 454 [M+H].

Example 158

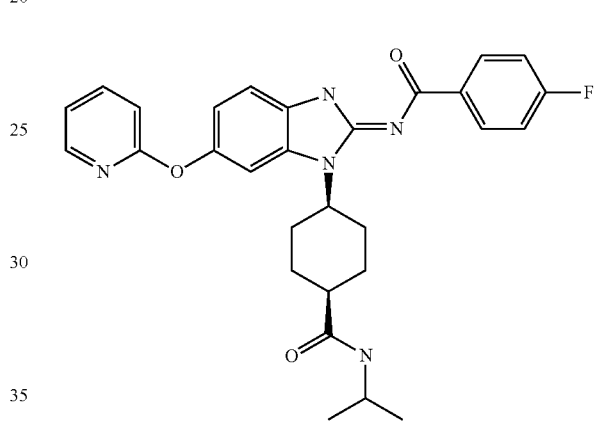

(E)-4-Fluoro-N-(1-(cis-4-(isopropylcarbamoyl)cyclohexyl)-6-(pyridin-2-yloxy)-1H-benzo[d]imidazol-2(3H)-ylidene)benzamide A microwave vial was charged with 4-fluoro-N-(6-hydroxy-1-(cis-4-(isopropylcarbamoyl)cyclohexyl)-1H-benzo[d]imidazol-2-yl)benzamide (56 mg, 0.128 mmol), 2-chloropyridine (0.036 mL, 0.383 mmol), cesium carbonate (166 mg, 0.511 mmol), and NMP (0.6 mL) then irradiated in the microwave at 160° C. for 6 hours. The mixture was diluted with EtOAc, washed with water, the water layer back extracted with EtOAc, and the combined organics were washed with brine. The organic layer was dried over $Na_2SO_4$ and filtered. The mixture was purified via flash chromatography using a linear gradient of 0% to 10% MeOH in DCM. The material was further purified by reverse-phase preparative HPLC using a 0.1% TFA in $ACN/H_2O$, gradient 10% to 90%. The material was partitioned between saturated aqueous $NaHCO_3$ and 5% IPA/DCM, the organic layer washed with brine, dried over $Na_2SO_4$, filtered and evaporated. The title compound was isolated as an off-white solid (32 mg, 35% yield). $^1$H NMR (400 MHz, DMSO-$d_6$) δ ppm 0.98 (d, J=8.00 Hz, 6H) 1.54-1.82 (m, 4H) 2.01-2.14 (m, 2H) 2.42-2.56 (m, 1H) 2.56-2.77 (m, 2H) 3.75-3.93 (m, 1H) 4.80-4.95 (m, 1H) 6.97 (dd, J=8.56, 2.10 Hz, 1H) 6.95-7.10 (m, 1H) 7.00-7.18 (m, 1H) 7.20-7.29 (m, 2H) 7.48 (d, J=2.05 Hz, 1H) 7.51-7.62 (m, 2H) 7.80-7.90 (m, 1H) 8.07-8.19 (m, 1H) 8.27-8.38 (m, 2H) 12.81 (s, 1H). M/Z calc'd for $C_{29}H_{30}FN_5O_3$: 515.58. found 516 [M+H].

Example 159

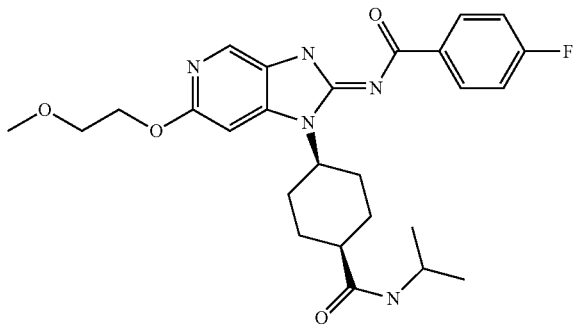 [SMILES: COCCOc1cc2c(cn1)[nH]/c(=N\C(=O)c1ccc(F)cc1)n2[C@H]1CC[C@@H](C(=O)NC(C)C)CC1]

(E)-4-Fluoro-N-(1-(cis-4-(isopropylcarbamoyl)cyclohexyl)-6-(2-methoxyethoxy)-1H-imidazo[4,5-c]pyridin-2(3H)-ylidene)benzamide Step A: cis-N-Isopropyl-4-(2-(2-methoxyethoxy)-5-nitropyridin-4-ylamino)cyclohexanecarboxamide To an ice-bath cooled solution of 2-methoxyethanol (0.296 mL, 3.76 mmol) in THF (2.3 mL) was added sodium hydride (150 mg, 3.76 mmol), and the mixture was stirred for 20 minutes. To the mixture was added cis-4-(2-chloro-5-nitropyridin-4-ylamino)-N-isopropylcyclohexanecarboxamide (400 mg, 1.174 mmol), and the flask was removed from the ice bath and the reaction was stirred for 2 hours. The reaction was quenched with water and diluted with DCM, washed with water, saturated aqueous $NaHCO_3$, and the organic layer dried over $Na_2SO_4$ and filtered through Celite® brand filter aid. The material was purified via flash chromatography using a linear gradient of 0% to 5% of 1% $NH_4OH$ in MeOH in $CH_2Cl_2$. The title compound was collected as a yellow solid (273 mg, 61% yield).

Step B: cis-4-(5-Amino-2-(2-methoxyethoxy)pyridin-4-ylamino)-N-isopropylcyclohexanecarboxamide The title compound was prepared from cis-N-isopropyl-4-(2-(2-methoxyethoxy)-5-nitropyridin-4-ylamino)cyclohexanecarboxamide using a procedure analogous to that used in the preparation of cis-4-(5-amino-2-chloropyridin-4-ylamino)-N-isopropylcyclohexanecarboxamide.

Step C: (E)-4-Fluoro-N-(1-(cis-4-(isopropylcarbamoyl)cyclohexyl)-6-(2-methoxyethoxy)-1H-imidazo[4,5-c]pyridin-2(3H)-ylidene)benzamide To an ice-bath cooled solution of cis-4-(5-amino-2-(2-methoxyethoxy)pyridin-4-ylamino)-N-isopropylcyclohexanecarboxamide (156 mg, 0.445 mmol) in THF (0.8 mL) was added 4-fluorobenzoyl isothiocyanate (161 mg, 0.890 mmol) as a solution in THF (2 mL). The mixture was stirred 15 minutes, and then stirred another 30 minutes at RT. DIPEA (0.194 mL, 1.113 mmol) and EDC (213 mg, 1.113 mmol) were added, and the mixture was heated to 60° C. for 1 hour. The mixture was evaporated, and the residue was dissolved with 5% IPA/EtOAc (5 mL), washed with 1:1 aqueous $NH_4Cl$ (sat)/water, [1 mL total volume (×2)], brine, and the organic layer was dried over $Na_2SO_4$ and filtered. The mixture was purified via flash chromatography using a linear gradient of 0% to 5% of 1% $NH_4OH$ in MeOH in DCM. The title compound was collected as a white solid (110 mg, 50% yield). M/Z calc'd for $C_{26}H_{32}FN_5O_4$: 497.56. found 498 [M+H].

Example 160

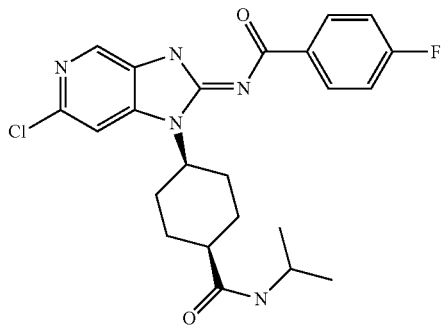 [SMILES: CC(C)NC(=O)[C@H]1CC[C@@H](n2/c(=N/C(=O)c3ccc(F)cc3)[nH]c3cnc(Cl)cc32)CC1]

(E)-N-(6-Chloro-1-(cis-4-(isopropylcarbamoyl)cyclohexyl)-1H-imidazo[4,5-c]pyridin-2(3H)-ylidene)-4-fluorobenzamide Step A: cis-4-(5-Amino-2-chloropyridin-4-ylamino)-N-isopropylcyclohexanecarboxamide To a solution of cis-4-(2-chloro-5-nitropyridin-4-ylamino)-N-isopropylcyclohexanecarboxamide (400 mg, 1.174 mmol) in MeOH (2.3 mL) was added $SnCl_2$ (890 mg, 4.69 mmol), and the mixture was stirred at reflux for 2 hours. The mixture was evaporated and partitioned between 10% IPA/DCM and saturated $NaHCO_3$. The solids were removed by filtration through Celite® brand filter aid, and the organic layer was washed with water, saturated $NaHCO_3$, dried over $Na_2SO_4$ and filtered. The mixture was purified via flash chromatography using a linear gradient of 0% to 10% of 1% $NH_4OH$ in MeOH in DCM. The title compound was collected as a white solid (160 mg, 44% yield).

Step B: (E)-N-(6-Chloro-1-(cis-4-(isopropylcarbamoyl)cyclohexyl)-1H-imidazo[4,5-c]pyridin-2(3H)-ylidene)-4-fluorobenzamide The title compound was prepared from cis-4-(5-amino-2-chloropyridin-4-ylamino)-N-isopropylcyclohexanecarboxamide using a procedure analogous to that used in the preparation of cis-methyl 4-((E)-2-(benzoylimino)-2,3-dihydro-1H-imidazo[4,5-c]pyridin-1-yl)cyclohexanecarboxylate. Isolated as an off-white solid (34 mg, 15% yield). M/Z calc'd for $C_{23}H_{25}ClFN_5O_2$: 457.93. found 458 [M+H].

Example 161

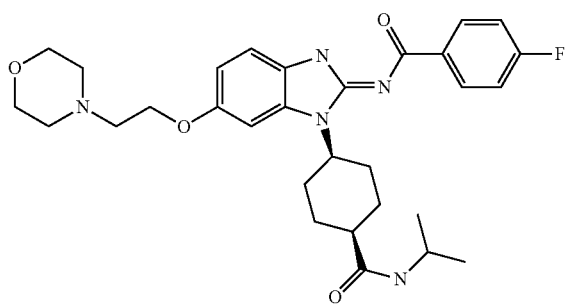 [SMILES: CC(C)NC(=O)[C@H]1CC[C@@H](n2/c(=N/C(=O)c3ccc(F)cc3)[nH]c3ccc(OCCN4CCOCC4)cc32)CC1]

(E)-4-Fluoro-N-(1-(cis-4-(isopropylcarbamoyl)cyclohexyl)-6-(2-morpholinoethoxy)-1H-benzo[d]imidazol-2(3H)-ylidene)benzamide Step A:
4-(2-(3-Fluoro-4-nitrophenoxy)ethyl)morpholine The title compound was prepared with 4-(2-chloroethyl)morpholine hydrochloride using a procedure analogous to that used for 1-(2-(3-fluoro-4-nitrophenoxy)ethyl)piperidine (4.37 g, 79% yield).

Step B: cis-N-Isopropyl-4-(5-(2-morpholinoethoxy)-2-nitrophenylamino)cyclohexanecarboxamide.

The title compound was prepared from 4-(2-(3-fluoro-4-nitrophenoxy)ethyl)morpholine using a procedure analogous to that used to prepare cis-N-isopropyl-4-(2-nitro-5-(2-(piperidin-1-yl)ethoxy)phenylamino)cyclohexanecarboxamide (425 mg, 98% yield).

Step C: (E)-4-Fluoro-N-(1-(cis-4-(isopropylcarbamoyl)cyclohexyl)-6-(2-morpholinoethoxy)-1H-benzo[d]imidazol-2(3H)-ylidene)benzamide.

To a solution of cis-N-isopropyl-4-(5-(2-morpholinoethoxy)-2-nitrophenylamino)-cyclohexanecarboxamide (425 mg, 0.978 mmol) in AcOH (1.0 mL) was added iron (273 mg, 4.89 mmol), and the mixture was heated to 100° C. for 40 minutes. The mixture was diluted with MeOH and filtered through a pad of Celite® brand filter aid and evaporated. The residue was dissolved in THF (5 mL) and zinc (512 mg, 7.82 mmol) and AcOH (0.560 mμL, 9.78 mmol) were added. The mixture was stirred at RT for 1 hour and was filtered through a pad of Celite® brand filter aid upon complete conversion. The mixture was purified via flash chromatography using a linear gradient of 0% to 10% of 1% NH$_4$OH in MeOH in DCM. The desired compound cis-4-(2-amino-5-(2-morpholinoethoxy)phenylamino)-N-isopropylcyclohexanecarboxamide was obtained as a red film.

The title compound was prepared from cis-4-(2-amino-5-(2-morpholinoethoxy)phenylamino)-N-isopropylcyclohexanecarboxamide using a procedure analogous to that used for (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. Isolated as an off-white solid (19 mg, 35% yield). M/Z calc'd for C$_{30}$H$_{38}$FN$_5$O$_4$: 551.65. found 552 [M+H].

Example 162

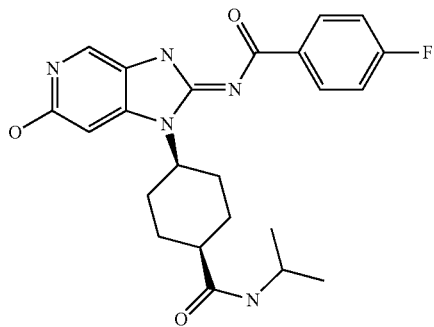 [SMILES: CC(C)NC(=O)[C@H]1CC[C@@H](n2/c(=N/C(=O)c3ccc(F)cc3)[nH]c3cnc(O)cc32)CC1]

(E)-4-Fluoro-N-(6-hydroxy-1-(cis-4-(isopropylcarbamoyl)cyclohexyl)-1H-imidazo[4,5-c]pyridin-2(3H)-ylidene)benzamide To a RT suspension of (E)-4-fluoro-N-(1-(cis-4-(isopropylcarbamoyl)cyclohexyl)-6-methoxy-1H-imidazo[4,5-c]pyridin-2(3H)-ylidene)benzamide (30 mg, 0.066 mmol) and sodium iodide (69.4 mg, 0.463 mmol) in ACN (0.6 mL) was added TMS-Cl (0.059 mL, 0.463 mmol) and water (10 μL), and the mixture was heated at 60° C. After 2 hours and 4 hours, additional TMS-Cl portions (0.059 mL, 0.463 mmol) were added, and the mixture was stirred at 60° C. for a total reaction time of 20 hours. The material was purified by reverse-phase preparative HPLC using 0.1% TFA in ACN/H$_2$O, gradient 10% to 90% over 15 minutes. The combined fractions were freebased with saturated aqueous NaHCO$_3$ and extracted with 10% IPA/DCM, dried over Na$_2$SO$_4$, filtered and evaporated. The title compound was obtained as a white solid (8 mg, 21% yield). $^1$H NMR (400 MHz, DMSO-d$_6$) δ ppm 1.08 (d, J=8 Hz, 6H) 1.50-1.60 (m, 2H) 1.62-1.82 (m, 2H) 2.05-2.08 (m, 2H) 2.49-2.51 (m, 1H) 2.55-2.74 (m, 2H) 3.97-4.02 (m, 1H) 4.60-4.70 (m, 1H) 6.38 (s, 1H) 7.20-7.30 (m, 2H) 7.48-7.52 (m, 1H) 7.64 (d, J=7.63 Hz, 1H) 8.29 (dd, J=8.22, 5.97 Hz, 2H) 11.10 (br. s., 1H) 12.26 (br. s., 1H). M/Z calc'd for C$_{23}$H$_{26}$FN$_5$O$_3$: 439.48. found 440 [M+H].

Example 163

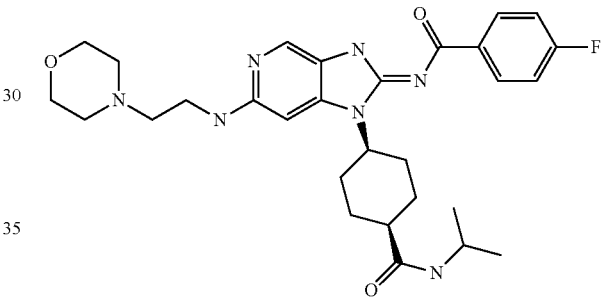

(E)-4-Fluoro-N-(1-(cis-4-(isopropylcarbamoyl)cyclohexyl)-6-(2-morpholinoethylamino)-1H-imidazo[4,5-c]pyridin-2(3H)-ylidene)benzamide A glass microwave reaction vessel was charged with cis-4-(2-chloro-5-nitropyridin-4-ylamino)-N-isopropylcyclohexanecarboxamide (200 mg, 0.587 mmol) and 2-morpholinoethanamine (0.092 mL, 0.704 mmol) in 2-propanol. A drop of HCl (2N in ether) was added, and the reaction mixture was stirred and irradiated in a microwave at 175° C. for 2 hours. Additional 2-morpholinoethanamine (0.030 mL, 0.24 mmol) was added, and the mixture was heated an additional 20 minutes. The mixture was evaporated and the residue diluted with 10% IPA/DCM, washed with water, brine, and the organic layer dried over Na$_2$SO$_4$. The mixture was purified via flash chromatography using a linear gradient of 0% to 10% of 1% NH$_4$OH in MeOH in DCM. Intermediate cis-N-isopropyl-4-(2-(2-morpholinoethylamino)-5-nitropyridin-4-ylamino)cyclohexanecarboxamide was isolated as a yellow film (128 mg).

Diamine cis-4-(5-amino-2-(2-morpholinoethylamino)pyridin-4-ylamino)-N-isopropylcyclohexanecarboxamide was prepared from cis-N-isopropyl-4-(2-(2-morpholinoethylamino)-5-nitropyridin-4-ylamino)cyclohexanecarboxamide using a procedure analogous to that used in the preparation of cis-4-(5-amino-2-chloropyridin-4-ylamino)-N-isopropylcyclohexanecarboxamide (73 mg).

The title compound was prepared from cis-4-(5-amino-2-(2-morpholinoethylamino)pyridin-4-ylamino)-N-isopropylcyclohexanecarboxamide using a procedure analogous to that used to prepare (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. Isolated as an off-white solid (23 mg, 23% yield). M/Z calc'd for $C_{29}H_{38}FN_7O_3$: 551.66. found 552 [M+H].

Example 164

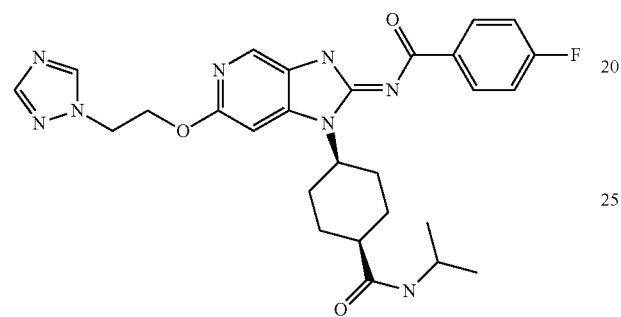

(E)-N-(6-(2-(1H-1,2,4-Triazol-1-yl)ethoxy)-1-(cis-4-(isopropylcarbamoyl)cyclohexyl)-1H-imidazo[4,5-c]pyridin-2(3H)-ylidene)-4-fluorobenzamide Intermediate cis-4-(2-(2-(1H-1,2,4-triazol-1-yl)ethoxy)-5-nitropyridin-4-ylamino)-N-isopropylcyclohexanecarboxamide was prepared in 2 steps from 2-(1H-1,2,4-triazol-1-yl)ethanol using a procedure analogous to that used to prepare cis-N-isopropyl-4-(2-(2-methoxyethoxy)-5-nitropyridin-4-ylamino)cyclohexanecarboxamide (104 mg).

Diamine cis-4-(2-(2-(1H-1,2,4-triazol-1-yl)ethoxy)-5-aminopyridin-4-ylamino)-N-isopropylcyclohexanecarboxamide was prepared from cis-4-(2-(2-(1H-1,2,4-triazol-1-yl)ethoxy)-5-nitropyridin-4-ylamino)-N-isopropylcyclohexanecarboxamide using a procedure analogous to that used for cis-4-(5-amino-2-chloropyridin-4-ylamino)-N-isopropylcyclohexanecarboxamide (104 mg).

The title compound was prepared from cis-4-(2-(2-(1H-1,2,4-triazol-1-yl)ethoxy)-5-aminopyridin-4-ylamino)-N-isopropylcyclohexanecarboxamide using a procedure analogous to that used to prepare (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. Isolated as an off-white solid (62 mg, 43% yield, last step). $^1$H NMR (400 MHz, DMSO-$d_6$) δ ppm 1.08 (d, J=6.55 Hz, 6H) 1.57-1.62 (m, 2H) 1.69-1.73 (m, 2H) 2.02-2.16 (m, 2H) 2.50-2.51 (m, 1H) 2.57-2.79 (m, 2H) 3.92-4.02 (m, 1H) 4.60-4.65 (m, 4H) 4.70-4.80 (m, 1H) 6.99 (s, 1H) 7.25 (dd, J=8.85, 8.85 Hz, 2H) 7.65 (d, J=7.82 Hz, 1H) 7.98 (s, 1H) 8.22 (s, 1H) 8.28-8.36 (m, 2H) 8.53 (s, 1H) 12.70 (s, 1H). M/Z calc'd for $C_{27}H_{31}FN_8O_3$: 534.59. found 535 [M+H].

Example 165

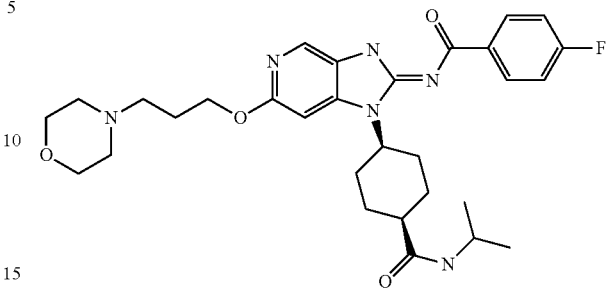

(E)-4-Fluoro-N-(1-(cis-4-(isopropylcarbamoyl)cyclohexyl)-6-(3-morpholinopropoxy)-1H-imidazo[4,5-c]pyridin-2(3H)-ylidene)benzamide Intermediate cis-N-isopropyl-4-(2-(3-morpholinopropoxy)-5-nitropyridin-4-ylamino)cyclohexanecarboxamide was prepared with 3-morpholinopropan-1-ol using a 2 step procedure analogous to that used to prepare cis-N-isopropyl-4-(2-(2-methoxyethoxy)-5-nitropyridin-4-ylamino)cyclohexanecarboxamide (200 mg).

Diamine cis-4-(5-amino-2-(3-morpholinopropoxy)pyridin-4-ylamino)-N-isopropylcyclohexanecarboxamide was prepared from cis-N-isopropyl-4-(2-(3-morpholinopropoxy)-5-nitropyridin-4-ylamino)cyclohexanecarboxamide using a procedure analogous to that used for cis-4-(5-amino-2-chloropyridin-4-ylamino)-N-isopropylcyclohexanecarboxamide (130 mg).

The title compound was prepared from cis-4-(5-amino-2-(3-morpholinopropoxy)pyridin-4-ylamino)-N-isopropylcyclohexanecarboxamide using a procedure analogous to that used to prepare (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide with 1.3 equivalents of 4-fluorobenzoyl isothiocyanate. Isolated as an off-white solid (98 mg, 104% yield). M/Z calc'd for $C_{30}H_{39}FN_6O_4$: 566.67. found 567 [M+H].

Example 166

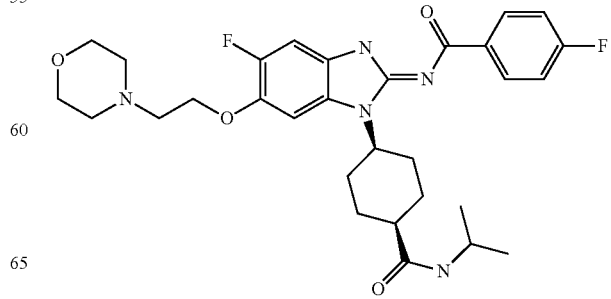

(E)-4-Fluoro-N-(5-fluoro-1-(cis-4-(isopropylcarbamoyl)cyclohexyl)-6-(2-morpholinoethoxy)-1H-benzo[d]imidazol-2(3H)-ylidene)benzamide Intermediate 4-(2-(2,5-difluoro-4-nitrophenoxy)ethyl)morpholine was prepared from 4-(2-chloroethyl)morpholine hydrochloride using a procedure analogous to that used to prepare 1-(2-(3-fluoro-4-nitrophenoxy)ethyl)piperidine (900 mg).

Intermediate cis-4-(4-Fluoro-5-(2-morpholinoethoxy)-2-nitrophenylamino)-N-isopropylcyclohexanecarboxamide was prepared from 4-(2-(2,5-difluoro-4-nitrophenoxy)ethyl)morpholine using a procedure analogous to that used to prepare cis-N-isopropyl-4-(5-(4-methoxybenzyloxy)-2-nitrophenylamino)cyclohexanecarboxamide (272 mg).

Diamine cis-4-(2-amino-4-fluoro-5-(2-morpholinoethoxy)phenylamino)-N-isopropylcyclohexanecarboxamide was prepared from cis-4-(4-fluoro-5-(2-morpholinoethoxy)-2-nitrophenylamino)-N-isopropylcyclohexanecarboxamide using a procedure analogous to that used to prepare 4-(3-aminopyridin-4-ylamino)-N-isopropylcyclohexanecarboxamide (161 mg, 81% yield).

The title compound was prepared from cis-4-(2-amino-4-fluoro-5-(2-morpholinoethoxy)phenylamino)-N-isopropylcyclohexanecarboxamide using a procedure analogous to that used to prepare (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. The product was isolated as an off-white solid (161 mg, 81% yield). $^1$H NMR (400 MHz, DMSO-$d_6$) δ ppm 1.08 (d, J=8 Hz, 6H) 1.53-1.66 (m, 2H) 1.70-1.80 (m, 2H) 2.00-2.08 (m, 2H) 2.52-2.60 (m, 1H) 2.70-2.91 (m, 8H) 3.49-3.70 (m, 4H) 3.89-4.08 (m, 1H) 4.27 (t, J=6.06 Hz, 2H) 4.93 (br. s., 1H) 7.24 (dd, J=8.85, 8.85 Hz, 2H) 7.38 (d, J=10.76 Hz, 1H) 7.77 (d, J=7.73 Hz, 2H) 8.29 (dd, J=8.61, 5.97 Hz, 2H) 12.73 (s, 1H). M/Z calc'd for $C_{30}H_{37}F_2N_5O_4$: 569.64. found 570 [M+H].

Example 167

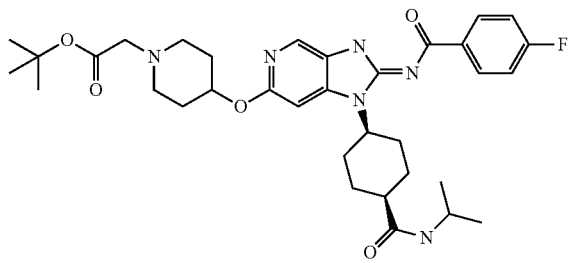 [SMILES: CC(C)NC(=O)[C@H]1CC[C@@H](n2/c(=N/C(=O)c3ccc(F)cc3)[nH]c3cnc(OC4CCN(CC(=O)OC(C)(C)C)CC4)cc32)CC1]

tert-Butyl 2-(4-((E)-2-(4-fluorobenzoylimino)-1-(cis-4-(isopropylcarbamoyl)cyclohexyl)-2,3-dihydro-1H-imidazo[4,5-c]pyridin-6-yloxy)piperidin-1-yl)acetate Step A: tert-Butyl 2-(4-hydroxypiperidin-1-yl)acetate To a heated (40° C.) solution of tert-butyl 2-bromoacetate (7.38 mL, 49.9 mmol) in THF (10 mL) was added dropwise a solution of piperidin-4-ol (5.050 g, 49.9 mmol) and TEA (6.96 mL, 49.9 mmol) in THF (50 mL). The mixture was refluxed for 2 hours and then cooled to RT and filtered through a pad of Celite® brand filter aid. The filtrate was evaporated and the residue diluted with EtOAc (50 mL), washed with water (50 mL), brine (10 mL), and the organic layer dried over $Na_2SO_4$, filtered and evaporated. The material was purified via flash chromatography using a linear gradient of 0% to 10% of 1% $NH_4OH$ in MeOH in DCM. The title compound was isolated as an off-white solid (4.865 g, 45% yield).

Step B: tert-Butyl 2-(4-((E)-2-(4-fluorobenzoylimino)-1-(cis-4-(isopropylcarbamoyl)cyclohexyl)-2,3-dihydro-1H-imidazo[4,5-c]pyridin-6-yloxy)piperidin-1-yl)acetate To a sealable tube charged with tert-butyl 2-(4-hydroxypiperidin-1-yl)acetate (379 mg, 1.761 mmol), 18-crown-6 (233 mg, 0.880 mmol), and cesium carbonate (574 mg, 1.761 mmol) in toluene (1.2 mL), was added cis-4-(2-chloro-5-nitropyridin-4-ylamino)-N-isopropylcyclohexanecarboxamide (200 mg, 0.587 mmol). The mixture was blanketed with nitrogen and sealed, and the reaction mixture was heated at 80° C. for 24 hours. The mixture was diluted with 1:2 toluene/EtOAc (6 mL), washed with brine (5 mL, 2 mL), and dried over $Na_2SO_4$. The mixture was purified via flash chromatography using a linear gradient of 0% to 10% of 1% $NH_4OH$ in MeOH in DCM. Intermediate cis-4-(2-chloro-5-nitropyridin-4-ylamino)-N-isopropylcyclohexanecarboxamide was collected as a tan film (172 mg).

Diamine tert-butyl 2-(4-(5-amino-4-(cis-4-(isopropylcarbamoyl)cyclohexylamino)pyridin-2-yloxy)piperidin-1-yl)acetate was prepared from tert-butyl 2-(4-(4-(cis-4-(isopropylcarbamoyl)cyclohexylamino)-5-nitropyridin-2-yloxy)piperidin-1-yl)acetate using a procedure analogous to that used to prepare cis-4-(5-amino-2-chloropyridin-4-ylamino)-N-isopropylcyclohexanecarboxamide (100 mg).

The title compound was prepared from tert-butyl 2-(4-(5-amino-4-(cis-4-(isopropylcarbamoyl)cyclohexylamino)pyridin-2-yloxy)piperidin-1-yl)acetate using a procedure analogous to that used for (E)-4-fluoro-N-(1-(cis-4-(isopropylcarbamoyl)cyclohexyl)-6-(2-methoxyethoxy)-1H-imidazo[4,5-c]pyridin-2(3H)-ylidene)benzamide. Isolated as an off-white solid (124 mg, 79% yield, last step). M/Z calc'd for $C_{34}H_{45}FN_6O_5$: 636.76. found 637 [M+H].

Example 168

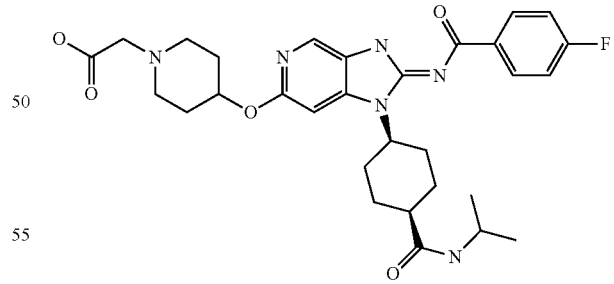

2-(4-((E)-2-(4-Fluorobenzoylimino)-1-(cis-4-(isopropylcarbamoyl)cyclohexyl)-2,3-dihydro-1H-imidazo[4,5-c]pyridin-6-yloxy)piperidin-1-yl)acetic acid hydrochloride To a solution of tert-butyl 2-(4-((E)-2-(4-fluorobenzoylimino)-1-(cis-4-(isopropylcarbamoyl)cyclohexyl)-2,3-dihydro-1H-imidazo[4,5-c]pyridin-6-yloxy)piperidin-1-yl)

acetate (81 mg, 0.127 mmol) in dioxane (1.2 mL) was added HCl (4N dioxane) (0.127 mL, 0.509 mmol) and 2 drops of concentrated HCl (0.010 mL, 0.127 mmol). The resulting mixture was stirred at RT for 4 hours. The reaction mixture was concentrated and triturated with about 2 mL of dioxane to produce a precipitate. The off-white solid was collected to afford the title compound (70 mg, 89% yield). M/Z calc'd for $C_{30}H_{37}FN_6O_5$: 580.28. found 581 [M+H].

Example 169

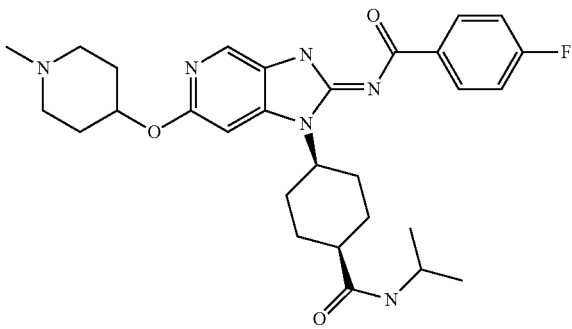 [SMILES: CC(C)NC(=O)[C@H]1CC[C@@H](n2/c(=N/C(=O)c3ccc(F)cc3)[nH]c3cnc(OC4CCN(C)CC4)cc32)CC1]

(E)-4-Fluoro-N-(1-(cis-4-(isopropylcarbamoyl)cyclohexyl)-6-(1-methylpiperidin-4-yloxy)-1H-imidazo[4,5-c]pyridin-2(3H)-ylidene)benzamide Intermediate cis-N-isopropyl-4-(2-(1-methylpiperidin-4-yloxy)-5-nitropyridin-4-ylamino)cyclohexanecarboxamide was prepared from 1-methylpiperidin-4-ol using a procedure analogous to that used for cis-4-(2-chloro-5-nitropyridin-4-ylamino)-N-isopropylcyclohexanecarboxamide (95 mg).

Diamine cis-4-(5-amino-2-(1-methylpiperidin-4-yloxy)pyridin-4-ylamino)-N-isopropylcyclohexanecarboxamide was prepared from cis-N-isopropyl-4-(2-(1-methylpiperidin-4-yloxy)-5-nitropyridin-4-ylamino)cyclohexanecarboxamide using a procedure analogous to that used to prepare cis-4-(5-amino-2-chloropyridin-4-ylamino)-N-isopropylcyclohexanecarboxamide (95 mg).

The title compound was prepared from cis-4-(5-amino-2-(1-methylpiperidin-4-yloxy)pyridin-4-ylamino)-N-isopropylcyclohexanecarboxamide using a procedure analogous to that used for (E)-4-fluoro-N-(1-(cis-4-(isopropylcarbamoyl)cyclohexyl)-6-(2-methoxyethoxy)-1H-imidazo[4,5-c]pyridin-2 (3H)-ylidene)benzamide. The product was isolated as an off-white solid (94 mg, 72% yield). $^1$H NMR (400 MHz, DMSO-d$_6$) δ ppm 1.10 (d, J=8H, 6H) 1.48-1.78 (m, 7H) 1.84-2.03 (m, 2H) 2.04-2.10 (m, 2H) 2.13-2.34 (m, 5H) 2.65 (m, 4H) 3.95-4.05 (m, 1H) 4.65-4.80 (m, 1H) 4.89-5.03 (m, 1H) 6.96 (s, 1H) 7.26 (dd, J=8.75 Hz, 2H) 7.68 (d, J=7.63 Hz, 1H) 8.23 (s, 1H) 8.31 (dd, J=8.56, 5.82 Hz, 2H) 12.60 (br. s., 1H). M/Z calc'd for $C_{29}H_{37}FN_6O_3$: 536.64. found 537 [M+H].

Example 170

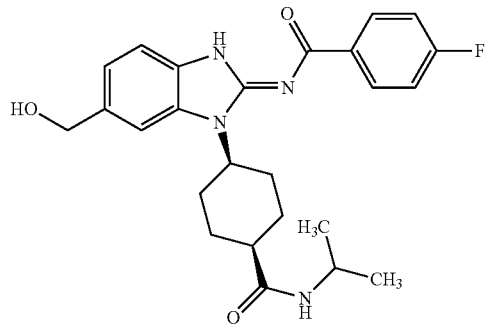 [SMILES: CC(C)NC(=O)[C@H]1CC[C@@H](n2/c(=N/C(=O)c3ccc(F)cc3)[nH]c3ccc(CO)cc32)CC1]

(E)-4-Fluoro-N-(6-(hydroxymethyl)-1-(cis-4-(isopropylcarbamoyl)cyclohexyl)-1H-benzo[d]imidazol-2(3H)-ylidene)benzamide Step A: cis-4-(tert-Butoxycarbonylamino)cyclohexanecarboxylic acid To a solution of cis-4-amino-1-cyclohexanecarboxylic acid (41.54 g, 290 mmol) in 1 N aqueous NaOH (300 mL) was added a solution of di-tert-butyl dicarbonate (76 g, 348 mmol) in dioxane (160 mL) with stirring. The reaction was stirred at RT for 24 hours. Hexanes (400 mL) was added, and the reaction was stirred for a further 10 minutes. After the layers were separated, the aqueous layer was chilled in an ice-water bath and carefully acidified to a pH of approximately 5 with stirring by addition of 6 N aqueous HCl (50 mL). The resulting white solid was removed by filtration, and the filtrate was extracted with EtOAc. The combined organic layers were washed with brine, and concentrated. The residue was dissolved in a minimum of hot EtOAc, diluted with an equal volume of hexanes, and allowed to stand at RT. The white precipitate was collected by filtration, combined with the first crop of precipitate, and dried in vacuo to generate cis-4-(tert-butoxycarbonylamino)cyclohexanecarboxylic acid (87.0 g, quantitative yield).

Step B: tert-Butyl cis-4-(isopropylcarbamoyl)cyclohexylcarbamate

To a solution of cis-4-(tert-butoxycarbonylamino)cyclohexanecarboxylic acid (54.58 g, 224 mmol) in dry DMF (200 mL) was added 1,1'-carbonyldiimidazole reagent grade (70 g, 432 mmol) portionwise with stirring. After the evolution of $CO_2$ had ceased, the resulting solution was stirred at RT for 10 minutes. The solution was cooled to 0° C., and isopropylamine (38.5 mL, 449 mmol) was added with stirring. The reaction was stirred at 0° C. for 10 minutes and at RT for 24 hours. The reaction was diluted slowly with water (1 L) with stirring in an ice-water bath and then allowed to age for 1 hour. The precipitate was collected by filtration, washed with water, and dried in vacuo to generate tert-butyl cis-4-(isopropylcarbamoyl)cyclohexyl-carbamate as a white solid (39.11 g, 61% yield).

Step C: cis-4-Amino-N-isopropylcyclohexanecarboxamide hydrochloride

To a solution of tert-butyl cis-4-(isopropylcarbamoyl)cyclohexylcarbamate (39.11 g, 138 mmol) in DCM (400 mL) was added 4 M HCl in dioxane (138 mL, 550 mmol), and 0.5 mL concentrated HCl. The reaction was stirred vigorously overnight at RT. A large amount of white precipitate had formed in the flask and it was collected by vacuum filtration, washed with DCM, and dried in vacuo, to generate cis-4-amino-N-isopropylcyclohexanecarboxamide hydrochloride as a white powder (31.08 g, 102% yield).

Step D: cis-4-(5-(Hydroxymethyl)-2-nitrophenylamino)-N-isopropylcyclohexanecarboxamide To a suspension of cis-4-amino-N-isopropylcyclohexanecarboxamide hydrochloride (7.09 g, 32.1 mmol) and DIPEA (15 mL, 88 mmol) in ACN (50 mL) was added (3-fluoro-4-nitrophenyl)methanol (5 g, 29.2 mmol). The reaction was stirred overnight at 80° C. The reaction mixture was concentrated, loaded onto a silica-gel pre column, and purified by column chromatography, eluting with 0-100% EtOAc in DCM, to provide cis-4-(5-(hydroxymethyl)-2-nitrophenylamino)-N-isopropylcyclohexanecarboxamide as an orange foam (7.0 g, 71.4% yield). MS, m/z ($C_{17}H_{25}N_3O_4$): calcd, 335.2. found, 336.0 [M+H].

Step E: (E)-4-Fluoro-N-(6-(hydroxymethyl)-1-(cis-4-(isopropylcarbamoyl)cyclohexyl)-1H-benzo[d]imidazol-2(3H)-ylidene)benzamide To a solution of cis-4-(5-(hydroxymethyl)-2-nitrophenylamino)-N-isopropylcyclohexane-carboxamide (2.0 g, 5.96 mmol) in EtOH (25 mL) was added 10% palladium on carbon (0.635 g, 0.596 mmol). The reaction was stirred under a hydrogen atmosphere (1 atm) at RT. After 3 hours, the reaction mixture was filtered through Celite® brand filter aid and concentrated to afford cis-4-(2-amino-5-(hydroxymethyl) phenylamino)-N-isopropylcyclohexanecarboxamide as a brown oil.

The diamine was dissolved in THF (30 mL), cooled to 0° C., and 4-fluorobenzoyl isothiocyanate (1.296 g, 7.15 mmol) was added. The reaction mixture was stirred at 0° C. for 15 minutes, and then EDC (1.714 g, 8.94 mmol) and DIPEA (1.561 mL, 8.94 mmol) were added. The reaction was stirred at 60° C. for 2 hours and for 16 hours at RT. The reaction mixture was concentrated and partitioned between DCM and water. The organic layer was dried over anhydrous magnesium sulfate, filtered, concentrated, and adsorbed onto a plug of silica gel. The residual product was purified by column chromatography, eluting with 0-100% EtOAc in DCM, to provide (E)-4-fluoro-N-(6-(hydroxymethyl)-1-(cis-4-(isopropylcarbamoyl)cyclohexyl)-1H-benzo[d]imidazol-2(3H)-ylidene)benzamide as a tan powder (2.14 g, 79% yield). $^1$H NMR (400 MHz, DMSO-$d_6$) δ ppm 12.76 (s, 1H), 8.33 (dd, J=5.9, 8.7 Hz, 2H), 7.62 (d, J=7.7 Hz, 1H), 7.59 (s, 1H), 7.49 (d, J=7.8 Hz, 1H), 7.24 (dd, J=8.9 Hz, 8.9 Hz, 2H), 7.18, (d, J=8.1 Hz, 1H), 5.20 (t, J=5.6 Hz, 1H), 4.80 (brs, 1H), 4.55 (s, 2H), 4.00-4.08 (m, 1H), 2.72-2.82 (m, 2H), 2.52 (brs, 1H), 2.11-2.19 (m, 2H), 1.68-1.78 (m, 2H), 1.61-1.63 (m, 2H), 1.10 (d, J=6.6 Hz, 6H). MS, m/z ($C_{25}H_{29}FN_4O_3$): calcd, 452.2. found, 452.7 [M+H].

Example 171

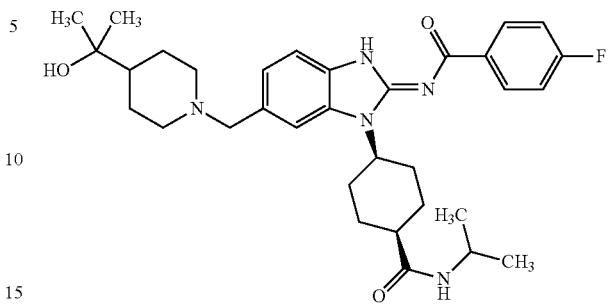

(E)-4-Fluoro-N-(6-((4-(2-hydroxypropan-2-yl)piperidin-1-yl)methyl)-1-(cis-4-(isopropylcarbamoyl) cyclohexyl)-1H-benzo[d]imidazol-2(3H)-ylidene) benzamide To a 0° C. (ice bath) cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was concentrated in vacuo and the residue was suspended in ACN (2 mL) and re-concentrated to remove residual thionyl chloride The residue was resuspended in ACN (2 mL), cooled to 0° C., and 2-(piperidin-4-yl)propan-2-ol (200 mg, 1.396 mmol) was added. The reaction was stirred overnight at RT. After 16 hours, the reaction was concentrated, and the residue was purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(6-((4-(2-hydroxypropan-2-yl)piperidin-1-yl) methyl)-1-(cis-4-(isopropylcarbamoyl)cyclohexyl)-1H-benzo[d]imidazol-2(3H)-ylidene)benzamide as a white powder (77 mg, 60.3% yield). $^1$H NMR (400 MHz, DMSO-$d_6$) δ ppm 12.75 (brs, 1H), 8.32 (dd, J=6.0, 8.6 Hz, 2H), 7.63 (d, J=7.7 Hz, 1H), 7.57 (s, 1H), 7.48 (d, J=7.9 Hz, 1H), 7.24 (dd, J=8.8 Hz, 8.8 Hz, 2H), 7.16, (d, J=7.8 Hz, 1H), 4.84 (brs, 1H), 4.00-4.08 (m, 2H), 3.51 (brs, 2H), 2.90 (brs, 2H), 2.65-2.80 (m, 2H), 2.53 (s, 1H), 2.11-2.20 (m, 2H), 1.78-1.90 (m, 2H), 1.59-1.78 (m, 7H), 1.18-1.33 (m, 3H), 1.11 (d, J=6.6 Hz, 6H), 1.02 (s, 6H). MS, m/z ($C_{33}H_{44}FN_5O_3$): calcd, 577.3. found, 578.1 [M+H].

Example 172

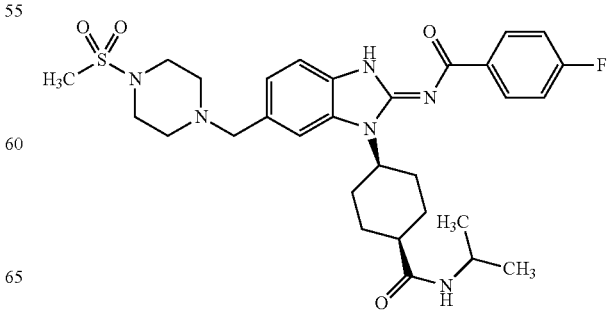

(E)-4-Fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed at reduced pressure, and the residue was suspended in ACN (2 mL) and re-concentrated to remove residual thionyl chloride.

The residue was resuspended in ACN (2 mL), cooled to 0° C., and 1-(methylsulfonyl)piperazine (AstaTech, Inc., Bristol, Pa.; 363 mg, 2.21 mmol) was added. The reaction was stirred overnight at RT. The reaction was concentrated, and the residue was purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide as a white powder (74 mg, 55.9% yield). MS, m/z (C$_{30}$H$_{39}$FN$_6$O$_4$S): calcd, 598.3. found, 598.8 [M+H].

Example 173

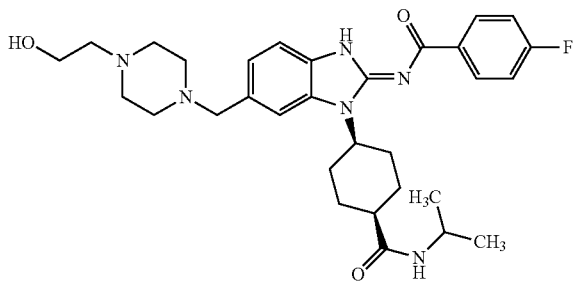 [SMILES: CC(C)NC(=O)[C@H]1CC[C@@H](n2/c(=N/C(=O)c3ccc(F)cc3)[nH]c3ccc(CN4CCN(CCO)CC4)cc32)CC1]

(E)-4-Fluoro-N-(6-((4-(2-hydroxyethyl)piperazin-1-yl)methyl)-1-(cis-4-(isopropylcarbamoyl)cyclohexyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and 2-(piperazin-1-yl)ethanol, using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (30 mg, 24% yield). $^1$H NMR (400 MHz, DMSO-d$_6$) δ ppm 1.11 (d, J=6.5 Hz, 6H), 1.20-1.32 (m, 1H), 1.55-1.83 (m, 5H), 2.09-2.21 (m, 2H), 2.28-2.45 (m, 6H), 2.54 (br. s, 1H), 2.64-2.82 (m, 2H), 3.44-3.66 (m, 5H), 3.96-4.12 (m, 1H), 4.38 (br. s., 1H), 4.86 (br. s., 1H), 7.14 (d, J=8.3 Hz, 1H), 7.24 (dd, J=8.4 Hz, 8.4 Hz, 2H), 7.48 (d, J=8.2 Hz, 1H), 7.59 (br. s., 1H), 7.64 (d, J=7.2 Hz, 1H), 8.32 (m, J=6.5 Hz, 2H), 12.74 (br. s., 1H). MS, m/z (C$_{31}$H$_{41}$FN$_6$O$_3$): calcd, 564.3. found, 564.9 [M+H].

Example 174

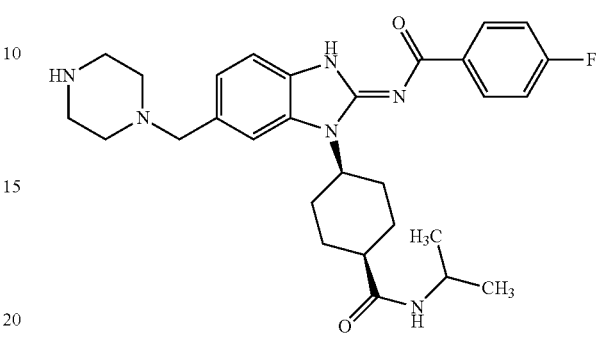

(E)-4-Fluoro-N-(1-(cis-4-(isopropylcarbamoyl)cyclohexyl)-6-(piperazin-1-ylmethyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and piperazine using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (58 mg, 50% yield). MS, m/z (C$_{29}$H$_{37}$FN$_6$O$_2$): calcd, 520.3. found, 521.1 [M+H].

Example 175

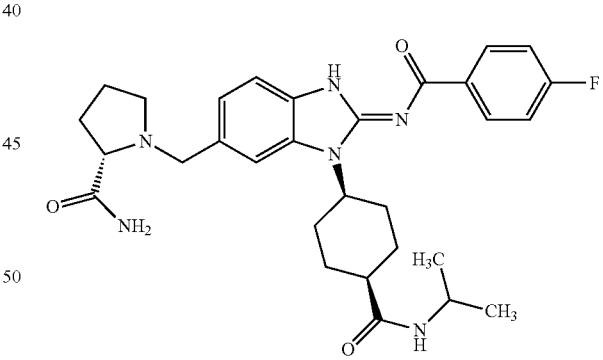

(S)-1-((E)-2-(4-Fluorobenzoylimino)-3-(cis-4-(isopropylcarbamoyl)-cyclohexyl)-2,3-dihydro-1H-benzo[d]imidazol-5-yl)methyl)pyrrolidine-2-carboxamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and (S)-pyrrolidine-2-carboxamide using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)

Example 176

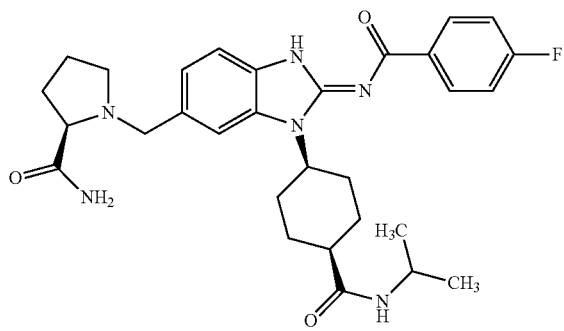 [SMILES: CC(C)NC(=O)[C@H]1CC[C@@H](n2/c(=N/C(=O)c3ccc(F)cc3)[nH]c3ccc(CN4CCC[C@@H]4C(N)=O)cc32)CC1]

(R)-1-(((E)-2-(4-Fluorobenzoylimino)-3-(cis-4-(isopropylcarbamoyl)-cyclohexyl)-2,3-dihydro-1H-benzo[d]imidazol-5-yl)methyl)pyrrolidine-2-carboxamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and (R)-pyrrolidine-2-carboxamide using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (47 mg, 39% yield). $^1$H NMR (400 MHz, DMSO-$d_6$) δ ppm 1.11 (d, J=6.6 Hz, 6H), 1.51-1.79 (m, 5H), 2.07-2.19 (m, 2H), 2.40 (br. s., 4H), 2.53 (br. s., 1H), 2.60-2.79 (m, 2H), 2.85 (br. s., 4H), 3.54 (s, 2H), 3.96-4.10 (m, 1H), 4.80-4.92 (m, 1H), 7.14 (d, J=8.1 Hz, 1H), 7.25 (dd, J=8.8 Hz, 8.8 Hz, 2H), 7.49 (d, J=8.0 Hz, 1H), 7.56-7.74 (m, 2H), 8.31 (dd, J=8.1, 6.1 Hz, 2H). MS, m/z ($C_{30}H_{37}FN_6O_3$): calcd, 548.3. found, 549.0 [M+H].

Example 177

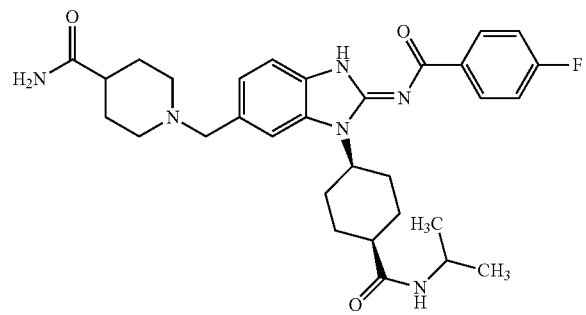 [SMILES: CC(C)NC(=O)[C@H]1CC[C@@H](n2/c(=N/C(=O)c3ccc(F)cc3)[nH]c3ccc(CN4CCC(C(N)=O)CC4)cc32)CC1]

1-(((E)-2-(4-Fluorobenzoylimino)-3-(cis-4-(isopropylcarbamoyl)-cyclohexyl)-2,3-dihydro-1H-benzo[d]imidazol-5-yl)methyl)piperidine-4-carboxamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and piperidine-4-carboxamide using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (57 mg, 46% yield). MS, m/z ($C_{31}H_{39}FN_6O_3$): calcd, 562.3. found, 563.1 [M+H].

Example 178

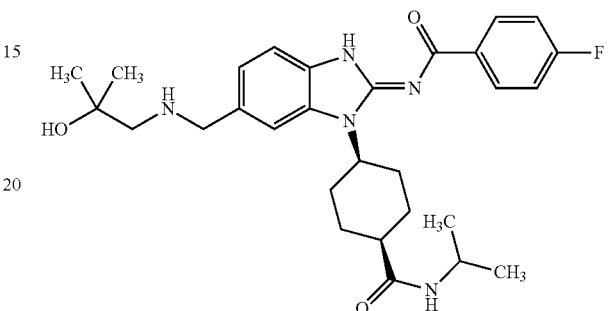

(E)-4-Fluoro-N-(6-((2-hydroxy-2-methylpropylamino)methyl)-1-(cis-4-(isopropylcarbamoyl)cyclohexyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and 1-amino-2-methylpropan-2-ol using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (33 mg, 29% yield). $^1$H NMR (400 MHz, DMSO-$d_6$) δ ppm 1.06-1.15 (m, 12H), 1.23-1.28 (m, 2H), 1.56-1.79 (m, 5H), 2.09-2.17 (m, 2H), 2.45 (br. s., 1H), 2.53 (br. s., 1H), 2.72-2.87 (m, 2H), 3.87 (br. s., 2H), 3.99-4.10 (m, 1H), 4.86 (br. s, 1H), 7.19-7.28 (m, 3H), 7.49 (d, J=8.2 Hz, 1H), 7.60-7.70 (m, 2H), 8.32 (dd, J=8.6, 5.8 Hz, 2H), 12.75 (s, 1H). MS, m/z ($C_{29}H_{38}FN_5O_3$): calcd, 523.3. found, 524.1 [M+H]

Example 179

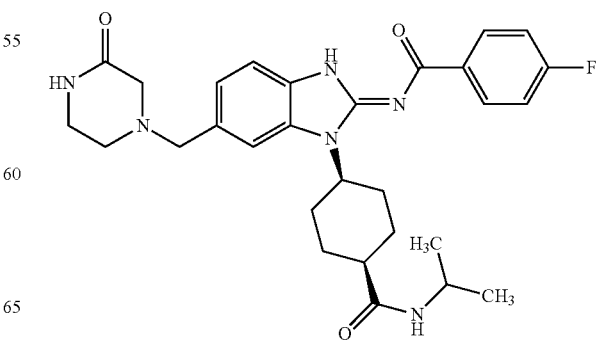

(E)-4-Fluoro-N-(1-(cis-4-(isopropylcarbamoyl)cyclohexyl)-6-((3-oxopiperazin-1-yl)methyl)-1H-benzo[d]imidazol-2(3H)-ylidene)benzamide 2,2,2-trifluoroacetate The title compound was prepared from (E)-4-fluoro-N-(6-(hydroxymethyl)-1-(cis-4-(isopropylcarbamoyl)cyclohexyl)-1H-benzo[d]imidazol-2 (3H)-ylidene)benzamide and piperazine-2-one using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (72 mg, 50% yield). MS, m/z ($C_{29}H_{35}FN_6O_3 \cdot C_2HF_3O_2$): calcd, 534.3. found, 535.4 [M+H].

Example 180

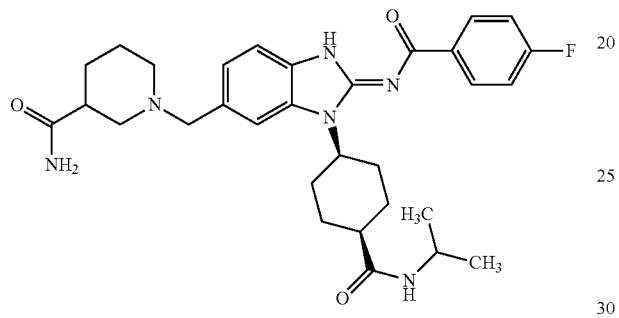

1-(((E)-2-(4-Fluorobenzoylimino)-3-(cis-4-(isopropylcarbamoyl)-cyclohexyl)-2,3-dihydro-1H-benzo[d]imidazol-5-yl)methyl)piperidine-3-carboxamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and piperidine-3-carboxamide using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (6 mg, 4% yield). MS, m/z ($C_{31}H_{39}FN_6O_3$): calcd, 562.3. found, 563.1 [M+H].

Example 181

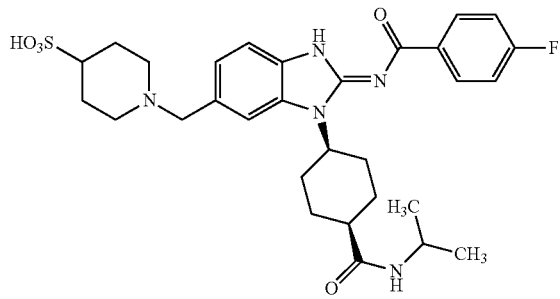 [SMILES: CC(C)NC(=O)[C@H]1CC[C@@H](n2/c(=N/C(=O)c3ccc(F)cc3)[nH]c3ccc(CN4CCC(S(=O)(=O)O)CC4)cc32)CC1]

1-(((E)-2-(4-Fluorobenzoylimino)-3-(cis-4-(isopropylcarbamoyl)-cyclohexyl)-2,3-dihydro-1H-benzo[d]imidazol-5-yl)methyl)piperidine-4-sulfonic acid The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and piperidine-4-sulfonic acid using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (24 mg, 18% yield). MS, m/z ($C_{30}H_{38}FN_5O_5S$): calcd, 599.3. found, 599.7 [M+H].

Example 182

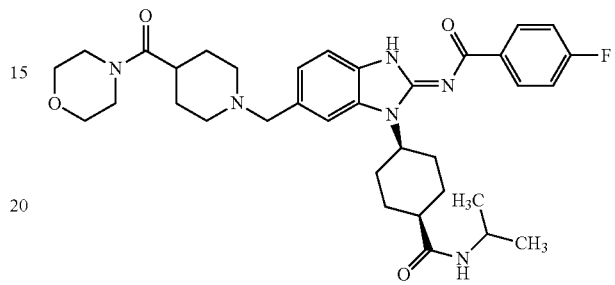

(E)-4-Fluoro-N-(1-(cis-4-(isopropylcarbamoyl)cyclohexyl)-6-((4-(morpholine-4-carbonyl)piperidin-1-yl)methyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and morpholino(piperidin-4-yl)methanone hydrochloride using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide, with a reaction temperature of 50° C. for 4 hours. The title compound was isolated as a white powder (49 mg, 35.0% yield). MS, m/z ($C_{35}H_{45}FN_6O_4$): calcd, 632.4. found, 633.0 [M+H].

Example 183

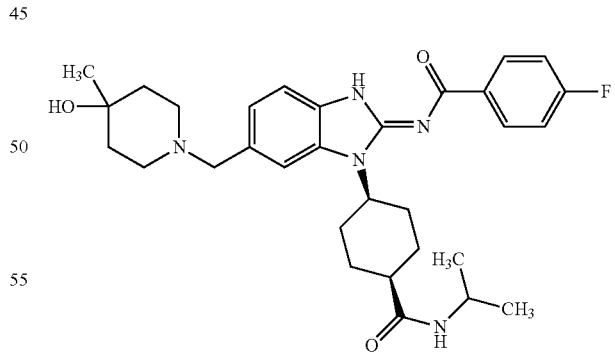

(E)-4-Fluoro-N-(6-((4-hydroxy-4-methylpiperidin-1-yl)methyl)-1-(cis-4-(isopropylcarbamoyl)cyclohexyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and 4-methylpiperidin-4-ol using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide. The title compound was isolated as a white powder (37 mg, 30% yield). MS, m/z ($C_{31}H_{40}FN_5O_3$): calcd, 549.3. found, 549.9 [M+H]

Example 184

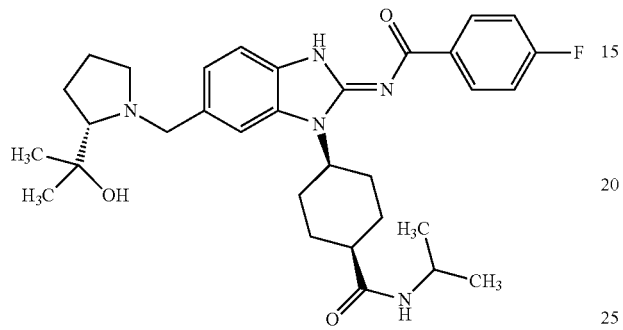

(E)-4-Fluoro-N-(6-(((S)-2-(2-hydroxypropan-2-yl)pyrrolidin-1-yl)methyl)-1-(cis-4-(isopropylcarbamoyl)cyclohexyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. After 30 minutes, the solvent was removed at reduced pressure, and the residue was suspended in ACN (2 mL) and re-concentrated to remove residual thionyl chloride.

The residue was resuspended in ACN (2 mL), cooled to 0° C., and (S)-2-(pyrrolidin-2-yl)propan-2-ol hydrochloride (183 mg, 1.105 mmol) and sodium hydride (60% dispersion in mineral oil, 44 mg, 1.105 mmol) were added. The reaction was stirred at RT for 16 hours. The reaction was concentrated, and the residue was purified by reverse-phase preparative HPLC, using 0.1% TFA in ACN/water (gradient 15% to 90%). The product fractions were combined, neutralized with saturated aqueous NaHCO₃, and extracted with EtOAc (×2). The combined organic layers were washed with brine, dried over anhydrous magnesium sulfate, filtered, and concentrated to provide (E)-4-fluoro-N-(6-(((S)-2-(2-hydroxypropan-2-yl)pyrrolidin-1-yl)methyl)-1-(cis-4-(isopropylcarbamoyl)cyclohexyl)-1H-benzo[d]imidazol-2(3H)-ylidene)benzamide as a purple powder (44 mg, 35.3% yield). ¹H NMR (400 MHz, DMSO-d₆) δ ppm 1.09 (dd, J=6.6, 1.6 Hz, 6H), 1.14 (s, 6H), 1.55-1.81 (m, 8H), 2.04-2.11 (m, 2H), 2.19-2.28 (m, 1H), 2.54 (br. s, 1H), 2.62-2.68 (m, 1H), 2.76-2.90 (m, 3H), 3.51 (d, J=14.4 Hz, 1H), 3.98-4.09 (m, 1H), 4.14 (s, 1H), 4.36 (d, J=13.3 Hz, 1H), 4.86-4.96 (m, 1H), 7.18 (d, J=8.0 Hz, 1H), 7.22-7.29 (m, 2H), 7.46 (d, J=8.0 Hz, 1H), 7.70 (d, J=8.0 Hz, 1H), 7.79 (s, 1H), 8.30 (dd, J=8.9, 5.9 Hz, 2H), 12.71 (s, 1H). MS, m/z ($C_{32}H_{42}FN_5O_3$): calcd, 563.3. found, 564.0 [M+H].

Example 185

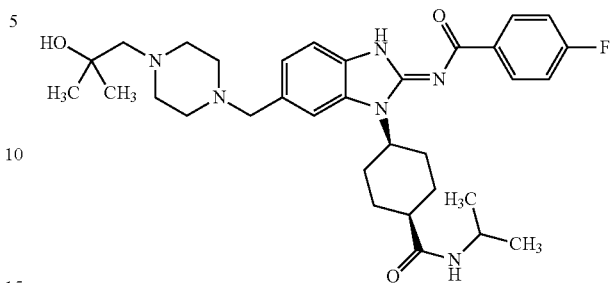

(E)-4-Fluoro-N-(6-((4-(2-hydroxy-2-methylpropyl)piperazin-1-yl)methyl)-1-(cis-4-(isopropylcarbamoyl)cyclohexyl)-1H-benzo[d]imidazol-2(3H)-ylidene)benzamide Step A: Benzyl 4-(2-methoxy-2-oxoethyl)piperazine-1-carboxylate To a solution of benzyl piperazine-1-carboxylate (0.5 g, 2.270 mmol) and TEA (0.949 mL, 6.81 mmol) in THF (10 mL) was added methyl 2-bromoacetate (0.230 mL, 2.497 mmol) dropwise. The reaction was stirred at 65° C. After 1 hour, the reaction mixture was concentrated, and the residue was partitioned between EtOAc and saturated aqueous NaHCO₃. The organic layer was dried over anhydrous magnesium sulfate, filtered, and concentrated to generate benzyl 4-(2-methoxy-2-oxoethyl)piperazine-1-carboxylate as a clear oil (0.61 g, 92% yield).

Step B: Benzyl 4-(2-hydroxy-2-methylpropyl)piperazine-1-carboxylate

To a solution of benzyl 4-(2-methoxy-2-oxoethyl)piperazine-1-carboxylate (0.61 g, 2.087 mmol) in THF (5 mL) at 0° C. was added methylmagnesium iodide (2.087 mL, 6.26 mmol) dropwise. The reaction was stirred at ambient temperature for 10 minutes then stirred at 35° C. for 3 hours, and overnight at ambient temperature. The reaction was quenched with saturated aqueous ammonium chloride and extracted with EtOAc. The organic layer was dried over anhydrous magnesium sulfate, filtered, and concentrated to provide benzyl 4-(2-hydroxy-2-methylpropyl)piperazine-1-carboxylate as a yellow oil (0.54 g, 89% yield). MS, m/z ($C_{16}H_{24}N_2O_3$): calcd, 292.2. found, 293.1 [M+H].

Step C: 2-Methyl-1-(piperazin-1-yl)propan-2-ol dihydrochloride

To a solution of benzyl 4-(2-hydroxy-2-methylpropyl)piperazine-1-carboxylate (0.54 g, 1.847 mmol) in EtOH (10 mL) was added 10% palladium on carbon (0.1 g, 0.094 mmol). The reaction was stirred overnight under a hydrogen atmosphere. After 16 hours, the reaction was filtered through Celite® brand filter aid (rinsed with MeOH and DCM). The filtrate was concentrated to a clear oil, the oil was diluted with EtOAc, and 4 N HCl/dioxane (0.5 mL; 2 mmol) was added dropwise. The white precipitate was collected by vacuum filtration, washed with diethyl ether, and dried in vacuo, to generate 2-methyl-1-(piperazin-1-yl)propan-2-ol hydrochloride as a brown powder (0.31 g, 86% yield).

Step D: (E)-4-Fluoro-N-(6-((4-(2-hydroxy-2-methylpropyl)piperazin-1-yl)methyl)-1-(cis-4-(isopropylcarbamoyl)cyclohexyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed at reduced pressure, and the residue was suspended in ACN (2 mL) and re-concentrated to remove residual thionyl chloride.

The residue was resuspended in ACN (2 mL), cooled to 0° C., and 2-methyl-1-(piperazin-1-yl)propan-2-ol dihydrochloride (153 mg, 0.663 mmol) and TEA (0.25 mL, 1.77 mmol) were added. The reaction was stirred for 16 hours at RT then 4 hours at 50° C. The reaction was concentrated, and the residue was redissolved in 2 mL MeOH. The residual material was purified by reverse-phase preparative HPLC, using 0.1% TFA in ACN/water (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated. The product was further purified by column chromatography, eluting with 0-100% (90:9:1) DCM/MeOH/NH$_4$OH in DCM, to provide (E)-4-fluoro-N-(6-((4-(2-hydroxy-2-methylpropyl)piperazin-1-yl)methyl)-1-(cis-4-(isopropylcarbamoyl)cyclohexyl)-1H-benzo[d]imidazol-2(3H)-ylidene)benzamide as an off-white powder (26 mg, 19.9% yield). MS, m/z (C$_{33}$H$_{45}$FN$_6$O$_3$): calcd, 592.3. found, 593.0 [M+H].

Example 186

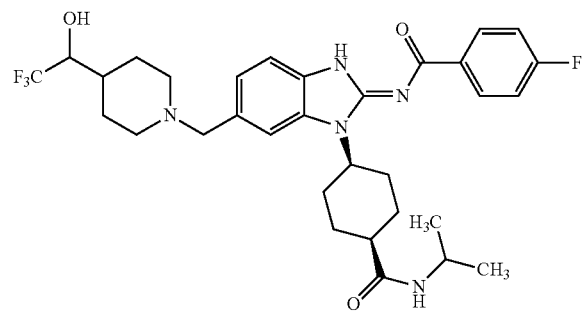 [SMILES: CC(C)NC(=O)[C@H]1CC[C@@H](n2/c(=N/C(=O)c3ccc(F)cc3)[nH]c3ccc(CN4CCC(C(O)C(F)(F)F)CC4)cc32)CC1]

(E)-4-Fluoro-N-(1-(cis-4-(isopropylcarbamoyl)-cyclohexyl)-6-((4-(2,2,2-trifluoro-1-hydroxyethyl)piperidin-1-yl)methyl)-1H-benzo[d]imidazol-2(3H)-ylidene)benzamide

Step A: tert-Butyl 4-(2,2,2-trifluoro-1-(trimethylsilyloxy)ethyl)piperidine-1-carboxylate To a solution of tert-butyl 4-formylpiperidine-1-carboxylate (AstaTech Inc., Bristol, Pa.; 1 g, 4.69 mmol) in THF (10 mL) at 0° C. was added trimethyl(trifluoromethyl)silane (0.832 mL, 5.63 mmol) and TBAF (1 drop of a 1M solution in THF). The reaction was allowed to warm to RT and stirred for 2 hours. The reaction was diluted with diethyl ether and washed with 1 N aqueous HCl and brine. The organic layer was dried over anhydrous magnesium sulfate, filtered, and concentrated to yield tert-butyl 4-(2,2,2-trifluoro-1-(trimethylsilyloxy)ethyl)piperidine-1-carboxylate as a yellow oil which crystallized upon standing (1.62 g, 97% yield).

Step B: 2,2,2-Trifluoro-1-(piperidin-4-yl)ethanol hydrochloride

To a solution of tert-butyl 4-(2,2,2-trifluoro-1-(trimethylsilyloxy)ethyl)piperidine-1-carboxylate (1.6 g, 4.50 mmol) in DCM (9 mL) and MeOH (1 mL) was added 2 M HCl in ether (11.25 mL, 22.51 mmol). The reaction was stirred at RT for 16 hours. The precipitate that formed was collected by vacuum filtration, washed with diethyl ether, and dried in vacuo to generate 2,2,2-trifluoro-1-(piperidin-4-yl)ethanol hydrochloride as a white powder (0.83 g, 84% yield).

Step C: (E)-4-Fluoro-N-(1-(cis-4-(isopropylcarbamoyl)-cyclohexyl)-6-((4-(2,2,2-trifluoro-1-hydroxyethyl)piperidin-1-yl)methyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. After 30 minutes, the solvent was removed at reduced pressure, and the residue was suspended in ACN (2 mL) and re-concentrated to remove residual thionyl chloride.

The residue was resuspended in ACN (2 mL), cooled to 0° C., and 2,2,2-trifluoro-1-(piperidin-4-yl)ethanol hydrochloride (146 mg, 0.663 mmol) and DBU (0.133 mL, 0.884 mmol) were added. The reaction was stirred for 48 hours at RT, and then the reaction was concentrated and the residue was purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(1-(cis-4-(isopropylcarbamoyl)-cyclohexyl)-6-((4-(2,2,2-trifluoro-1-hydroxyethyl)piperidin-1-yl)methyl)-1H-benzo[d]imidazol-2(3H)-ylidene)benzamide as a white powder (56 mg, 41.0% yield). MS, m/z (C$_{32}$H$_{39}$F$_4$N$_5$O$_3$): calcd, 617.3. found, 618.0 [M+H].

Example 187

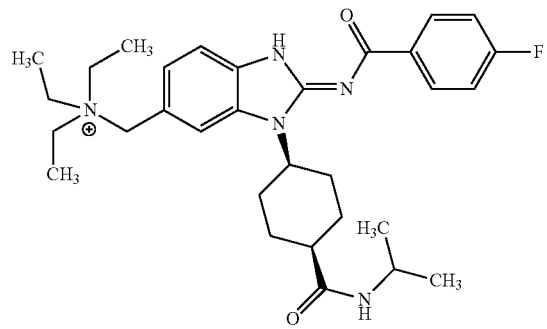 [SMILES: CC[N+](CC)(CC)Cc1ccc2[nH]/c(=N\C(=O)c3ccc(F)cc3)n([C@H]3CC[C@@H](C(=O)NC(C)C)CC3)c2c1]

N,N-Diethyl-N-(((E)-2-(4-fluorobenzoylimino)-3-(cis-4-(isopropylcarbamoyl)cyclohexyl)-2,3-dihydro-1H-benzo[d]imidazol-5-yl)methyl)ethanaminium chloride To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. After 30 minutes, the solvent was removed at reduced pressure, and the residue was suspended in ACN (2 mL) and re-concentrated to remove residual thionyl chloride.

The residue was resuspended in ACN (2 mL), cooled to 0° C., and 2,2,2-trifluoro-1-(piperidin-4-yl)ethanol hydrochloride (146 mg, 0.663 mmol) and TEA (0.154 mL, 1.105 mmol) were added. The reaction was stirred for 48 hours at RT, followed by 4 hours at 50° C. The reaction was concentrated, and the residue was purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide N,N-diethyl-N-(((E)-2-(4-fluorobenzoylimino)-3-(cis-4-(isopropylcarbamoyl)cyclohexyl)-2,3-dihydro-1H-benzo[d]imidazol-5-yl)methyl)ethanaminium chloride as an off-white powder (76 mg, 60.1% yield). $^1$H NMR (400 MHz, DMSO-d$_6$) δ ppm 1.10 (d, J=6.7 Hz, 6H), 1.36 (t, J=7.1 Hz, 9H), 1.59-1.83 (m, 4H), 2.01-2.09 (m, 2H), 2.56 (br. s, 1H), 2.71-2.89 (m, 2H), 3.22 (q, J=7.2 Hz, 6H), 3.92-4.02 (m, 1H), 4.54 (s, 2H), 4.86-5.04 (m, 1H), 7.27 (dd, J=8.9 Hz, 8.9 Hz, 2H), 7.36 (d, J=8.0 Hz, 1H), 7.64 (d, J=8.2 Hz, 1H), 7.78 (d, J=7.7 Hz, 1H), 7.88 (s, 1H), 8.32 (dd, J=8.9, 5.8 Hz, 2H), 12.94 (s, 1H). MS, m/z (C$_{31}$H$_{43}$FN$_5$O$_2$.Cl): calcd, 536.3. found, 536.1 [M+H].

Example 188

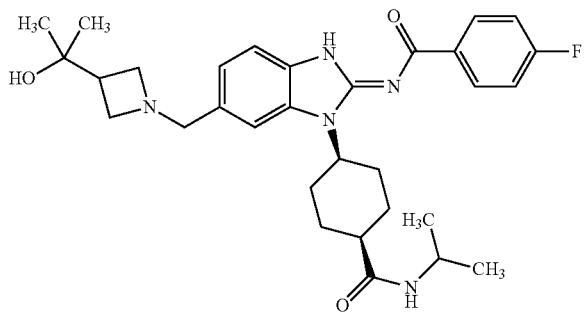 [SMILES: CC(C)NC(=O)[C@H]1CC[C@@H](n2/c(=N/C(=O)c3ccc(F)cc3)[nH]c3ccc(CN4CC(C(C)(C)O)C4)cc32)CC1]

(E)-4-Fluoro-N-(6-((3-(2-hydroxypropan-2-yl)azetidin-1-yl)methyl)-1-(cis-4-(isopropylcarbamoyl)cyclohexyl)-1H-benzo[d]imidazol-2(3H)-ylidene)benzamide

Step A: tert-Butyl 3-(2-hydroxypropan-2-yl)azetidine-1-carboxylate

To a solution of 1-tert-butyl 3-methyl azetidine-1,3-dicarboxylate (900 mg, 4.18 mmol) in THF (25 mL) at 0° C. was added 3 M methylmagnesium iodide in ether (4.18 mL, 12.54 mmol) dropwise. The reaction was stirred overnight at RT. The reaction was quenched with saturated aqueous ammonium chloride and extracted with EtOAc. The organic layer was concentrated, adsorbed onto a plug of silica gel, and purified by column chromatography, eluting with 20-100% (90:9:1 DCM/MeOH/NH$_4$OH)/DCM, to provide tert-butyl 3-(2-hydroxypropan-2-yl)azetidine-1-carboxylate as a yellow oil (867 mg, 96% yield).

Step B: 2-(Azetidin-3-yl)propan-2-ol hydrochloride

To a solution of tert-butyl 3-(2-hydroxypropan-2-yl)azetidine-1-carboxylate (0.87 g, 4.04 mmol) in DCM (15 mL) at 0° C. was added 4 M HCl in dioxane (8.08 mL, 16.16 mmol) dropwise. The reaction was stirred overnight at RT. The reaction mixture was concentrated and dried in vacuo to generate 2-(azetidin-3-yl)propan-2-ol hydrochloride as a brown solid (0.44 g, 71.8% yield).

Step C: (E)-4-Fluoro-N-(6-((3-(2-hydroxypropan-2-yl)azetidin-1-yl)methyl)-1-(cis-4-(isopropylcarbamoyl)cyclohexyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. The solvent was removed on a rotovap, and the residue suspended in ACN (2 mL) and re-concentrated to remove residual thionyl chloride. The residue was resuspended in DMF (2 mL), cooled to 0° C., and 2-(azetidin-3-yl)propan-2-ol hydrochloride (101 mg, 0.663 mmol) and DBU (0.10 mL, 0.663 mmol) were added. After stirring for 16 hours at RT, the reaction mixture was concentrated and purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(6-((3-(2-hydroxypropan-2-34)azetidin-1-yl)methyl)-1-(cis-4-(isopropylcarbamoyl)cyclohexyl)-1H-benzo[d]imidazol-2(3H)-ylidene) as a white powder benzamide (26 mg, 21.4% yield). MS, m/z (C$_{31}$H$_{40}$FN$_5$O$_3$): calcd, 549.3. found, 549.9 [M+H].

Example 189

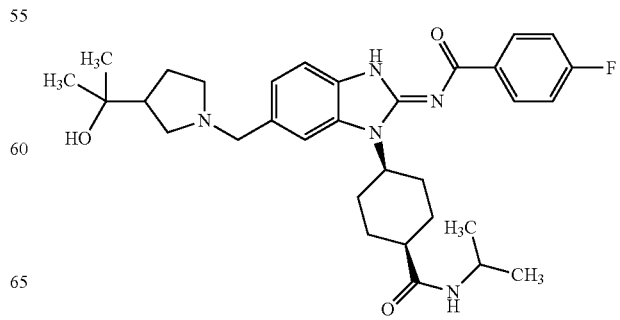

(E)-4-Fluoro-N-(6-((3-(2-hydroxypropan-2-yl)pyrrolidin-1-yl)methyl)-1-(cis-4-(isopropylcarbamoyl)cyclohexyl)-1H-benzo[d]imidazol-2(3H)-ylidene)benzamide

Step A: tert-Butyl 3-(2-hydroxypropan-2-yl)pyrrolidine-1-carboxylate

To a solution of 1-tert-butyl 3-methylpyrrolidine-1,3-dicarboxylate (0.98 g, 4.27 mmol) in diethyl ether (5 mL) at 0° C. was added 3 M methylmagnesium iodide in ether (4.27 mL, 12.82 mmol) dropwise. A large amount of precipitate formed, so THF (5 mL) was added to improve the solubility. The reaction was stirred at RT for 10 minutes and then stirred at reflux for 3 hours, and at RT for 16 hours. The reaction was quenched with saturated aqueous ammonium chloride and extracted with EtOAc. The organic layer was dried over anhydrous magnesium sulfate, filtered, and concentrated to provide tert-butyl 3-(2-hydroxypropan-2-yl)pyrrolidine-1-carboxylate as a yellow oil (0.69 g, 70.4% yield).

Step B: 2-(Pyrrolidin-3-yl)propan-2-ol hydrochloride

To a solution of tert-butyl 3-(2-hydroxypropan-2-yl)pyrrolidine-1-carboxylate (0.69 g, 3.01 mmol) in DCM (15 mL) and EtOAc (5 mL) was added 4 M HCl in dioxane (3.01 mL, 12.04 mmol). The reaction was stirred overnight at RT and then concentrated to generate 2-(pyrrolidin-3-yl)propan-2-ol hydrochloride as a yellow oil (0.51 g, 102% yield).

Step C: (E)-4-Fluoro-N-(6-((3-(2-hydroxypropan-2-yl)pyrrolidin-1-yl)methyl)-1-(cis-4-(isopropylcarbamoyl)cyclohexyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. The solvent was removed at reduced pressure, and the residue was suspended in ACN (2 mL) and re-concentrated to remove residual thionyl chloride. The residue was resuspended in ACN (2 mL), cooled to 0° C., and 2-(pyrrolidin-3-yl)propan-2-ol hydrochloride (110 mg, 0.663 mmol) and TEA (0.154 mL, 1.105 mmol) were added. The reaction was stirred for 16 hours at RT, followed by 4 hours at 50° C. and 6 hours at 80° C. The reaction was cooled to RT, DBU (0.17 mL, 1.105 mmol) was added, and the reaction was stirred overnight at 40° C. The reaction was concentrated, adsorbed onto a plug of silica gel, and purified by column chromatography, eluting with 0-100% (90:9:1 DCM/MeOH/NH$_4$OH)/DCM, to provide (E)-4-fluoro-N-(6-((3-(2-hydroxypropan-2-yl)pyrrolidin-1-yl)methyl)-1-(cis-4-(isopropylcarbamoyl)cyclohexyl)-1H-benzo[d]imidazol-2(3H)-ylidene)benzamide as a light-yellow powder (65 mg, 52.2% yield). $^1$H NMR (400 MHz, DMSO-d$_6$) δ ppm 1.03 (s, 6H), 1.11 (d, J=6.7 Hz, 6H), 1.54-1.79 (m, 7H), 2.09-2.19 (m, 3H), 2.36 (br. s., 2H), 2.52 (br. s., 1H), 2.59 (br. s., 1H), 2.69-2.84 (m, 2H), 3.55 (br. s., 1H), 3.68 (br. s., 1H), 3.99-4.10 (m, 2H), 4.83 (br. s., 1H), 7.14-7.19 (m, 1H), 7.24 (dd, J=8.9 Hz, 8.9 Hz, 2H), 7.48 (d, J=8.0 Hz, 1H), 7.55-7.66 (m, 2H), 8.32 (dd, J=8.7, 6.0 Hz, 2H), 12.74 (br. s., 1H). MS, m/z (C$_{32}$H$_{42}$FN$_5$O$_3$): calcd, 563.3. found, 564.0 [M+H].

Example 190

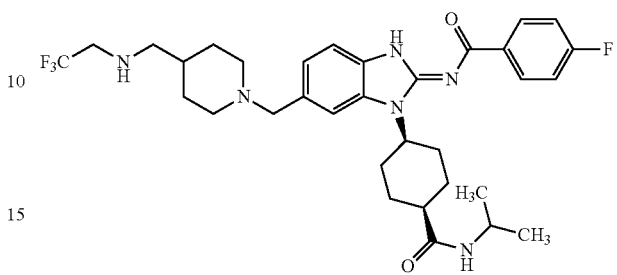

(E)-4-Fluoro-N-(1-(cis-4-(isopropylcarbamoyl)cyclohexyl)-6-((4-((2,2,2-trifluoroethylamino)methyl)piperidin-1-yl)methyl)-1H-benzo[d]imidazol-2(3H)-ylidene)benzamide

Step A: tert-Butyl 4-((2,2,2-trifluoroethylamino)methyl)piperidine-1-carboxylate To a solution of tert-butyl 4-formylpiperidine-1-carboxylate (1 g, 4.69 mmol) in DCM (25 mL) was added 2,2,2-trifluoroethanamine (0.464 g, 4.69 mmol) and AcOH (0.05 mL). The reaction was stirred at RT for 3 hours and then sodium triacetoxyborohydride (1.292 g, 6.10 mmol) was added, and the reaction was stirred at RT for 16 hours. The reaction was diluted with DCM and saturated aqueous NaHCO$_3$. The aqueous layer was adjusted to a pH of approximately 10 with 1 N aqueous NaOH, and extracted with DCM. The combined organic layers were dried over anhydrous magnesium sulfate, filtered, and concentrated to generate tert-butyl 4-((2,2,2-trifluoroethylamino)methyl)piperidine-1-carboxylate as a colorless oil (1.49 g, 107% yield).

Step B: 2,2,2-Trifluoro-N-(piperidin-4-ylmethyl)ethanamine dihydrochloride

To a solution of tert-butyl 4-((2,2,2-trifluoroethylamino)methyl)piperidine-1-carboxylate (1.49 g, 5.03 mmol) in DCM (25 mL) was added 4 N HCl in dioxane (5.03 mL, 20.11 mmol). The reaction was stirred at RT. After 16 hours, the white precipitate was collected by vacuum filtration, washed with diethyl ether, and dried in vacuo, to generate 2,2,2-trifluoro-N-(piperidin-4-ylmethyl)ethanamine dihydrochloride as a white powder (1.07 g, 3.98 mmol, 79% yield).

Step C: (E)-4-Fluoro-N-(1-(cis-4-(isopropylcarbamoyl)cyclohexyl)-6-((4-((2,2,2-trifluoroethylamino)methyl)piperidin-1-yl)methyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. The solvent was removed at reduced pressure, and the residue was suspended in ACN (2 mL) and re-concentrated to remove residual thionyl chloride.

The residue was resuspended in ACN (2 mL), cooled to 0° C., and 2,2,2-trifluoro-N-(piperidin-4-ylmethyl)ethanamine dihydrochloride (178 mg, 0.663 mmol) and DBU (0.233 mL, 1.547 mmol) were added. The reaction was stirred for 3 days at RT, and then the reaction was concentrated and the residual material was purified by reverse-phase preparative HPLC, using 0.1% TFA in ACN/water, (gradient 15% to 75%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(1-(cis-4-(isopropylcarbamoyl)cyclohexyl)-6-((4-((2,2,2-trifluoroethylamino)methyl)piperidin-1-yl)methyl)-1H-benzo[d]imidazol-2(3H)-ylidene)benzamide as a white powder (35 mg, 25.1% yield). $^1$H NMR (400 MHz, DMSO-d$_6$) δ ppm 1.11 (d, J=1.0 Hz, 6H), 1.16-1.27 (m, 2H), 1.33 (br. s., 1H), 1.56-1.77 (m, 6H), 1.91 (br. s., 2H), 2.05-2.33 (m, 4H), 2.53 (br. s., 1H), 2.65-2.93 (m, 4H), 3.09-3.24 (m, 3H), 3.52 (br. s., 2H), 3.94-4.16 (m, 1H), 4.86 (br. s., 1H), 7.14 (d, J=8.0 Hz, 1H), 7.24 (t, J=8.8 Hz, 2H), 7.48 (d, J=8.2 Hz, 1H), 7.56-7.65 (m, 2H), 8.31 (dd, J=8.3, 6.2 Hz, 2H), 12.73 (br. s., 1H). MS, m/z (C$_{33}$H$_{42}$F$_4$N$_6$O$_2$): calcd, 630.3. found, 631.2 [M+H].

Example 191

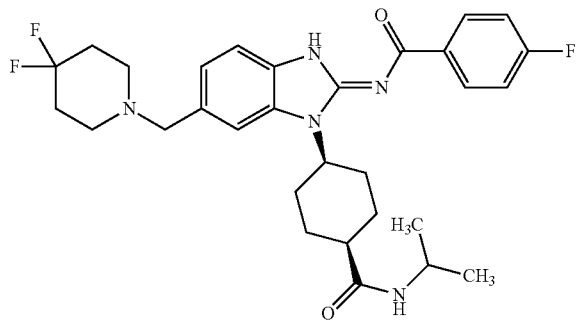 [SMILES: CC(C)NC(=O)[C@H]1CC[C@@H](n2/c(=N/C(=O)c3ccc(F)cc3)[nH]c3ccc(CN4CCC(F)(F)CC4)cc32)CC1]

(E)-N-(6-((4,4-Difluoropiperidin-1-yl)methyl)-1-(cis-4-(isopropylcarbamoyl)cyclohexyl)-1H-benzo[d]imidazol-2(3H)-ylidene)-4-fluorobenzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed, and the residue was resuspended in 2 mL DMSO, cooled to 0° C., and 4,4-difluoropiperidine hydrochloride (348 mg, 2.210 mmol) and TEA (0.308 mL, 2.210 mmol) were added. The reaction was stirred for 30 minutes at 0° C. and then at RT for 16 hours. The reaction was concentrated, and the residue was purified by reverse-phase preparative HPLC, using 0.1% TFA in AC/water (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-N-(6-((4,4-difluoropiperidin-1-yl)methyl)-1-(cis-4-(isopropylcarbamoyl)cyclohexyl)-1H-benzo[d]imidazol-2(3H)-ylidene)-4-fluorobenzamide as a white powder (71 mg, 57.8% yield). $^1$H NMR (400 MHz, DMSO-d$_6$) δ ppm 1.11 (s, 6H), 1.54-1.83 (m, 5H), 1.94-2.18 (m, 7H), 2.53 (br. s., 3H), 2.67-2.86 (m, 2H), 3.64 (s, 2H), 3.94-4.09 (m, 1H), 4.91 (br. s., 1H), 7.13 (d, J=8.0 Hz, 1H), 7.25 (dd, J=8.8 Hz, 8.8 Hz, 2H), 7.49 (d, J=8.1 Hz, 1H), 7.60-7.82 (m, 2H), 8.20-8.43 (m, 2H), 12.75 (br. s., 1H). MS, m/z (C$_{30}$H$_{36}$F$_3$N$_5$O$_2$): calcd, 555.3. found, 555.9 [M+H].

Example 192

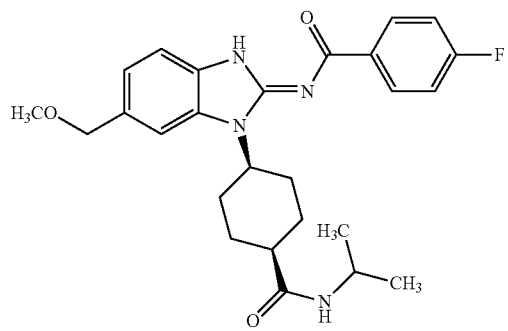 [SMILES: COCc1ccc2[nH]/c(=N\C(=O)c3ccc(F)cc3)n([C@H]3CC[C@@H](C(=O)NC(C)C)CC3)c2c1]

(E)-4-Fluoro-N-(1-(cis-4-(isopropylcarbamoyl)cyclohexyl)-6-(methoxymethyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed and the residue was resuspended in ACN (2 mL), cooled to 0° C., and sodium methoxide (478 mg, 2.210 mmol) was added. The reaction was stirred overnight at RT. The solvent was removed on a rotovap, and the residue was partitioned between water and DCM. The aqueous layer was neutralized (pH approximately 8) with concentrated HCl and extracted with DCM. The combined organic layers were concentrated, adsorbed onto a plug of silica gel, and purified by column chromatography, eluting with 0-10% MeOH in DCM, to provide (E)-4-fluoro-N-(1-(cis-4-(isopropylcarbamoyl)cyclohexyl)-6-(methoxymethyl)-1H-benzo[d]imidazol-2(3H)-ylidene)benzamide as a white powder (45 mg, 43.6% yield). MS, m/z (C$_{26}$H$_{31}$FN$_4$O$_3$): calcd, 466.2. found, 466.8 [M+H].

Example 193

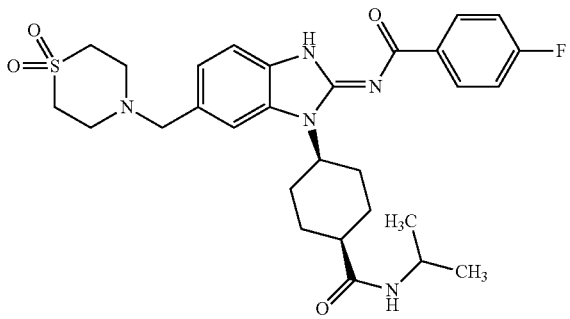 [SMILES: CC(C)NC(=O)[C@H]1CC[C@@H](n2/c(=N/C(=O)c3ccc(F)cc3)[nH]c3ccc(CN4CCS(=O)(=O)CC4)cc32)CC1]

N-((2E)-6-((1,1-Dioxido-4-thiomorpholinyl)methyl)-1-(cis-4-((1-methylethyl)carbamoyl)cyclohexyl)-1,3-dihydro-2H-benzimidazol-2-ylidene)-4-fluorobenzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and thiomorpholine-1,1-dioxide using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (67 mg, 53% yield). $^1$H NMR (400 MHz, DMSO-$d_6$) δ ppm 12.75 (s, 1H), 8.31 (dd, J=6.2, 8.7 Hz, 2H), 7.80 (s, 1H), 7.68 (d, J=7.8 Hz, 1H), 7.49 (d, J=8.2 Hz, 1H), 7.25 (dd, J=8.6 Hz, 8.6 Hz, 2H), 7.13, (d, J=8.6 Hz, 1H), 4.86-4.97 (m, 1H), 4.00-4.07 (m, 1H), 3.76 (s, 2H), 3.22 (brs, 4H), 2.92 (brs, 4H), 2.75-2.84 (m, 2H), 2.54 (brs, 1H), 2.05-2.14 (m, 2H), 1.69-1.79 (m, 2H), 1.59-1.65 (m, 2H), 1.11 (d, J=6.6 Hz, 6H). MS, m/z ($C_{29}H_{36}FN_5O_4S$): calcd, 569.3. found, 569.7 [M+H].

Example 194

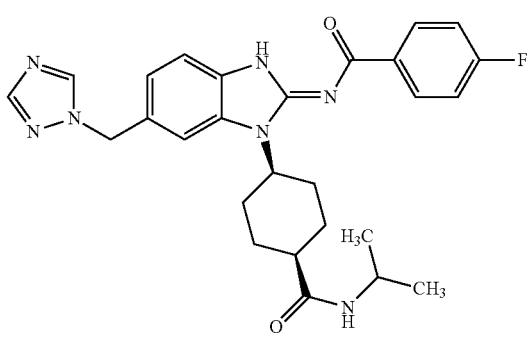 [SMILES: CC(C)NC(=O)[C@H]1CC[C@@H](n2/c(=N/C(=O)c3ccc(F)cc3)[nH]c3ccc(Cn4cncn4)cc32)CC1]

(E)-N-(6-((1H-1,2,4-Triazol-1-yl)methyl)-1-(cis-4-(isopropylcarbamoyl)cyclohexyl)-1H-benzo[d]imidazol-2(3H)-ylidene)-4-fluorobenzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed at reduced pressure, and the residue was dried in vacuo for 5 minutes. The residue was resuspended in ACN (2 mL), cooled to 0° C., and 1H-1,2,4-triazole (153 mg, 2.210 mmol), potassium carbonate (305 mg, 2.210 mmol), and sodium iodide (33.1 mg, 0.221 mmol) were added. The reaction was stirred at RT. After 16 hours, the solvent was removed, and the residue was partitioned between water and DCM. The aqueous layer was neutralized (pH approximately 8) with 2 N aqueous HCl and extracted with DCM. The combined organic layers were concentrated, adsorbed onto a plug of silica gel, and purified by column chromatography, eluting with 0-10% MeOH in DCM, to provide (E)-N-(6-((1H-1,2,4-triazol-1-yl)methyl)-1-(cis-4-(isopropylcarbamoyl)cyclohexyl)-1H-benzo[d]imidazol-2(3H)-ylidene)-4-fluorobenzamide (35 mg, 31% yield). $^1$H NMR (400 MHz, DMSO-$d_6$) δ ppm 12.80 (s, 1H), 8.69 (s, 1H), 8.33 (dd, J=6.0, 8.6 Hz, 2H), 7.95 (s, 1H), 7.76 (s, 1H), 7.67 (d, J=7.6 Hz, 1H), 7.50 (d, J=8.1 Hz, 1H), 7.24 (dd, J=8.8 Hz, 8.8 Hz, 2H), 7.15, (d, J=8.2 Hz, 1H), 5.45 (s, 2H), 4.78 (brs, 1H), 4.02-4.14 (m, 1H), 2.74-2.85 (m, 2H), 2.54 (brs, 1H), 2.10-2.13 (d, J=12.8 Hz, 2H), 1.69-1.76 (m, 2H), 1.59-1.62 (m, 2H), 1.11 (d, J=6.6 Hz, 6H). MS, m/z ($C_{27}H_{30}FN_7O_2$): calcd, 503.2; found, 503.7 [M+H].

Example 195

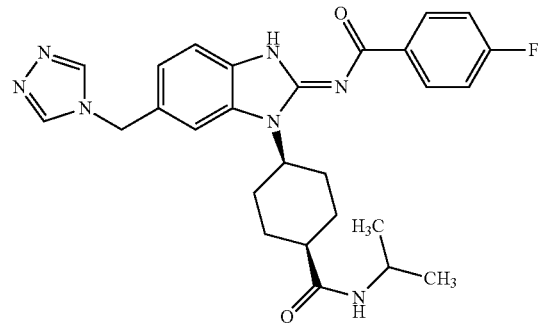 [SMILES: CC(C)NC(=O)[C@H]1CC[C@@H](n2/c(=N/C(=O)c3ccc(F)cc3)[nH]c3ccc(Cn4cnnc4)cc32)CC1]

(E)-N-(6-((4H-1,2,4-Triazol-4-yl)methyl)-1-(cis-4-(isopropylcarbamoyl)cyclohexyl)-1H-benzo[d]imidazol-2(3H)-ylidene)-4-fluorobenzamide The title compound was isolated from the reaction to prepare (E)-N-(6-((1H-1,2,4-triazol-1-yl)methyl)-1-(cis-4-(isopropylcarbamoyl)cyclohexyl)-1H-benzo[d]imidazol-2(3H)-ylidene)-4-fluorobenzamide (17 mg, 15% yield). MS, m/z ($C_{27}H_{30}FN_7O_2$): calcd, 503.2. found, 503.7 [M+H].

Example 196

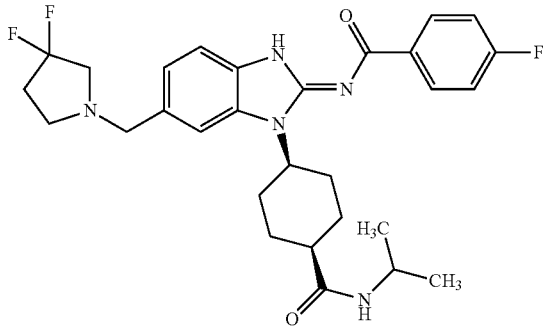 [SMILES: CC(C)NC(=O)[C@H]1CC[C@@H](n2/c(=N/C(=O)c3ccc(F)cc3)[nH]c3ccc(CN4CCC(F)(F)C4)cc32)CC1]

(E)-N-(6-((3,3-Difluoropyrrolidin-1-yl)methyl)-1-(cis-4-(isopropylcarbamoyl)cyclohexyl)-1H-benzo[d]imidazol-2(3H)-ylidene)-4-fluorobenzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (2.5 mL) was added thionyl chloride (0.081 mL, 1.105 mmol) dropwise, and the reaction was stirred at 0° C. for 30 minutes. The solvent was removed at reduced pressure, and the residue was dried in vacuo for 5 minutes. The residue was resuspended in ACN (1 mL) and cooled to 0° C. A suspension of 3,3-difluoropyrrolidine hydrochloride (317 mg, 2.210 mmol) and sodium hydride (88 mg, 2.210 mmol) in ACN (1 mL) was added, and the reaction was stirred overnight at RT. The solvent was removed at reduced pressure, and the residue was redissolved in 2 mL of MeOH. The residual material was purified by reverse-phase preparative HPLC, using 0.1% TFA in ACN/water, (gradient 15% to 90%). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-N-(6-((3,3-difluoropyrrolidin-1-yl)methyl)-1-(cis-4-(isopropylcarbamoyl)cyclohexyl)-1H-benzo[d]imidazol-2(3H)-ylidene)-4-fluorobenzamide as a white powder (59 mg, 49.3% yield). $^1$H NMR (400 MHz, DMSO-d$_6$) δ ppm 12.77 (s, 1H), 8.32 (s, 2H), 7.63 (brs, 2H), 7.50 (d, J=7.3 Hz, 1H), 7.24 (brs, 2H), 7.15, (d, J=8.0 Hz, 1H), 4.87 (brs, 1H), 4.02-4.05 (m, 1H), 3.69 (s, 2H), 2.89 (t, J=13.1 Hz, 2H), 2.71-2.77 (m, 4H), 2.53 (brs, 1H), 2.27 (m, 2H), 2.12-2.15 (m, 2H), 1.62-1.73 (m, 4H), 1.10 (d, J=5.6 Hz, 6H). MS, m/z (C$_{29}$H$_{34}$F$_3$N$_5$O$_2$): calcd, 541.3. found, 541.8 [M+H].

Example 197

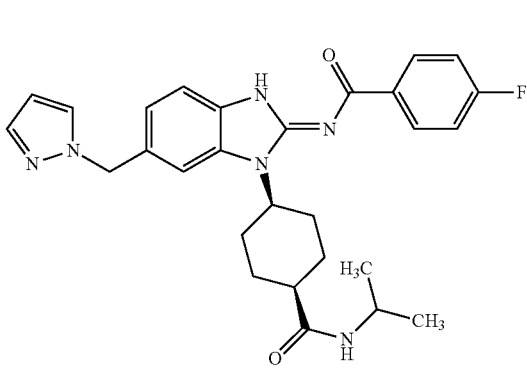 [SMILES: CC(C)NC(=O)[C@H]1CC[C@@H](n2/c(=N/C(=O)c3ccc(F)cc3)[nH]c3ccc(Cn4cccn4)cc32)CC1]

(E)-N-(6-((1H-Pyrazol-1-yl)methyl)-1-(cis-4-(isopropylcarbamoyl)cyclohexyl)-1H-benzo[d]imidazol-2(3H)-ylidene)-4-fluorobenzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and 1H-pyrazole using a method analogous to that used in the preparation of (E)-N-(6-((3,3-difluoropyrrolidin-1-yl)methyl)-1-(cis-4-(isopropylcarbamoyl)cyclohexyl)-1H-benzo[d]imidazol-2(3H)-ylidene)-4-fluorobenzamide (23 mg, 21% yield). MS, m/z (C$_{28}$H$_{31}$FN$_6$O$_2$): calcd, 502.2. found, 502.8 [M+H].

Example 198

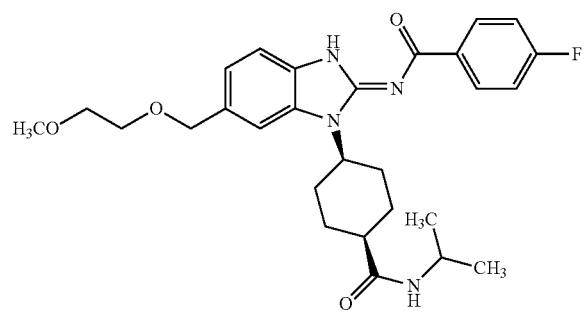 [SMILES: COCCOCc1ccc2[nH]/c(=N\C(=O)c3ccc(F)cc3)n([C@H]3CC[C@@H](C(=O)NC(C)C)CC3)c2c1]

(E)-4-Fluoro-N-(1-(cis-4-(isopropylcarbamoyl)cyclohexyl)-6-((2-methoxyethoxy)methyl)-1H-benzo[d]imidazol-2(3H)-ylidene)benzamide The title compound was prepared from (E)-4-fluoro-N-(6-(hydroxymethyl)-1-(cis-4-(isopropylcarbamoyl)cyclohexyl)-1H-benzo[d]imidazol-2(3H)-ylidene)benzamide and 2-methoxyethanol using a method analogous to that used in the preparation of (E)-N-(6-((3,3-difluoropyrrolidin-1-yl)methyl)-1-(cis-4-(isopropylcarbamoyl)cyclohexyl)-1H-benzo[d]imidazol-2(3H)-ylidene)-4-fluorobenzamide (14 mg, 12% yield). MS, m/z (C$_{28}$H$_{35}$FN$_4$O$_4$): calcd, 510.2. found, 510.9 [M+H].

Example 199

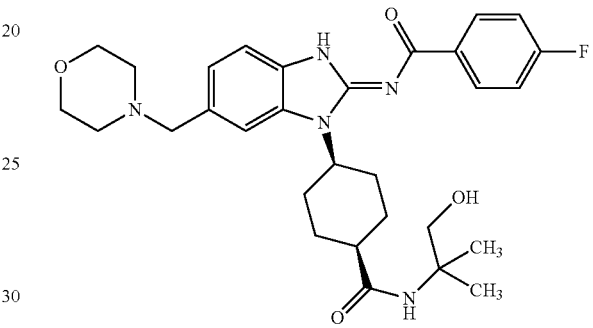

(E)-4-Fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide Step A: cis-Methyl 4-((E)-2-(4-fluorobenzoylimino)-6-(morpholinomethyl)-2,3-dihydro-1H-benzo[d]imidazol-1-yl)cyclohexanecarboxylate The title compound was prepared from cis-methyl 4-((E)-2-(4-fluorobenzoylimino)-6-(hydroxymethyl)-2,3-dihydro-1H-benzo[d]imidazol-1-yl)cyclohexanecarboxylate and morpholine using a method analogous to that used in the preparation of (E)-4-fluoro-N-(1-(cis-4-(isopropylcarbamoyl)cyclohexyl)-6-((4-(methylsulfonyl)piperazin-1-yl)methyl)-1H-benzo[d]imidazol-2(3H)-ylidene)benzamide (2.34 g, quantitative yield). MS, m/z (C$_{27}$H$_{31}$FN$_4$O$_4$): calcd, 494.2. found, 495.0 [M+H].

Step B: cis-4-((E)-2-(4-Fluorobenzoylimino)-6-(morpholinomethyl)-2,3-dihydro-1H-benzo[d]imidazol-1-yl)cyclohexanecarboxylic acid To a suspension of cis-methyl 4-((E)-2-(4-fluorobenzoylimino)-6-(morpholinomethyl)-2,3-dihydro-1H-benzo[d]imidazol-1-yl)cyclohexanecarboxylate (2.3 g, 4.65 mmol) in MeOH (46.5 mL) was added 1 N aqueous sodium hydroxide (46.5 mL, 46.5 mmol). The suspension wa stirred overnight at RT. The resulting solution was concentrated, adjusted to a pH of approximately 4 with 2 N aqueous HCl, and extracted with DCM. The organic layer was dried over anhydrous magnesium sulfate, filtered, and concentrated to generate cis-4-((E)-2-(4-fluorobenzoylimino)-6-(morpholinomethyl)-2,3-dihydro-1H-benzo[d]imidazol-1-yl)

cyclohexanecarboxylic acid as a white powder (2.29 g, 102% yield). MS, m/z ($C_{26}H_{29}FN_4O_4$): calcd, 480.2. found, 480.2 (M).

Step C: cis-4-((E)-2-(4-Fluorobenzoylimino)-6-(morpholinomethyl)-2,3-dihydro-1H-benzo[d]imidazol-1-yl)cyclohexanecarbonyl chloride To a 0° C. suspension of cis-4-((E)-2-(4-fluorobenzoylimino)-6-(morpholinomethyl)-2,3-dihydro-1H-benzo[d]imidazol-1-yl)cyclohexanecarboxylic acid (0.5 g, 1.041 mmol) in DCM (10.41 mL) was added thionyl chloride (0.380 mL, 5.20 mmol). The suspension was stirred for 30 minutes at 0° C. The reaction was concentrated, resuspended in ACN (5 mL), and reconcentrated to generate cis-4-((E)-2-(4-fluorobenzoylimino)-6-(morpholinomethyl)-2,3-dihydro-1H-benzo[d]imidazol-1-yl)cyclohexanecarbonyl chloride (0.50 g, 96% yield) as a white powder.

Step D: (E)-4-Fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene) benzamide To a 0° C. suspension of cis-4-((E)-2-(4-fluorobenzoylimino)-6-(morpholinomethyl)-2,3-dihydro-1H-benzo[d]imidazol-1-yl)cyclohexanecarbonyl chloride (50 mg, 0.100 mmol) in THF (1 mL) was added 2-amino-2-methylpropan-1-ol (17.8 mg, 0.401 mmol). The mixture was stirred for 1 hour at RT. The solvent was removed, and the residue was purified by reverse-phase preparative HPLC, using 0.1% $NH_4OH$ in ACN/water. The product fractions were combined and concentrated to provide (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide as a white powder (8.5 mg, 15.4% yield). MS, m/z ($C_{30}H_{38}FN_5O_4$): calcd, 551.3. found, 552.4 [M+H].

Example 200

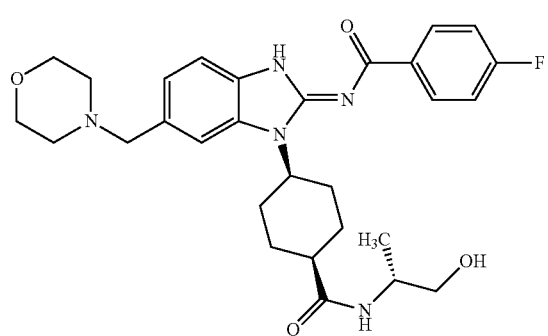 [SMILES: C[C@H](CO)NC(=O)[C@H]1CC[C@@H](n2/c(=N/C(=O)c3ccc(F)cc3)[nH]c3ccc(CN4CCOCC4)cc32)CC1]

(E)-4-Fluoro-N-(1-(cis-4-((R)-1-hydroxypropan-2-ylcarbamoyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and (R)-2-aminopropan-1-ol using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (26.5 mg, 49% yield). MS, m/z ($C_{29}H_{36}FN_5O_4$): calcd, 537.3. found, 538.4 [M+H].

Example 201

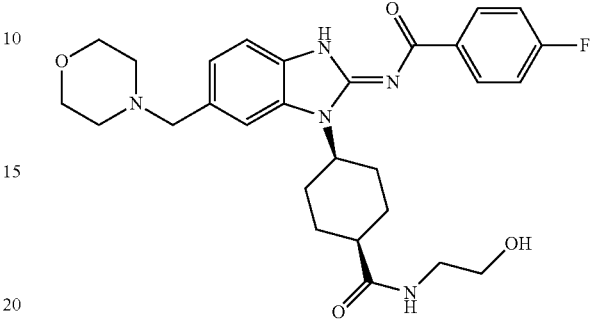

(E)-4-Fluoro-N-(1-(cis-4-(2-hydroxyethylcarbamoyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and 2-aminoethanol using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (25.3 mg, 48% yield). MS, m/z ($C_{28}H_{34}FN_5O_4$): calcd, 523.3. found, 524.3 [M+H].

Example 202

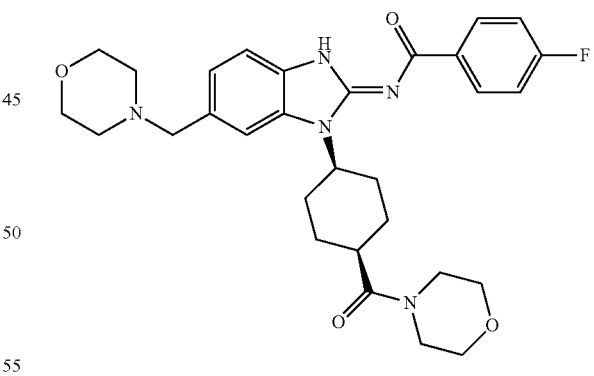

(E)-4-Fluoro-N-(1-(cis-4-(morpholine-4-carbonyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and morpholine using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (7.4 mg, 13% yield). MS, m/z ($C_{30}H_{36}FN_5O_4$): calcd, 549.3. found, 550.4 [M+H].

Example 203

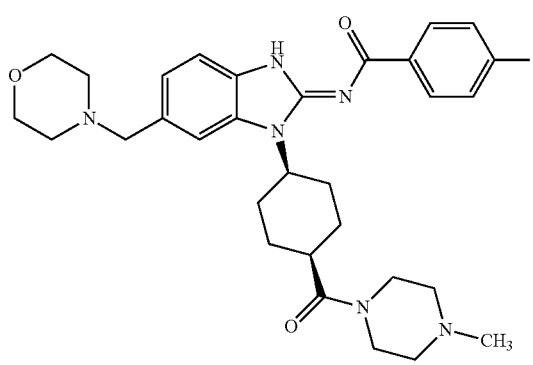

(E)-4-Fluoro-N-(1-(cis-4-(4-methylpiperazine-1-carbonyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and 1-methylpiperazine using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (15.2 mg, 27% yield). MS, m/z ($C_{31}H_{39}FN_6O_3$): calcd, 562.3. found, 563.4 [M+H].

Example 204

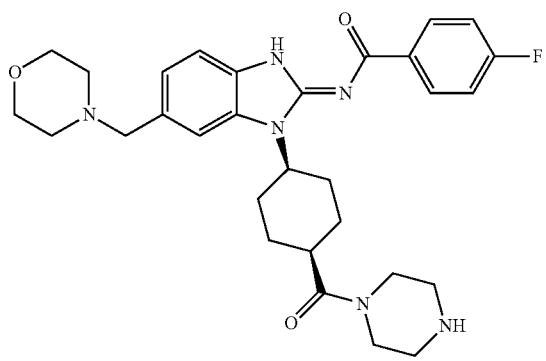 [SMILES: O=C(/N=c1\[nH]c2ccc(CN3CCOCC3)cc2n1[C@H]1CC[C@@H](C(=O)N2CCNCC2)CC1)c1ccc(F)cc1]

(E)-4-Fluoro-N-(6-(morpholinomethyl)-1-(cis-4-(piperazine-1-carbonyl)cyclohexyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and piperazine using a method analogous to that used in the preparation of (E)-4-fluoro-N-(1-(cis-4-(1-hydroxy-2-methylpropan-2-ylcarbamoyl)cyclohexyl)-6-(morpholinom-ethyl)-1H-benzo[d]imidazol-2(3H)-ylidene)benzamide (3.8 mg, 7% yield). $^1$H NMR (400 MHz, DMSO-$d_6$) δ ppm 1.63 (d, J=11.5 Hz, 2H), 1.73-1.84 (m, 2H), 1.95-2.03 (m, 2H), 2.39 (br. s., 4H), 2.73 (br. s., 4H), 2.79-2.94 (m, 2H), 3.03 (br. s., 1H), 3.46 (br. s., 2H), 3.51-3.65 (m, 9H), 4.83 (br. s., 1H), 7.15 (d, J=8.2 Hz, 1H), 7.24 (dd, J=8.9 Hz, 8.9 Hz, 2H), 7.48 (d, J=8.1 Hz, 1H), 7.68 (s, 1H), 8.33 (dd, J=8.6, 5.8 Hz, 2H). MS, m/z ($C_{30}H_{37}FN_6O_3$): calcd, 548.3. found, 549.4 [M+H].

Example 205

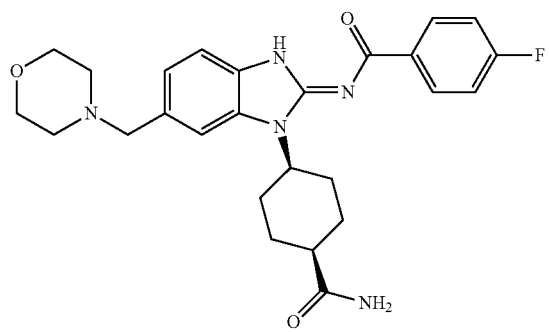 [SMILES: NC(=O)[C@H]1CC[C@@H](n2/c(=N/C(=O)c3ccc(F)cc3)[nH]c3ccc(CN4CCOCC4)cc32)CC1]

(E)-N-(1-(cis-4-Carbamoylcyclohexyl)-6-(morpholinomethyl)-1H-benzo[d]imidazol-2(3H)-ylidene)-4-fluorobenzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and 1 M ammonia in MeOH using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (19.5 mg, 40% yield). MS, m/z ($C_{26}H_{30}FN_5O_3$): calcd, 479.2. found, 480.2 [M+H].

Example 206

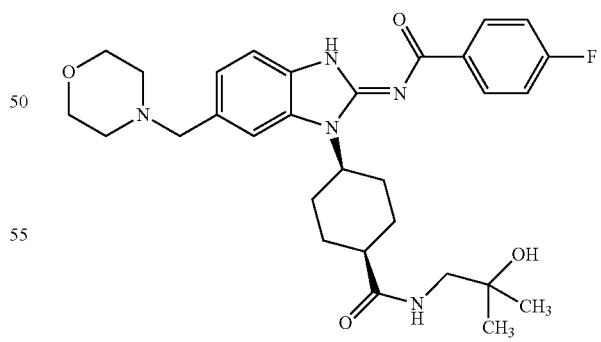

(E)-4-Fluoro-N-(1-(cis-4-(2-hydroxy-2-methylpropylcarbamoyl)-cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro- 1H-benzo[d]imidazol-1-yl)cyclohexanecarbonyl chloride and 1-amino-2-methylpropan-2-ol using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (26.4 mg, 48% yield). MS, m/z ($C_{30}H_{38}FN_5O_4$): calcd, 551.3. found, 552.4 [M+H].

Example 207

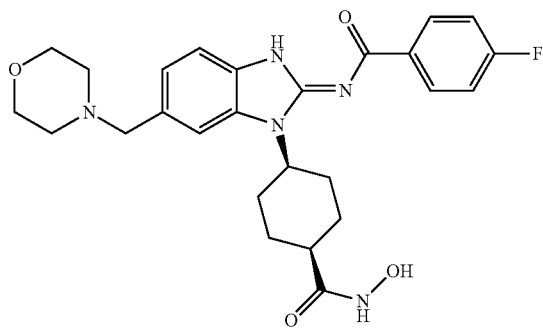 [SMILES: O=C(/N=c1\[nH]c2ccc(CN3CCOCC3)cc2n1[C@H]1CC[C@@H](C(=O)NO)CC1)c1ccc(F)cc1]

(E)-4-Fluoro-N-(1-(cis-4-(hydroxycarbamoyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and hydroxylamine using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (12.5 mg, 25% yield). MS, m/z ($C_{26}H_{30}FN_5O_4$): calcd, 495.2. found, 496.2 [M+H].

Example 208

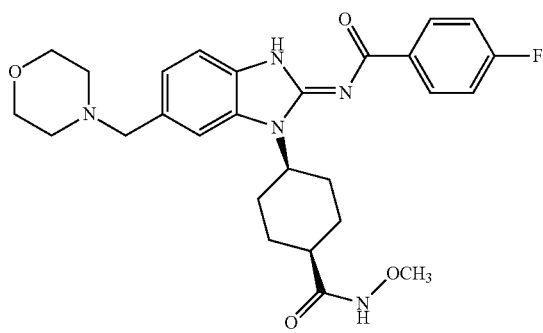 [SMILES: CONC(=O)[C@H]1CC[C@@H](n2/c(=N/C(=O)c3ccc(F)cc3)[nH]c3ccc(CN4CCOCC4)cc32)CC1]

(E)-4-Fluoro-N-(1-(cis-4-(methoxycarbamoyl)cyclohexyl)-6-(morpholinomethyl)-1H-benzo[d]imidazol-2(3H)-ylidene)benzamide The title compound was prepared from cis-4-((E)-2-(4-fluorobenzoylimino)-6-(morpholinomethyl)-2,3-dihydro-1H-benzo[d]imidazol-1-yl)cyclohexanecarbonyl chloride and O-methylhydroxylamine using a method analogous to that used in the preparation of (E)-4-fluoro-N-(1-(cis-4-(1-hydroxy-2-methylpropan-2-ylcarbamoyl)cyclohexyl)-6-(morpholinomethyl)-1H-benzo[d]imidazol-2(3H)-ylidene)benzamide (27.4 mg, 54% yield). MS, m/z ($C_{27}H_{32}FN_5O_4$): calcd, 509.2. found, 510.2 [M+H].

Example 209

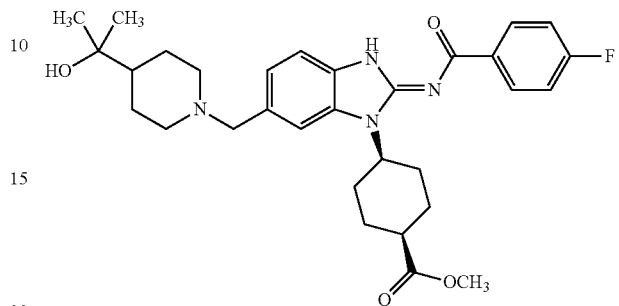

cis-Methyl 4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylate To a 0° C. cooled solution of cis-methyl 4-((E)-2-(4-fluorobenzoylimino)-6-(hydroxymethyl)-2,3-dihydro-1H-benzo[d]imidazol-1-yl)cyclohexanecarboxylate (1 g, 2.350 mmol) in DCM (25 mL) was added thionyl chloride (0.858 mL, 11.75 mmol) dropwise, and the reaction was stirred at 0° C. for 30 minutes. After 30 minutes, the solvent was removed at reduced pressure, and the residue was suspended in ACN (5 mL) and re-concentrated to remove residual thionyl chloride. The residue was resuspended in ACN (15 mL), cooled to 0° C., and 2-(piperidin-4-yl)propan-2-ol (1.010 g, 7.05 mmol) and TEA (0.655 mL, 4.70 mmol) were added. The reaction was stirred overnight at RT. After 16 hours, the reaction mixture was concentrated and partitioned between EtOAc and water. The organic layer was concentrated and the residual product was purified by column chromatography, eluting with 0-100% (90:9:1 DCM/MeOH/NH$_4$OH)/DCM to provide cis-methyl 4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylate as a white powder (1.05 g, 81% yield). $^1$H NMR (400 MHz, DMSO-d$_6$) δ ppm 1.03 (s, 6H), 1.09-1.35 (m, 3H), 1.56-1.91 (m, 8H), 2.21-2.29 (m, 2H), 2.53-2.64 (m, 2H), 2.77-2.95 (m, 3H), 3.50 (s, 2H), 3.77 (s, 3H), 3.99 (s, 1H), 4.74 (br. s., 1H), 7.14 (d, J=6.9 Hz, 1H), 7.26 (dd, J=8.8 Hz, 8.8 Hz, 2H), 7.37-7.58 (m, 2H), 8.26 (dd, J=8.7, 5.9 Hz, 2H), 12.77 (s, 1H). MS, m/z ($C_{31}H_{39}FN_4O_4$): calcd, 550.3. found, 551.1 [M+H].

Example 210

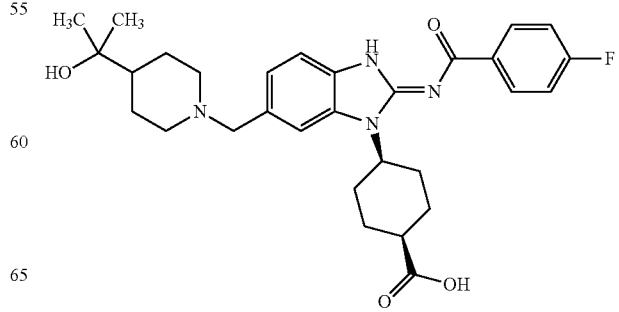

cis-4-((E)-2-(4-Fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid To a solution of cis-methyl 4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylate (1.05 g, 1.907 mmol) in MeOH (20 mL) was added 1 N aqueous NaOH (19.07 mL, 19.07 mmol). The solution was stirred overnight at RT. After 2 days, the reaction solution was concentrated, the pH was adjusted to 4 with 2 N aqueous HCl, and the mixture was extracted with 9:1 DCM/2-propanol. The organic layer was dried over anhydrous magnesium sulfate, filtered, and concentrated to generate cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid (1.01 g, 1.882 mmol, 99% yield) as a white powder. MS, m/z ($C_{30}H_{37}PN_4O_4$): calcd, 536.3. found, 537.0 [M+H].

Example 211

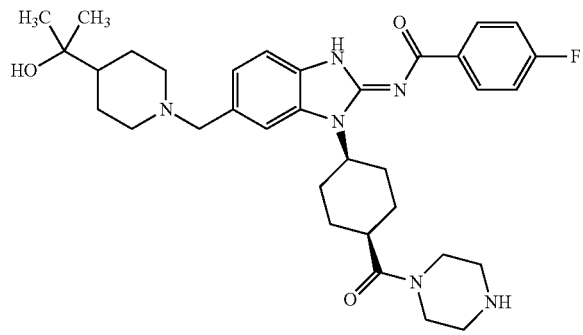 [SMILES: CC(C)(O)C1CCN(Cc2ccc3[nH]/c(=N\C(=O)c4ccc(F)cc4)n([C@H]4CC[C@@H](C(=O)N5CCNCC5)CC4)c3c2)CC1]

(E)-4-Fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide To a suspension of cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid (100 mg, 0.186 mmol) in DMF (3 mL) was added HATU (74.4 mg, 0.196 mmol) and DIPEA (0.036 mL, 0.205 mmol). The suspension was stirred for 15 minutes at RT. A solution of piperazine (161 mg, 1.863 mmol) in DMF (1 mL) was added, and the reaction was stirred at RT overnight. The reaction mixture was partitioned between water and EtOAc. The organic layer was concentrated and the residue purified by HPLC (15-90% ACN/0.1% TFA). The product fractions were combined, neutralized with saturated aqueous NaHCO$_3$, and extracted with EtOAc (×2). The combined organic layers were washed with brine, dried over anhydrous magnesium sulfate, filtered, and concentrated to provide (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide as a white powder (67 mg, 59.5% yield). MS, m/z ($C_{34}H_{45}FN_6O_3$): calcd, 604.3. found, 605.1 [M+H].

Example 212

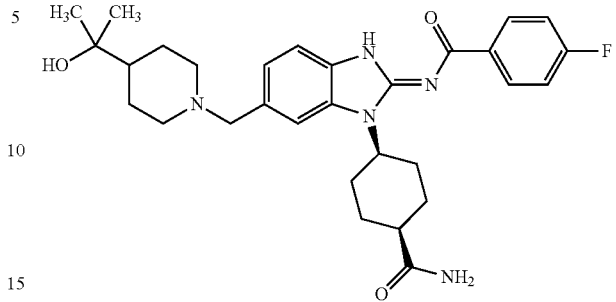

(E)-N-(1-(cis-4-Carbamoylcyclohexyl)-6-((4-(2-hydroxypropan-2-yl)piperidin-1-yl)methyl)-1H-benzo[d]imidazol-2(3H)-ylidene)-4-fluorobenzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid and 0.5-M ammonia in dioxane using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (68 mg, 68% yield). $^1$H NMR (400 MHz, DMSO-d$_6$) δ ppm 1.03 (s, 6H), 1.20-1.35 (m, 3H), 1.55-1.78 (m, 6H), 1.78-1.90 (m, 2H), 2.16-2.24 (m, 2H), 2.55 (br. s., 1H), 2.71-2.94 (m, 4H), 3.50 (br. s., 2H), 4.01 (s, 1H), 4.76 (br. s., 1H), 6.91 (br. s., 1H), 7.16 (d, J=7.6 Hz, 1H), 7.29 (dd, J=8.9 Hz, 8.9 Hz, 2H), 7.35 (s, 1H), 7.48 (d, J=8.4 Hz, 1H), 7.55 (s, 1H), 8.29 (dd, J=8.7, 6.1 Hz, 2H), 12.73 (br. s., 1H). MS, m/z ($C_{30}H_{38}FN_5O_3$): calcd, 535.3. found, 536.1 [M+H].

Example 213

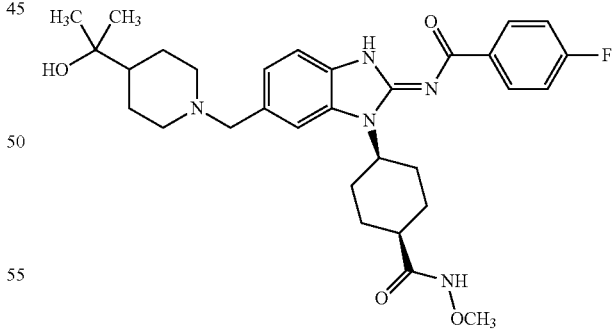

(E)-4-Fluoro-N-(6-((4-(2-hydroxypropan-2-yl)piperidin-1-yl)methyl)-1-(cis-4-(methoxycarbamoyl)cyclohexyl)-1H-benzo[d]imidazol-2(3H)-ylidene)benzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl) cyclohexanecarboxylic acid and O-methylhydroxylamine hydrochloride using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (76 mg, 72% yield). MS, m/z ($C_{31}H_{40}FN_5O_4$): calcd, 565.3. found, 566.1 [M+H].

Example 214

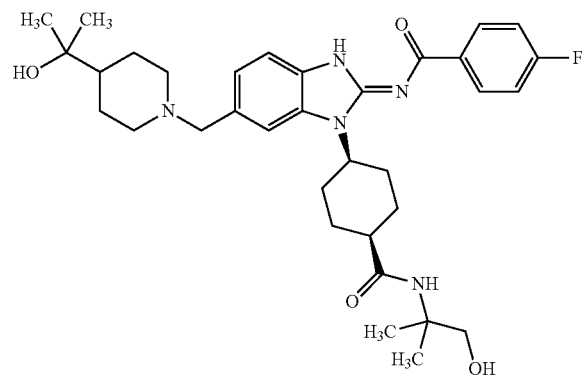 [SMILES: CC(C)(CO)NC(=O)[C@H]1CC[C@@H](n2/c(=N/C(=O)c3ccc(F)cc3)[nH]c3ccc(CN4CCC(C(C)(C)O)CC4)cc32)CC1]

(E)-4-Fluoro-N-(1-(cis-4-(1-hydroxy-2-methylpropan-2-ylcarbamoyl)cyclohexyl)-6-((4-(2-hydroxypropan-2-yl)piperidin-1-yl)methyl)-1H-benzo[d]imidazol-2(3H)-ylidene)benzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid and 2-amino-2-methylpropan-1-ol using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (76 mg, 72% yield). MS, m/z ($C_{34}H_{46}FN_5O_4$): calcd, 607.3. found, 608.1 [M+H].

Example 215

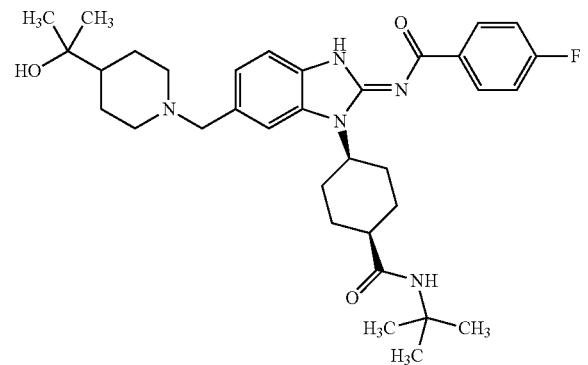 [SMILES: CC(C)(C)NC(=O)[C@H]1CC[C@@H](n2/c(=N/C(=O)c3ccc(F)cc3)[nH]c3ccc(CN4CCC(C(C)(C)O)CC4)cc32)CC1]

(E)-N-(1-(cis-4-(tert-Butylcarbamoyl)cyclohexyl)-6-((4-(2-hydroxypropan-2-yl)piperidin-1-yl)methyl)-1H-benzo[d]imidazol-2(3H)-ylidene)-4-fluorobenzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid and 2-methylpropan-2-amine using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (88 mg, 80% yield). MS, m/z ($C_{34}H_{46}FN_5O_3$): calcd, 591.4. found, 592.1 [M+H].

Example 216

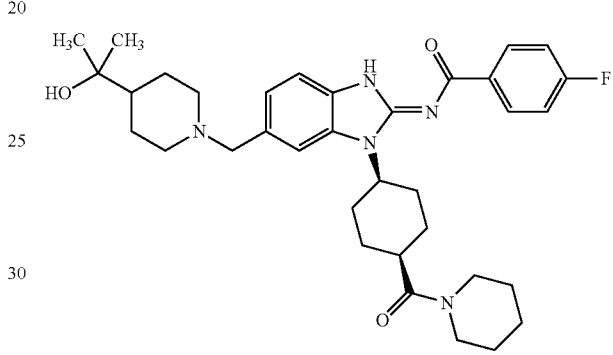

(E)-4-Fluoro-N-(6-((4-(2-hydroxypropan-2-yl)piperidin-1-yl)methyl)-1-(cis-4-(piperidine-1-carbonyl)cyclohexyl)-1H-benzo[d]imidazol-2(3H)-ylidene)benzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid and piperidine using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (80 mg, 71% yield). MS, m/z ($C_{35}H_{46}FN_5O_3$): calcd, 603.4. found, 604.1 [M+H].

Example 217

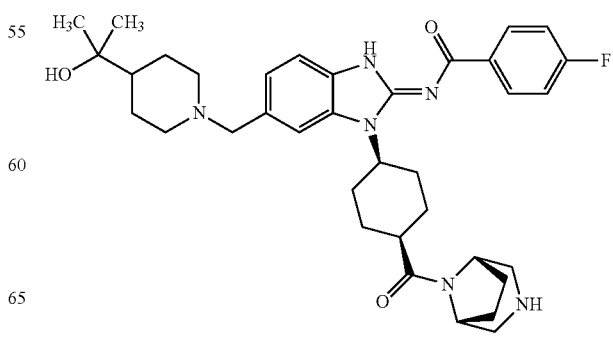

(E)-N-(1-(cis-4-(3,8-Fiazabicyclo[3.2.1]octane-8-carbonyl)cyclohexyl)-6-((4-(2-hydroxypropan-2-yl)piperidin-1-yl)methyl)-1H-benzo[d]imidazol-2(3H)-ylidene)-4-fluorobenzamide dihydrochloride Step A: tert-Butyl 8-(cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarbonyl)-3,8-diazabicyclo[3.2.1]octane-3-carboxylate The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid and tert-butyl 3,8-diazabicyclo[3.2.1]octane-3-carboxylate using a method analogous to that used in the preparation of (E)-4-fluoro-N-(6-((4-(2-hydroxypropan-2-yl)piperidin-1-yl)methyl)-1-(cis-4-(piperazine-1-carbonyl)cyclohexyl)-1H-benzo[d]imidazol-2(3H)-ylidene)benzamide (70 mg, 51% yield). MS, m/z ($C_{41}H_{55}FN_6O_5$): calcd, 730.4. found, 731.1 [M+H].

Step B: (E)-N-(1-(cis-4-(3,8-Diazabicyclo[3.2.1]octane-8-carbonyl)cyclohexyl)-6-((4-(2-hydroxypropan-2-yl)piperidin-1-yl)methyl)-1H-benzo[d]imidazol-2(3H)-ylidene)-4-fluorobenzamide dihydrochloride To a solution of tert-butyl 8-(cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarbonyl)-3,8-diazabicyclo[3.2.1]octane-3-carboxylate (70 mg, 0.096 mmol) in DCM (2 mL) was added 4 M HCl in dioxane (0.120 mL, 0.479 mmol). The suspension was stirred overnight at RT. After 16 hours, the reaction was concentrated to provide (E)-N-(1-(cis-4-(3,8-diazabicyclo[3.2.1]octane-8-carbonyl)cyclohexyl)-6-((4-(2-hydroxypropan-2-yl)piperidin-1-yl)methyl)-1H-benzo[d]imidazol-2(3H)-ylidene)-4-fluorobenzamide dihydrochloride as a white powder (68 mg, 101% yield). MS, m/z ($C_{36}H_{47}FN_6O_3 \cdot 2HCl$): calcd, 630.4. found, 631.2 [M+H].

Example 218

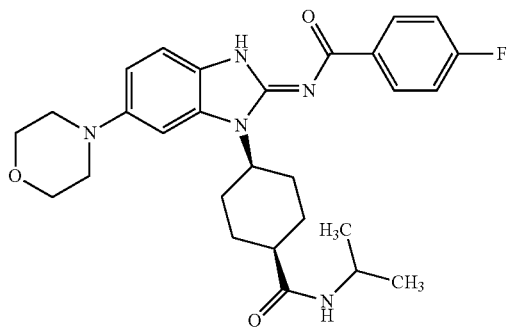 [SMILES: CC(C)NC(=O)[C@H]1CC[C@@H](n2/c(=N/C(=O)c3ccc(F)cc3)[nH]c3ccc(N4CCOCC4)cc32)CC1]

(E)-4-Fluoro-N-(1-(cis-4-(isopropylcarbamoyl)cyclohexyl)-6-morpholino-1H-benzo[d]imidazol-2(3H)-ylidene)benzamide Step A: cis-4-(5-Chloro-2-nitrophenylamino)-N-isopropylcyclohexane-carboxamide To a solution of cis-4-amino-N-isopropylcyclohexanecarboxamide hydrochloride (2.5 g, 11.33 mmol) and DIPEA (5.93 mL, 34.0 mmol) in ACN (25.2 mL) was added 4-chloro-2-fluoro-1-nitrobenzene (1.988 g, 11.33 mmol). The reaction mixture was stirred overnight at 80° C. After 16 hours, the reaction mixture was concentrated, and a large amount of yellow crystals formed in the flask. The crystals were collected by vacuum filtration, washed with ether, and dried in vacuo to generate 2.5 g of clean product. The filtrate was concentrated, and the residue was purified by column chromatography, eluting with 0-50% EtOAc in DCM, to provide an additional 0.84 g of product as a yellow powder, which was combined with the crystals to afford cis-4-(5-chloro-2-nitrophenylamino)-N-isopropylcyclohexane-carboxamide (3.33 g, 87% yield).

Step B: cis-N-Isopropyl-4-(5-morpholino-2-nitrophenylamino)-cyclohexanecarboxamide A suspension of cis-4-(5-chloro-2-nitrophenylamino)-N-isopropylcyclohexanecarboxamide (300 mg, 0.883 mmol) in morpholine (2 mL, 22.93 mmol) was irradiated in a microwave reactor for 1 hour at 150° C. The reaction mixture was partitioned between water and DCM. The organic layer was dried over anhydrous magnesium sulfate, filtered, and concentrated to a yellow oil. The residue was concentrated, adsorbed onto a plug of silica gel, and purified by column chromatography, eluting with 0-100% EtOAc in DCM, to provide cis-N-isopropyl-4-(5-morpholino-2-nitrophenylamino)cyclohexanecarboxamide as a yellow powder (0.38 g, 110% yield). MS, m/z ($C_{20}H_{30}N_4O_4$): calcd, 390.2. found, 390.9 [M+H].

Step C: cis-4-(2-Amino-6-morpholino-1H-benzo[d]imidazol-1-yl)-N-isopropylcyclohexanecarboxamide To a suspension of cis-N-isopropyl-4-(5-morpholino-2-nitrophenylamino)cyclohexanecarboxamide (380 mg, 0.973 mmol) in EtOH (10 mL) was added ammonium formate (614 mg, 9.73 mmol) and 10% palladium on carbon (104 mg, 0.097 mmol). The reaction was stirred at RT. After 1 hour, the reaction mixture was filtered through Celite® brand filter aid, concentrated, diluted with DCM, and washed with water and brine. The residue was concentrated and used in the next reaction without further purification.

The cis-4-(2-amino-5-morpholinophenylamino)-N-isopropylcyclohexanecarboxamide (315 mg, 0.874 mmol) was dissolved in EtOH (5 mL), and cyanogen bromide (139 mg, 1.311 mmol) was added. The reaction was stirred at RT. After 16 hours, the reaction was diluted with DCM (50 mL) and washed with 1 N aqueous NaOH. The organic layer was concentrated to provide cis-4-(2-amino-6-morpholino-1H-benzo[d]imidazol-1-yl)-N-isopropylcyclohexanecarboxamide as a light purple solid (210 mg, 62.3% yield). MS, m/z ($C_{21}H_{31}N_5O_2$): calcd, 385.2. found, 385.8 [M+H].

Step D: (E)-4-Fluoro-N-(1-(cis-4-(isopropylcarbamoyl)cyclohexyl)-6-morpholino-1H-benzo[d]imidazol-2(3H)-ylidene)benzamide To a solution of TEA (0.091 mL, 0.654 mmol) and 1H-benzo[d][1,2,3]triazol-1-ol hydrate (100 mg, 0.654 mmol) in DCM (2 mL) was added 4-fluorobenzoyl chloride (0.064 mL, 0.545 mmol) dropwise, and the reaction was stirred at RT for 30 minutes. After 30 minutes, the suspension was added to a solution of cis-4-(2-amino-6-morpholino-1H-benzo[d]imidazol-1-yl)-N-isopropylcyclohexanecarboxamide (210 mg, 0.545 mmol) in DCM (5 mL). The reaction was stirred at RT. After 3 days, the reaction mixture was concentrated, adsorbed onto a plug of silica gel, and purified by column chromatography, eluting with 0-10% MeOH in DCM, to provide (E)-4-fluoro-N-(1-(cis-4-(isopropylcarbamoyl)cyclohexyl)-6-morpholino-1H-benzo[d]imidazol-2(3H)-ylidene)benzamide as a grey powder (95 mg, 34.4% yield). $^1$H NMR (400 MHz, DMSO-$d_6$) δ ppm 12.57 (s, 1H), 8.29 (dd, J=6.1, 8.8 Hz, 2H), 7.73 (d, J=7.5 Hz, 1H), 7.44 (s, 1H), 7.39 (d, J=8.7 Hz, 1H), 7.24 (dd, J=8.8 Hz, 8.8 Hz, 2H), 6.87, (d, J=8.8 Hz, 1H), 4.94 (brs, 1H), 3.90-3.99 (m, 1H), 3.78 (t, J=4.7 Hz, 4H), 3.18 (t, J=4.8 Hz, 4H), 2.74-2.84 (m, 2H), 2.55 (brs, 1H), 2.03-2.11 (m, 2H), 1.67-1.78 (m, 2H), 1.54-1.63 (m, 2H), 1.10 (d, J=6.5 Hz, 6H). MS, m/z ($C_{28}H_{34}FN_5O_3$): calcd, 507.3. found, 507.9 [M+H].

Example 219

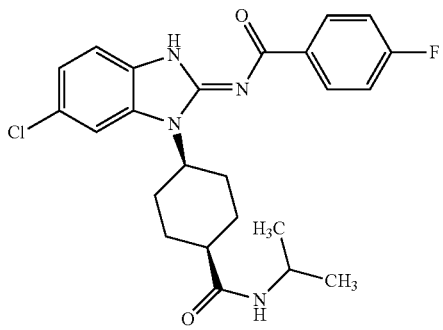 [SMILES: CC(C)NC(=O)[C@H]1CC[C@@H](n2/c(=N/C(=O)c3ccc(F)cc3)[nH]c3ccc(Cl)cc32)CC1]

(E)-N-(6-Chloro-1-(cis-4-(isopropylcarbamoyl)cyclohexyl)-1H-benzo[d]imidazol-2(3H)-ylidene)-4-fluorobenzamide Step A: cis-4-(2-Amino-6-chloro-1H-benzo[d]imidazol-1-yl)-N-isopropylcyclohexanecarboxamide To a solution of cis-4-(5-chloro-2-nitrophenylamino)-N-isopropylcyclohexanecarboxamide (2.27 g, 6.68 mmol) in EtOH (66.8 mL) was added tin(II) chloride dihydrate (6.03 g, 26.7 mmol). The reaction was stirred at 80° C. for 90 minutes. The reaction mixture was concentrated, and the residue was partitioned between EtOAc and 1 N aqueous NaOH. The organic layer was dried over anhydrous magnesium sulfate, filtered, and concentrated. The cis-4-(2-amino-5-chlorophenylamino)-N-isopropylcyclohexanecarboxamide intermediate (2.07 g, 6.68 mmol) was dissolved in EtOH (20 mL), and cyanogen bromide (1.061 g, 10.02 mmol) was added. The reaction was stirred at RT for 1 hour The reaction was diluted with 200 mL DCM and washed with 1 N aqueous NaOH. The organic layer was concentrated to provide cis-4-(2-amino-6-chloro-1H-benzo[d]imidazol-1-yl)-N-isopropylcyclohexanecarboxamide (2.77 g, 124% yield) as a brown oil. MS, m/z ($C_{17}H_{23}ClN_4O$): calcd, 334.2. found, 334.8 [M+H].

Step B: (E)-N-(6-Chloro-1-(cis-4-(isopropylcarbamoyl)cyclohexyl)-1H-benzo[d]imidazol-2(3H)-ylidene)-4-fluorobenzamide The title compound was prepared from cis-4-(2-amino-6-chloro-1H-benzo[d]imidazol-1-yl)-N-isopropylcyclohexanecarboxamide and 4-fluorobenzoyl chloride using a method analogous to that used in the preparation of (E)-4-fluoro-N-(1-(cis-4-(isopropylcarbamoyl)cyclohexyl)-6-morpholino-1H-benzo[d]imidazol-2(3H)-ylidene)benzamide (0.87 g, 28% yield). MS, m/z ($C_{24}H_{26}ClFN_4O_2$): calcd, 456.2. found, 456.9 [M+H].

Example 220

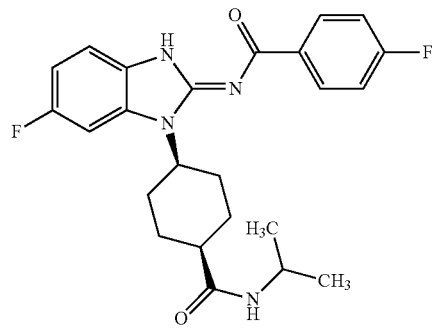 [SMILES: CC(C)NC(=O)[C@H]1CC[C@@H](n2/c(=N/C(=O)c3ccc(F)cc3)[nH]c3ccc(F)cc32)CC1]

(E)-4-Fluoro-N-(6-fluoro-1-(cis-4-(isopropylcarbamoyl)cyclohexyl)-1H-benzo[d]imidazol-2(3H)-ylidene)benzamide Step A: cis-4-(5-Fluoro-2-nitrophenylamino)-N-isopropylcyclohexane-carboxamide To a solution of cis-4-amino-N-isopropylcyclohexanecarboxamide hydrochloride (0.1 g, 0.453 mmol) and DIPEA (0.237 mL, 1.359 mmol) in ACN (3 mL) was added 2,4-difluoro-1-nitrobenzene (0.072 g, 0.453 mmol). The reaction was stirred overnight at 80° C. The reaction mixture was concentrated, adsorbed onto a plug of silica gel, and purified by column chromatography, eluting with 0-100% EtOAc in DCM, to provide cis-4-(5-fluoro-2-nitrophenylamino)-N-isopropylcyclohexanecarboxamide as a yellow powder (0.123 g, 84% yield).

Step B: (E)-4-Fluoro-N-(6-fluoro-1-(cis-4-(isopropylcarbamoyl)-cyclohexyl)-1H-benzo[d]imidazol-2(3H)-ylidene)benzamide To a solution of cis-4-(5-fluoro-2-nitrophenylamino)-N-isopropylcyclohexanecarboxamide (123 mg, 0.380 mmol) in EtOH (5 mL) was added ammonium formate (240 mg, 3.80 mmol) and 10% palladium on carbon (40.5 mg, 0.038 mmol). The reaction was stirred at RT for 1 hour. The reaction mixture was filtered through Celite® brand filter aid (washed with MeOH), concentrated, and redissolved in DCM (10 mL). The solution was washed with water, dried over anhydrous magnesium sulfate, filtered, and concentrated to afford cis-4-(2-amino-5-fluorophenylamino)-N-isopropylcyclohexanecarboxamide as a purple oil that crystallized upon standing. The diamine was dissolved in THF (5 mL), cooled to 0° C., and 4-fluorobenzoyl isothiocyanate (97 mg, 0.534 mmol) was added. The reaction was stirred at 0° C. for 15 minutes, and then DIPEA (0.100 mL, 0.573 mmol) and EDC (110 mg, 0.573 mmol) were added, and the reaction was stirred for 1 hour at 60° C. The reaction mixture was concentrated, adsorbed onto a plug of silica gel, and purified by column chromatography, eluting with 0-100% EtOAc in DCM, to provide (E)-4-fluoro-N-(6-fluoro-1-(cis-4-(isopropylcarbamoyl)cyclohexyl)-1H-benzo[d]imidazol-2(3H)-ylidene)benzamide as an off-white powder (137 mg, 81% yield). $^1$H NMR (400 MHz, DMSO-$d_6$) δ ppm 1.09 (d, J=6.7 Hz, 6H), 1.55-1.80 (m, 4H), 2.04-2.12 (m, 2H), 2.53 (br. s., 1H), 2.68-2.82 (m, 2H), 3.94-4.08 (m, 1H), 4.86 (br. s., 1H), 7.02-7.12 (m, 1H), 7.25 (dd, J=8.9 Hz, 8.9 Hz, 2H), 7.53 (dd, J=8.8, 4.9 Hz, 1H), 7.60 (dd, J=9.5, 1.9 Hz, 1H), 7.70 (d, J=7.4 Hz, 1H), 8.32 (dd, J=8.8, 5.9 Hz, 2H), 12.82 (s, 1H). MS, m/z ($C_{24}H_{26}F_2N_4O_2$): calcd, 440.2. found, 440.7 [M+H].

Example 221

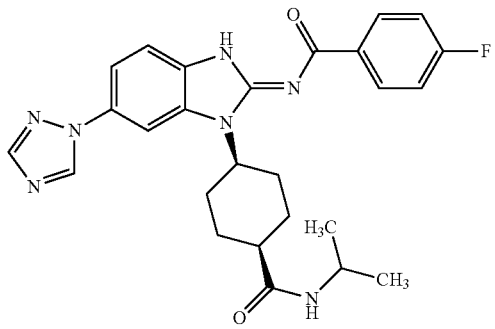 [SMILES: CC(C)NC(=O)[C@H]1CC[C@@H](n2/c(=N/C(=O)c3ccc(F)cc3)[nH]c3ccc(-n4cncn4)cc32)CC1]

(E)-4-Fluoro-N-(1-(cis-4-(isopropylcarbamoyl)cyclohexyl)-6-(1H-1,2,4-triazol-1-yl)-1H-benzo[d]imidazol-2(3H)-ylidene)benzamide Step A: cis-N-Isopropyl-4-(2-nitro-5-(1H-1,2,4-triazol-1-yl)phenylamino)-cyclohexanecarboxamide To a suspension of sodium hydride (70.6 mg, 2.94 mmol) and 1H-1,2,4-triazole (203 mg, 2.94 mmol) in NMP (1 mL) was added cis-4-(5-chloro-2-nitrophenylamino)-N-isopropylcyclohexanecarboxamide (100 mg, 0.294 mmol). The resulting suspension was irradiated in a microwave reactor for 1 hour at 150° C. The reaction mixture was partitioned between water and EtOAc. The aqueous layer was extracted with EtOAc (×2). The combined organic layers were then washed with brine, dried over anhydrous magnesium sulfate, filtered, and concentrated to provide a yellow oil that crystallized upon standing to provide cis-N-isopropyl-4-(2-nitro-5-(1H-1,2,4-triazol-1-yl)phenylamino)cyclohexanecarboxamide as a yellow solid (100 mg, 91% yield).

Step B: (E)-4-Fluoro-N-(1-(cis-4-(isopropylcarbamoyl)cyclohexyl)-6-(1H-1,2,4-triazol-1-yl)-1H-benzo[d]imidazol-2(3H)-ylidene)benzamide To a solution of cis-N-isopropyl-4-(2-nitro-5-(1H-1,2,4-triazol-1-yl)phenylamino)-cyclohexanecarboxamide (100 mg, 0.269 mmol) in EtOH (3 mL) was added tin(II) chloride dihydrate (242 mg, 1.074 mmol). The reaction was stirred at 80° C. After 3 hours, another four equivalents of tin(II) chloride dihydrate (242 mg, 1.074 mmol) was added, and the reaction was stirred at 80° C. for an additional 3 hours, and then at RT overnight. The reaction mixture was concentrated, and the residue was partitioned between EtOAc and 1 N aqueous sodium hydroxide. The aqueous layer was extracted with EtOAc; the combined organic layers were dried over anhydrous magnesium sulfate, filtered, and concentrated. The diamine was dissolved in THF (3 mL), cooled to 0° C., and 4-fluorobenzoyl isothiocyanate (53.5 mg, 0.296 mmol) was added. The reaction was stirred at 0° C. for 30 minutes, then DIPEA (0.070 mL, 0.403 mmol) and EDC (77 mg, 0.403 mmol) were added, and the reaction was stirred for 1 hour at 60° C. The residual material was concentrated, adsorbed onto a plug of silica gel, and purified by column chromatography, eluting with 20-100% EtOAc in DCM, to provide (E)-4-fluoro-N-(1-(cis-4-(isopropylcarbamoyl)cyclohexyl)-6-(1H-1,2,4-triazol-1-yl)-1H-benzo[d]imidazol-2(3H)-ylidene)benzamide as an off-white powder (44 mg, 33.5% yield). MS, m/z ($C_{26}H_{28}FN_7O_2$): Calc'd, 489.2. found, 489.9 [M+H].

Example 222

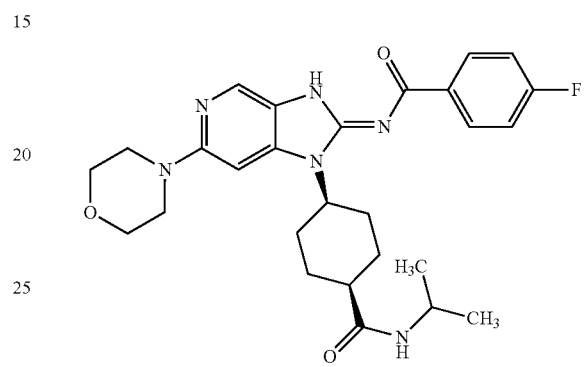

(E)-4-Fluoro-N-(1-(cis-4-(isopropylcarbamoyl)cyclohexyl)-6-morpholino-1H-imidazo[4,5-c]pyridin-2(3H)-ylidene)benzamide Step A: cis-N-Isopropyl-4-(2-morpholino-5-nitropyridin-4-ylamino)cyclohexane-carboxamide A suspension of cis-4-(2-chloro-5-nitropyridin-4-ylamino)-N-isopropylcyclohexanecarboxamide (100 mg, 0.293 mmol) and morpholine (0.256 mL, 2.93 mmol) in 2-propanol (1 mL) was irradiated in the microwave for 1 hour at 150° C. The reaction mixture was concentrated, adsorbed onto a plug of silica gel, and purified by column chromatography, eluting with 0-100% EtOAc in DCM, to provide cis-N-isopropyl-4-(2-morpholino-5-nitropyridin-4-ylamino)cyclohexanecarboxamide as a yellow powder (121 mg, quantitative yield). MS, m/z ($C_{19}H_{29}N_5O_4$): Calcd, 508.3. found, 509.1 [M+H].

Step B: (E)-4-Fluoro-N-(1-(cis-4-(isopropylcarbamoyl)cyclohexyl)-6-morpholino-1H-imidazo[4,5-c]pyridin-2(3H)-ylidene)benzamide To a solution of cis-N-isopropyl-4-(2-morpholino-5-nitropyridin-4-ylamino)cyclohexanecarboxamide (121 mg, 0.309 mmol) in EtOH (5 mL) and EtOAc (3 mL) was added 10% palladium on carbon (32.9 mg, 0.031 mmol). The reaction was stirred under a hydrogen atmosphere ($H_2$ balloon) at RT. After 3 hours, the reaction mixture was filtered through Celite® brand filter aid (washed with MeOH and DCM), and concentrated to afford cis-4-(5-amino-2-morpholinopyridin-4-ylamino)-N-isopropylcyclohexane-carboxamide as a dark oil. The diamine was dissolved in THF (3 mL), and 4-fluorobenzoyl isothiocyanate (61.8 mg, 0.341 mmol) was added. The reaction was stirred at 0° C. for 15 minutes, and then EDC (89 mg, 0.465 mmol) and DIPEA (0.081 mL, 0.465 mmol) were added. The reaction was stirred at 60° C. for 2 hours and then overnight at RT. After 16 hours, the reaction mixture was concentrated, and adsorbed onto a plug of silica gel. The residue was purified by column chromatography, eluting with 0-100% EtOAc in DCM, to provide (E)-4-fluoro-N-(1-(cis-4-(isopropylcarbamoyl)cyclohexyl)-6-morpholino-1H-imidazo[4,5-c]pyridin-2(3H)-ylidene)benzamide as a light-yellow powder (38 mg, 24.11% yield). MS, m/z ($C_{27}H_{33}FN_6O_3$): calcd, 508.3. found, 509.1 [M+H].

Example 223

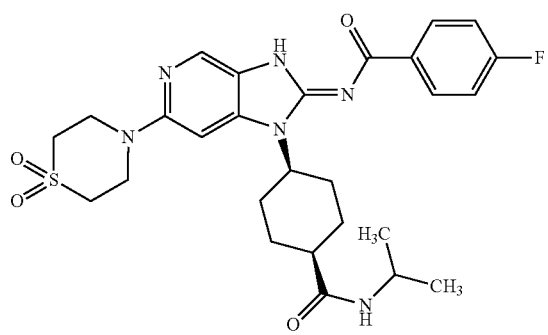 [SMILES: CC(C)NC(=O)[C@H]1CC[C@@H](n2/c(=N/C(=O)c3ccc(F)cc3)[nH]c3cnc(N4CCS(=O)(=O)CC4)cc32)CC1]

N-((2E)-6-(1,1-Dioxido-4-thiomorpholinyl)-1-(cis-4-((1-methylethyl)carbamoyl)cyclohexyl)-1,3-dihydro-2H-imidazo[4,5-c]pyridin-2-ylidene)-4-fluorobenzamide Step A: cis-N-Isopropyl-4-(5-nitro-2-(1,1-dioxido-4-thiomorpholinyl)pyridin-4-ylamino)cyclohexanecarboxamide A suspension of cis-4-(2-chloro-5-nitropyridin-4-ylamino)-N-isopropylcyclohexanecarboxamide (100 mg, 0.293 mmol) and thiomorpholine-1,1-dioxide (198 mg, 1.467 mmol) in 2-propanol (1 mL) was irradiated in the microwave for 90 minutes at 170° C. The reaction mixture was concentrated, adsorbed onto a plug of silica gel, and purified by column chromatography, eluting with 0-100% EtOAc in DCM, to provide cis-N-isopropyl-4-(5-nitro-2-(1,1-dioxido-4-thiomorpholinyl)pyridin-4-ylamino)cyclohexanecarboxamide as a yellow powder (112 mg, 87% yield). MS, m/z ($C_{19}H_{29}N_5O_5S$): Calcd, 439.2. found, 440.1 [M+H].

Step B: N-((2E)-6-(1,1-Dioxido-4-thiomorpholinyl)-1-(cis-4-((1-methylethyl)carbamoyl)cyclohexyl)-1,3-dihydro-2H-imidazo[4,5-c]pyridin-2-ylidene)-4-fluorobenzamide The title compound was prepared in 2 steps from cis-N-isopropyl-4-(5-nitro-2-(1,1-dioxido-4-thiomorpholinyl)pyridin-4-ylamino)cyclohexanecarboxamide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide as a light-yellow powder (24 mg, 17% yield). $^1$H NMR (400 MHz, DMSO-$d_6$) δ ppm 1.08 (d, J=6.6 Hz, 6H), 1.52-1.81 (m, 4H), 1.93-2.12 (m, 2H), 2.54 (br. s., 1H), 2.73-2.90 (m, 2H), 3.12 (br. s., 4H), 3.92-4.07 (m, 1H), 4.14 (br. s., 4H), 4.87 (br. s., 1H), 7.20-7.32 (m, 2H), 7.50 (s, 1H), 7.78 (d, J=7.6 Hz, 1H), 7.89-7.99 (m, 1H), 8.30 (br. s., 2H), 12.61 (br. s., 1H). MS, m/z ($C_{27}H_{33}FN_6O_4S$): calcd, 556.2. found, 557.1 [M+H].

Example 224

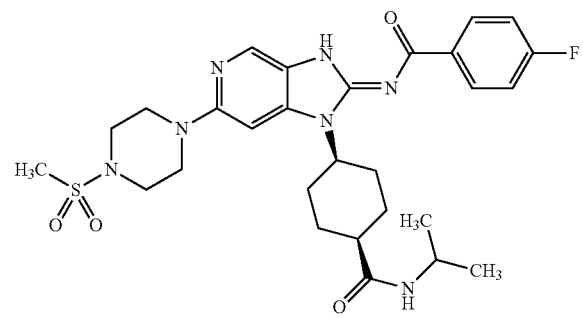 [SMILES: CC(C)NC(=O)[C@H]1CC[C@@H](n2/c(=N/C(=O)c3ccc(F)cc3)[nH]c3cnc(N4CCN(S(C)(=O)=O)CC4)cc32)CC1]

(E)-4-Fluoro-N-(1-(cis-4-(isopropylcarbamoyl)cyclohexyl)-6-(4-(methylsulfonyl)-piperazin-1-yl)-1H-imidazo[4,5-c]pyridin-2(3H)-ylidene)benzamide Step A: cis-N-Isopropyl-4-(2-(4-(methylsulfonyl)piperazin-1-yl)-5-nitropyridin-4-ylamino)cyclohexanecarboxamide The title compound was prepared using a method analogous to the preparation of cis-N-isopropyl-4-(2-morpholino-5-nitropyridin-4-ylamino)cyclohexane-carboxamide as a yellow powder (133 mg, 97% yield). MS, m/z ($C_{20}H_{32}N_6O_5S$): calcd, 468.2. found, 468.9 [M+H].

Step B: (E)-4-Fluoro-N-(1-(cis-4-(isopropylcarbamoyl)cyclohexyl)-6-(4-(methylsulfonyl)piperazin-1-yl)-1H-imidazo[4,5-c]pyridin-2(3H)-ylidene)benzamide The title compound was prepared in 2 steps from cis-N-isopropyl-4-(2-(4-(methylsulfonyl)piperazin-1-yl)-5-nitropyridin-4-ylamino)cyclohexanecarboxamide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide (125 mg, 76% yield). MS, m/z ($C_{28}H_{36}FN_7O_4S$): calcd, 585.2. found, 585.9 [M+H].

Example 225

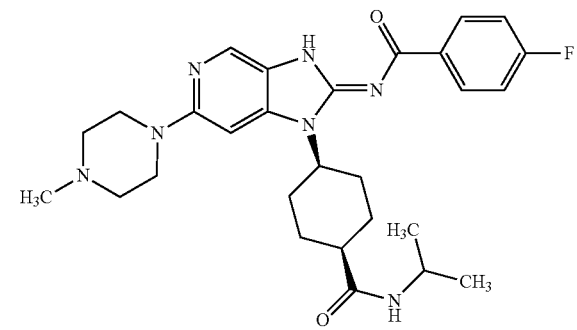 [SMILES: CC(C)NC(=O)[C@H]1CC[C@@H](n2/c(=N/C(=O)c3ccc(F)cc3)[nH]c3cnc(N4CCN(C)CC4)cc32)CC1]

(E)-4-Fluoro-N-(1-(cis-4-(isopropylcarbamoyl)cyclohexyl)-6-(4-methylpiperazin-1-yl)-1H-imidazo[4,5-c]pyridin-2(3H)-ylidene)benzamide Step A: cis-N-Isopropyl-4-(2-(4-methylpiperazin-1-yl)-5-nitropyridin-4-ylamino)cyclohexanecarboxamide The title compound was prepared using a method analogous to the preparation of cis-N-isopropyl-4-(2-morpholino-5-nitropyridin-4-ylamino)cyclohexane-carboxamide to provide cis-N-isopropyl-4-(2-(4-methylpiperazin-1-yl)-5-nitropyridin-4-ylamino)cyclohexanecarboxamide as a yellow powder (123 mg, quantitative yield). MS, m/z ($C_{20}H_{32}N_6O_3$): calcd, 404.2. found, 405.0 [M+H].

Step B: (E)-4-Fluoro-N-(1-(cis-4-(isopropylcarbamoyl)cyclohexyl)-6-(4-methylpiperazin-1-yl)-1H-imidazo[4,5-c]pyridin-2(3H)-ylidene)benzamide The title compound was prepared in 2 steps from cis-N-isopropyl-4-(2-(4-methylpiperazin-1-yl)-5-nitropyridin-4-ylamino)cyclohexanecarboxamide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide (139 mg, 88% yield). MS, m/z ($C_{28}H_{36}FN_7O_2$): calcd, 521.3. found, 522.0 [M+H].

Example 226

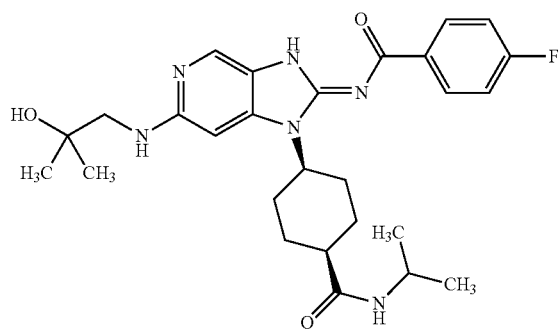 [SMILES: CC(C)NC(=O)[C@H]1CC[C@@H](n2/c(=N/C(=O)c3ccc(F)cc3)[nH]c3cnc(NCC(C)(C)O)cc32)CC1]

(E)-4-Fluoro-N-(6-(2-hydroxy-2-methylpropylamino)-1-(cis-4-(isopropylcarbamoyl)cyclohexyl)-1H-imidazo[4,5-c]pyridin-2(3H)-ylidene)benzamide Step A: cis-4-(2-(2-Hydroxy-2-methylpropylamino)-5-nitropyridin-4-ylamino)-N-isopropylcyclohexanecarboxamide The title compound was prepared using a method analogous to the preparation of cis-N-isopropyl-4-(2-morpholino-5-nitropyridin-4-ylamino)cyclohexane-carboxamide. The product was obtained as a yellow powder (90 mg, 78% yield). MS, m/z ($C_{19}H_{31}N_5O_4$): calcd, 393.2. found, 394.2 [M+H].

Step B: (E)-4-Fluoro-N-(6-(2-hydroxy-2-methylpropylamino)-1-(cis-4-(isopropylcarbamoyl)cyclohexyl)-1H-imidazo[4,5-c]pyridin-2(3H)-ylidene)benzamide The title compound was prepared in 2 steps from (cis-4-(2-(2-hydroxy-2-methylpropylamino)-5-nitropyridin-4-ylamino)-N-isopropylcyclohexanecarboxamide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide (32 mg, 27.4% yield). $^1$H NMR (400 MHz, DMSO-$d_6$) δ ppm 1.09 (d, J=6.6 Hz, 6H), 1.17 (s, 6H), 1.55-1.77 (m, 4H), 2.03-2.11 (m, 2H), 2.53-2.56 (m, 1H), 2.70-2.81 (m, 2H), 3.19 (d, J=6.0 Hz, 2H), 3.92-4.08 (m, 1H), 4.65 (s, 1H), 4.74 (br. s., 1H), 5.80 (t, J=5.8 Hz, 1H), 6.80 (s, 1H), 7.24 (dd, J=8.9 Hz, 8.9 Hz, 2H), 7.71 (d, J=8.0 Hz, 1H), 8.11 (s, 1H), 8.29 (dd, J=8.9, 5.9 Hz, 2H), 12.48 (s, 1H). MS, m/z ($C_{27}H_{35}FN_6O_3$): calcd, 510.3. found, 511.2 [M+H].

Example 227

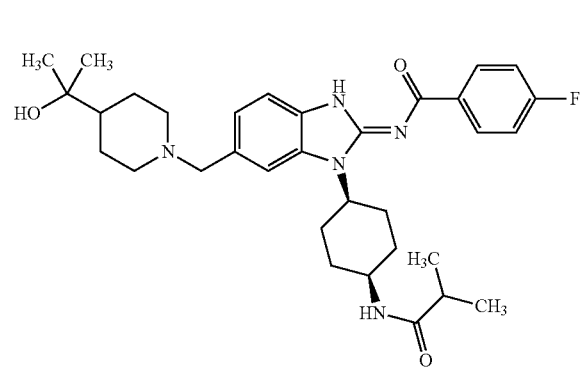 [SMILES: CC(C)C(=O)N[C@H]1CC[C@@H](n2/c(=N/C(=O)c3ccc(F)cc3)[nH]c3ccc(CN4CCC(C(C)(C)O)CC4)cc32)CC1]

(E)-4-Fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide Step A: N-(cis-4-Aminocyclohexyl)isobutyramide hydrochloride To a solution of tert-butyl cis-4-aminocyclohexylcarbamate (500 mg, 2.333 mmol) in DCM (20 mL) was added isobutyric anhydride (0.407 mL, 2.450 mmol). The solution was stirred overnight at RT. After 16 hours, 4 M HCl in dioxane (2.333 mL, 9.33 mmol) was added, and the reaction was stirred at RT overnight. The resulting white precipitate was collected by vacuum filtration and dried in vacuo to generate N-(cis-4-aminocyclohexyl)isobutyramide hydrochloride as an off-white powder (508 mg, 99% yield).

Step B: N-(cis-4-(5-(Hydroxymethyl)-2-nitrophenylamino)cyclohexyl)-isobutyramide To a suspension of N-(cis-4-aminocyclohexyl)isobutyramide hydrochloride (200 mg, 0.906 mmol) and DIPEA (0.432 mL, 2.471 mmol) in ACN (2 mL) was added (3-fluoro-4-nitrophenyl)methanol (141 mg, 0.824 mmol). The reaction was stirred overnight at 80° C. After 16 hours, the reaction mixture was concentrated and the residue purified by column chromatography, eluting with 0-100% EtOAc in DCM, to provide N-(cis-4-(5-(hydroxymethyl)-2-nitrophenylamino)cyclohexyl)isobutyramide as an orange foam (176 mg, 63.7% yield). MS, m/z ($C_{17}H_{25}N_3O_4$): calcd, 335.2. found, 336.0 [M+H].

Step C: (E)-4-Fluoro-N-(6-(hydroxymethyl)-1-(cis-4-isobutyramidocyclohexyl)-1H-benzo[d]imidazol-2(3H)-ylidene)benzamide The desired compound was prepared in 2 steps from N-(cis-4-(5-(hydroxymethyl)-2-nitrophenylamino)cyclohexyl)isobutyramide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide (75 mg, 63.3% yield). MS, m/z ($C_{25}H_{29}FN_4O_3$): calcd, 452.2. found, 453.0 [M+H].

Step D: (E)-4-Fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide To a 0° C. cooled solution of (E)-4-fluoro-N-(6-(hydroxymethyl)-1-(cis-4-isobutyramidocyclohexyl)-1H-benzo[d]imidazol-2(3H)-ylidene)benzamide (75 mg, 0.166 mmol) in DCM (5 mL) was added thionyl chloride (0.060 mL, 0.829 mmol) dropwise. The resulting mixture was stirred at 0° C. for 30 minutes. After 30 minutes, the solvent was removed, and the residue was suspended in ACN (5 mL) and re-concentrated to remove residual thionyl chloride. The residue was resuspended in ACN (3 mL), cooled to 0° C., and 2-(piperidin-4-yl)propan-2-ol (95 mg, 0.663 mmol) was added. The reaction was stirred overnight at RT. After 16 hours, the reaction mixture was concentrated and partitioned between EtOAc and water. The organic layer was concentrated and the residue was purified by column chromatography, eluting with 0-100% (90:9:1 DCM/MeOH/NH$_4$OH) in DCM to provide (E)-4-fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide as a white powder (30 mg, 31.3% yield). MS, m/z ($C_{33}H_{44}FN_5O_3$): calcd, 577.3. found, 578.1 [M+H].

Example 228

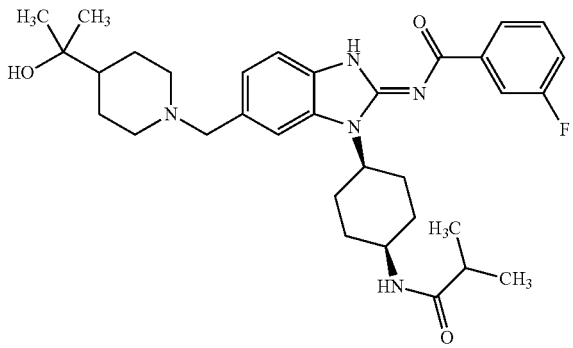 [SMILES: CC(C)C(=O)N[C@H]1CC[C@@H](n2/c(=N/C(=O)c3cccc(F)c3)[nH]c3ccc(CN4CCC(C(C)(C)O)CC4)cc32)CC1]

(E)-3-Fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide The title compound was prepared from (E)-4-fluoro-N-(6-(hydroxymethyl)-1-(cis-4-isobutyramidocyclohexyl)-1H-benzo[d]imidazol-2(3H)-ylidene)benzamide and 2-(piperidin-4-yl)propan-2-ol using a method analogous to that used in the preparation of (E)-4-fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide (58 mg, 46.4% yield). MS, m/z ($C_{33}H_{44}FN_5O_3$): calcd, 577.3. found, 578.1 [M+H].

Example 229

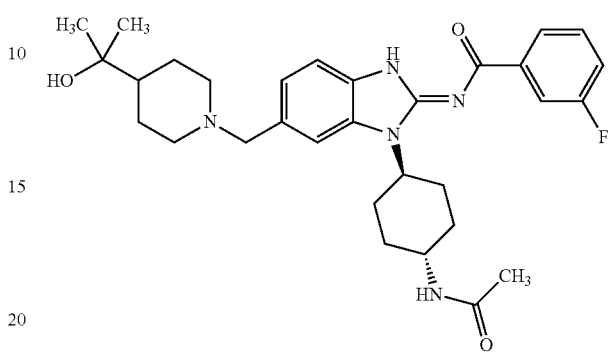

(E)-N-(1-(trans-4-Acetamidocyclohexyl)-6-((4-(2-hydroxypropan-2-yl)piperidin-1-yl)methyl)-1H-benzo[d]imidazol-2(3H)-ylidene)-4-fluorobenzamide Step A: N-(trans-4-Aminocyclohexyl)acetamide hydrochloride To a solution of tert-butyl trans-4-aminocyclohexylcarbamate (500 mg, 2.333 mmol) in DCM (20 mL) was added acetic anhydride (0.231 mL, 2.450 mmol). The solution was stirred overnight at RT. After 16 hours, 4 M HCl in dioxane (2.333 mL, 9.33 mmol) was added, and the reaction was stirred at RT for 3 days. The resulting white solid was collected by vacuum filtration and dried in vacuo to generate N-(trans-4-aminocyclohexyl)acetamide hydrochloride as a white powder (0.49 g, 109% yield).

Step B: N-(trans-4-(5-(Hydroxymethyl)-2-nitrophenylamino)cyclohexyl)-acetamide

To a suspension of N-(trans-4-aminocyclohexyl)acetamide hydrochloride (200 mg, 1.038 mmol) and DIPEA (0.494 mL, 2.83 mmol) in ACN (2 mL) was added (3-fluoro-4-nitrophenyl)methanol (161 mg, 0.944 mmol). The resulting mixture was stirred overnight at 80° C. After 16 hours, the reaction was concentrated and the residue purified by column chromatography, eluting with 0-10% MeOH in DCM, to provide N-(trans-4-(5-(hydroxymethyl)-2-nitrophenylamino)cyclohexyl)acetamide as a yellow powder (50 mg, 17.24% yield). MS, m/z ($C_{15}H_{21}N_3O_4$): calcd, 307.2. found, 308.1 [M+H].

Step C: (E)-N-(1-(trans-4-Acetamidocyclohexyl)-6-(hydroxymethyl)-1H-benzo[d]imidazol-2(3H)-ylidene)-4-fluorobenzamide The title compound was prepared in 2 steps from N-(trans-4-(5-(hydroxymethyl)-2-nitrophenylamino)cyclohexyl)-acetamide using a method analogous to that used in the preparation of (E)-4-fluoro-N-(1-(cis-4-(isopropylcarbamoyl)cyclohexyl)-6-morpholino-1H-imidazo[4,5-c]pyridin-2(3H)-ylidene)benzamide (41 mg, 53.6% yield). MS, m/z ($C_{23}H_{25}FN_4O_3$): calcd, 424.2. found, 425.1 [M+H].

Step D: (E)-N-(1-(trans-4-Acetamidocyclohexyl)-6-((4-(2-hydroxypropan-2-yl)piperidin-1-ylmethyl)-1H-benzo[d]imidazol-2(3H)-ylidene)-4-fluorobenzamide The title compound was prepared from (E)-N-(1-(trans-4-acetamidocyclohexyl)-6-(hydroxymethyl)-1H-benzo[d]imidazol-2(3H)-ylidene)-4-fluorobenzamide and 2-(piperidin-4-yl)propan-2-ol using a method analogous to that used in the preparation of (E)-4-fluoro-N-(6-((4-(2-hydroxypropan-2-yl)piperidin-1-yl)methyl)-1-(cis-4-isobutyramidocyclohexyl)-1H-benzo[d]imidazol-2(3H)-ylidene)benzamide (11 mg, 20.7% yield). $^1$H NMR (400 MHz, DMSO-d$_6$) δ ppm 1.02 (s, 6H), 1.13-1.30 (m, 5H), 1.40-1.54 (m, 2H), 1.60-1.68 (m, 2H), 1.76-1.91 (m, 7H), 1.97-2.06 (m, 2H), 2.85-2.94 (m, 2H), 3.53 (s, 2H), 3.82 (br. s., 1H), 3.99 (s, 1H), 4.83 (br. s., 1H), 7.16 (d, J=7.3 Hz, 1H), 7.28 (dd, J=8.9 Hz, 8.9 Hz, 2H), 7.48 (d, J=7.9 Hz, 1H), 7.60 (s, 1H), 7.81 (d, J=7.3 Hz, 1H), 8.20-8.29 (m, 2H), 12.76 (br. s., 1H). MS, m/z (C$_{31}$H$_{40}$FN$_5$O$_3$): calcd, 549.3. found, 550.2 [M+H].

Example 230

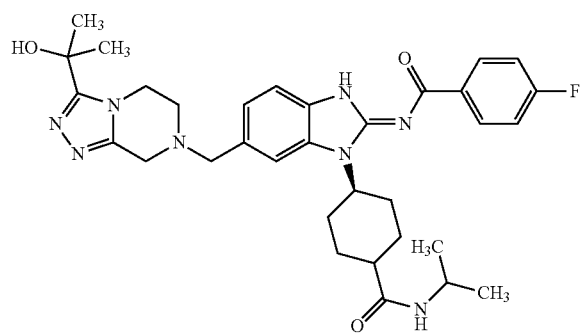

(E)-4-Fluoro-N-(6-((3-(2-hydroxypropan-2-yl)-5,6-dihydro-[1,2,4]-triazolo[4,3-a]pyrazin-7(8H)-yl)methyl)-1-(cis-4-(isopropylcarbamoyl)cyclohexyl)-1H-benzo[d]imidazol-2(3H)-ylidene)benzamide

Step A: tert-Butyl 3-(2-hydroxypropan-2-yl)-5,6-dihydro-[1,2,4]triazolo[4,3-a]pyrazine-7(8H)-carboxylate To a solution of 7-tert-butyl 3-ethyl 5,6-dihydro-[1,2,4]triazolo[4,3-a]pyrazine-3,7(8H)-dicarboxylate (0.9 g, 3.04 mmol) in THF (20 mL) at 0° C., was added 3 M methylmagnesium iodide in diethyl ether (3.04 mL, 9.11 mmol) dropwise. The reaction was stirred overnight at RT. After 16 hours, the reaction was quenched with saturated aqueous ammonium chloride and extracted with EtOAc. The organic layer was concentrated to provide tert-butyl 3-(2-hydroxypropan-2-yl)-5,6-dihydro-[1,2,4]triazolo[4,3-a]pyrazine-7(8H)-carboxylate as a white powder (0.4 g, 46.6% yield).

Step B: 2-(5,6,7,8-Tetrahydro-[1,2,4]triazolo[4,3-a]pyrazin-3-yl)propan-2-ol dihydrochloride To a solution of tert-butyl 3-(2-hydroxypropan-2-yl)-5,6-dihydro-[1,2,4]triazolo[4,3-a]pyrazine-7(8H)-carboxylate (0.40 g, 1.417 mmol) in DCM (10 mL) at 0° C., was added 2 M HCl in diethyl ether (3.54 mL, 7.08 mmol) dropwise. The reaction was stirred overnight at RT. After 16 hours, the white precipitate was collected by vacuum filtration, washed with ether, and dried in vacuo. The residue was resuspended in 1,4-dioxane (10 mL) and 4 M HCl in dioxane (1.78 mL, 7.08 mmol) was added. The mixture was heated to 60° C. and stirred vigorously overnight. After 16 hours, the suspension was concentrated to a white powder and dried in vacuo to generate 2-(5,6,7,8-tetrahydro-[1,2,4]triazolo[4,3-a]pyrazin-3-yl)propan-2-ol dihydrochloride (0.373 g, 103% yield).

Step C: (E)-4-Fluoro-N-(6-((3-(2-hydroxypropan-2-yl)-5,6-dihydro-1,2,41-triazolo[4,3-a]pyrazin-7(8H)-yl)methyl)-1-(cis-4-(isopropylcarbamoyl)cyclohexyl)-1H-benzo[d]imidazol-2(3H)-ylidene)benzamide To a 0° C. cooled solution of (E)-4-fluoro-N-(6-(hydroxymethyl)-1-(cis-4-(isopropylcarbamoyl)cyclohexyl)-1H-benzo[d]imidazol-2(3H)-ylidene)benzamide (100 mg, 0.221 mmol) in DCM (5 mL) was added thionyl chloride (0.081 mL, 1.105 mmol) dropwise, and the reaction was stirred at 0° C. for 30 minutes. After 30 minutes, the solvent was removed at reduced pressure, and the residue was suspended in ACN (2 mL) and re-concentrated to remove residual thionyl chloride. The residue was added to a suspension of the 2-(5,6,7,8-tetrahydro-[1,2,4]triazolo[4,3-a]pyrazin-3-yl)propan-2-ol dihydrochloride (169 mg, 0.663 mmol) and potassium carbonate (244 mg, 1.768 mmol) in 4 mL DMF. The reaction was stirred overnight at RT. After 16 hours, the reaction mixture was partitioned between water and EtOAc. The aqueous layer was extracted with EtOAc. The combined organic layers were washed with water and brine, and concentrated to a brown oil. The residue was purified by HPLC (0.1% NH$_4$OH in ACN/water) to generate (E)-4-fluoro-N-(6-((3-(2-hydroxypropan-2-O-5,6-dihydro-[1,2,4]triazolo[4,3-a]pyrazin-7(8H)-yl)methyl)-1-(cis-4-(isopropylcarbamoyl)cyclohexyl)-1H-benzo[d]imidazol-2(3H)-ylidene)benzamide as a white powder (13 mg, 9.54% yield). MS, m/z (C$_{33}$H$_{41}$FN$_8$O$_3$): calcd, 616.3. found, 617.4 [M+H].

Example 231

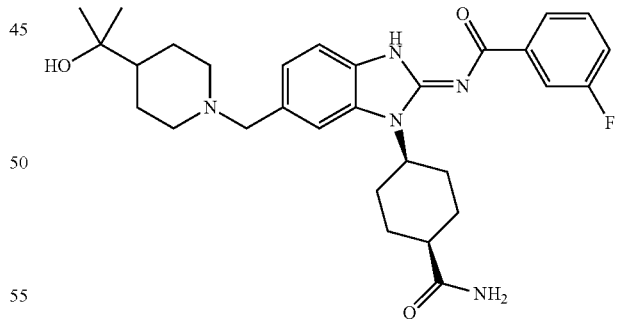

(E)-N-(1-(cis-4-Carbamoylcyclohexyl)-6-((4-(2-hydroxypropan-2-yl)piperidin-1-ylmethyl)-1H-benzo[d]imidazol-2(3H)-ylidene)-3-fluorobenzamide

Step A: 2-(1-(3-Fluoro-4-nitrobenzyl)piperidin-4-yl)propan-2-ol

To a solution of 3-fluoro-4-nitrobenzaldehyde (0.5 g, 2.96 mmol) and 2-(piperidin-4-yl)propan-2-ol (0.466 g, 3.25 mmol) in DCM (25 mL) was added AcOH (0.017 mL, 0.296 mmol) and sodium triacetoxyborohydride (0.689 g, 3.25 mmol), and the reaction was stirred at RT for 1 hour. After 1 hour, the reaction was quenched by the addition of 1 N aqueous NaOH (15 mL), and the layers were separated. The aqueous layer was extracted with DCM, and the combined organic layers were washed with brine, dried over anhydrous magnesium sulfate, filtered, and concentrated. The residual product was adsorbed onto a plug of silica gel, and purified by column chromatography, eluting with 0-100% EtOAc in DCM, to provide 2-(1-(3-fluoro-4-nitrobenzyl)piperidin-4-yl)propan-2-ol as a yellow oil (0.75 g, 86% yield).

Step B: cis-4-(5-((4-(2-Hydroxypropan-2-yl)piperidin-1-yl)methyl)-2-nitrophenylamino)cyclohexanecarboxylic acid To a suspension of cis-4-aminocyclohexanecarboxylic acid (0.199 g, 1.392 mmol) and DIPEA (0.553 mL, 3.16 mmol) in ACN (5 mL) was added 2-(1-(3-fluoro-4-nitrobenzyl)piperidin-4-yl)propan-2-ol (0.375 g, 1.265 mmol). The reaction was stirred at 75° C. After 48 hours, the reaction mixture was concentrated, diluted with water (10 mL), and extracted with DCM and EtOAc. The combined organic layers were dried over anhydrous magnesium sulfate, filtered, and concentrated to provide cis-4-(5-((4-(2-hydroxypropan-2-yl)piperidin-1-yl)methyl)-2-nitrophenylamino)cyclohexanecarboxylic acid as an orange powder (0.76 g, 143% yield).

Step C: cis-4-(5-((4-(2-Hydroxypropan-2-yl)piperidin-1-yl)methyl)-2-nitrophenylamino)cyclohexanecarboxamide To a solution of cis-4-(5-((4-(2-hydroxypropan-2-yl)piperidin-1-yl)methyl)-2-nitrophenylamino)cyclohexanecarboxylic acid (0.53 g, 1.263 mmol) in DMF (7 mL) was added CDI (0.410 g, 2.53 mmol) and aqueous ammonium hydroxide (100 µL, 2.53 mmol). The reaction was stirred overnight at RT. After 16 hours, the reaction mixture was partitioned between water and DCM and the aqueous layer was extracted with DCM. The combined organic layers were washed with water and brine, dried over anhydrous magnesium sulfate, filtered, and concentrated. The residue was purified by column chromatography, eluting with 0-100% (90:9:1 DCM/MeOH/NH$_4$OH)/DCM, to provide cis-4-(5-(4-(2-hydroxypropan-2-yl)piperidin-1-yl)methyl)-2-nitrophenylamino)cyclohexane-carboxamide as an orange foam (0.213 g, 40.3% yield). MS, m/z ($C_{22}H_{34}FN_4O_4$): calcd, 418.3. found, 419.1 [M+H].

Step D: (E)-N-(1-(cis-4-Carbamoylcyclohexyl)-6-((4-(2-hydroxypropan-2-yl)piperidin-1-371)methyl)-1H-benzo[d]imidazol-2(3H)-ylidene)-3-fluorobenzamide To a solution of cis-4-(5-(4-(2-hydroxypropan-2-yl)piperidin-1-yl)methyl)-2-nitrophenylamino)cyclohexanecarboxamide (213 mg, 0.509 mmol) in EtOH (5 mL) was added 10% palladium on carbon (54.2 mg, 0.051 mmol). A hydrogen balloon was placed on the vessel, and the reaction was stirred vigorously under a hydrogen atmosphere at RT. After 2 hours, the reaction mixture was filtered through Celite® brand filter aid (washed with 1:1 MeOH/DCM) to provide cis-4-(2-amino-5-((4-(2-hydroxypropan-2-yl)piperidin-1-yl)methyl)phenylamino)cyclohexanecarboxamide as a dark oil.

The diamine was dissolved in THF (3 mL), cooled to 0° C., and 3-fluorobenzoyl isothiocyanate (56.0 mg, 0.309 mmol) was added. The reaction was stirred at 0° C. for 15 minutes, then EDC (74.0 mg, 0.386 mmol) and DIPEA (0.067 mL, 0.386 mmol) were added, and the reaction was stirred at 60° C. for 2 hours. The reaction mixture was concentrated and partitioned between DCM and water. The organic layer was dried over anhydrous magnesium sulfate, filtered, concentrated, and the residue was purified by column chromatography, eluting with 0-100% EtOAc in DCM, to provide (E)-N-(1-(cis-4-carbamoylcyclohexyl)-6-((4-(2-hydroxypropan-2-yl)piperidin-1-yl)methyl)-1H-benzo[d]imidazol-2(3H)-ylidene)-3-fluorobenzamide as an off-white powder (75 mg, 54.4% yield). MS, m/z ($C_{30}H_{38}FN_5O_3$): calcd, 535.3. found, 536.1 [M+H].

Example 232

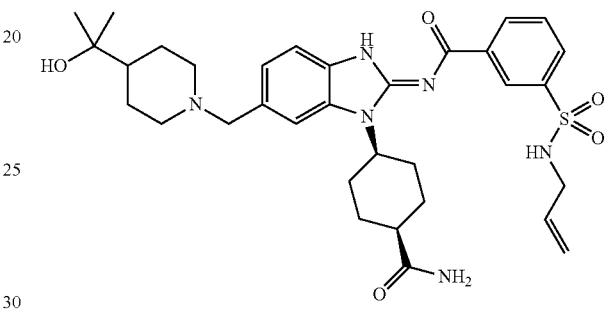

(E)-3-(N-Allylsulfamoyl)-N-(1-(cis-4-carbamoylcyclohexyl)-6-((4-(2-hydroxypropan-2-yl)piperidin-1-yl)methyl)-1H-benzo[d]imidazol-2(3H)-ylidene)benzamide Step A: 3-(N-Allylsulfamoyl)benzoyl isothiocyanate To a suspension of 3-(N-allylsulfamoyl)benzoic acid (2 g, 8.29 mmol) in 1,2-dichloroethane (25 mL) was added thionyl chloride (1.271 mL, 17.41 mmol) dropwise. The suspension was stirred for 2 hours at 80° C. After 2 hours, the reaction mixture was concentrated to an off-white solid. The solid was redissolved in 25 mL acetone, and potassium isothiocyanate (0.967 g, 9.95 mmol) was added. A precipitate formed immediately upon addition. The reaction was stirred at 50° C. After 2 hours, the reaction was filtered, concentrated, and adsorbed onto a silca-gel pre column. The residue was purified by column chromatography, eluting with 20-100% EtOAc in hexanes, to provide 3-(N-allylsulfamoyl)benzoyl isothiocyanate as an off-white solid (0.71 g, 30.3% yield). MS, m/z ($C_{11}H_{10}N_2O_3S_2$): calcd, 282.0. found, 282.9 [M+H].

Step B: (E)-3-(N-Allylsulfamoyl)-N-(1-(cis-4-carbamoylcyclohexyl)-6-((4-(2-hydroxypropan-2-yl)piperidin-1-yl)methyl)-1H-benzo[d]imidazol-2(3H)-ylidene)benzamide The title compound was prepared from cis-4-(5-((4-(2-hydroxypropan-2-yl)piperidin-1-yl)methyl)-2-nitrophenylamino)cyclohexane-carboxamide and 3-(N-allylsulfamoyl)benzoyl isothiocyanate using a method analogous to that used for the preparation of (E)-N-(1-(cis-4-carbamoylcyclohexyl)-6-((4-(2-hydroxypropan-2-yl)piperidin-1-yl)methyl)-1H-benzo[d]imidazol-2(3H)-ylidene)-3-fluorobenzamide (75 mg, 46% yield). $^1$H NMR (400 MHz, DMSO-d$_6$) δ ppm 1.03 (br. s., 6H), 1.24 (br. s., 3H), 1.56-1.78 (m, 6H), 1.85 (br. s., 2H), 2.13-2.27 (m, 2H), 2.59 (br. s., 1H), 2.69-3.04 (m, 4H), 3.48 (br. s., 4H), 4.02 (br. s., 1H), 4.79 (br. s., 1H), 5.03 (d, J=11.1 Hz, 1H), 5.16 (d, J=17.5 Hz, 1H), 5.62-5.78 (m, 1H), 6.87 (br. s., 1H), 7.20 (br. s., 1H), 7.39-7.64 (m, 3H), 7.69-7.79 (m, 1H), 7.93 (d, J=7.3 Hz, 1H), 8.09 (br. s., 1H), 8.45-8.68 (m, 2H), 12.81 (br. s., 1H). MS, m/z ($C_{33}H_{44}N_6O_5S$): calcd, 636.3. found, 636.9 [M+H].

Example 233

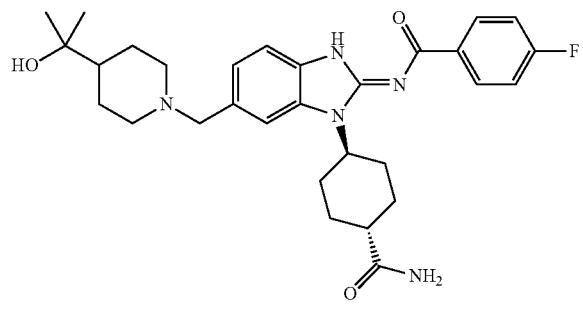 [SMILES: CC(C)(O)C1CCN(Cc2ccc3[nH]/c(=N\C(=O)c4ccc(F)cc4)n([C@H]4CC[C@H](C(N)=O)CC4)c3c2)CC1]

(E)-N-(1-(trans-4-Carbamoylcyclohexyl)-6-((4-(2-hydroxypropan-2-yl)piperidin-1-yl)methyl)-1H-benzo[d]imidazol-2(3H)-ylidene)-4-fluorobenzamide Step A: trans-4-(5-((4-(2-Hydroxypropan-2-yl)piperidin-1-yl)methyl)-2-nitrophenylamino)cyclohexanecarboxylic acid To a suspension of trans-4-aminocyclohexanecarboxylic acid (0.199 g, 1.392 mmol) and DIPEA (0.553 mL, 3.16 mmol) in ACN (5 mL) was added 2-(1-(3-fluoro-4-nitrobenzyl)piperidin-4-yl)propan-2-ol (0.375 g, 1.265 mmol). The reaction was stirred at 75° C. After 48 hours, the reaction mixture was concentrated, diluted with water (10 mL) and extracted with DCM and EtOAc. The combined organic layers were dried over anhydrous magnesium sulfate, filtered, and concentrated to provide trans-4-(5-((4-(2-hydroxypropan-2-yl)piperidin-1-yl)methyl)-2-nitrophenylamino)cyclohexanecarboxylic acid (0.524 g, 1.249 mmol, 99% yield) as an orange powder.

Step B: trans-4-(5-(4-(2-Hydroxypropan-2-yl)piperidin-1-yl)methyl)-2-nitrophenylamino)cyclohexanecarboxamide To a solution of trans-4-(5-((4-(2-hydroxypropan-2-yl)piperidin-1-yl)methyl)-2-nitrophenylamino)cyclohexanecarboxylic acid (0.53 g, 1.263 mmol) in DMF (5 mL) was added CDI (0.410 g, 2.53 mmol). The reaction was stirred at RT for 1 hour, and then concentrated aqueous ammonium hydroxide (0.098 mL, 2.53 mmol) was added, and the reaction was stirred overnight. After 16 hours, the reaction mixture was partitioned between water and EtOAc. The aqueous layer was extracted with EtOAc, and the combined organic layers were washed with water and brine, dried over anhydrous magnesium sulfate, filtered, and concentrated. The residue was purified by column chromatography, eluting with 50-100% (90:9:1 DCM/MeOH/NH$_4$OH)/DCM, to provide trans-4-(5-((4-(2-hydroxypropan-2-yl)piperidin-1-yl)methyl)-2-nitrophenylamino)cyclohexanecarboxamide as an orange powder (0.39 g, 73.8% yield). MS, m/z ($C_{22}H_{34}FN_4O_4$): calcd, 418.3. found, 419.1 [M+H].

Step C: (E)-N-(1-(trans-4-Carbamoylcyclohexyl)-6-((4-(2-hydroxypropan-2-yl)piperidin-1-yl)methyl)-1H-benzo[d]imidazol-2(3H)-ylidene)-4-fluorobenzamide The title compound was prepared in 2 steps from trans-4-(5-((4-(2-hydroxypropan-2-yl)piperidin-1-yl)methyl)-2-nitrophenylamino)cyclohexane-carboxamide using a method analogous to that used in the preparation of (E)-N-(1-(cis-4-carbamoylcyclohexyl)-6-((4-(2-hydroxypropan-2-yl)piperidin-1-yl)methyl)-1H-benzo[d]imidazol-2(3H)-ylidene)-3-fluorobenzamide (75 mg, 45% yield). $^1$H NMR (400 MHz, DMSO-d$_6$) δ ppm 1.03 (s, 6H), 1.15-1.33 (m, 3H), 1.59-1.73 (m, 5H), 1.80-1.93 (m, 4H), 1.96-2.04 (m, 2H), 2.30-2.47 (m, 3H), 2.91 (br. s., 2H), 3.53 (br. s., 2H), 4.78 (br. s., 1H), 6.77 (br. s., 1H), 7.14-7.21 (m, 1H), 7.25-7.34 (m, 3H), 7.46-7.59 (m, 2H), 8.27 (dd, J=8.5, 5.9 Hz, 2H), 12.77 (br. s., 1H). MS, m/z ($C_{30}H_{38}FN_5O_3$): calcd, 535.3. found, 536.1 [M+H].

Example 234

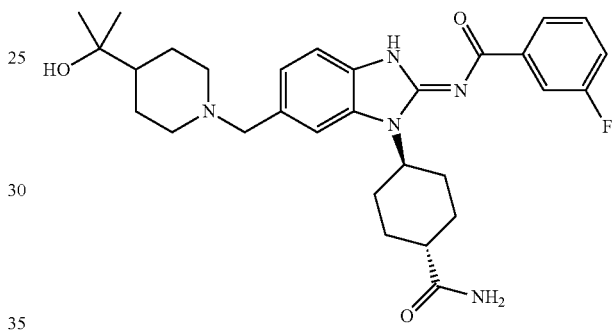

(E)-N-(1-(trans-4-Carbamoylcyclohexyl)-6-((4-(2-hydroxypropan-2-yl)piperidin-1-yl)methyl)-1H-benzo[d]imidazol-2(3H)-ylidene)-3-fluorobenzamide The title compound was prepared in 2 steps from trans-4-(5-((4-(2-hydroxypropan-2-yl)piperidin-1-yl)methyl)-2-nitrophenylamino)cyclohexane-carboxamide using a method analogous to the preparation of (E)-N-(1-(cis-4-carbamoylcyclohexyl)-6-((4-(2-hydroxypropan-2-yl)piperidin-1-yl)methyl)-1H-benzo[d]imidazol-2(3H)-ylidene)-3-fluorobenzamide (75 mg, 45%). MS, m/z ($C_{30}H_{38}FN_5O_3$): calcd, 535.3. found, 536.1 [M+H].

Example 235

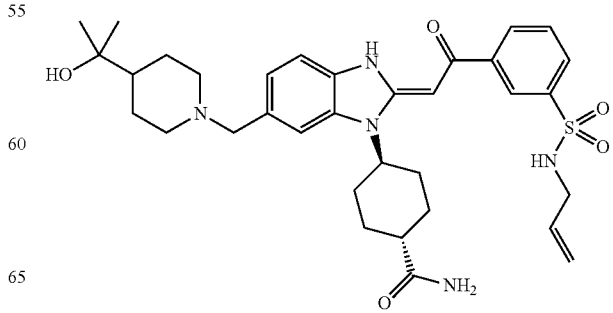

(E)-3-(N-Allylsulfamoyl)-N-(1-(trans-4-carbamoyl-cyclohexyl)-6-((4-(2-hydroxypropan-2-yl)piperidin-1-yl)methyl)-1H-benzo[d]imidazol-2(3H)-ylidene)benzamide The title compound was prepared in 2 steps from trans-4-(5-(4-(2-hydroxypropan-2-yl)piperidin-1-yl)methyl)-2-nitrophenylamino)cyclohexane-carboxamide using a method analogous to the preparation of (E)-N-(1-(cis-4-carbamoyl-cyclohexyl)-6-((4-(2-hydroxypropan-2-yl)piperidin-1-yl)methyl)-1H-benzo[d]imidazol-2(3H)-ylidene)-3-fluorobenzamide (69 mg, 35% yield). MS, m/z ($C_{30}H_{38}FN_5O_3$): calcd, 636.3. found, 636.9 [M+H].

Example 236

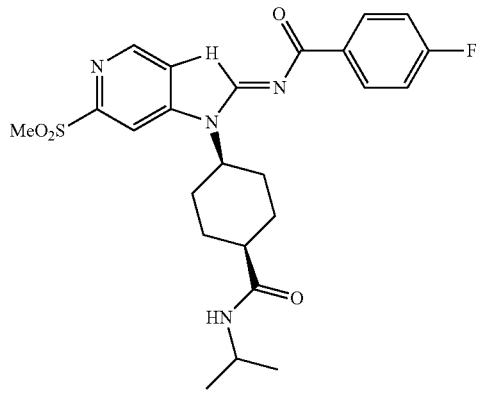

(E)-4-Fluoro-N-(1-(cis-4-(isopropylcarbamoyl)cyclohexyl)-6-(methylsulfonyl)-1H-imidazo[4,5-c]pyridin-2(3H)-ylidene)benzamide

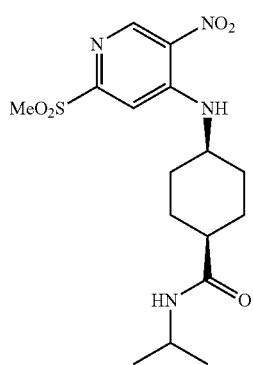 [SMILES: CC(C)NC(=O)[C@H]1CC[C@@H](Nc2cc(S(C)(=O)=O)ncc2[N+](=O)[O-])CC1]

Step A: cis-N-Isopropyl-4-(2-(methylsulfonyl)-5-nitropyridin-4-ylamino)cyclohexanecarboxamide To a solution of cis-4-(2-chloro-5-nitropyridin-4-ylamino)-N-isopropylcyclohexanecarboxamide (0.100 g, 0.293 mmol) in DMF (0.6 mL) was added sodium methanesulfinate (0.042 g, 0.352 mmol), and the reaction mixture was heated at 100° C. for 2 hours. The reaction was conducted twice and the mixtures were combined and concentrated under reduced pressure and the yellow residue purified by flash chromatography, eluting with 0-80% 9:1 DCM/MeOH:DCM to afford cis-N-isopropyl-4-(2-(methylsulfonyl)-5-nitropyridin-4-ylamino)cyclohexanecarboxamide as a yellow solid. MS (ESI pos. ion) m/z: 385.0 [M+H].

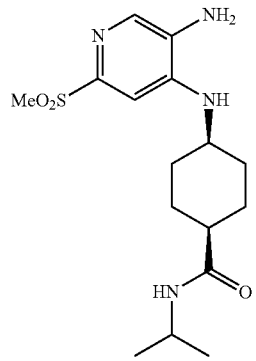 [SMILES: CC(C)NC(=O)[C@H]1CC[C@@H](Nc2cc(S(C)(=O)=O)ncc2N)CC1]

Step B: cis-4-(5-Amino-2-(methylsulfonyl)pyridin-4-ylamino)-N-isopropylcyclohexanecarboxamide To a solution of cis-N-isopropyl-4-(2-(methylsulfonyl)-5-nitropyridin-4-ylamino)cyclohexanecarboxamide (0.177 g, 0.460 mmol) in MeOH (2 mL) was added anhydrous tin (II) chloride (0.349 g, 1.842 mmol). The reaction mixture was heated at 80° C. for 3 hours and was concentrated under vacuum. The remaining residue was dissolved in EtOAc and washed with 1N aqueous NaOH followed by brine. The organic layer was dried over sodium sulfate and concentrated under vacuum. The residue was purified by flash chromatography, eluting with 0-100% 90/10/1 DCM/MeOH/NH$_4$OH:DCM to afford cis-4-(5-amino-2-(methylsulfonyl)pyridin-4-ylamino)-N-isopropylcyclohexanecarboxamide (0.150 g, 92% yield). MS (ESI pos. ion) m/z: 355.2 [M+H].

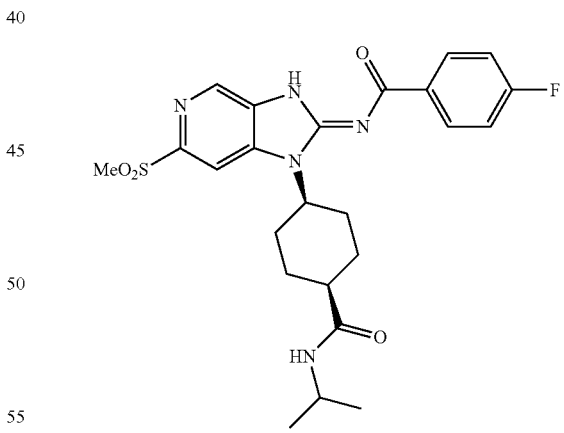

Step C: (E)-4-Fluoro-N-(1-(cis-4-(isopropylcarbamoyl)cyclohexyl)-6-(methylsulfonyl)-1H-imidazo[4,5-c]pyridin-2(3H)-ylidene)benzamide A solution of cis-4-(5-Amino-2-(methylsulfonyl)pyridin-4-ylamino)-N-isopropylcyclohexanecarboxamide (0.069 g, 0.195 mmol) in THF (0.5 mL) was cooled to 0° C. and 4-fluorobenzoyl isothiocyanate (0.053 g, 0.292 mmol) was added as a THF solution. The mixture was stirred at 0° C. for 30 minutes and then was warmed to 20° C. and stirred for 1 hour. To the mixture was added DIPEA (0.051 mL, 0.292 mmol) and EDC (0.056 g, 0.292 mmol), and the reaction was heated at 60° C. for 1 hour. The reaction mixture was diluted with DCM and then washed with water and brine. The organic layer was concentrated under vacuum. The sample was purified by flash chromatography, eluting with 0-70% 90/10/1 DCM/MeOH/NH₄OH:DCM to afford impure product as a light yellow solid. The impure material was further purified by preparative TLC, eluting with 90/10/1 DCM/MeOH/NH₄OH:DCM to afford (E)-4-fluoro-N-(1-(cis-4-(isopropylcarbamoyl)cyclohexyl)-6-(methylsulfonyl)-1H-imidazo[4,5-c]pyridin-2(3H)-ylidene)benzamide as a pale yellow solid (0.046 g, 47.1% yield). MS, m/z (C₂₄H₂₈FN₅O₄S); Calcd, 501.58. found 502.2 [M+H].

Example 237

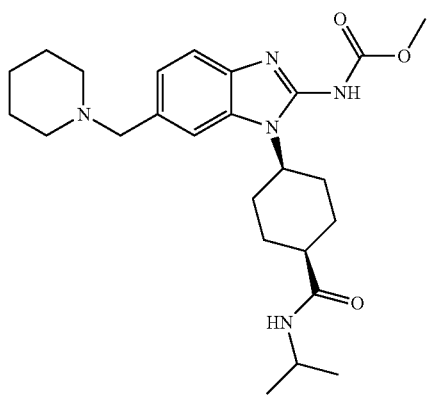 [SMILES: COC(=O)Nc1nc2ccc(CN3CCCCC3)cc2n1[C@H]1CC[C@@H](C(=O)NC(C)C)CC1]

Methyl 1-(cis-4-(isopropylcarbamoyl)cyclohexyl)-6-(piperidin-1-ylmethyl)-1H-benzo[d]imidazol-2-yl-carbamate

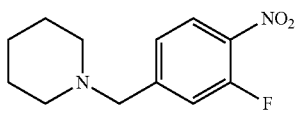 [SMILES: O=[N+]([O-])c1ccc(CN2CCCCC2)cc1F]

Step A: 1-(3-Fluoro-4-nitrobenzyl)piperidine

To a mixture of 3-fluoro-4-nitrobenzaldehyde (4.85 g, 28.7 mmol), piperidine (3.12 mL, 31.5 mmol) and 20 drops of AcOH in DCM was added sodium triacetoxyborohydride (6.69 g, 31.5 mmol), and the resulting suspension was stirred at RT for 30 minutes. The reaction was made basic with 2N aqueous NaOH, and extracted with DCM. The organic layer was washed with brine and was dried over sodium sulfate, filtered and concentrated in vacuo to yield a red oil. The residual oil was purified via MPLC, eluting with a gradient of 0-100% EtOAc in hexane to yield 1-(3-fluoro-4-nitrobenzyl)piperidine (3.98 g, 16.70 mmol, 58.2% yield) as an orange oil.

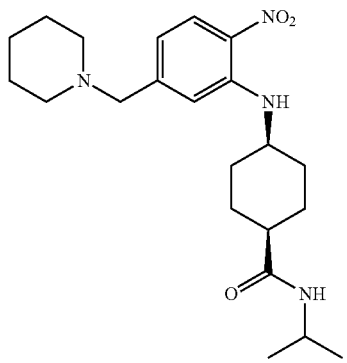 [SMILES: CC(C)NC(=O)[C@H]1CC[C@@H](Nc2cc(CN3CCCCC3)ccc2[N+](=O)[O-])CC1]

Step B: cis-N-Isopropyl-4-(2-nitro-5-(piperidin-1-ylmethyl)phenylamino)cyclohexanecarboxamide cis-4-Amino-N-isopropylcyclohexanecarboxamide hydrochloride (1.734 g, 7.86 mmol) was suspended in ACN (4.09 mL, 6.55 mmol), and DIPEA (1.144 mL, 6.55 mmol) was added. After stirring for 10 minutes at RT, the solution was added to a solution of 1-(3-fluoro-4-nitrobenzyl)piperidine (1.56 g, 6.55 mmol) in ACN (8.73 mL) and DIPEA (2.287 mL, 13.10 mmol). The reaction was heated at reflux for three days. The reaction was diluted with water and DCM, and the layers were separated. The organic layer was dried over Na₂SO₄, filtered and concentrated to yield the product as a dark red solid. The residue was purified via HPLC (eluting with 100% 90:10:1 DCM:MeOH:NH₄OH to yield cis-N-isopropyl-4-(2-nitro-5-(piperidin-1-ylmethyl)phenylamino)cyclohexanecarboxamide as an orange-red solid.

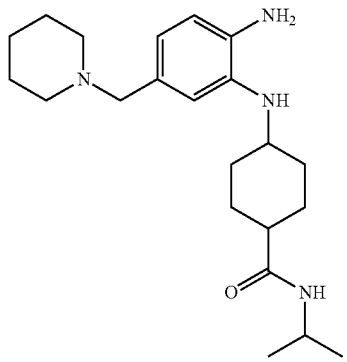 [SMILES: CC(C)NC(=O)C1CCC(Nc2cc(CN3CCCCC3)ccc2N)CC1]

Step C: 4-(2-Amino-5-(piperidin-1-ylmethyl)phenylamino)-N-isopropylcyclohexanecarboxamide To a round bottom flask was added cis-N-isopropyl-4-(2-nitro-5-(piperidin-1-ylmethyl)phenylamino)cyclohexanecarboxamide (1.400 g, 3.48 mmol) under nitrogen. Palladium on carbon (0.370 g, 0.348 mmol) was added, followed by EtOH (28.3 mL) via syringe. To the reaction was added ammonium formate (2.193 g, 34.8 mmol), and the reaction mixture was stirred at RT overnight. The reaction mixture was filtered through Celite® brand filter aid, concentrated and diluted with 90:10:1 DCM:MeOH:NH₄OH and water. The layers were separated, and the aqueous layer was washed once more. The organics were dried over sodium sulfate, filtered and concentrated to yield cis-4-(2-amino-5-(piperidin-1-ylmethyl)phenylamino)-N-isopropylcyclohexanecarboxamide (1.18 g, 3.17 mmol, 91% yield) as a dark red solid.

Step D: Methyl 1-(cis-4-(isopropylcarbamoyl)cyclohexyl)-6-(piperidin-1-ylmethyl)-1H-benzo[d]imidazol-2-ylcarbamate To a solution of cis-4-(2-amino-5-(piperidin-1-ylmethyl)phenylamino)-N-isopropylcyclohexanecarboxamide (0.300 g, 0.805 mmol) in MeOH (4.5 mL) was added 1,3-bis(methoxycarbonyl)-2-methyl-2-thiopseudourea (0.166 g, 0.805 mmol) and p-toluenesulfonic acid monohydrate (0.168 g, 0.886 mmol). The reaction mixture was heated at 80° C. for 2 hours and then concentrated under vacuum. The residue was dissolved in DCM and was washed with saturated aqueous NaHCO$_3$. The organic layer was dried over sodium sulfate and concentrated under vacuum. The residue was purified by flash chromatography, eluting with 0-100% 90:10:1 DCM/MeOH/NH$_4$OH:DCM to afford methyl 1-(cis-4-(isopropylcarbamoyl)cyclohexyl)-6-(piperidin-1-ylmethyl)-1H-benzo[d]imidazol-2-ylcarbamate (0.239 g, 65.1% yield). MS, m/z (C$_{25}$H$_{37}$N$_5$O$_3$); calcd, 455.59. found 456.2 [M+H]. $^1$H NMR (400 MHz, CDCl$_3$) δ ppm 1.23 (d, J=6.55 Hz, 6H) 1.38-1.49 (m, 2H) 1.52-1.67 (m, 4H) 1.67-1.85 (m, 6H) 2.10-2.20 (m, 2H) 2.34-2.51 (m, 4H) 2.58-2.73 (m, 2H) 3.54-3.66 (m, 1H) 3.79 (s, 3H) 4.20 (dt, J=13.70, 6.70 Hz, 1H) 4.86 (tt, J=12.79, 4.47 Hz, 1H) 5.34 (br. d, J=7.20 Hz, 1H) 7.13-7.25 (m, 2H) 7.61 (br. s., 1H) 11.29 (br. s., 1H).

Example 238

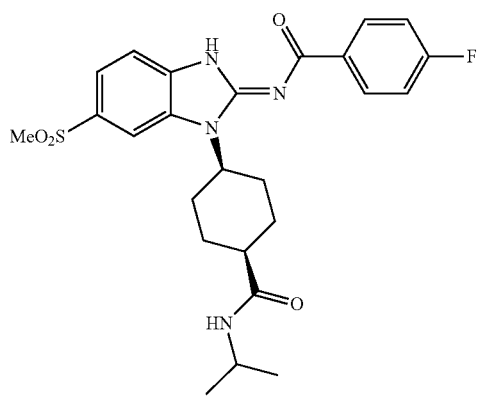 [SMILES: CC(C)NC(=O)[C@H]1CC[C@@H](n2/c(=N/C(=O)c3ccc(F)cc3)[nH]c3ccc(S(C)(=O)=O)cc32)CC1]

(E)-4-Fluoro-N-(1-(cis-4-(isopropylcarbamoyl)cyclohexyl)-6-(methylsulfonyl)-1H-benzo[d]imidazol-2(3H)-ylidene)benzamide

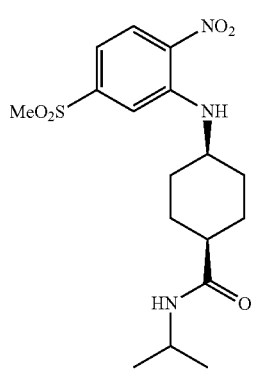

Step A: cis-N-Isopropyl-4-(5-(methylsulfonyl)-2-nitrophenylamino)cyclohexanecarboxamide To a solution of cis-4-(5-fluoro-2-nitrophenylamino)-N-isopropylcyclohexanecarboxamide (0.100 g, 0.309 mmol) in DMF (0.55 mL) was added sodium methanesulfinate (0.045 g, 0.371 mmol), and the reaction mixture was heated at 100° C. for 2 hours. The mixture was concentrated under vacuum, and the residue was purified by flash chromatography, eluting with 0-70% 9:1 DCM/MeOH to cis-N-isopropyl-4-(5-(methylsulfonyl)-2-nitrophenylamino)cyclohexanecarboxamide as a bright orange solid (0.124 g, 105% yield). MS (ESI pos. ion) m/z: 384.0 [M+H].

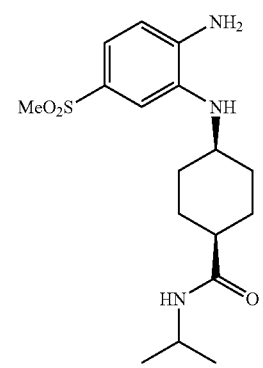

Step B: cis-4-(2-Amino-5-(methylsulfonyl)phenylamino)-N-isopropylcyclohexanecarboxamide To a solution of cis-N-Isopropyl-4-(5-(methylsulfonyl)-2-nitrophenylamino)cyclohexanecarboxamide (0.120 g, 0.313 mmol) in MeOH (1.2 mL) was added 5% Pd/C (0.067 g, 0.031 mmol) and ammonium formate (0.154 mL, 3.13 mmol) (exotherm). The reaction mixture was stirred at 20° C. for 1 hour and then the mixture was filtered through a pad of Celite® brand filter aid, washing with MeOH. The filtrate was concentrated under vacuum, and the remaining residue was dissolved in DCM then washed with water. The organic layer was concentrated under vacuum. The residue was purified by flash chromatography, eluting with 0-80% 90:10:1 DCM/MeOH/NH$_4$OH:DCM to afford cis-4-(2-amino-5-(methylsulfonyl) phenylamino)-N-isopropylcyclohexanecarboxamide as a pale yellow oil (0.107 g, 97% yield). MS (ESI pos. ion) m/z: 354.2 [M+H].

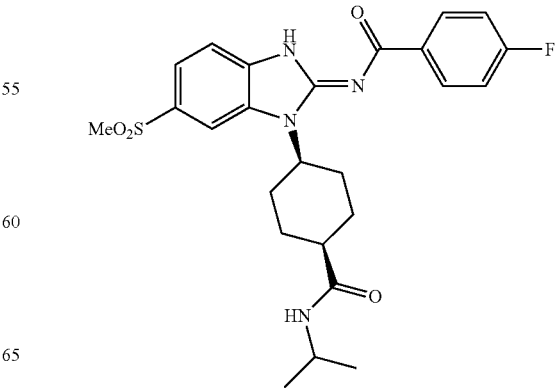

Step C: (E)-4-Fluoro-N-(1-(cis-4-(isopropylcarbamoyl)cyclohexyl)-6-(methylsulfonyl)-1H-benzo[d]imidazol-2(3H)-ylidene)benzamide The title compound was prepared from cis-4-(2-amino-5-(methylsulfonyl) phenylamino)-N-isopropylcyclohexanecarboxamide using a method analogous to that used in the preparation of (E)-4-fluoro-N-(1-(cis-4-(isopropylcarbamoyl)cyclohexyl)-6-(methylsulfonyl)-1H-imidazo[4,5-c]pyridin-2(3H)-ylidene)benzamide, as an off-white solid (0.111 g, 75% yield). MS, m/z ($C_{25}H_{29}FN_4O_4S$): calcd, 500.59. found 501.2 [M+H]. $^1$H NMR (400 MHz, DMSO-$d_6$) d ppm 1.09 (d, J=6.55 Hz, 6H) 1.62-1.81 (m, 4H) 2.14 (m, J=13.10 Hz, 2H) 2.51-2.57 (m, 2H) 2.75-2.91 (m, 2H) 3.28 (s, 3H) 3.99-4.10 (m, 1H) 4.72-4.88 (m, 1H) 7.22-7.29 (m, 2H) 7.64 (d, J=7.73 Hz, 1H) 7.68-7.79 (m, 2H) 8.23-8.27 (m, 1H) 8.32-8.40 (m, 2H) 13.04 (br. s, 1H). $^1$H NMR (400 MHz, DMSO-$d_6$) δ ppm 1.09 (d, J=6.55 Hz, 6H) 1.62-1.81 (m, 4H) 2.09-2.19 (m, 2H) 2.51-2.57 (m, 2H) 2.75-2.91 (m, 2H) 3.28 (s, 3H) 4.05 (sxt, J=6.94 Hz, 1H) 4.72-4.88 (m, 1H) 7.25 (s, 2H) 7.64 (d, J=7.73 Hz, 1H) 7.68-7.79 (m, 2H) 8.23-8.27 (m, 1H) 8.32-8.40 (m, 2H) 13.04 (br. s, 1H).

Example 239

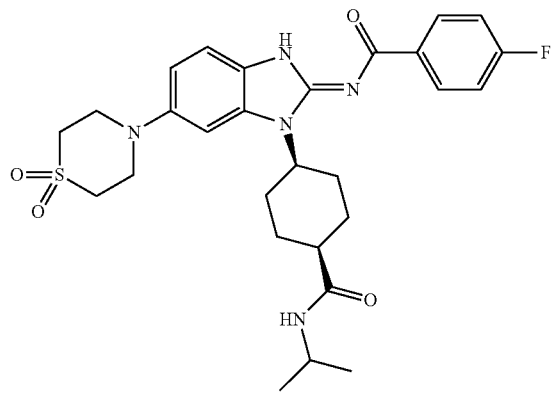 [SMILES: CC(C)NC(=O)[C@H]1CC[C@@H](n2/c(=N/C(=O)c3ccc(F)cc3)[nH]c3ccc(N4CCS(=O)(=O)CC4)cc32)CC1]

(E)-4-Fluoro-N-(1-(cis-4-(isopropylcarbamoyl)cyclohexyl)-6-(thiomorpholine 1,1-dioxide)-1H-benzo[d]imidazol-2(3H)-ylidene)benzamide

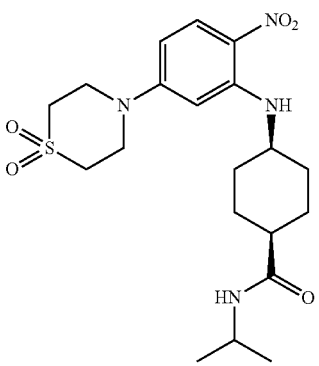 [SMILES: CC(C)NC(=O)[C@H]1CC[C@@H](Nc2cc(N3CCS(=O)(=O)CC3)ccc2[N+](=O)[O-])CC1]

Step A: cis-N-Isopropyl-4-(5-(thiomorpholine 1,1-dioxide)-2-nitrophenylamino)cyclohexanecarboxamide To a solution of cis-4-(5-fluoro-2-nitrophenylamino)-N-isopropylcyclohexanecarboxamide (0.100 g, 0.309 mmol) in NMP (0.5 mL) was added thiomorpholine 1,1-dioxide (0.209 g, 1.546 mmol), and the reaction mixture was irradiated at 200° C. in a microwave reactor for 2.5 hours. The mixture was diluted with EtOAc and washed with water, brine, and the organic layer concentrated under vacuum. The sample was purified by flash chromatography, eluting with 0-70% 90:10:1 DCM/MeOH/NH$_4$OH:DCM to afford cis-N-isopropyl-4-(5-(thiomorpholine 1,1-dioxide)-2-nitrophenylamino)cyclohexanecarboxamide as an orange oil (0.044 g, 32.4% yield). MS (ESI pos. ion) m/z: 439.2 [M+H].

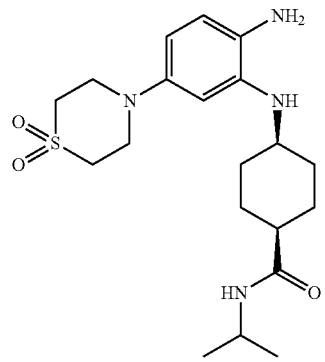 [SMILES: CC(C)NC(=O)[C@H]1CC[C@@H](Nc2cc(N3CCS(=O)(=O)CC3)ccc2N)CC1]

Step B: cis-4-(2-Amino-5-(thiomorpholine 1,1-dioxide)phenylamino)-N-isopropylcyclohexanecarboxamide The title compound was prepared from cis-N-isopropyl-4-(5-(thiomorpholine 1,1-dioxide)-2-nitrophenylamino)cyclohexanecarboxamide using a method analogous to the preparation of cis-4-(2-amino-5-(methylsulfonyl) phenylamino)-N-isopropylcyclohexanecarboxamide, as a purple oil (25 mg). MS (ESI pos. ion) m/z: 409.2 [M+H].

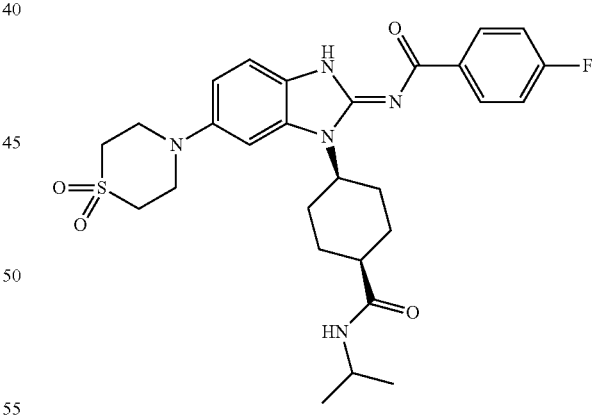

Step C: (E)-4-Fluoro-N-(1-(cis-4-(isopropylcarbamoyl)cyclohexyl)-6-(thiomorpholine 1,1-dioxide)-1H-benzo[d]imidazol-2(3H)-ylidene)benzamide The title compound was prepared from cis-4-(2-amino-5-(thiomorpholine 1,1-dioxide)phenylamino)-N-isopropylcyclohexanecarboxamide (0.025 g, 0.061 mmol) using a method analogous to that used in the preparation of (E)-4-fluoro-N-(1-(cis-4-(isopropylcarbamoyl)cyclohexyl)-6-(methylsulfonyl)-1H-imidazo[4,5-c]pyridin-2(3H)-ylidene)benzamide, as a light yellow solid. MS m/z ($C_{28}H_{34}FN_5O_4S$), calcd 555.67. found 556.2 [M+H].

Example 240

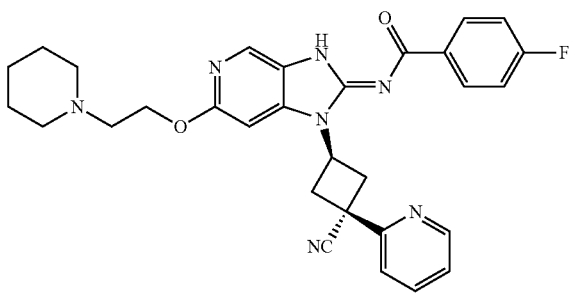 [SMILES: N#C[C@]1(c2ccccn2)C[C@@H](n2/c(=N/C(=O)c3ccc(F)cc3)[nH]c3cnc(OCCN4CCCCC4)cc32)C1]

(E)-N-(1-(trans-3-Cyano-3-(pyridin-2-yl)cyclobutyl)-6-(2-(piperidin-1-yl)ethoxy)-1H-imidazo[4,5-c]pyridin-2(3H)-ylidene)-4-fluorobenzamide

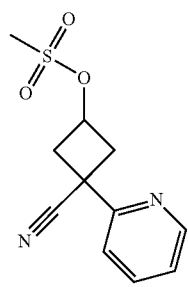 [SMILES: CS(=O)(=O)OC1CC(C#N)(c2ccccn2)C1]

Step A: 3-Cyano-3-(pyridin-2-yl)cyclobutyl methanesulfonate

To a solution of 3-hydroxy-1-(pyridin-2-yl)cyclobutanecarbonitrile (WO 2007/060484)(10.996 g, 63.1 mmol) in dry DCM (100 mL) and pyridine (20.59 mL, 252 mmol), was added (with stirring and cooling in an ice water bath) methane sulfonyl chloride (4.88 mL, 63.1 mmol). The mixture was stirred at RT for 25 hours. The solvent was removed at reduced pressure, and the residue was partitioned between EtOAc and aqueous NaHCO$_3$. The organic phase was washed with aqueous NaHCO$_3$ and was concentrated at reduced pressure. The residue was eluted through a short pad of silica gel (eluent 30%-50% EtOAc/hexane). The solvent was removed, and the resulting oil was crystallized from toluene on dilution with hexane to afford the title compound as a 3:1 mixture of geometrical isomers (assessed by NMR).

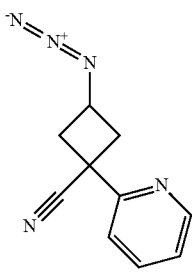

Step B: 3-Azido-1-(pyridin-2-yl)cyclobutanecarbonitrile

To a solution of 3-cyano-3-(pyridin-2-yl)cyclobutyl methanesulfonate (4.008 g, 15.89 mmol) in dry DMF (20 mL) was added sodium azide (2.066 g, 31.8 mmol), and the mixture was stirred in an oil bath at 90° C. for 48 hours under a N$_2$ atmosphere. The reaction was diluted with EtOAc and water, and the layers were separated. The organic layer was washed with water and concentrated under vacuum. The residue was chromatographed on silica gel, eluting with 40% EtOAc/hexane to afford the title compound, a 3:1 mixture of geometrical isomers, as a colourless oil m/z 200 MH+.

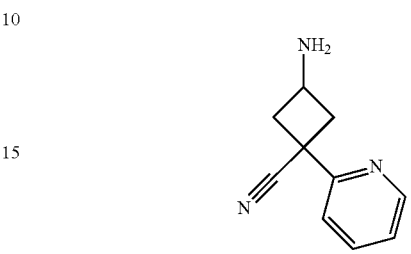

Step C: 3-Amino-1-(pyridin-2-yl)cyclobutanecarbonitrile

To a solution of 3-azido-1-(pyridin-2-yl)cyclobutanecarbonitrile (3.375 g, 16.94 mmol) in THF (30 mL) and water (8 mL) was added triphenylphosphine (5.33 g, 20.33 mmol) with cooling and stirring in an ice-water bath. The mixture was stirred at RT overnight. The reaction was diluted with 1N aqueous HCl and EtOAc. The acidic aqueous layer was separated and retained. The organic layer was washed with water, and then the combined aqueous layers were washed with EtOAc and basified by addition of 6 N aq NaOH. The product amine was extracted with EtOAc. The organic phase was concentrated to afford the title compound as a colorless oil and a 3:1 mixture of geometrical isomers, which was dried under vacuum and used without further purification.

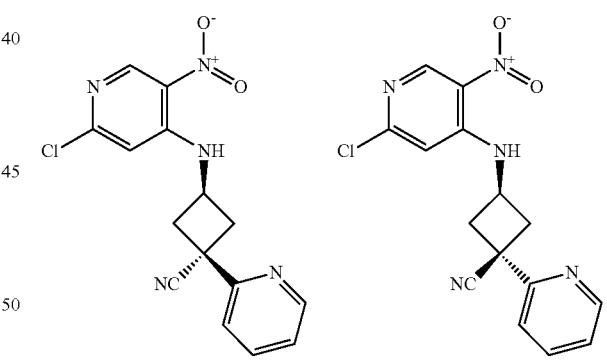

Step D: cis-3-(2-Chloro-5-nitropyridin-4-ylamino)-1-(pyridin-2-yl)cyclobutanecarbonitrile and trans-3-(2-chloro-5-nitropyridin-4-ylamino)-1-(pyridin-2-yl)cyclobutanecarbonitrile To a suspension of 2,4-dichloro-5-nitropyridine (2.39 g, 12.38 mmol) in ACN (20 mL) was added DIPEA (4.33 mL, 24.77 mmol) and 3-amino-1-(pyridin-2-yl)cyclobutanecarbonitrile (2.252 g, 13.00 mmol). The reaction mixture was heated at 80° C. for 8 hours. The reaction mixture was concentrated under vacuum, and the remaining residue was dissolved in DCM then washed with water and brine. The organic layer was concentrated under vacuum. The residue was purified by flash chromatography, eluting with 0-70% EtOAc/hexane to afford a mixture of diastereomers as an orange foam/solid. The diastereomers were separated by flash chromatography, eluting with 0-100% EtOAc/hexane to afford the minor diastereomer as a gold solid and assigned as trans-3-(2-chloro-5-nitropyridin-4-ylamino)-1-(pyridin-2-yl)cyclobutanecarbonitrile (0.618 g, 15.13% yield) based on NOE experiments. MS (ESI pos. ion) m/z: 330.0 [M+H]. Also obtained 1.56 g of the major diastereomer as a gold solid and assigned as cis-3-(2-chloro-5-nitropyridin-4-ylamino)-1-(pyridin-2-yl)cyclobutanecarbonitrile (1.56 g, 38.2% yield) based on NOE experiments. MS (ESI pos. ion) m/z: 330.0 [M+H].

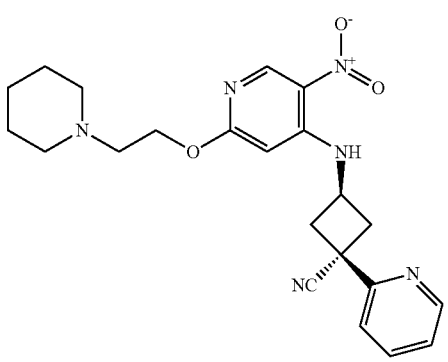 [SMILES: N#C[C@]1(c2ccccn2)C[C@@H](Nc2cc(OCCN3CCCCC3)ncc2[N+](=O)[O-])C1]

Step E: trans-3-(5-Nitro-2-(2-(piperidin-1-yl)ethoxy)pyridin-4-ylamino)-1-(pyridin-2-yl)cyclobutanecarbonitrile To a solution of trans-3-(2-chloro-5-nitropyridin-4-ylamino)-1-(pyridin-2-yl)cyclobutanecarbonitrile (0.150 g, 0.455 mmol) in toluene (3 mL) was added 1-piperidineethanol (0.300 mL, 2.275 mmol), 18-crown-6 (0.180 g, 0.682 mmol) and cesium carbonate (0.445 g, 1.365 mmol). The reaction mixture was heated at 80° C. overnight. The reaction mixture was diluted with EtOAc and was washed with water and brine. The organic layer was concentrated under vacuum. The sample was purified by flash chromatography, eluting with 0-100% 90:10:1 DCM/MeOH/NH$_4$OH:DCM to afford 161 mg of impure product as an orange-red oil. The impure sample was further purified by flash chromatography, eluting with 0-80% 90:10:1 DCM/MeOH/NH$_4$OH:DCM to afford trans-3-(5-nitro-2-(2-(piperidin-1-yl)ethoxy)pyridin-4-ylamino)-1-(pyridin-2-yl)cyclobutanecarbonitrile (0.134 g, 69.7% yield) as a dark orange oil. MS (ESI pos. ion) m/z: 423.2 [M+H].

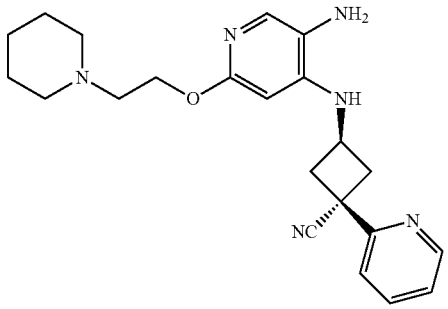 [SMILES: N#C[C@]1(c2ccccn2)C[C@@H](Nc2cc(OCCN3CCCCC3)ncc2N)C1]

Step F: trans-3-(5-Amino-2-(2-(piperidin-1-yl)ethoxy)pyridin-4-ylamino)-1-(pyridin-2-yl)cyclobutanecarbonitrile To a solution of trans-3-(5-nitro-2-(2-(piperidin-1-yl)ethoxy)pyridin-4-ylamino)-1-(pyridin-2-yl)cyclobutanecarbonitrile (0.131 g, 0.310 mmol) in MeOH (1.2 mL) was added anhydrous tin (II) chloride (0.235 g, 1.240 mmol). The reaction mixture was heated at 80° C. for 2 hours. The reaction mixture was concentrated under vacuum, and the remaining residue was dissolved in DCM and was washed with 1N aqueous NaOH followed by brine. The organic layer was dried over sodium sulfate and concentrated under vacuum. The sample was purified by flash chromatography, eluting with 20-100% 90:10:1 DCM/MeOH/NH$_4$OH:DCM to afford trans-3-(5-amino-2-(2-(piperidin-1-yl)ethoxy)pyridin-4-ylamino)-1-(pyridin-2-yl)cyclobutanecarbonitrile (0.091 g, 74.8% yield) as a red oil. MS (ESI pos. ion) m/z: 393.3 [M+H].

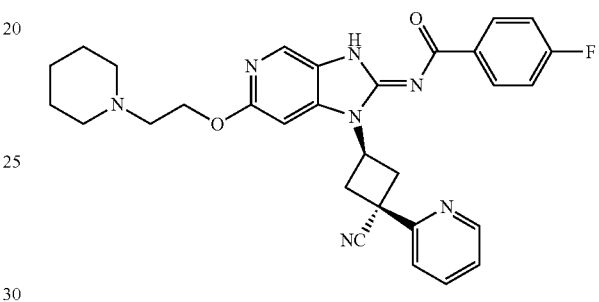

Step G: (E)-N-(1-(trans-3-Cyano-3-(pyridin-2-yl)cyclobutyl)-6-(2-(piperidin-1-yl)ethoxy)-1H-imidazo[4,5-c]pyridin-2(3H)-ylidene)-4-fluorobenzamide trans-3-(5-Amino-2-(2-(piperidin-1-yl)ethoxy)pyridin-4-ylamino)-1-(pyridin-2-yl)cyclobutanecarbonitrile (0.088 g, 0.224 mmol) was dissolved in THF (1.2 mL) and cooled to 0° C. 4-Fluorobenzoyl isothiocyanate (0.045 g, 0.247 mmol) was added as a THF solution. The resulting mixture was stirred at 0° C. for 30 minutes, warmed to 20° C., and stirred for 1 hour. DIPEA (0.047 mL, 0.269 mmol) and EDC (0.052 g, 0.269 mmol) were added to the reaction mixture, and the reaction was heated at 60° C. for 1 hour. The reaction mixture was diluted with DCM and washed with water and brine. The organic layer was concentrated under vacuum. The residue was purified by flash chromatography, eluting with 0-100% 90:10:1 DCM/MeOH/NH$_4$OH:DCM to afford (E)-N-(1-(trans-3-cyano-3-(pyridin-2-yl)cyclobutyl)-6-(2-(piperidin-1-yl)ethoxy)-1H-imidazo[4,5-c]pyridin-2(3H)-ylidene)-4-fluorobenzamide (0.053 g, 43.8% yield) as a tan solid. MS m/z (C$_{30}$H$_{30}$FN$_7$O$_2$); calcd 539.61. found 540.2 [M+H].

Example 241

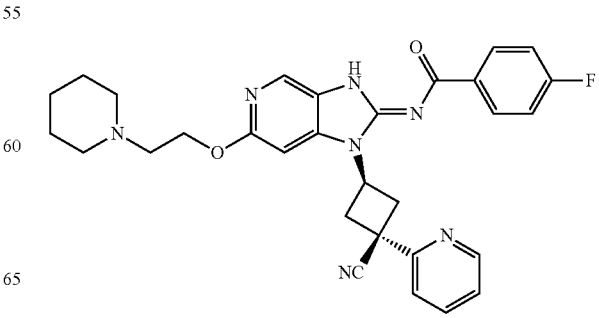

(E)-N-(1-(cis-3-Cyano-3-(pyridin-2-yl)cyclobutyl)-
6-(2-(piperidin-1-yl)ethoxy)-1H-imidazo[4,5-c]
pyridin-2(3H)-ylidene)-4-fluorobenzamide The title compound was prepared as previously described for (E)-N-(1-(trans-3-cyano-3-(pyridin-2-yl)cyclobutyl)-6-(2-(piperidin-1-yl)ethoxy)-1H-imidazo[4,5-c]pyridin-2(3H)-ylidene)-4-fluorobenzamide. MS m/z ($C_{30}H_{30}FN_7O_2$); calcd 539.61. found 540.3 [M+H]. $^1$H NMR (400 MHz, DMSO-$d_6$) δ ppm 1.31-1.42 (m, 2H) 1.43-1.55 (m, 4H) 2.33-2.47 (m, 4H) 2.57-2.71 (m, 2H) 3.21-3.27 (m, 2H) 4.07-4.23 (m, 2H) 4.34 (t, J=5.92 Hz, 2H) 5.36 (quin, J=8.90 Hz, 1H) 6.95 (s, 1H) 7.19-7.34 (m, 2H) 7.45-7.55 (m, 1H) 7.77-7.90 (m, 1H) 7.92-8.07 (m, 1H) 8.23 (s, 1H) 8.32-8.48 (m, 2H) 8.67-8.85 (m, 1H) 12.77 (br. s., 1H).

Example 242

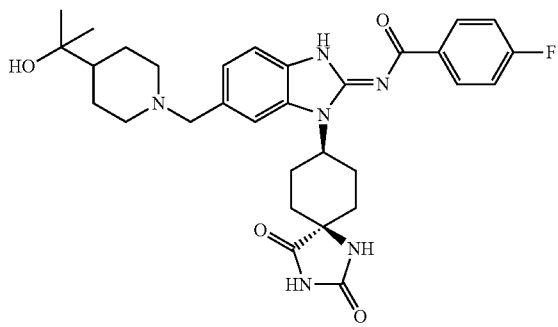 [SMILES: CC(C)(O)C1CCN(Cc2ccc3[nH]/c(=N\C(=O)c4ccc(F)cc4)n([C@H]4CC[C@]5(CC4)NC(=O)NC5=O)c3c2)CC1]

(E)-N-(1-((5S,8S)-2,4-Dioxo-1,3-diazaspiro[4.5]
decan-8-yl)-6-((4-(2-hydroxypropan-2-yl)piperidin-
1-yl)methyl)-1H-benzo[d]imidazol-2(3H)-ylidene)-
4-fluorobenzamide Step A. 1,3-Diazaspiro[4.5]decane-2,4,8-trione A suspension of 9,12-dioxa-1,3-diazadispiro[4.2.4.2]tetradecane-2,4-dione (6.33 g, 28.0 mmol) in HCl (6N) (28 mL, 168 mmol) and EtOH (66.0 mL) was stirred at RT for 18 hours. The mixture was partially evaporated (about ½ volume), cooled in an ice bath and brought to a pH of approximately 10. The aqueous layer was extracted with DCM (2×200 mL), and the aqueous layer concentrated. The residue was triturated with THF (2×100 mL), and solids were removed by filtration. The filtrate was evaporated to afford the title compound as a white solid.

Step B.
8-Amino-1,3-diazaspiro[4.5]decane-2,4-dione

To a suspension of 1,3-diazaspiro[4.5]decane-2,4,8-trione (5.00 g, 27.4 mmol) in MeOH (91 mL) was added ammonium acetate (6.35 g, 82 mmol), and the mixture was stirred at RT for 25 minutes. To the suspension was added sodium cyanoborohydride (5.17 g, 82 mmol), and the mixture was stirred at RT. After 90 minutes, the flask was cooled, and the contents were quenched by careful addition of aqueous concentrated HCl, adjusting the pH to 7 with solid NaHCO$_3$. The mixture was filtered through a pad of Celite® brand filter aid and concentrated in vacuo. The material was used directly in the next step.

Step C. 8-(5-(Hydroxymethyl)-2-nitrophenylamino)-
1,3-diazaspiro[4.5]decane-2,4-dione The title compound was prepared using a method analogous to that used in the preparation of cis-methyl 4-(3-nitropyridin-4-ylamino)cyclohexanecarboxylate starting from 8-amino-1,3-diazaspiro[4.5]decane-2,4-dione.

Step D. 8-(5-((4-(2-Hydroxypropan-2-yl)piperidin-1-
yl)methyl)-2-nitrophenylamino)-1,3-diazaspiro[4.5]
decane-2,4-dione The title compound was prepared using a method analogous to that used in the preparation of cis-methyl 4-((E)-2-(4-fluorobenzoylimino)-6-(piperidin-1-ylmethyl)-2,3-dihydro-1H-benzo[d]imidazol-1-yl)cyclohexanecarboxylate starting from 8-(5-(hydroxymethyl)-2-nitrophenylamino)-1,3-diazaspiro[4.5]decane-2,4-dione.

Step E. 8-(2-Amino-5-(4-(2-hydroxypropan-2-yl)
piperidin-1-yl)methyl)phenylamino)-1,3-diazaspiro
[4.5]decane-2,4-dione The title compound was synthesized using a method analogous to the preparation of cis-4-(5-amino-2-(2-(piperidin-1-yl)ethoxy)pyridin-4-ylamino)-N-isopropylcyclohexanecarboxamide starting from 8-(5-((4-(2-hydroxypropan-2-yl)piperidin-1-yl)methyl)-2-nitrophenylamino)-1,3-diazaspiro[4.5]decane-2,4-dione.

Step F. (E)-N-(1-((5S,8S)-2,4-Dioxo-1,3-diazaspiro
[4.5]decan-8-yl)-6-((4-(2-hydroxypropan-2-yl)pip-
eridin-1-yl)methyl)-1H-benzo[d]imidazol-2(3H)-
ylidene)-4-fluorobenzamide The title compound was prepared from 8-(2-amino-5-((4-(2-hydroxypropan-2-yl)piperidin-1-yl)methyl)phenylamino)-1,3-diazaspiro[4.5]decane-2,4-dione (467 mg, 1.087 mmol) using a method analogous to that used in the preparation of (E)-4-fluoro-N-(1-((1S,4S)-4-(isopropylcarbamoyl)cyclohexyl)-6-(methylsulfonyl)-1H-imidazo[4,5-c]pyridin-2(3H)-ylidene)benzamide, and obtained as a white solid. MS m/z ($C_{31}H_{37}FN_6O_4$), calcd 576.66. found 577 [M+H].

Example 243

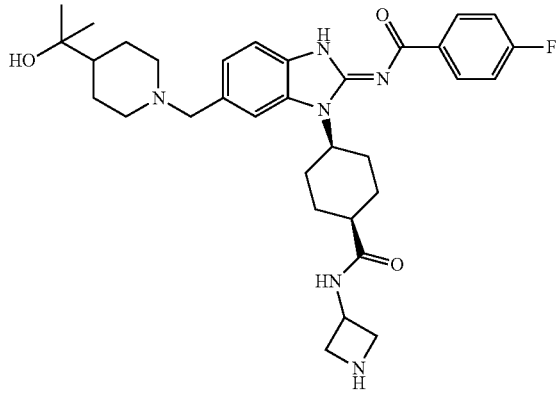 [SMILES: CC(C)(O)C1CCN(Cc2ccc3[nH]/c(=N\C(=O)c4ccc(F)cc4)n([C@H]4CC[C@@H](C(=O)NC5CNC5)CC4)c3c2)CC1]

(E)-N-(1-(cis-4-(Azetidin-3-ylcarbamoyl)cyclohexyl)-6-((4-(2-hydroxypropan-2-yl)piperidin-1-ylmethyl)-1H-benzo[d]imidazol-2(3H)-ylidene)-4-fluorobenzamide The title compound was prepared from cis-4-((E)-2-(4-fluorobenzoylimino)-6-((4-(2-hydroxypropan-2-yl)piperidin-1-yl)methyl)-2,3-dihydro-1H-benzo[d]imidazol-1-yl)cyclohexanecarboxylic acid using a method analogous to that used in the preparation of (E)-N-(1-(cis-4-(cis-2,5-diazabicyclo[2.2.1]heptane-2-carbonyl)cyclohexyl)-6-(2-(4-(2-hydroxypropan-2-yl)piperidin-1-yl)ethoxy)-1H-imidazo[4,5-c]pyridin-2(3H)-ylidene)-3-fluorobenzamide. MS m/z ($C_{33}H_{43}FN_6O_3$), calcd 590.3. found 591.2 [M+H].

Example 244

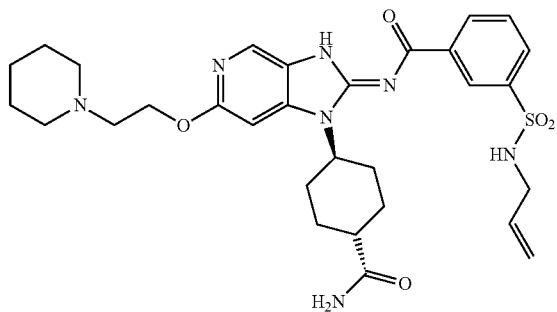

(E)-3-(N-Allylsulfamoyl)-N-(1-(trans-4-carbamoylcyclohexyl)-6-(2-(piperidin-1-yl)ethoxy)-1H-imidazo[4,5-c]pyridin-2(3H)-ylidene)benzamide Step A: trans-4-(2-Chloro-5-nitropyridin-4-ylamino)cyclohexanecarboxylic acid hydrochloride Trans-4-Aminocyclohexanecarboxylic acid (5.01 g, 35.0 mmol) and potassium carbonate (4.83 g, 35.0 mmol) were dissolved in water (20.00 mL). 2,4-Dichloro-5-nitropyridine (6.75 g, 35.0 mmol) was added to the reaction mixture as a dioxane (40 mL) solution. The reaction mixture was stirred at 80° C. for 8 hours. The reaction mixture was concentrated under vacuum to remove the dioxane and the remaining aqueous solution was acidified with aqueous 2N HCl (approximately pH 2-3). A precipitate formed which was collected on a glass frit washing well with water and then with DCM. The solid was dried under high vacuum at 37° C. 8.79 g of trans-4-(2-chloro-5-nitropyridin-4-ylamino)cyclohexanecarboxylic acid hydrochloride (74.8% yield) was collected as a yellow solid. Mass cal'd: 299.1; MS (ESI pos. ion) m/z: 300.0 [M+H].

Step B. Trans-4-(2-chloro-5-nitropyridin-4-ylamino)cyclohexanecarboxamide

Trans-4-(2-Chloro-5-nitropyridin-4-ylamino)cyclohexanecarboxylic acid hydrochloride (5.00 g, 14.87 mmol) was suspended in THF (30 mL), and the mixture was cooled to 0° C. Thionyl chloride (4.34 mL, 59.5 mmol) was slowly added via syringe. The suspension became thicker and lighter yellow in color. The reaction mixture was stirred at 0° C. for 15 minutes and then warmed to 20° C. and stirred for an additional 2 hours. The reaction was concentrated to dryness under vacuum. The remaining solid was concentrated from THF again and dried under high vacuum. The solid was resuspended in THF (75 mL), cooled to 0° C. and then ammonia gas was bubbled through the mixture for approximately 5 minutes. The reaction mixture was stirred at 0° C. for 30 minutes then warmed to 20° C. and stirred overnight. A precipitate was present in the reaction mixture. Water was added to the mixture and stirring was continued for about 15 minutes. The mixture was filtered and the solid was washed with water and THF and dried under high vacuum to yield 3.93 g of product as a yellow solid. The filtrate was also extracted with DCM, and the organic layer was dried over sodium sulfate and concentrated under vacuum to yield an additional 981 mg of product as a yellow solid. Mass cal'd: 298.1; MS (ESI pos. ion) m/z: 299.0 [M+H].

Step C. trans-4-(5-Nitro-2-(2-(piperidin-1-yl)ethoxy)pyridin-4-ylamino)cyclohexanecarboxamide Trans-4-(2-Chloro-5-nitropyridin-4-ylamino)cyclohexanecarboxamide (3.00 g, 10.04 mmol) was suspended in toluene (30 mL). 1-Piperidine ethanol (6.62 mL, 50.2 mmol), 18-crown-6 (3.98 g, 15.06 mmol) and cesium carbonate (9.82 g, 30.1 mmol) were then added to the reaction. The resulting reaction mixture was heated at 80° C. overnight followed by additional heating at 90° C. for 8 hours. The reaction mixture was diluted with DCM and washed with water and brine. The organic layer was concentrated under vacuum to yield 6.43 g of crude material as a yellow oil/residue. The sample was purified by flash chromatography, eluting with 0-100% 90:10:1 dichloromethane/methanol/NH$_4$OH:dichloromethane to afford 1.62 g of trans-4-(5-nitro-2-(2-(piperidin-1-yl)ethoxy)pyridin-4-ylamino)cyclohexanecarboxamide (41.2% yield) as a yellow solid. Mass cal'd: 391.2; MS (ESI pos. ion) m/z: 392.2 [M+H].

Step D. trans-4-(5-Amino-2-(2-(piperidin-1-yl)ethoxy)pyridin-4-ylamino)cyclohexanecarboxamide The title compound was prepared as previously described for cis-4-(5-amino-2-(methylsulfonyl)pyridin-4-ylamino)-N-isopropylcyclohexanecarboxamide. The sample was purified via trituration with DCM to yield 914 mg of trans-4-(5-amino-2-(2-(piperidin-1-yl)ethoxy)pyridin-4-ylamino)cyclohexanecarboxamide (61.1% yield) as a light red solid. Mass cal'd: 361.2; MS (ESI pos. ion) m/z: 362.2 [M+H].

Step E. (E)-3-(N-Allylsulfamoyl)-N-(1-(trans-4-carbamoylcyclohexyl)-6-(2-(piperidin-1-yl)ethoxy)-1H-imidazo[4,5-c]pyridin-2(3H)-ylidene)benzamide The title compound was prepared as previously described for (E)-4-fluoro-N-(1-(cis-4-(isopropylcarbamoyl)cyclohexyl)-6-(methylsulfonyl)-1H-imidazo[4,5-c]pyridin-2(3H)-ylidene)benzamide. The sample was purified by flash chromatography, eluting with 20-100% 90:10:1 DCM/MeOH1/NH$_4$OH:DCM followed by trituration with DCM to afford 77 mg of (E)-3-(N-allylsulfamoyl)-N-(1-(trans-4-carbamoylcyclohexyl)-6-(2-(piperidin-1-yl)ethoxy)-1H-imidazo[4,5-c]pyridin-2 (3H)-ylidene)benzamide (76% yield) as a pale yellow solid. Mass cal'd: 609.3; MS (ESI pos. ion) m/z: 610.0 [M+H].

Example 245

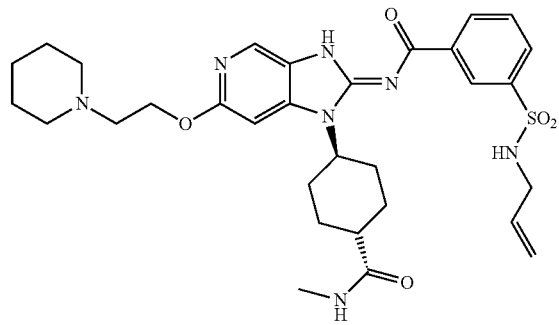

(E)-3-(N-Allylsulfamoyl)-N-(1-((1R,4R)-4-(methyl-carbamoyl)cyclohexyl)-6-(2-(piperidin-1-yl)ethoxy)-1H-imidazo[4,5-c]pyridin-2(3H)-ylidene)benzamide The title compound was prepared in an analogous manner to Example 244. The sample was purified by flash chromatography, eluting with 0-100% 90:10:1 DCM/MeOH/NH$_4$OH:DCM followed by trituration with ACN to afford 58 mg of (E)-3-(N-allylsulfamoyl)-N-(1-(trans-4-(methylcarbamoyl)cyclohexyl)-6-(2-(piperidin-1-yl)ethoxy)-1H-imidazo[4,5-c]pyridin-2(3H)-ylidene)benzamide (46.6% yield) as a white solid. Mass cal'd: 623.3; MS (ESI pos. ion) m/z: 624.3 [M+H].

Example 246

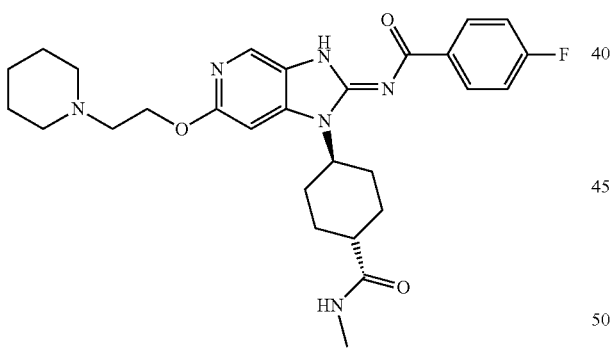

(E)-4-Fluoro-N-(1-(trans-4-(methylcarbamoyl)cyclo-hexyl)-6-(2-(piperidin-1-yl)ethoxy)-1H-imidazo[4,5-c]pyridin-2(3H)-ylidene)benzamide The title compound was prepared in an analogous manner to Example 244 The sample was purified by flash chromatography, eluting with 0-100% 90:10:1 DCM/MeOH/NH$_4$OH:DCM followed by trituration with ACN to afford 87 mg of (E)-4-fluoro-N-(1-(trans-4-(methylcarbamoyl)cyclohexyl)-6-(2-(piperidin-1-yl)ethoxy)-1H-imidazo[4,5-c]pyridin-2(3H)-ylidene)benzamide (0.087 g, 0.166 mmol, 83% yield) as a white solid. Mass cal'd: 522.3; MS (ESI pos. ion) m/z: 523.2 [M+H].

Example 247

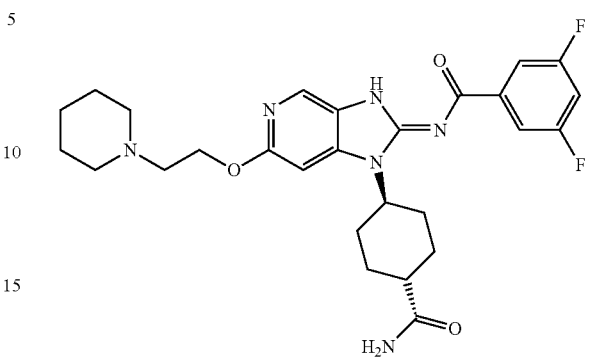

(E)-N-(1-(trans-4-Carbamoylcyclohexyl)-6-(2-(piperidin-1-yl)ethoxy)-1H-imidazo[4,5-c]pyridin-2(3H)-ylidene)-3,5-difluorobenzamide The title compound was prepared in an analogous manner to Example 244. The sample was purified by flash chromatography, eluting with 10-100% 90:10:1 DCM/MeOH/NH$_4$OH:DCM followed by trituration with DCM and then ACN to afford 63 mg of (E)-N-(1-(trans-4-carbamoylcyclohexyl)-6-(2-(piperidin-1-yl)ethoxy)-1H-imidazo[4,5-c]pyridin-2(3H)-ylidene)-3,5-difluorobenzamide (0.063 g, 0.120 mmol, 72.1% yield) as a white solid. Mass cal'd: 526.2; MS (ESI pos. ion) m/z: 527.2 [M+H].

Example 248

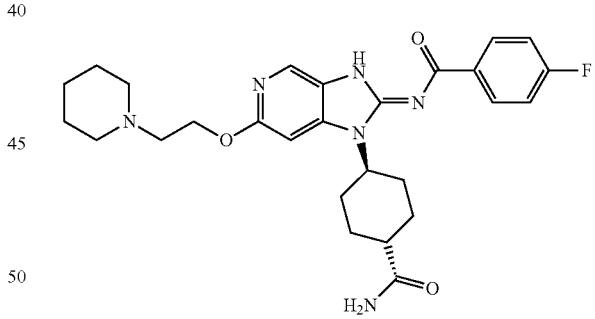

(E)-N-(1-(trans-4-Carbamoylcyclohexyl)-6-(2-(piperidin-1-yl)ethoxy)-1H-imidazo[4,5-c]pyridin-2(3H)-ylidene)-4-fluorobenzamide The title compound was prepared in an analogous manner to Example 244. The sample was purified by flash chromatography, eluting with 0-100% 90:10:1 DCM/MeOH/NH$_4$OH:DCM to afford 27 mg of (E)-N-(1-(trans-4-carbamoylcyclohexyl)-6-(2-(piperidin-1-yl)ethoxy)-1H-imidazo[4,5-c]pyridin-2(3H)-ylidene)-4-fluorobenzamide (0.027 g, 0.053 mmol, 32.0% yield) as a pale yellow solid. Mass cal'd: 508.3; MS (ESI pos. ion) m/z: 509.2 [M+H].

Example 249

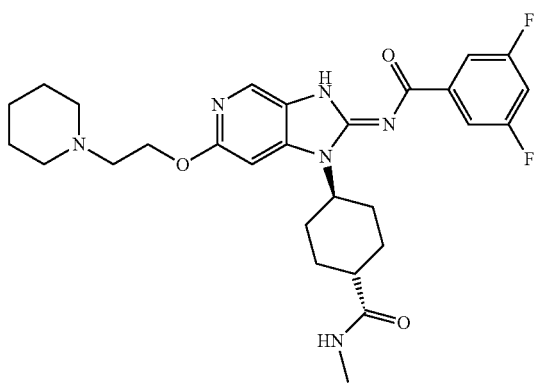

(E)-3,5-Difluoro-N-(1-(trans-4-(methylcarbamoyl)cyclohexyl)-6-(2-(piperidin-1-yl)ethoxy)-1H-imidazo[4,5-c]pyridin-2(3H)-ylidene)benzamide The title compound was prepared in an analogous manner to Example 245. The sample was purified by flash chromatography, eluting with 10-100% 90:10:1 DCM/MeOH/NH₄OH:DCM followed by trituration with ACN to afford 51 mg of (E)-3,5-difluoro-N-(1-(trans-4-(methylcarbamoyl)cyclohexyl)-6-(2-(piperidin-1-yl)ethoxy)-1H-imidazo[4,5-c]pyridin-2(3H)-ylidene)benzamide (0.051 g, 0.094 mmol, 47.2% yield) as a white solid. Mass cal'd: 540.3; MS (ESI pos. ion) m/z: 541.2 [M+H].

Example 250

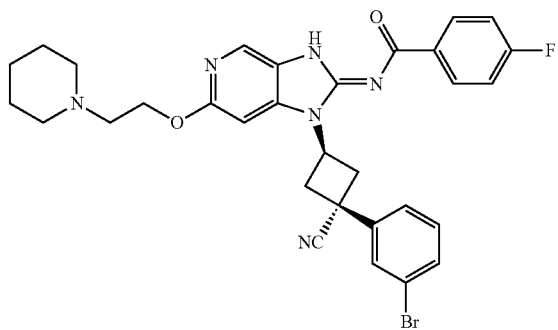 [SMILES: N#C[C@]1(c2cccc(Br)c2)C[C@@H](n2/c(=N/C(=O)c3ccc(F)cc3)[nH]c3cnc(OCCN4CCCCC4)cc32)C1]

(E)-N-(1-(trans-3-(3-Bromophenyl)-3-cyanocyclobutyl)-6-(2-(piperidin-1-yl)ethoxy)-1H-imidazo[4,5-c]pyridin-2(3H)-ylidene)-4-fluorobenzamide

Step A.
1-(3-Bromophenyl)-3-oxocyclobutanecarbonitrile

To 3-bromophenylacetonitrile (7.55 g, 38.5 mmol) and 1,3-dibromo-2,2-dimethyoxypropane (10.09 g, 38.5 mmol) in dry DMSO (100 ml) was added in two portions sodium hydride (3.23 g of 60% dispersion in oil, 81 mmol) while the mixture was cooled in a water bath. The mixture was stirred at RT for 10 minutes, and heated at 60° C. in an oil bath for 6 hours. The reaction was diluted with water and extracted with EtOAc. The organic layer was separated, washed with water and the solvent removed. The residual red oil was eluted through a short pad of silica, eluent 10% EtOAc/Hexane. The resulting ketal was dissolved in acetone (100 ml) and 1N aqueous HCl (10 ml) and heated at reflux for 6 hours under a nitrogen atmosphere. The solvent was removed and the residue was neutralized by treatment with aqueous NaHCO₃ and extracted with EtOAc. The solvent was removed and the residue was chromatographed (SiO₂, eluent 10% EtOAc in hexane) to give a yellow oil which solidified on drying under vacuum.

Step B.
1-(3-Bromophenyl)-3-hydroxycyclobutanecarbonitrile 1-(3-Bromophenyl)-3-oxocyclobutanecarbonitrile (2.00 g, 8.00 mmol) was dissolved in DCM (15 mL) and MeOH (15.00 mL), and the mixture was cooled to 0° C. Sodium borohydride (0.333 g, 8.80 mmol) was added to the reaction mixture, and stirring was continued at 0° C. for 1.5 hours. The reaction mixture was quenched with water at 0° C. then warmed to RT. DCM was added, and the mixture was washed with water and brine. The organic layer was dried over sodium sulfate and concentrated under vacuum to afford 2.02 g of 1-(3-bromophenyl)-3-hydroxycyclobutanecarbonitrile (2.02 g, 8.01 mmol, 100% yield) as a pale yellow oil. Mass cal'd: 250.99; MS (ESI pos. ion) m/z: 252.0 [M+H].

Step C. (E)-N-(1-(trans-3-(3-Bromophenyl)-3-cyanocyclobutyl)-6-(2-(piperidin-1-yl)ethoxy)-1H-imidazo[4,5-c]pyridin-2(3H)-ylidene)-4-fluorobenzamide The title compound was prepared from 1-(3-bromophenyl)-3-hydroxycyclobutanecarbonitrile in an analogous manner to Example 240. The sample was purified by flash chromatography, eluting with 0-100% 90:10:1 DCM/MeOH/NH₄OH:DCM followed by the separation of diastereomers via SFC chromatography eluting with 45% MeOH (0.1% DEA)/CO₂, 100 bar to afford 116 mg of (E)-N-(1-(trans-3-(3-bromophenyl)-3-cyanocyclobutyl)-6-(2-(piperidin-1-yl)ethoxy)-1H-imidazo[4,5-c]pyridin-2(3H)-ylidene)-4-fluorobenzamide (0.116 g, 0.188 mmol, 24.9% yield) as a tan solid. Mass cal'd: 616.2; MS (ESI pos. ion) m/z: 617.0 [M+H].

Example 251

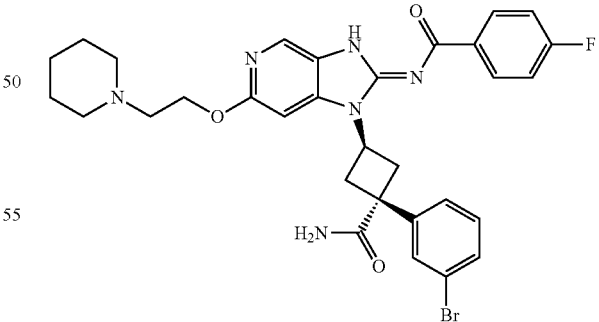

(E)-N-(1-(trans-3-(3-Bromophenyl)-3-carbamoylcyclobutyl)-6-(2-(piperidin-1-yl)ethoxy)-1H-imidazo[4,5-c]pyridin-2(3H)-ylidene)-4-fluorobenzamide (E)-N-(1-(trans-3-(3-Bromophenyl)-3-cyanocyclobutyl)-6-(2-(piperidin-1-yl)ethoxy)-1H-imidazo[4,5-c]pyridin-2

(3H)-ylidene)-4-fluorobenzamide (0.055 g, 0.089 mmol) was dissolved in concentrated sulfuric acid (0.570 μL, 10.69 mmol) and then stirred at 20° C. for 2 hours. The reaction mixture was slowly poured into cold saturated aqueous sodium carbonate. A precipitate formed which was collected on a glass frit, washing with water, acetonitrile and dichloromethane. The solid was transferred to a flask with DCM/MeOH and concentrated under vacuum. The residue was then dried under high vacuum to afford 37 mg of (E)-N-(1-(trans-3-(3-bromophenyl)-3-carbamoylcyclobutyl)-6-(2-(piperidin-1-yl)ethoxy)-1H-imidazo[4,5-c]pyridin-2(3H)-ylidene)-4-fluorobenzamide (0.037 g, 0.058 mmol, 65.4% yield) as a tan solid. Mass cal'd: 634.2; MS (ESI pos. ion) m/z: 635.0 [M+H].

Example 252

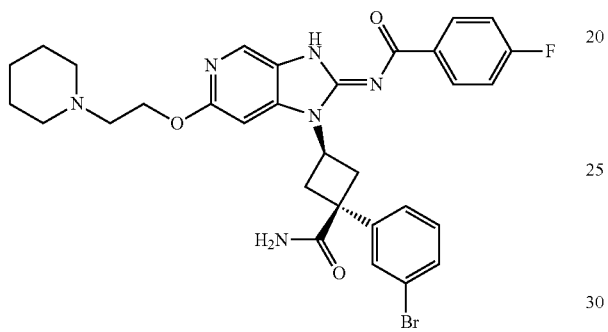

(E)-N-(1-(cis-3-(3-Bromophenyl)-3-carbamoylcyclobutyl)-6-(2-(piperidin-1-yl)ethoxy)-1H-imidazo[4,5-c]pyridin-2(3H)-ylidene)-4-fluorobenzamide The title compound was prepared in an analogous manner to Example 251 to afford 54 mg of (E)-N-(1-(cis-3-(3-bromophenyl)-3-carbamoylcyclobutyl)-6-(2-(piperidin-1-yl)ethoxy)-1H-imidazo[4,5-c]pyridin-2(3H)-ylidene)-4-fluorobenzamide. Mass cal'd: 634.2; MS (ESI pos. ion) m/z: 635.0 [M+H].

ALK Inhibition in Enzyme Assay

The cytoplasmic domain (amino acids 1058-1620) of wild-type human ALK was expressed in SF9 cells as an N-terminal GST fusion protein. Kinase activity of the purified protein was assessed using a Lance® TR-FRET assay. The kinase reaction was performed in a 384-well microtiter plate using 2 nM enzyme in 20 mM HEPES (pH 7.5), 0.05% BSA, 2 mM DTT, 10 mM $MgCl_2$, 1 μM peptide substrate (Biotin-Ahx-EQEDEPEGIYGVLF-OH) (SEQ ID NO: 1), and ATP at 40 μM (the Km apparent). The reaction was allowed to proceed for 90 minutes at room temperature and was then terminated with 20 mM EDTA in 50 mM Tris (pH 7.5), 100 mM NaCl, 0.05% BSA, and 0.1% Tween-20. Phosphorylation of the peptide substrate was detected using the Lance® detection reagents streptavidin-allophycocyanin (SA-APC) and Eu-W1024 anti-phosphotyrosine antibody (PT66) from Perkin Elmer Life Sciences (Waltham, Mass.). The plates were read on a RUBY star plate reader (BMG LABTECH, Cary, N.C.) with an excitation wavelength of 320 nm. Emission was monitored at 615 nm and 665 nm, with increased emission at 665 nm indicative of peptide phosphorylation. Compound $IC_{50}$ values were calculated from the magnitude of signal in the 655 nm emission channel and were expressed as the mean of three replicates.

The following table includes ALK $IC_{50}$ values obtained using the procedure set forth above for the Example compounds described herein.

| Table of ALK $IC_{50}$ values of Example Compounds | |
|---|---|
| Example | ALK $IC_{50}$ (μM)[a] |
| 1 | ++++ |
| 2 | ++++++ |
| 3 | ++++++ |
| 4 | ++++++ |
| 5 | ++++++ |
| 6 | ++++++ |
| 7 | ++++++ |
| 8 | ++++++ |
| 9 | ++++++ |
| 10 | ++++ |
| 11 | ++++++ |
| 12 | ++++ |
| 13 | ++++ |
| 14 | ++++++ |
| 15 | ++++++ |
| 16 | +++++ |
| 17 | ++++++ |
| 18 | ++++++ |
| 19 | ++++++ |
| 20 | ++++++ |
| 21 | ++++++ |
| 22 | ++++++ |
| 23 | ++++++ |
| 24 | ++++++ |
| 25 | +++ |
| 26 | ++++++ |
| 27 | ++++ |
| 28 | ++++ |
| 29 | ++++++ |
| 30 | ++++++ |
| 31 | ++++++ |
| 32 | ++++++ |
| 33 | ++++++ |
| 34 | ++++ |
| 35 | ++++++ |
| 36 | ++++ |
| 37 | ++++ |
| 38 | ++++++ |
| 39 | ++++++ |
| 40 | +++++ |
| 41 | ++++++ |
| 42 | +++ |
| 43 | ++++++ |
| 44 | ++++++ |
| 45 | ++++++ |
| 46 | ++++++ |
| 47 | ++++++ |
| 48 | ++++++ |
| 49 | +++++ |
| 50 | ++++++ |
| 51 | ++++++ |
| 52 | ++++++ |
| 53 | ++++++ |
| 54 | ++++++ |
| 55 | NA[b] |
| 56 | ++++ |
| 57 | ++++++ |
| 58 | ++++++ |
| 59 | ++++++ |
| 60 | +++ |
| 61 | ++++++ |
| 62 | +++++ |
| 63 | +++++ |
| 64 | ++++ |
| 65 | +++ |
| 66 | ++++ |
| 67 | ++++ |
| 68 | ++ |
| 69 | ++++ |
| 70 | +++ |
| 71 | ++++ |

Table of ALK IC$_{50}$ values of Example Compounds

| Example | ALK IC$_{50}$ (μM)$^a$ |
|---|---|
| 72 | ++++++ |
| 73 | ++++ |
| 74 | ++++++ |
| 75 | ++++ |
| 76 | +++ |
| 77 | ++++++ |
| 78 | ++++++ |
| 79 | +++ |
| 80 | ++++++ |
| 81 | ++++ |
| 82 | +++ |
| 83 | ++++ |
| 84 | ++++ |
| 85 | ++++++ |
| 86 | ++ |
| 87 | +++++ |
| 88 | +++++ |
| 89 | ++++++ |
| 90 | ++++++ |
| 91 | ++++++ |
| 92 | ++++++ |
| 93 | +++ |
| 94 | +++++ |
| 95 | ++++++ |
| 96 | ++++++ |
| 97 | +++++ |
| 98 | ++++++ |
| 99 | ++++ |
| 100 | +++++ |
| 101 | ++++++ |
| 102 | ++++ |
| 103 | ++++++ |
| 104 | ++++ |
| 105 | +++ |
| 106 | ++++++ |
| 107 | ++++++ |
| 108 | ++++++ |
| 109 | +++ |
| 110 | +++ |
| 111 | ++++++ |
| 112 | ++ |
| 113 | ++++ |
| 114 | +++++ |
| 115 | ++++++ |
| 116 | +++++ |
| 117 | +++++ |
| 118 | ++++++ |
| 119 | ++++++ |
| 120 | ++++ |
| 121 | +++++ |
| 122 | ++++ |
| 123 | ++++++ |
| 124 | ++++ |
| 125 | ++++++ |
| 126 | ++++++ |
| 127 | ++++++ |
| 128 | ++++++ |
| 129 | ++++++ |
| 130 | ++++++ |
| 131 | ++++ |
| 132 | ++++ |
| 133 | ++++ |
| 134 | +++++ |
| 135 | ++++++ |
| 136 | +++ |
| 137 | ++++++ |
| 138 | ++++++ |
| 139 | ++++++ |
| 140 | ++++++ |
| 141 | ++++++ |
| 142 | ++++++ |
| 143 | ++++++ |
| 144 | ++++++ |
| 145 | ++++++ |
| 146 | ++++++ |
| 147 | ++++++ |
| 148 | ++++++ |
| 149 | ++++++ |
| 150 | ++++++ |
| 151 | ++++++ |
| 152 | ++++++ |
| 153 | ++++++ |
| 154 | ++++++ |
| 155 | ++++++ |
| 156 | ++++++ |
| 157 | ++++++ |
| 158 | ++++++ |
| 159 | ++++++ |
| 160 | ++++++ |
| 161 | ++++++ |
| 162 | ++++++ |
| 163 | ++++++ |
| 164 | ++++++ |
| 165 | ++++++ |
| 166 | ++++++ |
| 167 | ++++++ |
| 168 | ++++++ |
| 169 | ++++++ |
| 170 | ++++++ |
| 171 | ++++++ |
| 172 | ++++++ |
| 173 | ++++++ |
| 174 | ++++++ |
| 175 | ++++++ |
| 176 | ++++++ |
| 177 | ++++++ |
| 178 | ++++++ |
| 179 | ++++++ |
| 180 | ++++++ |
| 181 | ++++++ |
| 182 | ++++++ |
| 183 | ++++++ |
| 184 | ++++++ |
| 185 | ++++++ |
| 186 | ++++++ |
| 187 | ++++++ |
| 188 | ++++++ |
| 189 | ++++++ |
| 190 | ++++++ |
| 191 | ++++++ |
| 192 | ++++++ |
| 193 | ++++++ |
| 194 | ++++++ |
| 195 | ++++++ |
| 196 | ++++++ |
| 197 | ++++++ |
| 198 | ++++++ |
| 199 | ++++++ |
| 200 | ++++++ |
| 201 | ++++++ |
| 202 | ++++ |
| 203 | ++++ |
| 204 | ++++++ |
| 205 | ++++++ |
| 206 | +++++ |
| 207 | +++++ |
| 208 | ++++++ |
| 209 | ++++++ |
| 210 | ++++ |
| 211 | ++++++ |
| 212 | ++++++ |
| 213 | ++++++ |
| 214 | ++++++ |
| 215 | ++++++ |
| 216 | ++++++ |
| 217 | ++++++ |
| 218 | ++++++ |
| 219 | ++++++ |

Table of ALK $IC_{50}$ values of Example Compounds

| Example | ALK $IC_{50}$ ($\mu$M)[a] |
|---|---|
| 220 | ++++++ |
| 221 | ++++++ |
| 222 | ++++++ |
| 223 | ++++++ |
| 224 | ++++++ |
| 225 | ++++++ |
| 226 | ++++++ |
| 227 | +++++ |
| 228 | ++++ |
| 229 | +++++ |
| 230 | ++++++ |
| 231 | ++++++ |
| 232 | ++++++ |
| 233 | +++++ |
| 234 | ++++ |
| 235 | ++++++ |
| 236 | ++++++ |
| 237 | ++++ |
| 238 | ++++++ |
| 239 | ++++++ |
| 240 | +++ |
| 241 | ++++ |
| 242 | ++++ |
| 243 | ++++++ |
| 244 | +++++ |
| 245 | +++++ |
| 246 | ++++ |
| 247 | +++ |
| 248 | +++ |
| 249 | +++ |
| 250 | ++++ |
| 251 | +++++ |
| 252 | +++ |

[a]$IC_{50}$ Ranges: + $IC_{50}$ > 10 $\mu$M ++ 5 $\mu$M ≤ $EC_{50}$ ≤ 10 $\mu$M +++ 1 $\mu$M ≤ $EC_{50}$ < 5 $\mu$M ++++ 0.1 $\mu$M ≤ $EC_{50}$ < 1 $\mu$M +++++ 0.05 $\mu$M ≤ $EC_{50}$ < 0.1 $\mu$M ++++++ $EC_{50}$ < 0.05 $\mu$M
[b]Not Applicable All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound of Formula I:

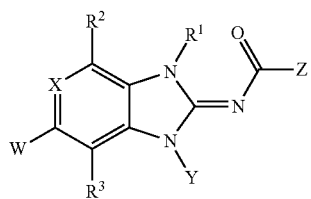

I or a pharmaceutically acceptable salt thereof, tautomer thereof, a pharmaceutically acceptable salt of the tautomer, or a stereoisomer of any of the foregoing, wherein:
$R^1$ is —H;
$R^2$ is —H;
$R^3$ is —H;
X is selected from $CR^4$;
$R^4$ is —H;
Y is selected from a $C_3$-$C_{12}$ cycloalkyl or a 3-10 membered heterocyclyl comprising 1, 2, or 3 heteroatoms selected from O, S, or N; wherein the $C_3$-$C_{12}$ cycloalkyl and the 3-10 membered heterocyclyl may be monocyclic, bicyclic, or tricyclic, and further wherein the $C_3$-$C_{12}$ cycloalkyl and the 3-10 membered heterocyclyl comprise a substituent selected from C(=O)$NH_2$, —C(=O)NH(($C_1$-$C_6$)alkyl), —C(=O)NH—($C_1$-$C_4$)alkylene-$CF_3$, —C(=O)NH—($C_1$-$C_4$)alkylene-F, —C(=O)NH—($C_2$-$C_4$)alkenyl, —C(=O)N(($C_1$-$C_6$)alkyl)$_2$, —C(=O)NH—OH, —C(=O)NH—O—($C_1$-$C_6$)alkyl, —C(=O)NH—Y", —C(=O)—($C_1$-$C_4$)alkylene-$CF_3$, —C(=O)N—($C_1$-$C_4$)alkylene-F, —C(=O)—($C_2$-$C_4$)alkenyl, —C(=O)—($C_1$-$C_4$)alkylene-$NH_2$, —C(=O)—($C_1$-$C_4$)alkylene-NH(($C_1$-$C_4$)alkyl), —C(=O)—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-O—($C_1$-$C_6$)alkyl, —C(=O)NH—($C_1$-$C_4$)alkylene-Y", —C(=O)—($C_1$-$C_6$)alkyl, —C(=O)—Y", —$CO_2$H, —C(=O)—O—($C_1$-$C_6$)alkyl, —C(=O)NH—($C_1$-$C_4$)alkylene-$NH_2$, —C(=O)NH—($C_1$-$C_4$)alkylene-NH(($C_1$-$C_6$)alkyl), and —C(=O)NH—($C_1$-$C_4$)alkylene-N(($C_1$-$C_6$)alkyl)$_2$, —($C_1$-$C_4$)alkylene-NH—C(=O)—($C_1$-$C_6$)alkyl; and
wherein Y optionally further comprises 1 or 2 substituents selected from Y', —F, —Cl, —Br, —I, —C≡N, —$NO_2$, —OH, —O-($C_1$-$C_6$)alkyl, —SH, —S—($C_1$-$C_6$)alkyl, —$OCF_3$, —$OCHF_2$—$CF_3$, —($C_1$-$C_6$)alkyl, —($C_2$-$C_6$)alkenyl, —($C_2$-$C_6$)alkynyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)NH—($C_1$-$C_4$)alkylene-$CF_3$, —C(=O)NH—($C_1$-$C_4$)alkylene-F, —C(=O)NH—($C_2$-$C_4$)alkenyl, —C(=O)N(($C_1$-$C_6$)alkyl)$_2$, —C(=O)NH—OH, —C(=O)NH—O—($C_1$-$C_6$)alkyl, —C(=O)NH—Y", —C(=O)—($C_1$-$C_4$)alkylene-$CF_3$, —C(=O)N—($C_1$-$C_4$)alkylene-F, —C(=O)—($C_2$-$C_4$)alkenyl, —C(=O)—($C_1$-$C_4$)alkylene-$NH_2$, —C(=O)—($C_1$-$C_4$)alkylene-NH(($C_1$-$C_4$)alkyl), —C(=O)—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-O—($C_1$-$C_6$)alkyl, —C(=O)NH—($C_1$-$C_4$)alkylene-Y", —C(=O)—($C_1$-$C_6$)alkyl, —C(=O)—Y", —$CO_2$H, —C(=O)—O—($C_1$-$C_6$)alkyl, —C(=O)NH—($C_1$-$C_4$)alkylene-$NH_2$, —C(=O)NH—($C_1$-$C_4$)alkylene-NH(($C_1$-$C_6$)alkyl), and —C(=O)NH—($C_1$-$C_4$)alkylene-N(($C_1$-$C_6$)alkyl)$_2$, —$SO_2NH_2$, —$SO_2$NH(($C_1$-$C_6$)alkyl), —$SO_2$N(($C_1$-$C_6$)alkyl)$_2$, —$SO_2$NH(($C_2$-$C_4$)alkenyl), —$SO_2$NH(($C_2$-$C_4$)alkynyl), —$SO_2$NH—Y", —$SO_2$NH—($C_1$-$C_4$)alkylene-OH, —$SO_2$NH—($C_1$-$C_4$)alkylene-O—($C_1$-$C_4$)alkyl, —$SO_2$—($C_1$-$C_6$)alkyl, —$SO_2$—Y", —SO—($C_1$-$C_6$)alkyl, —($C_1$-$C_4$)alkylene-NH—C(=O)—($C_1$-$C_6$)alkyl, —($C_1$-$C_4$)alkylene-NH—($C_1$-$C_6$)alkyl, —($C_1$-$C_4$)alkylene-N(($C_1$-$C_6$)alkyl)$_2$-($C_1$-$C_4$)alkylene-OH, —($C_1$-$C_4$)alkylene-O—($C_1$-$C_6$)alkyl, —($C_1$-$C_4$)alkylene-C(=O)—($C_1$-$C_6$)alkyl, —($C_1$-$C_4$)alkylene-C(=O)—O—($C_1$-$C_6$)alkyl, or —($C_1$-$C_4$)alkylene-C(=O)—OH, wherein two substituents on a carbon ring member of the Y cycloalkyl or heterocyclyl may join to form a 3-7 membered cycloalkyl group or a 3-7 membered heterocyclyl group that comprises 1 to 3 heteroatoms selected from N, O, or S; and further wherein 1 or 2 carbon atom ring members of the 3-7 membered cycloalkyl or the 3-7 membered heterocyclyl group formed from the two substituents on the carbon ring member of the Y cycloalkyl or heterocyclyl may be double bonded to an O atom;

Y' may be absent or is a $C_6$-$C_{10}$ aryl, a 5-10 membered heteroaryl comprising 1, 2, 3, or 4 heteroatoms independently selected from O, S, or N, or a 3-7 membered heterocyclyl comprising 1, 2, or 3 heteroatoms selected from O, S, or N, wherein the $C_6$-$C_{10}$ aryl, the 5-10 membered heteroaryl, or the 3-7 membered heterocyclyl Y' groups are unsubstituted or are optionally substituted with 1, 2, or 3 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_6$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-$CF_3$, —C(=O)NH—($C_1$-$C_4$)alkylene-O—($C_1$-$C_4$)alkyl, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

Y" may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl Y" groups are unsubstituted or are optionally substituted with 1, 2, or 3 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_6$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-$CF_3$, —C(=O)NH—($C_1$-$C_4$)alkylene-O—($C_1$-$C_4$)alkyl, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

W is selected from —($CR^aR^{a'}$)$_q$—O—($C_1$-$C_6$)alkyl, —($CR^aR^{a'}$)$_q$—O—W', —O—($CR^aR^{a'}$)$_q$—W', —($CR^aR^{a'}$)$_q$—OH, —O—($CR^aR^{a'}$)$_q$—O—($C_1$-$C_6$)alkyl, —($CR^aR^{a'}$)$_q$—O—($CR^aR^{a'}$)$_q$—OH, —($CR^aR^{a'}$)$_q$—O—($CR^aR^{a'}$)$_q$—O—($C_1$-$C_6$)alkyl, —($CR^aR^{a'}$)$_q$—SH, —($CR^aR^{a'}$)$_q$—S—($C_1$-$C_6$)alkyl, —($CR^aR^{a'}$)$_q$—S—W', —S—($CR^aR^{a'}$)$_q$—W', —($CR^aR^{a'}$)$_q$—S(O)$_2$—($C_1$-$C_6$)alkyl, —($CR^aR^{a'}$)$_q$—S(O)$_2$—W', —S(O)$_2$—($CR^aR^{a'}$)$_q$—W', —($CR^aR^{a'}$)$_q$—$NH_2$, —($CR^aR^{a'}$)$_q$—NH—($C_1$-$C_6$)alkyl, —($CR^aR^{a'}$)$_q$—N—(($C_1$-$C_6$)alkyl,)$_2$, —($CR^aR^{a'}$)$_q$—$N^+$-(($C_1$-$C_6$)alkyl,)$_3$, —($CR^aR^{a'}$)$_q$—NH—W', —($CR^aR^{a'}$)$_q$—NH—($CR^aR^{a'}$)$_q$—OH, —NH—($CR^aR^{a'}$)$_q$—W', or —($CR^aR^{a'}$)$_q$—W';

W' may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl W' groups are unsubstituted or are optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —CH($CF_3$)(OH), —($C_1$-$C_4$)alkylene-$NH_2$, —($C_1$-$C_4$)alkylene-NH(($C_1$-$C_4$)alkyl), —($C_1$-$C_4$)alkylene-NH—($C_1$-$C_4$)alkylene-$CF_3$, —($C_1$-$C_4$)alkylene-N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_6$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —C(=O)NH—($C_1$-$C_4$)alkylene-OH, —C(=O)NH—($C_1$-$C_4$)alkylene-$CF_3$, —C(=O)NH—($C_1$-$C_4$)alkylene-O—($C_1$-$C_4$)alkyl, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —($C_1$-$C_4$)alkylene-OH, —OH, —O—($C_1$-$C_6$)alkyl, —SH, —S—($C_1$-$C_6$)alkyl, —$SO_3$H, —$OCF_3$, —$OCHF_2$, or —C(=O)—W"; and further wherein W' may include 0, 1, or 2=O groups when W' is a $C_3$-$C_{10}$ cycloalkyl or a 3-10 membered heterocyclyl, and further wherein the =O groups may be bonded to a ring carbon atom or a ring S atom;

W" may be absent or is selected from a $C_3$-$C_{10}$ cycloalkyl; a 3-10 membered heterocyclyl comprising 1, 2, or 3 heteroatoms selected from N, O, and S; a $C_6$-$C_{10}$ aryl; or a 5-10 membered heteroaryl comprising 1, 2, 3, or 4 heteroatoms independently selected from N, O, or S; wherein the $C_3$-$C_{10}$ cycloalkyl and the 3-10 membered heterocyclyl may be monocyclic or bicyclic, and further wherein the $C_3$-$C_{10}$ cycloalkyl, the 3-10 membered heterocyclyl, the $C_6$-$C_{10}$ aryl, or the 5-10 membered heteroaryl W" groups are unsubstituted or are optionally substituted with 1, 2, 3, or 4 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —OH, —$NH_2$, —NH(($C_1$-$C_4$)alkyl), —N(($C_1$-$C_4$)alkyl)$_2$, —$CF_3$, —$CO_2$H, —C(=O)—O—($C_1$-$C_4$)alkyl, —SH, —S—($C_1$-$C_6$)alkyl, —$OCF_3$, or —$OCHF_2$; and further wherein W" may include 0, 1, or 2=O groups when W" is a $C_3$-$C_{10}$ cycloalkyl or a 3-10 membered heterocyclyl, and further wherein the =O groups may be bonded to a ring carbon atom or a ring S atom;

the subscript q is, in each instance, independently selected from 0, 1, 2, 3, or 4;

$R^a$ is, in each instance, independently selected from —H, —CH$_3$, —CH$_2$CH$_3$, —F, —CF$_3$, or —C≡N;

$R^{a'}$ is, in each instance, independently selected from —H, —CH$_3$, —CH$_2$CH$_3$, —F, —CF$_3$, or —C≡N; or $R^a$ and $R^{a'}$ may join to form a cyclopropyl ring together with the carbon atom to which they are attached;

Z is selected from —OMe or —NH-cyclohexyl; or a phenyl, pyridyl, benzothiophenyl, thiazolyl, pyradizinyl, pyrimidinyl, indolyl, cyclohexyl, morpholinyl, pyrrolidinyl, piperazinyl, or piperidinyl group; wherein the —NH-cyclohexyl, phenyl, pyridyl, benzothiophenyl, thiazolyl, pyradizinyl, pyrimidinyl, indolyl, cyclohexyl, morpholinyl, pyrrolidinyl, piperazinyl, or piperidinyl group is unsubstituted or is optionally substituted with 1, 2, or 3 substituents independently selected from —F, —Cl, —Br, —I, —C≡N, —NO$_2$, —CF$_3$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_6$)alkyl), —N((C$_1$-C$_6$)alkyl)$_2$, —C(=O)NH$_2$, —C(=O)NH((C$_1$-C$_6$)alkyl), —C(=O)N((C$_1$-C$_6$)alkyl)$_2$, —SO$_2$NH$_2$, —SO$_2$NH((C$_1$-C$_6$)alkyl), —SO$_2$N((C$_1$-C$_6$)alkyl)$_2$, —SO$_2$NH((C$_2$-C$_6$)alkenyl), —SO$_2$NH((C$_2$-C$_6$)alkynyl), —SO$_2$NH—(C$_1$-C$_4$)alkylene-OH, —SO$_2$NH—(C$_1$-C$_4$)alkylene-O—(C$_1$-C$_6$)alkyl, —NHSO$_2$—(C$_1$-C$_6$)alkyl, —NHC(=O)—(C$_1$-C$_6$)alkyl, —SO$_2$—(C$_1$-C$_6$)alkyl, —SO—(C$_1$-C$_6$)alkyl, —(C$_1$-C$_4$)alkylene-NH—C(=O)—(C$_1$-C$_6$)alkyl, —C(=O)—(C$_1$-C$_6$)alkyl, —CO$_2$H, —C(=O)—O—(C$_1$-C$_6$)alkyl, —C(=O)NH—(C$_1$-C$_4$)alkylene-NH$_2$, —C(=O)NH—(C$_1$-C$_4$)alkylene-NH((C$_1$-C$_6$)alkyl), —C(=O)NH—(C$_1$-C$_4$)alkylene-N((C$_1$-C$_6$)alkyl)$_2$, —(C$_1$-C$_4$)alkylene-C(=O)—(C$_1$-C$_6$)alkyl, —(C$_1$-C$_4$)alkylene-C(=O)—O—(C$_1$-C$_6$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$.

2. The compound of claim 1, wherein Z is an unsubstituted or substituted phenyl, pyridyl, benzothiophenyl, thiazolyl, pyradizinyl, pyrimidinyl, indolyl, cyclohexyl, morpholinyl, pyrrolidinyl, piperazinyl, or piperidinyl group, or a pharmaceutically acceptable salt thereof, tautomer thereof, a pharmaceutically acceptable salt of the tautomer, or a stereoisomer of any of the foregoing.

3. The compound of claim 1, wherein Z is an unsubstituted or substituted phenyl or pyridyl, or a pharmaceutically acceptable salt thereof, tautomer thereof, a pharmaceutically acceptable salt of the tautomer, or a stereoisomer of any of the foregoing.

4. The compound of claim 1, wherein Z is selected from

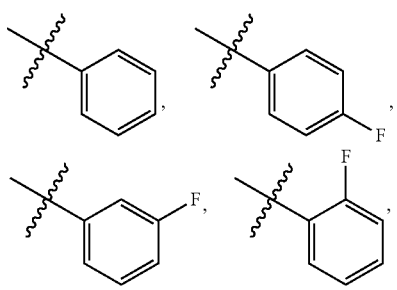

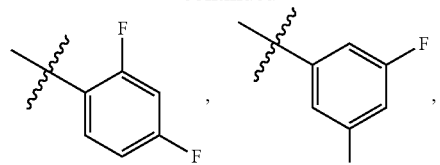

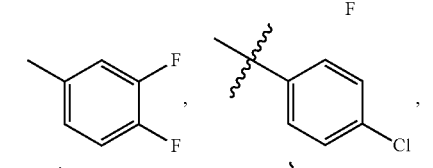

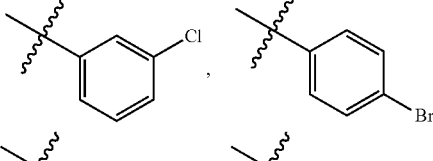

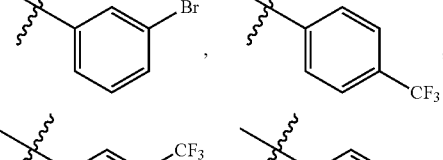

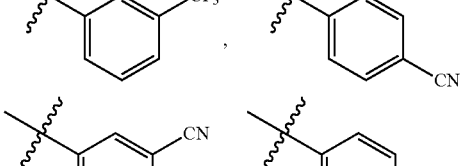

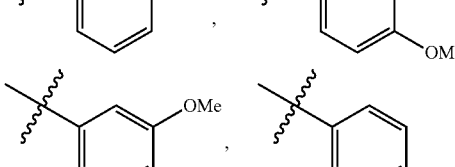

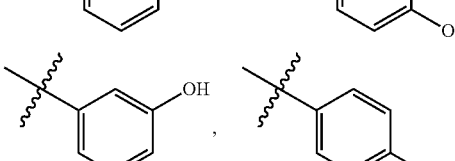

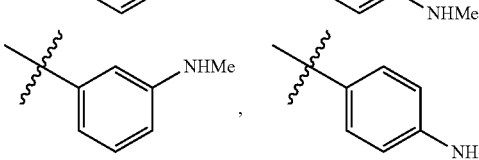

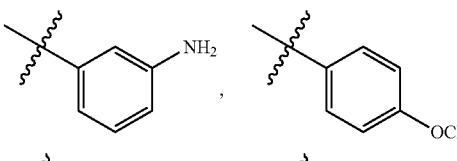

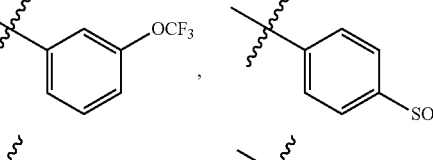

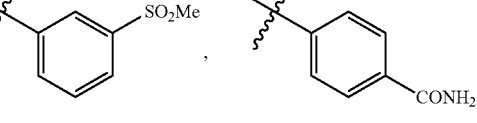

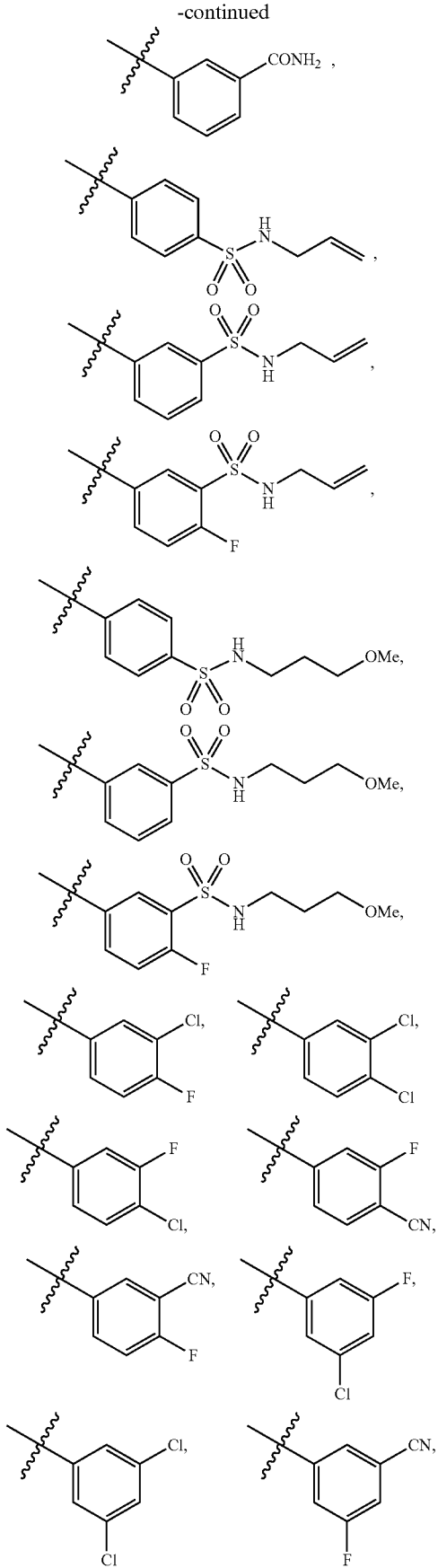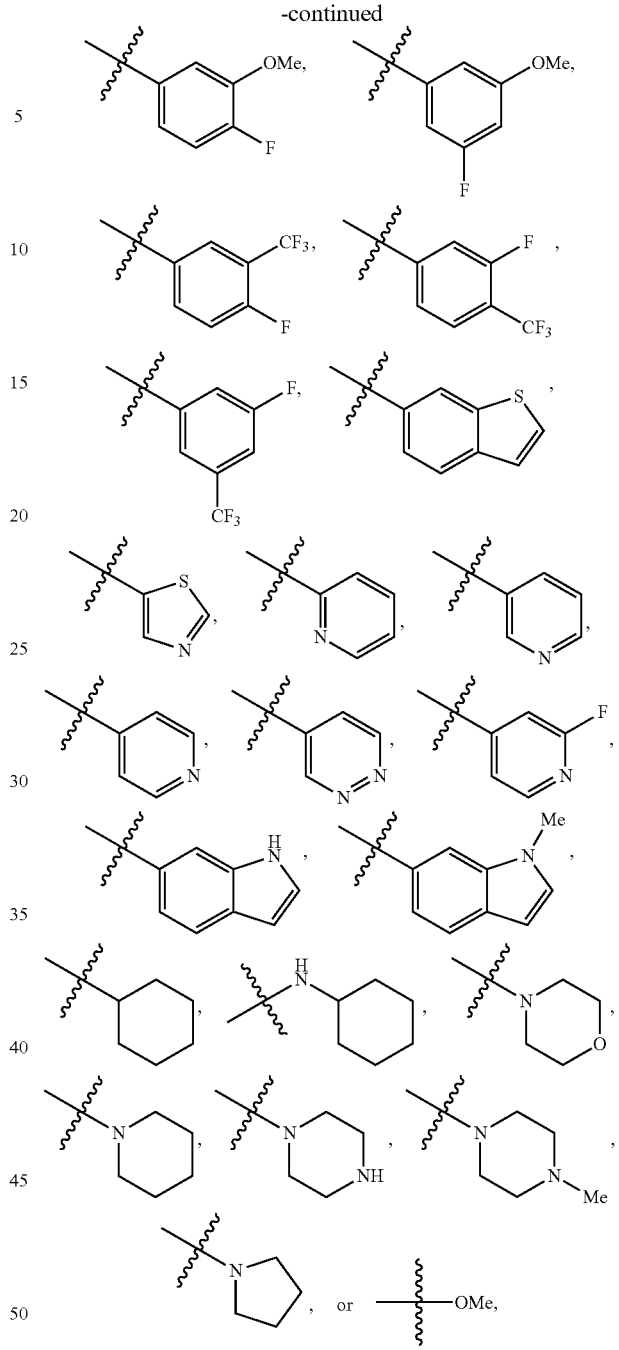
or a pharmaceutically acceptable salt thereof, tautomer thereof, a pharmaceutically acceptable salt of the tautomer, or a stereoisomer of any of the foregoing, wherein the symbol ⌇, when drawn across a bond, indicates the point of attachment to the rest of the molecule.
5. The compound of claim 1, wherein Z is selected from
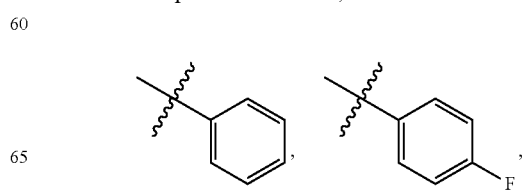

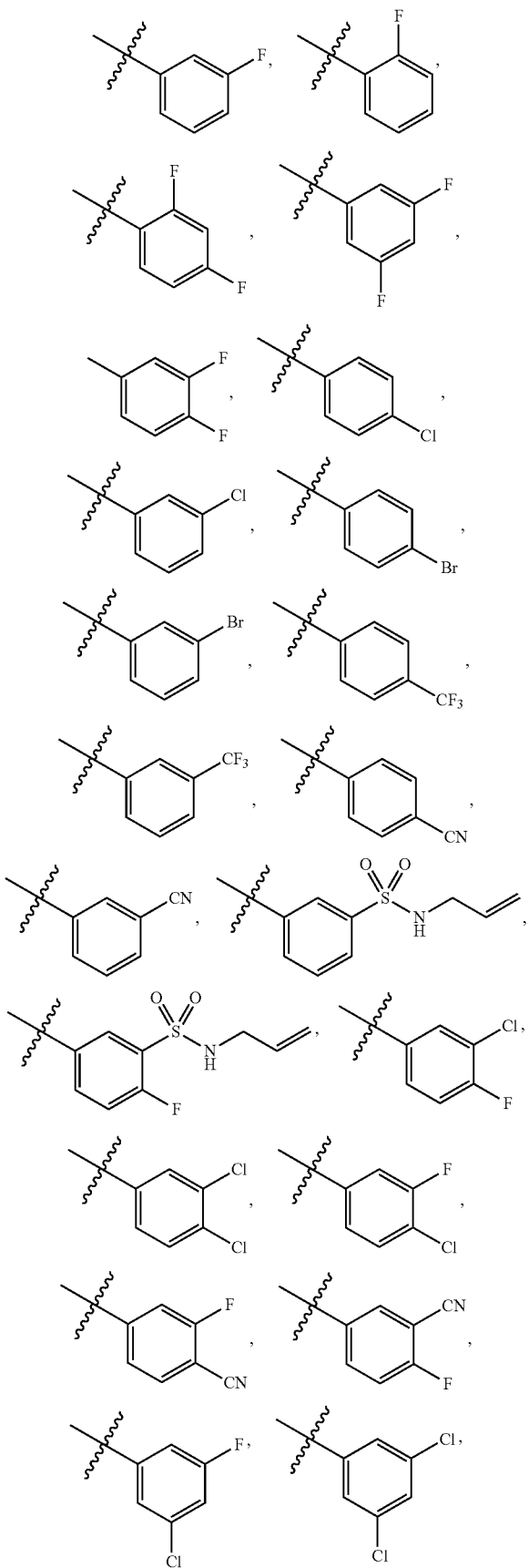

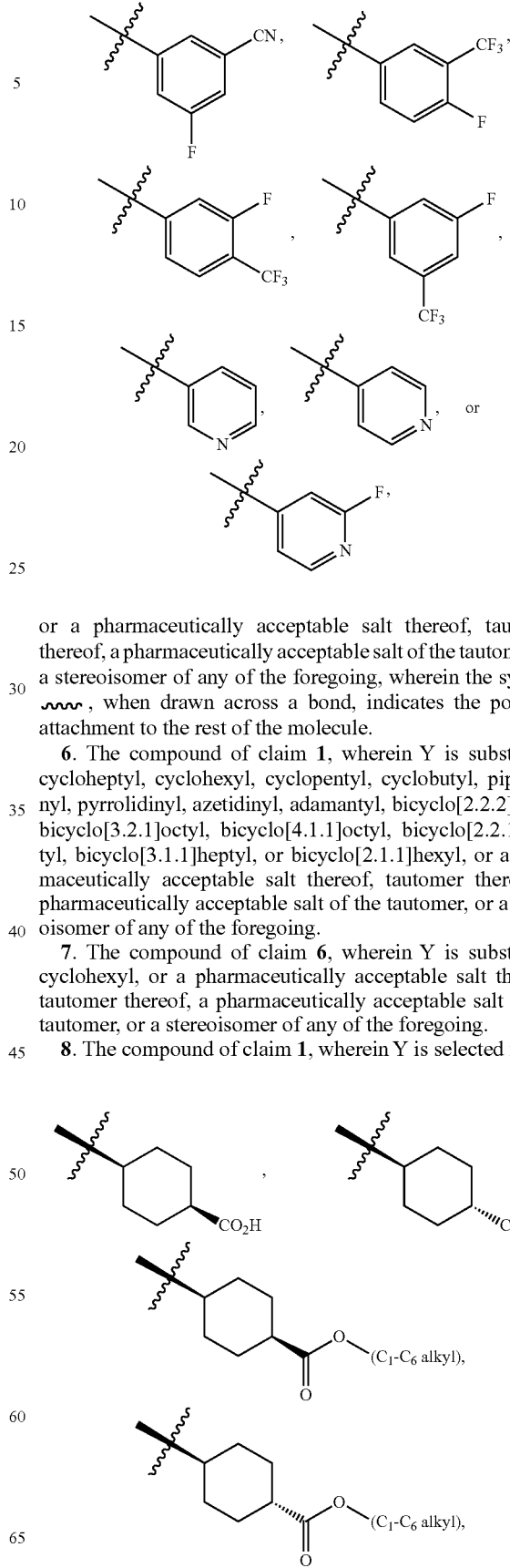

or a pharmaceutically acceptable salt thereof, tautomer thereof, a pharmaceutically acceptable salt of the tautomer, or a stereoisomer of any of the foregoing, wherein the symbol ⌇, when drawn across a bond, indicates the point of attachment to the rest of the molecule.

6. The compound of claim 1, wherein Y is substituted cycloheptyl, cyclohexyl, cyclopentyl, cyclobutyl, piperidinyl, pyrrolidinyl, azetidinyl, adamantyl, bicyclo[2.2.2]octyl, bicyclo[3.2.1]octyl, bicyclo[4.1.1]octyl, bicyclo[2.2.1]heptyl, bicyclo[3.1.1]heptyl, or bicyclo[2.1.1]hexyl, or a pharmaceutically acceptable salt thereof, tautomer thereof, a pharmaceutically acceptable salt of the tautomer, or a stereoisomer of any of the foregoing.

7. The compound of claim 6, wherein Y is substituted cyclohexyl, or a pharmaceutically acceptable salt thereof, tautomer thereof, a pharmaceutically acceptable salt of the tautomer, or a stereoisomer of any of the foregoing.

8. The compound of claim 1, wherein Y is selected from

-continued
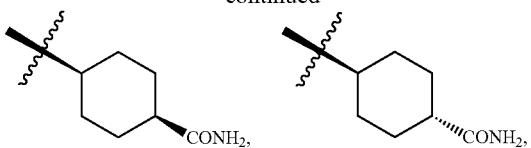
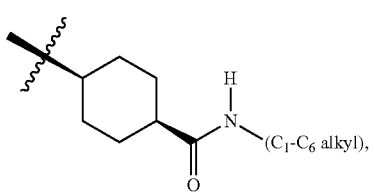
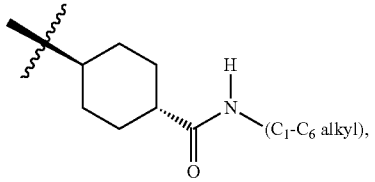
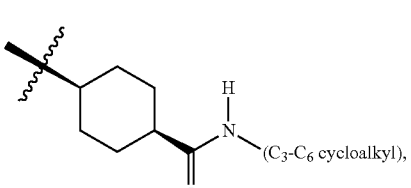
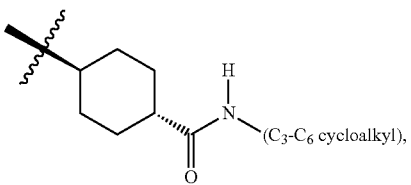
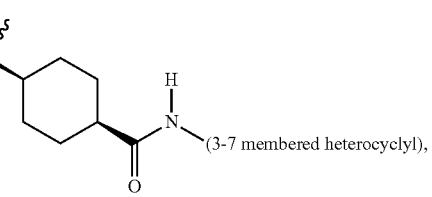
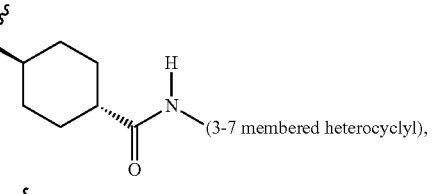
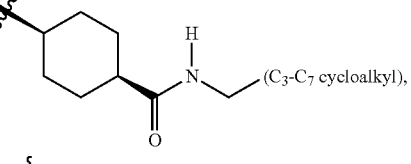
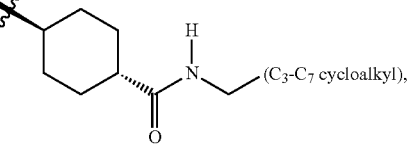
-continued
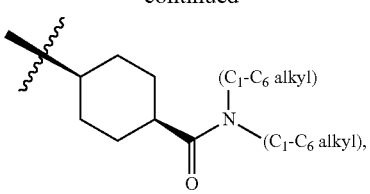
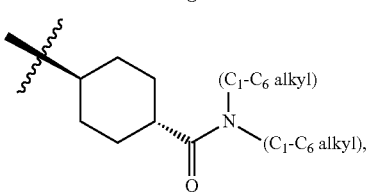
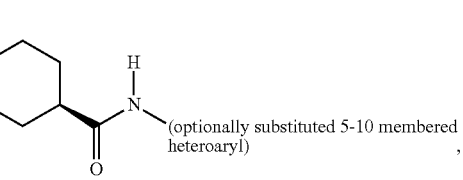
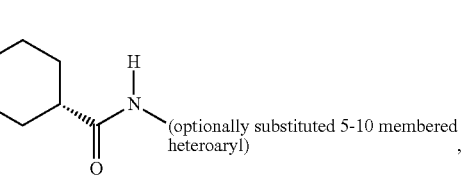
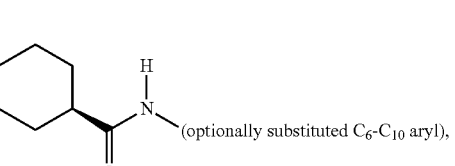
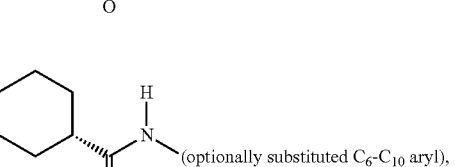
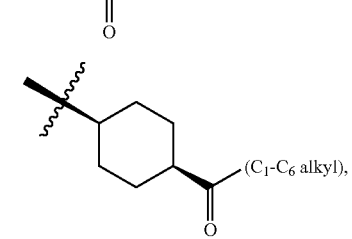
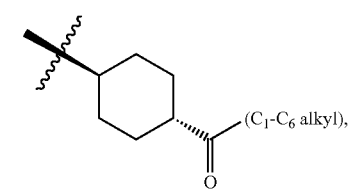
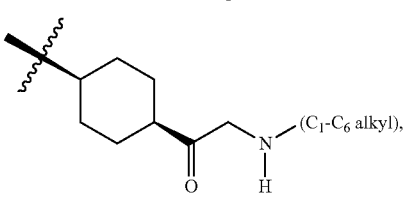

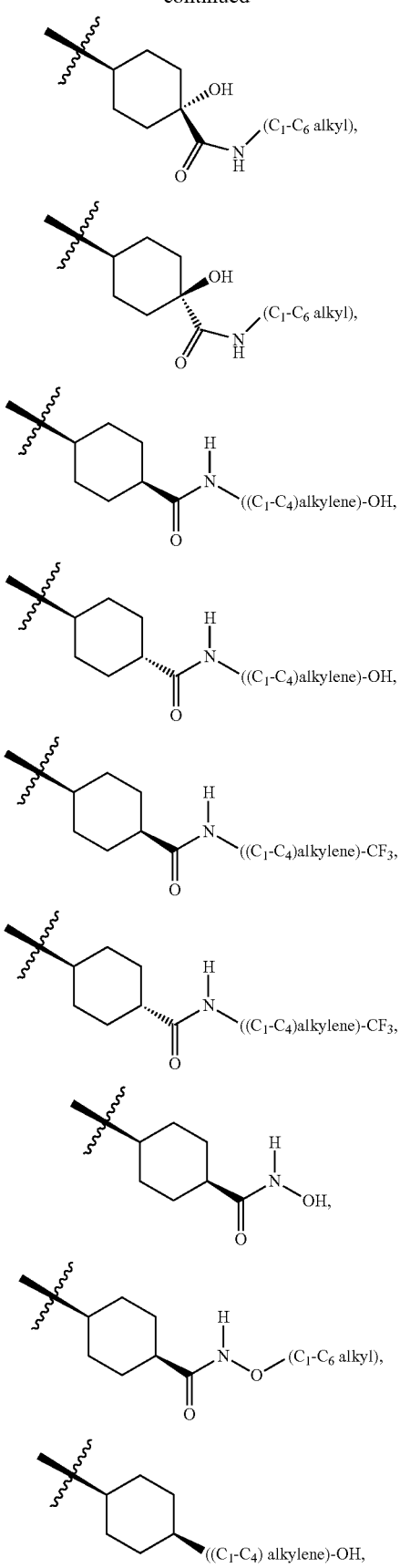
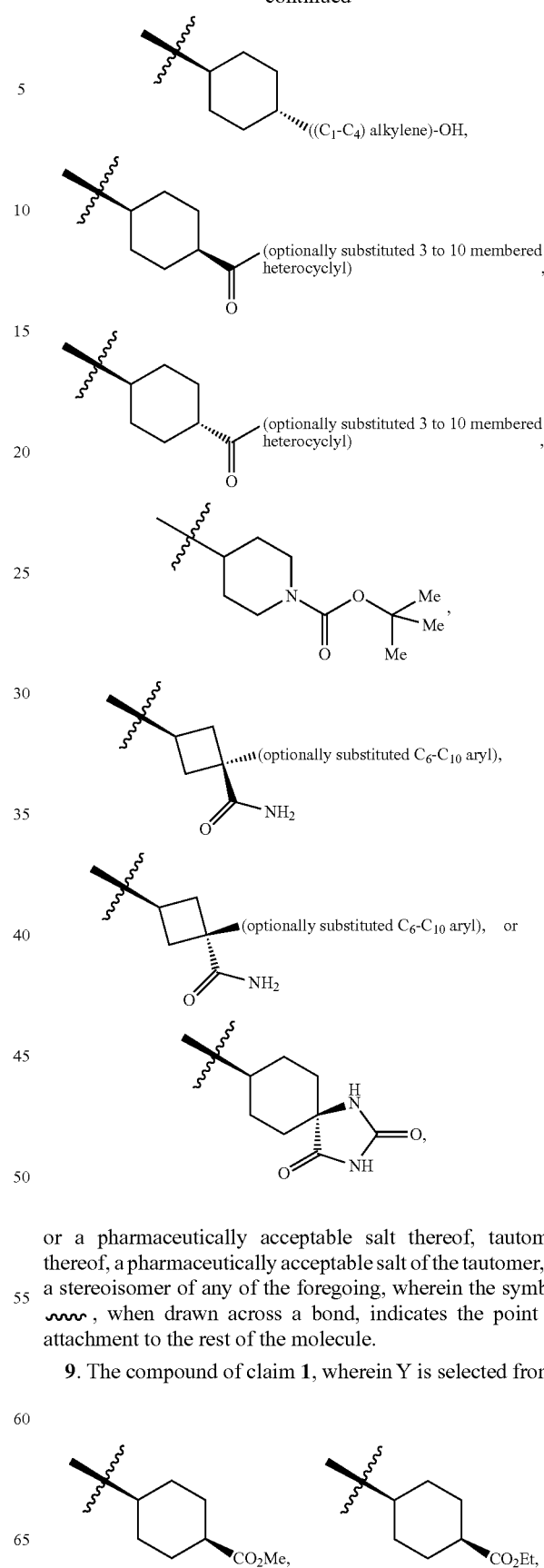
or a pharmaceutically acceptable salt thereof, tautomer thereof, a pharmaceutically acceptable salt of the tautomer, or a stereoisomer of any of the foregoing, wherein the symbol ⌇, when drawn across a bond, indicates the point of attachment to the rest of the molecule.
9. The compound of claim 1, wherein Y is selected from

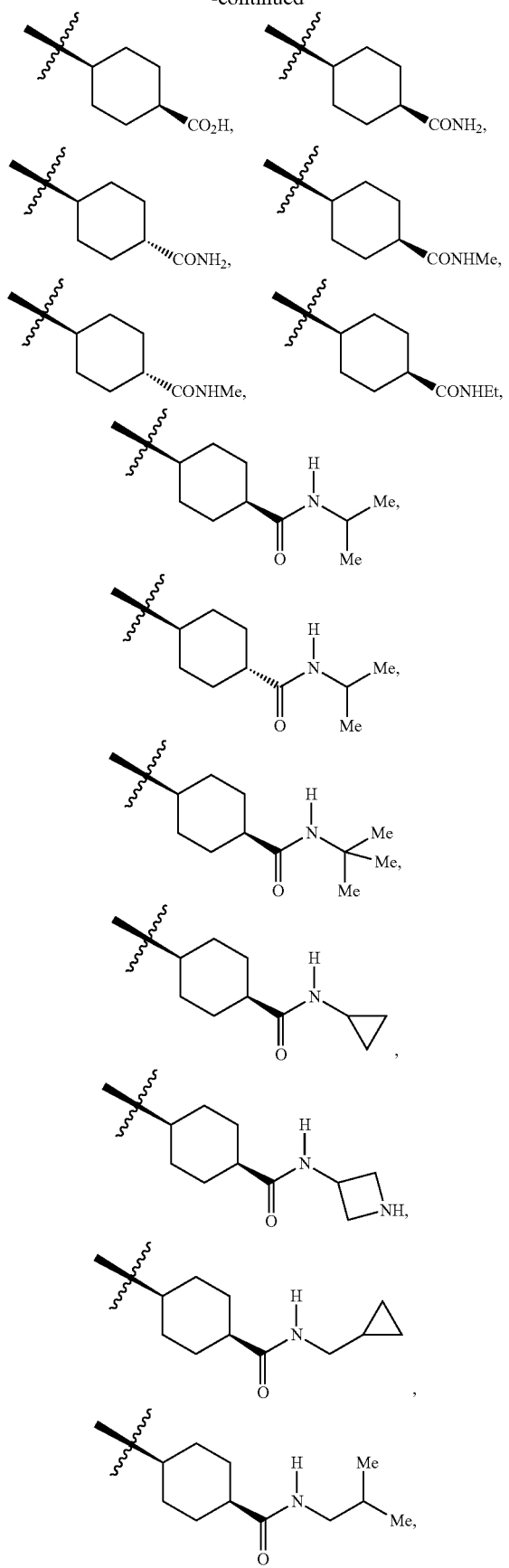
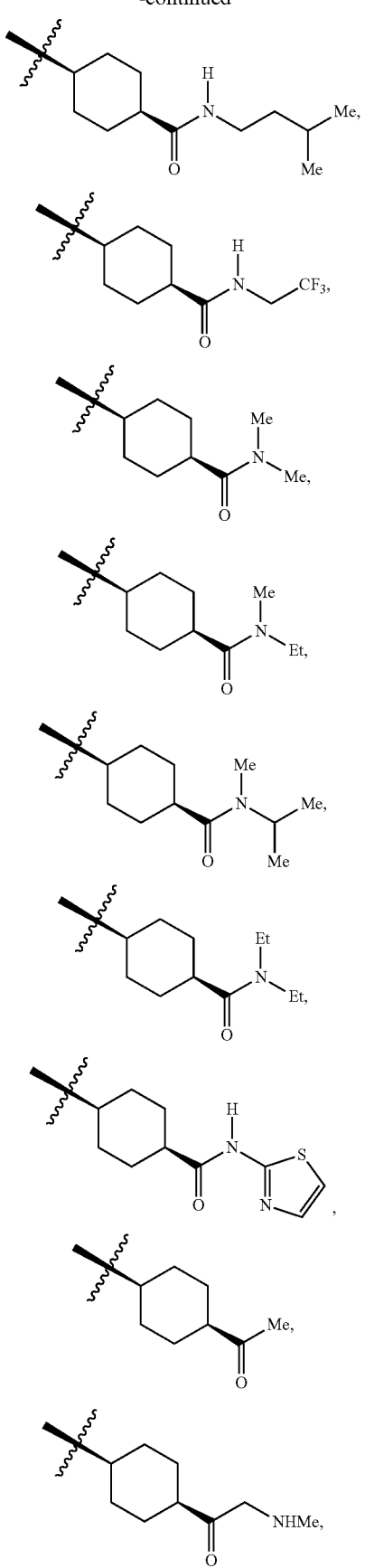

329
-continued
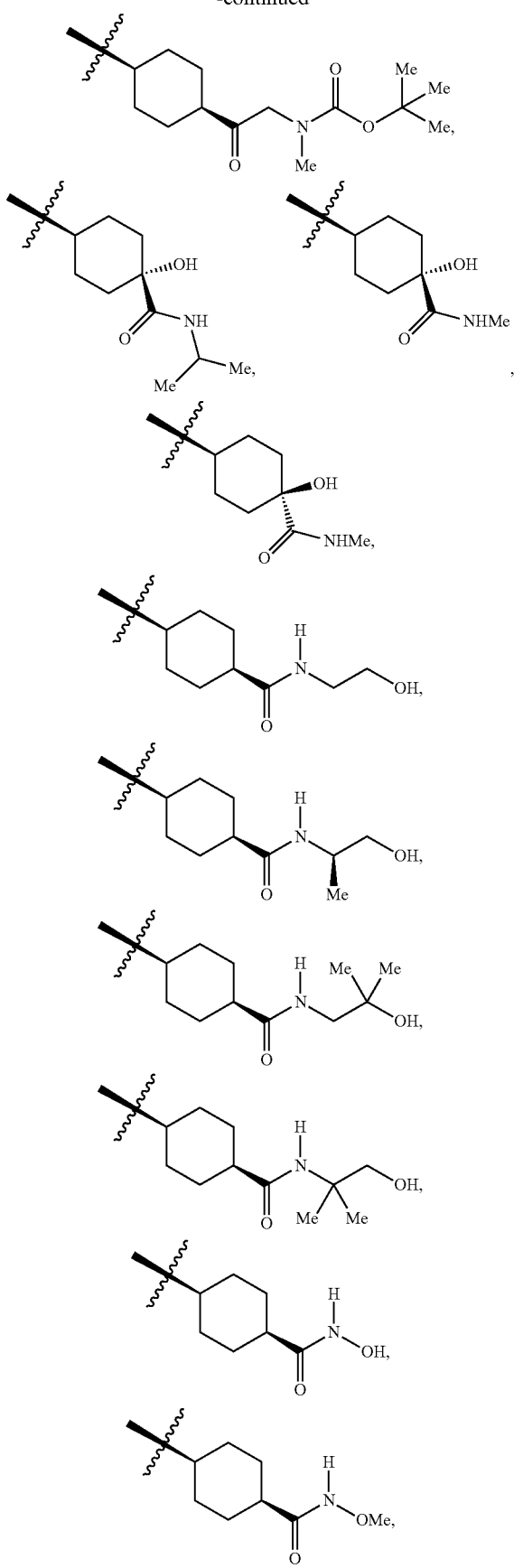
330
-continued
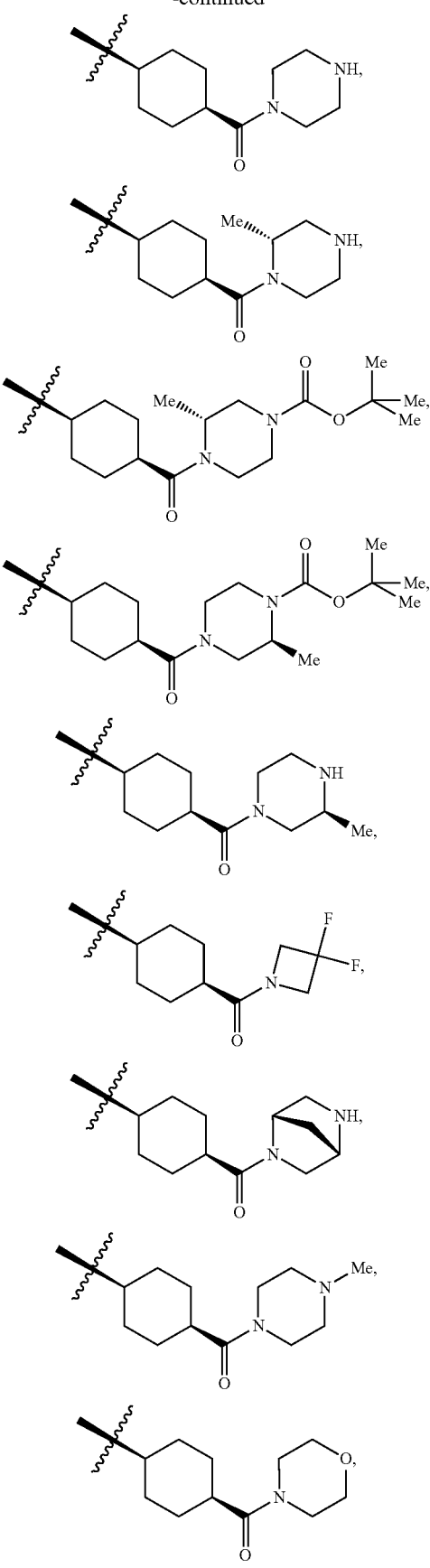

331
-continued
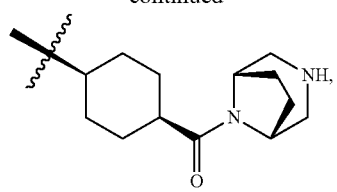
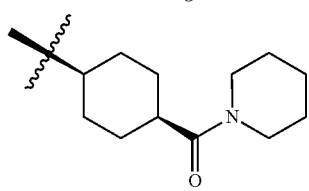
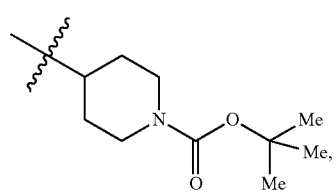
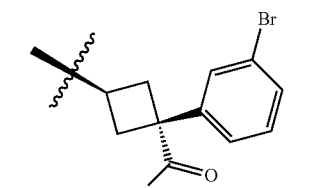
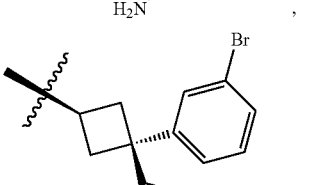
, or
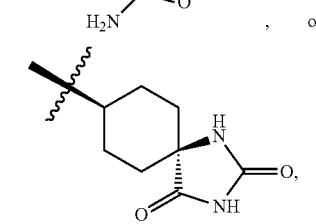
or a pharmaceutically acceptable salt thereof, tautomer thereof, a pharmaceutically acceptable salt of the tautomer, or a stereoisomer of any of the foregoing, wherein the symbol ⌇⌇, when drawn across a bond, indicates the point of attachment to the rest of the molecule.
10. The compound of claim 1, wherein Y is selected from
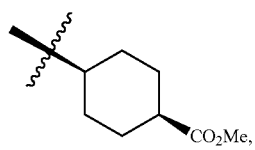
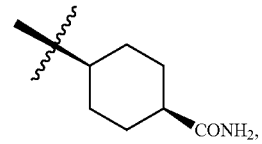
332
-continued
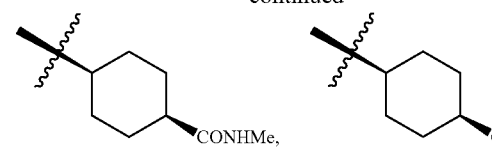
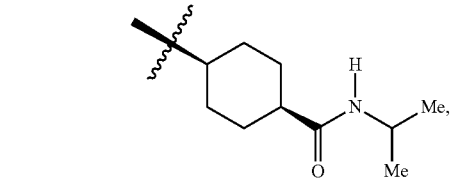
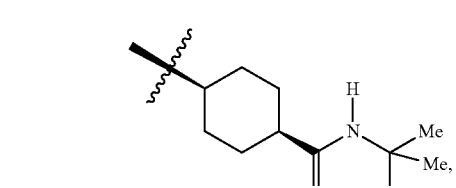
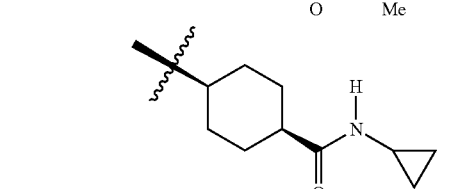
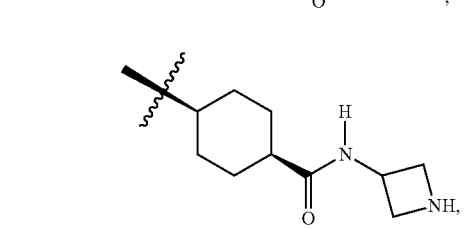
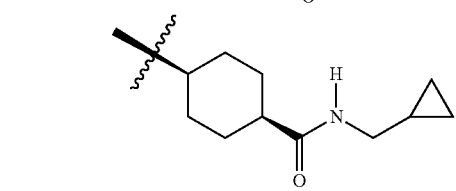
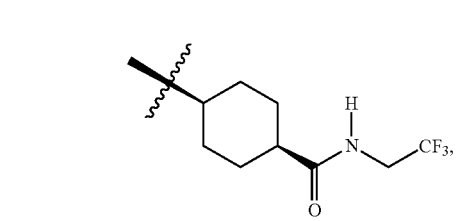
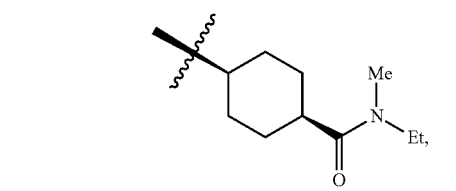
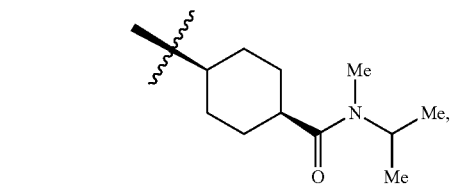

333
-continued

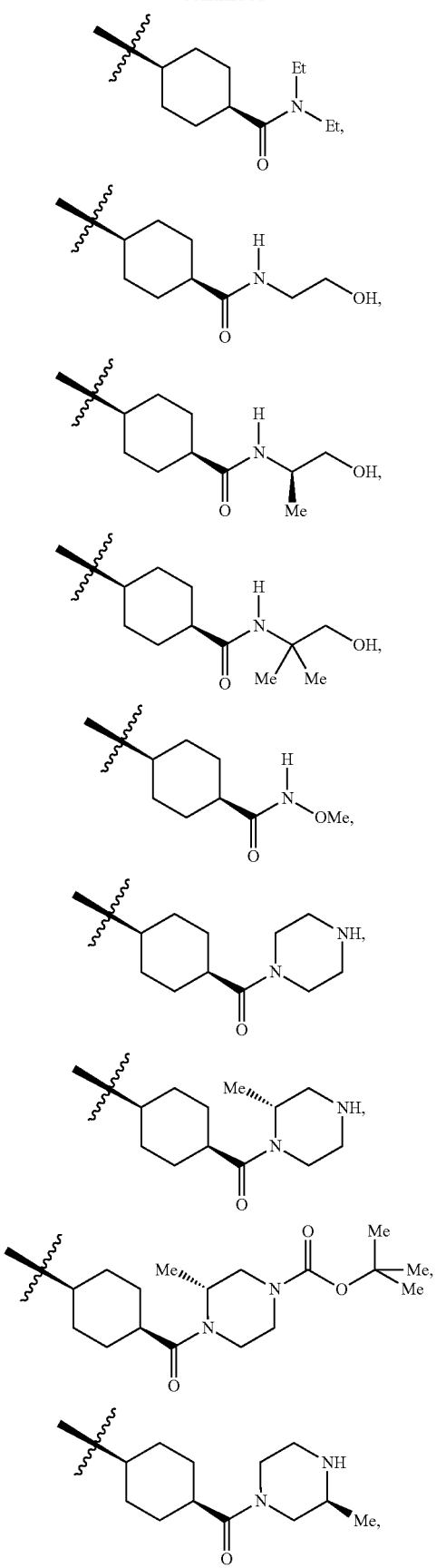

334
-continued

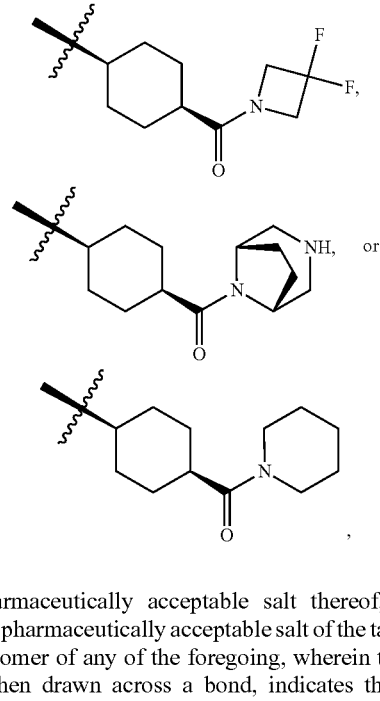

or a pharmaceutically acceptable salt thereof, tautomer thereof, a pharmaceutically acceptable salt of the tautomer, or a stereoisomer of any of the foregoing, wherein the symbol ⌇⌇⌇, when drawn across a bond, indicates the point of attachment to the rest of the molecule.

11. The compound of claim 10, wherein Y is

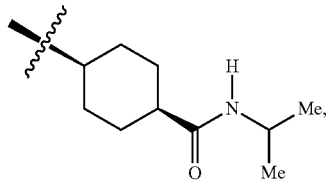

or a pharmaceutically acceptable salt thereof, tautomer thereof, a pharmaceutically acceptable salt of the tautomer, or a stereoisomer of any of the foregoing, wherein the symbol ⌇⌇⌇, when drawn across a bond, indicates the point of attachment to the rest of the molecule.

12. The compound of claim 1, wherein W is selected from —CH$_2$OCH$_3$, —CH$_2$OCH$_2$CH$_2$OH, —CH$_2$OCH$_2$CH$_2$OCH$_3$, —OCH$_2$CH$_2$OH, —OCH$_2$CH$_2$OMe, —W', —CH$_2$W', —OW', —OCH$_2$W', —OCH$_2$CH$_2$W', —OCH$_2$CH$_2$CH$_2$W', —NHW', —NHCH$_2$W', —NHCH$_2$CH$_2$W', —NHCH$_2$CH$_2$CH$_2$W', or —W'—C(=O)—W"; wherein W', if present, is selected from a 3-10 membered heterocyclyl comprising 1 or 2 heteroatoms selected from N, O, and S; a C$_6$-C$_{10}$ aryl; or a 5-10 membered heteroaryl comprising 1, 2, 3, or 4 heteroatoms independently selected from N, O, or S; wherein the 3-10 membered heterocyclyl W' group may be monocyclic or bicyclic, and further wherein the 3-10 membered heterocyclyl, the C$_6$-C$_{10}$ aryl, or the 5-10 membered heteroaryl W' groups are unsubstituted or are substituted with 1, 2, 3, or 4 substituents independently selected from —F, —Cl, —Br, —(C$_1$-C$_6$)alkyl, —CH(CF$_3$)(OH), —(C$_1$-C$_4$)alkylene-NH$_2$, —(C$_1$-C$_4$)alkylene-NH—(C$_1$-C$_4$)alkylene-CF$_3$, —C(=O)NH$_2$, —SO$_2$—(C$_1$-C$_6$)alkyl, —CF$_3$, —CO$_2$H, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —(C$_1$-C$_4$)alkylene-OH, —OH, —O—(C$_1$-C$_6$)alkyl, or —SO$_3$H; and further wherein W' may include 0, 1, or 2=O groups when W' is a 3-10 membered heterocyclyl, and further wherein the =O groups may be bonded to a ring carbon atom or a ring S atom; and further wherein W", if present, is a 3-10 membered heterocyclyl comprising 1, 2, or 3 heteroatoms selected from N, O, and S, wherein the 3-10 membered heterocyclyl W" group may be monocyclic or bicyclic, and further wherein the 3-10 membered heterocyclyl W" group is unsubstituted or is optionally substituted with 1, 2, 3, or 4 substituents independently selected from —F, —Cl, —Br, —I, —C≡N, —NO₂, —(C₁-C₆)alkyl, —(C₂-C₆)alkenyl, —(C₂-C₆)alkynyl, —OH, —NH₂, —NH((C₁-C₄)alkyl), —N((C₁-C₄)alkyl)₂, —CF₃, —CO₂H, —C(=O)—O—(C₁-C₄)alkyl, —SH, —S—(C₁-C₆)alkyl, —OCF₃, or —OCHF₂, or a pharmaceutically acceptable salt thereof, tautomer thereof, a pharmaceutically acceptable salt of the tautomer, or a stereoisomer of any of the foregoing.

13. The compound of claim 1, wherein W is selected from —OMe, —SO₂Me, —CH₂OMe, —OCH₂CH₂OH, —OCH₂CH₂OMe, or a group selected from

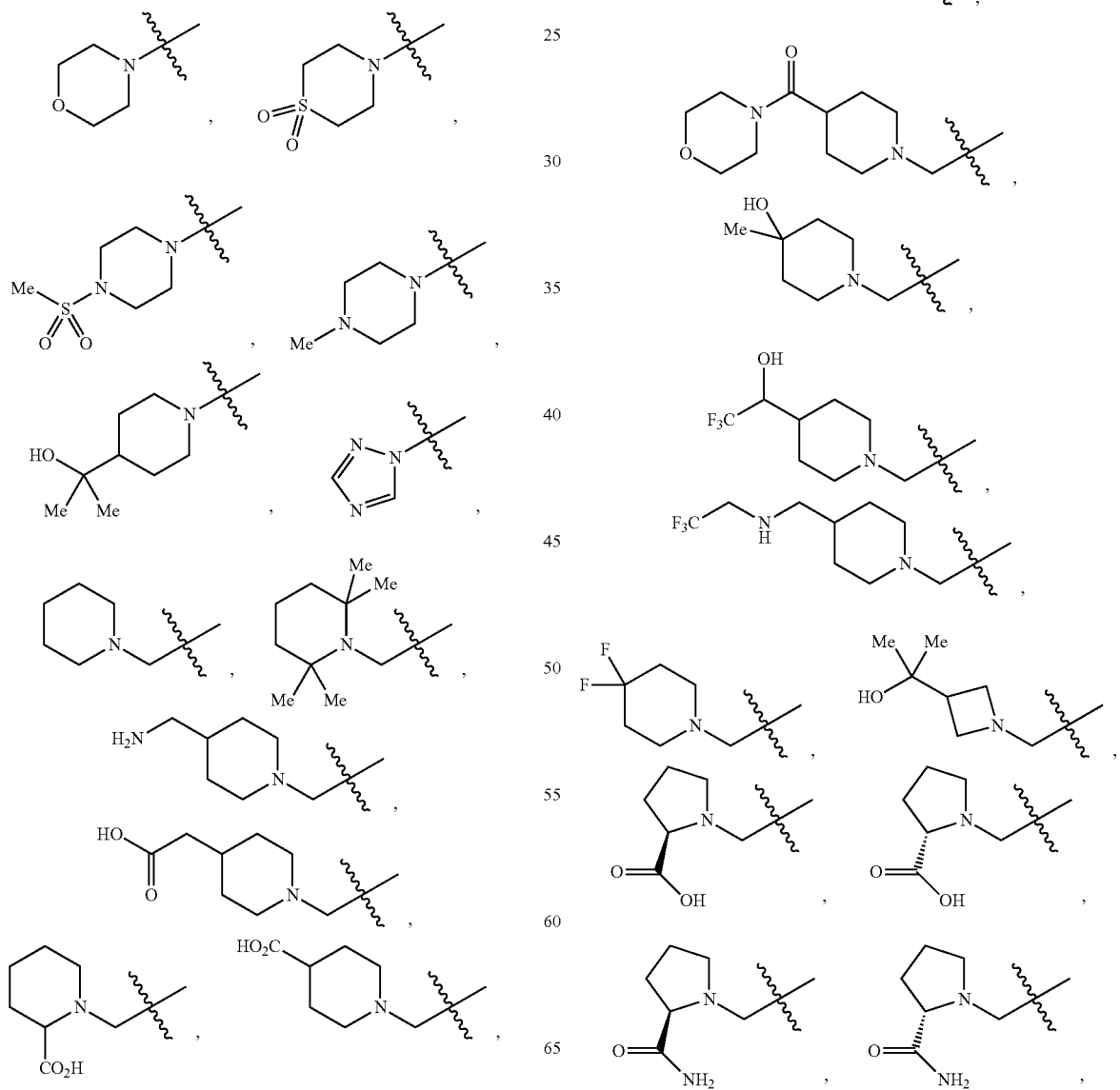

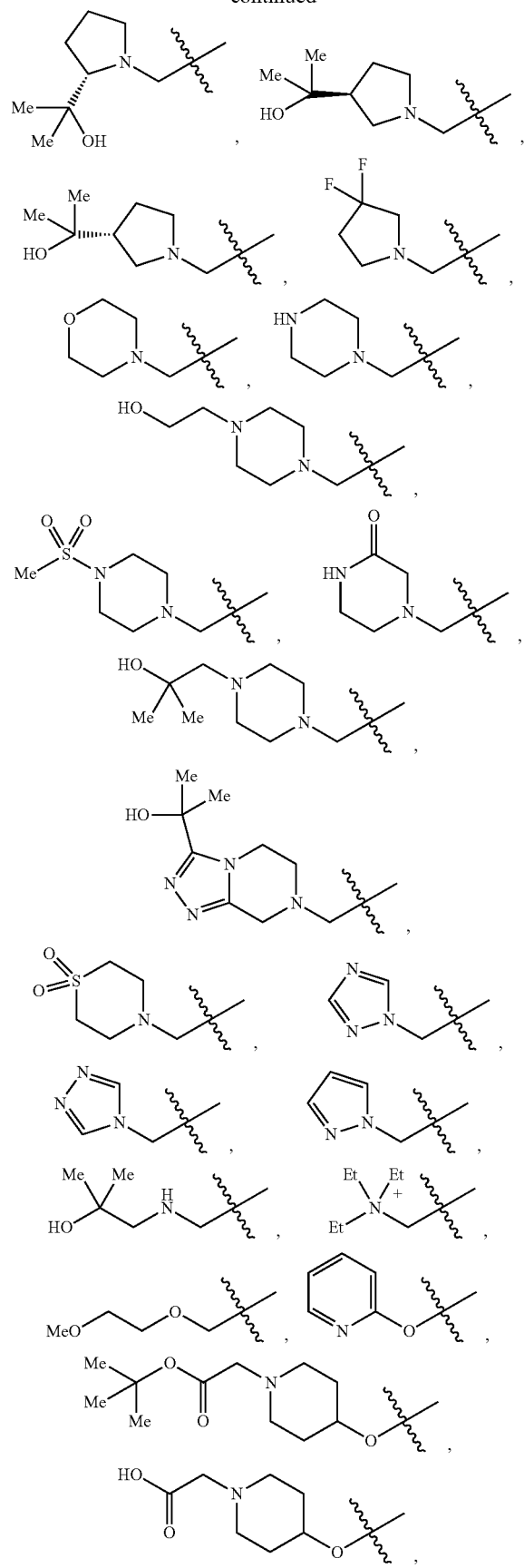

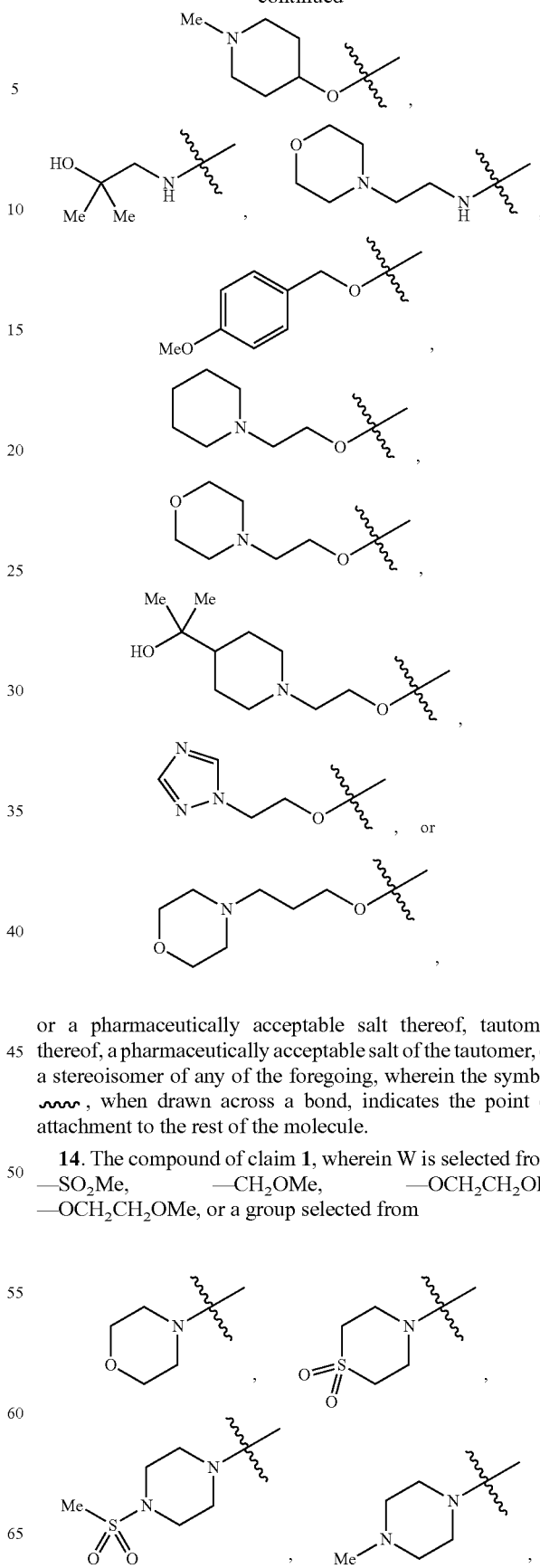

or a pharmaceutically acceptable salt thereof, tautomer thereof, a pharmaceutically acceptable salt of the tautomer, or a stereoisomer of any of the foregoing, wherein the symbol ⁓, when drawn across a bond, indicates the point of attachment to the rest of the molecule.

14. The compound of claim 1, wherein W is selected from —SO₂Me, —CH₂OMe, —OCH₂CH₂OH, —OCH₂CH₂OMe, or a group selected from

-continued
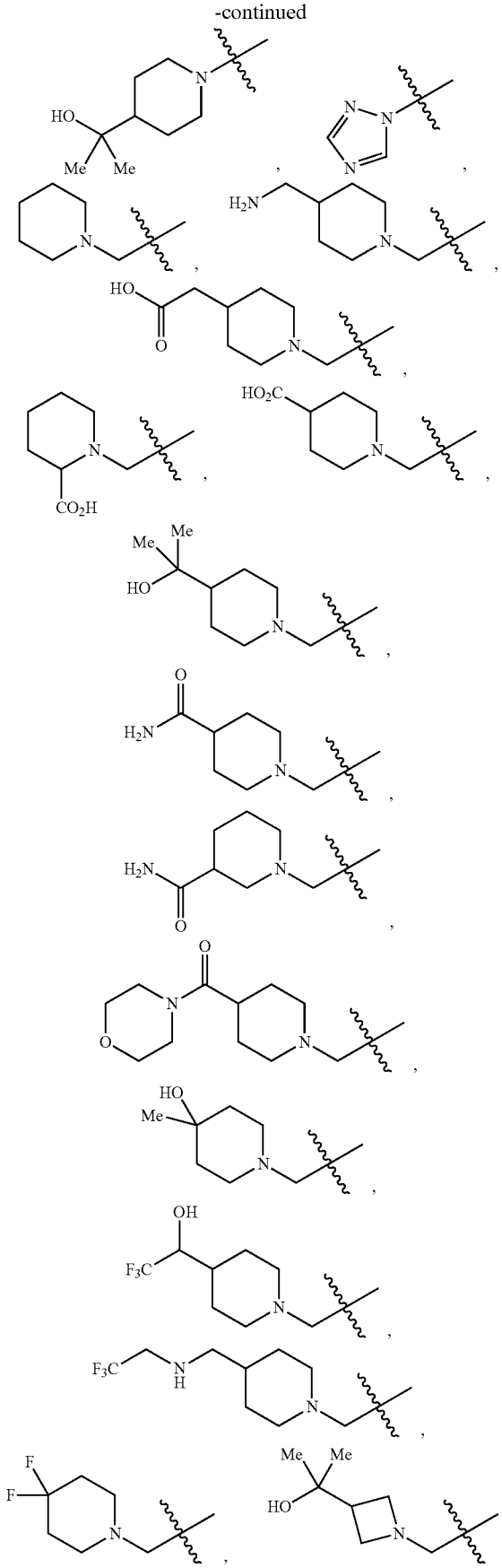
-continued
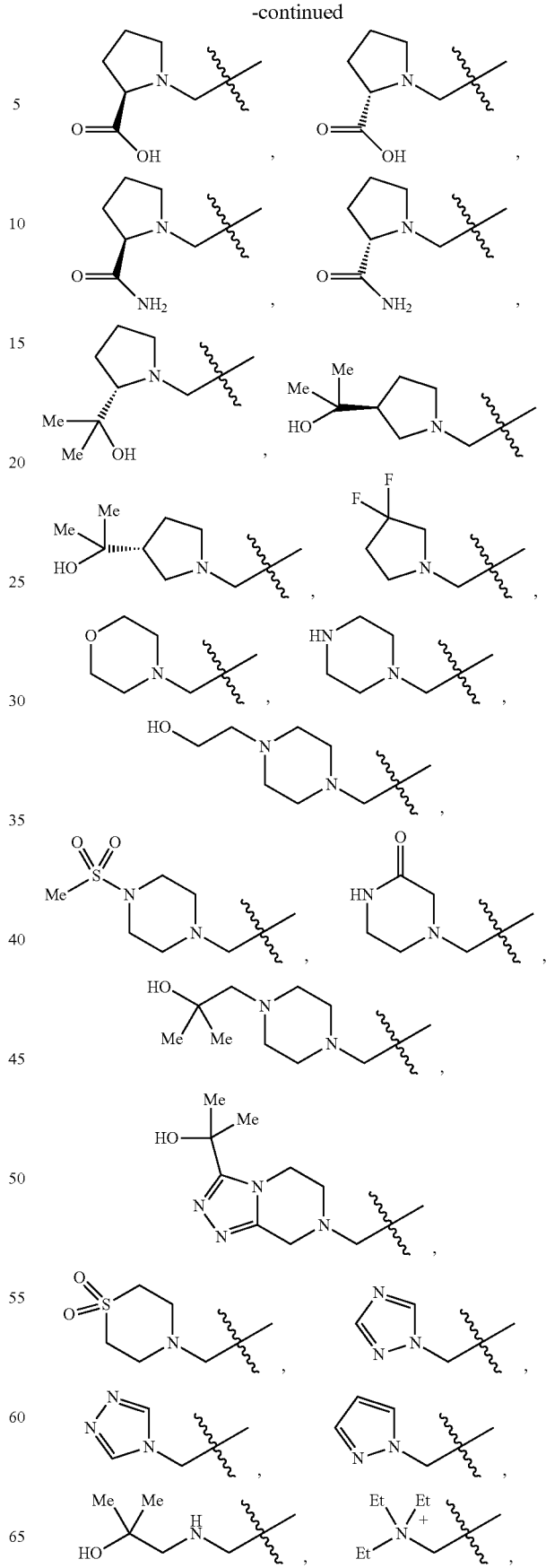

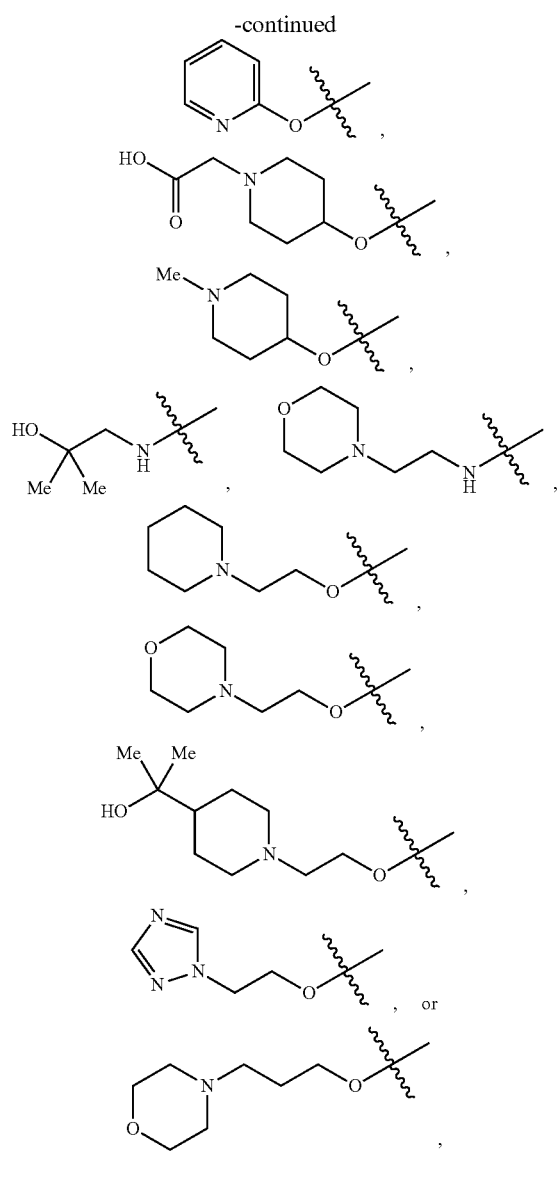
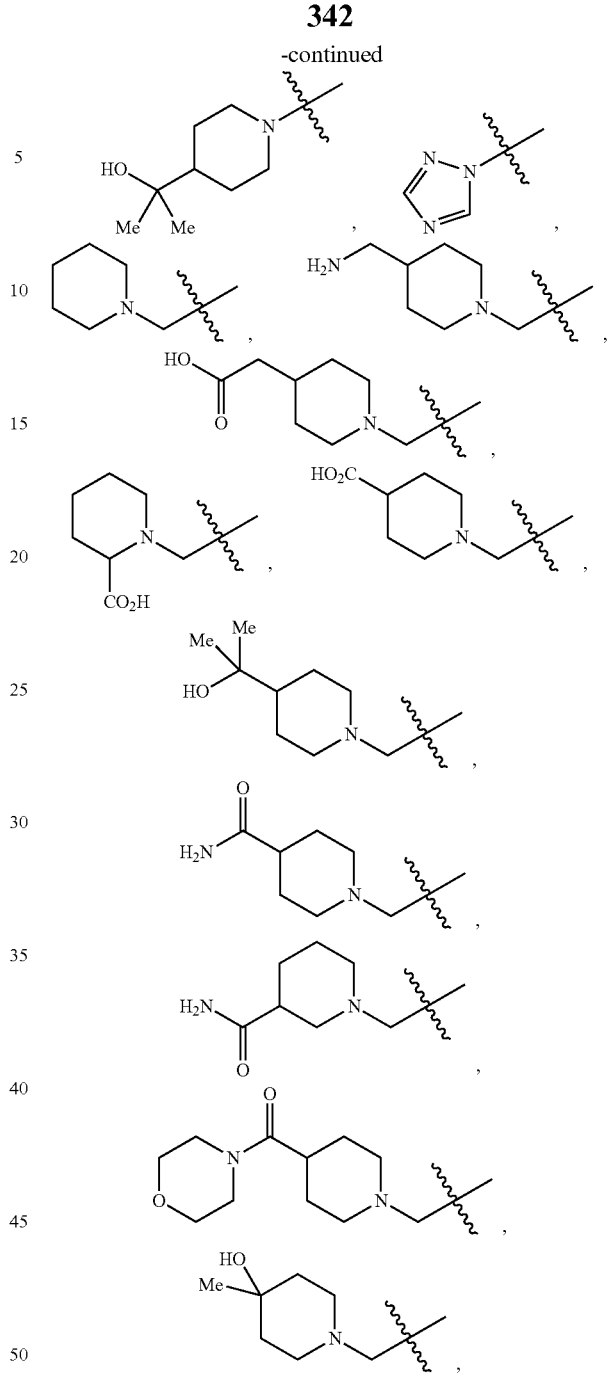
or a pharmaceutically acceptable salt thereof, tautomer thereof, a pharmaceutically acceptable salt of the tautomer, or a stereoisomer of any of the foregoing, wherein the symbol ⌇, when drawn across a bond, indicates the point of attachment to the rest of the molecule.
15. The compound of claim 1, wherein W is selected from
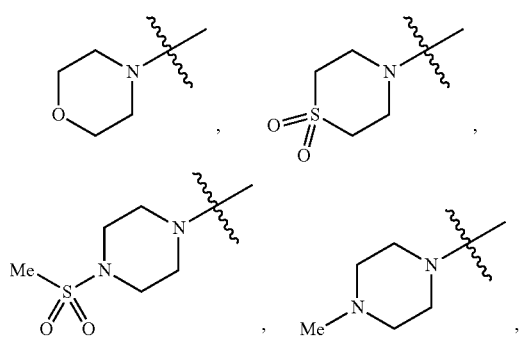

343
-continued
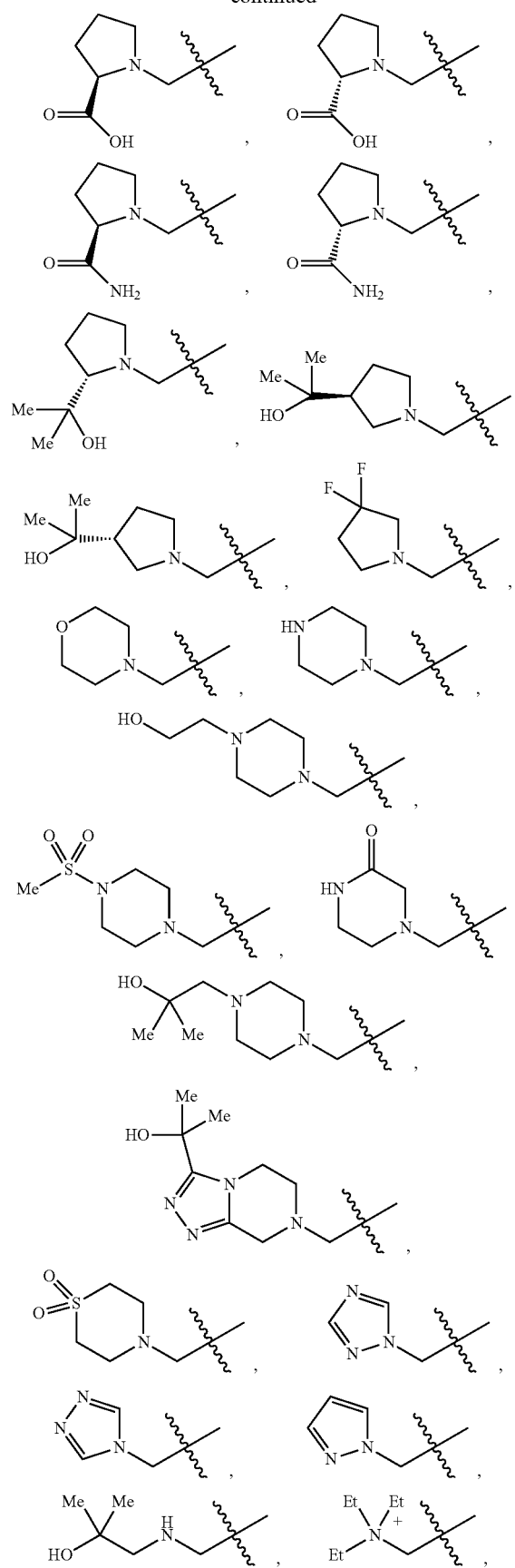
344
-continued
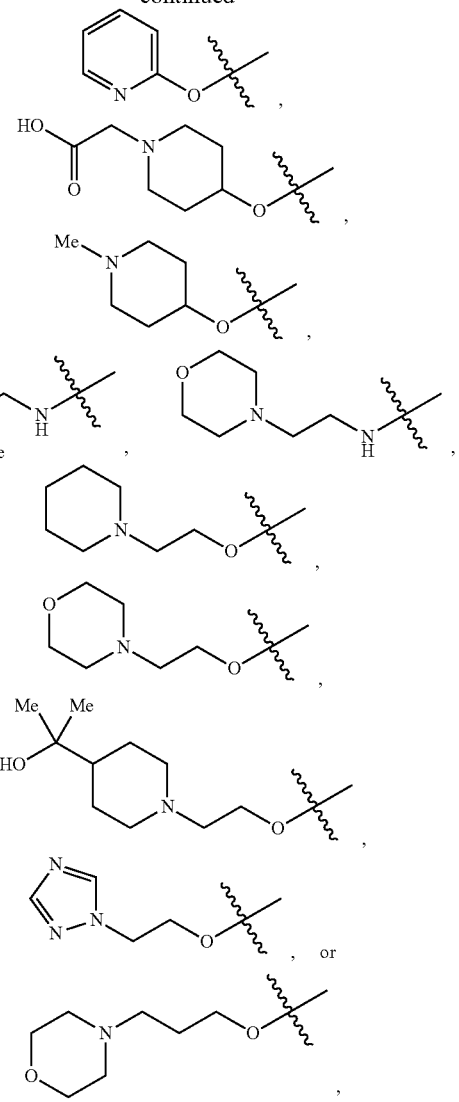
or a pharmaceutically acceptable salt thereof, tautomer thereof, a pharmaceutically acceptable salt of the tautomer, or a stereoisomer of any of the foregoing, wherein the symbol ⁓, when drawn across a bond, indicates the point of attachment to the rest of the molecule.
16. The compound of claim 1, wherein the compound is selected from,
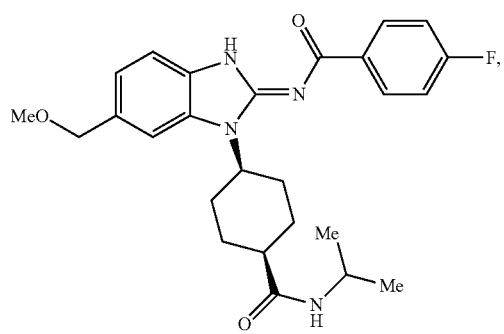 [SMILES: COCc1ccc2[nH]/c(=N\C(=O)c3ccc(F)cc3)n([C@H]3CC[C@@H](C(=O)NC(C)C)CC3)c2c1]

345
-continued
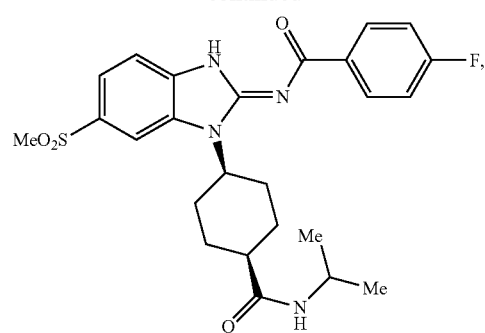
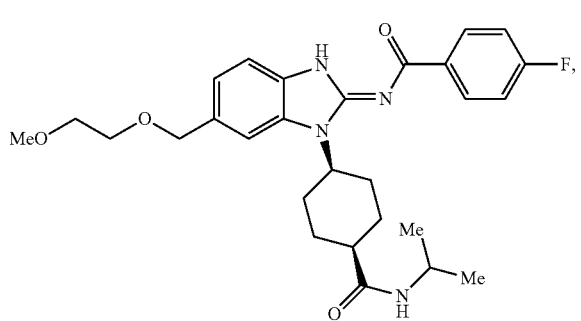
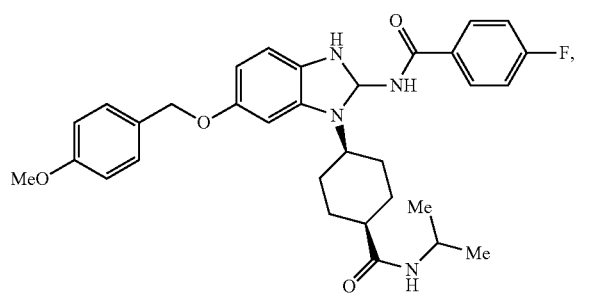
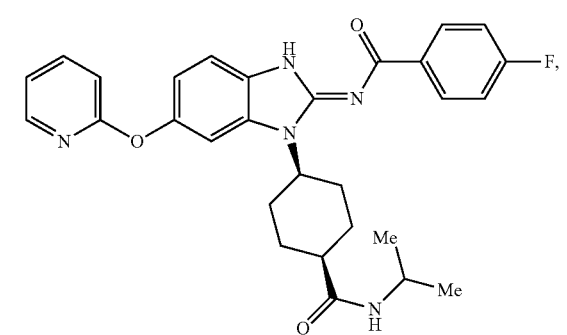
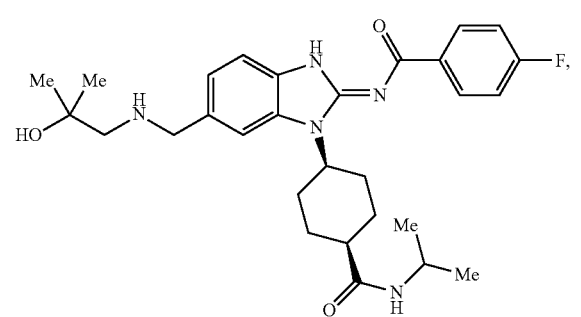
346
-continued
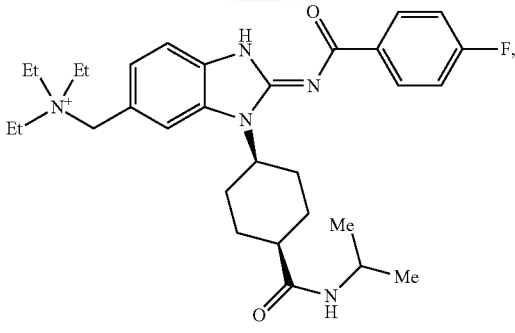
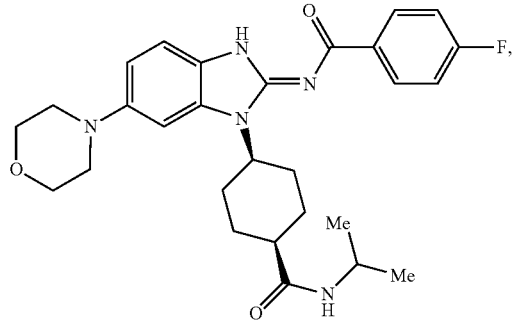
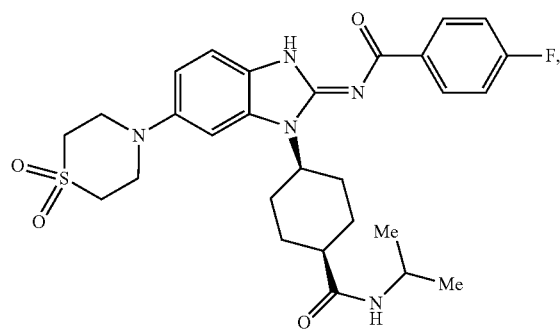
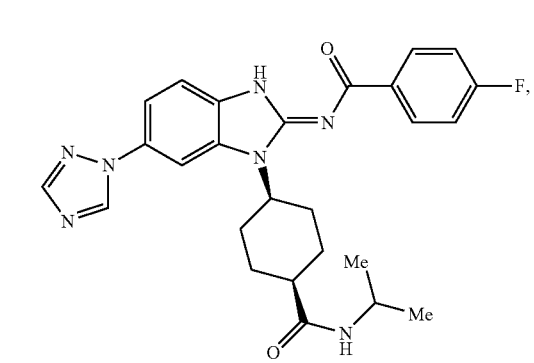 [SMILES: CC(C)NC(=O)[C@H]1CC[C@@H](n2/c(=N/C(=O)c3ccc(F)cc3)[nH]c3ccc(-n4cncn4)cc32)CC1]
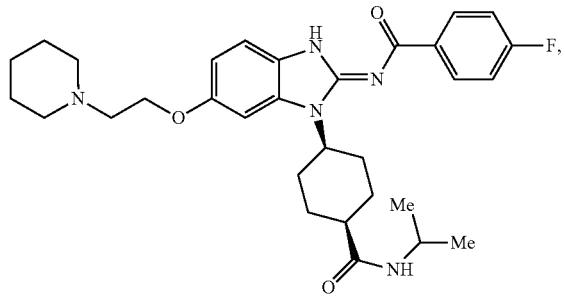

347
-continued
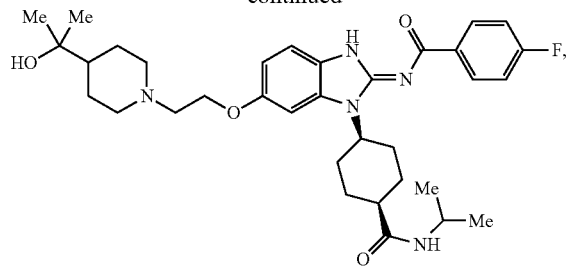
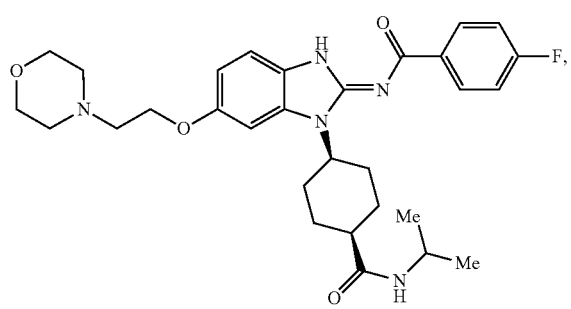
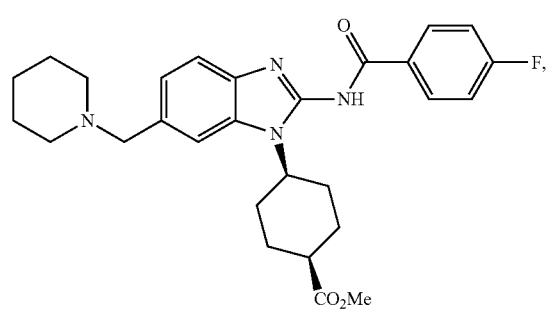
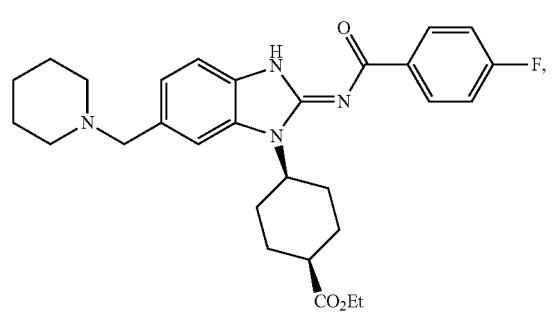
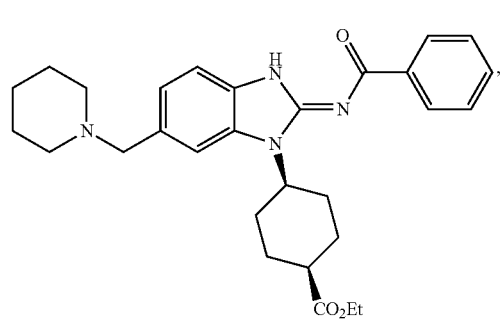
348
-continued
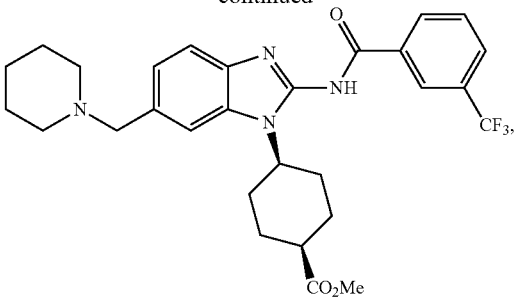

349
-continued
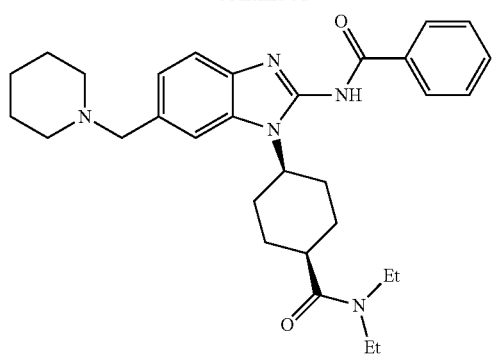
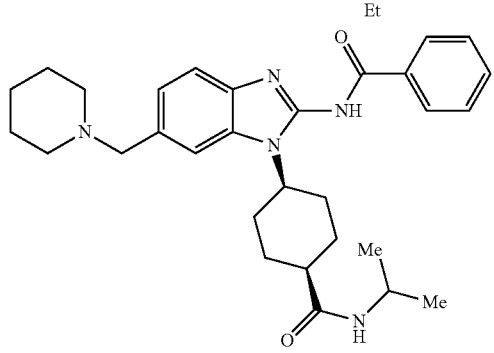
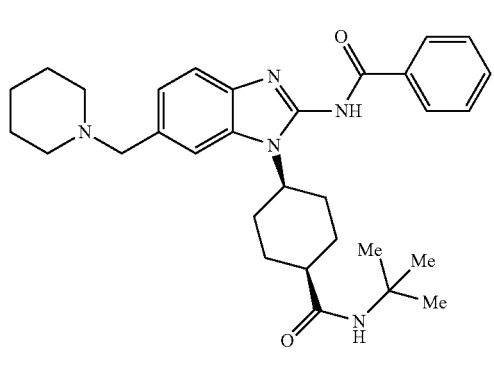
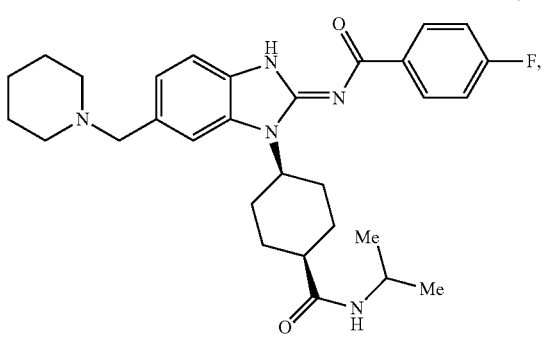
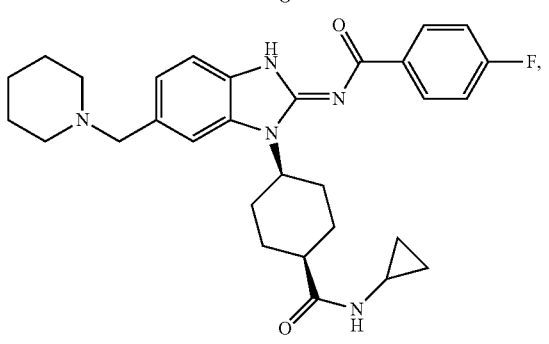
350
-continued
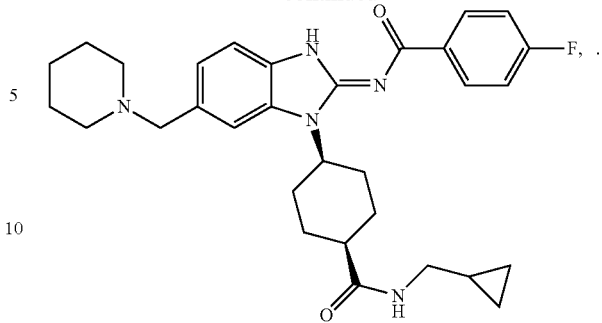
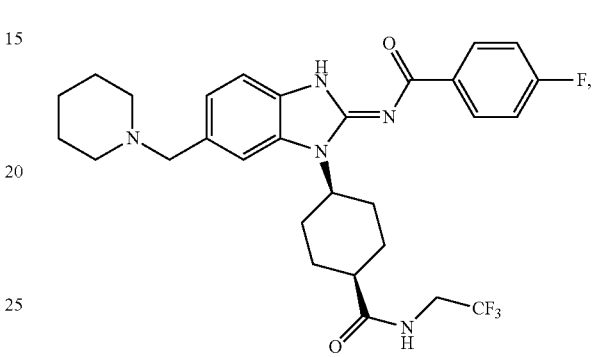
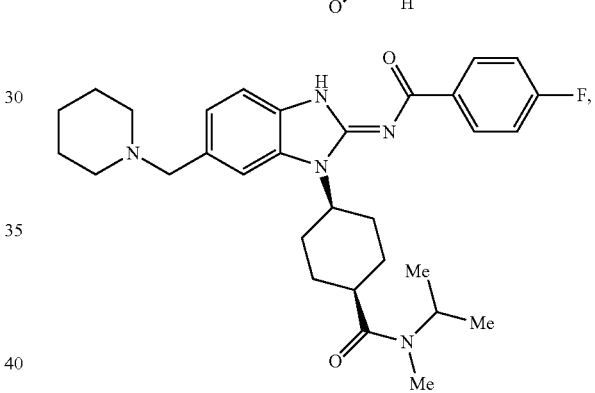
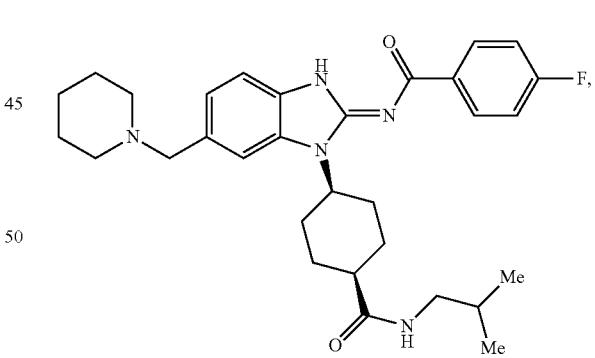
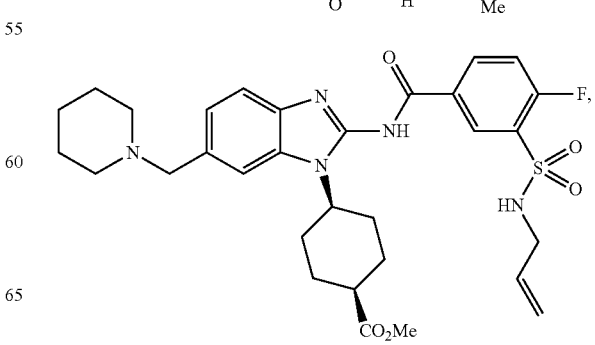

351
-continued
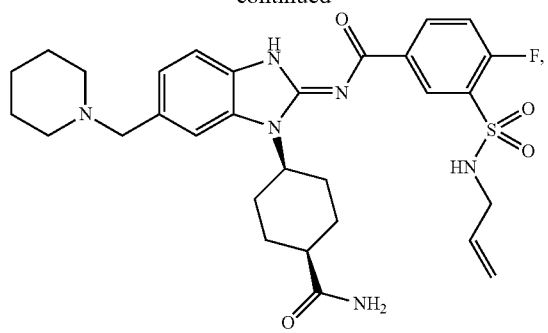
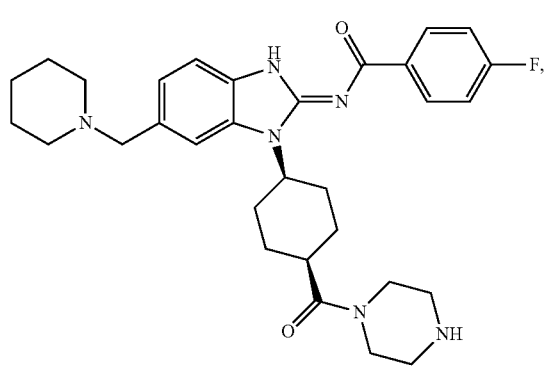
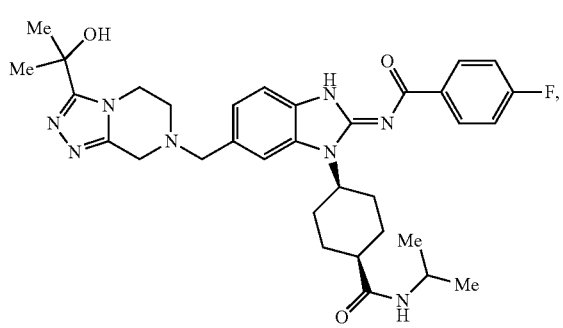
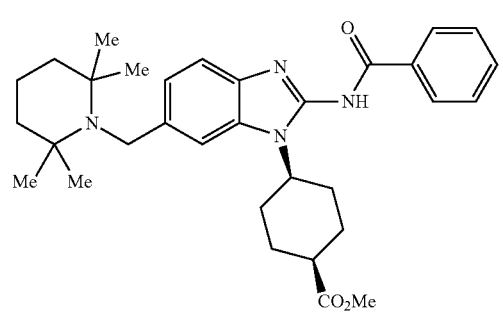
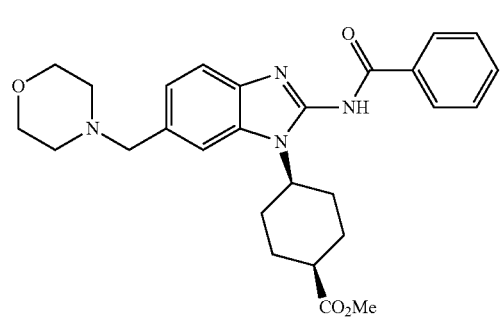
352
-continued
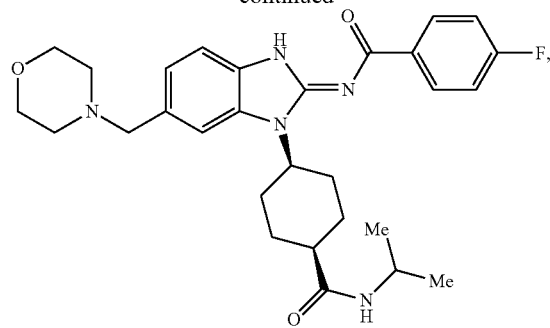
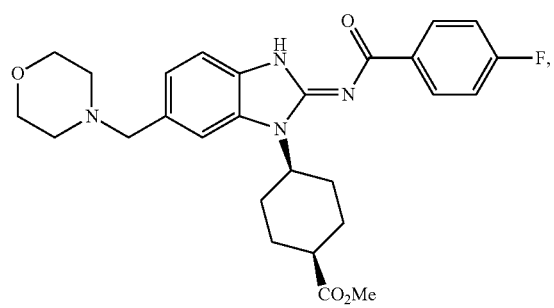
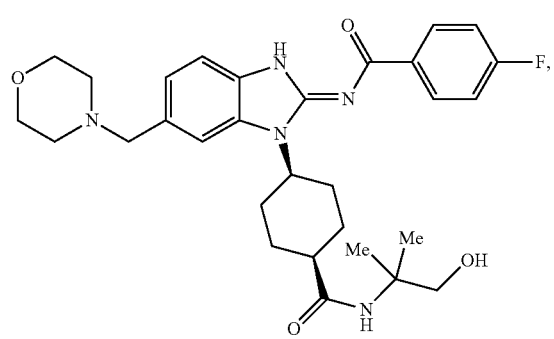
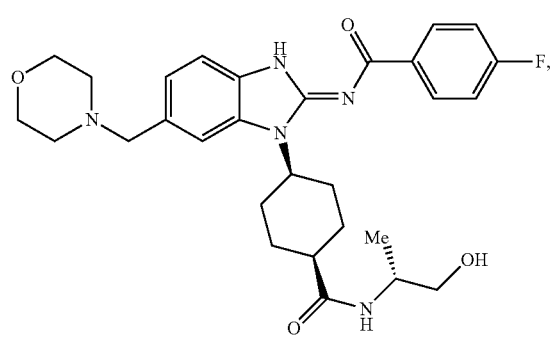
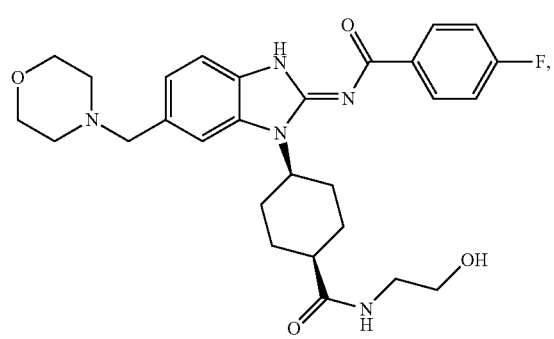

| 353 -continued | 354 -continued |
|---|---|
| 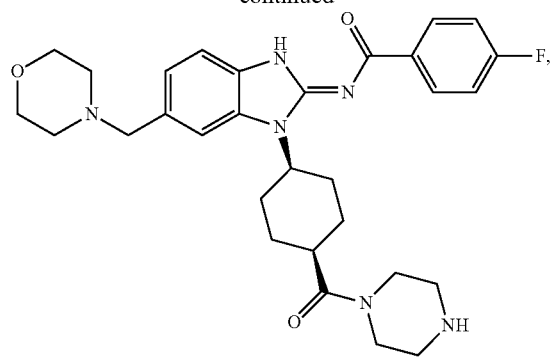 | 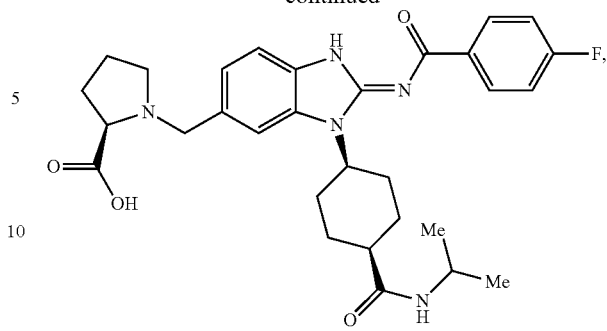 |
| 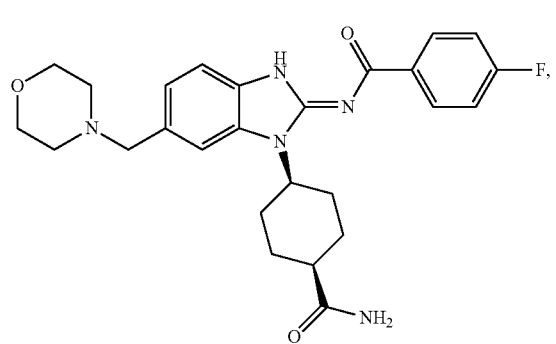 | 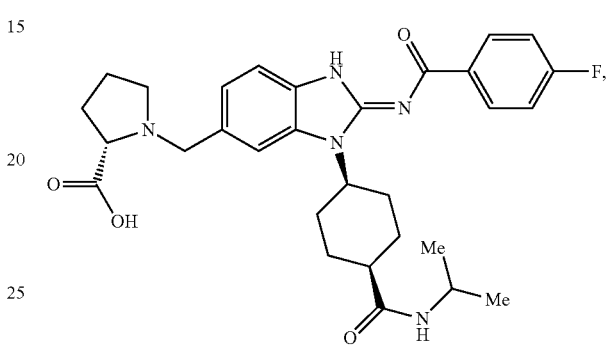 |
| 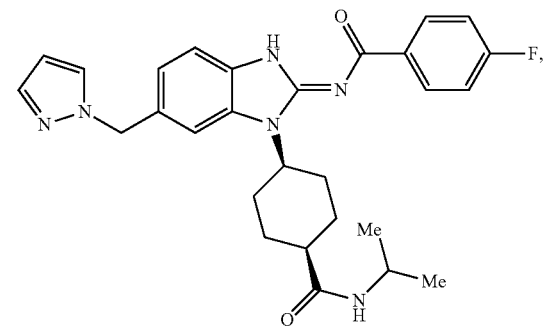 | 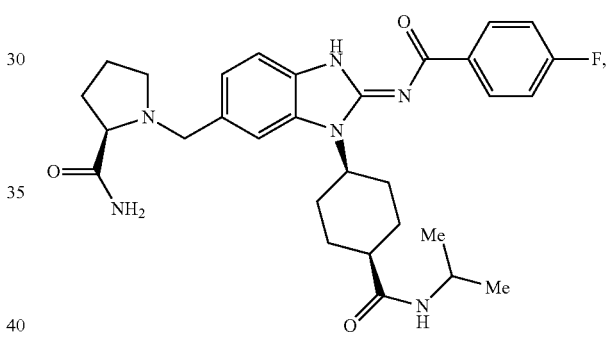 |
| 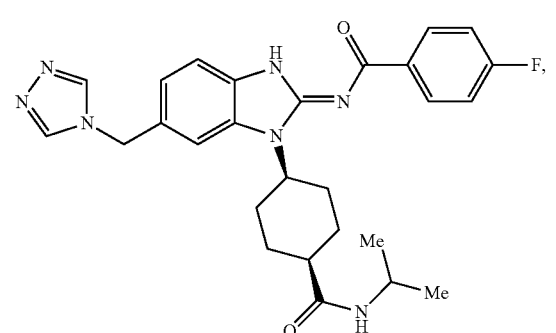 | 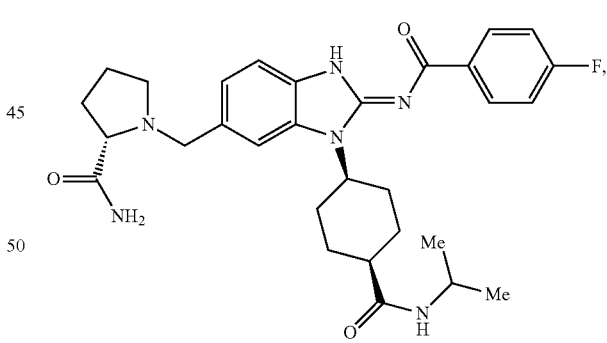 |
| 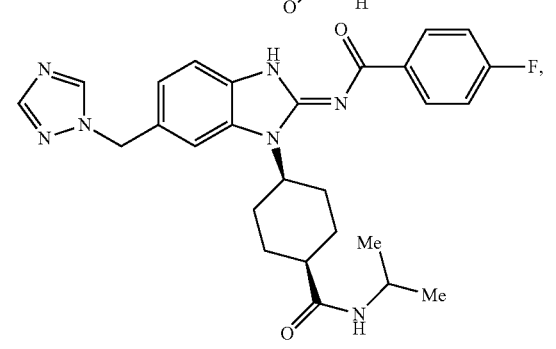 | 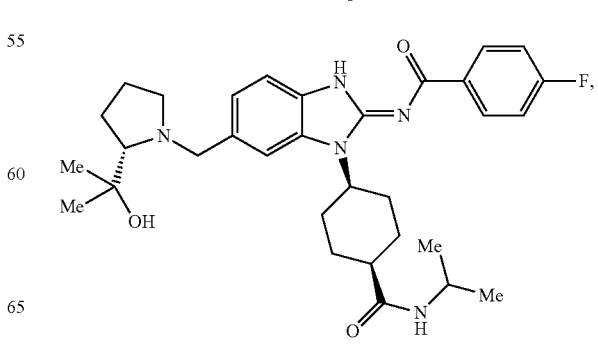 |

355
-continued
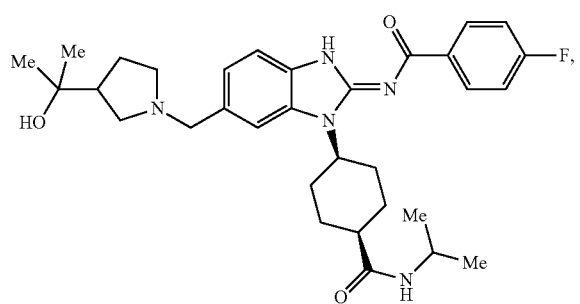
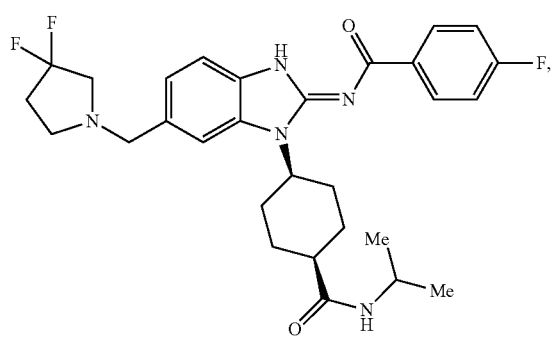
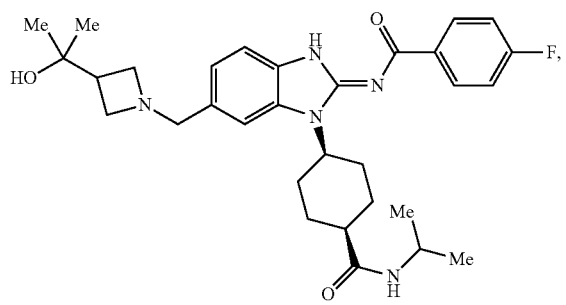
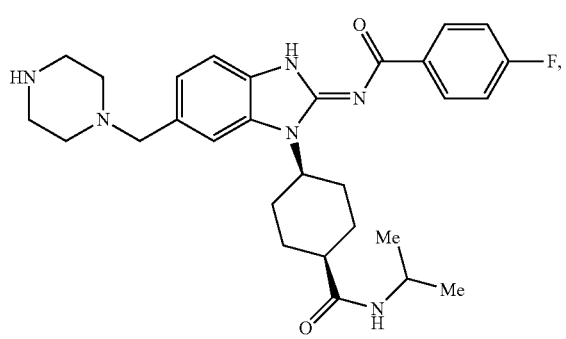
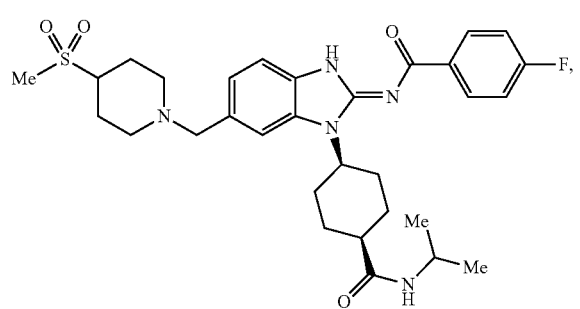
356
-continued
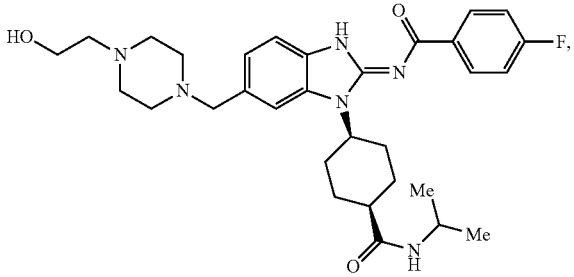
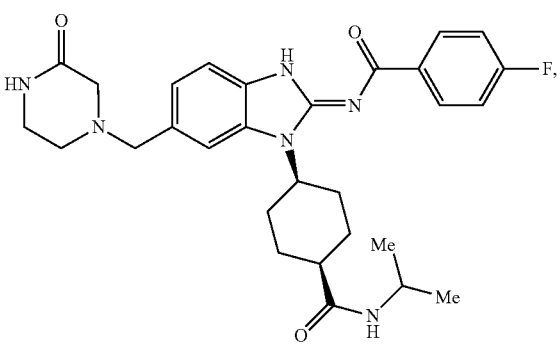
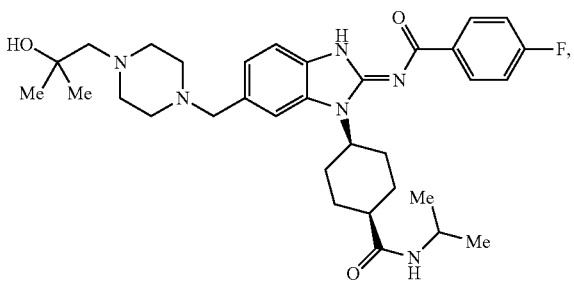
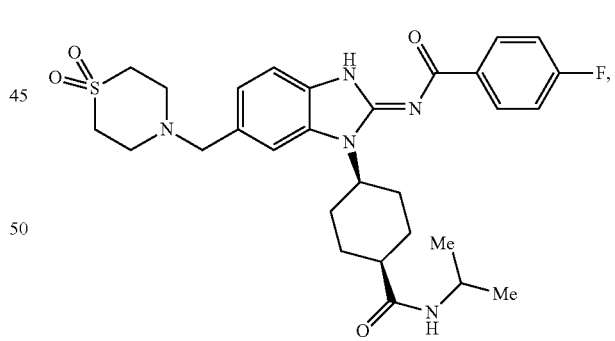
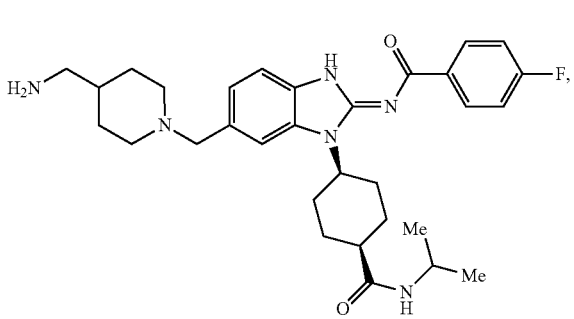

357
-continued
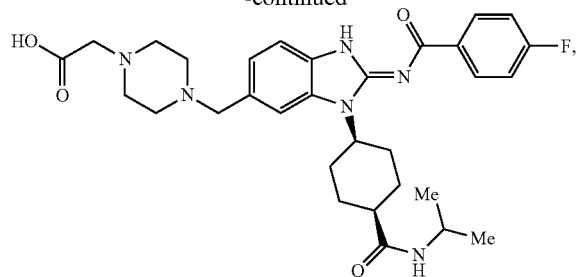
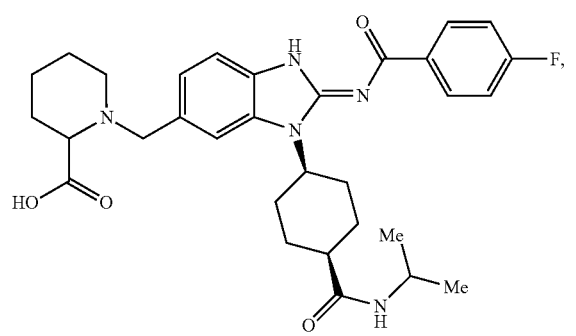
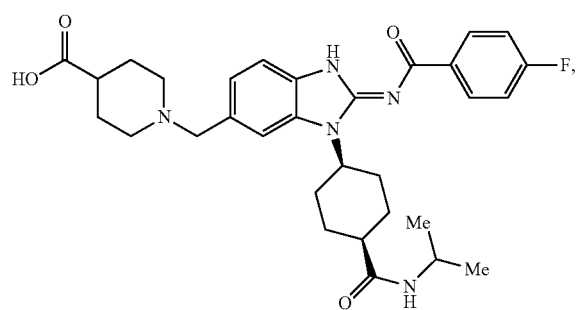
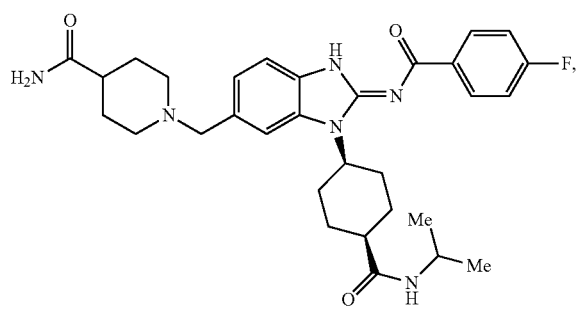
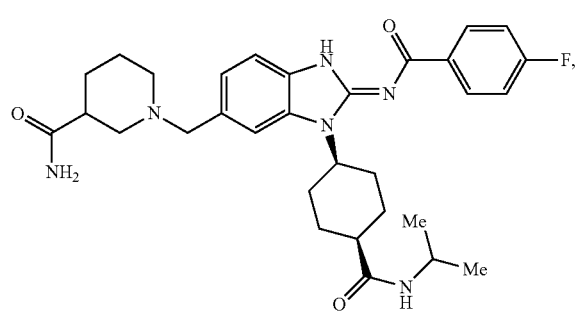
358
-continued
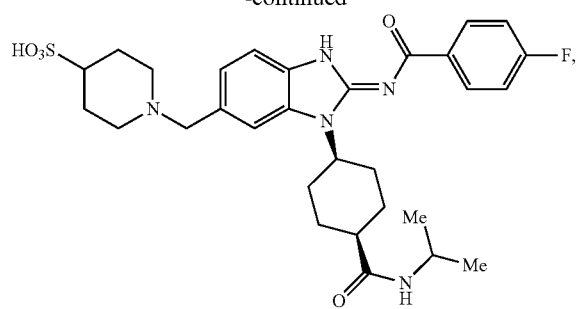
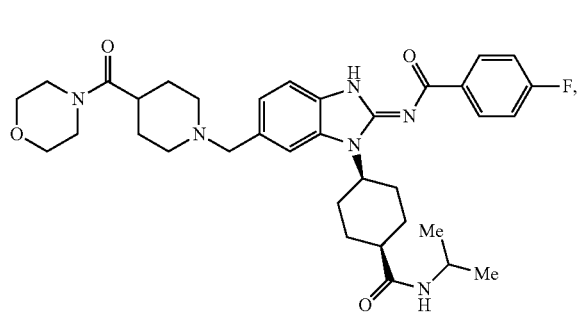
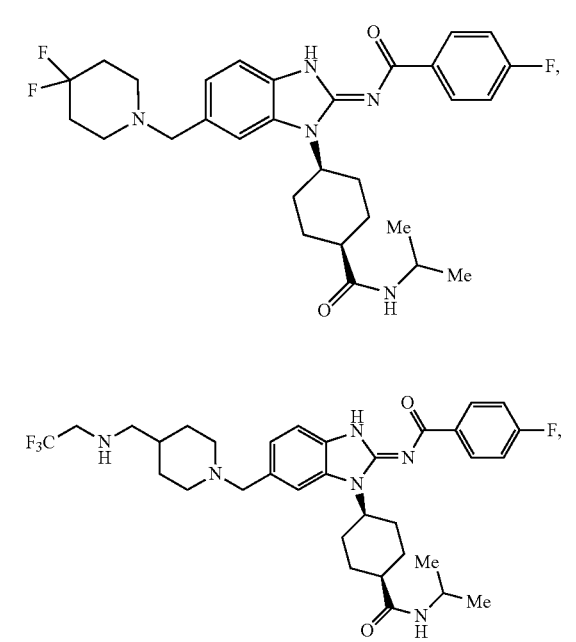

359
-continued
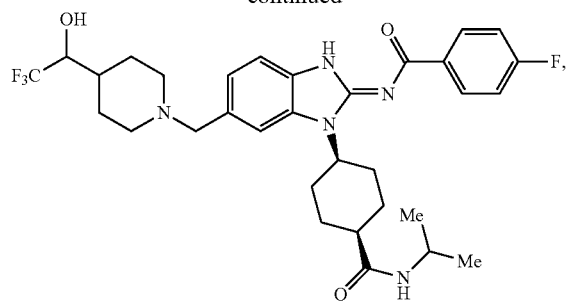
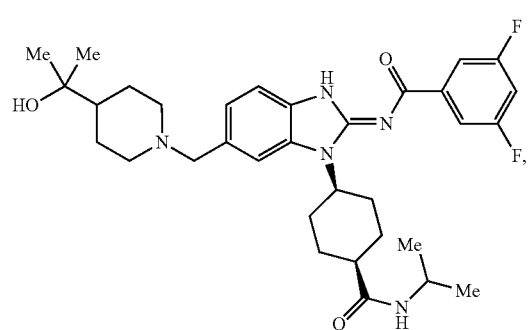
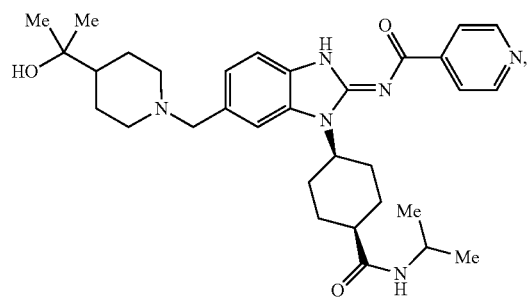
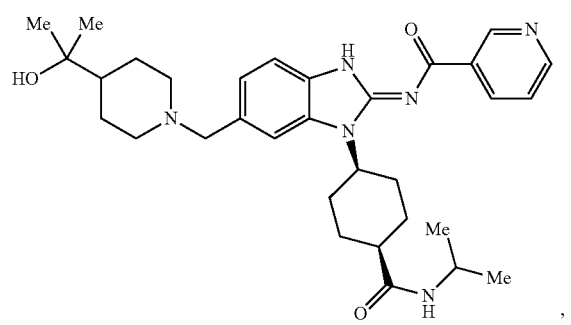
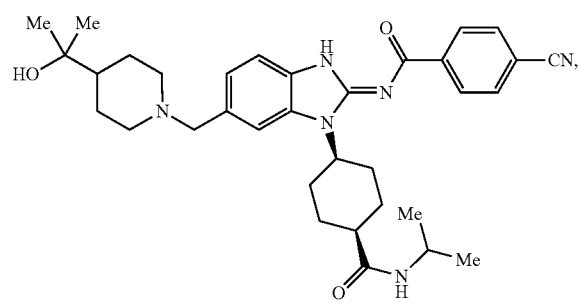
360
-continued
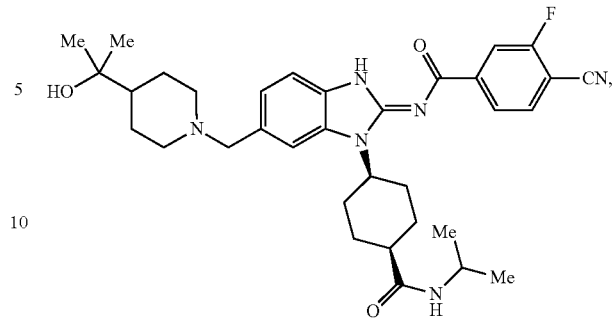
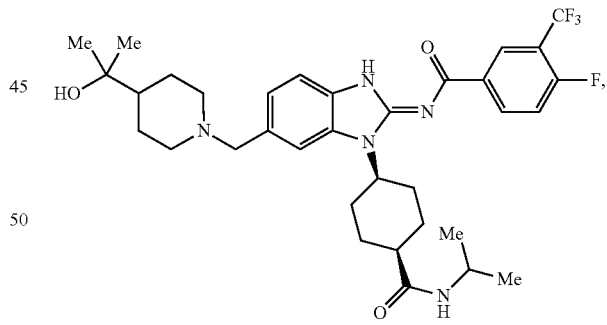
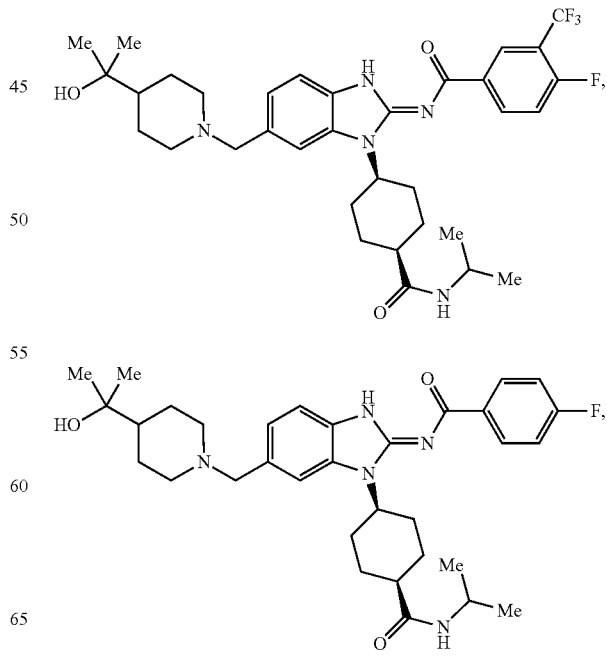

361
-continued
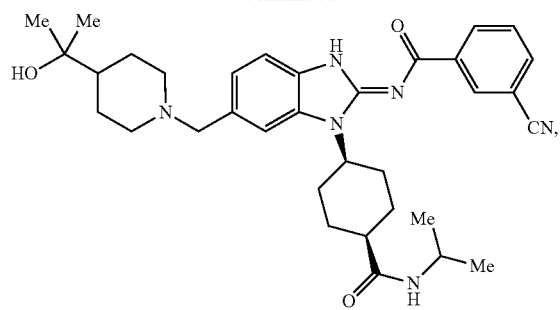
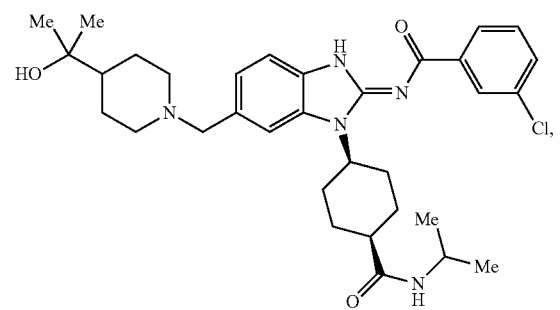
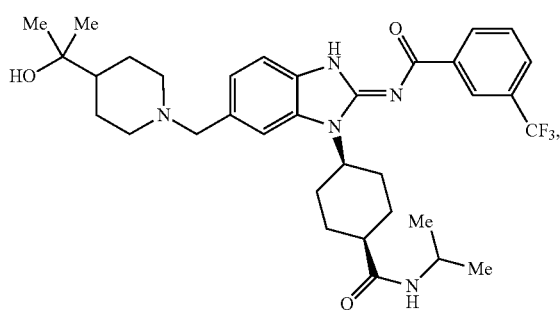
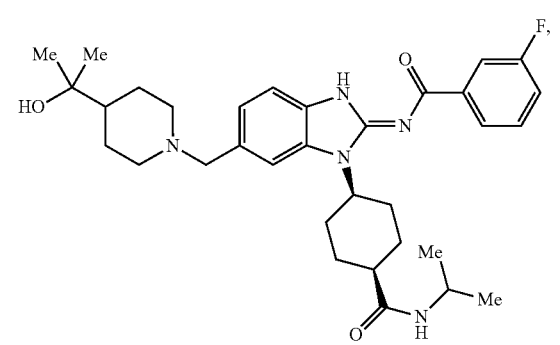
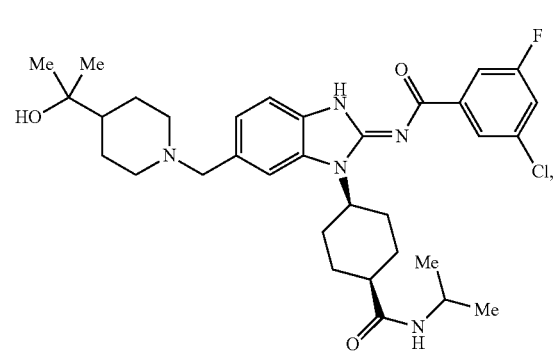
362
-continued
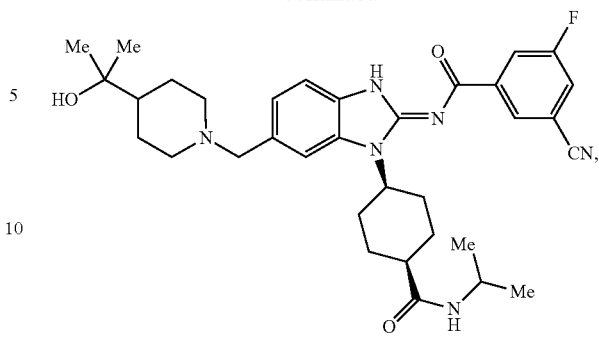
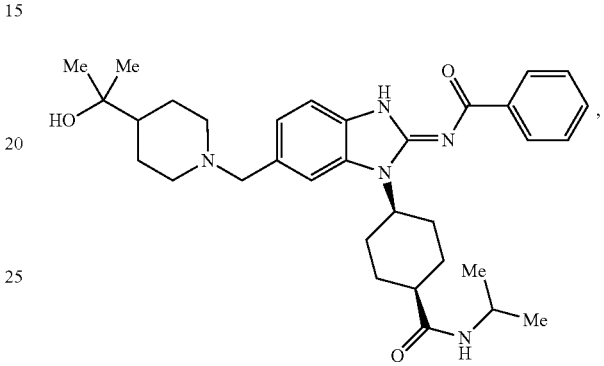
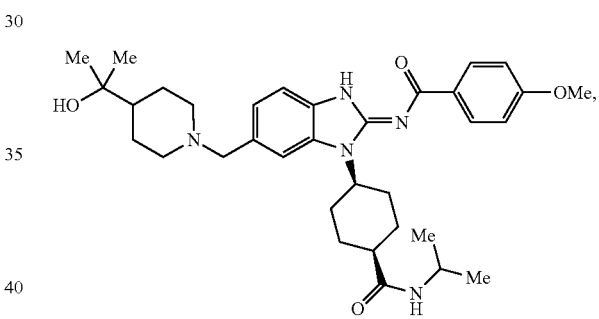
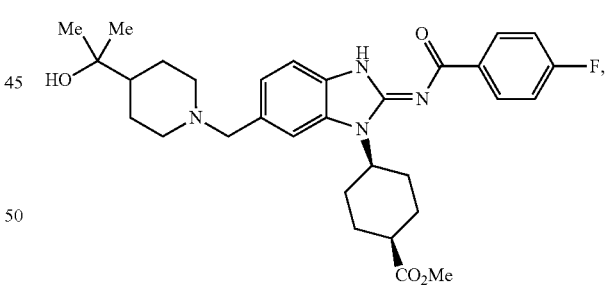
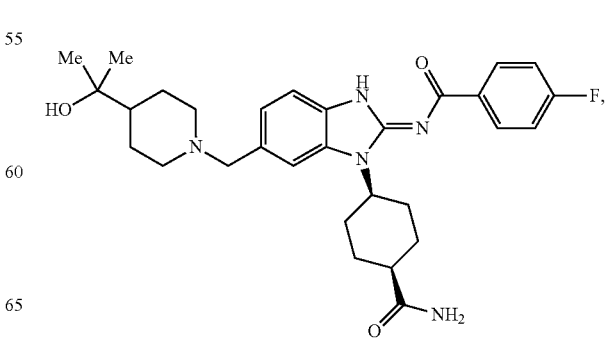

363
-continued

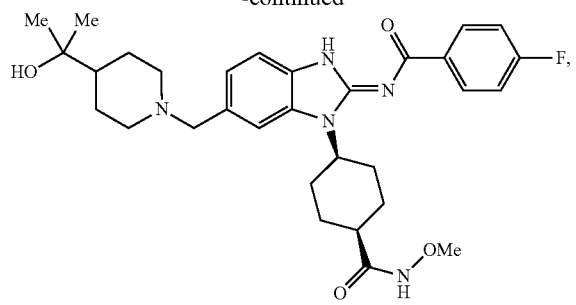

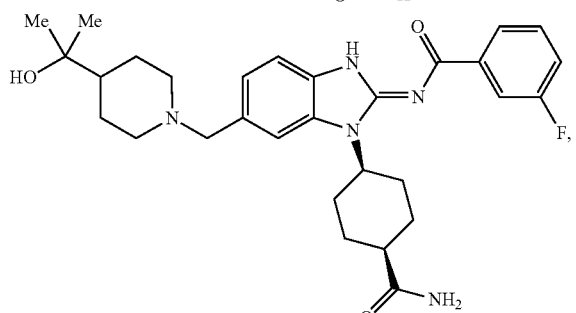

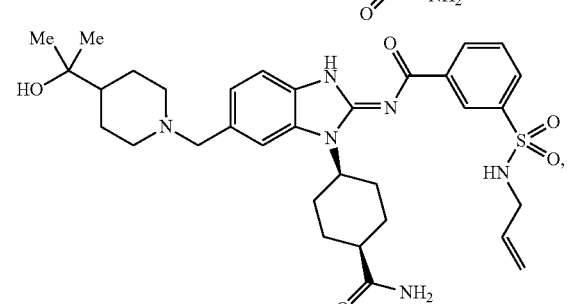

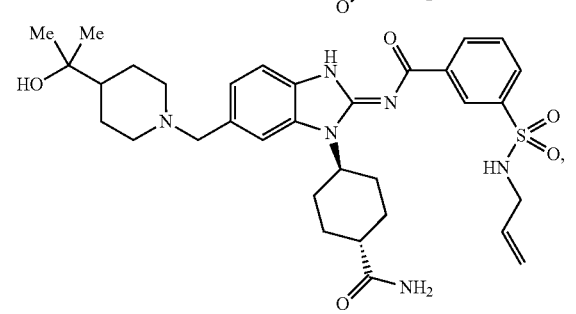

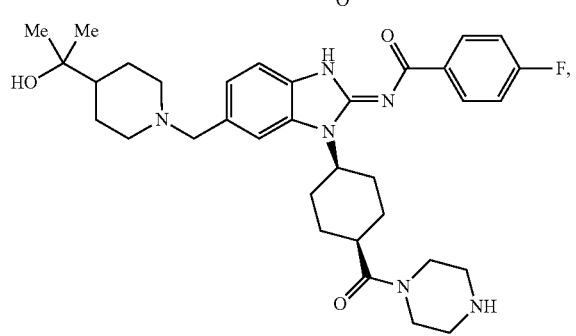

364
-continued

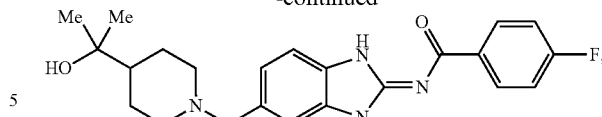

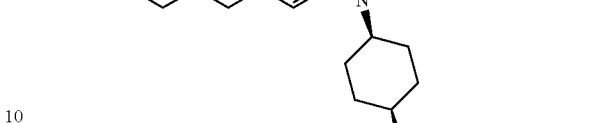

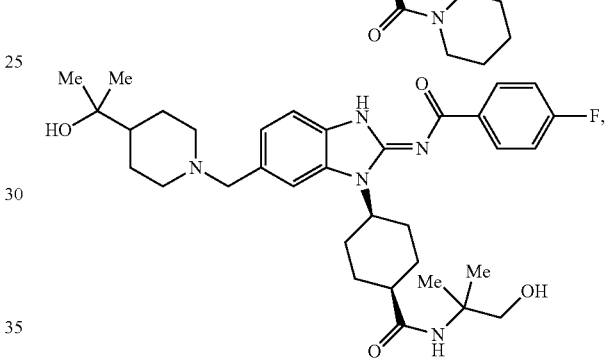

or

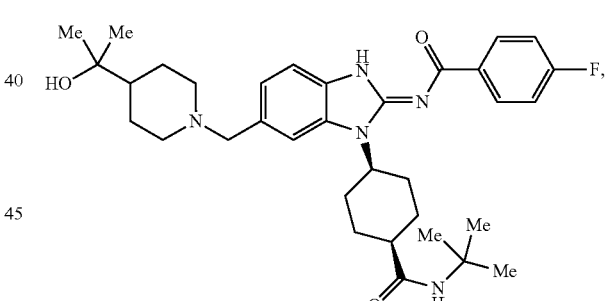

or a pharmaceutically acceptable salt thereof, tautomer thereof, a pharmaceutically acceptable salt of the tautomer, or a stereoisomer of any of the foregoing.

17. A pharmaceutical composition comprising a therapeutically effective amount of the compound or the pharmaceutically acceptable salt thereof, tautomer thereof, the pharmaceutically acceptable salt of the tautomer, or the stereoisomer of any of the foregoing, according to claim 1 and at least one pharmaceutically acceptable excipient, carrier, or diluent.

* * * * *